(12) United States Patent
Zemolka et al.

(10) Patent No.: US 8,138,187 B2
(45) Date of Patent: Mar. 20, 2012

(54) SUBSTITUTED HETEROARYL DERIVATIVES

(75) Inventors: Saskia Zemolka, Aachen (DE); Stefan Schunk, Aachen (DE); Werner Englberger, Stolberg (DE); Babette-Yvonne Kögel, Langerwehe-Hamich (DE); Klaus Linz, Wachtberg (DE); Hans Schick, Berlin (DE); Helmut Sonnenschein, Berlin (DE); Heinz Graubaum, Berlin (DE); Claudia Hinze, Bonn (DE)

(73) Assignee: Gruenenthal GmbH, Aachen (DE)

( * ) Notice: Subject to any disclaimer, the term of this patent is extended or adjusted under 35 U.S.C. 154(b) by 285 days.

(21) Appl. No.: 12/373,947

(22) Filed: Jan. 15, 2009

(65) Prior Publication Data
US 2010/0009986 A1    Jan. 14, 2010

Related U.S. Application Data

(63) Continuation of application No. PCT/EP2007/006325, filed on Jul. 17, 2007.

(30) Foreign Application Priority Data

Jul. 18, 2006 (DE) .................. 10 2006 033 109

(51) Int. Cl.
*A61K 31/53* (2006.01)
*A61K 31/44* (2006.01)
*A61K 31/40* (2006.01)
*A61K 31/38* (2006.01)
*A61K 31/34* (2006.01)

(52) U.S. Cl. ........ 514/247; 514/279; 514/410; 514/443; 514/468

(58) Field of Classification Search .................. 514/247, 514/279, 410, 443, 468
See application file for complete search history.

(56) References Cited

FOREIGN PATENT DOCUMENTS

| DE | 101 35 636 | 2/2003 |
|---|---|---|
| DE | 101 35 637 | 2/2003 |
| DE | 102 52 874 | 9/2004 |
| WO | 9951576 A | 10/1999 |
| WO | 2004043967 A | 5/2004 |

OTHER PUBLICATIONS

Vippagunta SR, Brittain HG, and Grant D J, "Crystalline solids," Advanced Drug Delivery Reviews, May 2001,48(1), 3-26.*
Calo et al; "Pharmacology of nociceptin and its receptor: a novel therapeutic target"; British Journal of Pharmaoclogy (2000), 129, pp. 1261-1283.
Manabe et al; "Facilitation of long-term potentiation and memory in mice lacking nociceptin receptors"; Nature, vol. 394, Aug. 6, 1998, pp. 577-581.
Nishi, et al; "Unrestrained nociceptive response and disregulation of hearin gability in mice lacking the nociceptin/orphaninFQ receptor": The EMBO Journal, vol. 16, No. 8, (1997) pp. 1858-1864.
Friderichs, Wiley-VCH Verlag GmbH, 2002, Analgesics, chapter 3, pp. 127-150.
Puetz, Wiley-VCH Verlag GmbH, 2002, Analgesics, chapter 9, pp. 455-476.

* cited by examiner

*Primary Examiner* — San-Ming Hui
*Assistant Examiner* — Paul Zarek
(74) *Attorney, Agent, or Firm* — Norris McLaughlin & Marcus, P.A.

(57) ABSTRACT

The invention relates to substituted heteroaryl derivatives, to methods for the production thereof, to medicaments containing said compounds and to the use of substituted heteroaryl derivatives for producing medicaments.

17 Claims, No Drawings

SUBSTITUTED HETEROARYL DERIVATIVES

This application is a continuation application of PCT/EP2007/006325 filed Jul. 17, 2007, which claims foreign priority benefit under 35 U.S.C. §119 of the German Patent Application No. 10 2006 033 109.5 filed Jul. 18, 2006.

The present invention relates to substituted heteroaryl derivatives, processes for the preparation thereof, medicaments containing these compounds and the use of substituted heteroaryl derivatives for the preparation of medicaments.

Treatment of chronic and non-chronic states of pain is of great importance in medicine. There is a worldwide need for pain therapies which are highly effective. The urgent need for action for targeted treatment of chronic and non-chronic states of pain appropriate for the patient, by which is to be understood successful and satisfactory pain treatment for the patient, is documented in the large number of scientific works which have been published recently in the field of applied analgesics and of basic research into nociception.

Conventional μ opioids, such as morphine, have a good action in the therapy of severe to very severe pain and are of very great importance for pain therapy. However, it may be advantageous if, in addition to the μ opioid receptor, other opioid receptors, in particular the ORL-1 receptor, are influenced, since pure μ opioids can also have undesirable side effects, such as constipation and respiratory depression, but can also lead to dependency. The δ, κ and ORL-1 opioid receptors are also involved in the pain event (Opioids: Introduction, p. 127-150, Further Opioid Receptors, 455-476 in: Analgesics—From Chemistry and Pharmacology to Clinical Application, Wiley VCH, 2002).

The ORL1 receptor moreover is also involved in regulation of further physiological and pathophysiological processes. These include, inter alia, learning and memory development (Manabe et al., Nature, 394, 1997, p. 577-581), hearing capacity (Nishi et al., EMBO J., 16, 1997, p. 1858-1864) and numerous further processes. A review article by Calo et al. (Br. J. Pharmacol., 129, 2000, 1261-1283) gives an overview of the indications or biological processes in which the ORL1 receptor plays a role or with high probability could play a role. There are mentioned, inter alia: analgesia, stimulation and regulation of food intake, influence on μ-agonists, such as morphine, treatment of withdrawal symptoms, reduction in the addiction potential of opioids, anxiolysis, modulation of motor activity, memory disorders, epilepsy; modulation of neurotransmitter secretion, in particular of glutamate, serotonin and dopamine, and therefore neurodegenerative diseases; influencing of the cardiovascular system, inducement of an erection, diuresis, antinatriuresis, electrolyte balance, arterial blood pressure, water retention diseases, intestinal motility (diarrhoea), relaxing effects on the respiratory tract, micturition reflex (urinary incontinence). The use of agonists and antagonists as anoretics, analgesics (also in co-administration with opioids) or nootropics is furthermore discussed.

The prior art (WO 02090317) discloses structurally related compounds which have an affinity for the ORL-1 receptor, but no affinity for the μ opioid receptor is described. In these compounds, however, the heteroaryl ring is linked to the cyclohexane ring via a nitrogen.

The object of the present invention was to provide further medicaments which act on the opioid receptor system and are therefore suitable for medicaments in particular for treatment of the various diseases associated with this system or for use in the indications associated therewith. The invention therefore provides substituted heteroaryl derivatives of the general formula I

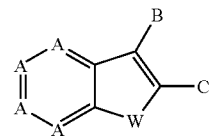

wherein
A represents N or $CR^{7-10}$ wherein A represents N at most twice
W represents O, S or $NR^4$
with the proviso that if W represents O or S. A denotes $CR^{7-10}$;
one of the radicals B or C represents H; $C_{1-8}$-alkyl, in each case saturated or unsaturated, branched or unbranched, mono- or polysubstituted or unsubstituted, $COR^{12}$; $SO_2R^{12}$; aryl, $C_{3-8}$-cycloalkyl or heteroaryl bonded via $C_{1-3}$-alkyl and in each case mono- or polysubstituted or unsubstituted; aryl-, or heteroaryl, in each case mono- or polysubstituted or unsubstituted; $C_{3-8}$-cycloalkyl, in each case mono- or polysubstituted or unsubstituted, and the other particular radical B or C represents

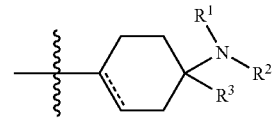

wherein
⇌ represents a single bond or a double bond,
$R^1$ and $R^2$ independently of one another represent H; $C_{1-5}$-alkyl, in each case saturated or unsaturated, branched or unbranched, mono- or polysubstituted or unsubstituted; $C_{3-8}$-cycloalkyl, in each case mono- or polysubstituted or unsubstituted; aryl or heteroaryl, in each case mono- or polysubstituted or unsubstituted; or aryl, $C_{3-8}$-cycloalkyl or heteroaryl, bonded via $C_{1-3}$-alkyl and in each case mono- or polysubstituted or unsubstituted;
or the radicals $R^1$ and $R^2$ together represent $CH_2CH_2OCH_2CH_2$, $CH_2CH_2NR^{11}CH_2CH_2$ or $(CH_2)_{3-6}$,
wherein $R^{11}$ denotes H; $C_{1-5}$-alkyl, in each case saturated or unsaturated, branched or unbranched, mono- or polysubstituted or unsubstituted; $C_{3-8}$-cycloalkyl, in each case mono- or polysubstituted or unsubstituted; aryl-, or heteroaryl, in each case mono- or polysubstituted or unsubstituted; or aryl, $C_{3-8}$-cycloalkyl or heteroaryl, bonded via $C_{1-3}$-alkyl and in each case mono- or polysubstituted or unsubstituted; C(O)phenyl, C(O)heteroaryl, $C(O)C_{1-5}$-alkyl, in each case substituted or unsubstituted;
and
R represents $C_{1-8}$-alkyl, in each case saturated or unsaturated, branched or unbranched, mono- or polysubstituted or unsubstituted; $C_{3-8}$-cycloalkyl, in each case mono- or polysubstituted or unsubstituted; aryl or heteroaryl, in each case unsubstituted or mono- or polysubstituted; aryl, heteroaryl or $C_{3-8}$-cycloalkyl, bonded via $C_{1-3}$-alkyl group and in each case unsubstituted or mono- or polysubstituted;
$R^4$ represents H; $C_{1-5}$-alkyl, saturated or unsaturated, branched or unbranched, unsubstituted or mono- or polysubstituted; aryl, or heteroaryl, in each case substituted or unsubstituted; aryl, heteroaryl or cycloalkyl, bonded via a $C_{1-3}$- alkyl group and in each case mono- or polysubstituted or unsubstituted; COR$^{12}$; SO$_2$R$^{12}$, wherein R$^{12}$ denotes H; C$_{1-5}$-alkyl, in each case saturated or unsaturated, branched or unbranched, mono- or polysubstituted or unsubstituted;

C$_{3-8}$-cycloalkyl, in each case saturated or unsaturated, mono- or polysubstituted or unsubstituted; aryl-, or heteroaryl, in each case mono- or polysubstituted or unsubstituted; or aryl, C$_{3-8}$-cycloalkyl or heteroaryl, bonded via C$_{1-3}$-alkyl and in each case mono- or polysubstituted or unsubstituted; OR$^{13}$; NR$^{14}$R$^{15}$;

R$^7$, R$^8$, R$^9$ and R$^{10}$ independently of one another represent H, F, Cl, Br, I, NO$_2$, CF$_3$, OR$^{13}$, SR$^{13}$, SO$_2$R$^{13}$, SO$_2$OR$^{13}$, CN, COOR$^{13}$, NR$^{14}$R$^{15}$; NHC(O)NHR$^{13}$, NHC(O)R$^{13}$, NH(CNR$^{13}$)NHR$^{13}$, SO$_2$NHR$^{13}$; C$_{1-5}$-alkyl C$_{3-8}$-cycloalkyl, unsubstituted or mono- or polysubstituted; aryl-, or heteroaryl, unsubstituted or mono- or polysubstituted; or aryl, C$_{3-8}$-cycloalkyl or heteroaryl, bonded via C$_{1-3}$-alkyl and unsubstituted or mono- or polysubstituted;

wherein R$^{13}$ denotes H; C$_{1-5}$-alkyl, in each case saturated or unsaturated, branched or unbranched, unsubstituted or mono- or polysubstituted;

C$_{3-8}$-cycloalkyl, in each case saturated or unsaturated, unsubstituted or mono- or polysubstituted; aryl-, or heteroaryl, unsubstituted or mono- or polysubstituted; or aryl, C$_{3-8}$-cycloalkyl or heteroaryl, bonded via C$_{1-3}$-alkyl and unsubstituted or mono- or polysubstituted;

or R$^7$, R$^8$ and R$^9$ have the abovementioned meaning and R$^{10}$ together with B represents —CH$_2$CH$_2$CH$_2$— and R$^{10}$ and B therefore form a six-membered ring, R$^{14}$ and R$^{15}$ independently of one another denote H; C$_{1-5}$-alkyl, in each case saturated or unsaturated, branched or unbranched, unsubstituted or mono- or polysubstituted; or C$_{3-8}$-cycloalkyl, in each case saturated or unsaturated, unsubstituted or mono- or polysubstituted; aryl-, or heteroaryl, unsubstituted or mono- or polysubstituted; or aryl, C$_{3-8}$-cycloalkyl or heteroaryl, bonded via C$_{1-3}$-alkyl and unsubstituted or mono- or polysubstituted;

or R$^{14}$ and R$^{15}$ together form CH$_2$CH$_2$OCH$_2$CH$_2$, CH$_2$CH$_2$NR$^{16}$CH$_2$CH$_2$ or (CH$_2$)$_{3-6}$, wherein R$^{16}$ denotes H; C$_{1-5}$-alkyl, saturated or unsaturated, branched or unbranched, unsubstituted or mono- or polysubstituted;

in the form of the racemate; of the enantiomers, diastereomers, mixtures of the enantiomers or diastereomers or of an individual enantiomer or diastereomer; of the bases and/or salts of physiologically acceptable acids.

If a radical, for example R$^{13}$ occurs more than once within a compound, e.g. in NH(CNR$^{13}$)NHR$^{13}$, the radical can assume different meanings within the same molecule. NH(CNR$^{13}$)NHR$^{13}$ can thus denote, for example,

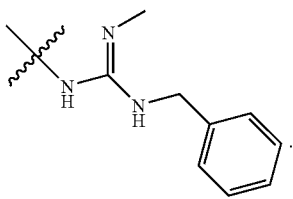

In the context of this invention, the expressions "C$_{1-8}$-alkyl", "C$_{1-3}$-alkyl," and "C$_{1-5}$-alkyl" include acyclic saturated or unsaturated hydrocarbon radicals, which can be branched- or straight-chain and unsubstituted or mono- or polysubstituted, having 1 to 8 or 1 to 3 C atoms or 1-5 C atoms, i.e. C$_{1-8}$-alkanyls, C$_{2-8}$-alkenyls and C$_{2-8}$-alkynyls or C$_{1-3}$-alkanyls, C$_{2-3}$-alkenyls and C$_{2-3}$-alkynyls, or C$_{1-5}$-alkanyls, C$_{2-5}$-alkenyls and C$_{2-5}$-alkynyls. In this context, alkenyls have at least one C—C double bond and alkynyls have at least one C—C triple bond. Alkyl is advantageously chosen from the group which includes methyl, ethyl, n-propyl, 2-propyl, n-butyl, iso-butyl, sec-butyl, tert-butyl, n-pentyl, iso-pentyl, neo-pentyl, n-hexyl, 2-hexyl, n-heptyl, n-octyl, 1,1,3,3-tetramethylbutyl; ethylenyl (vinyl), ethynyl, propenyl (—CH$_2$CH═CH$_2$, —CH═CH—CH$_3$, —C(═CH$_2$)—CH$_3$), propynyl (—CH—C≡CH, —C≡C—CH$_3$), butenyl, butynyl, pentenyl, pentynyl, hexenyl, hexynyl, heptenyl, heptynyl, octenyl and octynyl. Methyl, ethyl, n-propyl, n-butyl, sec-butyl, iso-butyl are particularly advantageous.

For the purpose of this invention, the expression "cycloalkyl" or "C$_{3-8}$-cycloalkyl" denotes cyclic hydrocarbons having 3, 4, 5, 6, 7 or 8 carbon atoms, wherein the hydrocarbons can be saturated or unsaturated (but not aromatic), unsubstituted or mono- or polysubstituted. With respect to cycloalkyl, the term also includes saturated or unsaturated (but not aromatic) cycloalkyls in which one or two carbon atoms are replaced by a hetero atom S, N or O. Cycloalkyl rings which contain a hetero atom are sometimes called "heterocyclyl rings" in the literature; in the context of this invention, these "heterocyclyl rings" are expressly covered by the term C$_{3-8}$-cycloalkyl. The term "C$_{3-8}$-cycloalkyl" in the description and the claims therefore in each case represents "C$_{3-8}$-cycloalkyl (without hetero atoms in the ring)" and at the same time also "a three- to eight-membered heterocyclyl ring". The cycloalkyl ring can also be condensed with a further ring, which can be saturated, unsaturated (also aromatic). C$_{3-8}$-Cycloalkyl is advantageously from the group which contains cyclopropyl, cyclobutyl, cyclopentyl, cyclohexyl, cycloheptyl, cyclooctyl, cyclopentenyl, cyclohexenyl, cycloheptenyl and cyclooctenyl, but also tetrahydropyranyl, dioxanyl, dioxolanyl, tetrahydroquinolinyl, tetrahydroisoquinolinyl, isoindolinyl, thiazolidinyl, morpholinyl, piperidinyl, piperazinyl, pyrazolinonyl and pyrrolidinyl. Cyclopropyl, cyclopentyl, cyclohexyl, pyrrolidinyl, tetrahydroquinolinyl, piperidyl, tetrahydroisoquinolinyl, isoindolinyl, piperazinyl, morpholinyl and thiazolinyl is particularly preferred.

In the context of this invention, the expression "aryl" denotes aromatic hydrocarbons, inter alia phenyls and naphthyls. The aryl radicals can also be condensed with further saturated, (partially) unsaturated or aromatic ring systems, so that the aryl radical forms an aromatic ring system having at most 20 C atoms. Each of these C$_{6-20}$-aryl radicals can be unsubstituted or mono- or polysubstituted, wherein the substituents on the aryl can be identical or different and can be in any desired and possible position of the aryl. Aryl is advantageously chosen from the group which contains phenyl, 1-naphthyl, 2-naphthyl, which can in each case be unsubstituted or mono- or polysubstituted. The phenyl radical is particularly advantageous.

The expression "heteroaryl" represents a 5-, 6- or 7-membered cyclic aromatic radical which contains at least 1, if appropriate also 2, 3, 4 or 5 hetero atoms, wherein the hetero atoms are identical or different and the heterocyclic ring can be unsubstituted or mono- or polysubstituted; in the case of substitution on the heterocyclic ring, the substituents can be identical or different and can be in any desired and possible position of the heteroaryl. The heterocyclic ring can also be part of a bi- or polycyclic system having up to 20 ring members in total. Preferred hetero atoms are nitrogen, oxygen and sulfur. It is preferable for the heteroaryl radical to be chosen from the group which contains pyrrolyl, indolyl, furyl (furanyl), benzofuranyl, thienyl (thiophenyl), benzothienyl, benzothiadiazolyl, benzothiazolyl, benzotriazolyl, benzodioxolanyl, benzodioxanyl, benzimidazolyl, phtalazinyl, pyrazolyl, imidazolyl, triazolyl, tetrazolyl, imidazolyl, thiazolyl, oxazolyl, isoxazolyl, pyridyl, pyridazinyl, pyrimidinyl, pyrazinyl, pyranyl, indazolyl, purinyl, indolizinyl, quinolinyl, isoquinolinyl, quinazolinyl, carbazolyl, phenazinyl, phenothiazinyl or oxadiazolyl, wherein bonding to the compounds of the general structure I can take place via any desired and possible ring member of the heteroaryl radical. Pyridyl, imidazolyl, thienyl, benzimidazolyl, pyrrolyl, triazolyl, pyrazolyl and tetrazolyl are particularly preferred.

For the purpose of the present invention, the expression "aryl or heteroaryl bonded via $C_{1-3}$-alkyl" means that $C_{1-3}$-alkyl and aryl or heteroaryl have the meanings defined above and the aryl or heteroaryl radical is bonded to the compound of the general structure I via a $C_{1-3}$-alkyl group. Benzyl, methylpyridyl and phenethyl are particularly advantageous in the context of this invention.

In connection with "alkyl" or "cycloalkyl", in the context of this invention the term "substituted" is understood as meaning replacement of a hydrogen atom by F, Cl, Br, I, —CN, $NH_2$, NH—$C_{1-6}$-alkyl, NH—$C_{1-6}$-alkyl-OH, N($C_{1-6}$-alkyl)$_2$, N($C_{1-6}$-alkyl-OH)$_2$, $NO_2$, SH, S—$C_{1-6}$-alkyl, OC(=O)$C_{1-6}$-alkyl, S-benzyl, $OCF_3$, O—$C_{1-6}$-alkyl, OH, O—$C_{1-6}$-alkyl-OH, =O, $C_{1-6}$-alkyl, benzyl, O-benzyl, O-phenyl, C(=O)$C_{1-6}$-alkyl, $CO_2H$, NHC(=O)$C_{1-6}$-alkyl, $CO_2$—$C_{1-6}$-alkyl, wherein polysubstituted radicals are to be understood as meaning those radicals which are substituted several times, e.g. two or three times, either on different or on the same atoms, for example three times on the same C atom, as in the case of $CF_3$ or —$CH_2CF_3$, or at different places, as in the case of —CH(OH)—CH=CH—$CHCl_2$. Polysubstitution can be by the same or by different substituents. For the purpose of the present invention, "mono- or polysubstituted" in connection with alkyl particularly preferably denotes F, Cl, $NH_2$, SH, S—$C_{1-6}$-alkyl, OC(=O)$C_{1-6}$-alkyl, O—$C_{1-6}$-alkyl, OH, =O, C(=O)$C_{1-6}$-alkyl, $CO_2H$, NHC(=O)$C_{1-6}$-alkyl and $CO_2$—$C_{1-6}$-alkyl.

With respect to "aryl" and "heteroaryl", in the context of this invention "mono- or polysubstituted" means the replacement once or several times, e.g. two, three or four times, of one or more hydrogen atoms of the ring system by F, Cl, Br, I, CN, $NH_2$, NH—$C_{1-6}$-alkyl, NH—$C_{1-6}$-alkyl-OH, N($C_{1-6}$ alkyl)$_2$, N($C_{1-6}$-alkyl-OH)$_2$, $NO_2$, SH, S—$C_{1-6}$-alkyl, OH, O—$C_{1-6}$-alkyl, O—$C_{1-6}$-alkyl-OH, C(=O)$C_{1-6}$-alkyl, $CO_2H$, $CO_2$—$C_{1-6}$-alkyl, $CF_3$, $OCF_3$, $C_{1-6}$-alkyl; on one or optionally various atoms (wherein a substituent can optionally be substituted in its turn). In this context, polysubstitution is by the same or by different substituents. In this context, preferred substituents for "aryl" and "heteroaryl" are F, Cl, CN, $NH_2$, $NO_2$, SH, OH, O—$C_{1-6}$-alkyl, C(=O)$C_{1-6}$-alkyl, $CO_2H$, $CO_2$—$C_{1-6}$-alkyl, $CF_3$, $OCF_3$ and $C_{1-6}$-alkyl. —F and —Cl are particularly preferred.

Compounds according to the invention in which $R^{10}$ together with B represents —$CH_2CH_2CH_2$— and $R^{10}$ and B therefore form a six-membered ring have the following general formula:

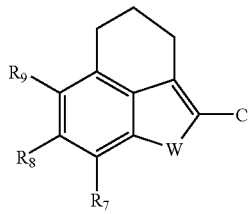

wherein the remaining radicals have the abovementioned meaning.

In the context of this invention, the term salt formed with a physiologically acceptable acid is understood as meaning salts of the particular active compound with inorganic or organic acids, which are physiologically acceptable—in particular when used on humans and/or mammals. The hydrochloride, the citrate, the hemicitrate and the methanesulfonate is preferred. The methanesulfonate is particularly preferred. Examples of physiologically acceptable acids are: hydrochloric acid, hydrobromic acid, sulfuric acid, methanesulfonic acid, formic acid, acetic acid, oxalic acid, succinic acid, tartaric acid, mandelic acid, fumaric acid, lactic acid, malic acid, maleic acid, citric acid, glutamic acid, 1,1-dioxo-1,2-dihydro11$\lambda^6$-benzo[d]isothiazol-3-one (saccharic acid), monomethylsebacic acid, 5-oxo-proline, hexane-1-sulfonic acid, nicotinic acid, 2-, 3- or 4-aminobenzoic acid, 2,4,6-trimethylbenzoic acid, α-liponic acid, acetylglycine, hippuric acid, phosphoric acid and/or aspartic acid. Citric acid, methanesulfonic acid and hydrochloric acid are preferred. Methanesulfonic acid is particularly preferred.

The term $(CH_2)_{3-6}$ or $(CH_2)_{4-5}$ is to be understood as meaning —$CH_2$—$CH_2$—$CH_2$—, —$CH_2$—$CH_2$—$CH_2$—$CH_2$—, —$CH_2$—$CH_2$—$CH_2$—$CH_2$—$CH_2$— and $CH_2$—$CH_2$—$CH_2$—$CH_2$—$CH_2$—$CH_2$—, or respectively, —$CH_2$—$CH_2$—$CH_2$—$CH_2$— and —$CH_2$—$CH_2$—$CH_2$—$CH_2$—$CH_2$—.

It is preferable for $R^1$ and $R^2$ not to simultaneously denote H.

Preferred compounds are those wherein C represents

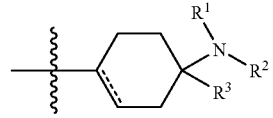

and B represents H; $C_{1-8}$-alkyl, in each case saturated or unsaturated, branched or unbranched, mono- or polysubstituted or unsubstituted, $COR^{12}$; $SO_2R^{12}$; aryl, $C_{3-8}$-cycloalkyl or heteroaryl bonded via $C_{1-3}$-alkyl and in each case mono- or polysubstituted or unsubstituted; aryl-, or heteroaryl, in each case mono- or polysubstituted or unsubstituted; $C_{3-8}$-cycloalkyl, in each case mono- or polysubstituted or unsubstituted.

Compounds which are furthermore preferred are those wherein ⁓ represents a single bond.

For a preferred embodiment of the compounds according to the invention, the abovementioned $C_{1-8}$-alkyls, $C_{1-5}$-alkyls, $C_{1-3}$-alkyls or $C_{1-3}$-alkylenes or $C_{3-8}$-cycloalkyl radicals can in each case be mono- or polysubstituted by F, Cl, Br, I, —CN, $NH_2$, NH—$C_{1-6}$-alkyl, NH—$C_{1-6}$-alkyl-OH, N($C_{1-6}$-alkyl)$_2$, N($C_{1-6}$-alkyl-OH)$_2$, $NO_2$, SH, S—$C_{1-6}$-alkyl, S-benzyl, $OCF_3$, O—$C_{1-6}$-alkyl, OH, O—$C_{1-6}$-alkyl-OH, =O, $C_{1-6}$-alkyl, benzyl, O-benzyl, O-phenyl, C(=O)$C_{1-6}$-alkyl, $CO_2H$, NHC(=O)$C_{1-6}$-alkyl, OC(=O)$C_{1-6}$-alkyl, $CO_2$—$C_{1-6}$-alkyl, the abovementioned aryl or heteroaryl radicals can in each case be mono- or polysubstituted by F, Cl, Br, I, CN, $NH_2$, NH—$C_{1-6}$-alkyl, NH—$C_{1-6}$-alkyl-OH, N($C_{1-6}$ alkyl)$_2$, N($C_{1-6}$-alkyl-OH)$_2$, $NO_2$, SH, S—$C_{1-6}$-alkyl, OH, O—$C_{1-6}$-alkyl, O—$C_{1-6}$alkyl-OH, C(=O)$C_{1-6}$-alkyl, $CO_2H$, $CO_2$—$C_{1-6}$-alkyl, $CF_3$, $OCF_3$, $C_{1-6}$-alkyl or phenoxy, in the form of the racemate; of the enantiomers, diastereomers, mixtures of the enantiomers or diastereomers or of an individual enantiomer or diastereomer; of the bases and/or salts of physiologically acceptable acids.

The radicals and groups or substituents described as preferred in the following can be combined in the compounds according to the invention with the broadest meaning of the remaining radicals, but also with preferred meanings of other radicals and groups or substituents.

Preferred substituted heteroaryl derivatives are those wherein W represents $NR^4$.

Heteroaryl derivatives which are furthermore preferred are also those wherein A represents $CR^{7-10}$ or the general formula I assumes the meanings of the general formulae Ia and Ib:

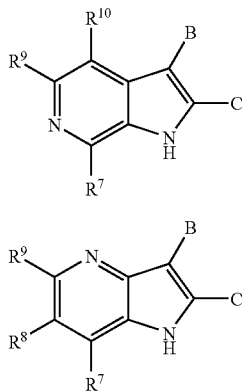

Preferred substituted heteroaryl derivatives are furthermore those wherein $R^1$ and $R^2$ independently of one another represent H; $C_{1-5}$-alkyl, saturated or unsaturated, branched or unbranched, mono- or polysubstituted or unsubstituted;

or the radicals $R^1$ and $R^2$ together form a ring and denote $CH_2CH_2OCH_2CH_2$, $CH_2CH_2NR^{11}CH_2CH_2$ or $(CH_2)_{3-6}$, Particularly preferred substituted heteroaryl derivatives are those wherein $R^1$ and $R^2$ independently of one another represent $CH_3$ or H, wherein $R^1$ and $R^2$ do not simultaneously denote H, or $R^1$ and $R^2$ form a ring and denote $CH_2CH_2OCH_2CH_2$, $CH_2CH_2N(CH_3)CH_2CH_2$, $CH_2CH_2CH_2$, $CH_2CH_2CH_2CH_2$ or $CH_2CH_2CH_2CH_2CH_2$.

Substituted heteroaryl derivatives which are very particularly preferred are those wherein $R^1$ and $R^2$ represent $CH_3$ or H, wherein $R^1$ and $R^2$ do not simultaneously denote H.

Substituted heteroaryl derivatives which are furthermore preferred are those wherein $R^3$ represents $C_{1-6}$-alkyl, cyclopentyl, cyclohexyl, phenyl, benzyl, naphthyl, thiazolyl, thiophenyl, triazolyl, benzimidazolyl, benzothiophenyl, furyl, benzofuranyl, benzodioxolanyl, indolyl, indanyl, benzodioxanyl, pyrrolyl, pyridyl, pyrimidyl or pyrazinyl, in each case unsubstituted or mono- or polysubstituted; cyclopentyl, cyclohexyl, phenyl, naphthyl, thiophenyl, benzothiophenyl, pyridyl, furyl, benzofuranyl, benzodioxolanyl, indolyl, indanyl, benzodioxanyl, pyrrolyl, pyrimidyl or pyrazinyl, bonded via a saturated, unbranched $C_{1-3}$-alkyl group and in each case unsubstituted or mono- or polysubstituted;

in particular $R^3$ denotes butyl, phenyl, thiophenyl, thiazolyl, cyclopentyl, cyclohexyl, naphthyl, benzyl, benzofuranyl, 1,2,4-triazolyl, benzimidazolyl, benzodioxanyl, benzodioxolanyl, pyridyl or benzothiophenyl, in each case unsubstituted or mono- or polysubstituted; phenyl, furyl or thiophenyl bonded via a saturated, unbranched $C_{1-3}$-alkyl group and in each case unsubstituted or mono- or polysubstituted.

Substituted heteroaryl derivatives which are particularly preferred are those wherein $R^3$ denotes phenyl, 4-fluorophenyl, benzyl, butyl or benzothiophenyl.

Preferred substituted heteroaryl derivatives are also those wherein B or C represent $C_{1-8}$-alkyl, in each case saturated or unsaturated, branched or unbranched, mono- or polysubstituted or unsubstituted; preferably $C_1$-$C_4$-alkyl, mono- or polysubstituted or unsubstituted.

Substituted heteroaryl derivatives which are furthermore preferred are those wherein B or C represent

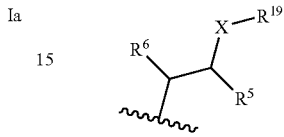

wherein

X represents O $NR^{20}$, S or $CH_2$;

$R^5$ represents =O; H; $COOR^{13}$, $CONR^{13}$, $OR^{13}$; $C_{1-5}$-alkyl, saturated or unsaturated, branched or unbranched, unsubstituted or mono- or polysubstituted; $C_{3-8}$-cycloalkyl, saturated or unsaturated, unsubstituted or mono- or polysubstituted; aryl-, or heteroaryl, unsubstituted or mono- or polysubstituted; or aryl, $C_{3-8}$-cycloalkyl or heteroaryl, bonded via $C_{1-3}$-alkyl and unsubstituted or mono- or polysubstituted;

$R^6$ represents H; F, Cl, $NO_2$, $CF_3$, $OR^{13}$, $SR^{13}$, $SO_2R^{13}$, $SO_2OR^{13}$, CN, $COOR^{13}$, $NR^{14}R^{15}$; $C_{1-5}$-alkyl, saturated or unsaturated, branched or unbranched, unsubstituted or mono- or polysubstituted; $C_{3-8}$-cycloalkyl, saturated or unsaturated, unsubstituted or mono- or polysubstituted; aryl-, or heteroaryl, unsubstituted or mono- or polysubstituted; or aryl, $C_{3-8}$-cycloalkyl or heteroaryl, bonded via $C_{1-3}$-alkyl and unsubstituted or mono- or polysubstituted;

or $R^5$ and $R^6$ together denote $(CH_2)_n$ where n=2, 3, 4, 5 or 6, wherein individual hydrogen atoms can also be replaced by F, Cl, Br, I, $NO_2$, $CF_3$, $OR^{13}$, CN or $C_{1-5}$-alkyl;

$R^{19}$ denotes H; aryl; benzyl; $C(=O)C_{1-5}$-alkyl and $R^{20}$ denotes H or —$C_{1-5}$-alkyl.

It is preferable for $R^5$ to represent H, $CH_3$, $CH_2OH$, COOH or $COOCH_3$, preferably H.

Preferred substituted heteroaryl derivatives are also those wherein $R^6$ represents H, $C_{1-5}$-alkyl, aryl or aryl linked via a $C_{1-3}$-alkyl group, preferably H.

Preferred substituted heteroaryl derivatives are moreover also those wherein B or C represents $(CH_2)_{1-4}$—$R^{21}$, wherein $R^{21}$ represents H, OH, SH, $COOC_{1-6}$-alkyl, COOH, OC(=O) $C_{1-6}$-alkyl, $NH_2$, $NHC(=O)C_{1-6}$-alkyl; or $C_{3-8}$-cycloalkyl, aryl or heteroaryl, in each case unsubstituted or mono- or polysubstituted, preferably phenyl, benzimidazole, pyridyl, triazolyl, phenyl, pyrazolyl, tetrazolyl or imidazolyl, pyrrolidinyl, tetrahydroquinolinyl, tetrahydroisoquinolinyl, thiazolidinyl, isoindolinyl, piperazinyl, morpholinyl, cyclohexyl, piperidyl, pyrrolidinyl or cyclopropyl, in each case unsubstituted or mono- or polysubstituted.

Particularly preferred substituted heteroaryl derivatives are those wherein $R^{21}$ represents OH, SH, $COOCH_3$, COOH, $OC(=O)CH_3$, $NH_2$, $NHC(=O)CH_3$, $NHC(=O)CH_2C$ $(CH_3)_2$; or phenyl, benzimidazole, pyridyl, triazolyl, phenyl, pyrazolyl, tetrazolyl or imidazolyl, in each case unsubstituted or substituted by $COOCH_3$, $CH_3$; or cyclopropyl, cyclohexyl, pyrrolidinyl tetrahydroquinolinyl, pyrrolidinyl, piperidyl, tetrahydroisoquinolinyl, isoindolinyl, piperazinyl, morpholinyl or thiazolinyl, in each case unsubstituted or substituted by =O or CH$_3$.

Preferred substituted heteroaryl derivatives are also those wherein B denotes C$_{3-8}$-cycloalkyl, in particular cyclopropyl.

Substituted heteroaryl derivatives which are moreover also preferred are those wherein R$^7$, R$^8$, R$^9$ and R$^{10}$ independently of one another represent H; methyl; ethyl; propyl; butyl; pyridyl, O-benzyl, F, Cl, Br, I, CN, CF$_3$, OCF$_3$, OH, OCH$_3$, NH$_2$, COOH, COOCH$_3$, NHCH$_3$ or N(CH$_3$)$_2$ or NO$_2$.

Particularly preferred substituted heteroaryl derivatives are those wherein R$^7$, R$^8$, R$^9$ and R$^{10}$ independently of one another represent H, F, Cl, NO$_2$, CN, CF$_3$, OCH$_3$, OCF$_3$ or OH.

Very particularly preferred substituted heteroaryl derivatives are those wherein R$^7$ R$^8$, R$^9$ and R$^{10}$ represent H.

Preferred substituted heteroaryl derivatives are also those wherein R$^4$ denotes H; C$_{1-3}$-alkyl-C$_{3-8}$-cycloalkyl, C$_{1-6}$-alkyl, unsubstituted or mono- or polysubstituted; or SO$_2$-phenyl or CO-phenyl, in each case unsubstituted or mono- or polysubstituted, in particular R$^4$ denotes methyloxirane, CH$_2$CH(OH)CH$_2$N(CH$_3$)$_2$, SO$_2$-phenyl, CH$_2$CH$_2$OH, CH$_2$CH(OH)CH$_2$NHCH$_3$ or CH$_3$.

Particularly preferred substituted heteroaryl derivatives are furthermore those wherein R$^4$ represents H.

Most preferred substituted heteroaryl derivatives are those from the group
(1) 2-(2-(4-(dimethylamino)-4-phenylcyclohexyl)-1H-indol-3-yl)ethanol, citrate
(3) (±) 2-(2-(4-(dimethylamino)-4-phenylcyclohex-1-enyl)-1H-indol-3-yl)ethyl acetate hydrochloride
(4) (±) 2-(4-(dimethylamino)-4-phenylcyclohex-1-enyl)-3-(3-aminopropyl)-1H-indole, citrate
(6) (±) 3-(2-(4-(dimethylamino)-4-phenylcyclohex-1-enyl)-1H-indol-3-yl)propan-1-ol hydrochloride
(7) (±) 2-(5,6-dichloro-2-(4-(dimethylamino)-4-phenylcyclohex-1-enyl)-1H-indol-3-yl)ethanol, citrate
(8) (±) 2-(2-(4-morpholino-4-phenylcyclohex-1-enyl)-1H-indol-3-yl)ethanol, citrate
(9) (±) 2-(4,6-dichloro-2-(4-(dimethylamino)-4-phenylcyclohex-1-enyl)-1H-indol-3-yl)ethanol, citrate
(10) (±) 2-(2-(4-(dimethylamino)-4-phenylcyclohex-1-enyl)-5-fluoro-1H-indol-3-yl)ethanol, citrate
(11) (±) 2-(2-(4-(dimethylamino)-4-phenylcyclohex-1-enyl)-5-(pyridin-3-yl)-1H-indol-3-yl)ethanol, citrate
(13) (±) 2-(2-(4-(dimethylamino)-4-phenylcyclohex-1-enyl)-5-nitro-1H-indol-3-yl)ethanol, citrate
(14) (±) 2-(2-(4-(benzo[b]thiophen-2-yl)-4-(dimethylamino) cyclohex-1-enyl)-1H-indol-3-yl)ethanol, citrate
(15) (±) 2-(2-(4-(benzo[b]thiophen-2-yl)-4-(dimethylamino) cyclohex-1-enyl)-5-fluoro-1H-indol-3-yl)ethanol, citrate
(16) (±) 2-(4-(dimethylamino)-4-phenylcyclohex-1-enyl)-3-methyl-1H-indole, citrate
(17) N,N-dimethyl-4-(3-methyl-1H-indol-2-yl)-1-phenylcyclohexanamine, citrate
(18) N,N-dimethyl-4-(3-methyl-1H-indol-2-yl)-1-phenylcyclohexanamine, citrate
(19) 2-(2-(2-(4-(dimethylamino)-4-phenylcyclohexyl)-1H-indol-3-yl)ethyl)isoindoline-1,3-dione, citrate
(20) N-(2-(2-(4-(dimethylamino)-4-phenylcyclohexyl)-1H-indol-3-yl)ethyl)acetamide, citrate
(21) N-(2-(2-(4-(dimethylamino)-4-phenylcyclohexyl)-1H-indol-3-yl)ethyl)acetamide, citrate
(22) (±)-2-(4-benzyl-4-(dimethylamino)cyclohex-1-enyl)-3-methyl-1H-indole-5-carbonitrile
(23) (±)-2-(4-(dimethylamino)-4-phenylcyclohex-1-enyl)-3-methyl-1H-indole-5-carbonitrile
(24) (±)-2-(4-(dimethylamino)-4-butylcyclohex-1-enyl)-3-methyl-5-trifluoromethyl-1H-indole
(25) (±)-2-(4-(dimethylamino)-4-phenylcyclohex-1-enyl)-3-methyl-5-trifluoromethyl-1H-indole, citrate
(26) (±)-2-(4-(dimethylamino)-4-benzylcyclohex-1-enyl)-3-methyl-5-fluoro-1H-indole, citrate
(27) (±)-2-(4-(dimethylamino)-4-butylcyclohex-1-enyl)-3-methyl-5-fluoro-1H-indole, citrate
(28) (±)-2-(4-(dimethylamino)-4-phenylcyclohex-1-enyl)-3-methyl-5-fluoro-1H-indole, citrate
(29) (±)-2-(4-(dimethylamino)-4-phenylcyclohex-1-enyl)-3-methyl-5-methoxy-1H-indole, citrate
(30) (±)-2-(4-(dimethylamino)-4-benzylcyclohex-1-enyl)-3-methyl-1H-indole, citrate
(31) (±)-2-(4-(dimethylamino)-4-butylcyclohex-1-enyl)-3-methyl-1H-indole, citrate
(32) (±)-2-(4-(dimethylamino)-4-phenylcyclohex-1-enyl)-3-methyl-1H-pyrrolo[2,3-b]pyridine, citrate
(33) (±)-2-(4-(dimethylamino)-4-benzylcyclohex-1-enyl)-3-cyclopropyl-1H-indole hydrochloride
(34) (±)-2-(4-(dimethylamino)-4-butylcyclohex-1-enyl)-3-cyclopropyl-1H-indole
(35) (±)-2-(4-(dimethylamino)-4-phenylcyclohex-1-enyl)-3-cyclopropyl-1H-indole
(36) (±)-2-(4-(dimethylamino)-4-benzylcyclohex-1-enyl)-3-(cyclohexylmethyl)-1H-indole
(37) (±)-2-(4-(dimethylamino)-4-benzylcyclohex-1-enyl)-3-benzyl-1H-indole hydrochloride
(38) (±)-2-(4-(dimethylamino)-4-butylcyclohex-1-enyl)-3-(cyclohexylmethyl)-1H-indole hydrochloride
(39) (±)-2-(4-(dimethylamino)-4-butylcyclohex-1-enyl)-3-benzyl-1H-indole
(40) (±)-2-(4-(dimethylamino)-4-phenylcyclohex-1-enyl)-3-(cyclohexylmethyl)-1H-indole hydrochloride
(41) (±)-2-(4-(dimethylamino)-4-phenylcyclohex-1-enyl)-3-benzyl-1H-indole hydrochloride
(42) (±)-2-(4-(dimethylamino)-4-benzylcyclohex-1-enyl)-3-propyl-1H-indole
(43) (±)-2-(4-(dimethylamino)-4-butylcyclohex-1-enyl)-3-propyl-1H-indole
(44) (±)-2-(4-(dimethylamino)-4-phenylcyclohex-1-enyl)-3-propyl-1H-indole
(45) (±) 2-(4-(dimethylamino)-4-benzylcyclohex-1-enyl)-3-(2-(pyridin-4-yl)ethyl)-1H-indole
(46) (±) 2-(4-(dimethylamino)-4-butylcyclohex-1-enyl)-3-(2-(pyridin-4-yl)ethyl)-1H-indole
(47) (±) 2-(4-(dimethylamino)-4-phenylcyclohex-1-enyl)-3-(2-(pyridin-4-yl)ethyl)-1H-indole
(48) (±)-3-(2-(4-benzyl-4-(dimethylamino)cyclohex-1-enyl)-1H-indol-3-yl)propan-1-ol, citrate
(49) (±)-3-(2-(4-butyl-4-(dimethylamino)cyclohex-1-enyl)-1H-indol-3-yl)propan-1-ol, citrate
(51) (±) 2-(2-(2-(4-(dimethylamino)-4-phenylcyclohex-1-enyl)-1H-indol-3-yl)ethyl)isoindoline-1,3-dione
(52) (±) 2-(4-(dimethylamino)-4-benzylcyclohex-1-enyl)-3-(2-(1H-benzo[d]imidazol-1-yl)ethyl)-5-fluoro-1H-indole
(53) (±) 2-(4-(dimethylamino)-4-butylcyclohex-1-enyl)-3-(2-(1H-benzo[d]imidazol-1-yl)ethyl)-5-fluoro-1H-indole
(54) (±) 2-(4-(dimethylamino)-4-phenylcyclohex-1-enyl)-3-(2-(1H-benzo[d]imidazol-1-yl)ethyl)-5-fluoro-1H-indole
(55) (±) 2-(4-(dimethylamino)-4-benzylcyclohex-1-enyl)-3-(2-(piperidin-1-yl)ethyl)-5-fluoro-1H-indole
(56) (±) 2-(4-(dimethylamino)-4-butylcyclohex-1-enyl)-3-(2-(piperidin-1-yl)ethyl)-5-fluoro-1H-indole
(57) (±) 2-(4-(dimethylamino)-4-phenylcyclohex-1-enyl)-3-(2-(piperidin-1-yl)ethyl)-5-fluoro-1H-indole

(58) (±) 2-(4-(dimethylamino)-4-phenylcyclohex-1-enyl)-3-(2-(piperidin-1-yl)ethyl)-1H-indole, citrate
(59) (±) 2-(4-(dimethylamino)-4-benzylcyclohex-1-enyl)-3-(2-(1H-1,2,3-triazol-1-yl)ethyl)-5-fluoro-1H-indole
(60) (±) 2-(4-(dimethylamino)-4-butylcyclohex-1-enyl)-3-(2-(1H-1,2,3-triazol-1-yl)ethyl)-5-fluoro-1H-indole
(61) (±) 2-(4-(dimethylamino)-4-phenylcyclohex-1-enyl)-3-(2-(1H-1,2,3-triazol-1-yl)ethyl)-5-fluoro-1H-indole
(62) N-(2-(2-(4-butyl-4-(dimethylamino)cyclohexyl)-1H-indol-3-yl)ethyl)-3,3-dimethylbutanamide, citrate
(63) (±) N-(2-(2-(4-(dimethylamino)-4-phenylcyclohex-1-enyl)-1H-indol-3-yl)ethyl)acetamide
(64) (±) N-(2-(2-(4-butyl-4-(dimethylamino)cyclohex-1-enyl)-1H-indol-3-yl)ethyl)-3,3-dimethylbutanamide
(65) (±)-2-(2-(4-(dimethylamino)-4-phenylcyclohex-1-enyl)-5-fluoro-6-methoxy-1H-indol-3-yl)ethanol, citrate
(66) (±)-2-(2-(4-benzyl-4-(4-methylpiperazin-1-yl)cyclohex-1-enyl)-5-fluoro-1H-indol-3-yl)ethanol
(67) (±)-2-(5-fluoro-2-(4-phenyl-4-(pyrrolidin-1-yl)cyclohex-1-enyl)-1H-indol-3-yl)ethanol
(68) 2-(4-benzyl-4-(dimethylamino)cyclohexyl)-3-methyl-1H-indole-5-carbonitrile, citrate
(69) 2-(4-benzyl-4-(dimethylamino)cyclohexyl)-3-methyl-1H-indole-5-carbonitrile, citrate
(70) 2-(4-butyl-4-(dimethylamino)cyclohexyl)-3-methyl-1H-indole-5-carbonitrile, citrate
(71) 2-(4-butyl-4-(dimethylamino)cyclohexyl)-3-methyl-1H-indole-5-carbonitrile, citrate
(72) 2-(4-(dimethylamino)-4-phenylcyclohexyl)-3-methyl-1H-indole-5-carbonitrile, citrate
(73) 1-benzyl-N,N-dimethyl-4-(3-methyl-5-(trifluoromethyl)-1H-indol-2-yl)cyclohexanamine, citrate
(74) 1-benzyl-N,N-dimethyl-4-(3-methyl-5-(trifluoromethyl)-1H-indol-2-yl)cyclohexanamine, citrate
(75) 1-butyl-N,N-dimethyl-4-(3-methyl-5-(trifluoromethyl)-1H-indol-2-yl)cyclohexanamine, citrate
(76) N,N-dimethyl-4-(3-methyl-5-(trifluoromethyl)-1H-indol-2-yl)-1-phenylcyclohexanamine, citrate
(77) 1-benzyl-4-(5-fluoro-3-methyl-1H-indol-2-yl)-N,N-dimethylcyclohexanamine, citrate
(78) 1-benzyl-4-(5-fluoro-3-methyl-1H-indol-2-yl)-N,N-dimethylcyclohexanamine, citrate
(79) 1-butyl-4-(5-fluoro-3-methyl-1H-indol-2-yl)-N,N-dimethylcyclohexanamine hydrochloride
(80) 4-(5-fluoro-3-methyl-1H-indol-2-yl)-N,N-dimethyl-1-phenylcyclohexanamine, citrate
(81) 4-(5-fluoro-3-methyl-1H-indol-2-yl)-N,N-dimethyl-1-phenylcyclohexanamine, citrate
(82) 4-(3-(2-(1H-benzo[d]imidazol-1-yl)ethyl)-5-fluoro-1H-indol-2-yl)-1-butyl-N,N-dimethylcyclohexanamine, citrate
(83) 4-(3-(2-(1H-benzo[d]imidazol-1-yl)ethyl)-5-fluoro-1H-indol-2-yl)-N,N-dimethyl-1-phenylcyclohexanamine, citrate
(84) 4-(3-(2-(1H-benzo[d]imidazol-1-yl)ethyl)-5-fluoro-1H-indol-2-yl)-N,N-dimethyl-1-phenylcyclohexanamine, citrate
(85) 1-benzyl-4-(5-fluoro-3-(2-(pyrrolidin-1-yl)ethyl)-1H-indol-2-yl)-N,N-dimethylcyclohexanamine, citrate
(86) 1-benzyl-4-(5-fluoro-3-(2-(pyrrolidin-1-yl)ethyl)-1H-indol-2-yl)-N,N-dimethylcyclohexanamine, citrate
(87) 1-butyl-4-(5-fluoro-3-(2-(pyrrolidin-1-yl)ethyl)-1H-indol-2-yl)-N,N-dimethylcyclohexanamine, citrate
(88) 1-butyl-4-(5-fluoro-3-(2-(pyrrolidin-1-yl)ethyl)-1H-indol-2-yl)-N,N-dimethylcyclohexanamine, citrate
(89) 4-(5-fluoro-3-(2-(pyrrolidin-1-yl)ethyl)-1H-indol-2-yl)-N,N-dimethyl-1-phenylcyclohexanamine, citrate
(90) 4-(5-fluoro-3-(2-(pyrrolidin-1-yl)ethyl)-1H-indol-2-yl)-N,N-dimethyl-1-phenylcyclohexanamine, citrate
(91) 1-benzyl-4-(5-fluoro-3-(2-(piperidin-1-yl)ethyl)-1H-indol-2-yl)-N,N-dimethylcyclohexanamine, citrate
(92) 1-benzyl-4-(5-fluoro-3-(2-(piperidin-1-yl)ethyl)-1H-indol-2-yl)-N,N-dimethylcyclohexanamine, citrate (2:3)
(93) 1-butyl-4-(5-fluoro-3-(2-(piperidin-1-yl)ethyl)-1H-indol-2-yl)-N,N-dimethylcyclohexanamine, citrate (4:3)
(94) 1-butyl-4-(5-fluoro-3-(2-(piperidin-1-yl)ethyl)-1H-indol-2-yl)-N,N-dimethylcyclohexanamine, citrate
(95) 4-(5-fluoro-3-(2-(piperidin-1-yl)ethyl)-1H-indol-2-yl)-N,N-dimethyl-1-phenylcyclohexanamine, citrate
(96) 4-(5-fluoro-3-(2-(piperidin-1-yl)ethyl)-1H-indol-2-yl)-N,N-dimethyl-1-phenylcyclohexanamine, citrate
(97) 4-(3-(2-(1H-pyrazol-1-yl)ethyl)-5-fluoro-1H-indol-2-yl)-1-benzyl-N,N-dimethylcyclohexanamine, citrate (2:3)
(98) 4-(3-(2-(1H-pyrazol-1-yl)ethyl)-5-fluoro-1H-indol-2-yl)-1-benzyl-N,N-dimethylcyclohexanamine, citrate
(99) 4-(3-(2-(1H-pyrazol-1-yl)ethyl)-5-fluoro-1H-indol-2-yl)-1-butyl-N,N-dimethylcyclohexanamine, citrate
(100) 4-(3-(2-(1H-pyrazol-1-yl)ethyl)-5-fluoro-1H-indol-2-yl)-1-butyl-N,N-dimethylcyclohexanamine, citrate
(101) 4-(3-(2-(1H-pyrazol-1-yl)ethyl)-5-fluoro-1H-indol-2-yl)-N,N-dimethyl-1-phenylcyclohexanamine, citrate
(102) 4-(3-(2-(1H-pyrazol-1-yl)ethyl)-5-fluoro-1H-indol-2-yl)-N,N-dimethyl-1-phenylcyclohexanamine, citrate
(103) 4-(3-(2-(1H-imidazol-1-yl)ethyl)-5-fluoro-1H-indol-2-yl)-1-benzyl-N,N-dimethylcyclohexanamine, citrate
(104) 4-(3-(2-(1H-imidazol-1-yl)ethyl)-5-fluoro-1H-indol-2-yl)-1-benzyl-N,N-dimethylcyclohexanamine, citrate
(105) 4-(3-(2-(1H-imidazol-1-yl)ethyl)-5-fluoro-1H-indol-2-yl)-1-butyl-N,N-dimethylcyclohexanamine, citrate (2:3)
(106) 4-(3-(2-(1H-imidazol-1-yl)ethyl)-5-fluoro-1H-indol-2-yl)-1-butyl-N,N-dimethylcyclohexanamine, citrate
(107) 4-(3-(2-(1H-imidazol-1-yl)ethyl)-5-fluoro-1H-indol-2-yl)-N,N-dimethyl-1-phenylcyclohexanamine, citrate
(108) 4-(3-(2-(1H-imidazol-1-yl)ethyl)-5-fluoro-1H-indol-2-yl)-N,N-dimethyl-1-phenylcyclohexanamine, citrate (2:3)
(109) 4-(3-(2-(1H-benzo[d]imidazol-1-yl)ethyl)-5-fluoro-1H-indol-2-yl)-1-benzyl-N,N-dimethylcyclohexanamine, citrate (4:3)
(110) 4-(3-(2-(1H-benzo[d]imidazol-1-yl)ethyl)-5-fluoro-1H-indol-2-yl)-1-benzyl-N,N-dimethylcyclohexanamine, citrate (2:3)
(111) 4-(3-(2-(1H-benzo[d]imidazol-1-yl)ethyl)-5-fluoro-1H-indol-2-yl)-1-butyl-N,N-dimethylcyclohexanamine, citrate (2:3)
(112) 4-(3-(2-(1H-1,2,3-triazol-1-yl)ethyl)-5-fluoro-1H-indol-2-yl)-1-benzyl-N,N-dimethylcyclohexanamine, citrate (4:1)
(113) 4-(3-(2-(1H-1,2,3-triazol-1-yl)ethyl)-5-fluoro-1H-indol-2-yl)-1-benzyl-N,N-dimethylcyclohexanamine, citrate
(114) 4-(3-(2-(1H-1,2,3-triazol-1-yl)ethyl)-5-fluoro-1H-indol-2-yl)-1-butyl-N,N-dimethylcyclohexanamine, citrate
(115) 4-(3-(2-(1H-1,2,3-triazol-1-yl)ethyl)-5-fluoro-1H-indol-2-yl)-1-butyl-N,N-dimethylcyclohexanamine, citrate
(116) 4-(3-(2-(1H-1,2,3-triazol-1-yl)ethyl)-5-fluoro-1H-indol-2-yl)-N,N-dimethyl-1-phenylcyclohexanamine, citrate
(117) 4-(3-(2-(1H-1,2,3-triazol-1-yl)ethyl)-5-fluoro-1H-indol-2-yl)-N,N-dimethyl-1-phenylcyclohexanamine, citrate
(118) 2-(4-(dimethylamino)-4-phenylcyclohexyl)-3-methyl-1H-indol-5-ol (119) 2-(4-(dimethylamino)-4-phenylcyclohexyl)-3-methyl-1H-indol-5-ol
(120) 1-benzyl-N,N-dimethyl-4-(3-methyl-5-(trifluoromethoxy)-1H-indol-2-yl)cyclohexanamine, citrate
(121) 1-butyl-N,N-dimethyl-4-(3-methyl-5-(trifluoromethoxy)-1H-indol-2-yl)cyclohexanamine, citrate
(122) 1-butyl-N,N-dimethyl-4-(3-methyl-5-(trifluoromethoxy)-1H-indol-2-yl)cyclohexanamine, citrate
(123) N,N-dimethyl-4-(3-methyl-5-(trifluoromethoxy)-1H-indol-2-yl)-1-phenylcyclohexanamine, citrate
(124) N,N-dimethyl-4-(3-methyl-5-(trifluoromethoxy)-1H-indol-2-yl)-1-phenylcyclohexanamine, citrate
(125) 1-butyl-4-(5-methoxy-3-methyl-1H-indol-2-yl)-N,N-dimethylcyclohexanamine, citrate
(126) 1-butyl-4-(5-methoxy-3-methyl-1H-indol-2-yl)-N,N-dimethylcyclohexanamine, citrate
(127) 4-(5-methoxy-3-methyl-1H-indol-2-yl)-N,N-dimethyl-1-phenylcyclohexanamine, citrate
(128) 4-(5-methoxy-3-methyl-1H-indol-2-yl)-N,N-dimethyl-1-phenylcyclohexanamine, citrate (4:3)
(129) 1-benzyl-N,N-dimethyl-4-(3-methyl-1H-indol-2-yl)cyclohexanamine, citrate
(130) 1-benzyl-N,N-dimethyl-4-(3-methyl-1H-indol-2-yl)cyclohexanamine, citrate
(131) 1-butyl-N,N-dimethyl-4-(3-methyl-1H-indol-2-yl)cyclohexanamine, citrate
(132) 1-butyl-N,N-dimethyl-4-(3-methyl-1H-indol-2-yl)cyclohexanamine, citrate
(133) 1-benzyl-4-(3-cyclopropyl-1H-indol-2-yl)-N,N-dimethylcyclohexanamine, citrate
(134) 1-benzyl-4-(3-cyclopropyl-1H-indol-2-yl)-N,N-dimethylcyclohexanamine, citrate
(135) 1-butyl-4-(3-cyclopropyl-1H-indol-2-yl)-N,N-dimethylcyclohexanamine hydrochloride
(136) 4-(3-cyclopropyl-1H-indol-2-yl)-N,N-dimethyl-1-phenylcyclohexanamine, citrate
(137) methyl 2-(2-(4-(dimethylamino)-4-phenylcyclohexyl)-1H-indol-3-yl)acetate, citrate
(138) methyl 2-(2-(4-(dimethylamino)-4-phenylcyclohexyl)-1H-indol-3-yl)acetate, citrate
(139) 1-benzyl-4-(3-(cyclohexylmethyl)-1H-indol-2-yl)-N,N-dimethylcyclohexanamine, citrate
(140) 1-benzyl-4-(3-(cyclohexylmethyl)-1H-indol-2-yl)-N,N-dimethylcyclohexanamine, citrate
(141) 1-benzyl-4-(3-benzyl-1H-indol-2-yl)-N,N-dimethylcyclohexanamine, citrate
(142) 1-benzyl-4-(3-benzyl-1H-indol-2-yl)-N,N-dimethylcyclohexanamine, citrate
(143) 1-butyl-4-(3-(cyclohexylmethyl)-1H-indol-2-yl)-N,N-dimethylcyclohexanamine, citrate
(144) 1-butyl-4-(3-(cyclohexylmethyl)-1H-indol-2-yl)-N,N-dimethylcyclohexanamine hydrochloride
(145) 4-(3-benzyl-1H-indol-2-yl)-1-butyl-N,N-dimethylcyclohexanamine, citrate
(146) 4-(3-benzyl-1H-indol-2-yl)-1-butyl-N,N-dimethylcyclohexanamine, citrate
(147) 4-(3-(cyclohexylmethyl)-1H-indol-2-yl)-N,N-dimethyl-1-phenylcyclohexanamine, citrate
(148) 4-(3-(cyclohexylmethyl)-1H-indol-2-yl)-N,N-dimethyl-1-phenylcyclohexanamine, citrate
(149) 4-(3-benzyl-1H-indol-2-yl)-N,N-dimethyl-1-phenylcyclohexanamine, citrate
(150) 4-(3-benzyl-1H-indol-2-yl)-N,N-dimethyl-1-phenylcyclohexanamine, citrate
(151) N,N-dimethyl-1-phenyl-4-(3-(pyridin-2-ylmethyl)-1H-indol-2-yl)cyclohexanamine
(152) N,N-dimethyl-1-phenyl-4-(3-(pyridin-2-ylmethyl)-1H-indol-2-yl)cyclohexanamine
(153) 3-(2-(4-(dimethylamino)-4-phenylcyclohexyl)-1H-indol-3-yl)propanoic acid hydrochloride
(156) 1-benzyl-N,N-dimethyl-4-(3-propyl-1H-indol-2-yl)cyclohexanamine, citrate
(157) 1-butyl-N,N-dimethyl-4-(3-propyl-1H-indol-2-yl)cyclohexanamine hydrochloride
(158) 1-butyl-N,N-dimethyl-4-(3-propyl-1H-indol-2-yl)cyclohexanamine, citrate
(159) N,N-dimethyl-1-phenyl-4-(3-propyl-1H-indol-2-yl)cyclohexanamine, citrate
(160) N,N-dimethyl-1-phenyl-4-(3-propyl-1H-indol-2-yl)cyclohexanamine, citrate
(161) 1-benzyl-N,N-dimethyl-4-(3-(2-(pyridin-4-yl)ethyl)-1H-indol-2-yl)cyclohexanamine, citrate
(162) 1-benzyl-N,N-dimethyl-4-(3-(2-(pyridin-4-yl)ethyl)-1H-indol-2-yl)cyclohexanamine, citrate
(163) 1-butyl-N,N-dimethyl-4-(3-(2-(pyridin-4-yl)ethyl)-1H-indol-2-yl)cyclohexanamine, citrate
(164) 1-butyl-N,N-dimethyl-4-(3-(2-(pyridin-4-yl)ethyl)-1H-indol-2-yl)cyclohexanamine, citrate
(165) N,N-dimethyl-1-phenyl-4-(3-(2-(pyridin-4-yl)ethyl)-1H-indol-2-yl)cyclohexanamine, citrate (1:4)
(166) N,N-dimethyl-1-phenyl-4-(3-(2-(pyridin-4-yl)ethyl)-1H-indol-2-yl)cyclohexanamine, citrate
(167) N,N-dimethyl-4-(3-(2-(1-methyl-1H-benzo[d]imidazol-2-yl)ethyl)-1H-indol-2-yl)-1-phenylcyclohexanamine, citrate
(168) N,N-dimethyl-4-(3-(2-(1-methyl-1H-benzo[d]imidazol-2-yl)ethyl)-1H-indol-2-yl)-1-phenylcyclohexanamine, citrate
(169) N,N-dimethyl-1-phenyl-4-(3-(2-(pyridin-2-yl)ethyl)-1H-indol-2-yl)cyclohexanamine, citrate
(170) N,N-dimethyl-1-phenyl-4-(3-(2-(pyridin-2-yl)ethyl)-1H-indol-2-yl)cyclohexanamine, citrate (2:3)
(171) 4-(2-(4-benzyl-4-(dimethylamino)cyclohexyl)-1H-indol-3-yl)butanoic acid hydrochloride
(172) 4-(2-(4-(dimethylamino)-4-phenylcyclohexyl)-1H-indol-3-yl)butanoic acid hydrochloride
(173) 4-(2-(4-(dimethylamino)-4-phenylcyclohexyl)-1H-indol-3-yl)butan-1-ol hydrochloride
(174) 4-(2-(4-benzyl-4-(dimethylamino)cyclohexyl)-1H-indol-3-yl)butyl acetate hydrochloride
(175) 4-(2-(4-benzyl-4-(dimethylamino)cyclohexyl)-1H-indol-3-yl)butyl acetate hydrochloride
(176) 4-(2-(4-butyl-4-(dimethylamino)cyclohexyl)-1H-indol-3-yl)butyl acetate hydrochloride
(177) 4-(2-(4-butyl-4-(dimethylamino)cyclohexyl)-1H-indol-3-yl)butyl acetate hydrochloride
(178) 4-(2-(4-(dimethylamino)-4-phenylcyclohexyl)-1H-indol-3-yl)butyl acetate hydrochloride
(179) 4-(2-(4-(dimethylamino)-4-phenylcyclohexyl)-1H-indol-3-yl)butyl acetate hydrochloride
(180) 3-(2-(4-benzyl-4-(dimethylamino)cyclohexyl)-1H-indol-3-yl)propan-1-ol, citrate
(181) 3-(2-(4-butyl-4-(dimethylamino)cyclohexyl)-1H-indol-3-yl)propan-1-ol hydrochloride
(182) 3-(2-(4-butyl-4-(dimethylamino)cyclohexyl)-1H-indol-3-yl)propan-1-ol hydrochloride
(183) 3-(2-(4-(dimethylamino)-4-phenylcyclohexyl)-1H-indol-3-yl)propan-1-ol hydrochloride
(184) 3-(2-(4-(dimethylamino)-4-phenylcyclohexyl)-1H-indol-3-yl)propan-1-ol hydrochloride
(185) 3-(2-(4-(dimethylamino)-4-phenylcyclohexyl)-1H-indol-3-yl)propyl acetate hydrochloride (186) 3-(2-(4-(dimethylamino)-4-phenylcyclohexyl)-1H-indol-3-yl)propyl acetate hydrochloride
(187) 1-(2-(2-(4-(dimethylamino)-4-phenylcyclohexyl)-1H-indol-3-yl)ethyl)pyrrolidine-2,5-dione
(188) 1-(2-(2-(4-(dimethylamino)-4-phenylcyclohexyl)-1H-indol-3-yl)ethyl)pyrrolidine-2,5-dione
(189) 4-(3-(2-(3,4-dihydroquinolin-1 (2H)-yl)ethyl)-1H-indol-2-yl)-N,N-dimethyl-1-phenylcyclohexanamine, citrate (4:3)
(190) 4-(3-(2-(3,4-dihydroquinolin-1 (2H)-yl)ethyl)-1H-indol-2-yl)-N,N-dimethyl-1-phenylclohexanamine, citrate
(191) methyl 1-(2-(2-(4-(dimethylamino)-4-phenylcyclohexyl)-1H-indol-3-yl)ethyl)-1H-1,2,3-triazole-4-carboxylate, citrate
(192) methyl 1-(2-(2-(4-(dimethylamino)-4-phenylcyclohexyl)-1H-indol-3-yl)ethyl)-1H-1,2,3-triazole-4-carboxylate, citrate
(193) 4-(3-(2-(isoindolin-2-yl)ethyl)-1H-indol-2-yl)-N,N-dimethyl-1-phenylcyclohexanamine, citrate
(194) 4-(3-(2-(isoindolin-2-yl)ethyl)-1H-indol-2-yl)-N,N-dimethyl-1-phenylcyclohexanamine, citrate
(195) 4-(3-(2-(3,4-dihydroisoquinolin-2(1H)-yl)ethyl)-1H-indol-2-yl)-N,N-dimethyl-1-phenylcyclohexanamine, citrate
(196) 4-(3-(2-(3,4-dihydroisoquinolin-2(1H)-yl)ethyl)-1H-indol-2-yl)-N,N-dimethyl-1-phenylcyclohexanamine, citrate (2:3)
(197) N,N-dimethyl-1-phenyl-4-(3-(2-(pyrrolidin-1-yl)ethyl)-1H-indol-2-yl)cyclohexanamine, citrate
(198) N,N-dimethyl-1-phenyl-4-(3-(2-(pyrrolidin-1-yl)ethyl)-1H-indol-2-yl)cyclohexanamine, citrate
(199) N,N-dimethyl-1-phenyl-4-(3-(2-(piperidin-1-yl)ethyl)-1H-indol-2-yl)cyclohexanamine, citrate
(200) N,N-dimethyl-4-(3-(2-(4-methylpiperazin-1-yl)ethyl)-1H-indol-2-yl)-1-phenylcyclohexanamine, citrate
(201) N,N-dimethyl-4-(3-(2-morpholinoethyl)-1H-indol-2-yl)-1-phenylcyclohexanamine, citrate
(202) N,N-dimethyl-4-(3-(2-morpholinoethyl)-1H-indol-2-yl)-1-phenylcyclohexanamine, citrate
(203) 4-(3-(2-(1H-benzo[d]imidazol-1-yl)ethyl)-1H-indol-2-yl)-N,N-dimethyl-1-phenylcyclohexanamine, citrate
(204) 4-(3-(2-(1H-benzo[d]imidazol-1-yl)ethyl)-1H-indol-2-yl)-N,N-dimethyl-1-phenylcyclohexanamine, citrate
(205) 4-(3-(2-(1H-imidazol-1-yl)ethyl)-1H-indol-2-yl)-N,N-dimethyl-1-phenylcyclohexanamine, citrate
(206) 4-(3-(2-(1H-imidazol-1-yl)ethyl)-1H-indol-2-yl)-N,N-dimethyl-1-phenylcyclohexanamine, citrate
(207) 4-(3-(2-(1H-1,2,4-triazol-1-yl)ethyl)-1H-indol-2-yl)-N,N-dimethyl-1-phenylcyclohexanamine, citrate
(208) 4-(3-(2-(1H-1,2,4-triazol-1-yl)ethyl)-1H-indol-2-yl)-N,N-dimethyl-1-phenylcyclohexanamine, citrate
(209) N,N-dimethyl-1-phenyl-4-(3-(2-(thiazolidin-3-yl)ethyl)-1H-indol-2-yl)cyclohexanamine, citrate
(210) N,N-dimethyl-1-phenyl-4-(3-(2-(thiazolidin-3-yl)ethyl)-1H-indol-2-yl)cyclohexanamine, citrate
(211) N,N-dimethyl-4-(3-(2-(5-methyl-2H-tetrazol-2-yl)ethyl)-1H-indol-2-yl)-1-phenylcyclohexanamine, citrate
(212) N,N-dimethyl-4-(3-(2-(5-methyl-2H-tetrazol-2-yl)ethyl)-1H-indol-2-yl)-1-phenylcyclohexanamine, citrate
(213) 4-(3-(2-(1H-pyrazol-1-yl)ethyl)-1H-indol-2-yl)-N,N-dimethyl-1-phenylcyclohexanamine, citrate
(214) 4-(3-(2-(1H-pyrazol-1-yl)ethyl)-1H-indol-2-yl)-N,N-dimethyl-1-phenylcyclohexanamine, citrate
(215) 4-(3-(2-(1H-1,2,3-triazol-1-yl)ethyl)-1H-indol-2-yl)-N,N-dimethyl-1-phenylcyclohexanamine, citrate
(216) 4-(3-(2-(1H-1,2,3-triazol-1-yl)ethyl)-1H-indol-2-yl)-N,N-dimethyl-1-phenylcyclohexanamine, citrate
(217) N,N-dimethyl-4-(3-(2-(5-methyl-1H-tetrazol-1-yl)ethyl)-1H-indol-2-yl)-1-phenylcyclohexanamine, citrate
(218) N,N-dimethyl-4-(3-(2-(5-methyl-1H-tetrazol-1-yl)ethyl)-1H-indol-2-yl)-1-phenylcyclohexanamine, citrate
(219) 2-(2-(4-(dimethylamino)-4-phenylcyclohexyl)-1H-indol-3-yl)ethanol
(220) 2-(2-(4-(dimethylamino)-4-phenylcyclohexyl)-1H-indol-3-yl)ethyl acetate
(221) N,N-dimethyl-4-(3-methyl-1H-pyrrolo[3,2-c]pyridin-2-yl)-1-phenylcyclohexanamine, citrate
(222) N,N-dimethyl-4-(3-methyl-1H-pyrrolo[3,2-c]pyridin-2-yl)-1-phenylcyclohexanamine, citrate
(223) N,N-dimethyl-4-(3-methyl-1H-pyrrolo[2,3-b]pyridin-2-yl)-1-phenylcyclohexanamine, citrate
(224) N,N-dimethyl-4-(3-methyl-1H-pyrrolo[2,3-b]pyridin-2-yl)-1-phenylcyclohexanamine, citrate
(225) N,N-dimethyl-4-(3-methylbenzofuran-2-yl)-1-phenylcyclohexanamine, citrate
(226) N,N-dimethyl-4-(3-methylbenzofuran-2-yl)-1-phenylcyclohexanamine, citrate
(227) 4-(1H-indol-3-yl)-N,N-dimethyl-1-phenylcyclohexanamine, citrate
(228) (±)-3-(4-(dimethylamino)-4-benzylcyclohex-1-enyl)-1H-pyrrolo[2,3-b]pyridine
(229) (±)-3-(4-(dimethylamino)-4-butylcyclohex-1-enyl)-1H-pyrrolo[2,3-b]pyridine
(230) (±)-3-(4-(dimethylamino)-4-phenylcyclohex-1-enyl)-1H-pyrrolo[2,3-b]pyridine, citrate
(231) (±)-4-(1H-indol-3-yl)-N,N-dimethyl-1-phenylcyclohex-3-enamine, citrate
(232) (±)-4-(1H-indol-3-yl)-N,N-dimethyl-1-phenylcyclohex-3-enamine
(233) (±)-2-(3-(4-(dimethylamino)-4-phenylcyclohex-1-enyl)benzo[b]thiophen-2-yl)ethanol hydrochloride
(234) (±)-2-(3-(4-(dimethylamino)-4-(pyridin-2-yl)cyclohex-1-enyl)benzo[b]thiophen-2-yl)ethanol hydrochloride
(235) 4-(1H-indol-2-yl)-N,N-dimethyl-1-phenylcyclohexanamine, citrate
(236) 4-(1H-indol-2-yl)-N,N-dimethyl-1-phenylcyclohexanamine, citrate
(237) 1-benzyl-N,N-dimethyl-4-(1H-pyrrolo[2,3-b]pyridin-3-yl)cyclohexanamine hydrochloride
(238) 1-butyl-N,N-dimethyl-4-(1H-pyrrolo[2,3-b]pyridin-3-yl)cyclohexanamine hydrochloride
(239) (±)-4-(benzofuran-2-yl)-1-benzyl-N,N-dimethylcyclohex-3-enamine hydrochloride
(240) (±)-N,N-dimethyl-4-(3-methylbenzofuran-2-yl)-1-phenylcyclohex-3-enamine, citrate
(241) (±)-2-(2-(4-(dimethylamino)-4-phenylcyclohex-1-enyl)benzofuran-3-yl)ethanethiol, citrate
(242) (±)-N,N-dimethyl-4-(3-methylbenzo[b]thiophen-2-yl)-1-phenylcyclohex-3-enamine, citrate
(243) N,N-dimethyl-4-(3-methylbenzo[b]thiophen-2-yl)-1-phenylcyclohexanamine, citrate
(244) N,N-dimethyl-1-phenyl-4-(1H-pyrrolo[2,3-b]pyridin-3-yl)cyclohexanamine, citrate
(246) 1-(dimethylamino)-3-(2-(4-(dimethylamino)-4-phenylcyclohexyl)-3-methyl-1H-indol-1-yl)propan-2-ol
(247) N,N-dimethyl-4-(3-methyl-1-(oxiran-2-ylmethyl)-1H-indol-2-yl)-1-phenylcyclohexanamine
(248) 4-(1,3-dimethyl-1H-indol-2-yl)-N,N-dimethyl-1-phenylcyclohexanamine
(249) 2-(4-butyl-4-(dimethylamino)cyclohexyl)-3-methyl-1H-indol-5-ol, citrate
(250) 2-(4-butyl-4-(dimethylamino)cyclohexyl)-3-methyl-1H-indol-5-ol, citrate (251) (±)-2-(4-(dimethylamino)-4-(thiophen-2-yl)-cyclohex-1-enyl)-3-(2-(pyridin-4-yl)ethyl)-1H-indole
(252) (±)-2-(4-(dimethylamino)-4-(3-fluorophenyl)-cyclohex-1-enyl)-3-(2-(pyridin-4-yl)ethyl)-1H-indole
(253) (±)-2-(4-butyl-4-(pyrrolidin-1-yl)cyclohex-1-enyl)-3-(2-(pyridin-4-yl)ethyl)-1H-indole
(254) (±)-2-(4-(methylamino)-4-phenylcyclohex-1-enyl)-3-(2-(pyridin-4-yl)ethyl)-1H-indole
(255) (±)-2-(4-(dimethylamino)-4-(thiophen-2-yl)-cyclohex-1-enyl)-3-methyl-1H-indole, citrate
(256) N,N-dimethyl-4-(3-methyl-1H-indol-2-yl)-1-(thiophen-2-yl)cyclohexanamine, citrate
(257) N,N-dimethyl-4-(3-methyl-1H-indol-2-yl)-1-(thiophen-2-yl)cyclohexanamine, citrate
(258) 2-(4-butyl-4-(pyrrolidin-1-yl)cyclohex-1-enyl)-3-methyl-1H-indole
(259) N-methyl-4-(3-methyl-1H-indol-2-yl)-1-phenylcyclohexanamine hydrobromide
(260) N-methyl-4-(3-methyl-1H-indol-2-yl)-1-phenylcyclohexanamine, citrate
(261) 1-(3-fluorophenyl)-N,N-dimethyl-4-(3-methyl-1H-indol-2-yl)cyclohexanamine, citrate
(262) 1-(3-fluorophenyl)-N,N-dimethyl-4-(3-methyl-1H-indol-2-yl)cyclohexanamine, citrate
(263) (±)-2-(4-(dimethylamino)-4-(3-fluorophenyl)-cyclohex-1-enyl)-3-methyl-1H-indole
(264) 2-(4-benzyl-4-(dimethylamino)cyclohexyl)-3-methyl-1H-indol-5-ol, citrate
(265) 2-(4-benzyl-4-(dimethylamino)cyclohexyl)-3-methyl-1H-indol-5-ol, citrate
(266) 2-(4-butyl-4-(pyrrolidin-1-yl)cyclohexyl)-3-(2-(pyridin-4-yl)ethyl)-1H-indole, citrate
(267) 2-(4-butyl-4-(pyrrolidin-1-yl)cyclohexyl)-3-(2-(pyridin-4-yl)ethyl)-1H-indole, citrate
(268) 2-(4-(azetidin-1-yl)-4-phenylcyclohexyl)-3-methyl-1H-indole, citrate
(269) 2-(4-(azetidin-1-yl)-4-phenylcyclohexyl)-3-methyl-1H-indole, citrate
(270) 2-(4-(azetidin-1-yl)-4-phenylcyclohexyl)-3-(2-(pyridin-4-yl)ethyl)-1H-indole hydrochloride
(271) 2-(4-(azetidin-1-yl)-4-phenylcyclohexyl)-3-(2-(pyridin-4-yl)ethyl)-1H-indole hydrochloride
(272) 2-(4-butyl-4-(pyrrolidin-1-yl)cyclohexyl)-3-methyl-1H-indole, citrate
(273) 3-(2-(4-(dimethylamino)-4-phenylcyclohexyl)-1H-pyrrolo[2,3-b]pyridin-3-yl)propan-1-ol, citrate
(274) 1-(2-(4-(dimethylamino)-4-phenylcyclohexyl)-3-methyl-1H-indol-1-yl)-3-(methylamino)propan-2-ol, citrate
(275) 1-benzyl-3-(2-(2-(4-(dimethylamino)-4-phenylcyclohexyl)-1H-indol-3-yl)ethyl)urea, citrate
(276) 1-benzyl-3-(2-(2-(4-(dimethylamino)-4-phenylcyclohexyl)-1H-indol-3-yl)ethyl)urea, citrate
(277) 1-(2-(2-(4-(dimethylamino)-4-phenylcyclohexyl)-1H-indol-3-yl)ethyl)-3-phenylurea, citrate
(278) 1-(2-(2-(4-(dimethylamino)-4-phenylcyclohexyl)-1H-indol-3-yl)ethyl)-3-phenylurea, citrate
(279) 1-cyclopentyl-3-(2-(2-(4-(dimethylamino)-4-phenylcyclohexyl)-1H-indol-3-yl)ethyl)urea, citrate
(280) 1-cyclopentyl-3-(2-(2-(4-(dimethylamino)-4-phenylcyclohexyl)-1H-indol-3-yl)ethyl)urea, citrate
(281) N-(2-(2-(4-(dimethylamino)-4-phenylcyclohexyl)-1H-indol-3-yl)ethyl)-cyclopentanesulfonamide, citrate
(282) N-(2-(2-(4-(dimethylamino)-4-phenylcyclohexyl)-1H-indol-3-yl)ethyl)cyclopentanesulfonamide, citrate
(283) N-(2-(2-(4-(dimethylamino)-4-phenylcyclohexyl)-1H-indol-3-yl)ethyl)benzenesulfonamide, citrate
(284) N-(2-(2-(4-(dimethylamino)-4-phenylcyclohexyl)-1H-indol-3-yl)ethyl)thiophene-2-sulfonamide, citrate
(285) N-(2-(2-(4-(dimethylamino)-4-phenylcyclohexyl)-1H-indol-3-yl)ethyl)thiophene-2-sulfonamide, citrate
(286) N-(2-(2-(4-(dimethylamino)-4-phenylcyclohexyl)-1H-indol-3-yl)ethyl)nicotinamide, citrate
(287) N-(2-(2-(4-(dimethylamino)-4-phenylcyclohexyl)-1H-indol-3-yl)ethyl)nicotinamide, citrate
(288) N-(2-(2-(4-(dimethylamino)-4-phenylcyclohexyl)-1H-indol-3-yl)ethyl)benzamide, citrate
(289) 1-(3-fluorophenyl)-N,N-dimethyl-4-(3-(2-(pyridin-4-yl)ethyl)-1H-indol-2-yl)cyclohexanamine
(290) 1-(3-fluorophenyl)-N,N-dimethyl-4-(3-(2-(pyridin-4-yl)ethyl)-1H-indol-2-yl)cyclohexanamine, citrate
(291) N-methyl-1-phenyl-4-(3-(2-(pyridin-4-yl)ethyl)-1H-indol-2-yl)cyclohexanamine, citrate
(292) N-methyl-1-phenyl-4-(3-(2-(pyridin-4-yl)ethyl)-1H-indol-2-yl)cyclohexanamine, citrate
(293) 2-(4-butyl-4-(pyrrolidin-1-yl)cyclohexyl)-3-methyl-1H-indole, citrate
(294) N,N-dimethyl-1-phenyl-4-(1-(phenylsulfonyl)-1H-indol-2-yl)cyclohexanamine
(295) N,N-dimethyl-1-phenyl-4-(1-(phenylsulfonyl)-1H-indol-2-yl)cyclohexanamine
(296) N,N-dimethyl-4-(3-methyl-1-(oxiran-2-ylmethyl)-1H-indol-2-yl)-1-phenylcyclohex-3-enamine
(297) N,N-dimethyl-4-(3-methyl-1-(oxiran-2-ylmethyl)-1H-indol-2-yl)-1-phenylcyclohexanamine, citrate
(298) 1-(dimethylamino)-3-(2-(4-(dimethylamino)-4-phenylcyclohex-1-enyl)-3-methyl-1H-indol-1-yl)propan-2-ol, citrate
(299) 1-(dimethylamino)-3-(2-(4-(dimethylamino)-4-phenylcyclohexyl)-3-methyl-1H-indol-1-yl)propan-2-ol, citrate
(300) 2-(3-(4-(dimethylamino)-4-phenylcyclohex-1-enyl)-1H-indol-1-yl)ethanol hydrochloride
(301) (±) 3-(4-(dimethylamino)-4-phenylcyclohex-1-enyl)-(1-(phenylsulfonyl)-1H-indole)hydrochloride
(302) 1-benzyl-N,N-dimethyl-4-(1-methyl-1H-indol-2-yl)cyclohex-3-enamine; hydrochloride
(303) N,N-dimethyl-4-(3-(2-(pyridin-4-yl)ethyl)-1H-indol-2-yl)-1-(thiophen-2-yl)cyclohexanamine hydrochloride
(304) N,N-dimethyl-4-(3-(2-(pyridin-4-yl)ethyl)-1H-indol-2-yl)-1-(thiophen-2-yl)cyclohexanamine hydrochloride
(305) N-methyl-4-(3-methyl-1H-indol-2-yl)-1-(4-methylthiazol-2-yl)cyclohexanamine
(306) N-methyl-4-(3-methyl-1H-indol-2-yl)-1-(4-methylthiazol-2-yl)cyclohexanamine
(307) 2-(2-(4-(dimethylamino)-4-phenylcyclohexyl)-1H-indol-3-yl)ethanol in the form of the racemate; of the enantiomers, diastereomers, mixtures of the enantiomers or diastereomers or of an individual enantiomer or diastereomer; of the bases and/or salts of physiologically acceptable acids.

The substances according to the invention act, for example, on the μ opioid receptor relevant in connection with various diseases, so that they are suitable as a pharmaceutical active compound in a medicament. The invention therefore also provides medicaments containing at least one substituted heteroaryl derivative according to the invention and optionally suitable additives and/or auxiliary substances and/or optionally further active compounds.

The medicaments according to the invention optionally contain, in addition to at least one substituted heteroaryl derivate according to the invention, suitable additives and/or auxiliary substances, that is to say also carrier materials, fillers, solvents, diluents, dyestuffs and/or binders, and can be administered as liquid medicament forms in the form of injection solutions, drops or juices or as semi-solid medicament forms in the form of granules, tablets, pellets, patches, capsules, plasters/spray-on plasters or aerosols. The choice of auxiliary substances etc. and the amounts thereof to be employed depend on whether the medicament is to be administered orally, perorally, parenterally, intravenously, intraperitoneally, intradermally, intramuscularly, intranasally, buccally, rectally or locally, for example on the skin, the mucous membranes or into the eyes. Formulations in the form of tablets, coated tablets, capsules, granules, drops, juices and syrups are suitable for oral administration, and solutions, suspensions, easily reconstitutable dry formulations and sprays are suitable for parenteral, topical and inhalatory administration. Substituted heteroaryl derivatives according to the invention in a depot, in dissolved form or in a plaster, optionally with the addition of agents which promote penetration through the skin, are suitable formulations for percutaneous administration. Formulation forms which can be used orally or percutaneously can release the substituted heteroaryl derivatives according to the invention in a delayed manner. The substituted heteroaryl derivatives according to the invention can also be used in parenteral long-term depot forms, such as e.g. implants or implanted pumps. In principle, other further active compounds known to the person skilled in the art can be added to the medicaments according to the invention.

The amount of active compound to be administered to patients varies as a function of the weight of the patient, of the mode of administration, the indication and the severity of the disease. 0.00005 to 50 mg/kg, preferably 0.01 to 5 mg/kg of at least one substituted heteroaryl derivative according to the invention are conventionally administered.

The ORL-1 receptor and the μ opioid receptor have been identified in particular in the pain event. Substituted heteroaryl derivatives according to the invention can accordingly be used for the preparation of a medicament for treatment of pain, in particular acute, neuropathic, chronic pain or inflammation pain.

The invention therefore also provides the use of a substituted heteroaryl derivative according to the invention for the preparation of a medicament for treatment of pain, in particular acute, visceral, neuropathic, chronic pain or inflammation pain.

The invention also provides the use of a substituted heteroaryl derivative according to the invention for the preparation of a medicament for treatment of anxiety states, of stress and syndromes associated with stress, depression, epilepsy, Alzheimer's disease, senile dementia, catalepsy, general cognitive dysfunctions, learning and memory disorders (as a nootropic), withdrawal symptoms, alcohol and/or drug and/or medicament abuse and/or dependency, sexual dysfunctions, cardiovascular diseases, hypotension, hypertension, tinnitus, pruritus, migraine, impaired hearing, lack of intestinal motility, impaired food intake, anorexia, obesity, locomotor disorders, diarrhoea, cachexia, urinary incontinence or as a muscle relaxant, anticonvulsive or anaesthetic or for co-administration in treatment with an opioid analgesic or with an anaesthetic, for diuresis or antinatriuresis, anxiolysis, for modulation of motor activity, for modulation of neurotransmitter secretion and treatment of neurodegenerative diseases associated therewith, for treatment of withdrawal symptoms and/or for reduction of the addiction potential of opioids.

In this context, in one of the above uses it may be preferable for a substituted heteroaryl derivative which is used to be present as the pure diastereomer and/or enantiomer, as a racemate or as a non-equimolar or equimolar mixture of the diastereomers and/or enantiomers.

The invention also provides a method for the treatment, in particular in one of the abovementioned indications, of a non-human mammal or a human requiring treatment of pain, in particular chronic pain, by administration of a therapeutically active dose of a substituted heteroaryl derivative according to the invention, or of a medicament according to the invention.

The invention also provides processes for the preparation of the substituted heteroaryl derivatives according to the invention as described in the following description and examples.

Process 1

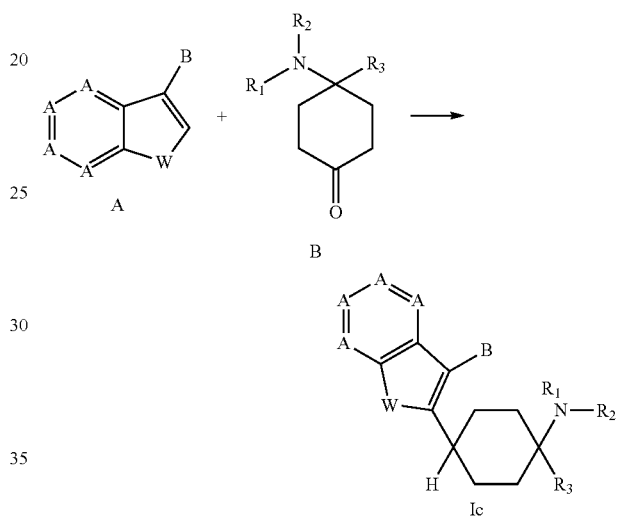

For the preparation of amines of the general formula Ic, ketones B are reacted with heteroaromatics A in organic solvents or solvent mixtures, for example ethyl acetate, chloroform, methylene chloride (MC), dichloroethane (DCE), diethyl ether (Et$_2$O), acetonitrile (MeCN) or nitromethane, with the addition of an organic or inorganic acid, for example HCl, HBr, trifluoromethanesulfonic acid, methanesulfonic acid, acetic acid, trifluoroacetic acid, or without a solvent in an organic or inorganic acid or acid mixtures at temperatures of between 0° C. and 150° C., optionally using microwave irradiation. An organic or inorganic reducing agent, e.g. triethylsilane or tin powder, is then added and the reaction is carried out at temperatures of between 0° C. and 150° C., optionally using microwave irradiation.

Process 2

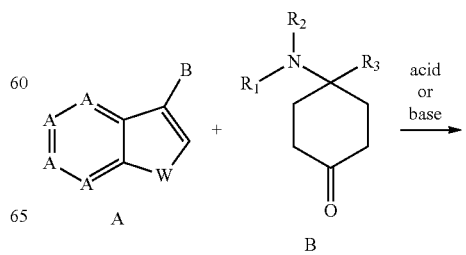

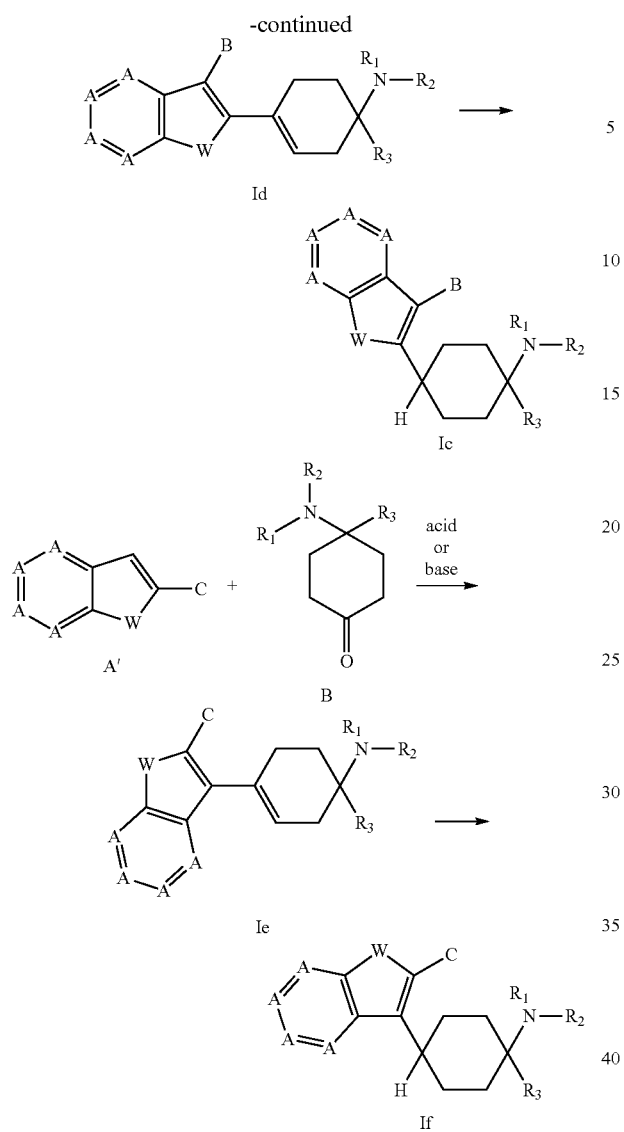

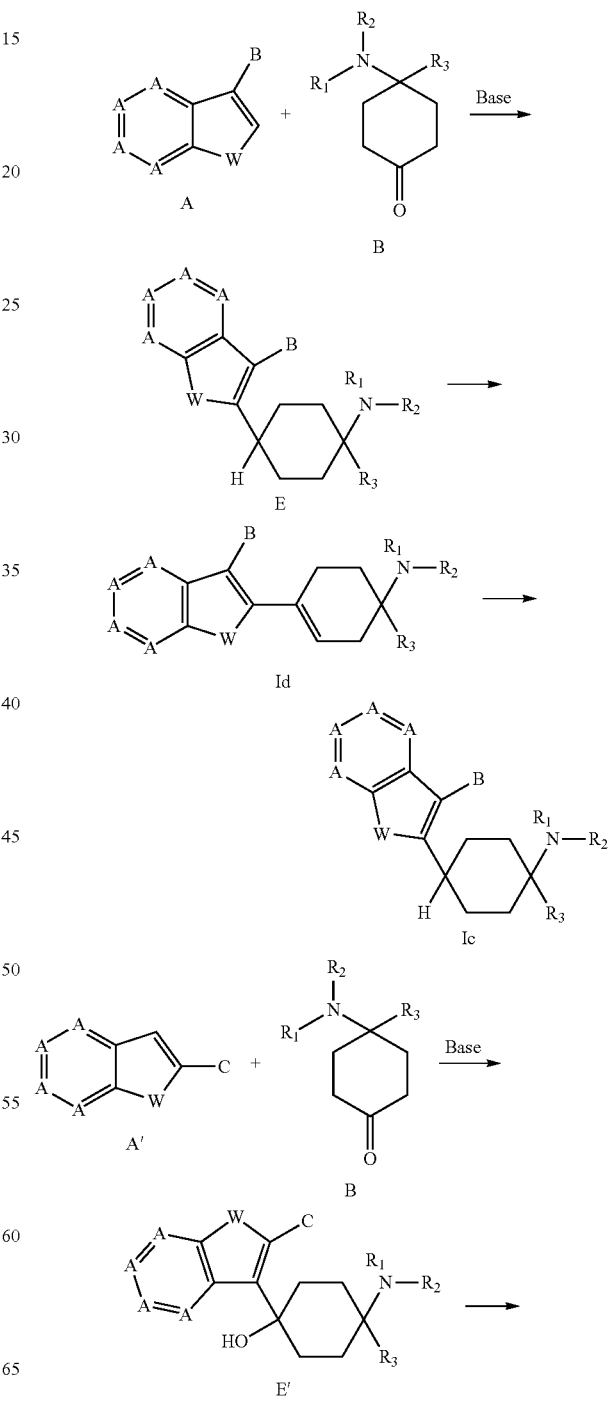

The reaction of heteroaromatics of the general formula A or A' with cyclohexanones of the general formula B to give cyclohexene-substituted heteroaromatics of the general formula Id or Ie can be carried out in organic solvents or solvent mixtures, for example chloroform, methylene chloride (DCM), dichloroethane (DCE), diethyl ether ($Et_2O$), acetonitrile (MeCN) or nitromethane, with the addition of an organic or inorganic acid, for example HCl, HBr, trifluoromethanesulfonic acid, methanesulfonic acid, acetic acid, trifluoroacetic acid, at temperatures of between 0° C. and 150° C., optionally using microwave irradiation. The reaction can also be carried out e.g. with the addition of trifluoromethanesulfonic acid trimethylsilyl ester. The reaction is preferably carried out with the addition of Brönsted acids.

Alternatively, compounds of the general formulae Id or Ie can also be obtained under basic conditions. In this context, a base, for example KOH or NaOH, is dissolved in an organic solvent, for example methanol. The heteroaromatic of the general formula A/A' and the ketone of the general formula B are reacted in this medium at temperatures of between 20 and 100° C. The product is optionally purified by column chromatography.

The double bond can be reduced by means of hydrogen in the form of HBr/glacial acetic acid//Sn or HCl/Sn (nascent hydrogen) or $H_2$ in the presence of a metal catalyst, such as e.g. palladium on charcoal, platinum on charcoal, platinum oxide, Raney nickel, rhodium or ruthenium complexes, in a suitable solvent or solvent mixture, such as, for example, methanol (MeOH), ethanol (EtOH), acetone, ethyl acetate (AcOEt), HBr or acetic acid (AcOH), at temperatures of between 0° C. and 150° C. The compounds of the general formulae Ic and If are obtained by this procedure. Hydrogen can also be generated in situ from hydrogen transfer agents, such as e.g. cyclohexene.

Process 3

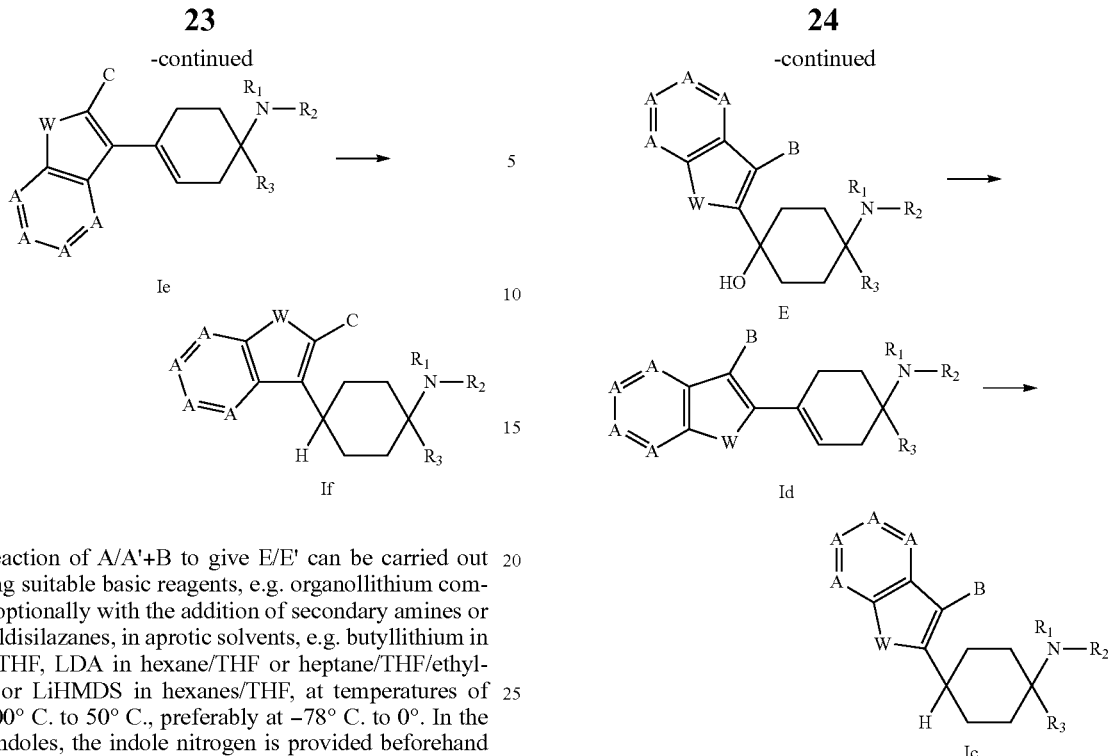

The reaction of A/A'+B to give E/E' can be carried out employing suitable basic reagents, e.g. organollithium compounds, optionally with the addition of secondary amines or hexaalkyldisilazanes, in aprotic solvents, e.g. butyllithium in hexanes/THF, LDA in hexane/THF or heptane/THF/ethylbenzene or LiHMDS in hexanes/THF, at temperatures of from −100° C. to 50° C., preferably at −78° C. to 0°. In the case of indoles, the indole nitrogen is provided beforehand with suitable protective groups known to the person skilled in the art, e.g. the benzenesulfonyl group, subst. or unsubst. benzyl groups or alkoxymethyl groups or substituted oxycarbonyl groups.

The reaction of E to give Id or Ie can be carried out under acidic or dehydrating conditions or after conversion of the hydroxyl group into a leaving group. In this context e.g. mineral acids, e.g. HCl or $H_2SO_4$ or dehydrating $P_4O_{10}$ can be employed, or the hydroxyl group can be converted into the chloride in situ by means of $SOCl_2$/pyridine. The double bond can optionally be reduced under the conditions described above.

Synthesis Via the Larock Reaction:

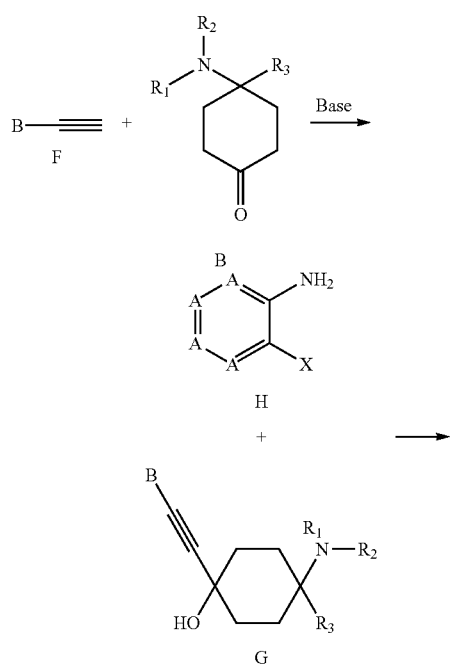

The reaction of F+B to give G can be carried out employing suitable basic reagents, e.g. organollithium compounds, optionally with the addition of secondary amines or hexaalkyldisilazanes, in aprotic solvents, e.g. butyllithium in hexanes/THF, LDA in hexane/THF or heptane/THF/ethylbenzene or LiHMDS in hexanes/THF, at temperatures of from −100° C. to 50° C., preferably at −78° C. to 0°. Further suitable conditions are e.g. Grignard reagents in aprotic solvents, e.g. ethylmagnesium bromide in THF or finely powdered alkali metal hydroxide, preferably KOH, in dry ether, with or without cooling with ice; alkali metal alcoholates, e.g. MeOK EtOK in THF at 0° C., KOtBu in THF at −10° C.

In stage 1, compounds of the general formula H given above, wherein X represents a halogen radical or a sulfonic acid ester, particularly preferably iodine, bromine or trifluoromethanesulfonate, are reacted in the sense of an indole synthesis by the Larock reaction with alkynes of the general formula G in a reaction medium preferably chosen from the group consisting of methanol, ethyl acetate, ethanol, isopropanol, n-butanol, dioxane, chloroform, methylene chloride, pyridine, dimethylsulfoxide, toluene, tetrahydrofuran, dimethylformamide, acetonitrile, diethyl ether, water and corresponding mixtures, particularly preferably chosen from the group consisting of dimethylformamide, ethyl acetate, tetrahydrofuran, water and corresponding mixtures, preferably with the addition of at least one palladium catalyst, preferably chosen from the group consisting of palladium(II) dichloride [$PdCl_2$], bis(triphenylphosphine)-palladium(II) acetate [Pd(PPh$_3$)$_2$(OAc)$_2$], bis(triphenylphosphine)-palladium(II) chloride [PdCl$_2$(PPh$_3$)$_2$], palladium(II) acetate [Pd(OAc)$_2$; Ac=acetate], bis(acetonitrile)-palladium(II) chloride [(CH$_3$CN)$_2$PdCl$_2$], bis(benzonitrile)-palladium(II) chloride [(PhCN)$_2$PdCl$_2$] and tetrakis(triphenylphosphine)palladium [(PPh$_3$)$_4$Pd], particularly preferably chosen from the group consisting of Pd(PPh$_3$)$_2$(OAc)$_2$, (PPh$_3$)$_4$Pd and PdCl$_2$(PPh$_3$)$_2$, optionally in the presence of at least one phosphine, preferably a phosphine chosen from the group consisting of triphenylphosphine, tri-(tert-butyl)-phosphine, triphenylarsine and tri-(ortho-toluyl)-phosphine, particularly preferably in the presence of triphenylphosphine, optionally with the addition of at least one inorganic salt, preferably with the addition of lithium chloride or tetrabutylammonium chloride, optionally with the addition of at least one inorganic base, preferably chosen from the group consisting of potassium carbonate, sodium carbonate, potassium acetate, sodium bicarbonate and caesium carbonate, and/or addition of at least one organic base chosen from the group consisting of triethylamine, diisopropylamine, diisopropylethylamine and [1,4]-diazabicyclo-[2.2.2]octane, at temperatures of from preferably −70° C. to 300° C., particularly preferably from −70° C. to 150° C., to give compounds of the general formula E and/or their regioisomers.

Compounds of the general formula H are commercially obtainable or known from the literature. By way of example, syntheses to give compounds of the general formula A are described in the examples part.

In stage 2, in the case where the radical B in compound G corresponds to a silyl protective group, the compounds of the general formula E are reacted in a reaction medium preferably chosen from the group consisting of methanol, ethyl acetate, ethanol, isopropanol, n-butanol, dioxane, chloroform, methylene chloride, pyridine, dimethylsulfoxide, toluene, tetrahydrofuran, dimethylformamide, acetonitrile, diethyl ether, water and corresponding mixtures, particularly preferably chosen from the group consisting of acetonitrile, tetrahydrofuran, methanol, ethanol, ethyl acetate, pyridine, water and corresponding mixtures, in the presence of fluoride, chosen from the group consisting of tetra-n-butylammonium fluoride, hydrofluoric acid (HF, HF-pyridine), potassium fluoride and/or sodium fluoride, caesium fluoride, or in the presence of an organic or inorganic acid, preferably HCl, acetic acid, trifluoroacetic acid, boron trifluoride, at temperatures of from preferably −70° C. to 300° C., particularly preferably from −70° C. to 150° C., to give compounds of the general formula E where B=H.

The reaction of E to give Id or Ic can be carried out under the abovementioned conditions.

The syntheses of the cyclohexanone derivatives with the general formula B are known in the literature (WO04043967, WO0290317, U.S. Pat. No. 4,065,573, Lednicer et al., J. Med. Chem., 23, 1980, 424-430). Derivatives of the general formula A or A' are commercially obtainable or described in the literature.

EXAMPLES

The following examples serve to explain the invention in more detail, but do not limit the general inventive idea.

The yields of the compounds prepared are not optimized.

In cases where isomers have been obtained, the isomer is called "non-polar isomer", which migrates further on silica gel thin-layer plates (normal phase) compared with the "polar isomer". The mobile phase used is e.g. MC/methanol 9:1, optionally with the addition of 5% of triethylamine.

All the temperatures are uncorrected.
Abbreviations:
days days
MC methylene chloride
DMF N,N-dimethylformamide
ether diethyl ether
EtOAc ethyl acetate
$H_2O$ water
MeOH methanol
$NEt_3$ triethylamine
RT room temperature.
TBAF tetrabutylammonium fluoride
THF Tetrahydrofuran
TMEDA N,N,N',N'-tetramethylethylenediamine Ketone Units Precursors 8-Dimethylamino-1,4-dioxa-spiro[4.5]decane-8-carbonitrile 40 per cent strength aqueous dimethylamine solution (116 ml, 0.92 mol), cyclohexane-1,4-dione monoethylene ketal (30.0 g, 0.192 mol) and potassium cyanide (30.0 g, 0.46 mol) was added to a mixture of 4 N hydrochloric acid (50 ml) and methanol (30 ml), while cooling with ice. The mixture was stirred at room temperature for 72 h and then, after addition of water (80 ml), extracted with ether (4×100 ml). After concentration of the solution, the residue was taken up in methylene chloride (200 ml) and dried with magnesium sulfate overnight. The organic phase was concentrated and the ketal was obtained as a white solid.

Yield: 38.9 g (96%); melting point: 86-88° C.
$^1$H-NMR (DMSO-$d_6$): 1.57 (2H, m); 1.72 (2H; m); 1.85 (2H, m); 1.99 (2H, m); 2.25 (6H, s); 3.87 (4H, m).
$^{13}$C-NMR (DMSO-$d_6$): 30.02; 31.32; 60.66; 63.77; 106.31; 118.40.

8-Methylamino-1,4-dioxa-spiro[4.5]decane-8-carbonitrile 40% strength aqueous methylamine solution (29.0 ml, 0.23 mol), cyclohexane-1,4-dione monoethylene ketal (7.50 g, 0.048 mol) and potassium cyanide (7.50 g) was added to a mixture of 4 N hydrochloric acid (12.5 ml) and methanol (7.5 ml), while cooling with ice. The mixture was stirred at room temperature for 7 d. After addition of water (20 ml), the mixture was extracted with ether (4×25 ml). After concentration of the solution, the residue was taken up in methylene chloride (50 ml) and dried with $MgSO_4$ overnight. The organic phase was concentrated and the ketal was obtained as an oil, which crystallized completely.

Yield: 7.05 g (80%)
$^1$H-NMR (DMSO-$d_6$): 1.54 (2H, m); 1.71 (4H, m); 1.95 (2H, m); 2.30 (3H, d); 2.72 (1H, q); 3.86 (4H, s).

Ketone Unit Ket-2

1-Methyl-4-(8-[1,2,3]triazol-1-yl-1,4-dioxaspiro[4.5]dec-8-yl)piperazine A solution of N-methylpiperazine (2.60 g, 2.88 ml, 26 mmol), 1.4-dioxaspiro[4.5]decan-8-one (3.90 g, 25 mmol) and 1,2,3-triazole (1.87 g, 27 mmol) in toluene (25 ml) was heated under reflux in a thoroughly heated flask using a water separator.

The reaction solution was then transferred into a closable measuring cylinder and the crude product was reacted further.

1-(8-Benzyl-1,4-dioxaspiro[4.5]dec-8-yl)-4-methylpiperazine A 2 M benzylmagnesium chloride solution in tetrahydrofuran (15 ml, 30 mmol) was added dropwise to a solution of 1-methyl-4-(8-[1,2,3]triazol-1-yl-1,4-dioxaspiro[4.5]dec-8-yl)piperazine (12.5 mmol) in toluene (12 ml) under argon such that the internal temperature remained below 24° C. When the addition had ended, the reaction mixture was stirred at room temperature for 2 h and then cooled to 0° C. and added dropwise to a 20% ammonium chloride solution (50 ml), the aqueous phase was extracted with diethyl ether (3×40 ml) and the combined organic phases were washed with 2 N sodium hydroxide solution (70 ml) and water (70 ml), dried with sodium sulfate and concentrated i. vac. The crude product (4.28 g) was reacted further.

4-Benzyl-4-(4-methylpiperazin-1-yl)cyclohexanone (Ket-2) First water (2.5 ml) and then concentrated hydrochloric acid (2.5 ml) was added to a solution of 1-(8-benzyl-1,4-dioxaspiro[4.5]dec-8-yl)-4-methylpiperazine (4.28 g, 13.0 mmol) in acetone (15 ml) and the mixture was stirred at room temperature overnight. The reaction mixture was then rendered alkaline (pH 10) with 2 M potassium carbonate solution and extracted with diethyl ether (3×40 ml) and the combined organic phases were dried with sodium sulfate and concentrated i. vac. The crude product was purified by means of flash chromatography (200 g, 20×5.7 cm) with methanol.

Yield: 2.63 g (71%), yellowish solid (Ket-2); melting point: 113-132° C.

$^1$H-NMR (DMSO-$d_6$): 1.36 (dt, 2H, J=13.8, 4.6 Hz); 1.92 (dd, 2H, J=14.9, 4.1 Hz), 2.05-2.14 (m, 2H); 2.17 (s, 3H); 2.34-2.47 (m, 6H); 2.61-2.69 (m, 4H); 2.72 (s, 2H); 7.12-7.28 (m, 5H).

$^{13}$C-NMR: 30.9 (2C); 35.8 (2C); 37.3; 43.7 (2C); 45.6; 55.6 (2C); 56.7; 125.8; 127.7 (2C); 130.5 (2C); 138.3; 210.0.

Ketone Unit Ket-3

Dimethyl-(8-benzyl-1,4-dioxa-spiro[4.5]dec-8-yl) amine hydrochloride

2 M benzylmagnesium chloride solution in THF (3, 285 ml, 570 mmol) was added to a solution of 8-dimethylamino-1,4-dioxa-spiro[4.5]decane-8-carbonitrile (39.8 g, 190 mmol) in THF (300 ml) in the course of 15 min, under argon and while cooling with ice. The mixture was then stirred at RT for 16 h. For working up of the reaction mixture, saturated ammonium chloride solution (200 ml) and water (100 ml) was added, while cooling with ice, and the mixture was extracted with diethyl ether (3×100 ml). The organic phase was extracted by shaking with water (50 ml) and saturated NaCl solution (50 ml) and the extract was then concentrated. A white solid (68.34 g) remained which, apart from the product, still contained the educt. The crude product was dissolved in ethyl methyl ketone (250 ml), and ClSiMe$_3$ (30 ml, 238 mmol) was added, while cooling with ice. After 16 h, dimethyl-(8-benzyl-1,4-dioxa-spiro[4.5]dec-8-yl)amine hydrochloride was isolated in a yield of 52% (40.33 g) as a white solid with a melting point of 276-280° C.

4-Dimethylamino-4-benzylcyclohexanone (Ket-3)

The hydrochloride (40.33 g, 130 mmol) was dissolved in water (55 ml), concentrated hydrochloric acid (100 ml, 1.21 mol) was added and the mixture was stirred at room temperature for 4 d. When the hydrolysis had ended, the reaction mixture was extracted with diethyl ether (2×100 ml) and the aqueous phase was rendered alkaline with 5 N sodium hydroxide solution, while cooling with ice, during which the product precipitated out. The solid was filtered off with suction, washed with H$_2$O (3×20 ml) and dried. It was possible to isolate 4-dimethylamino-4-benzylcyclohexanone (Ket-3) in this way in a yield of 87% (26 g) as a yellow solid with a melting point of 80-84° C.

Ketone Unit Ket-4

(8-Butyl-1,4-dioxa-spiro[4.5]dec-8-yl)-dimethyl-amine hydrochloride

8-Dimethylamino-1,4-dioxa-spiro[4.5]decane-8-carbonitrile (10.5 g, 50 mmol) was initially introduced into THF (150 ml), while cooling with ice and under argon. 2 M butylmagnesium chloride in THF (62.5 ml, 125 mmol) was added dropwise in the course of 15 min and the mixture was stirred at RT for 16 h.

20% strength ammonium chloride solution (37 ml) and water (50 ml) were added to the mixture, while cooling with ice, and the mixture was extracted with ether (3×50 ml). The org. phase was washed with water (1×50 ml) and saturated sodium chloride solution (1×50 ml) and the organic phase was dried with Na$_2$SO$_4$ and concentrated i. vac.

The crude product (2.05 g) was dissolved in ethyl methyl ketone (75 ml), ClSiMe$_3$ (9.5 ml, 75 mmol) was added, while cooling with ice, and the mixture was stirred at RT for 6 h. The white precipitate which had precipitated out was filtered off with suction and dried i. vac. Yield: 3.1 g (22%)

1H-NMR (DMSO-$d_6$): 0.91 (3H, t); 1.31 (4H, m); 1.56 (2H, m); 1.75 (8H, m); 2.64 (6H, s); 3.87 (4H, s); 9.87 (1H, s).

4-Butyl-4-dimethylamino-cyclohexanone (Ket-4)

8-Butyl-1,4-dioxa-spiro[4.5]dec-8-yl)-dimethyl-amine hydrochloride (3.10 g, 11.1 mmol) was initially introduced into H$_2$O (4.7 ml) and conc. HCl (7 ml) and the mixture was stirred at RT for 24 h. The mixture was extracted with ether (1×15 ml), the aqueous phase was rendered alkaline with 5 N NaOH, while cooling with ice, and the mixture was extracted with methylene chloride (3×20 ml). The org. phase was dried over Na$_2$SO$_4$ and concentrated i. vac. Yield: 1.96 g (89%), oil $^1$H-NMR (DMSO-$d_6$): 0.88 (3H, t); 1.23 (4H, m); 1.40 (2H, m); 1.68 (2 H, m); 1.91 (2H, m); 2.31 (2H, m); 2.22 (6H, s); 2.42 (2H, m).

$^{13}$C-NMR (DMSO-$d_6$): 13.91; 23.21; 26.06; 29.53; 31.07; 37.04; 38.88; 55.36; 210.37.

Ketone Unit Ket-6

2-Iodo-benzo[b]thiophene

Butyllithium 1.6 M in hexane (112.5 ml, 180 mmol) and abs. ether (70 ml) was initially introduced into a 500 ml three-necked flask under an argon atmosphere and the mixture was cooled to 0° C. in an ice bath. Benzothiophene (20.1 g, 150 mmol) then dissolved in abs. ether (40 ml) and the solution added dropwise in the course of 30 minutes, while cooling with ice, and the mixture subsequently stirred in an ice bath for 2.5 h. The reaction mixture stood in a refrigerator overnight. Iodine (75.0 g) and abs. ether (50 ml) were initially introduced into a 500 ml three-necked flask under an argon atmosphere and the solution of the lithium compound was added dropwise, while cooling with ice. The mixture was warmed slowly to room temperature, hydrolysed with water and washed with sodium thiosulfate solution and the organic phase was dried over sodium sulfate. The reaction solution was then concentrated i. vac. and the residue was purified by means of flash chromatography with cyclohexane. Yield: 24.1 g (62%) semi-solid, pale brown crystals $^1$H-NMR (DMSO-$d_6$): 7.32 (2H, m); 7.75 (1H, s); 7.81 (1H, m); 7.93 (1H, m).

(8-Benzo[b]thiophen-2-yl-1,4-dioxa-spiro[4.5]dec-8-yl)-dimethyl-amine hydrochloride Mg (238 mg) was initially introduced into abs. ether (2 ml) in a 100 ml three-necked flask under argon, and 2-iodo-benzo[b]thiophene (2.51 g, 9.6 mmol) in abs. ether (8 ml) was slowly added dropwise thereto. After addition of abs. ether (10 ml), the mixture was boiled under reflux for 5 h. The reaction solution was cooled in an ice bath and 8-dimethylamino-1,4-dioxa-spiro[4.5]decane-8-carbonitrile (1.03 g, 4.9 mmol) in THF (10 ml) was added dropwise at 10° C. The mixture stirred at room temperature overnight, NH$_4$Cl solution (5 ml) and water (7 ml) was added to the reaction mixture, while cooling with ice, and the mixture was extracted with ether (3×30 ml). The org. phase was washed with water (30 ml) and then with saturated NaCl solution (20 ml), dried over Na$_2$SO$_4$ and concentrated i. vac.

Yield: 1.99 g (66%)

The crude product was dissolved in ethyl methyl ketone (19 ml), trimethylchlorosilane (1.63 ml, 12.8 mmol) was added, while cooling with ice, and the mixture was stirred at room temperature for 5 h. The precipitate formed was filtered off with suction and dried i. vac.

Yield: 600 mg (35%)

$^1$H-NMR (DMSO-d$_6$): 1.46 (2H, m); 1.79 (2H, m); 2.37 (2H, m); 2.63 (6H, s); 2.75 (2 H, m); 7.47 (2H, m); 7.91 (1H, s); 7.95 (1H, m); 8.06 (1H, m); 11.40 (1H, s).

$^{13}$C-NMR (DMSO-d$_6$): 30.43; 31.13; 37.84; 63.88; 66.42; 105.84; 122.48; 124.55; 124.89; 125.71; 128.99; 135.00; 138.91; 139.58.

4-Benzo[b]thiophen-2-yl-4-dimethylamino-cyclohexanone (Ket-6)

(8-Benzo[b]thiophen-2-yl-1,4-dioxa-spiro[4.5]dec-8-yl)-dimethyl-amine hydrochloride (0.60 g, 1.7 mmol) was dissolved in water (0.8 ml), concentrated hydrochloric acid (1.04 ml, 151 mmol) was added and the mixture was stirred at room temperature for 3 d. When the hydrolysis had ended, the reaction mixture was extracted with diethyl ether (2×25 ml) and the aqueous phase was rendered alkaline with 5 N sodium hydroxide solution, the mixture was extracted with methylene chloride (3×25 ml) and the extract was dried over sodium sulfate and concentrated i. vac. Yield: 0.44 g (95%) Ket-6

$^1$H-NMR (DMSO-d$_6$): 2.19 (10H, m); 2.52 (4H, m); 7.35 (3H, m); 7.84 (1H, m); 7.91 (1 H, m).

$^{13}$C-NMR (DMSO-d$_6$): 33.74; 36.51; 38.05; 58.60; 121.87; 121.94; 123.35; 124.02; 124.16; 138.19; 139.17; 144.28; 209.50.

Ketone Unit Ket-8

8-Pyrrolidin-1-yl-1,4-dioxaspiro[4.5]decane-8-carbonitrile

Pyrrolidine (22.5 ml, 0.306 mol), cyclohexane-1,4-dione monoethylene ketal (10.0 g, 0.064 mol) and potassium cyanide (10.0 g, 0.15 mol) was added to a mixture of 4 N hydrochloric acid (17 ml) and methanol (10 ml), while cooling with ice. The mixture was stirred at room temperature for 74 h and then, after addition of water (80 ml), extracted with diethyl ether (4×70 ml). After concentration, the residue was taken up in methylene chloride (70 ml) and the mixture was dried with magnesium sulfate overnight. The organic phase was concentrated and 8-pyrrolidin-1-yl-1,4-dioxaspiro[4.5]decane-8-carbonitrile was obtained as a white solid with a melting point of 65-67° C. in a yield of 68% (10.2 g).

4-(8-Phenyl-1,4-dioxaspiro[4.5]dec-8-yl)pyrrolidine hydrochloride

8-Pyrrolidin-1-yl-1,4-dioxaspiro[4.5]decane-8-carbonitrile (10.0 g, 42.6 mmol), dissolved in THF (90 ml), was added to a 1.82 M phenylmagnesium chloride solution in THF (70 ml, 0.127 mol) in the course of 15 min, under argon and while cooling with ice, and the mixture was stirred at room temperature for 16 h. For working up of the reaction mixture, saturated ammonium chloride solution (100 ml) was added, while cooling with ice, and the mixture was then extracted with diethyl ether (3×100 ml). The organic phase was extracted by shaking with water (70 ml) and saturated NaCl solution (70 ml) and the extract was concentrated. A yellow crystal slurry (11.8 g) remained which, apart from the desired product, still contained educt. The crude product was dissolved in ethyl methyl ketone (70 ml), and ClSiMe$_3$ (8 ml, 0.063 mol) was added, while cooling with ice. After a reaction time of 6 h, it was possible to isolate 4-(8-phenyl-1,4-dioxaspiro[4.5]dec-8-yl)pyrrolidine hydrochloride in a yield of 43% (5.9 g) as a white solid.

4-Pyrrolidin-4-yl-4-phenylcyclohexanone (Ket-8)

4-(8-Phenyl-1,4-dioxaspiro[4.5]dec-8-yl)pyrrolidine hydrochloride (5.8 g, 17.9 mmol) was dissolved in 7.5 N hydrochloric acid (16 ml) and the mixture was stirred at room temperature for 24 h. When the hydrolysis had ended, the reaction mixture was extracted with diethyl ether (2×50 ml), and the aqueous phase was rendered alkaline with 5 N sodium hydroxide solution, while cooling with ice, and extracted with methylene chloride (3×50 ml) and the extract was concentrated. It was possible to isolate the ketone Ket-8 as a yellow solid with a melting point of 75-79° C. and a yield of 96% (4.1 g).

Ketone Unit Ket-9

4-(8-Phenyl-1,4-dioxaspiro[4.5]dec-8-yl)morpholine hydrochloride

Bromobenzene (3.0 g, 0.019 mol) and a little iodine was added to a mixture of magnesium (2.9 g, 0.119 mol) and anhydrous THF (15 ml) under argon. After 30 min the mixture was heated to 50° C., the Grignard reaction starting with boiling. Further bromobenzene (15.7 g, 0.1 mol), dissolved in THF (50 ml), was added in the course of 20 min and the mixture was boiled under reflux for 1.5 h. 8-Pyrrolidin-1-yl-1,4-dioxaspiro[4.5]decane-8-carbonitrile (10.0 g, 0.0396 mol), dissolved in THF (60 ml), was added to the mixture in the course of 20 min, while cooling with ice. The reaction mixture was then heated to 70° C. for 4 h. After a further reaction time of 16 h at room temperature, the reaction was interrupted by addition of NH$_4$Cl solution (60 ml), while cooling with ice. The aqueous phase was extracted with diethyl ether (2×70 ml), the organic phase was extracted by shaking with water (50 ml) and saturated NaCl solution (50 ml) and the extract was concentrated. A yellow crystal slurry (11 g) remained which, apart from the desired phenyl compound, also contained the unreacted aminonitrile educt. The crude product obtained was dissolved in methyl ethyl ketone (140 ml), and trimethylchlorosilane (7.5 ml, 0.059 mol) was added, while cooling with ice. After 15 min a white precipitate started to precipitate out, and was filtered off with suction after 6 h. It was possible to obtain 6.5 g (49%) of the hydrochloride 5 with a melting point of 250-252° C.

4-Morpholin-4-yl-4-phenylcyclohexanone (Ket-9)

The hydrochloride just obtained (6.5 g, 19.1 mmol) was dissolved in 7.5 N hydrochloric acid (22 ml) and the solution was stirred at room temperature for 24 h. When the hydrolysis had ended, the reaction mixture was extracted by shaking with Et$_2$O (2×50 ml). The aqueous phase was rendered alkaline with 5 N sodium hydroxide solution, while cooling with ice, and extracted with methylene chloride (3×50 ml) and the extract was concentrated. It was possible to isolate the ketone Ket-9 in this way as a beige-coloured solid with a melting point of 116-119° C. and a yield of 84% (4.1 g).

Ketone Unit Ket-10

Dimethyl-(8-phenyl-1,4-dioxaspiro[4.5]dec-8-yl) amine hydrochloride

8-Dimethylamino-1,4-dioxaspiro[4.5]decane-8-carbonitrile (21 g, 0.1 mmol), dissolved in THF (210 ml), was added to a 1.82 M phenylmagnesium chloride solution in THF (109 ml, 0.198 mol) in the course of 15 min, under argon and while cooling with ice, and the mixture was then stirred at room temperature for 16 h. For working up of the reaction mixture, saturated ammonium chloride solution (150 ml) was added, while cooling with ice, and the mixture was extracted with diethyl ether (3×100 ml). The organic phase was extracted by shaking with water (100 ml) and saturated NaCl solution (100 ml) and the extract was concentrated. A yellow oil (25.2 g) remained. The crude product was dissolved in ethyl methyl ketone (280 ml), and ClSiMe$_3$ (18.8 ml, 0.15 mol) was added, while cooling with ice. After a reaction time of 6 h, it was possible to isolate dimethyl-(8-phenyl-1,4-dioxaspiro[4.5] dec-8-yl)amine hydrochloride in a yield of 35% (10.5 g) as a white solid.

4-Dimethylamino-4-phenylcyclohexanone (Ket-10)

Dimethyl-(8-phenyl-1,4-dioxaspiro[4.5]dec-8-yl)amine hydrochloride (10.5 g, 35.2 mmol) was dissolved in 7.5 N hydrochloric acid (36 ml) and the solution was stirred at room temperature for 96 h. When the hydrolysis had ended, the reaction mixture was extracted with diethyl ether (2×50 ml). The aqueous phase was rendered alkaline with 5 N sodium hydroxide solution, while cooling with ice, and extracted with methylene chloride (3×50 ml) and the extract was concentrated. It was possible to isolate 4-dimethylamino-4-phenylcyclohexanone (Ket-10) in this way as a yellow solid with a melting point of 104-108° C. in a yield of 97% (7.4 g).

Ketone Unit Ket-11

A solution of 4.5 g of 8-dimethylamino-1,4-dioxa-spiro [4.5]decane-8-carbonitrile, 50 mg of cyclopentadienyl-cycloocta-1,5-diene-cobalt(l) [cpCo(cod)] and 100 ml of toluene was transferred into the reaction vessel in an inert gas/ acetylene countercurrent. After saturation with acetylene, the reaction solution was irradiated at a temperature of 25° C. over a period of 6 hours, with vigorous stirring. The reaction was interrupted by switching off the lamp and supplying air and the reaction solution was concentrated. The crude product obtained (5.47 g) was taken up in a mixture of water (8.7 ml) and conc. hydrochloric acid (15 ml) and the mixture was stirred at RT overnight. For working up, the mixture was washed with diethyl ether (3×100 ml), the phases were separated, the aqueous phase was rendered alkaline with 32 per cent strength by weight sodium hydroxide solution and extracted with methylene chloride (3×100 ml) and the combined extracts were dried (Na$_2$SO$_4$), filtered and concentrated. 3.72 g of 4-dimethylamino-4-pyridine-2-ylcyclohexanone (Ket-11) were obtained.

Ketone Unit Ket-12

Dimethyl-(8-thiophen-2-yl-1,4-dioxaspiro[4.5]dec-8-yl)amine hydrochloride

2-Iodothiophene (22.9 g, 109 mmol) was dissolved in THF (80 ml) under argon and 2 M isopropylmagnesium chloride (35.7 ml, 72 mmol) in THF was added at 0° C. in the course of 30 min. After a reaction time of 1 h at 3-5° C., 8-dimethylamino-1,4-dioxa-spiro[4.5]decane-8-carbonitrile (10 g, 47.6 mmol), dissolved in tetrahydrofuran (20 ml), was added and the mixture was stirred at room temperature for 20 h. Working up of the mixture was carried out by addition of saturated NH$_4$Cl solution (85 ml) and extraction with diethyl ether (3×100 ml). The organic phase was extracted by shaking with water (50 ml) and saturated NaCl solution (50 ml) and the extract was concentrated. A dark brown oil (21.3 g) was obtained. The crude product was dissolved in ethyl methyl ketone (140 ml), and ClSiMe$_3$ (9.1 ml, 71.4 mmol) was added. After a reaction time of 6 h, dimethyl-(8-thiophen-2-yl-1,4-dioxaspiro[4.5]dec-8-yl)amine hydrochloride was isolated as a white crystalline compound in a yield of 60% (8.74 g).

4-Dimethylamino-4-thiophen-2-ylcyclohexanone (Ket-12)

Dimethyl-(8-thiophen-2-yl-1,4-dioxaspiro[4.5]dec-8-yl) amine hydrochloride (8.68 g, 28.6 h hydrolysis had ended the reaction mixture was extracted with diethyl ether (2×50 ml). The aqueous phase was rendered alkaline with 5 N sodium hydroxide solution, while cooling with ice, and extracted with methylene chloride (3×50 ml) and the extract was concentrated. Ket-12 was obtained in this way as a yellow solid with a melting point of 108-110° C. in a yield of 89% (5.66 g).

Ketone Unit Ket-13

Variant 1:
[8-(3-Fluorophenyl)-1,4-dioxaspiro[4.5]dec-8-yl]di methylamine hydrochloride 0.5 M 3-fluorophenylmagnesium bromide solution in THF (3, 750 ml, 375 mmol) was added to a solution of 8-dimethylamino-1,4-dioxa-spiro[4.5]decane-8-carbonitrile (19.8 g, 94 mmol) in THF (100 ml) in the course of 15 min, under argon and while cooling with ice, and the mixture was then stirred at room temperature for 16 h. For working up of the reaction mixture, saturated ammonium chloride solution (150 ml) and water (60 ml) was added, while cooling with ice, and the mixture was extracted with diethyl ether (3×100 ml). The organic phase was extracted by shaking with water (50 ml) and saturated NaCl solution (50 ml) and the extract was concentrated. A brown oil (26.5 g) remained which, apart from the phenyl compound 4, still contained the ketal 2. The crude product was dissolved in ethyl methyl ketone (156 ml), and ClSiMe3 (17.8 ml, 141 mmol) was added, while cooling with ice. After a reaction time of 6 h, it was possible to isolate the hydrochloride in a yield of 55% (16.3 g) as a white solid with a melting point of 275-278° C.

Variant 2: [8-(3-Fluoro-phenyl)-1,4-dioxa-spiro[4.5] dec-8-yl]-dimethyl-amine hydrochloride A solution of 1-bromo-3-fluorobenzene (5.00 g, 28.6 mmol) in abs. ether (15 ml) was added dropwise to a suspension of magnesium (694 mg, 28.6 mmol) in abs. ether (10 ml) such that the ether boiled. When the addition had ended, the mixture was subsequently stirred at RT for 10 min, and thereafter the magnesium was dissolved completely. The reaction solution was cooled in an ice bath and 8-dimethylamino-1,4-dioxa-spiro[4.5]decane-8-carbonitrile (3.00 g, 14.3 mmol) in abs. THF (30 ml) was added dropwise at 10° C. The mixture stirred at room temperature overnight, 20% strength NH$_4$Cl solution (20 ml) and water (30 ml) were added to the reaction mixture, while cooling with ice, and the mixture was extracted with ether (3×50 ml). The org. phase was washed with water (50 ml) and then with saturated NaCl solution (50 ml), dried over $Na_2SO_4$ and concentrated i. vac.

The crude product was dissolved in ethyl methyl ketone (25 ml), $ClSiMe_3$ (3.2 ml, 25 mmol) was added, while cooling with ice, and the mixture was stirred at room temperature for 5 h. The precipitate formed was filtered off and dried i. vac. Yield: 2.8 g (62%)

$^1$H-NMR (DMSO-$d_6$): 1.91 (8H, m); 2.54 (6H, s); 3.91 (4H, d); 7.37 (1H, m); 7.61 (3 H, m).

Variant 1: 4-Dimethylamino-4-(3-fluoro-phenyl)-cyclohexanone (Ket-13)

[8-(3-Fluoro-phenyl)-1,4-dioxa-spiro[4.5]dec-8-yl]-dimethyl-amine hydrochloride (7.2 g, 22.75 mmol) was dissolved in water (9.6 ml), concentrated hydrochloric acid (14 ml, 455 mmol) was added and the mixture was stirred at room temperature for 4 d. When the hydrolysis had ended, the reaction mixture was extracted with diethyl ether (2×50 ml) and the aqueous phase was rendered alkaline with 5 N sodium hydroxide solution, while cooling with ice, during which the product precipitated out. It was possible to isolate the ketone Ket-13 as a yellow solid with a melting point of 83-88° C. and a yield of 50% (6.05 g).

Variant 2

4-Dimethylamino-4-(3-fluoro-phenyl)-cyclohexanone (Ket-13)

[8-(3-Fluoro-phenyl)-1,4-dioxa-spiro[4.5]dec-8-yl]-dimethyl-amine hydrochloride (2.80 g, 8.86 mmol) was dissolved in water (3.7 ml), concentrated hydrochloric acid (5.5 ml) was added and the mixture was stirred at RT for 4 d. When the hydrolysis had ended, the reaction mixture was extracted with ether (2×10 ml) and the aqueous solution was rendered alkaline with 5 N sodium hydroxide solution, while cooling with ice, the reaction mixture was extracted with methylene chloride (3×50 ml) and the organic phase was dried over sodium sulfate and concentrated i. vac. The crude product was purified by flash chromatography with $CHCl_3$/MeOH (20:1).

Yield of Ket-13: 676 mg (32%), colourless solid; melting point: 62-67° C.

$^1$H-NMR (DMSO-$d_6$): 2.02 (6H, s); 2.12 (5H, m); 2.45 (3H, m); 7.24 (3H, m); 7.43 (1H, m).

Ketone Unit Ket-14

1-(8-Pyrrolidin-1-yl-1,4-dioxaspiro[4.5]dec-8-yl)-1H-[1,2,3]triazole Pyrrolidine (1.95 g, 2.29 ml, 27.5 mmol), 1,2,3-triazole (2.07 g, 30 mmol) and molecular sieve 4 Å (7.14 g) were added to a solution of 1,4 dioxaspiro[4,5]decan-8-one (3.9 g, 25 mmol) in toluene (40 ml). The mixture was stirred at 90° C. for 7 h. The solution was then decanted and immediately reacted further.

1-(8-Butyl-1,4-dioxaspiro[4.5]dec-8-yl)pyrrolidine The reaction solution of 1-(8-pyrrolidin-1-yl-1,4-dioxaspiro[4.5]dec-8-yl)-1H-[1,2,3]triazole (approx. 6.9 g, 25 mmol toluene (38 ml) was added dropwise to a 2 M solution of n-butylmagnesium chloride (25 ml, 50 mmol) in tetrahydrofuran, while cooling with ice and under argon. The reaction mixture was stirred at room temperature overnight and then poured into saturated ammonium chloride solution (60 ml). The phases were separated and the aqueous phase was extracted with diethyl ether (3×70 ml). The combined organic phases were dried with sodium sulfate and concentrated i. vac. and the residue (12 g) was purified by flash chromatography (400 g, 20×7.6 cm) with ethyl acetate/methanol (9:1).

Yield: 2.70 g (40% over two stages)

$^1$H-NMR (DMSO-$d_6$): 0.87 (t, 3H, J=7.1 Hz); 1.12-1-29 (m, 4H); 1.30-1.45 (m, 4H); 1.46-1.60 (m, 4H); 1.61-1.75 (m, 6H); 1.93 (t, 1H, J=7.1 Hz); 2.36 (t, 1H, J=7.0 Hz), 2.58 (br s, 2H), 3.83 (s, 4H).

4-Butyl-4-pyrrolidin-1-yl-cyclohexanone (Ket-14)

Water (10.0 ml) and 37% hydrochloric acid (14.0 ml) were added to a solution of 1-(8-butyl-1,4-dioxaspiro[4.5]dec-8-yl)pyrrolidine (2.70 g, 10.1 mmol) in acetone (100 ml) and the mixture was stirred at room temperature overnight. 4 M sodium hydroxide solution was then slowly added dropwise to the mixture until pH 10 was reached. The mixture was extracted with diethyl ether (4×40 ml) and the combined organic phases were dried with sodium sulfate and concentrated i. vac. The crude produce (2.6 g) was purified by flash chromatography (260 g, 30×5.6 cm) with ethyl acetate/methanol (9:1).

Yield: 1.06 g (47%), brownish oil Ket-14

$^1$H-NMR (DMSO-$d_6$): 0.88 (t, 3H, J=6.7 Hz); 1.14-1.34 (m, 4H); 1.40-1.50 (m, 2H); 1.62-1.88 (m, 8H); 2.04 (dt, 2H, J=15.0, 3.9 Hz); 2.42 (ddd, 2H, J=6.3, 11.8, 15.5 Hz); 2.63 (t, 4H, J=6.0 Hz).

Ketone Unit Ket-15

4-Cyano-4-phenylheptanedioic acid dimethyl ester

Phenylacetonitrile (11.7 g, 0.1 mol) and methyl acrylate (47 ml, 0.5 mol) were initially introduced into tert-butanol (60 ml) and the mixture was heated to the boiling point. The heat source was then removed. Triton B (benzyltrimethylammonium hydroxide, 40 per cent in methanol, 15.2 ml), dissolved in tert-butanol (23 ml), was added dropwise, first slowly, later swiftly. After the dropwise addition, the mixture was boiled under reflux for 4 h. The reaction mixture was cooled to room temperature overnight.—For working up, toluene (100 ml) and water (70 ml) were added to the mixture. The organic phase was separated off and washed with water (1×70 ml) and saturated sodium chloride solution (1×50 ml). After drying with $Na_2SO_4$, the solvent was distilled off in a fume cupboard because of the severe odour nuisance. Purification was carried out by a bulb tube distillation under a pressure of $7.8 \times 10^{-2}$ mbar at a temperature of 235° C. It was possible to isolate the desired 4-cyano-4-phenylheptanedioic acid dimethyl ester in a yield of 21.45 g (72%) as a colourless, viscous substance.

5-Cyano-2-oxo-5-phenylcyclohexanecarboxylic acid methyl ester

4-Cyano-4-phenylheptanedioic acid dimethyl ester (14.45 g, 0.05 mol) was dissolved in dry tetrahydrofuran (350 ml). Sodium tert-butylate (9.6 g, 0.1 mol) was then added in portions. During this addition the reaction mixture became orange in colour. Thereafter, the mixture was boiled under reflux for 5 h. During the boiling a beige-colouring, slurry-like suspension formed. The reaction mixture was cooled to room temperature overnight. 2.5 N glacial acetic acid (170 ml) was slowly added dropwise to the reaction mixture, while cooling with ice. Toluene (100 ml) was then added to the mixture. The organic phase was separated off and washed with saturated sodium bicarbonate solution (3×70 ml), water (3×50 ml) and sodium chloride solution (1×70 ml). After drying with Na$_2$SO$_4$, the solvent was distilled off on a rotary evaporator and the residue was recrystallized from methanol. It was possible to obtain the desired product in a yield of 10.7 g (83%) as a yellow solid with a melting point of 75-80° C.

4-Cyano-4-phenylcyclohexanone

5-Cyano-2-oxo-5-phenylcyclohexanecarboxylic acid methyl ester (7.71 g, 0.03 mol) was dissolved in 10 per cent strength H$_2$SO$_4$ and concentrated acetic acid (240 ml). The reaction mixture was stirred at 100° C. for 24 h. The course of the reaction was monitored by TLC. For working up, the mixture was diluted with water (400 ml), while cooling with ice, and extracted with ethyl acetate (3×100 ml). The organic phase was then washed thoroughly with water (6×100 ml), saturated sodium bicarbonate solution (10×100 ml) and saturated sodium chloride solution (1×100 ml). After drying with Na$_2$SO$_4$, the solvent was distilled off on a rotary evaporator. It was possible to isolate the desired product in a yield of 5.46 g (92%) with a melting point of 106-107° C.

8-Cyano-8-phenyl-1,4-dioxaspiro[4.5]decane

4-Cyano-4-phenylcyclohexanone (5.97 g, 30 mmol) was taken up in toluene (200 ml), and ethylene glycol (4 ml, 71.6 mmol) was added. After addition of p-toluenesulfonic acid (86 mg, 0.5 mmol), the mixture was heated to the boiling point using a water separator. The course of the reaction was monitored by TLC chromatography. After 20 h starting substance was no longer detectable in the TLC. After cooling, the toluene solution was extracted by shaking with water (5×30 ml) and saturated aqueous NaCl solution (3×20 ml) and the extract was dried over Na$_2$SO$_4$. After removal of the solvent on a rotary evaporator, the desired ketal is obtained in a yield of 6.8 g (94%) as a white solid with a melting point of 108-110° C.

8-Phenyl-1,4-dioxaspiro[4.5]decane-8-carboxylic acid (Schneider, Woldemar; Krombholz, Gottfried; ARPMAS; Arch. Pharm. (Weinheim Ger.); 313; 6; 1980; 487-498) 8-Cyano-8-phenyl-1,4-dioxaspiro[4.5]decane (4.86 g, 20 mmol) was dissolved in ethylene glycol (40 ml), NaOH (4 g, 100 mmol) was added and the mixture was then heated under reflux to the boiling point. The course of the reaction was monitored by means of TLC. After 20 h nitrile was no longer detectable. For working up, ice (approx. 100 g) was added to the mixture and the mixture was covered with a layer of ether (40 ml) and acidified by slowly adding half-concentrated HCl (50 ml). The aqueous phase was extracted with ether (3×30 ml). The combined organic extracts were washed with saturated NaCl solution (2×30 ml), dried over Na$_2$SO$_4$ and concentrated to dryness on a rotary evaporator. By recrystallization of the solid obtained from toluene, the desired carboxylic acid was obtained as a crystalline solid with a melting point of 134-139° C. in a yield of 3.1 g (59%).

8-Isocyanato-8-phenyl-1,4-dioxaspiro[4.5]decane

8-Phenyl-1,4-dioxaspiro[4.5]decane-8-carboxylic acid (3 g, 11.5 mmol) was initially introduced into anisole (30 ml). The suspension obtained was cooled to a temperature of 0° C. in an ice/sodium chloride bath and triethylamine (2.25 ml, 16 mmol) was added. A clear solutions was formed and was stirred at 0° C. for a further 15 min. Phosphoric acid diphenyl ester azide (2.5 ml, 11.5 mmol) was then added to the mixture in the course of 5 min. The reaction mixture was stirred at 0° C. for 20 min, allowed to come to RT in the course of a further 20 min and then heated in an oil bath at 100° C. (bath temperature) for 2 h. For working up, the anisole was distilled off under an oil pump vacuum. Purification by chromatography was carried out on silica gel with toluene. The desired product was obtained as a crystalline solid with a melting point of 38-41° C. in a yield of 2.7 g (91%).

Methyl-(8-phenyl-1,4-dioxaspiro[4.5]dec-8-yl)amine

LiAlH$_4$ (535 mg, 14.08 mmol) was suspended in dry THF (4 ml) with exclusion of moisture from the atmosphere. 8-Isocyanato-8-phenyl-1,4-dioxaspiro[4.5]decane (2.29 g, 8.8 mmol, dissolved in 40 ml of dry THF) was added dropwise in the course of 20 min. When the addition was complete, the reaction mixture was heated to the boiling point under reflux for 4 h. After cooling, first aqueous THF (1 ml of H$_2$O in 3 ml) was cautiously added to the reaction mixture, while cooling with ice, then 1.7 ml of 15 per cent strength sodium hydroxide solution and finally 5 ml of H$_2$O. The mixture was stirred for 20 min and then filtered over silica gel. The solvent mixture obtained after washing the filter cake with ethyl acetate several times was concentrated to dryness on a rotary evaporator. The desired product was obtained in a yield of 2.1 g (97%) as a viscous oil.

4-Methylamino-4-phenylcyclohexanone (Ket-15)
(Upjohn_Lednicer, U.S. Pat. No. 4,065,573A1, 1977)

A mixture of conc. HCl (15 ml) and water (8 ml) was poured over methyl-(8-phenyl-1,4-dioxaspiro[4.5]dec-8-yl) amine (2.1 g, 8.4 mmol) and the mixture was stirred at RT for 5 days. For working up, the reaction mixture was diluted with water (20 ml) and extracted with ether (3×30 ml). The ethereal phase was discarded. The aqueous phase was then rendered basic with 2N NaOH and extracted with methylene chloride (3×30 ml). The organic phase obtained in this way was dried with Na$_2$SO$_4$ and then concentrated on a rotary evaporator. By purification by chromatography on silica gel with ethyl acetate/ethanol (4:1), it was possible to obtain the ketone Ket-15 in a yield of 1.38 g (81%) as a solid with a melting point of 32-38° C.

Ketone Unit Ket-16

8-Azetidin-1-yl-1,4-dioxaspiro[4.5]decane-8-carbonitrile

First 1,4-dioxaspiro[4,5]decan-8-one (4.84 g, 31 mmol) and thereafter potassium cyanide (4.85 g, 74.4 mmol) in water (15 ml) was added to a mixture of 4N hydrochloric acid (8.1 ml), methanol (4.9 ml) and azetidine (8.5 g, 10 ml, 149 mmol), while cooling with ice. The mixture was stirred at room temperature for 5 d, water (50 ml) was then added and the mixture was extracted with diethyl ether (3×50 ml). The combined organic phases were dried with sodium sulfate and concentrated i. vac.; yield: 6.77 g (98%), oil $^1$H-NMR (DMSO-d$_6$): 1.45-1.63 (m, 4H); 1.67-1.82 (m, 4H); 1.99 (q, 2H, J=7.1 Hz); 3.21 (t, 4H, J=7.1 Hz); 3.86 (s, 4H).

1-(8-Phenyl-1,4-dioxaspiro[4.5]dec-8-yl)azetidine

A solution of the nitrile just prepared (2.20 g, 9.9 mmol) in anhydrous tetrahydrofuran (25 ml) was added dropwise to a 2 M solution of phenylmagnesium chloride in tetrahydrofuran (12 ml, 24 mmol), under argon and while cooling with ice, and thereafter the mixture was stirred at room temperature overnight. After addition of saturated ammonium chloride solution (5 ml) and water (5 ml), the phases were separated and the aqueous phase was extracted with diethyl ether (3×50 ml). The combined organic phases were dried with sodium sulfate and concentrated i. vac. The crude product was purified by flash chromatography (100 g, 20×4.0 cm) with ethyl acetate/cyclohexane (1:1); yield: 670 mg (25%), colourless oil $^1$H-NMR (DMSO-$d_6$): 1.27-1.40 (m, 2H); 1.55-2.00 (m, 8H); 2.86 (t, 4H, J=6.8 Hz); 3.76-3.89 (m, 4H); 7.24-7.45 (m, 5H).

4-Azetidin-1-yl-4-phenylcyclohexanone (Ket-16)

6N hydrochloric acid (2 ml) was added to a solution of the acetal just prepared (370 mg, 1.3 mmol) in acetone (30 ml) and the mixture was stirred at room temperature overnight. The mixture was adjusted to pH 10 by addition of 5N sodium hydroxide solution and the aqueous phase was extracted with methylene chloride (3×20 ml). The combined organic phases were dried with sodium sulfate and concentrated i. vac.

Yield: 274 mg (92%), white solid (Ket-16)
$^1$H-NMR (DMSO-$d_6$): 1.67 (td, 2H, J=13.8, 6.9 Hz); 1.95-2.13 (m, 4H); 2.20-2.33 (m, 2H); 2.40-2.47 (m, 1H); 2.52-2.57 (m, 1H); 2.94 (t, 4H; J=6.9 Hz); 7.28-7.47 (m, 5H).

Ketone Unit Ket-17

1-(8-Pyrrolidin-1-yl-1,4-dioxaspiro[4.5]dec-8-yl)-1H-[1,2,3]triazole

Pyrrolidine (1.95 g, 2.29 ml, 27.5 mmol), 1,2,3-triazole (2.07 g, 30 mmol) and molecular sieve 4 Å (7.14 g) were added to a solution of 1,4 dioxaspiro[4.5]decan-8-one (3.9 g, 25 mmol) in toluene (40 ml). The mixture was stirred at 90° C. for 7 h. The solution was then decanted and immediately reacted further.

1-(8-Butyl-1,4-dioxaspiro[4.5]dec-8-yl)pyrrolidine

The reaction solution of the triazole derivative just prepared (approx. 6.9 g, 25 mmol) in toluene (38 ml) was added dropwise to a 2 M solution of n-butylmagnesium chloride (25 ml, 50 mmol) in tetrahydrofuran, while cooling with ice and under argon. The reaction mixture was stirred at room temperature overnight and then poured into saturated ammonium chloride solution (60 ml). The phases were separated and the aqueous phase was extracted with diethyl ether (3×70 ml). The combined organic phases were dried with sodium sulfate and concentrated i. vac. and the residue (12 g) was purified by flash chromatography (400 g, 20×7.6 cm) with ethyl acetate/methanol (9:1).

Yield: 2.70 g (40% over two stages), brown oil
$^1$H-NMR (DMSO-$d_6$): 0.87 (t, 3H, J=7.1 Hz); 1.12-1-29 (m, 4H); 1.30-1.45 (m, 4H); 1.46-1.60 (m, 4H); 1.61-1.75 (m, 6H); 1.93 (t, 1H, J=7.1 Hz); 2.36 (t, 1H, J=7.0 Hz), 2.58 (br s, 2H), 3.83 (s, 4H).

4-Butyl-4-pyrrolidin-1-yl-cyclohexanone (Ket-17)

Water (10.0 ml) and 37% hydrochloric acid (14.0 ml) were added to a solution of the acetal just obtained (2.70 g, 10.1 mmol) in acetone (100 ml) and the mixture was stirred at room temperature overnight. 4 M sodium hydroxide solution was then slowly added dropwise to the mixture until pH 10 was reached. The mixture was extracted with diethyl ether (4×40 ml) and the combined organic phases were dried with sodium sulfate and concentrated i. vac. The crude product (2.6 g) was purified by flash chromatography (260 g, 30×5.6 cm) with ethyl acetate/methanol (9:1).

Yield: 1.06 g (47%), brown oil (Ket-17)
$^1$H-NMR (DMSO-$d_6$): 0.88 (t, 3H, J=6.7 Hz); 1.14-1.34 (m, 4H); 1.40-1.50 (m, 2H); 1.62-1.88 (m, 8H); 2.04 (dt, 2H, J=15.0, 3.9 Hz); 2.42 (ddd, 2H, J=6.3, 11.8, 15.5 Hz); 2.63 (t, 4H, J=6.0 Hz).

Ketone Unit Ket-18

Variant 1

Methyl-[8-(4-methyl-thiazol-2-yl)-1,4-dioxa-spiro[4.5]dec-8-yl]-amine

Butyllithium (2.5 M in hexane, 9.2 ml, 23.0 mmol) was initially introduced into the reaction vessel under an argon atmosphere and cooled to −78° C. in a cooling bath. 4-Methyl-thiazole (2.09 ml, 23 mmol) was dissolved in abs. tetrahydrofuran (60.0 ml) and the solution was added dropwise at −78° C., while cooling with ice, and the mixture was subsequently stirred at this temperature for 10 min.

8-Methylamino-1,4-dioxa-spiro[4.5]decane-8-carbonitrile (2.12 g, 10.8 mmol) in abs. tetrahydrofuran (15 ml) was added rapidly dropwise to this solution at −78° C. After the addition, the reaction solution was subsequently stirred in a cooling bath for 1 h and then warmed slowly to 0° C. The reaction mixture was stirred at room temperature overnight. Hydrolysis was then carried out with water (10 ml) at 0° C., the aqueous phase was extracted with chloroform (3×50 ml) and the organic phase was washed with water (1×50 ml) and saturated NaCl solution (50 ml), dried over $Na_2SO_4$ and concentrated i. vac.

The product was purified by means of flash chromatography with cyclohexane/ethyl acetate (1:4) and ethyl acetate. Yield: 2.71 g (94%)

$^1$H-NMR (DMSO-$d_6$): 1.54 (2H, m); 1.82 (4H, m); 2.02 (2H, m); 2.08 (3H, d); 2.32 (3H, s); 2.38 (1H, q); 3.86 (4H, s); 7.09 (1H, s).

$^{13}$C-NMR (DMSO-$d_6$): 16.96; 28.92; 30.04; 33.03; 58.29; 63.48; 63.59; 107.67; 113.69; 151.07; 178.75.

4-(Methylamino)-4-(4-methylthiazol-2-yl)cyclohexanone (Ket-18)

5% strength sulfuric acid (6 ml) was added to methyl-[8-(4-methyl-thiazol-2-yl)-1,4-dioxa-spiro[4.5]dec-8-yl]-amine (100 mg, 0.37 mmol) and the mixture was stirred at RT overnight. When the hydrolysis had ended, the reaction mixture was extracted with ether (1×5 ml), the aqueous solution was rendered alkaline with 5N NaOH, while cooling with ice, the reaction mixture was extracted with methylene chloride (3×10 ml) and the organic phase was dried over $Na_2SO_4$ and concentrated i. vac. Yield: 74 mg (88%), oil.

$^{13}$C-NMR (DMSO-$d_6$): 17.19; 29.52; 35.48; 37.00; 58.58; 113.06; 152.54; 176.03; 210.85.

Variant 2

Ethyl 5-cyano-5-(4-methylthiazol-2-yl)-2-oxocyclohexanecarboxylate

Sodium amide (58.0 g, 1.48 mol) was added in portions to a solution of (4-methyl-thiazol-2-yl)-acetonitrile (24.4 g, 0.175 mol) and bromo-propionic acid ethyl ester (51.6 ml, 0.4 mol) in abs. toluene (700 ml) at 0-5° C. and the mixture was then boiled under reflux for 3 h. The reaction solution was cooled to 0° C. and hydrolysed slowly with acetic acid/water (2/1, 240 ml). The organic phase was separated off, washed with sat. $NaHCO_3$ solution (2×400 ml) and water (2×400 ml), dried over sodium sulfate and concentrated i. vac.

Yield: 45.0 g (88%), brown oil $^1$H-NMR (DMSO-d$_6$): 1.26 (3H, t); 2.30-2.62 (4H, m); 2.38 (3H, s); 2.84 (1H, d); 2.93 (1H, d); 4.22 (2H, q); 7.39 (1H, s); 12.21 (1H, s).

1-(4-Methyl-thiazol-2-yl)-4-oxo-cyclohexanecarbonitrile Ethyl 5-cyano-5-(4-methylthiazol-2-yl)-2-oxocyclohexanecarboxylate (45.0 g, 0.153 mol) was dissolved in acetic acid (1.23 l) and 10% strength sulfuric acid (540 ml) and the solution was boiled under reflux for 4 d.

For working up, water (850 ml) was added to the mixture, while cooling with ice, and the mixture was extracted with ethyl acetate (three times 300 ml; sat. NaCl solution was added for better separation of the phases). The organic phase was washed with water (6×100 ml) and stirred thoroughly with sat. NaHCO$_3$ solution (1 l) for 20 min, and the organic phase was then washed once more with sat. NaHCO$_3$ solution and sat. NaCl solution, dried over sodium sulfate and concentrated i. vac.

Yield: 13.3 g (39%), pale brown solid $^1$H-NMR (DMSO-d$_6$): 2.38-2.69 (11H, m); 7.39 (1H, s).

$^{13}$C-NMR (DMSO-d$_6$): 16.68; 34.88; 37.32; 41.43; 115.76; 120.09; 152.37; 166.26: 206.05.

8-(4-Methyl-thiazol-2-yl)-1,4-dioxa-spiro[4.5]decane-8-carbonitrile 1-(4-Methyl-thiazol-2-yl)-4-oxo-cyclohexanecarbonitrile (13.3 g, 61 mmol) and ethylene glycol (6.8 ml, 122 mmol) were dissolved in toluene (250 ml), a catalytic amount of p-toluenesulfonic acid was added and the mixture was boiled for 3 h using a water separator.

For working up, the organic solution was washed with water (125 ml), sat. NaHCO$_3$ solution, water and sat. NaCl solution, dried over sodium sulfate and concentrated i. vac. Yield: 15.8 g (99%), pale brown oil $^1$H-NMR (DMSO-d$_6$): 1.80 (4H, m); 2.11-2.42 (7H, m); 4.22 (4H, s); 7.35 (1H, s).

8-(4-Methyl-thiazol-2-yl)-1,4-dioxa-spiro[4.5]decane-8-carboxylic acid amide A solution of KOH (12.9 g, 230 mmol) in water (200 ml) was added to 8-(4-methyl-thiazol-2-yl)-1,4-dioxa-spiro[4.5]decane-8-carbonitrile (15.2 g, 58 mmol), dissolved in ethanol (200 ml), and the mixture was stirred at RT for 48 h. Since according to TLC (EA/cyclohexane 4:1) educt was still present, the mixture was subsequently stirred at 80° C. for a further 3 h.

For working up, ethanol was removed i. vac., a solid precipitated out of the aqueous solution and was separated off and boiled up briefly with half-concentrated acetic acid and the mixture was cooled and filtered with suction.

Yield: 6.5 g (40%), colourless crystals; melting point: 167-170° C.

$^1$H-NMR (DMSO-d$_6$): 1.61 (4H, m); 2.10 (2H, m); 2.38 (5H, m); 3.91 (4H, s); 7.12 (3H, m).

$^{13}$C-NMR (DMSO-d$_6$): 16.84; 31.57; 31.92; 34.12; 50.93; 66.65; 107.17; 114.11; 151.12; 172.27; 173.14.

Methyl 8-(4-methylthiazol-2-yl)-1,4-dioxaspiro[4.5]decane-8-ylcarbamate 8-(4-Methyl-thiazol-2-yl)-1,4-dioxa-spiro[4.5]decane-8-carboxylic acid amide (2.82 g, 10 mmol) and mercury(II) acetate (4.58 g, 12 mmol) were dissolved in absol. DMF (50 ml). Methanol (12 ml, 300 mmol) and a solution of N-bromosuccinimide (1.96 g, 11 mmol) in absol. DMF (15 ml) were added at RT and the mixture was stirred for 18 h. For working up, the solvent was removed i. vac. and the solid residue was extracted with ether (4×50 ml). The organic phase was concentrated and the product mixture was separated by flash chromatography with EA/cyclohexane (1:2). Yield: 541 mg (19%)

$^1$H-NMR (DMSO-d$_6$): 1.66 (2H, m); 1.72 (2H, m); 2.03 (2H, m); 2.25 (5H, m); 3.57 (3H, s); 3.87 (4H, s); 7.09 (1H, s).

$^{13}$C-NMR (DMSO-d$_6$): 16.84; 31.57; 31.92; 34.12; 50.93; 66.65; 107.17; 114.11; 151.12; 172.27; 173.14.

Methyl-[8-(4-methyl-thiazol-2-yl)-1,4-dioxa-spiro[4.5]dec-8-yl]-amine LiAlH$_4$ (125 mg, 3.3 mmol) was added in portions to a solution of methyl 8-(4-methylthiazol-2-yl)-1,4-dioxaspiro[4.5]decan-8-ylcarbamate (520 mg, 1.7 mmol) in absol THF (20 ml) and the mixture was boiled under reflux for 5 h. The reaction mixture was hydrolysed with sat. Na$_2$SO$_4$ solution at 0° C., filtered over Celite, washed with THF and concentrated i. vac. The residue was taken up in EA and the mixture was washed with water and dried over sodium sulfate. Purification was carried out by flash chromatography with EA/cyclohexane (4:1). Yield: 106 mg (24%), oil $^1$H-NMR (DMSO-d$_6$): 1.55 (2H, m); 1.82 (4H, m); 1.98 (2H, m); 2.05 (3H, s); 2.32 (3H, s); 3.86 (4H, s); 7.10 (1H, s).

Indole Units

Indole Building Block Precursors

3-(2-Bromo-ethyl)-5-fluoro-1H-indole 2-(5-Fluoro-1H-indol-3-yl)-ethanol (20.0 g, 112 mmol) was dissolved in abs. CH$_2$Cl$_2$ (250 ml), and tetrabromomethane (56.0 g, 170 mmol) was added at RT. Triphenylphosphine (44.0 g, 165 mmol) was then added in portions at RT, while cooling with water. The solution was stirred at RT for 2.5 h and then concentrated i. vac. The residue was absorbed on to silica gel and divided into two equal portions. The crude product was purified by flash chromatography over 2 columns each with 500 g of silica gel and cyclohexane/ethyl acetate (9:1→4:1). Yield: 25.4 g (93%), red solid $^1$H-NMR (DMSO-d$_6$): 3.18 (2H, t); 3.69 (2H, t); 6.91 (1H, m); 7.32 (3H, m); 11.03 (1H, s).

$^{13}$C-NMR (DMSO-d$_6$): 28.36; 34.22; 102.83: 108.96; 111.96; 125.55; 126.95; 132.74; 155.60; 157.90.

Indole Unit Ind-1

2-(2-(1H-Indol-3-yl)ethyl)isoindoline-1,3-dione (Ind-1)

Tryptamine (3.04 g, 19.0 mmol) and phthalic anhydride (3.00 g, 20.0 mmol) were boiled for 12 h in a water separator. The solvent was distilled off i. vac. and the residue was dissolved in methylene chloride. Product was precipitated out by addition of cyclohexane and the precipitate was filtered off with suction and dried. Yield: 4.46 g (Ind-1; 87%)

$^1$H-NMR (DMSO-d$_6$): 3.03 (2H, t); 3.85 (2H, t); 7.04 (2H, m); 7.18 (1H, s); 7.34 (1H, d); 7.54 (1H, d); 7.83 (4H, m); 10.83 (1H, s).

Indole Unit Ind-2

N-(2-(1H-Indol-3-yl)ethyl)acetamide (Ind-2)

Tryptamine (192 mg/1.2 mmol) was initially introduced into abs. THF (5 ml), and triethylamine (179 µl/1.3 mmol) was added. Acetic anhydride (132 mg/1.3 mmol) was then added and the mixture was stirred at RT for 4 h. The mixture was concentrated to dryness i. vac. The residue was taken up in ethyl acetate and this solution was washed with saturated NaHCO$_3$ solution (two times 20 ml) and with NaCl solution (two times 20 ml). The organic phase was dried over Na$_2$SO$_4$ and concentrated i. vac.

Yield: 236 mg (Ind-2; 97%)

$^1$H-NMR (DMSO-d$_6$): 1.81 (3H, s); 2.83 (2H, m); 3.33 (2H, m); 6.96 (1H, m); 7.05 (1H, m); 7.14 (1H, s); 7.35 (1H, m); 7.53 (1H, d); 7.92 (1H, t, NH); 10.79 (1H, s).

$^{13}$C-NMR (DMSO-d$_6$): 22.65; 25.19; 33.11; 39.50; 111.31; 111.86; 118.16; 120.84; 122.52; 127.21; 136.21; 168.99.

N-(2-(1H-Indol-3-yl)ethyl)acetamide (Ind-2)

Tryptamine (192 mg/1.2 mmol) was initially introduced into abs. THF (5 ml), and triethylamine (179 µl/1.3 mmol) was added. Acetic anhydride (132 mg/1.3 mmol) was then added and the mixture was stirred at RT for 4 h. The mixture was concentrated to dryness i. vac. The residue was taken up in ethyl acetate and this solution was washed with saturated NaHCO$_3$ solution (two times 20 ml) and with NaCl solution (two times 20 ml). The organic phase was dried over Na$_2$SO$_4$ and concentrated i. vac.

Yield: 236 mg (Ind-2, 97%)

$^1$H-NMR (DMSO-d$_6$): 1.81 (3H, s); 2.83 (2H, m); 3.33 (2H, m); 6.96 (1H, m); 7.05 (1H, m); 7.14 (1H, s); 7.35 (1H, m); 7.53 (1H, d); 7.92 (1H, t, NH); 10.79 (1H, s).

$^{13}$C-NMR (DMSO-d$_6$): 22.65; 25.19; 33.11; 39.50; 111.31; 111.86; 118.16; 120.84; 122.52; 127.21; 136.21; 168.99.

Indole Unit Ind-4

(5-Fluoro-3-hydroxy-2-oxo-2,3-dihydro-1H-indol-3-yl) acetic acid ethyl ester 5-Fluoroindoline-2,3-dione (10 mmol) was dissolved in a mixture of ethanol/pyridine/acetic acid (50 ml, 15:5:2), ethyl potassium malonate (1.87 g, 11 mmol) was added and the mixture was accordingly heated under reflux for 14 h. The course of the reaction was monitored by means of TLC (eluent: ethyl acetate/hexane (1:1). For working up, the solvent mixture was distilled off in vacuo. The residue was taken up in ethyl acetate (50 ml) and the mixture was extracted by shaking with water (50 ml). After separation of the phases, the aqueous phase was extracted twice with ethyl acetate (30 ml each time). The combined organic phases were washed with 2N HCl (50 ml), dried over Na$_2$SO$_4$ and concentrated to 20 ml in vacuo. Hexane was added to the solution until crystallization started. To bring the crystallization to completion, the mixture was cooled to 10° C. for 12 h. The solid was filtered off with suction and dried in vacuo (S. J. Garden, R. B. da Silva, A. C. Pinto, Tetrahedron 2002, 58, 8399-8412 (specifically page 8406)).

Yield (5-fluoro-3-hydroxy-2-oxo-2,3-dihydro-1H-indol-3-yl)acetic acid ethyl ester: 89%

Melting point: 133-135° C.

2-(5-Fluoro-1H-indol-3-yl)ethanol (Ind-4)[1]

(5-Fluoro-3-hydroxy-2-oxo-2,3-dihydro-1H-indol-3-yl) acetic acid ethyl ester (10 mmol) was dissolved in absolute THF (20 ml) under an argon atmosphere. BH$_3$×THF (40 ml, 1 M solution, 40 mmol) was then added to the mixture, while cooling with a water bath, and the mixture was stirred at room temperature for 14 h. The course of the reaction was monitored by means of TLC. When the reaction had ended, the reaction solution was added to a mixture of ethyl acetate (50 ml) and H$_2$O (50 ml). After separation of the phases, the aqueous phase was extracted twice with ethyl acetate (30 ml each time). The combined organic phases were dried over Na$_2$SO$_4$ and concentrated in vacuo. The residue was filtered over silica gel with ethyl acetate. The product obtained after removal of the solvent was in the form of a sufficiently pure oil and crystallized spontaneously.

Yield (Ind-4): 95%; melting point: 47-50° C.)

Indole unit Ind-5: 2-(1H-indol-3-yl)ethanol (Ind-5)

Commercially obtainable under CAS 526-55-6 e.g. from Sigma-Aldrich

Indole Unit Ind-6

3-Methyl-2-trimethylsilanyl-1H-indole-5-carbonitrile 1-(Trimethylsilyl)propyne (2.23 ml, 1.68 g, 15.0 mmol), 4-amino-3-iodobenzonitrile (3.33 g, 13.65 mmol), lithium chloride (606 mg, 14.3 mmol) and sodium carbonate (4.35 g, 40.95 mmol) were added successively to abs. dimethylformamide (60 ml) under argon. Pd(dppf)Cl$_2$ (1.116 g, 1.365 mmol) was added to this mixture and the reaction mixture was heated at 100° C. with exclusion of moisture for 6 h and then stirred at room temperature for 16 h. For working up of the mixture, water (150 ml) and ethyl acetate (300 ml) was added and the mixture was stirred for 10 min. After separation of the phases, the aqueous phase was extracted with ethyl acetate (3×100 ml). The combined organic phases were washed with saturated sodium chloride solution (3×100 ml), dried and concentrated. The residue was a brown oil (5.5 g) which, apart from 3-methyl-2-trimethylsilanyl-1H-indole-5-carbonitrile, contained traces of the isomer 2-methyl-3-trimethylsilanyl-1H-indole-5-carbonitrile and DMF.

3-Methyl-1H-indole-5-carbonitrile (Ind-6)

Splitting off of the trimethylsilyl groups was carried out in two stages. The mixture of the nitriles from the previous stage (5.15 g, crude product) was dissolved in tetrahydrofuran (60 ml), tetrabutylammonium fluoride×3H$_2$O (5.58 g, 17.7 mmol) was added and the mixture was stirred at room temperature for 4 h. Water (150 ml) was added to the reaction mixture and the mixture was stirred for 10 min. After the addition of diethyl ether (50 ml), the phases were separated. The aqueous phase was extracted with diethyl ether (3×150 ml). The combined organic phases were dried and concentrated. The residue was a brown oil (3.4 g), which was separated by chromatography [silica gel 60 (170 g); ethyl acetate/cyclohexane (1:10, 1,600 ml), ethyl acetate/cyclohexane (1:4, 500 ml)]. 3-Methyl-2-trimethylsilanyl-1H-indole-5-carbonitrile was obtained by this procedure as a beige-coloured solid in a yield of 60% (1.92 g) with a melting point of 128-131° C. A product mixture of the indole 3-methyl-1H-indole-5-carbonitrile and 2-methyl-1H-indole-5-carbonitrile (264 mg), which were present virtually in a ratio of 1:1, was furthermore isolated. The silyl compound 3-Methyl-2-trimethylsilanyl-1H-indole-5-carbonitrile (1.9 g, 8.32 mmol) was dissolved in tetrahydrofuran (60 ml) and the solution was heated at 60° C. for 2 h. The mixture was then concentrated, water (150 ml) was added and the mixture was stirred for 10 min. After addition of diethyl ether (100 ml), the phases were separated. The aqueous phase was extracted with diethyl ether (2×50 ml). The organic phases were dried and concentrated. 3-Methyl-1H-indole-5-carbonitrile (Ind-6) was obtained by this procedure as a beige-coloured solid in a yield of 99% (1.33 g) with a melting point of 110-112° C.

Indole Unit Ind-7

3-Methyl-5-trifluoromethyl-2-trimethylsilanyl-1H-indole2-Iodo-4-trifluoromethylaniline (1.15 g, 4 mmol), trimethylsilylpropyne (494 mg, 0.656 ml. 4.4 mmol), lithium chloride (178 mg, 4.2 mmol) and sodium carbonate (1.27 g, 12 mmol) were combined in abs. dimethylformamide (20 ml) in an argon atmosphere.

[Pd(dppf)Cl$_2$×CH$_2$Cl$_2$]; 327 mg, 0.4 mmol) was then added. The reaction mixture was stirred at 100° C. (oil bath temperature) for 6 h and at room temperature for 18 h. The reaction mixture was then cooled with ice water, water (50 ml) and ethyl acetate (100 ml) were added and the mixture was stirred for 30 min. In order to separate off the catalyst, the dark brown mixture was filtered over Celite. The phases of the filtrate were separated. The aqueous phase was extracted with ethyl acetate (5×35 ml). The combined organic phases were washed with saturated sodium chloride solution (3×35 ml), subsequently dried with sodium sulfate, filtered and concentrated in vacuo. The dark brown oil obtained (1.8 g) which, apart from 3-methyl-5-trifluoromethyl-2-trimethylsilanyl-1H-indole, contained traces of DMF and also the isomer 2-methyl-5-trifluoromethyl-3-trimethylsilanyl-1H-indole, was employed as the crude product for the next stage.

3-Methyl-5-trifluoromethyl-1H-indole (Ind-7)

Splitting off of the trimethylsilyl group was carried out in two stages. The crude product from the preceding stage (1.8 g, 4 mmol, based on the precursor) was stirred with THF (20 ml) and tetrabutylammonium fluoride (1.64 g, 5.5 mmol) at RT for 5 h. The mixture was then worked up. After addition of water (20 ml), the mixture was stirred for 15 min. The phases were then separated. The aqueous phase was extracted with diethyl ether (3×30 ml). The combined organic phases were dried with sodium sulfate, filtered and concentrated in vacuo. 1.8 g of a viscous dark brown oil were obtained, and the oil was separated into its constituents by chromatography [silica gel 60 (60 g); cyclohexane/ethyl acetate (15:1; 500 ml, 10:1; 500 ml)]. 763 mg (2.8 mmol, 70%, based on the preceding stage) of 3-methyl-5-trifluoromethyl-2-trimethylsilanyl-1H-indole were obtained. THF (20 ml) and tetrabutylammonium fluoride (1.15 g, 3.6 mmol) were added to this again and the mixture was heated under reflux for 2 h. After the working up described above, 550 mg (69%) of 3-methyl-5-trifluoromethyl-1H-indole (Ind-7) were obtained as a beige-coloured solid with a melting point of 63-65° C.

Indole unit Ind-8: 5-Fluoro-3-methylindole (Ind-8)

Commercially obtainable under CAS no. 392-13-2 from e.g. Chempur

Indole Unit Ind-9

5-Methoxy-3-methyl-1H-indole (5-methoxyskatole) (Ind-9)

4-Methoxyphenylhydrazine hydrochloride (3.5 g, 20 mmol) was dissolved in H$_2$O (100 ml), and sodium carbonate (2.1 g, 20 mmol) was added. The mixture was stirred, a clear solution forming within a few minutes after transient precipitation of the free base.

Propionaldehyde (0.98 g, 16.8 mmol) and ethanol (5 ml, as a solubilizing agent) was added to the mixture. The mixture was stirred at RT for 14 h, an oily precipitate precipitating out of the solution. For working up, the mixture was extracted with ethyl acetate (3×20 ml). The combined organic phases were dried over MgSO$_4$ and then concentrated to dryness on a rotary evaporator. The brown residue obtained (3.2 g) was dissolved in DMF (20 ml) without further purification, the solution was heated to 110° C. (bath temperature) and 12 per cent sulfuric acid (10 ml) was added. Immediate decolorization took place. To bring the reaction to completion, the mixture was stirred at 110° C. for a further 3 h and then left to stand at RT overnight.—For working up, the reaction solution was added to ice (100 g). The aqueous mixture formed was extracted with ethyl acetate (4×20 ml) and the combined organic phases were dried over MgSO$_4$. The residue (3.3 g) obtained after evaporating off the solvent was purified by chromatography [silica gel 60 (100 g); cyclohexane/EtOAc 4:1, (300 ml)]. 5-Methoxy-3-methyl-1H-indole (Ind-9) was obtained in this way in a yield of 2.3 g (85%) as a tacky solid.

Indole Unit Ind-10: 3-Methyl-1H-indole (Ind-10)

Commercially obtainable under CAS 83-34-1 from e.g. Sigma-Aldrich

Indole Unit Ind-11

3-Cyclopropyl-2-trimethylsilanyl-1H-indoleCyclopropylethynyl)trimethylsilane (1.38 g, 10.0 mmol), 2-iodoaniline (1.94 g, 9.1 mmol), lithium chloride (404 mg, 9.54 mmol) and sodium carbonate (2.9 g, 27.3 mmol) were added successively to abs. dimethylformamide (40 ml) under argon. Pd(dppf)Cl$_2$ (744 mg, 0.91 mmol) was added to this mixture. The reaction mixture was heated at 100° C. with exclusion of moisture for 6 h and then stirred at room temperature for 16 h. For working up of the mixture, water (100 ml) and ethyl acetate (200 ml) were added. The mixture was then stirred for 10 min. The mixture was filtered over Celite. After separation of the phases, the aqueous phase was extracted with ethyl acetate (3×70 ml). The combined organic phases were washed with saturated sodium chloride solution (3×70 ml), dried with sodium sulfate and concentrated. The residue was a brown oil (3.6 g) which still contained traces of by-products and dimethylformamide. After purification by chromatography [silica gel 60 (120 g); ethyl acetate/cyclohexane 1:20 (700 ml)], 3-cyclopropyl-2-trimethylsilanyl-1H-indole was obtained as a beige-coloured solid in a yield of 75% (1.56 g) with a melting point of 78-81° C.

3-Cyclopropyl-1H-indole (Ind-11) 3-Cyclopropyl-2-trimethylsilanyl-1H-indole (1.56 g, 6.0 mmol)) was dissolved in tetrahydrofuran (40 ml), tetrabutylammonium fluoridex 3H$_2$O (2.79 g, 8.84 mmol) was added and the mixture was stirred at 70° C. for 2 h. The reaction mixture was concentrated, water (90 ml) and diethyl ether (70 ml) were added and the mixture was stirred for 10 min. The phases were separated. The aqueous phase was extracted with diethyl ether (2×50 ml). The combined organic phases were dried with sodium sulfate and concentrated. Ind-11 was isolated as a brown oil in a yield of 99% (1.04 g).

Indole Unit Ind-12

(3-Cyclohexyl prop-1-ynyl)trimethylsilaneProp-2-ynyl-cyclohexane (5.00 g, 40.9 mmol) was initially introduced into tetrahydrofuran (60 ml) at −25° C. and n-butyllithium (17.2 ml, 43.0 mmol; 2.5 M in hexane) was added dropwise. The temperature was kept at −15 to −20° C. (approx. 5 minutes). The reaction mixture was then stirred at 0 to −5° C. for 30 min. Thereafter, triethylchlorosilane (6.6 g, 43.8 mmol) was added dropwise (approx. 5 min) at 0 to −5° C. and the mixture was then subsequently stirred at room temperature overnight. The reaction mixture was concentrated in vacuo and water (50 ml) was added to the residue. The mixture was extracted with cyclohexane (3×30 ml). The combined organic phases were dried with sodium sulfate. The volatile constituents were removed completely in vacuo. (3-Cyclohexylprop-1-ynyl)trimethylsilane was obtained as a yellow oil (9.61 g, 99%).

3-Cyclohexylmethyl-2-triethylsilanyl-1H-indole2-Iodoaniline (5.48 g, 25.02 mmol), (3-cyclohexylprop-1-ynyl)trimethylsilane (6.50 g, 27.45 mmol), lithium chloride (1.11 g, 26.19 mmol) and sodium carbonate (7.95 g, 75.01 mmol) were combined in dimethylformamide (absolute, 70 ml) in an argon atmosphere. The catalyst ([Pd(dppf)Cl$_2$×CH$_2$Cl$_2$], 2.05 g, 2.51 mmol) was then added. The solution was stirred at 100-106° C. for 6 h. The black reaction mixture was cooled to room temperature and water (300 ml) and ethyl acetate (150 ml) were added in succession. After stirring for one hour, the mixture was filtered over Celite. The phases were separated. The aqueous phase was extracted with ethyl acetate (3×50 ml). The combined organic phases were dried with sodium sulfate. After filtration, the volatile constituents were removed completely in vacuo. The residue (10.8 g, brown oil) was separated by chromatography [silica gel 60 (300 g); cyclohexane/ethyl acetate 20:1 (1,050 ml), cyclohexane/ethyl acetate 10:1 (500 ml), cyclohexane/ethyl acetate 3:1 (750 ml)]. 3-Cyclohexylmethyl-2-triethylsilanyl-1H-indole was isolated as a brown oil (5.79 g, 71%).

3-Cyclohexylmethyl-1H-indole (Ind-12)5N hydrochloric acid (20 ml, 100 mmol) was metered into a solution of 3-cyclohexylmethyl-2-triethylsilanyl-1H-indole (5.70 g, 17.40 mmol) in MeOH (106 ml). The reaction mixture was stirred at room temperature overnight. Methanol was distilled off and the aqueous residue was extracted with methylene chloride (3×20 ml). The combined organic phases were dried with sodium sulfate. After filtration, the volatile constituents were removed completely in vacuo. The solid residue (brown solid, 4.50 g) was recrystallized from hexane (15 ml). 2.70 g (73%) of 3-cyclohexylmethyl-1H-indole (Ind-12) (melting point: 71-73° C.) were obtained.

Indole Unit Ind-13

3-Propyl-2-trimethylsilanyl-1H-indole

2-Iodoaniline (4.65 g, 21.2 mmol), trimethyl(pent-1-ynyl) silane (3.27 g, 23.3 mmol), lithium chloride (0.96 g, 22.6 mmol) and sodium carbonate (6.75 g, 63.7 mmol) were combined in dimethylformamide (absolute, 64 ml) in an argon atmosphere. The catalyst ([Pd(dppf)Cl$_2$×CH$_2$Cl$_2$], 1.78 g, 2.2 mmol) was then added. The solution was stirred at 105-112° C. (oil bath temperature) for 7 h. The black reaction mixture was cooled to room temperature and water (200 ml) and ethyl acetate (200 ml) were added in succession. After stirring for one hour, the mixture was filtered over Celite. The phases were separated. The organic phase was washed with 10 per cent strength citric acid solution (100 ml) and with saturated sodium chloride solution (100 ml). The organic phase was dried with sodium sulfate. After filtration, the volatile constituents were removed completely in vacuo. The residue (7.03 g of brown oil) was separated by chromatography [silica gel 60 (150 g); cyclohexane/trichloromethane 10:1 (550 ml); cyclohexane/trichloromethane 5:1 (1,650 ml)]. 2.35 g (50%) of 3-propyl-2-trimethylsilanyl-1H-indole were isolated as a brown oil (contaminated).

3-Propyl-1H-indole (Ind-13)3-Propyl-2-trimethylsilanyl-1H-indole (3.76 g, 16.25 mmol)) was dissolved in MeOH (70 ml), and 2N hydrochloric acid (45 ml, 90 mmol) was metered in. The reaction mixture was stirred overnight at room temperature. Methanol was distilled off and the aqueous residue was extracted with methylene chloride (3×20 ml). The combined organic phases were dried with sodium sulfate. After filtration, the volatile constituents were removed completely in vacuo. 2.66 g (100%) of 3-propyl-1H-indole (Ind-13) were obtained as a brown oil.

Indole Unit Ind-14

3-(2-(Pyridin-4-yl)ethyl)-1H-indole (Ind-14)

Indole (5.85 g, 50 mmol) was dissolved in glacial acetic acid (25 ml) together with 4-vinylpyridine (5.80 g, 55 mmol). The reaction mixture was boiled under reflux for 6 h. For working up, the glacial acetic acid was distilled off. Saturated NaHCO$_3$ solution (75 ml) and water (15 ml) were then added to the mixture. The mixture was extracted with ethyl acetate (1×100 ml, 3×15 ml). (The insoluble oil remaining between the phases contained only polar impurities.) The organic phase was dried over Na$_2$SO$_4$ and then evaporated. The residue was recrystallized twice from ethyl acetate (30 ml each time). The product Ind-14 was obtained as a pale yellow solid in a yield of 7.06 g (31.8 mmol, 63%, m.p.: 154-158° C.).

Indole Unit Ind-15

3-(1H-Indol-3-yl)propanoic acid cyanomethyl ester 3-(1H-Indol-3-yl)propanoic acid (5 g, 26 mmol) was dissolved in acetone (50 ml), and caesium carbonate (4.2 g, 13.0 mmol), chloroacetonitrile (1.8 ml, 28.6 mmol) and potassium iodide (20 mg) were added in succession. After a reaction time of 3 d at room temperature with exclusion of moisture, the solid residues were separated off by filtration and the filtrate was concentrated. The crude product of the ester was obtained only in a yield of 3.6 g by this procedure. The filtrate was taken up again in acetone (25 ml) and, for better solubility of the caesium salt formed as an intermediate product, DMF (25 ml) was added. The residue separated off previously, chloroacetonitrile (1.8 ml, 18.6 mmol) and potassium iodide (20 mg) was added to this solution. The reaction mixture was stirred at 60° C. for 3 h and at room temperature for 16H, with exclusion of water. The solid residues was separated off by filtration and the filtrate was concentrated. It was possible to obtain further crude product of the ester, which still contained DMF. The two crude products were combined and purified by chromatography on silica gel with ethyl acetate/cyclohexane (1:3). The desired cyanomethyl ester was obtained as a beige-coloured compound with a melting point of 72° C. in a yield of 91% (5.36 g).

3-(Indol-3-yl)propionic acid amide

The cyanomethyl ester just prepared (5.1 g, 22.3 mmol), in tetrahydrofuran (100 ml), was added to a 25 per cent strength ammonia solution (125 ml), while stirring, and the mixture was stirred at room temperature for 20 h. After this reaction time, the reaction was complete. Working up of the mixture was carried out by phase separation and extraction of the aqueous phase with tetrahydrofuran (2×30 ml). The organic phases were combined, dried and concentrated. The residue was washed with water (3×10 ml) and diethyl ether (3×10 ml) and dried. The desired amide remained as a white solid in a yield of 76% (3.2 g) with a melting point of 140° C.

3-(Indol-3-yl)propylamine (Ind-15)

Lithium aluminium hydride (1.42 g, 34 mmol) was added in portions to abs. THF (70 ml), under argon and while stirring. A solution of the amide just prepared (3.2 g, 17 mmol), in abs. THF (60 ml), was added to the LiAlH$_4$ suspension at 60° C. in the course of 30 min, while stirring. After a reaction time of 12 h at 60° C. under argon, THF (30 ml) was added to the mixture, and water (35 ml) was slowly added, while cooling with ice. The aluminium compounds obtained by this procedure were separated off by filtration and washed with THF (3×10 ml). The filtrate was concentrated until an oil precipitated out. After addition of water (30 ml), the amine was extracted with ethyl acetate (3×40 ml) and the extracts were combined and washed with water (40 ml). After drying and concentrating the organic phase, 3-(indol-3-yl)propylamine (Ind-15) was obtained as a colourless solid in a yield of 94% (2.77 g) with a melting point of 65° C.

Indole Unit Ind-16

3-(1H-Indol-3-yl)propanol

LiAlH$_4$ (1.21 mg, 31.71 mmol) was initially introduced into dry THF (50 ml). A solution of 3-indolepropionic acid (2.5 g, 13.21 mmol) in dry THF (80 ml) was added dropwise to the suspension in the course of 30 min. Thereafter, the reaction mixture was heated under reflux for 3 h at 10° C. and then stirred at RT for 18. H$_2$O (60 ml) was subsequently added, and then a mixture of conc. H$_2$SO$_4$ (10 ml) and H$_2$O (30 ml). The mixture was stirred for 20 min and ether (50 ml) was finally added. The organic phase was separated off and the aqueous phase was extracted with ether (3×40 ml). The combined ethereal extracts were dried over Na$_2$SO$_4$ and, after filtration of the drying agent, concentrated to dryness on a rotary evaporator. 3-(1H-Indol-3-yl)propanol was obtained as a viscous oil (2.28 g, 99%).

3-(3-Trimethylsilanyloxypropyl)-1H-indole (Ind-16)

3-(1H-Indol-3-yl)propanol (1.75 g, 10 mmol) was initially introduced into dry THF (30 ml), and first hexamethyldisilazane (10 ml, 47 mmol), followed by trimethylchlorosilane (2 ml, 15.7 mmol) was added at RT. The mixture was stirred at RT for 20 h, the solvent was then removed on a rotary evaporator and the residue was rendered basic with saturated NaHCO$_3$ solution. The aqueous solution was extracted with ether (3×30 ml). The combined organic phases were washed with H$_2$O (2×20 ml) and dried over Na$_2$SO$_4$. Removal of the solvent on a rotary evaporator gave 3-(3-trimethylsilanyloxypropyl)-1H-indole (2.46 g, 100%, m.p.: 34-38° C.) as a crystalline solid.

Indole Unit Ind-18

2-(2-(1H-Indol-3-yl)ethyl)isoindoline-1,3-dione

A solution of tryptamine (3.04 g, 19.0 mmol) and phthalic anhydride (3.0 g, 20.0 mmol) in toluene (300 ml) was boiled under reflux for 12 h using a water separator. The solvent was removed i. vac. and the residue was recrystallized from methylene chloride/cyclohexane. Yield: 4.46 g (81%)

Indole Unit Ind-19

1-(2-(5-Fluoro-1H-indol-3-yl)ethyl)-1H-benzo[d]imidazole (Ind-19)

A solution of 3-(2-bromo-ethyl)-5-fluoro-1H-indole (7.26 g, 30 mmol), benz-imidazole (3.54 g, 30 mmol) and ethyldiisopropylamine (5.1 ml, 30 mmol) in abs. chloroform (80 ml) was boiled under reflux for 20 h. The reaction solution was then washed twice with water, dried over Na$_2$SO$_4$ and concentrated i. vac. and the residue which remained was purified by flash chromatography with CHCl$_3$/MeOH (50:1).

An insoluble solid separated out in the water, and was filtered off with suction and likewise purified over a silica gel column. This was likewise the desired product.

Yield: 2.95 g (35%)

$^1$H-NMR (DMSO-d$_6$): 3.21 (2H, t); 4.51 (2H, t); 6.90 (1H, m); 7.21 (5H, m); 7.62 (1H, d); 8.09 (1H, s); 10.95 (1H, s).

Indole Unit Ind-20

5-Fluoro-3-(2-(piperidin-1-yl)ethyl)-1H-indole (Ind-20)

Piperidine (3.52 g, 4.08 ml, 41.3 mmol) was dissolved in abs dioxane (100 ml), 3-(2-bromo-ethyl)-5-fluoro-1H-indole (5.00 g, 20.7 mmol) was added at RT and the mixture was stirred at 70° C. for 16 h. The solution was concentrated, the residue was taken up in CHCl$_3$ (150 ml) and the mixture was washed with water (2×50 ml). The organic phase was dried over Na$_2$SO$_4$, filtered and concentrated i. vac. The residue obtained was purified by flash chromatography with 200 g of silica gel and ethyl acetate/ethanol (9:1→1:2).

Yield: 3.80 g (75%), colourless solid $^1$H-NMR (DMSO-d$_6$): 1.43 (2H, m); 1.59 (4H, m); 2.67 (6H, m); 2.92 (2H, t); 6.89 (1H, m); 7.24 (1H, s); 7.31 (2H, m); 11.05 (1H, s).

Indole Unit Ind-21

3-(2-(Piperidin-1-yl)ethyl)-1H-indole (Ind-21)

Piperidine (11.2 ml, 113 mmol) was added to a solution of 3-(2-bromo-ethyl)-indole (5.00 g, 22.31 mmol) in dry chloroform (25 ml) at room temperature and the mixture was then heated at the boiling point for 5 h. After cooling, the organic phase was extracted with dilute sulfuric acid (2×50 ml).

The aqueous phase was rendered alkaline with 5N NaOH, while cooling with ice, and extracted with ether (3×50 ml). The organic phase was dried over Na$_2$SO$_4$ and concentrated i. vac. For further purification, the residue was recrystallized from toluene (100 ml).

Yield: 2.00 g (40%)

$^1$H-NMR (DMSO-d$_6$): 1.38 (2H, m); 1.52 (4H, m); 2.42 (4H, m); 2.55 (2H; t); 3.31 (2H, t); 7.03 (3H, m); 7.31 (1H, d); 7.50 (1H, d); 10.73 (1H, s).

Indole Unit Ind-22

3-(2-(1H-1,2,3-Triazol-1-yl)ethyl)-5-fluoro-1H-indole (Ind-22)

A solution of 3-(2-bromo-ethyl)-5-fluoro-1H-indole (7.26 g, 30 mmol), 1,2,3-triazole (2.07 g, 30 mmol) and ethyldiisopropylamine (5.1 ml, 30 mmol) in abs. chloroform (70 ml) was boiled under reflux for 24 h. The reaction solution was then washed twice with water, dried over $Na_2SO_4$ and concentrated i. vac. and the residue which remained was purified by flash chromatography with EA/cyclohexane (1:1→4:1).).

Yield: 2.35 g (34%)

$^1$H-NMR (DMSO-$d_6$): 3.24 (2H, t); 4.64 (2H, t); 6.89 (1H, m); 7.12 (1H, s); 7.30 (2H, m); 7.67 (1H, s); 8.07 (1H, s); 10.96 (1H, s).

Indole Unit Ind-26

(4-Fluoro-3-methoxyphenyl)hydrazine hydrochloride All the working steps were carried out at 0° C. 4-Fluoro-3-methoxy-aniline (4.92 g, 34.8 mmol) was added to concentrated hydrochloric acid (30 ml), while stirring. After 10 min, an aqueous sodium nitrite solution (10 ml, 2.41 g, 34.8 mmol) was added dropwise to the suspension. After a further 10 min, a tin(II) chloride solution (10 ml, 13.6 g, 73 mmol) in concentrated hydrochloric acid was added. After formation of a yellowish precipitate, further concentrated hydrochloric acid (30 ml) was added. The precipitate was filtered off, washed with a little hydrochloric acid and dried i. vac. by repeated addition of toluene.

Yield: 9.81 g (146%), colourless solid. Melting point: 126-127° C.

$^1$H-NMR (300 MHz, $d_6$-DMSO): 3.80 (s, 3H), 6.53 (ddd, J=11.2, 5.2, 2.4 Hz, 1H), 6.99 (dd, J=7.5, 1.6 Hz, 1H), 7.11 (dd, J=11.4, 8.8 Hz, 1H), 8.20 (s, 1H), 10.28 (s, 3H).

$^{13}$C-NMR (100 MHz, $d_6$-DMSO): 55.9; 101.9; 106.3 (J=6 Hz); 115.7 (J=19 Hz); 142.5; 146.2; 147.2 (J=237 Hz); 147.3.

2-(5-Fluoro-6-methoxy-1H-indol-3-yl)ethanol (Ind-26) A solution of dihydrofuran (242 mg, 3.46 mmol) in acetonitrile (10 ml) was added dropwise to a solution of (4-fluoro-3-methoxyphenyl)hydrazine hydrochloride [1.00 g, 3.46 mmol (based on a purity of the educt of 68%)] in acetonitrile (30 ml) and 4% aqueous sulfuric acid (30 ml) at room temperature. Thereafter, the temperature was increased to 80° C. and the reaction mixture was stirred at this temperature for 2 h and then cooled to room temperature and the solvent was removed i. vac. 5% sodium bicarbonate solution was added to the residue and the mixture was extracted with ethyl acetate (3×50 ml). The combined organic phases were dried with sodium sulfate and concentrated i. vac.

Yield: 570 mg (78%)

Indole Unit Ind-27 & 28

(3-Hydroxy-2-oxo-2,3-dihydro-1H-indol-3-yl)acetic acid ethyl ester (S. J. Garden, R. B. da Silva, A. C. Pinto, Tetrahedron 2002, 58, 8399-8412 (specifically page 8406))

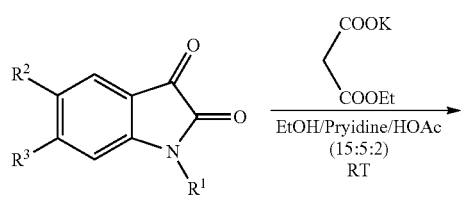

1a-1d

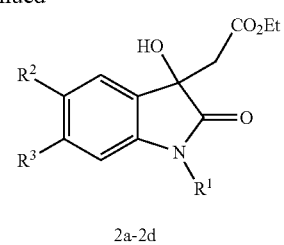

2a-2d

TABLE 1

| Product | Reaction time | Yield Melting point |
|---|---|---|
| 2a R1 = H, R2 = Br, R3 = H, (5-Bromo-3-hydroxy-2-oxo-2,3-dihydro-1H-indol-3-yl)acetic acid ethyl ester | 15 h | 80% 168-170° C. |
| 2b R1 = H, R2 = F, R3 = H, (5-Fluoro-3-hydroxy-2-oxo-2,3-dihydro-1H-indol-3-yl)acetic acid ethyl ester | 14 h | 89% 133-135° C. |
| 2c R1 = Me, R2 = H, R3 = H, (3-Hydroxy-1-methyl-2-oxo-2,3-dihydro-1H-indol-3-yl)acetic acid ethyl ester | 36 h | 73% 97-98° C. |
| 2d R1 = H, R2 = NO2, R3 = H, (3-Hydroxy-5-nitro-2-oxo-2,3-dihydro-1H-indol-3-yl)acetic acid ethyl ester | 26 h | 86% 194-197° C. |

The corresponding isatin 1a-1d (10 mmol) was dissolved in a mixture of ethanol/pyridine/acetic acid (50 ml, 15:5:2), ethyl potassium malonate (1.87 g, 11 mmol) was added and the mixture was heated under reflux in accordance with the times stated in the table. The course of the reaction was monitored by means of TLC (eluent: ethyl acetate/hexane 1:1). For working up, the solvent mixture was distilled off in vacuo. The residue was taken up in ethyl acetate (50 ml) and the mixture was extracted by shaking with water (50 ml). After separation of the phases, the aqueous phase was extracted twice with ethyl acetate (30 ml each time). The combined organic phases were washed with 2N HCl (50 ml), dried over $Na_2SO_4$ and concentrated to 20 ml in vacuo. Hexane was added to the solution until crystallization of the corresponding 3-hydroxy-2-oxo-2,3-dihydro-1H-indol-3-yl) acetic acid ethyl ester (2a-2d) started. To bring the crystallization to completion, the mixture was cooled to 10° C. for 12 h. The solid was filtered off with suction and dried in vacuo.

(1H-Indol-3-yl)ethanol

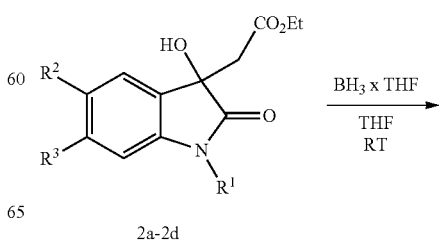

2a-2d

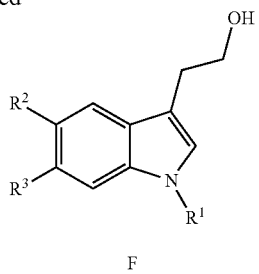

F

TABLE 2

|  | Product | Reaction time | Yield Melting point |
|---|---|---|---|
| 5-Bromotryptophol | R1 = H, R2 = Br, R3 = H, 2-(5-Bromo-1H-indol-3-yl)ethanol | 12 h | 75% 78-79° C. |
|  | R1 = H, R2 = F, R3 = H, 2-(5-Fluoro-1H-indol-3-yl)ethanol | 14 h | 95% 47-50° C. |
|  | R1 = Me, R2 = H, R3 = H, 2-(1-Methyl-1H-indol-3-yl)ethanol | 20 h | 98% oil |
| Ind-27 | R1 = H, R2 = NO2, R3 = H, 2-(5-Nitro-1H-indol-3-yl)ethanol | 24 h | 70%** 78-81° C. |

**Purification by column chromatography: silica gel; eluent: ethyl acetate/cyclohexane (1:4)

The aldol product 2a-2d (10 mmol) was dissolved in absolute THF (20 ml) under an Ar atmosphere. BH$_3$×THF (40 ml, 1 M solution, 40 mmol) was then added to the mixture, while cooling in a water bath, and the mixture was stirred at room temperature in accordance with the times stated in the table. The course of the reaction was monitored by means of TLC. When the reaction had ended, the reaction solution was added to a mixture of ethyl acetate (50 ml) and H2O (50 ml). After separation of the phases, the aqueous phase was extracted twice with ethyl acetate (30 ml each time). The combined organic phases were dried over Na$_2$SO$_4$ and concentrated in vacuo. The residue was filtered over silica gel with ethyl acetate. The product obtained after removal of the solvent was in the form of a sufficiently pure oil and as a rule crystallized spontaneously. If appropriate, purification by column chromatography on silica gel with the mobile phases stated in the table was carried out.

2-(5-Pyridin-4-yl-1H-indol-3-yl)ethanol (Ind-28)

5-Bromotryptophol (1.05 g, 4.39 mmol; see Table 1 and 2) and pyridine-4-boronic acid (10 mg, 6.59 mmol) were suspended in tetrahydrofuran (65 ml), and Na$_2$CO$_3$ solution (4.65 g, 43.9 mmol) in 44 ml of H$_2$O) were added. Bistriphenylphosphinepalladium dichloride (456.2 mg, 0.65 mmol) was then added. The reaction mixture, which was clear when hot, was boiled at 65° C. for 14 h, while stirring. The course of the reaction was monitored by TLC. For working up, the reaction solution was filtered. The filtrate comprised two phases. The organic phase was separated off. The solvent was distilled off on a rotary evaporator. The viscous residue was purified by flash chromatography [silica gel 60 (45 g); eluent: EtOAc (800 ml)].

Yield: 282 mg (27%), Ind-28, pale yellow solid; melting point: 169-171° C.

Indole Unit Ind-31

N-(3,5-Dichlorophenyl)-2-hydroxyiminoacetamide

A suspension of 3,5-difluoroaniline (10 g, 0.0617 mol) in water (40 ml) and 37 per cent strength hydrochloric acid (5.3 ml, 0.066 mol) was added to a solution of chloral hydrate (11 g, 0.066 mol) and sodium sulfate (70 g) in water (240 ml). A solution of hydroxylamine hydrochloride (13.5 g, 0.195 mmol) in water (60 ml) was added to this mixture. The reaction mixture was boiled under reflux for 1 h, during which a clear reaction solution formed, from which a reaction product already precipitated out when hot. The mixture was stirred at room temperature for 16 h and, after filtration and washing with water (3×50 ml), the desired oxime was obtained in a yield of 84% (12.1 g) with a melting point of 179° C. as a yellow solid.

4,6-Dichloro-1H-indole-2,3-dione

The N-(3,5-dichlorophenyl)-2-hydroxyiminoacetamide just prepared (12.1 g, 0.052 mol) was added to 96 per cent strength sulfuric acid (56 ml) at 50-75° C. in the course of 15 min. The reaction mixture was then heated at 90° C. for 15 min, while stirring. After cooling, the mixture was poured slowly on to ice (500 g). The solid formed was filtered off with suction after 30 min. The desired isatin was isolated in a yield of 81% (9.12 g) as an orange-coloured solid. It was not possible to determine a melting point.

(4,6-Dichloro-3-hydroxy-2-oxo-2,3-dihydro-1H-indol-3-yl)acetic acid ethyl ester

Malonic acid monoethyl ester potassium salt (3.9 g, 22.88 mmol) was added to a solution of 4,6-dichloro-1H-indole-2, 3-dione (4.5 g, 20.8 mmol) in a mixture of ethanol/pyridine/acetic acid [(15:5:2), 100 ml] and the mixture was boiled under reflux for 7 h. The reaction mixture was concentrated, the residue was taken up in ethyl acetate (50 ml) and the mixture was washed with water (50 ml). The aqueous phase was extracted with ethyl acetate (2×30 ml). The organic phases was combined and washed with 2N hydrochloric acid (50 ml), dried and concentrated. The desired hydroxy ester was obtained as a yellow oil in a yield of 82% (5.19 g).

2-(4,6-Dichloro-1H-indol-3-yl)ethanol (Ind-31)

A 1 M borane/THF solution (68 ml. 68 mmol) was added to a solution of the (4,6-dichloro-3-hydroxy-2-oxo-2,3-dihydro-1H-indol-3-yl)acetic acid ethyl ester just prepared (5.19 g, 17.0 mmol), in abs. tetrahydrofuran (50 ml), in an ice bath in the course of 20 min. The reaction mixture was stirred at room temperature for 48 h and, for working up, a mixture of ethyl acetate (100 ml) and water (100 ml) was added, while stirring. The phases were separated and the aqueous phase was extracted with ethyl acetate (2×50 ml). The organic phases were combined, dried and concentrated. The residue was taken up again in a mixture of water (50 ml) and ethyl acetate (50 ml). The organic phase was washed with water (3×50 ml), dried and concentrated. The crude indole unit Ind-31 was obtained as a yellow oil (3.74 g) by this procedure. Purification by chromatography [silica gel G (120 g); ethyl acetate/cyclohexane 1:2 (3.5 l)] gave 2-(4,6-dichloro-1H-indol-3-yl)ethanol as a beige-coloured oil in a yield of 69% (2.4 g).

Indole Unit Ind-36

5-Fluoro-3-(2-(pyrrolidin-1-yl)ethyl)-1H-indole (Ind-36)

Pyrrolidine (2.94 g, 3.4 ml, 41.3 mmol) was dissolved in abs dioxane (100 ml), 3-(2-bromo-ethyl)-5-fluoro-1H-indole (5.00 g, 20.7 mmol) was added at RT and the mixture was stirred at 70° C. for 8 h. The solution was concentrated, the residue was taken up in CHCl$_3$ (150 ml) and the mixture was washed with water (2×50 ml). The organic phase was dried over Na$_2$SO$_4$, filtered and concentrated i. vac. The residue obtained was purified by flash chromatography with 500 g of silica gel and chloroform/methanol (20:1→9:1→4:1→methanol. Only with methanol was a salt of the compound obtained, and it was then possible to liberate this by stirring with 2N NaOH and CHCl$_3$. The phases were separated, the aqueous phase was extracted twice with CHCl$_3$ and the combined organic phases were dried over Na$_2$SO$_4$, filtered and concentrated i. vac. The chloroform used was probably contaminated with HCl.

Yield: 3.27 g (Ind-36, 68%), colourless solid $^1$H-NMR (DMSO-d$_6$): 1.72 (4H, m); 2.62 (4H, m); 2.83 (4H, m); 6.89 (1H, m); 7.25 (3H, m); 10.93 (1H, s).

$^{13}$C-NMR (DMSO-d$_6$): 23.05; 23.90; 53.39; 56.07; 102.77; 108.72; 112.25; 124.68; 127.29; 132.84; 155.46; 157.75.

Indole Unit Ind-38

3-(2-(1H-Pyrazol-1-yl)ethyl)-5-fluoro-1H-indole (Ind-38)

A solution of 3-(2-bromo-ethyl)-5-fluoro-1H-indole (7.26 g, 30 mmol), pyrazole (2.04 g, 30 mmol) and ethyl-diisopropylamine (5.1 ml, 30 mmol) in abs. chloroform (80 ml) was stirred at 90° C. for 12 h. The reaction solution was then washed twice with water, dried over Na$_2$SO$_4$ and concentrated i. vac. and the residue which remained was purified by flash chromatography with CHCl$_3$/MeOH (20:1).

Yield: 1.91 g (Ind-38, 28%)

$^1$H-NMR (DMSO-d$_6$): 3.16 (2H, t); 4.35 (2H, t); 6.17 (1H, s); 6.86 (1H, m); 7.24 (3H, d); 7.44 (1H, s); 7.64 (1H, s); 10.93 (1H, s).

Indole Unit Ind-39

3-(2-(1H-Imidazol-1-yl)ethyl)-5-fluoro-1H-indole (Ind-39)

A solution of 3-(2-bromo-ethyl)-5-fluoro-1H-indole (4.84 g, 20 mmol), imidazole (1.36 g, 20 mmol) and ethyl-diisopropylamine (3.4 ml, 20 mmol) in abs. dioxane (50 ml) was stirred at 90° C. for 8 h until according to TLC educt was no longer present. The solvent was then removed i. vac., CHCl$_3$ (100 ml) was added to the residue and the organic phase was washed twice with water. The organic phase was dried over Na$_2$SO$_4$ and concentrated i. vac. and the residue which remained was purified by flash chromatography with CHCl$_3$/MeOH (9:1).

Yield: 1.29 g (Ind-39; 28%)

$^1$H-NMR (DMSO-d$_6$): 3.10 (2H, t); 4.20 (2H, t); 6.90 (2H, m); 7.12 (1H, s); 7.20 (1H, s); 7.33 (2H, m); 7.55 (1H, s); 10.9 (1H, s).

Indole Unit Ind-40

1-(2-(5-Fluoro-1H-indol-3-yl)ethyl)-1H-benzo[d]imidazole (Ind-40)

A solution of 3-(2-bromo-ethyl)-5-fluoro-1H-indole (7.26 g, 30 mmol), benz-imidazole (3.54 g, 30 mmol) and ethyl-diisopropylamine (5.1 ml, 30 mmol) in abs. chloroform (80 ml) was boiled under reflux for 20 h. The reaction solution was then washed twice with water, dried over Na$_2$SO$_4$ and concentrated i. vac. and the residue which remained was purified by flash chromatography with CHCl$_3$/MeOH (50:1).

An insoluble solid separated out in the water, and was filtered off with suction and likewise purified over a silica gel column. This was likewise the desired product. Yield: 2.95 g (35%)

$^1$H-NMR (DMSO-d$_6$): 3.21 (2H, t); 4.51 (2H, t); 6.90 (1H, m); 7.21 (5H, m); 7.62 (1H, d); 8.09 (1H, s); 10.95 (1H, s).

Indole Unit Ind-43

3-Methyl-5-trifluoromethoxy-2-trimethylsilanyl-1H-indole

2-Iodo-4-trifluoromethoxyaniline (1, 2.42 g, 8 mmol), trimethylsilylpropyne (2, 988 mg, 1.31 ml. 8.8 mmol), lithium chloride (356 mg, 8.4 mmol) and sodium carbonate (2.54 g, 24 mmol) were combined in abs. dimethylformamide (20 ml) in an argon atmosphere. The catalyst ([Pd(dppf)Cl2× CH$_2$Cl$_{12}$], 654 mg, 0.8 mmol) was then added. The reaction mixture was stirred at 100° C. (oil bath temperature) for 6 h and at room temperature for 18 h. The reaction mixture was then cooled with ice water, water (100 ml) and ethyl acetate (200 ml) was added and the mixture was stirred for 30 min. In order to separate off the catalyst, the dark brown mixture was filtered over Celite. The phases of the filtrate were separated. The aqueous phase was extracted with ethyl acetate (5×35 ml). The combined organic phases were washed with saturated sodium chloride solution (3×35 ml), subsequently dried with sodium sulfate, filtered and concentrated in vacuo. The dark brown oil (2.95 g) obtained which, apart from 3-methyl-5-trifluoromethoxy-2-trimethylsilanyl-1H-indole, also contained the isomeric 2-methyl-5-(trifluoromethoxy)-3-(trimethylsilyl)-1H-indole, was employed as the crude product for the next stage.

3-Methyl-5-trifluoromethoxy-1H-indole (Ind-43)

Splitting off of the trimethylsilyl group was carried out in two stages. The crude product of the silyl compounds (3-methyl-5-trifluoromethoxy-2-trimethylsilanyl-1H-indole and 2-methyl-5-(trifluoromethoxy)-3-(trimethylsilyl)-1H-indole) (2.95 g, 8 mmol, based on the precursor) was stirred with THF (40 ml) and tetrabutylammonium fluoride (3.28 g, 11 mmol) at RT for 4 h. The mixture was then worked up. After addition of water (40 ml), the mixture was stirred for 15 min. The phases were then separated. The aqueous phase was extracted with diethyl ether (3×60 ml). The combined organic phases were dried with sodium sulfate, filtered and concentrated in vacuo. A viscous dark brown oil was obtained, which was separated into its constituents by chromatography [silica gel 60 (100 g); cyclohexane/ethyl acetate (15:1; 1,000 ml; 10:1; 400 ml)]. 1.44 g (5 mmol, 63%, based on the precursor) of pure 3-methyl-5-trifluoromethoxy-2-trimethylsilanyl-1H-indole were obtained. THF (30 ml) and tetrabutylammonium fluoride (2.05 g, 6.5 mmol) were added to this again and the mixture was heated under reflux for 2 h. After the working up described above, 1.018 g (59%, based on the 1st stage) of 3-methyl-5-trifluoromethoxy-1H-indole (Ind-43) were obtained as a brown oil.

Indole Unit Ind-47: Methyl 2-(1H-indol-3-yl)acetate (Ind-47)

CAS no. 1912-33-0, commercially obtainable e.g. from Fluka

Indole Unit Ind-49

3-Hydroxy-3-pyridin-2-ylmethyl-1,3-dihydroindol-2-one A mixture of isatin (12.0 g, 82 mmol) and 2-picoline (25.1 g, 24 ml, 0.27 mol) was heated under reflux for 5 h. The reaction mixture was then concentrated i. vac. and toluene was repeatedly added to the residue and the mixture was in each case concentrated again i. vac. 2-Picoline still present was distilled off by bulb tube distillation at 60° C. Chloroform (100 ml) and 1 M hydrochloric acid (80 ml) were added to the residue, the aqueous phase was separated off, 1 M hydrochloric acid (40 ml) was again added to the chloroform phase and this phase was extracted. The combined acidic aqueous phases were adjusted to pH 10 with 25% ammonia solution and the product which had precipitated out was filtered off, washed with water and dried at 100° C.

Yield: 21.0 g (100%), yellow solid; melting point: 165-170° C.

1H-NMR (DMSO-d6): 3.17 (d, 1H, J=13.0 Hz); 3.30 (d, 1H, J=13.1 Hz); 6.29 (s, 1H); 6.64 (d, 1H, J=7.6 Hz); 6.82 (t, 1H, J=7.3 Hz); 6.91 (d, 1H, J=6.9 Hz); 7.04-7.17 (m, 3H); 7.57 (dt, 1H, J=6.9 and 1.4 Hz); 8.29 (d, 1H, J=4.3 Hz); 10.13 (s, 1H).

3-Pyridin-2-ylmethyl-1H-indole (Ind-49) A 2 M solution of borane-dimethyl sulfide complex (20 ml, 40 mmol) was added to a solution of 3-hydroxy-3-pyridin-2-ylmethyl-1,3-dihydroindol-2-one (4.80 g, 20 mmol) in anhydrous tetrahydrofuran (250 ml) and the mixture was stirred at room temperature overnight. Methanol (10 ml) was cautiously added to the reaction mixture and the mixture was concentrated i. vac. Methanol was repeatedly added to the residue, the mixture was in each case concentrated again i. vac., and the residue was taken up in 1N hydrochloric acid. The aqueous suspension was extracted with ethyl acetate (2×40 ml). The aqueous phase was adjusted to pH 10 with saturated potassium carbonate solution and extracted with ethyl acetate (3×30 ml). The combined organic phases were dried with sodium sulfate and concentrated i. vac. The crude product (4.0 g) was purified by flash chromatography (400 g, 20×7.6 cm) first with ethyl acetate/cyclohexane (2:1) and then chloroform.

Yield (Ind-49): 2.00 g (48%), reddish solid; melting point: 80-82° C.

1H-NMR (DMSO-d6): 4.18 (s, 2H); 6.92 (ddd, 1H, J=8.0, 7.0 and 1.1 Hz); 7.05 (ddd, 1H, J=8.2, 7.1 and 1.2 Hz); 7.15 (m, 1H); 7.18-7.24 (m, 2H); 7.34 (dt, 1H, J=8.1 and 0.9 Hz); 7.45 (br d, 1H, J=7.8 Hz); 7.64 (dt, 1H, J=7.7 and 1.9 Hz); 8.47 (ddd, 1H, J=4.9, 1.8 and 0.9 Hz); 10.86 (s, 1H).

Indole Unit Ind-50: 3-(1H-Indol-3-yl)propionic acid (Ind-50)

CAS no: 830-96-6, commercially obtainable e.g. from Fluka

Indole Unit Ind-54

2-(2-(1H-Indol-3-yl)ethyl)-1-methyl-1H-benzo[d]imidazole (Ind-54)

A mixture of 3-indolepropionic acid (2.85 g, 15 mmol) and N-methyl-1,2-phenylenediamine (611 mg, 5.0 mmol) was stirred at 130° C. for 5H, during which a dark brown viscous mass forms, which was dissolved in chloroform (100 ml). The organic solution was then washed with 10% strength $Na_2CO_3$ solution (2×30 ml) and water, dried over $Na_2SO_4$ and concentrated i. vac. and the residue was purified by flash chromatography with cyclohexane/EA (1:1). Yield: 863 mg (Ind-54, 63%), colourless solid 1H-NMR (DMSO-$d_6$): 3.22 (4H, t); 3.65 (3H, s); 6.95-7.56 (5H, m); 7.35 (1H, d); 7.45 (1H, d); 7.59 (2H, m); 10.81 (1H, s).

Indole unit Ind-55: 2-(2-(1H-Indol-3-yl)ethyl)-1-methyl-H-benzo[d]imidazole (Ind-61)

CAS no: 16571-51-0, commercially obtainable e.g. from Sigma-Aldrich

Indole unit Ind-56: 4-(1H-Indol-3-yl)butanoic acid (Ind-56)

CAS no: 133-32-4, commercially obtainable e.g. from ACROS

Indole Unit Ind-57

4-(1H-Indol-3-yl)-butan-1-ol (Ind-57)

LiAlH$_4$ (1.14 g, 30 mmol) was initially introduced into dry THF (100 ml) with exclusion of oxygen. 4-(1H-Indol-3-yl) butanoic acid (2.03 g, 10 mmol, dissolved in 80 ml of dry THF) was added dropwise to the suspension in the course of 30 min. Thereafter, the mixture was heated under reflux at the boiling point for 3 h. The reaction mixture was stirred at room temperature overnight. Water (30 ml) was then cautiously added to the mixture. The mixture was stirred for 20 min and 2N NaOH (10 ml) was added. The organic phase was separated off and the aqueous solution which remained was extracted with diethyl ether (3×40 ml). The ethereal solution was dried over $Na_2SO_4$ and concentrated to dryness on a rotary evaporator. Ind-57 was obtained in this way in a yield of 1.8 g (95%) as a colourless oil.

Indole Unit Ind-61

1-(2-(1H-Indol-3-yl)ethyl)pyrrolidine-2,5-dione (Ind-61)

Succinic anhydride (2.27 g, 22.7 mmol) was added in portions to a hot solution of tryptamine (3.30 g, 20.6 mmol) and potassium acetate (2.23 g, 22.7 mmol) in acetic acid (10 ml). The reaction solution was heated at the boiling point for 3 h and subsequently stirred at RT overnight and the precipitate which had precipitated out was filtered off and washed with acetic acid and EtOH. Yield: 3.00 g (Ind-61, 60%)

1H-NMR (DMSO-$d_6$): 2.61 (4H, s); 2.88 (2H, t); 3.61 (2H, t); 7.01 (2H, m); 7.20 (1H, s); 7.36 (1H, d); 7.53 (1H, t); 10.86 (1H, bs).

13C-NMR (DMSO-$d_6$): 23.06; 27.98; 38.60; 110.60; 111.41: 117.86; 118.33; 120.95; 122.83; 127.01; 136.19; 177.54.

Indole Unit Ind-62

1-(2-(1H-Indol-3-yl)ethyl)-1,2,3,4-tetrahydroquinoline (Ind-62)

1,2,3,4-Tetrahydroquinoline (5.94 g, 5.6 ml, 44.6 mmol) was added to a solution of 3-(2-bromoethyl)-indole (5.00 g, 22.3 mmol) in dry chloroform (25 ml) at room temperature and the mixture was then stirred under reflux for 5 h. The reaction mixture cooled overnight. The organic phase was extracted with dil. sulfuric acid (2×50 ml). The aqueous phase was rendered basic with 5N NaOH, while cooling with ice, and extracted with ether (3×50 ml). The organic phase was dried over $Na_2SO_4$ and concentrated i. vac. Yield: 5.35 g (Ind-62, 88%)

$^1$H-NMR (DMSO-$d_6$): 1.83 (2H, m); 2.67 (2H, m); 2.92 (2H, m); 3.50 (2H; m); 6.47 (1H, m); 6.66 (1H, m); 6.87 (1H, m); 7.08 (3H, m); 7.20 (1H, m); 7.36 (1H, m); 7.55 (1H, m); 10.82 (1H, s).

Indole Unit Ind-63

Methyl 1-(2-(1H-indol-3-yl)ethyl)-1H-1,2,3-triazole-4-carboxylate (Ind-63)

The resin (4-(bromomethyl)-phenoxyethyl-polystyrene HL) (5.00 g, 5.5 mmol) was suspended in N,N-dimethylacetamide (DMA) (30 ml), sodium azide (178 g, 27.5 mmol, 5 eq.) was added and the mixture was stirred at RT for 48 h. The resin was filtered off, washed with methanol and dried. The resin was suspended in DMA (100 ml) again, 3-(2-bromoethyl)indole (0.60 g, 2.67 mmol) was added and the mixture was stirred at RT for 5 d. Propiolic acid methyl ester (0.24 ml, 2.67 mmol) was then added, the mixture was stirred at 80° C. for 20 h and the solvent was removed i. vac. The residue was separated by flash chromatography with $CHCl_3$/MeOH (9:1). In addition to the desired product, 3-(2-bromoethyl)indole (103 mg, 17%) was recovered. Yield: 342 mg (Ind-63, 47%)

$^1$H-NMR (DMSO-$d_6$): 3.36 (2H, m); 3.80 (3H; m); 4.73 (2H, m); 7.03 (3H, m); 7.33 (1H, d); 7.53 (1H, d); 8.73 (1H, s); 10.85 (1H, s).

$^{13}$C-NMR (DMSO-$d_6$): 25.65; 50.29; 51.63; 109.60; 111.39; 118.09; 121.05; 123.18; 126.80; 129.00; 136.11; 137.34; 138.30; 160.73.

Indole Unit Ind-64

3-(2-(Isoindolin-2-yl)ethyl)-1H-indole (Ind-64)

A solution of 3-(2-bromo-ethyl)-1H-indole (4.48 g, 20 mmol) and isoindole (4.76 g, 40 mmol) in abs. dioxane (50 ml) was stirred at 80° C. for 6 h. The solvent was then removed i. vac., $CHCl_3$ (100 ml) was added to the residue and the mixture was washed twice with water. The organic phase was dried over $Na_2SO_4$ and concentrated i. vac. and the residue which remained was purified by flash chromatography with $CHCl_3$/MeOH (20:1).

Yield: 3.01 g (Ind-64, 57%), brown solid $^1$H-NMR (DMSO-$d_6$): 2.95 (4H, m); 3.93 (4H, m); 7.18 (2H, m); 7.20 (5H, m); 7.35 (1H, d); 7.57 (1H, d); 10.79 (1H, s).

Indole Unit Ind-65

2-(2-(1H-Indol-3-yl)ethyl)-1,2,3,4-tetrahydroisoquinoline (Ind-65)

A solution of 3-(2-bromo-ethyl)-1H-indole (4.48 g, 20 mmol) and isoquinoline (5.33 g, 40 mmol) in abs. dioxane (50 ml) was stirred at 80° C. for 6 h. The solvent was then removed i. vac., $CHCl_3$ (100 ml) was added to the residue and the mixture was washed twice with water. The organic phase was dried over $Na_2SO_4$ and concentrated i. vac. and the residue which remained was purified by flash chromatography with $CHCl_3$/MeOH (50:1). Yield: 4.78 g (Ind-65, 86%), white solid $^1$H-NMR (DMSO-$d_6$): 2.76 (6H, m); 2.95 (2H, m); 3.66 (2H, s); 7.06 (6H, m); 7.18 (1H, s); 7.34 (1H, d); 7.56 (1H, d); 10.77 (1H, s).

Indole Unit Ind-66

3-(2-(Pyrrolidin-1-yl)ethyl)-1H-indole (Ind-66)

Pyrrolidine (3.17 g, 3.7 ml, 44.6 mmol) was dissolved in abs. dioxane (100 ml), 3-(2-bromo-ethyl)-1H-indole (5 g, 22.3 mmol) was added at RT and the mixture was stirred at 70° C. for 8 h. The solution was concentrated, the residue was taken up in $CHCl_3$ (150 ml) and the mixture was washed with water (2×50 ml). The organic phase was dried over $Na_2SO_4$, filtered and concentrated i. vac.

Yield: 3.00 g (Ind-66, 63%)

$^1$H-NMR (DMSO-$d_6$): 1.73 (4H, m); 2.54 (4H, m); 2.74 (2H, t); 2.61 (2H, t); 6.99 (2H, m); 7.15 (1H, s); 7.35 (1H, d); 7.52 (1H, d); 10.79 (1H, s).

Indole Unit Ind-68

3-(2-(4-Methylpiperazin-1-yl)ethyl)-1H-indole (Ind-68)

3-(2-Bromo-ethyl)-indole (3.00 g, 13.39 mmol) was initially introduced into abs. $CHCl_3$ (25 ml), and 1-methylpiperazine (2.68 g, 26.8 mmol) was added. The mixture was stirred at a bath temperature of 75° C. for 5 h and at RT overnight. The mixture was extracted dilute sulfuric acid (2×30 ml), the acidic aqueous phase was rendered alkaline with 5N NaOH, while cooling with ice, and the mixture was extracted with ether (3×30 ml). The organic phase was dried over $Na_2SO_4$ and concentrated i. vac. Yield: 1.45 g (Ind-68, 45%)

$^1$H-NMR (DMSO-$d_6$): 2.18 (3H, s); 2.38 (4H, m); 2.58 (4H, m); 2.83 (2H, t); 3.43 (2H, t); 6.98 (2H, m); 7.13 (1H, s); 7.34 (1H, m); 7.49 (1H, m); 10.77 (1H, s).

Indole Unit Ind-69

4-(2-(1H-Indol-3-yl)ethyl)morpholine (Ind-69)

Morpholine (2.33 g, 2.33 ml, 26.8 mmol) was dissolved in abs. dioxane (50 ml), and 3-(2-bromo-ethyl)-1H-indole (3.00 g, 13.4 mmol) was added at RT. The solution was stirred at 70° C. for 14 h and concentrated i. vac., the residue was taken up in $CHCl_3$ (100 ml) and the mixture was washed with water (2×30 ml). The organic phase was dried over $Na_2SO_4$, filtered and concentrated i. vac. The residue obtained was recrystallized from aqueous methanol.

Yield: 1.09 g (35%)

$^1$H-NMR (DMSO-$d_6$): 2.45 (4H, m); 2.58 (2H, t); 2.83 (2H, t); 3.59 (4H, m); 7.04 (2H, m); 7.15 (1H, s); 7.32 (1H, d); 7.50 (1H, d); 10.77 (1H, s).

Indole Unit Ind-70

1-(2-(1H-Indol-3-yl)ethyl)-1H-benzo[d]imidazole (Ind-70)

A solution of 3-(2-bromo-ethyl)-1H-indole (4.48 g, 20 mmol) and benzimidazole (4.72 g, 40 mmol) in abs. dioxane (50 ml) was stirred at 90° C. for 13 h. The solvent was then removed i. vac., CHCl₃ (200 ml) was added to the residue and the mixture was washed twice with water. The organic phase was dried over Na₂SO₄ and concentrated i. vac. and the residue which remained was purified by flash chromatography with CHCl₃/MeOH (40:1). Yield: 1.32 g (25%), pale brown solid ¹H-NMR (DMSO-d₆): 3.24 (2H, t); 4.53 (2H, t); 7.10 (3H, m); 7.27 (3H, m); 7.62 (3H, m); 8.09 (1H, s); 10.85 (1H, s).

Indole Unit Ind-71

3-(2-(1H-Imidazol-1-yl)ethyl)-1H-indole (Ind-71)

A solution of 3-(2-bromo-ethyl)-1H-indole (1.12 g, 5 mmol) and imidazole (0.68 g, 10 mmol) in abs. dioxane (10 ml) was stirred at 80° C. for 4 h until according to TLC educt was no longer present. The solvent was then removed i. vac., CHCl₃ (100 ml) was added to the residue and the mixture was washed twice with water. The organic phase was dried over Na₂SO₄ and concentrated i. vac. and the residue which remained was purified by flash chromatography with CHCl₃/MeOH (20:1). Yield: 507 mg (Ind-71, 48%), colourless solid ¹H-NMR (DMSO-d₆): 3.16 (2H, t); 4.23 (2H, t); 6.86 (1H, s); 7.05 (3H, m); 7.19 (1H, s); 7.32 (1H, m); 7.55 (2H, m); 10.86 (1H, s).

Indole Unit Ind-72

3-(2-(1H-1,2,4-Triazol-1-yl)ethyl)-1H-indole (Ind-72)

A solution of 3-(2-bromo-ethyl)-1H-indole (4.92 g, 22 mmol) and 1,2,4-triazole (3.03 g, 44 mmol) in abs. dioxane (50 ml) was stirred at 80° C. for 24 h. The solvent was then removed i. vac., CHCl₃ (100 ml) was added to the residue and the mixture was washed twice with water. The organic phase was dried over Na₂SO₄ and concentrated i. vac. and the residue which remained was purified by flash chromatography with CHCl₃/MeOH (50:1). Yield: 0.792 g (Ind-72, 17%), colourless oil ¹H-NMR (DMSO-d₆): 3.20 (2H, t); 4.44 (2H, t); 7.05 (3H, m); 7.35 (1H, d); 7.49 (1H, s); 7.96 (1H, s); 8.37 (1H, s); 10.83 (1H, s).

Indole Unit Ind-73

3-(2-(1H-Indol-3-yl)ethyl)thiazolidine (Ind-73)

3-(2-Bromo-ethyl)-indole (3.00 g, 13.4 mmol) and thiazolidine (2.38 g, 26.8 mmol) were stirred in abs. CHCl₃ (25 ml) at a bath temperature of 75° C. for 5 h. The mixture was cooled to RT and extracted with dilute sulfuric acid (2×30 ml). The acidic aqueous phase was rendered alkaline with 5N NaOH, while cooling with ice, and extracted with ether (3×30 ml). The organic phase was dried over Na₂SO₄ and concentrated i. vac. and the residue was purified by flash chromatography with CHCl₃/MeOH (20:1→4:1→MeOH).

Yield: 564 mg (Ind-73, 18%)

¹H-NMR (DMSO-d₆): 2.68-3.05 (10H, m); 6.97 (2H, m); 7.18 (1H, m); 7.32 (1H, m); 7.57 (1H, m); 10.84 (1H, s).

Indole Unit Ind-74

3-(2-(5-Methyl-2H-tetrazol-2-yl)ethyl)-1H-indole (Ind-74)

A solution of 3-(2-bromo-ethyl)-1H-indole (2.24 g, 10 mmol), 5-methyl-1,2,3,4-tetrazole (0.84 g, 10 mmol) and ethyl-diisopropylamine (1.7 ml, 10 mmol) in abs. dioxane (25 ml) was stirred at 90° C. for 8 h until according to TLC educt was no longer present. The solvent was then removed i. vac., CHCl₃ (100 ml) was added to the residue and the organic phase was washed twice with water. The organic phase was dried over Na₂SO₄ and concentrated i. vac. and the residue which remained was purified by flash chromatography with EA/cyclohexane (1:4→1:1→MeOH).

Yield: 843 mg (37%), 3-[2-(5-methyl-tetrazol-2-yl)-ethyl]-1H-indole (Ind-74) 936 mg (41%), 3-[2-(5-methyl-tetrazol-1-yl)-ethyl]-1H-indole (Ind-77)

Ind-74

¹H-NMR (DMSO-d₆): 2.44 (3H, s); 3.36 (2H, t); 4.87 (2H, t); 7.05 (3H, m); 7.35 (1H, m); 7.49 (1H, m); 10.85 (1H, s).

Ind-77

¹H-NMR (DMSO-d₆): 2.16 (3H, s); 3.25 (2H, t); 4.58 (2H, t); 7.07 (3H, m); 7.36 (1H, m); 7.43 (1H, m); 10.87 (1H, s).

Indole Unit Ind-75

3-(2-(1H-Pyrazol-1-yl)ethyl)-1H-indole (Ind-75)

A solution of 3-(2-bromo-ethyl)-1H-indole (2.24 g, 10 mmol) and pyrazole (1.36 g, 20 mmol) in abs. dioxane (20 ml) was stirred at 80° C. for 16 h. The solvent was then removed i. vac., CHCl₃ (100 ml) was added to the residue and the mixture was washed twice with water. The organic phase was dried over Na₂SO₄ and concentrated i. vac. and the residue which remained was purified by flash chromatography with CHCl₃/MeOH (50:1).

Yield: 0.62 g (Ind-75, 29%), brown oil

¹H-NMR (DMSO-d₆): 3.20 (2H, t); 4.37 (2H, t); 6.18 (1H, s); 7.04 (3H, m); 7.32 (1H, d); 7.44 (1H, s); 7.52 (1H, d); 7.66 (1H, s); 10.80 (1H, s).

Indole Unit Ind-76

3-(2-(1H-1,20.3-Triazol-1-yl)ethyl)-1H-indole (Ind-76)

A solution of 3-(2-bromo-ethyl)-1H-indole (4.92 g, 22 mmol) and 1,2,3-triazole (3.03 g, 44 mmol) in abs. dioxane (50 ml) was stirred at 80° C. for 22 h. The solvent was then removed i. vac., CHCl₃ (100 ml) was added to the residue and the mixture was washed twice with water. The organic phase was dried over Na₂SO₄ and concentrated i. vac. and the residue which remained was purified by flash chromatography with CHCl₃/MeOH (50:1). Yield: 0.50 g (Ind-76, 11%), brown oil ¹H-NMR (DMSO-d₆): 3.31 (2H, t); 4.67 (2H, t); 6.97 (1H, m); 7.08 (2H, m); 7.34 (1H, d); 7.51 (1H, d); 7.65 (1H, s); 8.01 (1H, s); 10.72 (1H, s).

Indole Unit Ind-77

3-(2-(5-Methyl-1H-tetrazol-1-yl)ethyl)-1H-indole (Ind-77)

The synthesis of the indole Ind-77 has been described in the context of the synthesis of indole unit 74.

Indole Unit Ind-83

N-(3,4-Dichlorophenyl)-2-hydroxyiminoacetamide

A suspension of 3.4-difluoroaniline (10 g, 0.0617 mol) in water (40 ml) and 37 per cent hydrochloric acid (5.3 ml, 0.064 mol) was added to a solution of chloral hydrate (11 g, 0.066 mol) and sodium sulfate (70 g) in water (240 ml). A solution of hydroxylamine hydrochloride (13.5 g, 0.195 mmol) in water (60 ml) was added to this mixture. The reaction mixture was boiled under reflux for 1 h, during which a clear reaction solution formed, from which are reaction product already precipitated out when hot. The mixture was stirred at room temperature for 16 h and, after filtration and washing with water (3×50 ml), the desired oxime was obtained in a yield of 91% (13.1 g) with a melting point of 179° C. as a yellow solid.

5,6-Dichloro-1H-indole-2,3-dione and 4,5-dichloro-1H-indole-2,3-dione

The oxime just prepared (13 g, 0.055 mol) was added to 96 per cent strength sulfuric acid (60 ml) at 50-60° C. in the course of 15 min. The reaction mixture was then heated at 80° C. for 15 min, while stirring. After cooling, the mixture was poured slowly on to ice (500 g). The solid formed was filtered off with suction after 30 min. A mixture of the of 5,6-dichloro-1H-indole-2,3-dione and 4,5-dichloro-1H-indole-2, 3-dione was obtained (10.6 g, 90%). The two isatins were present in a ratio of 1:4. By separation of the isomer mixture by chromatography [silica gel G (500 g); ethyl acetate/cyclohexane 1:2 (4.8 l), 1:1(2.0 l), ethyl acetate (1.8 l)], 5,6-dichloro-1H-indole-2,3-dione was obtained in a yield of 14% (1.7 g) and 4,5-dichloro-1H-indole-2,3-dione in a yield of 22% (2.55 g, m.p. 252-253° C.). Both compounds were orange-coloured solids.

(5,6-Dichloro-3-hydroxy-2-oxo-2,3-dihydro-1H-indol-3-yl)acetic acid ethyl ester Malonic acid monoethyl ester potassium salt (1.49 g, 8.74 mmol) was added to a solution of 5,6-dichloro-1H-indole-2, 3-dione (1.7 g, 7.9 mmol) in a mixture of ethanol/pyridine/acetic acid [(15:5:2), 39.5 ml] and the mixture was boiled under reflux for 23 h. The reaction mixture was concentrated and the residue was co-distilled with toluene (3×10 ml). A solid red residue was obtained, which was stirred in a mixture of water (30 ml) and ethyl acetate (30 ml) for 20 min. The aqueous phase was extracted with ethyl acetate (2×20 ml). The organic phases was combined and washed with 2N hydrochloric acid, dried and concentrated. The desired hydroxy ester was obtained by this procedure as a red solid in a yield of 89% (2.13 g) with a melting point of 204-208° C.

2-(5,6-Dichloro-1H-indol-3-yl)ethanol (Ind-83)

A 1 M borane/THF solution (28.0 ml. 28.0 mmol) was added to a solution of the (5,6-dichloro-3-hydroxy-2-oxo-2, 3-dihydro-1H-indol-3-yl)acetic acid ethyl ester just prepared (2.13 g, 7.0 mmol), in abs. tetrahydrofuran (15 ml), in an ice bath in the course of 15 min. The reaction mixture was stirred at room temperature for 57 h and, for working up, was added to a mixture of ethyl acetate (50 ml) and water (50 ml), while stirring. The phases were separated and the aqueous phase was extracted with ethyl acetate (2×30 ml). The organic phases were combined, dried and concentrated. The crude indole was obtained as a yellow oil (1.9 g) by this procedure. Purification by chromatography [silica gel G (80 g); ethyl acetate/cyclohexane 1:2 (2 l)] gave the desired 2-(5,6-dichloro-1H-indol-3-yl)ethanol (Ind-83) as a beige-coloured solid in a yield of 60% (0.96 g) (m.p. 65-67° C.).

Indole Unit Ind-85: 1H-Indole (Ind-85)

Indole, CAS no.: 120-72-9, commercially obtainable e.g. from Sigma-Aldrich

Indole Unit Ind-86: 1H-Pyrrolo[2,3-b]pyridine (Ind-86)

7-Azaindole, CAS no.: 271-63-6, commercially obtainable e.g. from Sigma-Aldrich

Indole Unit Ind-89

2-(Benzo[b]thiophen-2-yl)ethanol (Ind-89)

A 2.5 M solution of n-buthyllithium in hexane (18 ml, 45 mmol) was added to a solution of benzothiophene (5 g, 37.2 mmol) in diethyl ether (40 ml) under argon at −70° C. in the course of 10 min. After 30 min the reaction mixture was warmed slowly to −15° C. (30 min). A solution of ethylene oxide (4.88 g, 112 mmol) in diethyl ether (20 ml) was added to this mixture at −10° C. in the course of 20 min. The ethylene oxide solution was prepared by condensation of gaseous ethylene oxide at −40° C. and taking up in diethyl ether. The reaction mixture was warmed slowly to room temperature and stirred for 16 h. Working up of the mixture was carried out by addition of saturated $NH_4Cl$ solution (30 ml), under argon and while cooling with ice. The slightly cloudy solution was filtered and water (10 ml) and diethyl ether (10 ml) were then added. The phases were separated. The aqueous phase was extracted with diethyl ether (2×30 ml). The organic phases were combined and washed with 2N HCl (30 ml) and saturated NaCl solution (30 ml). The organic phase was concentrated, after drying, the crude product of the alcohol being obtained as a yellow solid. After purification by chromatography on silica gel (160 g) with ethyl acetate/cyclohexane (1:5), the alcohol was obtained as a white solid with a melting point of 82-84° C. in a yield of 59%.

Indole Unit Ind-90: 1-Phenylsulfonyl-1H-indole (Ind-90)

Commercially obtainable CAS: 40899-71-6; e.g. Sigma-Aldrich.

Indole Unit Ind-92: Benzofuran (Ind-92)

Commercially obtainable CAS: 271-89-6 e.g. from Sigma-Aldrich.

Indole Unit Ind-94

Benzofuran-3-ylacetic acid methyl ester

KOtBu (0.673 g, 6 mmol) was dissolved in dry DMF (10 ml) with exclusion of oxygen. Phosphonoacetic acid triethyl ester (0.87 ml, 6 mmol) was then added to the mixture. After 20 min a solution of benzofuran-3(2H)-one (0.536 g, 4 mmol) in dry DMF (10 ml, argon atmosphere) was added to this mixture. The reaction mixture was stirred at room temperature for 1 h and thereafter poured on to ice (50 ml) for working up. The mixture obtained was extracted with diethyl ether (4×20 ml). The organic phase was washed with water (4×20 ml), dried with Na₂SO₄ and then concentrated. The product formed was purified by column chromatography [silica gel 60 (50 g); cyclohexane, ethyl acetate (4:1)] and obtained in a yield of 0.372 g (48%) as a yellowish oil.

2-(Benzofuran-3-yl)ethanol

LiAlH₄ (1.025 g, 37.95 mmol) was suspended in diethyl ether with exclusion of oxygen. A solution of the benzofuran-3-ylacetic acid methyl ester just prepared (2.546 g, 13.4 mmol) in diethyl ether (15 ml) was then slowly added to the mixture and the mixture was stirred at room temperature for 30 min. The course of the reaction was monitored by TLC. For complete hydrolysis of the excess hydride, a mixture of water (2 ml) and diethyl ether (5 ml) was cautiously added dropwise to the mixture. The ethereal solution obtained was filtered over kieselguhr and the filter cake was rinsed with diethyl ether. After removal of the solvent, the desired alcohol was obtained in a yield of 1.93 g (89%) as a pale yellow oil and was employed for the further synthesis without further purification.

3-(2-Bromoethyl)benzofuran

Triphenylphosphane dibromide (5.52 g, 14.41 mmol) was suspended in abs. acetonitrile (15 ml) under argon, the suspension was brought to 19° C. in a water batch and 2-(benzofuran-3-yl)ethanol (2.11 g, 13.1 mmol), dissolved in abs. acetonitrile (7 ml) was added in the course of 15 min. During the addition the temperature of the reaction mixture was kept between 19 and 21° C. The mixture was then left to stand for 12 h without further cooling. The triphenylphosphane which had precipitated out during this period of time was removed from the reaction mixture by filtration. The filtrate obtained was concentrated. For complete removal of the phosphane, the residue obtained was taken up in cyclohexane (20 ml) and the mixture was filtered over a layer of silica gel (15 g) about 3 cm thick. The silica gel was washed with cyclohexane (5×20 ml). The solution obtained in t his way, which contains the desired bromide in a pure form, was concentrated on a rotary evaporator. This was isolated in a yield of 2.47 g (87%) as a yellowish oil.

Thiosulfuric acid S-[2-(benzofuran-3-yl)ethyl]ester sodium salt

Sodium thiosulfate (5.44 g, pentahydrate, 21.9 mmol) was dissolved in water (22 ml), and 3-(2-bromoethyl)benzofuran (2.90 g, 12.9 mmol), dissolved in ethanol (40 ml), was added in the course of 10 min, while stirring. The reaction mixture was then boiled under reflux. After 4H, the reaction had ended (TLC control). For working up, the ethanol contained in the solvent mixture was distilled off in vacuo. The aqueous residue was extracted with diethyl ether (3×20 ml) and the organic phase was washed with water (2×20 ml). The combined aqueous phases were evaporated on a rotary evaporator. The white-yellowish residue (3.63 g) obtained in this way contains x mol of water. The reaction to give the thiol was carried out without further purification.

2-(Benzofuran-3-yl)ethanethiol (Ind-94)

The thiosulfuric acid S-[2-(benzofuran-3-yl)ethyl]ester sodium salt just prepared (3.63 g, contains x mol of water) was suspended in 50 per cent strength phosphoric acid (60 ml) with exclusion of oxygen (argon atmosphere). The reaction mixture obtained was then covered with a layer of diethyl ether (75 ml) and heated under reflux (7 h), with vigorous stirring, until solid was no longer to be observed in the aqueous phase. After cooling, the two phases were separated and the aqueous phase was extracted with diethyl ether (4×15 ml). The combined ethereal phases were washed with water (2×10 ml) and dried over sodium sulfate. The residue (yellowish oil, 1.71 g) obtained after removal of the diethyl ether contained, according to NMR, approx. 80% of the desired thiol Ind-94. Simple purification and dissolving experiments showed that Ind-94 is relatively unstable and by-products already form on standing in an ethereal solution (detection by NMR spectroscopy). The crude product obtained was therefore employed for the thioether synthesis without further working up.

Indole Unit Ind-95: 3-Methylbenzo[b]thiophene (Ind-95)

Commercially obtainable CAS 1455-18-1 from e.g. Acros Organics.

Indole Unit Ind-100

1-Benzyl-3-[2-(1H-indol-3-yl)-ethyl]-urea (Ind-100)

Tryptamine (1.04 g, 6.5 mmol) was dissolved in a mixture of acetone (20 ml) and triethylamine (1 ml) under a nitrogen atmosphere. Benzyl isocyanate (952 mg, 7.15 mmol, 0.88 ml) was swiftly added dropwise at 0° C. and the mixture was then subsequently stirred for 2 h, while cooling with ice, and at RT for 2 h. A subsequent TLC in chloroform/methanol 20:1 showed only small amounts still of tryptamine. The mixture was concentrated i. vac. The residue obtained was purified by flash chromatography with 100 g of silica gel and chloroform/methanol 20:1→9:1→4:1.

Yield: 1.72 g (90%)

Indole Unit Ind-101

1-(2-(1H-Indol-3-yl)ethyl)-3-phenyl-urea (Ind-101)

Tryptamine (1.04 g, 6.5 mmol) was dissolved in a mixture of acetone (20 ml) and triethylamine (1 ml) under a nitrogen atmosphere. Phenyl isocyanate (852 mg, 7.15 mmol, 0.78 ml) was swiftly added dropwise at 0° C. and the mixture was then subsequently stirred for 2 h, while cooling with ice, and at RT overnight. A subsequent TLC in chloroform/methanol 20:1 showed only small amounts still of tryptamine. The mixture was concentrated i. vac. The residue obtained was purified by flash chromatography with 100 g of silica gel and chloroform/methanol 50:1→9:1.

Yield: 928 mg (51%)

Indole Unit Ind-102

1-Cyclopentyl-3-[2-(1H-indol-3-yl)-ethyl]-urea (Ind-102)

Tryptamine (1.04 g, 6.5 mmol) was dissolved in a mixture of acetone (20 ml) and triethylamine (1 ml) under a nitrogen atmosphere. Cyclopentyl isocyanate (795 mg, 7.15 mmol, 0.81 ml) was swiftly added dropwise at 0° C. and the mixture was then subsequently stirred for 2H, while cooling with ice, and at RT overnight. A white solid had precipitated out of the solution, and was filtered off with suction and rinsed with acetone. It was 641 mg of pure product. The filtrate was concentrated i. vac. and the residue was then stirred thoroughly with acetone (10 ml). The undissolved white solid was filtered off with suction and rinsed with acetone, and a further 612 mg of pure product were obtained in this way.

Yield: 1.25 g (71%)

Indole Unit Ind-103

Cyclopentanesulfonic acid [2-(1H-indol-3-yl)-ethyl]-amide (Ind-103)

Tryptamine (950 mg, 5.93 mmol) was initially introduced into abs. THF (30 ml), and triethylamine (0.82 ml, 5.93 mmol) was added at RT. Cyclopentanesulfonyl chloride (1.00 g, 5.93 mmol) was then swiftly added dropwise at RT and the mixture was stirred at RT for 1 d. A subsequent TLC in chloroform/methanol 20:1 showed only small amounts still of tryptamine. The mixture was concentrated i. vac., the residue obtained was taken up in ethyl acetate (20 ml) and the mixture was washed with saturated $NaHCO_3$ solution (2×20 ml). A precipitate precipitated out of the solution, this was filtered off with suction, but according to TLC it was not the product. The organic phase was washed with saturated NaCl solution (2×20 ml), dried over $Na_2SO_4$ and concentrated i. vac.

Yield: 749 mg (43%)

Indole Unit Ind-104

N-[2-(1H-Indol-3-yl)-ethyl]-benzenesulfonamide[2-(1H-indol-3-yl)-ethyl]-amide (Ind-104)

Tryptamine (955 mg, 5.96 mmol) was initially introduced into abs. THF (30 ml). TEA (888 µl, 6.45 mmol) and benzenesulfonyl chloride (826 µl, 6.45 mmol) was then added and the mixture was stirred at RT for 16 h. The mixture was concentrated to dryness i. vac. The residue was taken up in EA (20 ml) and washed with saturated $NaHCO_3$ solution (2×20 ml) and with NaCl solution (2×20 ml). The organic phase was dried over $Na_2SO_4$ and concentrated i. vac. Yield: 1.80 g (100%)

Indole Unit Ind-105

Thiophen-2-sulfonic acid [2-(1H-indol-3-yl)-ethyl]-amide [2-(1H-indol-3-yl)-ethyl]-amide (Ind-105)

Tryptamine (640 mg, 4.0 mmol) was initially introduced into abs. THF (30 ml). TEA (596 µl, 4.3 mmol) and 2-thiophenesulfonyl chloride (785 mg, 4.3 mmol) was then added and the mixture was stirred at RT for 5 h. The mixture was concentrated to dryness i. vac. The residue was taken up in EA (20 ml) and washed with saturated $NaHCO_3$ solution (2×20 ml) and with NaCl solution (2×20 ml). The organic phase was dried over $Na_2SO_4$ and concentrated i. vac. Yield: 1.38 g (100%)

Indole Unit Ind-106

N-[2-(1H-Indol-3-yl)-ethyl]-nicotinamide (Ind-106)

Tryptamine (640 mg, 4.0 mmol) was initially introduced into abs. THF (30 ml). TEA (596 µl, 4.3 mmol) and nicotinic acid chloride hydrochloride (770 mg, 4.3 mmol) was then added and the mixture was stirred at RT for 5 h. The mixture was concentrated to dryness i. vac. The residue was taken up in EA (20 ml) and the mixture was washed with saturated $NaHCO_3$ solution (2×20 ml) and with NaCl solution (2×20 ml). The organic phase was dried over $Na_2SO_4$ and concentrated i. vac. Yield: 482 mg (45%)

Indole Unit Ind-107

2-(1-Benzenesulfonyl-1H-indol-2-yl)ethanol

LDA was prepared from diisopropylamine (6.7 ml, 48 mmol) and 2.5 M n-BuLi solution in hexane (17.6 ml, 44 mmol) in dry THF (100 ml) in a sulfonating flask with a magnetic stirrer, internal thermometer, dropping funnel, gas inlet tube and outlet tube and septum cap under argon at −5° C. The mixture was subsequently stirred at −5° C. for 20 min and then cooled to −75° C. and 1-(phenylsulfonyl)indole (10.3 g, 40 mmol) in dry THF (80 ml) was added dropwise over a period of 2 h such that the internal temperature did not exceed −70° C. When the addition had ended, the mixture was subsequently stirred at this temperature for 90 min. Ethylene oxide (6 ml. 120 mmol) in dry THF (25 ml) was then added dropwise at −15° C. The reaction mixture was left in a cooling bath overnight. The clear red-brown solution was poured into a saturated $NH_4Cl$ solution (100 ml). After addition of water (30 ml), phase separation occurred. The aqueous phase was extracted with diethyl ether (2×50 ml) and the organic phase was washed with 2N HCl (30 ml) and saturated NaCl solution (30 ml). After drying, the organic phase was concentrated, the crude product being a mixture of 2-(1-(phenylsulfonyl)-1H-indol-2-yl)ethanol, 2-(1H-indol-1-yl)ethanol and the starting substance. It was possible to separate off the starting substance by chromatography [silica gel G (300 g); cyclohexane/EtOAc (7:1)]. The mixture of the two alcohols (4.7 g) was employed in this form for the next stage.

2-(1H-indol-1-yl)ethanol (Ind-107)

For splitting off the phenylsulfonyl radical from 2-(1-(phenylsulfonyl)-1H-indol-2-yl)ethanol, the mixture just obtained (4.7 g) was dissolved in ethanol (80 ml) and 2 M sodium hydroxide solution (80 ml) and the solution was heated under reflux for 32 h, while stirring. The ethanol was stripped off on a rotary evaporator and the residue was diluted with water (20 ml). The aqueous solution was extracted with ether (3×70 ml). The combined organic phases were washed with water (30 ml) and saturated NaCl solution (30 ml). After drying, the organic phase was concentrated. A dark brown oil (3.08 g) was obtained, which was separated on silica gel G (200 g); cyclohexane/EtOAc (3:1) into the by-product (1.23 g, 16%, based on the 1st stage) and the desired alcohol 2-(1H-indol-1-yl)ethanol (1.12 g, 14%).

Indole Unit Ind-108

Triethyl-(3-phenylprop-1-ynyl)silane n-Butyllithium (18.1 ml, 45.3 mmol; 2.5 M in hexane) was added dropwise to a solution of prop-2-ynylbenzene (5.00 g, 43.0 mmol) in tetrahydrofuran (60 ml) at −25° C. The temperature was kept at −15 to −20° C. (approx. 5 minutes). The reaction mixture was then stirred at 0 to −5° C. for 30 min Thereafter, triethylchlorosilane (6.9 g, 45.8 mmol) was added dropwise (approx. 5 min) at 0 to −5° C. and the mixture was then stirred overnight at room temperature. The reaction mixture was concentrated in vacuo and water (50 ml) was added to the residue. The mixture was extracted with cyclohexane (3×30 ml). The combined organic phases were dried with sodium sulfate. The volatile constituents were removed completely in vacuo.

Triethyl-(3-phenylprop-1-ynyl)silane was obtained as a yellow oil (9.46 g, 95%, AS 11024).

3-Benzyl-2-triethylsilanyl-1H-indole2-Iodoaniline (5.48 g, 25.02 mmol), triethyl-(3-phenylprop-1-ynyl)silane (6.34 g, 27.51 mmol), lithium chloride (1.11 g, 26.19 mmol) and sodium carbonate (7.95 g, 75.01 mmol) were combined in dimethylformamide (absolute, 70 ml) in an argon atmosphere. The catalyst ([Pd(dppf)Cl$_2$×CH$_2$Cl$_2$], 2.05 g, 2.51 mmol) was then added. The solution was stirred at 100-106° C. for 6 h. The black reaction mixture was cooled to room temperature and water (300 ml) and ethyl acetate (150 ml) were added in succession. After stirring for one hour, the mixture was filtered over Celite. The phases were separated. The aqueous phase was extracted with ethyl acetate (3×50 ml). The combined organic phases were dried with sodium sulfate. After filtration, the volatile constituents were removed completely in vacuo. The residue (10.5 g of brown oil) was purified by chromatography [silica gel 60 (300 g); cyclohexane/ethyl acetate 10:1 (2,200 ml)]. 3-Benzyl-2-triethylsilanyl-1H-indole was isolated as a brown oil (6.44 g, (80%).

3-Benzyl-1H-indole (Ind-108) 3-Benzyl-2-triethylsilanyl-1H-indole (6.37 g, 19.81 mmol)) was dissolved in MeOH (119 ml), and hydrochloric acid (5N. 22 ml, 110 mmol) was metered in. The reaction mixture was stirred overnight at room temperature. Methanol was distilled off and the aqueous residue was extracted with methylene chloride (3×20 ml). The combined organic phases were dried with sodium sulfate. After filtration, the volatile constituents were removed completely in vacuo. The residue (brown solid, 4.97 g) was recrystallized from toluene/hexane (5+30 ml). 3.53 g (86%) of 3-benzyl-1H-indole (melting point: 108-110° C.) were obtained.

EXAMPLES

Example 1

2-(2-(4-(Dimethylamino)-4-phenylcyclohexyl)-1H-indol-3-yl)ethanol, citrate (1:1) diastereomer mixture Successive Sn powder (3.00 g, 25.40 mmol) was added to a suspension of N,N-dimethyl-N-{4-phenyl-2',3',4',9'-tetrahydrospiro[cyclohexane-1,1'-pyrano[3,4-b]indol]-4-yl}-amine (non-polar diastereomer, cf. WO2004043967) (0.72 g, 2.00 mmol) in conc. HCl (60 ml) in the course of 2 h. A clear solutions was formed during the addition, and was stirred at RT for a further 2 h. For working up, the mixture was rendered basic with saturated Na$_2$CO$_3$ solution, and EtOAc (50 ml) was added to the mixture formed. Since the phase separation was incomplete, the constituents insoluble both in H$_2$O and in EtOAc were separated off by means of filtration. The filter cake was washed with EtOAc (5×20 ml) and the aqueous phase was extracted with the particular ethyl acetate fractions (5×). The combined organic extracts were dried over Na$_2$SO$_4$. After filtration of the drying agent, the solvent was removed on a rotary evaporator and the residue (600 mg) was recrystallized from toluene (100 ml). 2-(2-(4-(Dimethylamino)-4-phenylcyclohexyl)-1H-indol-3-yl)ethanol was obtained as a diastereomer mixture (0.22 g, 30%). The solid (0.22 g, 0.60 mmol) was dissolved in boiling EtOH (30 ml), and citric acid (0.13 mg, 0.67 mmol), dissolved in hot EtOH (5 ml), was added. The ethanolic solution was concentrated (to approx. 10 ml) and ether (10 ml) was added. The precipitate formed was separated off by means of a frit and dried. The citrate (Ex. 1) (0.20 g, 60%, m.p.: from 114° C.) was obtained as a white solid.

Example 3

(±)-2-(2-(4-(Dimethylamino)-4-phenylcyclohex-1-enyl)-1H-indol-3-yl)ethyl acetate hydrochloride Tryptophol (Ind-5, 161 mg, 1 mmol) and ketone (Ket-10, 217 mg, 1 mmol) were dissolved in HBr/glacial acetic acid (33%) (5 ml) at 0° C. under argon. The mixture was kept at RT overnight. NaHCO$_3$ was added in portions, while stirring, and the volatile constituents were distilled off in vacuo. The residue was dissolved in EtOAc (20 ml) and the solution was washed with saturated aqueous NaHCO$_3$ solution (3×10 ml). After removal of the solvent on a rotary evaporator, the residue was purified by recrystallization from MeOH (15 ml). The free base of the desired product was obtained as a white solid (289 mg, 72%). This was suspended in ethyl methyl ketone (5 ml), and chlorotrimethylsilane (137 μl, 1.1 mmol) was added. The desired product (Ex. 3) precipitated out as a solid, which was filtered off with suction and dried (315 mg, 100%, m.p.: 120-122° C.

Example 4

(±)-2-(4-(Dimethylamino)-4-phenylcyclohex-1-enyl)-3-(3-aminopropyl)-1H-indole, citrate (1:1)

Ketone (Ket-10, 435 mg, 2 mmol) and 3-(1H-indol-3-yl)propan-1-amine (Ind-15, 348 mg, 2 mmol) were dissolved in DCE (20 ml). A rapid addition of methanesulfonic acid (4 ml) then took place. The mixture was stirred at RT for 1 h. The clear red reaction mixture was diluted with H$_2$O (10 ml) and adjusted to pH 11 with 2N NaOH. After separation of the phases, the aqueous phase was extracted with DCE (3×20 ml). The organic extracts were combined and dried over Na$_2$SO$_4$ and the solvent was removed on a rotary evaporator. The residue was purified by means of column chromatography (MeOH) and the free base of the desired product was obtained as a yellow solid (400 mg, 54%)

For preparation of the citrate, the olefin just obtained (380 mg, 1.02 mmol) was dissolved in hot EtOH (10 ml) and a hot solution of citric acid (196 mg, 1.02 mmol) in EtOH (2 ml) was added. The mixture was then kept at 5° C. for 16 h. Ethanol was removed on a rotary evaporator and the desired citrate (Ex. 4) was obtained as a yellow solid (576 mg, 100%, m.p.: 150-155° C.

$^1$H NMR (400 MHz, DMSO-d$_6$) δ ppm: 1.33 (s, broad, 2H), 1.43-1.57 (m, 2H), 1.65-1.82 (m, 2H), 1.99-2.17 (m, 8H), 2.37-2.47 (m, 1H), 2.47-2.54 (m, 3H), 2.54-2.68 (m, 3H), 2.68-2.79 (m, 1H), 6.11-6.19 (m, 1H), 6.85-7.02 (m, 1H), 7.16-7.25 (m, 2H), 7.25-7.35 (m, 2H), 7.37-7.43 (m, 1H),), 7.43-7.52 (m, 2H), 10.52 (s, 1H)

$^{13}$C NMR (101 MHz, DMSO-d$_6$) δ ppm: 21.8, 26.6, 27.0, 32.7, 35.2, 38.5, 41.74, 60.1, 110.4, 110.8, 117.8 117.9, 120.5, 124.6, 126.0, 126.8, 127.2, 128.3, 129.7, 134.8, 134.9, 142.5

Example 6

(±)-3-(2-(4-(Dimethylamino)-4-phenylcyclohex-1-enyl)-1H-indol-3-yl)propan-1-ol hydrochloride Trifluoromethanesulfonic acid trimethylsilyl ester (1 ml, 5 mmol) was added to a solution of ketone (Ket-10, 1.1 g, 5.07 mmol) and indole (Ind-16, 1.48 g, 6.0 mmol) in MC (30 ml) at −78° C. in the course of 5 min under argon. The reaction mixture was stirred at −78° C. for 60 min and triethylsilane (0.9 ml, 5.6 mmol) was finally added. The mixture was warmed to RT over a period of approx. 4 h and stirred at RT for a further 10 h. 1N NaOH (40 ml) was added and the mixture was stirred for 60 min. A precipitate formed, which partly dissolved on addition of MC (30 ml). After separation of the phases, the aqueous phase was extracted with MC (3×30 ml) and the organic extracts were combined and washed with 1N NaOH (1×30 ml) and $H_2O$ (2×30 ml). After drying over $Na_2SO_4$, the solvent was removed on a rotary evaporator and the residue was purified by column chromatography (EtOAc, then EtOAc/EtOH (8:2)) and the desired olefin (134 mg, 7%, m.p.: 163-167° C.) was obtained. For conversion into the hydrochloride, the olefin (120 mg, 0.31 mmol) was dissolved in ethyl methyl ketone (10 ml), $Me_3SiCl$ (76 μl, 0.6 mmol) was added and the mixture was stirred at RT for 3 h. The hydrochloride (Ex. 6) precipitated out as a white solid (67 mg, 52%, m.p.: 212-216° C.) by this procedure.

Example 7

(±)-2-(5,6-Dichloro-2-(4-(dimethylamino)-4-phenyl-cyclohex-1-enyl)-1H-indol-3-yl)ethanol, citrate (1:1)

Trifluoromethanesulfonic acid (0.1 ml, 1.1 mmol) was added to ketone (Ket-10, 217 mg, 1 mmol) and indole (Ind-83, 230 mg, 1 mmol) in absolute MC (50 ml) under argon. The reaction mixture was stirred at RT for 21 h. A brown solid precipitated out. 1N NaOH (20 ml) was added to the reaction mixture and the mixture was stirred at RT for 1 h. The phases were separated and the aqueous phase was extracted with MC (20 ml). The organic phases were combined and dried over $Na_2SO_4$ and, after filtration of the drying agent, the solvent was removed on a rotary evaporator. The residue was stirred with 2-propanol (3 ml) for 10 min and the residue was separated off by filtration and washed with 2-propanol (3×2 ml). The filtrate was concentrated (312 mg) on a rotary evaporate and the residue was purified by chromatography (MeOH=10:1 (1.0 l), 4:1 (0.5 l), MeOH (0.5 l). The desired olefin was obtained as a yellow solid (87 mg, 20%, m.p.: 116-119° C.) by this procedure. For preparation of the citrate, EtOH (15 ml) was added to this and the mixture was heated to 50° C. Citric acid (42 mg, 0.22 mmol), dissolved in warm EtOH (4 ml), was added to the cloudy solution. A clear solution resulted, from which a solid precipitated out on cooling to RT. The mixture was stirred at RT for 16 h and kept at 5° C. for 2 h. The desired citrate (Ex. 7) was filtered off with suction and washed with EtOH (2×5 ml) (59 mg, 48%, m.p.: 210-212° C.).

$^1$H NMR (300 MHz, DMSO-$d_6$) δ ppm: 1.64-1.78 (m, 1H), 2.16-2.05 (m, 2H), 2.21 (s, 6H), 2.37-2.48, (m, 2H), 2.60 (dd, 4H), 2.73-2.88 (m, 3H), 6.16 (t, 1H), 7.17-7.23 (m, 1H), 7.23-7.31 (m, 2H), 7.38 (d, 1H), 7.43 (d, 2H), 7.66 (d, 1H), 10.97 (s, 1H)

Example 8

(±)-2-(2-(4-Morpholino-4-phenylcyclohex-1-enyl)-1H-indol-3-yl)ethanol, citrate (1:1)

Ketone (Ket-9, 259 mg, 1 mmol) and tryptophol (Ind-5, 1 mg, 1 mmol) were initially introduced into absolute MC (50 ml), and trifluoromethanesulfonic acid (0.1 ml, 1.1 mmol) was added. The mixture was stirred at RT for 15 h. A pale brown precipitate formed. 1N NaOH (20 ml) was added to the reaction mixture and the mixture was stirred at RT for 16 h. After separation of the phases, the aqueous phase was extracted with MC (2×20 ml). The organic phases were combined and dried over $Na_2SO_4$. Removal of the solvent on a rotary evaporator gave the desired olefin as a beige-coloured solid (401 mg, 99%). This was dissolved in EtOH (5 ml), and citric acid (211 mg, 1.1 mmol), dissolved in EtOH (5 ml), was added. The mixture was stirred at RT for 16 h and kept at 5° C. for 2 h. The solid was filtered off, the filtrate was concentrated to 5 ml and ether (50 ml) was added. The solid which had precipitated out was filtered off with suction and washed with EtOH (2×10 ml). It was possible to isolate the desired citrate (Ex. 8) as a yellow solid (269 mg, 45%, m.p.: 125-137° C.).

Example 9

(±)-2-(4,6-Dichloro-2-(4-(dimethylamino)-4-phenyl-cyclohex-1-enyl)-1H-indol-3-yl)ethanol, citrate (1:1)

Ketone (Ket-10, 217.3 mg, 1 mmol) was initially introduced into absolute MC (40 ml) with indole (Ind-31, (230.1 mg, 1 mmol). The addition of trifluoromethanesulfonic acid (0.1 ml, 1.1 mmol) then took place. The mixture was stirred at RT for 20 h. 1N NaOH (20 ml) was added to the clear pale brown solution and the mixture was stirred vigorously for a further hour. A white solid settled out between the phases. This was filtered off with suction and washed with MC (20 ml) and the desired olefin (416 mg, 97%, m.p.: 255-258° C.) was obtained in this manner. For preparation of the citrate, some of the solid (341 mg, 0.79 mmol) was dissolved in EtOH (60 ml), while heating, and citric acid (168 mg, 0.87 mmol), dissolved in EtOH (5 ml), was added. The mixture was stirred at RT for 6 h and kept at 5° C. for 20 h. The solution was concentrated to approx. 10 ml on a rotary evaporator, ether (20 ml) was added and the mixture was stirred for 1 h. The solid which had precipitated out was filtered off with suction and washed with ether (10 ml). The citrate (9) was obtained as a white solid (444 mg (91% m.p.: 151-154° C.).

Example 10

(±)-2-(2-(4-(Dimethylamino)-4-phenylcyclohex-1-enyl)-5-fluoro-1H-indol-3-yl)ethanol, citrate (1:1)

A suspension von N,N-dimethyl-N-{4-phenyl-6'-fluoro-1',3',4',9'-tetrahydrospiro[cyclo-hexane-1,1'-pyrano[3,4-b] indol]-4-yl}amine (non-polar diastereomer, cf. WO2004043967) (400 mg, 1.06 mmol) (20 ml) was stirred in conc. HCl at RT for 18 h. The initially cloudy solution became clear in the course of time. The mixture was then rendered basic with saturated $Na_2CO_3$ solution. The solid which had precipitated out was separated off over a frit and the desired olefin (340 mg, 84%, m.p.: 216-221° C.) was obtained in this way. This (340 mg, 0.89 mmol) was dissolved in 30 ml of boiling isopropanol, and citric acid (170 mg, 0.88 mmol), dissolved in hot isopropanol (5 ml), was added. The reaction mixture was cooled to RT and the mixture was concentrated to approx. 10 ml on a rotary evaporator. A precipitate thereby precipitated out, which was separated off by means of a frit. Drying in vacuo gave Example 10 (180 mg, 42%).

Example 11

2',3',4',9'-Tetrahydro-N,N-dimethyl-4-(phenyl)-6'-(pyridin-4-yl)-spiro[cyclohexane-1,1'(1'H)-pyrido[3,4-b]indol]-4-amine (diastereomer mixture)

The ketone (Ket-10, 245.4 mg, 1.13 mmol) was initially introduced into absolute 1,2-dichloroethane (35 ml) with the indole (Ind-28, (270.0 mg, 1.13 mmol). The dropwise addition of methanesulfonic acid (220.6 µl, 3.39 mmol) then took place. The mixture was stirred at RT for 16 h. The reaction mixture was now heated to 75° C. and stirred at this temperature for 7 h A pale yellow precipitate thereby precipitated out. This was filtered off with suction at room temperature and washed with 1,1-dichloroethane (3×2 ml) and with diethyl ether (2×2 ml) and then dried. Yield (diastereomer mixture): 660 mg (93%); melting point: 190-197° C.

(±)-2-(2-(4-(Dimethylamino)-4-phenylcyclohex-1-enyl)-5-(pyridin-3-yl)-1H-indol-3-yl)ethanol, citrate (1:1)

The sulfonate just prepared (763 mg, 1.21 mmol) was soluble in water (28 ml) to give a clear solution. 1N NaOH (pH 11) was added to the solution and the mixture was stirred vigorously for one hour. The voluminous precipitate dissolved in methylene chloride (100 ml). The clear phases were separated. The aqueous phase was extracted with methylene chloride (3×10 ml). The organic extracts were combined, dried and then concentrated. The residue was a pale yellow solid (477.5 mg), which corresponded to the mixture of the spiro ether and to the desired olefin in the TLC. Separation of the mixture was achieved by flash chromatography twice [silica gel 60 each time (50 g); 1st column eluent: MeOH/EtOAc (1:7; 400 ml), MeOH/EtOAc (1:1; 1,000 ml); 2nd column eluent: $CH_2Cl_2$/MeOH/EtOAc (10:1:1; 480 ml), $CH_2Cl_2$/MeOH/EtOAc (2:1:1; 800 ml)]. The olefin was obtained in this way in a yield of (20 mg, m.p. 202-207° C., 4%).

$^1$H NMR (300 MHz, CDCl$_3$-d$_6$) δ ppm: 1.61-1.78 (m, 2H), 2.15-2.18 (m, 2H), 2.21 (s, 6H), 2.32-2.46 (m, 1H), 2.58-2.85 (m, 2H), 3.03 (t, J=6.93, 6.93 Hz, 2H), 3.78 (t, J=6.75, 6.75 Hz, 2H), 6.21-6.34 (m, 1H), 7.23-7.28 (m, 1H), 7.29-7.40 (m, 4H), 7.42-7.51 (m, 2H), 7.71 (s, 1H), 7.88-7.94 (m, 1H), 7.94-7.99 (m, 1H), 8.53 (dd, J=4.78, 1.56 Hz, 1H), 8.86 (d, J=1.64 Hz, 1H)

$^{13}$C NMR (101 MHz, CDCl$_3$) δ ppm: 27.1, 27.5, 28.2, 33.2, 38.5, 60.9, 63.2, 108.4, 111.1, 117.3, 121.5, 123.4, 126.7, 127.1, 127.2, 127.8, 130.1, 134.4, 137.8, 142.6, 147.5, 148.5

The racemate of the olefin I just obtained (20 mg, 0.046 mmol) was dissolved in ethanol (5 ml), while heating, and citric acid (19.3 mg, 0.101 mmol), dissolved in ethanol (1 ml), was added. The mixture was stirred at RT for 1 h. No precipitate precipitated out even on cooling. The solution was concentrated down to approx. 1 ml, diethyl ether (3 ml) was added and the mixture was stirred for 2 h. The mother liquor above the solid deposited was cautiously decanted. The solid was rinsed twice with diethyl ether (2 ml) and the supernatant solution was pipetted off again. The residue was dried in vacuo. The citrate of the olefin (Ex. 11) was obtained as a yellow solid in a yield of 98% (28.2 mg, melting point cannot be determined).

Example 13

(±)-2-(2-(4-(Dimethylamino)-4-phenylcyclohex-1-enyl)-5-nitro-1H-indol-3-yl)ethanol The ketone (Ket-10, 1.305 g, 6.0 mmol) was dissolved in dry methylene chloride (60 ml) together with the indole (Ind-27, 1.24 g, 6 mmol). Trifluoromethanesulfonic acid (1.19 ml, 6 mmol) was added rapidly at RT, the solution becoming brown in colour. The mixture was stirred at RT for a further 48 h. The reaction was monitored by TLC. For working up, 5N NaOH (50 ml) was added to the mixture and the mixture was stirred for 30 min. The organic phase was separated off. The aqueous phase was extracted with methylene chloride (5×30 ml). The organic phase was dried over Na$_2$SO$_4$ and then evaporated. The yellow oil which remained was a mixture of the desired olefin and a by-product. It was possible to separate and purify the mixture by column chromatography [silica gel 60 (200 g); MeOH (2,000 ml)]. The olefin was obtained as a yellow solid in a yield of 1.23 g (51%).

$^1$H NMR (400 MHz, DMSO-d$_6$) δ ppm: 1.58-1.83 (m, 1H), 1.94-2.18 (m, 8H), 2.32-2.46 (m, 1H), 2.52-2.70 (m, 2H), 2.85-3.03 (m, 2H), 3.34-3.50 (m, 2H), 6.18-6.27 (m, 1H), 7.09-7.17 (m, 1H), 7.18-7.26 (m, 2H), 7.32-7.41 (m, 3H), 7.92 (dd, J=8.92, 2.27 Hz, 1H), 8.45 (t, J=2.01 Hz, 1H), 11.43 (s, 1H)

$^{13}$C NMR (101 MHz, DMSO-d$_6$) δ ppm: 24.9, 26.3, 26.9, 32.5, 60.0, 70.6, 110.0, 111.9, 115.5, 116.4, 126.3, 126.8, 127.4, 127.7, 128.0, 128.8, 138.5, 139.7, 140.2, 142.5

(±)-2-(2-(4-(Dimethylamino)-4-phenylcyclohex-1-enyl)-5-nitro-1H-indol-3-yl)ethanol, citrate (2:1)

For preparation of the citrate, the olefin (360 mg, 1 mmol) was dissolved in hot ethanol (50 ml), and a similarly hot solution of citric acid (194 mg, 1 mmol) in ethanol (5 ml) was added. After cooling to 5° C., the mixture was left to stand for 16 h. The solid formed was filtered off with suction and dried. The desired hemicitrate was obtained in this way in a yield of 276 mg (50%) as a white solid (melting point: 199-203° C.).

$^1$H NMR (300 MHz, DMSO-d$_6$) δ ppm: 1.58-1.82 (m, 1H), 2.00-2.21 (m, 8H), 2.33-2.82 (m), 2.82-3.02 (m, 2H), 3.25-3.48 (m, 2H), 6.14-6.29 (m, 1H), 7.10-7.21 (m, 1H), 7.21-7.31 (m, 2H), 7.32-7.47 (m, 3H), 7.93 (dd, J=8.95, 2.22 Hz, 1H), 8.41-8.51 (m, 1H), 11.47 (s, 1H)

Example 14

(±)-2-(2-(4-(Benzo[b]thiophen-2-yl)-4-(dimethylamino)cyclohex-1-enyl)-1H-indol-3-yl)ethanol, citrate (1:1)

Ketone (Ket-6, 0.220 g, 0.804 mmol) and tryptophol (Ind-5, 0.130 g, 0.804 mmol) were initially introduced into abs. methylene chloride (10 ml) under argon, methanesulfonic acid (0.078 ml, 0.881 mmol) was then added and the mixture was stirred at room temperature overnight. 1N NaOH was added to the mixture and the mixture was extracted with methylene chloride (3×15 ml), the org. phase was dried over Na$_2$SO$_4$ and concentrated i. vac. and the product was then purified by means of flash chromatography with chloroform/methanol (9:1).

Yield: 0.07 g, 21.2%

$^1$H-NMR (DMSO-d$_6$): 2.01 (2H, m); 2.19 (1H, m); 2.24 (6H, s); 2.73 (2H, s); 2.91 (2H, t); 3.34 (1H, m); 3.53 (2H, m); 4.71 (1H, t, OH); 6.25 (1H, bs); 6.96 (2H, m); 7.27 (4H, m); 7.41 (1H, m); 7.73 (1H, m); 7.88 (1H, m); 10.66 (1H, bs).

$^{13}$C-NMR (DMSO-d$_6$): 26.44; 28.74; 28.97; 33.81; 38.32; 59.98; 61.84; 79.12; 107.53; 110.65; 118.09; 118.26; 120.85; 121.46; 122.07; 123.12; 123.84; 124.39; 128.72; 129.29; 135.18; 135.81; 138.87; 139.17; 150.93.

The olefin just obtained (0.07 g, 0.168 mmol) was dissolved in hot ethanol (2.5 ml), and citric acid (0.033 g, 0.168 mmol), dissolved in hot ethanol (1 ml), was added at room temperature. The reaction solution was then concentrated i. vac. and a brownish solid remained.

Yield: 99 mg (97%) Example 14; melting point: 95-97° C.

Example 15

(±)-2-(2-(4-(Benzo[b]thiophen-2-yl)-4-(dimethylamino)cyclohex-1-enyl)-5-fluoro-1H-indol-3-yl)ethanol, citrate (1:1)

Ketone (Ket-6, 0.220 g, 0.804 mmol) and indole (Ind-4, 0.194 g, 0.804 mmol) were initially introduced into abs. methylene chloride (10 ml) under argon, methanesulfonic acid (0.078 ml, 0.881 mmol) was then added and the mixture was stirred at room temperature overnight. 1N NaOH was added to the mixture and the mixture was extracted with methylene chloride (3×15 ml), the org. phase was dried over $Na_2SO_4$ and concentrated i. vac. and the product was then purified by means of flash chromatography with chloroform/methanol (9:1). Yield: 0.130 g (37%)

$^1$H-NMR (DMSO-$d_6$): 2.01 (2H, m); 2.25 (7H, m); 2.74 (2H, s); 2.87 (2H, t); 3.29 (1H, m); 3.53 (2H, m); 4.63 (1H, t, OH); 6.26 (1H, bs); 6.82 (2H, m); 7.20 (3H, m); 7.73 (1H, m); 7.86 (1H, m); 10.72 (1H, bs).

$^{13}$C-NMR (DMSO-$d_6$): 26.38; 28.61; 28.97; 33.77; 38.31; 59.94; 61.70; 79.12; 102.72; 102.95; 108.08; 108.65; 108.90; 111.54; 121.48; 122.07; 123.13; 123.85; 125.09; 129.10; 131.78; 137.91; 138.88; 139.15; 150.83; 157.79.

The olefin just obtained (0.130 g, 0.298 mmol) was dissolved in hot ethanol (2.5 ml), and citric acid (0.058 g, 0.298 mmol), dissolved in hot ethanol (1.5 ml), was added. The reaction solution was then concentrated i. vac. and a brownish solid remained.

Yield: 0.151 g (83%) Example 15; melting point: 92-104° C.

Example 16

(±)-2-(4-(Dimethylamino)-4-phenylcyclohex-1-enyl)-3-methyl-1H-indole, citrate (1:1)

Skatole (Ind-10, 262 mg, 2 mmol) was dissolved in methylene chloride (20 ml) together with the ketone (Ket-10, 434 mg, 2 mmol), and trifluoromethanesulfonic acid (0.2 ml, 2.3 mmol) was added. The mixture was stirred at RT for 3 days.—For working up, 2N NaOH (10 ml) was added to the reaction mixture. After separation of the phases, the aqueous phase was extracted with methylene chloride (2×20 ml). The combined organic extracts were dried over $Na_2SO_4$ and then concentrated. The crude product obtained (720 mg) was recrystallized from methanol (20 ml). The desired olefin (Ex. 16) was obtained in this way in a yield of 412 mg (62%) with a melting point of 168-180° C.

The citrate precipitation was carried out analogously to Example 15.

Example 17

N,N-Dimethyl-4-(3-methyl-1H-indol-2-yl)-1-phenylcyclohexanamine, citrate (2:1)

Example 18

N,N-Dimethyl-4-(3-methyl-1H-indol-2-yl)-1-phenylcyclohexanamine, citrate (2:1)

Variant 1

(±)-N,N-Dimethyl-N-[4-(3-methyl-1H-indol-2-yl)-1-phenylcyclohex-3-enyl]amine

3-Methylindole (Ind-10, 262 mg, 2 mmol) was dissolved in methylene chloride (20 ml) together with Ket-10 (434 mg, 2 mmol), and trifluoromethanesulfonic acid (0.2 ml, 2.3 mmol) was added. The mixture was stirred at RT for 3 days.—For working up, 2N NaOH (10 ml) was added to the reaction mixture. After separation of the phases, the aqueous phase was extracted with methylene chloride (2×20 ml). The combined organic extracts were dried over $Na_2SO_4$ and then concentrated. The crude product obtained (720 mg) was recrystallized from methanol (20 ml). (±)-N,N-Dimethyl-N-[4-(3-methyl-1H-indol-2-yl)-1-phenylcyclohex-3-enyl]amine was obtained in this way in a yield of 412 mg (62%) with a melting point of 168-180° C.

N,N-Dimethyl-N-[4-(3-methyl-1H-indol-2-yl)-1-phenylcyclohexyl]amine (polar and non-polar diastereomer)

(±)-N,N-Dimethyl-N-[4-(3-methyl-1H-indol-2-yl)-1-phenylcyclohex-3-enyl]amine (550 mg, 1.66 mmol) were dissolved in HBr/glacial acetic acid (33% HBr, 20 ml). Sn powder (1 g, 8.5 mmol) was then added to the mixture in portions in the course of 30 min. When the addition had ended, the reaction mixture was stirred for a further 30 min.—For working up, the mixture was concentrated to dryness on a rotary evaporator. The residue which remained was rendered basic by addition of 2N NaOH (20 ml). The aqueous mixture obtained was extracted with ethyl acetate (4×20 ml). The combined organic phases were dried with $Na_2SO_4$ and then concentrated. The residue obtained (530 mg) was recrystallized from methanol (60 ml). N,N-Dimethyl-N-[4-(3-methyl-1H-indol-2-yl)-1-phenylcyclohexyl]amine (less polar isomer) was obtained in this way in a yield of 222 mg (40%, melting point: from 204° C.).

The methanolic mother liquor was concentrated. NMR analyses of the residue which remained (305 mg, 55% yield) showed that it was predominantly the second, more polar diastereoisomer. The compound was employed for the citrate formation without further purification.

Variant 2

N,N-Dimethyl-N-[4-(3-methyl-1H-indol-2-yl)-1-phenylcyclohexyl]amine (non-polar diastereomer)

HBr/glacial acetic acid (33% HBr, 20 ml) was added to 3-methylindole (Ind-10, 262 mg, 2 mmol) together with Ket-10 (434 mg, 2 mmol) and the mixture was stirred at RT for 22 h*). Sn powder (0.5 g) was then added to the mixture in portions at RT in the course of 30 min. When the addition had ended, the mixture was stirred for a further 30 min.—For working up, the reaction mixture was concentrated to dryness on a rotary evaporator. The mixture was rendered basic with 2N NaOH. Ethyl acetate was added (20 ml) to the aqueous mixture. The insoluble constituents of the mixture were separated off by means of a frit. The filter cake was washed with ethyl acetate (3×20 ml). The phases of the mother liquor were separated and the aqueous phase was extracted with ethyl acetate (4×20 ml). The combined organic phases were dried over $MgSO_4$ and then concentrated. The residue obtained (550 mg) was recrystallized from methanol (70 ml, solid largely dissolved). 110 mg of product were isolated in this manner. A further 40 mg of dimethyl-[4-(3-methyl-1H-indol-2-yl)-1-phenylcyclohexyl]amine were isolated from the methanolic mother liquor by flash chromatography (eluent: ethyl acetate) (yield: 150 mg (28%); melting point: from 204° C.).

N,N-Dimethyl-4-(3-methyl-1H-indol-2-yl)-1-phenyl-cyclohexanamine, citrate (2:1), non-polar diastereomer (Ex. 17)

N,N-Dimethyl-[4-(3-methyl-1H-indol-2-yl)-1-phenylcyclohexyl]amine (non-polar isomer, 222 mg, 0.68 mmol) was dissolved in 2-propanol (50 ml) at the boiling point and citric acid (192 mg, 1 mmol), dissolved in hot isopropanol (2 ml), was added. The solution was cooled to 5° C. (refrigerator) and left to stand for 12 h. The precipitate formed was separated off by means of a frit. Example 17 was obtained in this way in a yield of 283 mg (99%, melting point: 244-252° C.).

N,N-Dimethyl-4-(3-methyl-1H-indol-2-yl)-1-phenyl-cyclohexanamine, citrate (2:1), polar diastereomer N,N-Dimethyl-[4-(3-methyl-1H-indol-2-yl)-1-phenylcyclohexyl]amine (polar isomer 290 mg, 0.87 mmol) was dissolved in isopropanol (150 ml) at the boiling point and citric acid (254 mg, 1.32 mmol, dissolved in 5 ml of isopropanol), was added. The reaction mixture was stirred for 10 min. After cooling to RT, the reaction mixture was concentrated to approx. 80 ml. The solution was stored at room temperature for 1 h and then at 5° C. overnight. The solid formed was filtered off with suction and discarded. The mother liquor was concentrated to dryness. Water (7 ml) was added to the residue and the mixture was stirred vigorously at RT for 30 min. The yellow solid formed was filtered off with suction and dried. Example 18 was obtained in this way in a yield of 185 mg (49%) as a yellow solid with a melting point of 224-236° C.

Example 19

(±)-2-(2-(2-(4-(Dimethylamino)-4-phenylcyclohex-1-enyl)-1H-indol-3-yl)ethyl)isoindoline-1,3-dione 2-hydroxypropane-1,2,3-tricarboxylate Ketone (Ket-10, 898 mg, 4.13 mmol) and indole (Ind-1, 1.20 g, 4.13 mmol) were dissolved in abs. methylene chloride (50 ml) under argon. Trifluoromethanesulfonic acid (480 µl/5.5 mmol) was then added rapidly and the mixture was stirred at RT overnight. The mixture was rendered alkaline with 1N NaOH and subsequently stirred at RT for 15 min. The phases were separated. The aqueous phase was extracted with methylene chloride (three times 20 ml). The organic phase was dried over $Na_2SO_4$ and concentrated i. vac. The residue was purified by flash chromatography with $CHCl_3$/MeOH (9:1).

Yield: 1.10 g (55%)
$^1$H-NMR (DMSO-$d_6$): 1.63 (2H, m); 2.09 (6H, m); 2.48 (2H, m); 2.64 (2H, m); 3.00 (2H, m); 3.69 (2H, m); 6.24 (1H, s); 6.97 (2H, m); 7.20-7.47 (5H, m); 7.68 (4H, m); 10.66 (1H, s).

2-(2-(2-(4-(Dimethylamino)-4-phenylcyclohexyl)-1H-indol-3-yl)ethyl)isoindoline-1,3-dione, citrate (1:1) One of 2 Possible Diatereomers The olefin just prepared (1.10 g, 2.24 mmol) was dissolved in HBr/glacial acetic acid (55 ml). Tin (2.60 g, 2.24 mmol) was added in the course of 30 min and the mixture was stirred at RT for 4 h. Ethanol was added to the mixture and the mixture was stirred at RT overnight. The mixture was then concentrated i. vac., 5N NaOH was added to the residue and the mixture was extracted with methylene chloride (three times 20 ml). The organic phase was dried over $Na_2SO_4$ and concentrated i. vac. The residue was purified by flash chromatography EA/EtOH (1:2 (MeOH+1% TEA).

Yield: 177 mg (16%) (mixed fraction)
432 mg (39%) of polar diastereomer

The polar diastereomer just obtained (80 mg, 0.162 mmol) was dissolved in hot ethanol (5 ml). Citric acid (30 mg, 0.162 mmol) was dissolved in hot ethanol (1 ml) and the solution was added. The mixture was cooled and concentrated to half and the precipitate which had precipitated out was filtered off with suction and dried i. vac.

Yield: 111 mg (Ex. 19; 100%)
Melting point: 108-110° C.
$^1$H-NMR (DMSO-$d_6$): 1.46 (2H, m); 1.74 (2H, m); 1.89 (2H, m); 2.37 (6H, s); 2.45-2.65 (4H, m); 2.97 (2H, m); 3.75 (2H, t); 6.89 (2H, m); 7.13 (1H, d); 7.46 (6H, m); 7.64 (4H, s); 10.44 (1H, s), citrate.

Example 20

(±)-N-(2-(2-(4-(Dimethylamino)-4-phenylcyclohex-1-enyl)-1H-indol-3-yl)ethyl)acetamide Ketone (Ket-10, 234 mg, 1.08 mmol) and indole (Ind-2, 219 mg, 1.08 mmol) were dissolved in abs. methylene chloride (10 ml) under argon, trifluoromethanesulfonic acid (188 µl, 12.16 mmol) was added rapidly and the mixture was stirred at RT for 16 h. The mixture was then rendered alkaline with 1N NaOH and subsequently stirred at RT for 15 min. The phases were separated. The aqueous phase was extracted with methylene chloride (three times 20 ml). The organic phase was dried over $Na_2SO_4$ and concentrated i. vac. The residue was purified by flash chromatography with CH/EA (1:1→1:4), EA/EtOH (4:1→1:1), EtOH, (methanol+1% TEA). 1N NaOH was added to the fractions and the mixture was extracted with methylene chloride (two times 10 ml). The organic phase was dried over $Na_2SO_4$ and concentrated i. vac.

Yield: 86 mg (19%)

N-(2-(2-(4-(Dimethylamino)-4-phenylcyclohexyl)-1H-indol-3-yl)ethyl)acetamide, citrate (1:1) Non-polar diastereomer The olefin just obtained (436 mg/1.08 mmol) was dissolved in HBr/glacial acetic acid (25 ml), tin (1.25 g, 1.08 mmol) was added in the course of 30 min and the mixture was stirred at RT for 4 h. Ethanol was added to the mixture and the mixture was stirred at RT overnight. The mixture was then concentrated to dryness i. vac. 5N NaOH was added to the residue and the mixture was extracted with methylene chloride (three times 20 ml). The organic phase was dried over $Na_2SO_4$ and concentrated i. vac. The solid still in the aqueous phase was filtered off with suction and dried i. vac. (non-polar diastereomer). The mother liquor was purified by flash chromatography with $CHCl_3$/MeOH (4:1→MeOH→MeOH+1% TEA).

Yield: 185 mg (42%) of non-polar diastereomer
250 mg (57%) of polar diastereomer The non-polar diastereomer just obtained (76 mg, 0.188 mmol) was dissolved in hot ethanol (5 ml). Citric acid (36 mg/0.188 mmol) was dissolved in hot ethanol (1 ml) and the solution was added. The mixture was cooled and ether was added. The precipitate which thereby precipitated out was filtered off with suction and dried i. vac.

Yield: 43 mg (Ex. 20; 38%)
Melting point: 245-247° C.

$^1$H-NMR (DMSO-d$_6$): 1.77 (5H, m); 2.35 (6H, s); 2.65-2.80 (6H, m); 2.97 (2H, m); 3.18 (2H, m); 6.96 (2H, m); 7.30-7.58 (6H, m); 7.89 (1H, s); 10.91 (1H, s), citrate.

Example 21

N-(2-(2-(4-(Dimethylamino)-4-phenylcyclohexyl)-1H-indol-3-yl)ethyl)acetamide, citrate (1:1) Polar diastereomer The polar diastereomer obtained under Example 20 (63 mg/0.155 mmol) was dissolved in hot ethanol (5 ml)/dioxane (5 ml). Citric acid (30 mg/0.155 mmol) was dissolved in hot ethanol (1 ml) and the solution was added. The mixture was cooled and ether was added, a precipitate thereby precipitating out. The precipitate was filtered off with suction and dried i. vac.

Yield: 52 mg (Ex. 21, 56%)

$^1$H-NMR (DMSO-d$_6$): 1.47 (2H, m); 1.81 (5H, m); 2.23 (2H, m); 2.43 (6H, s); 2.58-2.71 (4H, m); 2.92 (1H, t); 3.11 (2H, m); 3.43 (2H, m); 6.90 (2H, m); 7.14 (1H, m); 7.39 (1H, d); 7.57 (3H, m); 7.74 (2H, m); 8.02 (1H, s); 10.40 (1H, s).

Example 22

(±)-2-(4-Benzyl-4-(dimethylamino)cyclohex-1-enyl)-3-methyl-1H-indole-5-carbonitrile The ketone Ket-3 (606 mg, 2.62 mmol) and Ind-6 (410 mg, 2.62 mmol) were dissolved in abs. methylene chloride (40 ml), trifluoromethanesulfonic acid (0.256 ml, 432 mg, 2.88 mmol) was added and the mixture was stirred at room temperature for 3 days. A light-coloured precipitate formed in the reaction mixture. Water (10 ml) and 1N sodium hydroxide solution (10 ml) were added to the mixture and the mixture was stirred for 1 h. The phases were separated. The aqueous phase was extracted with methylene chloride (40 ml). The organic phases were combined, washed with water (20 ml), dried and concentrated. The residue was a brown oil (950 mg), which was separated by chromatography [silica gel 60 (80 g), ethyl acetate (500 ml), ethyl acetate/methanol (4:1, 500 ml)]. Example 22 was obtained as a colourless solid in a yield of 34% (318 mg) with a melting point of 120-123° C.

Example 23

(±)-2-(4-(Dimethylamino)-4-phenylcyclohex-1-enyl)-3-methyl-1H-indole-5-carbonitrile The ketone Ket-10 (568 mg, 2.62 mmol) and the indole Ind-6 (410 mg, 2.62 mmol) were dissolved in abs. methylene chloride (40 ml), trifluoromethanesulfonic acid (0.256 ml, 432 mg, 2.88 mmol) was added and the mixture was stirred at room temperature for 3 days. A light-coloured precipitate formed in the reaction mixture. Water (20 ml) and 1N sodium hydroxide solution (15 ml) were added to the mixture and the mixture was stirred for 30 min. The phases were separated. The aqueous phase was extracted with methylene chloride (30 ml). The organic phases were combined, washed with water (20 ml), dried and concentrated. The residue was a brown oil (983 mg), which was separated by chromatography [silica gel 60 (120 g); ethyl acetate (500 ml), trichloromethane/methanol (40:1, 1,600 ml), trichloromethane/methanol (20:1, 400 ml), trichloromethane/methanol (10:1, 700 ml)]. Example 23 was obtained as a colourless solid in a yield of 84% (824 mg) with a melting point of 180-185° C.

Example 24

(±)-2-(4-(Dimethylamino)-4-butylcyclohex-1-enyl)-3-methyl-5-trifluoromethyl-1H-indole The ketone (Ket-4, 395 mg, 2 mmol) was dissolved in methylene chloride (20 ml) together with Ind-7 (398 mg, 2 mmol). The addition of trifluoromethanesulfonic acid (0.2 ml, 338 mg 2.25 mmol) then took place, the mixture becoming dark in colour. The mixture was stirred at RT for 3 d. For working up, 1 N NaOH (10 ml) was added to the reaction mixture and the mixture was stirred for 10 min. During this procedure, the colour changed from dark red to pale brown. After separation of the phases, the aqueous phase was extracted with methylene chloride (2×10 ml). The combined organic phases were dried with sodium sulfate, filtered and concentrated in vacuo. 741 mg of pale brown solid were obtained, which was separated by chromatography [silica gel 60 (80 g); ethyl acetate/methanol 15:1; 1.5 l); (10:1; 500 ml); (1:1; 500 ml)]. Example 24 (140 mg, 18%, m.p.: 118-120° C.) was obtained.)

Example 25

(±)-2-(4-(Dimethylamino)-4-phenylcyclohex-1-enyl)-3-methyl-5-trifluoromethyl-1H-indole, citrate (1:1)

The ketone (Ket-10, 599 mg, 2.76 mmol) was dissolved in methylene chloride (20 ml) together with Ind-7 (550 mg, 2.76 mmol). The addition of trifluoromethanesulfonic acid (0.276 ml, 3.1 mmol) then took place, the mixture becoming dark in colour. The mixture was stirred at RT for 3 d. The course of the reaction was monitored by means of TLC. For working up, 1 N NaOH (10 ml) was added to the reaction mixture and the mixture was stirred for 10 min. During this procedure, the colour changed from dark red to pale brown. After separation of the phases, the aqueous phase was extracted with methylene chloride (2×10 ml). The combined organic phases were dried with sodium sulfate, filtered and concentrated in vacuo. 1.1 g of pale brown solid was obtained, which was purified by chromatography [silica gel 60 (80 g); ethyl acetate/methanol 15:1; 900 ml)]. 740 mg (67%) of N,N-dimethyl-4-(3-methyl-5-(trifluoromethyl)-1H-indol-2-yl)-1-phenylcyclohex-3-enamine, which, however, still contained approx. 10% of Ket-10, were obtained.

Citric acid (80 mg, 0.413 mmol), dissolved in ethanol (2 ml), was added to (±)-2-(4-(dimethylamino)-4-phenylcyclohex-1-enyl)-3-methyl-5-trifluoromethyl-1H-indole (150 mg, 0.375 mmol), dissolved in ethanol (5 ml). The clear green solution was stirred at RT for 20 h and then concentrated down to approx. 0.5 ml, and diethyl ether (5 ml) was subsequently added until crystallization occurred. After filtration with suction, Example 25 was obtained in a yield of 56% (124 mg) with a melting point which cannot be determined. It was not possible for the ketone Ket-10 already still present in the precursor to be separated off during the citrate preparation.

Example 26

(±)-2-(4-(Dimethylamino)-4-benzylcyclohex-1-enyl)-3-methyl-5-fluoro-1H-indole, citrate (1:1)

5-Fluoro-3-methylindole (Ind-8, 596 mg, 4 mmol) was dissolved in methylene chloride (20 ml) together with Ket-3 (932 mg, 4 mmol), and trifluoromethanesulfonic acid (0.4 ml, 4.6 mmol) was added. The mixture was stirred at RT for 22 h.—For working up, 2 N NaOH (10 ml) was added to the reaction mixture. The mixture was stirred for a further 20 min. After separation of the phases, the aqueous phase was extracted with methylene chloride (2×20 ml). The combined organic extracts were dried over MgSO$_4$ and then concentrated. The crude product obtained (1.50 g) was taken up in ethanol (10 ml), while heating. The clear solution was cooled and left at 5° C. for 14 h. Further EtOH (10 ml) was added to the crystal slurry formed and the crystal slurry was separated off by means of a frit. (±)-2-(4-(Dimethylamino)-4-benzyl-cyclohex-1-enyl)-3-methyl-5-fluoro-1H-indole was obtained in this way in a yield of 558 mg (38%, m.p.: 62-65° C.) in crystalline form. Further product (109 mg) was obtained by separation by column chromatography (mobile phase: ethyl acetate), so that the total yield was 667 mg (46%).

(±)-2-(4-(Dimethylamino)-4-benzylcyclohex-1-enyl)-3-methyl-5-fluoro-1H-indole (150 mg, 0.41 mmol) was dissolved in methanol (10 ml) with gentle heating, and citric acid (80 mg, 0.42 mmol), dissolved in methanol (2 ml), was added. The solvent was then concentrated on a rotary evaporator. The residue obtained was triturated with H$_2$O (approx. 5 ml). A tacky oil was formed, which solidified to a vitreous solid on drying in vacuo. Example 26 was obtained in this way in a yield of 161 mg (70%)

Example 27

(±)-2-(4-(Dimethylamino)-4-butylcyclohex-1-enyl)-3-methyl-5-fluoro-1H-indole, citrate (1:1)

5-Fluoro-3-methylindole (Ind-8) (596 mg, 4 mmol) was dissolved in methylene chloride (30 ml) together with the ketone Ket-4 (788 mg, 4 mmol), and trifluoromethanesulfonic acid (400 µl, 4.6 mmol) was added. The mixture was stirred at RT for 24 h. For working up, 2 N NaOH (30 ml) was added to the reaction mixture and the mixture was stirred at RT for 20 min. After the organic phase had been separated off, the aqueous phase was extracted with methylene chloride (3×15 ml). The combined organic extracts were dried over Na$_2$SO$_4$ and then concentrated. The crude product obtained (1.4 g) was purified by column chromatography [silica gel 60 (50 g); ethyl acetate (500 ml)] (±)-2-(4-(Dimethylamino)-4-butylcyclohex-1-enyl)-3-methyl-5-fluoro-1H-indole was obtained in this way in a yield of 160 mg (13%) as a white solid.

(±)-2-(4-(Dimethylamino)-4-butylcyclohex-1-enyl)-3-methyl-5-fluoro-1H-indole (160 mg, 0.49 mmol) was dissolved in isopropanol (10 ml) at the boiling point and citric acid (94 mg, 0.49 mmol), dissolved in hot isopropanol (2 ml), was added. The solution was cooled to 5° C. and kept in a refrigerator for 16 h. Since no solid precipitated out by this procedure, isopropanol was distilled off on a rotary evaporator. Example 27( ) was obtained in a yield of 254 mg (100%, melting point: 31-35° C.).

Example 28

(±)-2-(4-(Dimethylamino)-4-phenylcyclohex-1-enyl)-3-methyl-5-fluoro-1H-indole, citrate (1:1)

5-Fluoro-3-methylindole (Ind-8) (498 mg, 2 mmol) was dissolved in methylene chloride (20 ml) together with the ketone Ket-10 (434 mg, 2 mmol), and trifluoromethanesulfonic acid (0.2 ml, 2.3 mmol) was added. The mixture was stirred at RT for 22 h.—For working up, 2 N NaOH (10 ml) was added to the reaction mixture. The mixture was stirred for a further 20 min. After separation of the phases, the aqueous phase was extracted with methylene chloride (2×20 ml). The combined organic extracts were dried over MgSO$_4$ and then concentrated. The crude product obtained (710 mg) was taken up in boiling ethanol (18 ml). The clear solution was cooled and left at 5° C. for 14 h. The precipitate formed was separated off by means of a frit. (±)-2-(4-(Dimethylamino)-4-phenyl-cyclohex-1-enyl)-3-methyl-5-fluoro-1H-indole was obtained in this way in a yield of 399 mg (57%, m.p.: 171-175° C.) in crystalline form.

(±)-2-(4-(Dimethylamino)-4-phenylcyclohex-1-enyl)-3-methyl-5-fluoro-1H-indole (150 mg, 0.43 mmol) was dissolved in isopropanol (10 ml) at the boiling point and citric acid (100 mg, 0.52 mmol), dissolved in hot isopropanol (5 ml), was added. The solution volume was reduced to approx. 6 ml and the mixture was then cooled to 5° C. (refrigerator) and left to stand for 12 h. The precipitate was separated off by means of a frit and then dried. Example 28 was obtained in this way in a yield of 151 mg (79%, melting point: 88-93° C.)( ).

Example 29

(±)-2-(4-(Dimethylamino)-4-phenylcyclohex-1-enyl)-3-methyl-5-methoxy-1H-indole, citrate (2:1)

5-Methoxyskatole (Ind-9) (644 mg, 4 mmol) was dissolved in methylene chloride (40 ml) together with the ketone Ket-10 (868 mg, 4 mmol), and trifluoromethanesulfonic acid (0.4 ml, 4.5 mmol) was added. The mixture was stirred at RT for 2.5 d.—For working up, 2 N NaOH (20 ml) was added to the reaction mixture and the mixture was stirred at RT for 60 min. After the organic phase had been separated off, the aqueous phase was extracted with methylene chloride (2×20 ml). The combined organic extracts were dried over MgSO$_4$ and then concentrated. It was possible for the crude product obtained (1.2 g) to be purified by column chromatography [silica gel 60 G (10 g); cyclohexane/EtOAc 1:1, (100 ml)]. (±)-2-(4-(Dimethylamino)-4-phenylcyclohex-1-enyl)-3-methyl-5-methoxy-1H-indole was obtained in a yield of 400 mg (27%) as a solid (melting point: 175-185° C.).

(±)-2-(4-(Dimethylamino)-4-phenylcyclohex-1-enyl)-3-methyl-5-methoxy-1H-indole (150 mg, 0.41 mmol) was dissolved in isopropanol (15 ml) at the boiling point, and citric acid (80 mg, 0.42 mmol), dissolved in hot isopropanol (2 ml), was added. After cooling of the solution, a precipitate precipitated out. To bring the precipitation to completion, the mixture was cooled to 5° C. (refrigerator) and left at this temperature for 17 h. The precipitate was separated off by means of a frit and then dried. Example 29 was obtained in this way in a yield of 124 mg (65%) as a pink solid with a melting point of 204-209° C.

Example 30

(±)-2-(4-(Dimethylamino)-4-benzylcyclohex-1-enyl)-3-methyl-1H-indole, citrate (2:1)

3-Methylindole (Ind-10, 524 mg, 4 mmol) was dissolved in methylene chloride (20 ml) together with the ketone Ket-3 (932 mg, 4 mmol), and trifluoromethanesulfonic acid (0.4 ml, 4.6 mmol) was added. The mixture was stirred at RT for 22 h.—For working up, 2 N NaOH (10 ml) was added to the reaction mixture. The mixture was stirred for a further 10 min. After separation of the phases, the aqueous phase was extracted with methylene chloride (2×20 ml). The combined organic extracts were dried over MgSO$_4$ and then concentrated. The crude product obtained (1.28 g) was triturated with methanol (7 ml) and the mixture formed was left at 5° C. for 14 h. The solid formed, which became vitreous on drying, was separated off by means of a frit. (±)-2-(4-(Dimethylamino)-4-benzylcyclohex-1-enyl)-3-methyl-1H-indole was obtained in this way in a yield of 510 mg (37%) in adequate purity.

(±)-2-(4-(Dimethylamino)-4-benzylcyclohex-1-enyl)-3-methyl-1H-indole (100 mg, 0.29 mmol) was dissolved in methanol (10 ml) with gentle heating, and citric acid (58 mg, 0.3 mmol), dissolved in methanol (1 ml), was added. The solvent was then concentrated on a rotary evaporator. The residue obtained was triturated with $H_2O$ (approx. 5 ml). A solid was formed, which was isolated by means of a frit. Example 30 was obtained in this way in a yield of 78 mg (61%).

Example 31

(±)-2-(4-(Dimethylamino)-4-butylcyclohex-1-enyl)-3-methyl-1H-indole, citrate (1:1)

3-Methylindole (Ind-10, 524 mg, 4 mmol) was dissolved in methylene chloride (30 ml) together with the ketone Ket-4 (788 mg, 4 mmol), and trifluoromethanesulfonic acid (0.4 ml, 4.6 mmol) was added. The mixture was stirred at RT for 22 h.—For working up, 2 N NaOH (10 ml) was added to the reaction mixture. The mixture was stirred for a further 20 min. After separation of the phases, the aqueous phase was extracted with methylene chloride (2×20 ml). The combined organic phases were dried over $MgSO_4$ and then concentrated. The crude product obtained (1.21 g) was purified by column chromatography (mobile phase: ethyl acetate). (±)-2-(4-(Dimethylamino)-4-butylcyclohex-1-enyl)-3-methyl-1H-indole was obtained as a fraction contaminated with about 10% of Ket-4 in a yield of 315 mg (23%) as a semi-solid substance.

(±)-2-(4-(Dimethylamino)-4-butylcyclohex-1-enyl)-3-methyl-1H-indole (120 mg, 0.39 mmol) was dissolved in methanol (10 ml) with gentle heating, and citric acid (80 mg, 0.42 mmol), dissolved in methanol (1 ml), was added. Since no precipitate was formed after cooling of the solution (5° C.), the solvent was concentrated on a rotary evaporator. The residue obtained was taken up in 4 ml of hot isopropanol. After cooling, a tacky precipitate precipitated out, which solidified to a vitreous solid on drying in vacuo. Example 31, which became tacky again on standing in air, was obtained in this way in a yield of 105 mg (53%) as the citrate.

Example 32

(±)-2-(4-(Dimethylamino)-4-phenylcyclohex-1-enyl)-3-methyl-1H-pyrrolo[2,3-b]pyridine, citrate (1:1)

4-(Dimethylamino)-4-phenyl-1-(prop-1-ynyl)cyclohexanol

The ketone Ket-10 (3,000 mg, 13.81 mmol) was initially introduced into tetrahydrofuran (absolute, 50 ml) at −78° C. Prop-1-ynyl magnesium bromide (31.8 ml, 15.88 mmol, 0.5 M in tetrahydrofuran) was added dropwise under argon. The reaction mixture was then stirred at −78° C. for 15 min. Thereafter, it was warmed to room temperature and stirred at this temperature for 1 h. Ammonium chloride solution (50 ml; 1.0 M) was then added. The phases were separated. The aqueous phase was extracted with tetrahydrofuran (3×50 ml). The combined organic phases were dried with sodium sulfate and the volatile constituents were then removed completely in vacuo. A pale brown oil remained, to which diethyl ether (20 ml) was added. A white solid precipitated out (990 mg, 4-dimethylamino-4-phenyl-1-(prop-1-ynyl)cyclohexanol, non-polar diastereomer). The wash solution was concentrated down to 5 ml in vacuo. A white solid again precipitated out (1,350 mg, diastereomer mixture). The wash solution was evaporated slowly to 3 ml. A product fraction again precipitated out (410 mg; both diastereomers). Yield: 2,750 mg (10.68 mmol; 77%, diastereomer mixture)

4-Dimethylamino-1-(3-methyl-1H-pyrrolo[2,3-b]pyridin-2-yl)-4-phenylcyclohexanol

2-Amino-3-iodopyridine (3,108 mg, 14.13 mmol), 4-(dimethylamino)-4-phenyl-1-(prop-1-ynyl)cyclohexanol (4,000 mg, 15.54 mmol), lithium chloride (630 mg, 14.83 mmol) and sodium carbonate (4.49 g, 42.38 mmol) were combined in dimethylformamide (absolute, 60 ml) in an argon atmosphere. The catalyst ([Pd(dppf)$Cl_2$×$CH_2Cl_2$], 1,154 mg, 1.41 mmol) was then added. The red solution was heated at 79° C. (oil bath temperature) for 5 h. To bring the reaction to completion, a further 0.3 equivalent of 2-amino-3-iodopyridine (932 mg, 4.24 mmol) and 0.05 equivalent of catalyst (577 mg, 0.71 mmol) were added. Thereafter, the mixture was stirred at 99° C. (oil bath temperature) for a further 2 h. The black reaction mixture was cooled to room temperature and water (50 ml; stirring for 10 min) and methylene chloride (50 ml) were added in succession. The phases were separated (the mixture was filtered over kieselguhr) and the aqueous phase was extracted with methylene chloride (3×20 ml). The combined organic phases were washed with saturated NaCl solution (3×20 ml) and dried over sodium sulfate. After filtration, the volatile constituents were removed completely in vacuo. The residue was absorbed on kieselguhr and separated by chromatography (silica gel [200 g]; chloroform/ethanol [9:1 1,000 ml]). 1,200 mg (3.43 mmol; 22% of the non-polar diastereomer were isolated as a colourless solid.

(±)-2-(4-(Dimethylamino)-4-phenylcyclohex-1-enyl)-3-methyl-1H-pyrrolo[2,3-b]pyridine, citrate (1:1)

4-Dimethylamino-1-(3-methyl-1H-pyrrolo[2,3-b]pyridin-2-yl)-4-phenylcyclohexanol (900 mg, 2.58 mmol) was dissolved in methanesulfonic acid (20 ml), $P_4O_{10}$ (approx. 1 g) was added and the slightly coloured (pale brown) solution was stirred at 77° C. (oil bath temperature) for 3 h. The reaction mixture was rendered basic with 5 M sodium hydroxide solution. Methylene chloride (30 ml) was then added and the mixture was stirred for 10 min. The phases were separated. The aqueous phase was extracted with methylene chloride (3×35 ml). The combined organic phases were dried with sodium sulfate and the volatile constituents were then removed completely in vacuo. 805 mg (2.43 mmol; 94%) of a dark brown solid ((±)-2-(4-(dimethylamino)-4-phenylcyclohex-1-enyl)-3-methyl-1H-pyrrolo[2,3-b]pyridine) remained.

(±)-N,N-Dimethyl-N-[4-(3-methyl-1H-pyrrolo[2,3-b]pyridin-2-yl)-1-phenylcyclohex-3-enyl]amine (43 mg, 0.13 mmol) was dissolved in ethanol (10 ml). Citric acid (27 mg, 0.14 mmol) was added to the dark solution. The mixture was stirred at the boiling point for 1 h. The reaction mixture was cooled to room temperature and concentrated to approx. 3 ml in vacuo. The flask was stored at room temperature and at 0° C. The solution was covered with a layer of approx. 5 ml of diethyl ether and left to stand at room temperature for 3 days.

A beige-coloured solid precipitated out. The supernatant solution was siphoned off and discarded. The pulverulent solid was dried in vacuo. 30 mg (0.057 mmol; 44%) of the target compound Example 32 were obtained (melting point: 107° C.).

$^1$H NMR (400 MHz, RT, CD$_3$OD) δ ppm: 2.08 (s, br, 1H), 2.19 (s, 3H), 2.46 (s, br, 1H), 2.72 (s, 6H), 2.79 (dd, 4H), 2.60-2.85 (among these, br, further 2H) 2.97 (d, br, 1H), 3.68 (d, br, 1H), 6.14 (s, 1H), 7.01 (m, 1H), 7.40-7.60 (m, 2H), 7.73 (d, 2H), 7.84 (dd, 1H), 8.08 (s, br, 1H).

Example 33

(±)-2-(4-(Dimethylamino)-4-benzylcyclohex-1-enyl)-3-cyclopropyl-1H-indole hydrochloride The ketone Ket-3 (693 mg, 3 mmol) and Ind-11 (472 mg, 3.0 mmol) were dissolved in abs. methylene chloride (40 ml), trifluoromethanesulfonic acid (0.293 ml, 495 mg, 3.3 mmol) was added and the mixture was stirred at room temperature for 67 h. Since the reaction was not complete, further trifluoromethanesulfonic acid (0.586 ml, 990 mg, 6.6 mmol) was again added and the mixture was stirred at room temperature for 5 h. Water (20 ml) and 1 N sodium hydroxide solution (15 ml) were added to the mixture and the mixture was stirred for 30 min. The phases were separated. The aqueous phase was extracted with methylene chloride (30 ml). The organic phases were combined, washed with water (20 ml), dried with sodium sulfate and concentrated. The residue was a brown oil (1.17 g), which was separated by chromatography [silica gel 60 (70 g); ethyl acetate (500 ml), ethyl acetate/methanol (4:1 (400 ml)]. (±)-2-(4-(Dimethylamino)-4-benzylcyclohex-1-enyl)-3-cyclopropyl-1H-indole was obtained as a colourless solid (100 mg). A mixed fraction obtained, of ketone Ket-3 and product, was separated again by chromatography [silica gel 60 (70 g); ethyl acetate (500 ml), ethyl acetate/methanol 4:1, (300 ml)]. In addition to the product (102 mg), a further mixed fraction (490 mg) was obtained, which was separated again by chromatography. [Silica gel 60 (70 g); ethyl acetate/cyclohexane 1:1, (800 ml), methanol (500 ml)]. Only a small amount (26 mg) of pure product was obtained. The mixed fraction (286 mg) was dissolved in ethyl acetate (30 ml), water (30 ml) and 1 N hydrochloric acid (5 ml) were added and the mixture was stirred at room temperature for 1 h. A colourless solid which formed between the phases was separated off by filtration and washed with water (2×10 ml) and with ethyl acetate (2×10 ml). The hydrochloride Example 33 (221 mg) was obtained in this way with a melting point of 222-224° C., total yield: 39%).

Example 34

(±)-2-(4-(Dimethylamino)-4-butylcyclohex-1-enyl)-3-cyclopropyl-1H-indole

The ketone Ket-4 (592 mg, 3 mmol) and Ind-11 (472 mg, 3.0 mmol) were dissolved in abs. methylene chloride (40 ml), trifluoromethanesulfonic acid (0.293 ml, 495 mg, 3.3 mmol) was added and the mixture was stirred at room temperature for 67 h. Since the reaction was not complete, trifluoromethanesulfonic acid (0.586 ml, 990 mg, 6.6 mmol) was again added and the mixture was stirred at room temperature for 5 h. Water (20 ml) and 1 N sodium hydroxide solution (15 ml) were added to the mixture and the mixture was stirred for 30 min. The phases were separated. The aqueous phase was extracted with methylene chloride (30 ml). The organic phases were combined, washed with water (20 ml), dried with sodium sulfate and concentrated. The residue was a brown oil (1.06 g), which was separated by chromatography [silica gel 60 (80 g), ethyl acetate (800 ml), ethyl acetate/methanol 4:1, (500 ml), methanol (300 ml)]. Example 34 was obtained as a beige-coloured solid (226 mg). n-Hexane (5 ml) was added to a mixed fraction (236 mg) and the mixture was stirred for 10 min. Example 34 remained in undissolved form and was separated off by filtration and washing with n-hexane (2×3 ml). Yield: 348 mg (34%)

Melting point: 126-130° C.

Example 35

(±)-2-(4-(Dimethylamino)-4-phenylcyclohex-1-enyl)-3-cyclopropyl-1H-indole

Variant 1: Ketone Ket-10 (652 mg, 3.0 mmol) and indole Ind-11 (472 mg, 3 mmol) were dissolved in abs. methylene chloride (40 ml), trifluoromethanesulfonic acid (0.293 ml, 495 mg, 3.3 mmol) was added and the mixture was stirred at room temperature for 4 days. No conversion was detectable. Water (20 ml) and 1 N sodium hydroxide solution (15 ml) were added to the mixture and the mixture was stirred for 30 min. The phases were separated. The aqueous phase was extracted with methylene chloride (20 ml). The organic phases were combined, washed with water (20 ml), dried with sodium sulfate and concentrated. The residue was a brown oil (1.1 g), which was dissolved in abs. 1,2-dichloroethane (40 ml). Trifluoromethanesulfonic acid (0.44 ml, 743 mg, 4.95 mmol) was added to a portion of the solution (20 ml, 1.5 mmol of educts) and the mixture was stirred at room temperature for 23 h. Water (10 ml) and 1 N sodium hydroxide solution (10 ml) were added to the mixture and the mixture was stirred for 30 min. The phases were separated. The aqueous phase was extracted with methylene chloride (20 ml). The organic phases were combined, washed with water (20 ml), dried with sodium sulfate and concentrated. The residue was a brown oil (593 mg), which was separated by chromatography [silica gel 60 (50 g); trichloromethane/methanol (40:1 (600 ml), trichloromethane/methanol (20:1 (400 ml)]. Example 35 was obtained as a beige-coloured solid in a yield of 60% (302 mg) with a melting point of 180-187° C.

Variant 2: Trifluoromethanesulfonic acid (0.147 ml, 248 mg, 1.65 mmol) was added to a solution of Ket-10 and Ind-11 in 1,2-dichloroethane (1.5 mmol, 20 ml) and the mixture was heated at 70° C. for 8 h. Further trifluoromethanesulfonic acid (0.293 ml, 495 mg, 3.3 mmol) was added and the mixture was stirred at room temperature for 24 h. Water (10 ml) and 1 N sodium hydroxide solution (10 ml) were added to the mixture and the mixture was stirred for 30 min. The phases were separated. The aqueous phase was extracted with methylene chloride (30 ml). The organic phases were combined, washed with water (20 ml), dried with sodium sulfate and concentrated. The residue was a brown oil (572 mg), which was separated by chromatography [silica gel 60 (50 g); trichloromethane/methanol (40:1 (650 ml), trichloromethane/methanol (20:1 (400 ml)]. Example 35 was obtained as a beige-coloured solid in a yield of 43% (217 mg).

Example 36

(±)-2-(4-(Dimethylamino)-4-benzylcyclohex-1-enyl)-3-(cyclohexylmethyl)-1H-indole hydrochloride 3-Cyclohexylmethyl-1H-indole (Ind-12, 640 mg, 3 mmol) was dissolved in abs. methylene chloride (40 ml) together with ketone Ket-3 (694 mg, 3 mmol), and trifluoromethanesulfonic acid (0.396 ml, 4.51 mmol) was added. The mixture was stirred at room temperature for 90 h. For working up, 5 N NaOH (10 ml) was added to the reaction solution. The mixture was stirred for a further 10 min. After separation of the phases, the aqueous phase was extracted with methylene chloride (3×10 ml). The combined organic extracts were dried over $Na_2SO_4$ and then concentrated. The crude product obtained (1.34 g of brown oil) was dissolved in diethyl ether (30 ml). 2.5 N HCl (20 ml) was added at room temperature. The mixture was stirred at room temperature for 5 h. The precipitate was filtered off, washed with a little water and diethyl ether and dried. Example 36 (761 mg, 55%, melting point: 152-160° C.) was obtained as a beige-coloured solid.

Example 37

(±)-2-(4-(Dimethylamino)-4-benzylcyclohex-1-enyl)-3-benzyl-1H-indole hydrochloride 3-Benzyl-1H-indole (Ind-108) (622 mg, 3 mmol) was dissolved in abs. methylene chloride (40 ml) together with the ketone Ket-3 (694 mg, 2 mmol), and trifluoromethanesulfonic acid (0.396 ml, 4.51 mmol) was added. The mixture was stirred at room temperature for 81 h. For working up, 5 N NaOH (10 ml) was added to the reaction solution. The mixture was stirred for a further 10 min. After separation of the phases, the aqueous phase was extracted with methylene chloride (3×10 ml). The combined organic phases were dried over $Na_2SO_4$ and then concentrated. The crude product obtained (1.30 g of brown oil) was dissolved in toluene (5 ml). 1 N HCl (10 ml) was added at room temperature. Thereafter, diethyl ether (25 ml) was also added. The mixture was stirred at room temperature for 3 h. The precipitate was filtered off, washed with a little water and diethyl ether and dried. Example 37 (824 mg, 60%, melting point: 235-250° C., beige-coloured solid.

Example 38

(±)-2-(4-(Dimethylamino)-4-butylcyclohex-1-enyl)-3-(cyclohexylmethyl)-1H-indole hydrochloride Ind-12 (640 mg, 3 mmol) was dissolved in abs. methylene chloride (40 ml) together with ketone Ket-4 (592 mg, 2 mmol), and trifluoromethanesulfonic acid (0.396 ml, 4.51 mmol) was added. The mixture was stirred at room temperature for 90 h. For working up, 5 N NaOH (10 ml) was added to the reaction solution. The mixture was stirred for a further 10 min. After separation of the phases, the aqueous phase was extracted with methylene chloride (3×10 ml). The combined organic extracts were dried over $Na_2SO_4$ and then concentrated. The crude product obtained (1.33 g of brown oil) was dissolved in diethyl ether (30 ml). 2.5 N HCl (20 ml) was added at room temperature. The mixture was stirred at room temperature for 3 h. The precipitate was filtered off, washed with a little water and diethyl ether and dried. Example 38 was obtained (836 mg, 65%, melting point: 241-244° C.) (as a beige-coloured solid.

Example 39

(±)-2-(4-(Dimethylamino)-4-butylcyclohex-1-enyl)-3-benzyl-1H-indole (39)

3-Benzyl-1H-indole (Ind-108, 622 mg, 3 mmol) was dissolved in abs. methylene chloride (40 ml) together with the ketone Ket-4 (592 mg, 3 mmol), and trifluoromethanesulfonic acid (0.396 ml, 4.51 mmol) was added. The mixture was stirred at room temperature for 81 h. For working up, 5 N NaOH (10 ml) was added to the reaction solution. The mixture was stirred for a further 10 min. After separation of the phases, the aqueous phase was extracted with methylene chloride (3×10 ml). The combined organic extracts were dried over $Na_2SO_4$ and then concentrated. It was possible for the crude product obtained (1.17 g, brown oil) to be purified by column chromatography [silica gel 60 (80 g); ethyl acetate/methanol 5:1, (1,800 ml)]. Example 39 was obtained (464 mg, 40%, melting point: 107-115° C.) (as an orange-coloured solid.

Example 40

(±)-2-(4-(Dimethylamino)-4-phenylcyclohex-1-enyl)-3-(cyclohexylmethyl)-1H-indole hydrochloride (40)

3-Cyclohexylmethyl-1H-indole (Ind-12) (640 mg, 3 mmol) was dissolved in abs. methylene chloride (40 ml) together with the ketone Ket-10 (652 mg, 3 mmol), and trifluoromethanesulfonic acid (0.396 ml, 4.51 mmol) was added. The mixture was stirred at room temperature for 90 h. For working up, 5 N NaOH (10 ml) was added to the reaction solution. The mixture was stirred for a further 10 min. After separation of the phases, the aqueous phase was extracted with methylene chloride (3×10 ml). The combined organic extracts were dried over $Na_2SO_4$ and then concentrated. The crude product obtained (1.34 g) was dissolved in hot toluene (5 ml). 2.5 N HCl (20 ml) and diethyl ether (25 ml) was added at room temperature. The mixture was stirred at room temperature for 3 h. The solid was filtered off, washed with a little water and diethyl ether and dried. (968 mg, 72%, melting point: 235-238° C.) Example 40 were obtained.

Example 41

(±)-2-(4-(Dimethylamino)-4-phenylcyclohex-1-enyl)-3-(cyclohexylmethyl)-1H-indole hydrochloride (41)

3-Benzyl-1H-indole (Ind-108, 622 mg, 3 mmol) was dissolved in abs. methylene chloride (40 ml) together with ketone Ket-10 (652 mg, 3 mmol), and trifluoromethanesulfonic acid (0.396 ml, 4.51 mmol) was added. The mixture was stirred at room temperature for 81 h. For working up, 5 N NaOH (10 ml) was added to the reaction solution. The mixture was stirred for a further 10 min. After separation of the phases, the aqueous phase was extracted with methylene chloride (3×10 ml). The combined organic extracts were dried over $Na_2SO_4$ and then concentrated. The crude product obtained (1.24 g) was dissolved in toluene (5 ml). 1 N HCl (10 ml) and diethyl ether (25 ml) were added at room temperature. The mixture was stirred at room temperature for 3 h. The solid which had precipitated out was filtered off, washed with a little water and diethyl ether and dried. 840 mg (63%) of Example 41 (melting point: 163-166° C.) were obtained.

Example 42

(±)-2-(4-(Dimethylamino)-4-benzylcyclohex-1-enyl)-3-propyl-1H-indole

3-Propyl-1H-indole (Ind-13, 797 mg, 5.0 mmol) was dissolved in abs. methylene chloride (60 ml) together with ketone Ket-3 (1,157 mg, 5.0 mmol), and trifluoromethanesulfonic acid (0.485 ml, 5.52 mmol) was added. The mixture was stirred at room temperature for 88 h. For working up, the reaction mixture was extracted with water (3×40 ml). The organic phase was then washed with 1 N NaOH solution (40 ml), dried over $Na_2SO_4$ and then concentrated. The crude product obtained (1.68 g, brown oil) was purified by chromatography [silica gel 60 (140 g); ethyl acetate/methanol 20:1 (1,260 ml)]. 1,031 mg (55%) of Example 42 (melting point: 104-107° C.) were obtained.

Example 43

(±)-2-(4-(Dimethylamino)-4-butylcyclohex-1-enyl)-3-propyl-1H-indole

3-Propyl-1H-indole (Ind-13) (797 mg, 5.0 mmol) was dissolved in abs. methylene chloride (60 ml) together with the ketone Ket-4 (987 mg, 5.0 mmol), and trifluoromethanesulfonic acid (0.485 ml, 5.52 mmol) was added. The mixture was stirred at room temperature for 88 h. For working up, the reaction solution was extracted with water (3×40 ml). The organic phase was washed with 1 N NaOH solution (40 ml), dried over $Na_2SO_4$ and then concentrated. The crude product obtained (1.44 g, brown oil) was purified by chromatography [silica gel 60 (140 g); ethyl acetate/methanol 10:1 (550 ml), ethyl acetate/methanol (5:1 (600 ml), ethyl acetate/methanol 2:1 (1,200 ml)]. 808 mg (48%) of Example 43 (melting point: 114-120° C.) were obtained.

Example 44

(±)-2-(4-(Dimethylamino)-4-phenylcyclohex-1-enyl)-3-propyl-1H-indole (44)

3-Propyl-1H-indole (Ind-13) (1,035 mg, 6.50 mmol) was dissolved in abs. methylene chloride (80 ml) together with ketone Ket-10 (1,413 mg, 6.50 mmol), and trifluoromethanesulfonic acid (0.630 ml, 7.17 mmol) was added. The mixture was stirred at room temperature for 88 h. For working up, the reaction solution was extracted with water (3×40 ml). The organic phase was then washed with 1 N NaOH solution (40 ml), dried over $Na_2SO_4$ and then concentrated. The crude product obtained (1.90 g, brown solid) was purified by chromatography [silica gel 60 (140 g); trichloromethane/methanol 10:1 (550 ml), trichloromethane/methanol 5:1 (600 ml)]. 1,130 mg (48%) of Example 44 (melting point: 168-178° C.) were obtained.

Example 45

(±)-2-(4-(Dimethylamino)-4-benzylcyclohex-1-enyl)-3-(2-(pyridin-4-yl)ethyl)-1H-indole 3-(2-Pyridin-4-ylethyl)-1H-indole (Ind-14, 667 mg, 3 mmol) was dissolved in abs. methylene chloride (45 ml) together with the ketone (Ket-3, 652 mg, 3 mmol), and trifluoromethanesulfonic acid (0.553 ml, 6.3 mmol) was added. The mixture was stirred at RT for 67 h, a brown oil precipitating out. For working up, 1 N NaOH (10 ml) and THF (10 ml) were added to the reaction solution. The mixture was stirred for a further 60 min. After separation of the phases, the aqueous phase was extracted with methylene chloride (3×10 ml). The combined organic phases were dried over $Na_2SO_4$ and then concentrated. The crude product obtained (1.22 g) was purified by column chromatography [silica gel 60 (100 g); ethyl acetate/methanol (10:1, 1,100 ml), ethyl acetate/methanol (2:1, 500 ml), ethyl acetate/methanol (1:2, 750 ml)]. In addition to a bisindole compound (152 mg, m.p.: 314-317° C.) the desired product (45) was obtained as a white solid (379 mg, 29%, m.p.: 154-157° C.).

Example 46

(±)-2-(4-(Dimethylamino)-4-butylcyclohex-1-enyl)-3-(2-(pyridin-4-yl)ethyl)-1H-indole 3-(2-Pyridin-4-ylethyl)-1H-indole (Ind-14, 667 mg, 3 mmol) was dissolved in methylene chloride (45 ml) together with the ketone (Ket-4, 592 mg, 3 mmol), and trifluoromethanesulfonic acid (0.553 ml, 6.3 mmol) was added. The mixture was stirred at RT for 67 h, a brown oil precipitating out. For working up, 1 N NaOH (10 ml) and THF (10 ml) were added to the reaction solution. The mixture was stirred for a further 60 min. After separation of the phases, the aqueous phase was extracted with methylene chloride (3×10 ml). The combined organic phases were dried over $Na_2SO_4$ and then concentrated. The crude product obtained (1.24 g) was purified by column chromatography [silica gel 60 (100 g); ethyl acetate/methanol (10:1, 1,200 ml), ethyl acetate/methanol (5:1, 600 ml), ethyl acetate/methanol (2:1, (700 ml), ethyl acetate/methanol (1:2, 750 ml), methanol (800 ml)]. In addition to a bisindole compound (121 mg, m.p.: 274-282° C., the desired product 46 was obtained as a white solid (437 mg, 36%, m.p.: 145-149° C.).

$^1$H NMR (400 MHz, $CDCl_3$) δ ppm: 0.93 (t, J=6.89, Hz, 3H), 1.16-1.60 (m, 6H), 1.63-1.87 (m, 2H), 1.92-2.06 (m, 1H), 2.06-2.51 (m, 9H), 2.95 (t, J=7.82 Hz, 2H), 3.12 (t, J=7.82 Hz, 2H), 5.82 (m, 1H), 7.02-7.20 (m, 4H), 7.24-7.34 (m, 1H), 7.53 (d, J=7.77 Hz, 1H), 8.05 (s, 1H), 8.46 (d, J=5.00 Hz, 1H)

$^{13}$C NMR (101 MHz, $CDCl_3$) δ ppm: 14.2, 23.7, 25.6, 26.0, 26.9, 28.5, 30.5, 32.2, 36.4, 38.0, 55.9, 110.4, 110.6, 118.3, 119.4, 121.8, 124.0, 126.5, 128.7, 129.2, 135.1, 136.3, 149.5, 151.2

Example 47

(±)-2-(4-(Dimethylamino)-4-phenylcyclohex-1-enyl)-3-(2-(pyridin-4-yl)ethyl)-1H-indole 3-(2-Pyridin-4-ylethyl)-1H-indole (Ind-14, 667 mg, 3 mmol) was dissolved in abs. methylene chloride (45 ml) together with the ketone (Ket-10, 652 mg, 3 mmol), and trifluoromethanesulfonic acid (0.553 ml, 6.3 mmol) was added. The mixture was stirred at RT for 64 h, a brown oil precipitating out. For working up, 1 N NaOH (10 ml) and THF (10 ml) were added to the reaction solution. The mixture was stirred for a further 60 min. After separation of the phases, the aqueous phase was extracted with methylene chloride (3×10 ml). The combined organic extracts were dried over $Na_2SO_4$ and then concentrated. The crude product obtained (1.34 g) was purified by column chromatography [silica gel 60 (100 g); ethyl acetate/methanol (20:1, 500 ml), ethyl acetate/methanol (5:1, 870 ml), ethyl acetate/methanol (2:1, 320 ml), ethyl acetate/methanol (1:2, 550 ml)]. The desired product 47 was obtained as a colourless solid (339 mg, 27%, m.p.: 193-198° C.).

$^1$H NMR (300 MHz, DMSO-$d_6$) δ ppm: 1.61-1.83 (m, 1H), 1.97-2.23 (m, 8H), 2.27-2.44 (m, 1H), 2.50-2.82 (m, 4H), 2.82-3.06 (m, 2H), 6.10 (m, 1H), 6.86-6.96 (m, 1H), 6.96-7.06 (m, 1H), 7.06-7.15 (m, 2H), 7.15-7.35 (m, 4H), 7.41-7.54 (m, 3H), 8.41 (dd, J=4.43, 1.51 Hz, 2H), 10.63 (s, 1H)

$^{13}$C NMR (101 MHz, DMSO-d$_6$) δ ppm: 25.5, 26.6, 27.1, 32.6, 35.9, 60.1, 109.3, 110.7, 117.9, 118.3, 120.8, 123.8, 125.6, 126.3, 127.0, 127.4, 128.1, 129.7, 135.1, 135.8, 142.6, 149.3, 150.5

Example 48

(±)-3-(2-(4-Benzyl-4-(dimethylamino)cyclohex-1-enyl)-1H-indol-3-yl)propan-1-ol, citrate (1:1)

Indole Ind-16 (350 mg, 2 mmol) was dissolved in methylene chloride (40 ml) together with ketone Ket-3 (463 mg, 2 mmol), and trifluoromethanesulfonic acid (270 μl, 3 mmol) was added. The mixture was stirred at RT for 24 h. For working up, 2 N NaOH (30 ml) was added to the reaction mixture and the mixture was stirred at RT for 20 min. After the organic phase had been separated off, the aqueous phase was extracted with methylene chloride (3×15 ml). The combined organic extracts were dried over Na$_2$SO$_4$ and then concentrated. It was possible for the crude product obtained (780 mg) to be purified by column chromatography [silica gel 60 (100 g); MeOH (500 ml)]. (±)-3-(2-(4-Benzyl-4-(dimethylamino)cyclohex-1-enyl)-1H-indol-3-yl)propan-1-ol was obtained in a yield of 356 mg (46%) as a white solid.

(±)-3-(2-(4-Benzyl-4-(dimethylamino)cyclohex-1-enyl)-1H-indol-3-yl)propan-1-ol (50 mg, 0.13 mmol) was dissolved in isopropanol (4 ml) at the boiling point and citric acid (25 mg, 0.13 mmol), dissolved in hot isopropanol (1 ml), was added. The solution was cooled to 5° C. in a refrigerator and left to stand for 16 h. The white precipitate formed was separated off by means of a frit. Example 48 was obtained in this way in a yield of 50 mg (67%, melting point: 95-98° C.).

Example 49

(±)-3-(2-(4-Butyl-4-(dimethylamino)cyclohex-1-enyl)-1H-indol-3-yl)propan-1-ol, citrate (1:2) (49)

Indole Ind-16 (350 mg, 2 mmol) was dissolved in methylene chloride (40 ml) with ketone Ket-4 (395 mg, 2 mmol), and trifluoromethanesulfonic acid (270 μl, 3 mmol) was added. The mixture was stirred at RT for 24 h. For working up, 2 N NaOH (30 ml) was added to the reaction mixture and the mixture was stirred at RT for 20 min. After the organic phase had been separated off, the aqueous phase was extracted with methylene chloride (3×15 ml). The combined organic extracts were dried over Na$_2$SO$_4$ and then concentrated. The crude product obtained (710 mg) was purified by column chromatography [silica gel 60 (50 g); MeOH (500 ml)]. (±)-3-(2-(4-Butyl-4-(dimethylamino)cyclohex-1-enyl)-1H-indol-3-yl)propan-1-ol was obtained in a yield of 344 mg (49%) as a yellow solid.

The solid was dissolved in isopropanol (4 ml) at the boiling point and citric acid (187 mg, 0.97 mmol), dissolved in hot isopropanol (2 ml), was added. The solution was cooled to 5° C. (refrigerator) and left to stand for 16 h. The isopropanol was distilled off on a rotary evaporator and Example 49 was obtained in this way in a yield of 531 mg (100%, melting point: 50-54° C.).

Example 51

(±)-2-(2-(2-(4-(Dimethylamino)-4-phenylcyclohex-1-enyl)-1H-indol-3-yl)ethyl)isoindoline-1,3-dione Ketone (Ket-10, 461 mg, 2.12 mmol) and indole (Ind-18, 615 mg, 2.12 mmol) were dissolved in abs. methylene chloride (20 ml) under argon. Trifluoromethanesulfonic acid (230 μl/2.64 mmol) was then added rapidly and the mixture was stirred at RT for 24 h. For working up, the mixture was rendered basic with 1 N NaOH and subsequently stirred at RT for 15 min. The phases were separated and the aqueous phase was extracted with methylene chloride (3×20 ml). The organic phase was dried over Na$_2$SO$_4$ and concentrated i. vac. The residue was purified by flash chromatography with CHCl$_3$/MeOH (9:1→4:1→1:1).

Yield: 560 mg (54%)

Example 52

(±)-2-(4-(Dimethylamino)-4-benzylcyclohex-1-enyl)-3-(2-(1H-benzo[d]imidazol-1-yl)ethyl)-5-fluoro-1H-indole Indole (Ind-19, 668 mg, 2.39 mmol) and ketone (Ket-3, 553 mg, 2.39 mmol) were dissolved in abs. methylene chloride (30 ml), and trifluoromethanesulfonic acid (0.64 ml, 7.2 mmol) was added rapidly. The mixture was stirred at RT for 72 h, during which a dark brown oil settled out. After addition of 1 N NaOH (20 ml) and CH$_2$Cl$_2$ (20 ml), the mixture was subsequently stirred for a further 20 min, the phases were separated, the aqueous phase was extracted twice with CH$_2$Cl$_2$, the combined organic phases were washed with water and dried (Na$_2$SO$_4$) and the solution was concentrated i. vac. The residue which remained was purified by flash chromatography with EA/EtOH (9:1→1:2).

Yield: 395 mg (52; 33%), porous solid $^1$H-NMR (DMSO-d$_6$): 1.23 (2H, m); 2.06 (2H, m); 2.41 (6H, bs); 3.22 (2H, t); 3.33 (2H, s); 4.43 (2H, t); 5.58 (1H, s); 6.84 (1H, m); 7.08 (3H, m); 7.29 (6H, m); 7.40 (1H, d); 7.56 (1H, d); 7.86 (1H, s); 10.92 (1H, s).

Example 53

(±)-2-(4-(Dimethylamino)-4-butylcyclohex-1-enyl)-3-(2-(1H-benzo[d]imidazol-1-yl)ethyl)-5-fluoro-1H-indole Indole (Ind-19, 977 mg, 3.5 mmol) and ketone (Ket-4; 690 mg, 3.5 mmol) were dissolved in abs. methylene chloride (30 ml), and trifluoromethanesulfonic acid (0.93 ml, 10.5 mmol) was added rapidly. The mixture was stirred at RT for 48 h, during which a dark brown oil settled out. After addition of 1 N NaOH (20 ml) and CH$_2$Cl$_2$ (20 ml), the mixture was subsequently stirred for a further 20 min, the phases were separated, the aqueous phase was extracted twice with CH$_2$Cl$_2$, the combined organic phases were washed with water and dried (Na$_2$SO$_4$) and the solution was concentrated i. vac. The residue which remained was purified by flash chromatography with EA/EtOH (1:4).

Yield: 522 mg (33%), porous solid $^1$H-NMR (DMSO-d$_6$): 0.88 (3H, t); 1.23 (10H, m); 2.11 (3H, bs); 2.22 (6H, bs); 3.22 (2H, t); 4.43 (2H, t); 5.62 (1H, s); 6.86 (1H, m); 7.20 (4H, m); 7.41 (1H, d); 7.61 (1H, d); 7.86 (1H, s); 10.83 (1H, s).

Example 54

(±)-2-(4-(Dimethylamino)-4-phenylcyclohex-1-enyl)-3-(2-(1H-benzo[d]imidazol-1-yl)ethyl)-5-fluoro-1H-indole Indole (Ind-19, 600 mg, 2.14 mmol) and ketone (Ket-10, 466 mg, 2.14 mmol) were dissolved in abs. methylene chloride (30 ml), and trifluoromethanesulfonic acid (0.57 ml, 6.4 mmol) was added rapidly. The mixture was stirred at RT for 72 h, during which a dark brown oil settled out. After addition of 1 N NaOH (20 ml) and $CH_2Cl_2$ (20 ml), the mixture was subsequently stirred for a further 20 min, the phases were separated, the aqueous phase was extracted twice with $CH_2Cl_2$, the combined organic phases were washed with water and dried ($Na_2SO_4$) and the solution was concentrated i. vac. The residue which remained was purified by flash chromatography with EA/EtOH (9:1→1:2).

Yield: 886 mg (87%), porous solid $^1$H-NMR (DMSO-d$_6$): 1.61 (2H, m); 1.91 (2H, m); 2.08 (6H, bs); 3.13 (2H, t); 4.31 (2H, t); 5.85 (1H, s); 6.82 (1H, m); 7.20 (9H, m); 7.64 (1H, m); 7.85 (1H, s); 10.79 (1H, s).

Example 55

(±)-2-(4-(Dimethylamino)-4-benzylcyclohex-1-enyl)-3-(2-(piperidin-1-yl)ethyl)-5-fluoro-1H-indole Indole (Ind-20, 739 mg, 3.00 mmol) and ketone (Ket-3, 694 mg, 3.0 mmol) were dissolved in abs. $CH_2Cl_2$ (30 ml) at RT and trifluoromethanesulfonic acid (1.35 g, 0.80 ml. 9.0 mmol) was added swiftly. A black oil then precipitated out. The mixture was stirred at RT for 2 d. 1 N NaOH (30 ml) was added and the mixture was stirred for 20 min. The organic phase was separated off and the aqueous phase was extracted with $CH_2Cl_2$ (2×30 ml). The combined organic phases were washed with water (15 ml), dried over $Na_2SO_4$, filtered and concentrated i. vac. By flash chromatography with 50 g of silica gel and acetonitrile/methanol/aqueous 1 N ammonium chloride solution (9:1:1), Ind-20 was obtained as the first fraction and the purified product as the second fraction. The second fraction was concentrated i. vac., the concentrate was rendered basic with 2 N NaOH, the mixture was extracted twice with $CH_2Cl_2$ and the extract was dried over $Na_2SO_4$ and concentrated i. vac.

Yield: 764 mg (55, 55%), colourless solid $^1$H-NMR (DMSO-d$_6$): 1.37 (2H, m); 1.49 (4H, m); 1.95 (2H, m); 2.31 (6H, s); 2.41 (8H, m); 2.80 (4H, m); 5.91 (1H, s); 6.83 (1H, m); 7.20 (7H, m); 10.73 (1H, s).

Example 56

(±)-2-(4-(Dimethylamino)-4-butylcyclohex-1-enyl)-3-(2-(piperidin-1-yl)ethyl)-5-fluoro-1H-indole Indole (Ind-20, 1.06 g, 4.30 mmol) and ketone (Ket-4, 848 mg, 4.30 mmol) were dissolved in abs. $CH_2Cl_2$ (50 ml) at RT and trifluoromethanesulfonic acid (1.96 g, 1.15 ml. 12.9 mmol) was added swiftly. A black oil then precipitated out. The mixture was stirred at RT for 3 d. 1 N NaOH (50 ml) was added and the mixture was subsequently stirred for 20 min. The organic phase was separated off and the aqueous phase was extracted with $CH_2Cl_2$ (2×50 ml). The combined organic phases were washed with water (20 ml), dried over $Na_2SO_4$, filtered and concentrated i. vac. By flash chromatography with 50 g of silica gel and acetonitrile/methanol/aqueous 1 N ammonium chloride solution (9:1:1), indole (Ind-20) was obtained as the first fraction and the purified product as the second fraction. The second fraction was concentrated i. vac., the concentrate was rendered basic with 2 N NaOH, the mixture was extracted twice with $CH_2Cl_2$ and the extract was dried over $Na_2SO_4$ and concentrated i. vac.

Yield: 1.08 g (56, 59%), colourless solid $^1$H-NMR (DMSO-d$_6$): 0.89 (3H, t); 1.25-1.61 (10H, m); 1.79 (2H, m); 1.96 (2H, m) 2.21 (6H, s); 2.39 (8H, m); 2.83 (2H, m); 5.97 (1H, s); 6.81 (1H, m); 7.16 (2H, m); 10.79 (1H, s).

Example 57

(±)-2-(4-(Dimethylamino)-4-phenylcyclohex-1-enyl)-3-(2-(piperidin-1-yl)ethyl)-5-fluoro-1H-indole Indole (Ind-20, 640 mg, 2.60 mmol) and ketone (Ket-10, 565 mg, 2.60 mmol) were dissolved in abs. $CH_2Cl_2$ (30 ml) at RT and trifluoromethanesulfonic acid (1.17 g, 0.69 ml. 7.8 mmol) was added swiftly. A black oil then precipitated out. The mixture was stirred at RT for 24 h. 1 N NaOH (30 ml) was added and the mixture was subsequently stirred for 20 min. The organic phase was separated off and the aqueous phase was extracted twice with $CH_2Cl_2$ (30 ml each time). The combined organic phases were washed with water (15 ml), dried over $Na_2SO_4$, filtered and concentrated i. vac. By flash chromatography with 50 g of silica gel and acetonitrile/methanol/aqueous 1 N ammonium chloride solution (9:1:1), indole (Ind-20) was obtained as the first fraction and the purified product as the second fraction. The second fraction was concentrated i. vac., the concentrate was rendered basic with 2 N NaOH, the mixture was extracted twice with $CH_2Cl_2$ and the extract was dried over $Na_2SO_4$ and concentrated i. vac.

Yield: 404 mg (35%), colourless solid $^1$H-NMR (DMSO-d$_6$): 1.37-1.49 (6H, m); 1.74 (2H, m); 2.09 (6H, s); 2.27 (6H, m); 2.73 (4H, m); 6.21 (1H, s); 6.81 (1H, m); 7.08-7.47 (7H, m); 10.72 (1H, s).

Example 58

(±)-2-(4-(Dimethylamino)-4-phenylcyclohex-1-enyl)-3-(2-(piperidin-1-yl)ethyl)-1H-indole, citrate (1:1)

Ketone (Ket-10, 1.73 g, 8.0 mmol) and indole (Ind-21, 1.82 g, 8.0 mmol) were dissolved in abs. methylene chloride (100 ml). Addition of trifluoromethanesulfonic acid in portions (in total 3.12 ml, 36 mmol within 3 d) then took place. For working up, 2 N NaOH (150 ml) was added to the mixture and the mixture was stirred at room temperature for 20 min. The organic phase was separated off and the aqueous phase was extracted with methylene chloride (2×25 ml). The combined organic phases were dried over $Na_2SO_4$ and concentrated i. vac. The residue was purified by flash chromatography with methanol.

Yield: 0.209 g (7%)

$^1$H-NMR (CDCl$_3$): 1.49-1.69 (6H, m); 2.02-2.18 (10H, m); 2.44 (4H, m); 2.70 (2H; m); 2.93 (2H, t); 3.43 (2H, t); 6.14 (1H, m); 7.07 (2H, m); 7.26 (5H, m); 7.47 (2H, m); 8.40 (1H, s).

Example 59

(±)-2-(4-(Dimethylamino)-4-benzylcyclohex-1-enyl)-3-(2-(1H-1,2,3-triazol-1-yl)ethyl)-5-fluoro-1H-indole Indole (Ind-22, 750 mg, 3.25 mmol) and ketone (Ket-3, 752 mg, 3.25 mmol) were dissolved in abs. methylene chloride (30 ml), and trifluoromethanesulfonic acid (0.87 ml, 9.8 mmol) was added rapidly. The mixture was stirred at RT for 48 h, during which a dark brown oil settled out. After addition of 1 N NaOH (20 ml) and CH$_2$Cl$_2$ (20 ml), the mixture was subsequently stirred for a further 20 min, the phases were separated, the aqueous phase was extracted twice with CH$_2$Cl$_2$, the combined organic phases were washed with water and dried (Na$_2$SO$_4$) and the solution was concentrated i. vac. The residue which remained was purified by flash chromatography with EA/EtOH (1:4).

Yield: 387 mg (27%), colourless solid; melting point: 175-183° C.

$^1$H-NMR (DMSO-d$_6$): 1.37 (1H, m); 1.97 (3H, m); 2.31 (6H, bs); 2.72 (4H, m); 3.24 (2H, t); 4.56 (2H, t); 6.86 (1H, m); 7.22 (7H, m); 7.62 (1H, s); 8.00 (1H, s); 10.91 (1H, s).

Example 60

(±)-2-(4-(Dimethylamino)-4-butylcyclohex-1-enyl)-3-(2-(1H-1,2,3-triazol-1-yl)ethyl)-5-fluoro-1H-indole Indole (Ind-22, 825 mg, 3.58 mmol) and ketone (Ket-4, 707 mg, 3.58 mmol) were dissolved in abs. methylene chloride (25 ml), and trifluoromethanesulfonic acid (0.96 ml, 10.8 mmol) was added rapidly. The mixture was stirred at RT for 48 h, during which a dark brown oil settled out. After addition of 1 N NaOH (20 ml) and CH$_2$Cl$_2$ (20 ml), the mixture was subsequently stirred for a further 20 min, the phases were separated, the aqueous phase was extracted twice with CH$_2$Cl$_2$, the combined organic phases were washed with water and dried (Na$_2$SO$_4$) and the solution was concentrated i. vac. The residue which remained was purified by flash chromatography with EA/EtOH (1:4).

Yield: 514 mg (35%), porous solid $^1$H-NMR (DMSO-d$_6$): 0.89 (3H, t); 1.33 (6H, m); 1.77 (2H, m); 1.99 (1H, m); 2.28 (6H, bs); 2.38 (2H, m); 3.25 (2H, t); 4.54 (2H, t); 5.83 (1H, s); 6.87 (1H, m); 7.22 (2H, m); 7.64 (1H, s); 7.98 (1H, s); 10.92 (1H, s).

Example 61

(±)-2-(4-(Dimethylamino)-4-phenylcyclohex-1-enyl)-3-(2-(1H-1,2,3-triazol-1-yl)ethyl)-5-fluoro-1H-indole Indole (Ind-22, 600 mg, 2.6 mmol) and ketone (Ket-10, 565 mg, 2.6 mmol) were dissolved in abs. methylene chloride (20 ml), and trifluoromethanesulfonic acid (0.7 ml, 7.8 mmol) was added rapidly. The mixture was stirred at RT for 20 h, during which a dark brown oil settled out. After addition of 1 N NaOH (20 ml) and CH$_2$Cl$_2$ (20 ml), the mixture was subsequently stirred for a further 20 min, the phases were separated, the aqueous phase was extracted twice with CH$_2$Cl$_2$, the combined organic phases were washed with water and dried (Na$_2$SO$_4$) and the solution was concentrated i. vac. The residue which remained was purified by flash chromatography with EA/EtOH (1:4).

Yield: 803 mg (72%), colourless solid, melting point: 90-97° C.

$^1$H-NMR (DMSO-d$_6$): 1.68 (1H m); 2.10 (6H, s); 2.39 (1H, m); 2.62 (2H, m); 3.20 (2H, t); 4.47 (2H, t); 6.06 (1H, s); 6.81 (1H, m); 7.16 (5H, m); 7.46 (2H, m); 7.66 (1H, s); 7.95 (1H, s); 10.82 (1H, s).

Example 62

2',3',4',9'-Tetrahydro-N,N-dimethyl-4-butyl-spiro[cyclohexanE-1,1'(1'H)-pyrido[3,4-b]indol]-4-amine less polar diastereomer Tryptamine (Ind-1, 2.43 g, 15.2 mmol) and the ketone (Ket-4, 3.0 g, 15.2 mmol) were dissolved in abs. methanol (90 ml) and the solution was stirred at room temperature for 25 h under argon. The reaction mixture was then concentrated. The residue was dissolved in abs. 1,2-dichloroethane (150 ml), trifluoroacetic acid (10.4 ml, 15.5 g, 136 mol) was added rapidly and the mixture was stirred at room temperature for 3 d. 1 N sodium hydroxide solution (130 ml) was added to the brown solution and the mixture was stirred at RT for 20 min. The phases of the solution were separated. The aqueous phase was extracted with 1,2-dichloroethane (2×70 ml). The organic phases was combined, washed with water (50 ml), dried and concentrated. Methanol (60 ml) was added to the brown oily residue, as a result of which crystallization occurred. The suspension was stirred for a further 10 min. The colourless crystals were filtered off with suction and washed (1.28 g) with methanol (60 ml). These were the pure less polar spiro-amine. The filtrate was concentrated and methanol (50 ml) was added again to the brown solid obtained and the mixture was stirred in an ice bath for 1 h. After filtration with suction and washing with cold methanol (20 ml), it was possible to obtain 673 mg of the less polar spiro-amine. The filtrate was concentrated and the residue (2.4 g) was separated by chromatography [silica gel 60 (130 g); methanol (500 ml), methanol/triethylamine (100:1, 1.5 l)]. The less polar spiro-amine was obtained together with impurities (1.02 g). Cold methanol (10 ml) was added to this fraction and the mixture was filtered with suction. The solid obtained (332 mg) was pure non-polar product. The less polar spiro-amine was obtained in a total yield of 44% (2.28 g) with a melting point of 180-182° C. The more polar spiro-amine was obtained in a further fraction in a yield of 12% (622 mg) with a melting point of 93-96° C.

(±)-N-(2-(2-(4-Butyl-4-(dimethylamino)cyclohex-1-enyl)-1H-indol-3-yl)ethyl)-3,3-dimethylbutanamide 3,3-Dimethylbutyric acid chloride (0.246 ml, 238 mg, 1.77 mmol) was dissolved in abs. methylene chloride (5 ml) under argon and the less polar spiro-amine just prepared (200 mg, 0.59 mmol), dissolved in methylene chloride (15 ml) was added in the course of 30 min. After a reaction time of 24 h, water (10 ml) and 1 N sodium hydroxide solution (5 ml) were added to the yellow reaction solution and the mixture was stirred for 1 h. The phases were separated. The aqueous phase was extracted with methylene chloride (20 ml). The combined organic phases were washed with water (20 ml), dried and concentrated. A beige-coloured oil (322 mg) was obtained by this procedure, and was separated by chromatography [silica gel 60 (40 g); ethyl acetate (250 ml), ethyl acetate/methanol (4:1, 400 ml), methanol (300 ml)]. The desired olefin was isolated in a yield of 58% (150 mg) with a melting point of 139-142° C.

N-(2-(2-(4-Butyl-4-(dimethylamino)cyclohexyl)-1H-indol-3-yl)ethyl)-3,3-dimethylbutanamide The olefin just prepared (82 mg, 0.187 mmol) was dissolved in methanol (20 ml), and palladium on charcoal 5% (16 mg) was added. The reaction mixture was hydrogenated at room temperature under a pressure of 3 bar for 4.5 h. The conversion was complete. The catalyst was separated off over Celite and the filtrate was concentrated. The solid residue (84 mg) was separated by chromatography [silica gel 60 (20 g); ethyl acetate/methanol (4:1, 150 ml), methanol (300 ml)]. The more polar amide obtained in a yield of 83% (68 mg).

N-(2-(2-(4-Butyl-4-(dimethylamino)cyclohexyl)-1H-indol-3-yl)ethyl)-3,3-dimethylbutanamide, citrate (1:1) (62:More polar diastereomer)

The more polar amide just prepared (47 mg, 0.107 mmol) was dissolved in ethanol (1 ml), and citric acid (23 mg), dissolved in ethanol (1 ml), was added. Since no crystallization took place after 6 h, diethyl ether (15 ml) was slowly added to the mixture and the mixture was stirred at room temperature for 16 h. The solvent was decanted. The colourless solid which remained was transferred into the delivery tube in the moist state and dried. The citrate 62 was obtained in a yield of 69% (46 mg).

Example 63

(±)-N-(2-(2-(4-(Dimethylamino)-4-phenylcyclohex-1-enyl)-1H-indol-3-yl)ethyl)acetamide Ketone (Ket-10, 234 mg, 1.08 mmol) and indole (Ind-2, 219 mg, 1.08 mmol) were dissolved in abs. methylene chloride (10 ml) under argon, trifluoromethanesulfonic acid (188 μl/12.16 mmol) was added rapidly and the mixture was stirred at RT for 16 h. The mixture was then rendered alkaline with 1 N NaOH and subsequently stirred at RT for 15 min. The phases were separated. The aqueous phase was extracted with methylene chloride (three times 20 ml). The organic phase was dried over $Na_2SO_4$ and concentrated i. vac. The residue was purified by flash chromatography with CH/EA (1:1→1: 4), EA/EtOH (4:1→1:1), EtOH, (methanol+1% TEA). 1 N NaOH was added to the fractions and the mixture was extracted with methylene chloride (two times 10 ml). The organic phase was dried over $Na_2SO_4$ and concentrated i. vac.
Yield: 86 mg, (63, 19%)

Example 64

(±)-N-(2-(2-(4-Butyl-4-(dimethylamino)cyclohex-1-enyl)-1H-indol-3-yl)ethyl)-3,3-dimethylbutanamide The substance (±)-N-(2-(2-(4-butyl-4-(dimethylamino) cyclohex-1-enyl)-1H-indol-3-yl)ethyl)-3,3-dimethylbutanamide described under Example 62 is presented in the following as Example 64.

Example 65

(±)-2-(2-(4-(Dimethylamino)-4-phenylcyclohex-1-enyl)-5-fluoro-6-methoxy-1H-indol-3-yl)ethanol, citrate (1:1)

Trifluoromethanesulfonic acid (1.52 g, 10.1 mmol) was added to a solution of Ind-26 (1.60 g, 7.63 mmol) and Ket-10 (1.65 g, 7.63 mmol) in anhydrous methylene chloride (40 ml) at room temperature and the mixture was stirred at room temperature for 16 h. 0.5 M sodium hydroxide solution (10 ml) was then added to the reaction solution and the mixture was stirred at room temperature for 2 h. The phases were separated and the aqueous phase was extracted with ethyl acetate (3×30 ml). The combined organic phases were dried with sodium sulfate and concentrated i. vac. The residue was purified by flash chromatography (200 g, 20×5.6 cm) with chloroform/methanol (10:1). The residue was taken up in 1 N sodium hydroxide solution and the mixture was extracted with methylene chloride (3×40 ml). The combined organic phases were dried with sodium sulfate and concentrated i. vac.
Methanesulfonic acid (69 mg, 0.72 mmol) was added to the residue (100 mg, 0.24 mmol) together with DL-methionine (107 ml, 0.72 mmol) in methylene chloride (10 ml) and the mixture was stirred at room temperature for 2 h. After addition of further methanesulfonic acid (69 mg, 0.72 mmol), the reaction mixture was stirred over the weekend, 1 N sodium hydroxide solution (30 ml) was then added and the mixture was extracted with methylene chloride (3×40 ml). The combined organic phases were dried with sodium sulfate and concentrated i. vac.
Yield (Ex. 65): 63 mg (66%), colourless solid
$^1$H-NMR (300 MHz, DMSO-$d_6$): 1.57-1.80 (m, 2H), 2.09 (s, 6H), 2.41 (d, J=17.1 Hz, 2H), 2.62 (t, J=16.6 Hz, 2H), 2.77 (t, J=7.3 Hz, 2H), 3.50 (dd, J=12.3, 4.8 Hz, 2H), 3.79 (s, 3H), 4.60 (t, J=5.4 Hz, 1H), 6.17 (s, 1H), 6.84 (d, J=7.5 Hz, 1H), 7.15 (s, 1H), 7.17-7.26 (m, 1H), 7.31 (t, J=7.5 Hz, 2H), 7.47 (d, J=7.4 Hz, 2H), 10.52 (s, 1H).

Example 66

(±)-2-(2-(4-benzyl-4-(4-methylpiperazin-1-yl)cyclohex-1-enyl)-5-fluoro-1H-indol-3-yl)ethanol Trifluoromethanesulfonic acid (450 mg, 265 μl, 3 mmol) was added to a solution of Ket-2 (700 mg, 2.44 mmol) and 5-fluorotryptophol (Ind-4) (449 mg, 2.5 mmol) in anhydrous methylene chloride (25 ml), while cooling with ice, and the mixture was stirred at room temperature overnight. In order to monitor the conversion, a sample (0.5 ml) was taken, this was washed with 0.5 N sodium hydroxide solution and the organic phase was dried with sodium sulfate. Trifluoromethanesulfonic acid (450 mg, 265 μl, 3 mmol) was added, while cooling with ice, and the mixture was stirred at room temperature over the weekend. 0.5 N sodium hydroxide solution (10 ml) was then added to the reaction mixture, the mixture was stirred at room temperature for 2 h, the aqueous phase was extracted with methylene chloride (2×20 ml) and the combined organic phases were dried with sodium sulfate and concentrated i. vac.
The crude product was purified by means of flash chromatography (200 g, 20×5.7 cm) with methanol.
Yield (66): 60 mg (0.1%), yellow solid, melting point: 91-97° C.
$^1$H-NMR (CDCl$_3$): 1.48-1.75 (m, 2H); 1.93-2.21 (m, 2H); 2.28 (s, 3H); 2.38-2.50 (m, 4H); 2.69-2.87 (m, 7H); 3.03 (t, 2H, J=6.8 Hz); 3.48 (s, 2H); 3.85 (t, 2H, J=6.6 Hz); 5.92 (s, 1H); 6.82-6.95 (m, 1H); 7.16-7.32 (m, 7H); 7.92 (s, 1H).

Example 67

(±)-2-(5-fluoro-2-(4-phenyl-4-(pyrrolidin-1-yl)cyclohex-1-enyl)-1H-indol-3-yl)ethanol (67)

Trifluoromethanesulfonic acid (399 mg, 232 μl, 2.66 mmol) was added to a solution of Ket-8 (486 mg, 2 mmol) and 5-fluorotryptophol (Ind-4) (358 mg, 2 mmol) in anhydrous methylene chloride (20 ml) at 5-10° C. and the mixture was stirred at room temperature overnight. After addition of 0.5 N sodium hydroxide solution (10 ml), the phases were separated and the aqueous phase was extracted with methylene chloride (3×10 ml). The combined organic phases were dried with sodium sulfate and concentrated i. vac. The crude product (596 mg) was purified by flash chromatography (18 g, 20×1.5 cm) with ethyl acetate/cyclohexane (1:9→2:1) and in each case 1% triethylamine. Yield. 140 mg (17%), white solid, melting point: 188-191° C.
$^1$H-NMR (DMSO-$d_6$): 1.59 (br s, 4H); 1.76-1.88 (m, 1H); 2.08-2.20 (m, 2H); 2.34-2.48 (m, 3H); 2.52-2.60 (m, 2H); 2.66 (d, 1H, J=18.5 Hz); 2.80 (t, 3H, J=7.3 Hz); 3.47 (dd, 2H, J=13.1, 7.3 Hz); 4.58 (t, 1H, J=5.3 Hz); 6.22 (s, 1H); 6.77-6.84 (m, 1H); 6.81 (dt, 1H, J=8.8, 1.9 Hz); 7.12-7.24 (m, 3H); 7.32 (t, 2H, J=7.6 Hz); 7.48 (d, 2H, J=7.9 Hz); 10.07 (s, 1H).

¹³C-NMR (DMSO-d₆): 22.9; 26.0; 28.6; 28.9; 33.4; 44.8; 58.2; 61.7; 102.7 (d, J=24 Hz); 107.9 (d, J=6 Hz); 108.7 (d, J=26 Hz); 111.4 (d, J=10 Hz); 125.7; 126.2; 126.8; 127.5; 129.1 (d, J=10 Hz); 129.3; 131.7; 138.0; 142.2; 156.6 (d, J=231 Hz).

Example 68

2-(4-Benzyl-4-(dimethylamino)cyclohexyl)-3-methyl-1H-indole-5-carbonitrile, citrate (1:1), non-polar diastereomer Example 69

2-(4-Benzyl-4-(dimethylamino)cyclohexyl)-3-methyl-1H-indole-5-carbonitrile, citrate (1:1), polar diastereomer 2-(4-Benzyl-4-(dimethylamino)cyclohexyl)-3-methyl-1H-indole-5-carbonitrile (non-polar and polar diastereomer)

Ex. 22 (280 mg, 0.758 mmol) was dissolved in methanol (100 ml), and palladium on charcoal (5 per cent strength; 110 mg) was added. The reaction mixture was hydrogenated at 40° C. under 3 bar for 4.5 h. The conversion was complete. The catalyst was separated off over Celite and the filtrate was concentrated. The solid residue was separated by chromatography [silica gel 60 (30 g); ethyl acetate/methanol (20:1, 200 ml), ethyl acetate/methanol (10:1, 200 ml), ethyl acetate/methanol (4:1, 350 ml), methanol (200 ml)]. The less polar diastereoisomer was obtained in a yield of 27% (77 mg) with a melting point of 205-213° C. and the more polar in a yield of 55% (155 mg) with a melting point of 175-182° C.

2-(4-Benzyl-4-(dimethylamino)cyclohexyl)-3-methyl-1H-indole-5-carbonitrile, citrate (1:1), non-polar diastereomer (68)

2-(4-Benzyl-4-(dimethylamino)cyclohexyl)-3-methyl-1H-indole-5-carbonitrile (non-polar diastereomer) (72 mg, 0.194 mmol) was dissolved in ethanol (9 ml) at 60° C. and an ethanolic solution (2 ml) of citric acid (41 mg, 0.213 mmol) was added. A precipitation started immediately. After a reaction time of 16 h at room temperature, the colourless citrate was separated off by filtration and washed with ethanol (2 ml). Example 68 was obtained in a yield of 46% (50 mg) with a melting point of 249-255° C.

2-(4-Benzyl-4-(dimethylamino)cyclohexyl)-3-methyl-1H-indole-5-carbonitrile, citrate (1:1), polar diastereomer (69)

2-(4-Benzyl-4-(dimethylamino)cyclohexyl)-3-methyl-1H-indole-5-carbonitrile (polar diastereomer) (158 mg, 0.425 mmol) was dissolved in ethanol (7 ml) at 60° C. and an ethanolic solution (2 ml) of citric acid (91 mg, 0.47 mmol) was added. After a reaction time of 16 h at room temperature, the colourless citrate was separated off by filtration and washed with ethanol (3 ml). Example 69 was obtained in a yield of 51% (122 mg) with a melting point of 193-195° C.

Example 70

2-(4-Butyl-4-(dimethylamino)cyclohexyl)-3-methyl-1H-indole-5-carbonitrile, citrate (2:1), non-polar diastereomer Example 71

2-(4-Butyl-4-(dimethylamino)cyclohexyl)-3-methyl-1H-indole-5-carbonitrile, citrate (1:1), polar diastereomer (±)-2-(4-Butyl-4-dimethylaminocyclohex-1-enyl)-3-methyl-1H-indole-5-carbonitrile The ketone Ket-4 (517 mg, 2.62 mmol) and indole Ind-6 (410 mg, 2.62 mmol) were dissolved in abs. methylene chloride (40 ml), trifluoromethanesulfonic acid (0.256 ml, 432 mg, 2.88 mmol) was added and the mixture was stirred at room temperature for 5 days. Water (20 ml) and 1 N sodium hydroxide solution (15 ml) were added to the clear mixture and the mixture was stirred for 30 min. The phases were separated. The aqueous phase was extracted with methylene chloride (20 ml). The organic phases was combined, washed with water (20 ml), dried and concentrated. The residue was a brown oil (942 mg), which was separated by chromatography [silica gel 60 (70 g); ethyl acetate (700 ml), ethyl acetate/methanol (10:1, 200 ml), ethyl acetate/methanol (4:1, 750 ml), methanol (200 ml)]. (±)-2-(4-Butyl-4-dimethylaminocyclohex-1-enyl)-3-methyl-1H-indole-5-carbonitrile was obtained as a beige-coloured oil in a yield of 33% (289 mg).

2-(4-Butyl-4-dimethylaminocyclohexyl)-3-methyl-1H-indole-5-carbonitrile (non-polar and polar diastereomer)

(±)-2-(4-Butyl-4-dimethylaminocyclohex-1-enyl)-3-methyl-1H-indole-5-carbonitrile (266 mg, 0.79 mmol) was dissolved in methanol (85 ml), and palladium on charcoal (5 per cent strength; 110 mg) was added. The reaction mixture was hydrogenated at 40° C. under 3 bar for 2 h. The reaction took place to completion. The catalyst was separated off over Celite and the filtrate was concentrated. The solid residue (239 mg) was separated by chromatography [silica gel 60 (40 g); ethyl acetate/methanol (10:1, 200 ml), ethyl acetate/methanol (4:1, 250 ml), methanol (400 ml)]. 2-(4-Butyl-4-dimethylaminocyclohexyl)-3-methyl-1H-indole-5-carbonitri (non-polar diastereoisomer) was obtained in a yield of 11% (30 mg) with a melting point of 176-180° C., and the more polar diastereoisomer was obtained in a yield of 57% (151 mg) with a melting point of 162-166° C.

2-(4-Butyl-4-(dimethylamino)cyclohexyl)-3-methyl-1H-indole-5-carbonitrile, citrate (2:1), non-polar diastereomer 2-(4-Butyl-4-dimethylaminocyclohexyl)-3-methyl-1H-indole-5-carbonitri (less polar diastereoisomer) (30 mg, 0.089 mmol) was dissolved in ethanol (3 ml) at 60° C. and ethanolic solution (2 ml) of citric acid (19 mg, 0.098 mmol) was added. After a reaction time of 20 h, the solution was concentrated to 1 ml, diethyl ether (20 ml) was added and the mixture was stirred for 15 min. The colourless citrate was separated off by filtration and washed with diethyl ether (2 ml). Example 70 obtained in a yield of 45% (21 mg).

2-(4-Butyl-4-(dimethylamino)cyclohexyl)-3-methyl-1H-indole-5-carbonitrile, citrate (1:1), polar diastereomer 2-(4-Butyl-4-dimethylaminocyclohexyl)-3-methyl-1H-indole-5-carbonitri (more polar diastereoisomer) (144 mg, 0.426 mmol) was dissolved in ethanol (6 ml) at 60° C. and an ethanolic solution (3 ml) of citric acid (90 mg, 0.47 mmol) was added. After a reaction time of 18 h, the cloudy mixture was concentrated to 1 ml, diethyl ether (20 ml) was added and the mixture was stirred for 15 min. The colourless citrate was separated off by filtration and washed with diethyl ether (3 ml). Example 71 was obtained in a yield of 76% (171 mg).

Example 72

2-(4-(Dimethylamino)-4-phenylcyclohexyl)-3-methyl-1H-indole-5-carbonitrile, citrate (2:1), polar diastereomer 2-(4-Dimethylamino-4-phenylcyclohexyl)-3-methyl-1H-indole-5-carbonitrile (polar diastereomer)

Ex. 23 (200 mg, 0.562 mmol) was dissolved in methanol (30 ml), and palladium on charcoal (5 per cent strength; 75 mg) was added. The reaction mixture was hydrogenated under 3 bar for 20 h. The conversion was complete. The catalyst was separated off over Celite and the filtrate was concentrated. The solid residue (150 mg) was separated by chromatography [silica gel 60 (30 g); ethyl acetate/methanol (4:1, 250 ml), methanol (300 ml)]. 2-(4-Dimethylamino-4-phenylcyclohexyl)-3-methyl-1H-indole-5-carbonitrile (polar diastereomer) was obtained in a yield of 50% (100 mg) with a melting point of 235-240° C.

2-(4-(Dimethylamino)-4-phenylcyclohexyl)-3-methyl-1H-indole-5-carbonitrile, citrate (2:1), polar diastereomer 2-(4-Dimethylamino-4-phenylcyclohexyl)-3-methyl-1H-indole-5-carbonitrile (polar diastereomer) (95 mg, 0.265 mmol) was dissolved in ethanol (7 ml), and citric acid (56 mg), dissolved in ethanol (2 ml) was added. Since no crystallization took place after 6 h, the mixture was concentrated to 2 ml, diethyl ether (30 ml) was added and the mixture was stirred at room temperature for 10 min. The solvent was decanted. The colourless solid which remained was transferred into the delivery tube in the moist state and dried. Example 72 was obtained in a yield of 75% (90 mg) with a melting point of 257-261° C.

Example 73

1-Benzyl-N,N-dimethyl-4-(3-methyl-5-(trifluoromethyl)-1H-indol-2-yl)cyclohexanamine, citrate (2:1), non-polar diastereomer Example 74

1-Benzyl-N,N-dimethyl-4-(3-methyl-5-(trifluoromethyl)-1H-indol-2-yl)cyclohexanamine, citrate (1:1), polar diastereomer (±)-[1-Benzyl-4-(3-methyl-5-trifluoromethyl-1H-indol-2-yl)cyclohex-3-enyl]-dimethylamine Ketone (Ket-3, 393 mg, 1.7 mmol) was dissolved in methylene chloride (20 ml) together with indole Ind-7 (340 mg, 1.7 mmol). The addition of trifluoromethanesulfonic acid (0.17 ml, 287 mg 1.9 mmol) then took place, the mixture becoming dark in colour. The mixture was stirred at RT for 3 d. The course of the reaction was monitored by means of TLC. For working up, 1 N NaOH (10 ml) was added to the reaction mixture and the mixture was stirred for 10 min. During this procedure, the colour changed from dark red to pale brown. After separation of the phases, the aqueous phase was extracted with methylene chloride (2×10 ml). The combined organic phases were dried with sodium sulfate, filtered and concentrated in vacuo. 1.25 g of brown oil were obtained, which was separated by chromatography [silica gel 60 (80 g); ethyl acetate/methanol (10:1; 1,500 ml)]. (±)-[1-Benzyl-4-(3-methyl-5-trifluoromethyl-1H-indol-2-yl)cyclohex-3-enyl]-dimethylamine was obtained in a yield of 31% (220 mg) with a melting point of 119-120° C. as a colourless solid.

N-[1-Benzyl-4-(3-methyl-5-trifluoromethyl-1H-indol-2-yl)cyclohexyl]-N,N-dimethylamine (non-polar and polar diastereomer)

(±)-[1-Benzyl-4-(3-methyl-5-trifluoromethyl-1H-indol-2-yl)cyclohex-3-enyl]-dimethylamine (220 mg, 0.53 mmol) was dissolved in methanol (50 ml), while heating, and Pd/C (5%, 100 mg) was added under argon. Hydrogenation was carried out at 40° C. under 3 bar for 4 h. The catalyst was then filtered off with suction over Celite and the filtrate was concentrated. The solid colourless residue was separated by chromatography [silica gel 60 (30 g); ethyl acetate/methanol (20:1; 500 ml); (4:1; 300 ml); (2:1; 300 ml)]. N-[1-Benzyl-4-(3-methyl-5-trifluoromethyl-1H-indol-2-yl)cyclohexyl]-N,N-dimethylamine (less polar diastereoisomer) was isolated in a yield of 46 mg (21%) as a colourless solid with a melting point of 180-210° C. The polar diastereoisomer was obtained in a yield of 152 mg (69%) as a colourless solid with a melting point of 166-174° C.

1-Benzyl-N,N-dimethyl-4-(3-methyl-5-(trifluoromethyl)-1H-indol-2-yl)cyclohexanamine, citrate (2:1), non-polar diastereomer (73)

N-[1-Benzyl-4-(3-methyl-5-trifluoromethyl-1H-indol-2-yl)cyclohexyl]-N,N-dimethylamine (non-polar diastereoisomer) (46 mg, 0.11 mmol) was dissolved in ethanol (10 ml), and citric acid (23 mg, 0.122 mmol), dissolved in hot ethanol (2 ml), was added. After stirring at RT for 10 min, a colourless solid started to precipitate out. Diethyl ether (5 ml) was added to the reaction mixture and the mixture was stirred for 16 h. Thereafter, it was filtered with suction. Example 73 was obtained in a yield of 42% (28 mg) with a melting point of 201-203° C.

1-Benzyl-N,N-dimethyl-4-(3-methyl-5-(trifluoromethyl)-1H-indol-2-yl)cyclohexanamine, citrate (1:1), polar diastereomer N-[1-Benzyl-4-(3-methyl-5-trifluoromethyl-1H-indol-2-yl)cyclohexyl]-N,N-dimethylamine (polar diastereoisomer) (135 mg, 0.33 mmol) was dissolved in ethanol (20 ml), and citric acid (70 mg, 0.36 mmol), dissolved in hot ethanol (5 ml), was added. The clear colourless solution was stirred for 24 h and then concentrated to approx. half. After stirring at RT for a further 2 h, it was possible for the precipitate which had precipitated out to be filtered off with suction. Example 74 was obtained in a yield of 76% (151 mg) with a melting point of 158-165° C.

Example 75

1-Butyl-N,N-dimethyl-4-(3-methyl-5-(trifluoromethyl)-1H-indol-2-yl)cyclohexanamine, citrate (1:1), polar diastereomer 1-Butyl-N,N-dimethyl-4-(3-methyl-5-(trifluoromethyl)-1H-indol-2-yl)cyclohexanamine, (non-polar and polar diastereomer)

Ex. 24 (110 mg, 0.29 mmol) was dissolved in methanol (25 ml) under an argon atmosphere and Pd/C (5%, 50 mg) was added. Hydrogenation was carried out at RT under 3 bar for 3 h. The catalyst was then filtered off with suction over Celite and the filtrate was concentrated. The solid colourless residue was separated by chromatography [silica gel 60 (20 g); ethyl acetate/methanol (4:1; 500 ml); (1:1; 300 ml)]. 1-Butyl-N,N-dimethyl-4-(3-methyl-5-(trifluoromethyl)-1H-indol-2-yl)cyclohexanamine (polar diastereomer) was obtained in a yield of 83 mg (75%) as a colourless solid with a melting point of 141-146° C.

The less polar diastereoisomer was isolated in a yield of 10 mg (9%) as a colourless oil.

1-Butyl-N,N-dimethyl-4-(3-methyl-5-(trifluoromethyl)-1H-indol-2-yl)cyclohexanamine, citrate (1:1), polar diastereomer The more polar (1r,4s)-1-butyl-N,N-dimethyl-4-(3-methyl-5-(trifluoromethyl)-1H-indol-2-yl)cyclohexanamine (82 mg, 0.21 mmol) was dissolved in ethanol (10 ml), and citric acid (44 mg, 0.23 mmol), dissolved in hot ethanol (2 ml), was added. The clear colourless solution was stirred for 24 h and then concentrated. After addition of diethyl ether (10 ml), the mixture was stirred at RT for 2 h and the precipitate was then filtered off with suction. Example 75 was obtained in a yield of 78% (94 mg) with a melting point of 191-193° C.

Example 76

N,N-Dimethyl-4-(3-methyl-5-(trifluoromethyl)-1H-indol-2-yl)-1-phenylcyclohexanamine, citrate (1:1), polar diasteromer N,N-Dimethyl-4-(3-methyl-5-(trifluoromethyl)-1H-indol-2-yl)-1-phenylcyclohexanamine (non-polar and polar diastereomer)

HBr/glacial acetic acid (33% HBr, 22 ml) was added to Ex. 25 (420 mg, 1.05 mmol). The suspension was stirred for about 10 min until solution was complete. Sn powder (1.22 g, 10.5 mmol) was then added to the mixture in portions in the course of 40 min. When the addition had ended, the reaction mixture was stirred for a further 1.5 h and, for working up, it was then concentrated to dryness on a rotary evaporator. The residue which remained was rendered basic by addition of 5 N NaOH (40 ml). The solution obtained was extracted with methylene chloride (4×30 ml). The combined organic phases were dried with $Na_2SO_4$ and then concentrated. The residue (420 mg) was separated by column chromatography [silica gel 60 (30 g); ethyl acetate/cyclohexane (1:1; 500 ml); ethyl acetate (500 ml); ethyl acetate/methanol (2:1; 450 ml)]. N,N-Dimethyl-4-(3-methyl-5-(trifluoromethyl)-1H-indol-2-yl)-1-phenylcyclohexanamine (polar diastereomer) was obtained in a yield of 176 mg (42%) as a colourless solid with a melting point of 244-251° C. The less polar diastereoisomer was obtained in this way in a yield of 13 mg (3%) as a colourless solid with a melting point of 204-217° C.

N,N-Dimethyl-4-(3-methyl-5-(trifluoromethyl)-1H-indol-2-yl)-1-phenylcyclohexanamine, citrate (1:1), polar diasteromer N,N-Dimethyl-4-(3-methyl-5-(trifluoromethyl)-1H-indol-2-yl)-1-phenylcyclohexanamine (polar diastereomer) (170 mg, 0.42 mmol) was dissolved in ethanol (10 ml), and citric acid (89 mg, 0.46 mmol), dissolved in hot ethanol (2 ml), was added. After stirring at RT for 30 min, a colourless solid started to precipitate out. After 1 h the mixture was filtered with suction. Example 76 was obtained in a yield of 76% (188 mg) with a melting point of 243-247° C.

Example 77

1-Benzyl-4-(5-fluoro-3-methyl-1H-indol-2-yl)-N,N-dimethylcyclohexanamine, citrate (2:1), non-polar diastereomer

Example 78

1-Benzyl-4-(5-fluoro-3-methyl-1H-indol-2-yl)-N,N-dimethylcyclohexanamine, citrate (1:1), polar diastereomer 1-Benzyl-4-(5-fluoro-3-methyl-1H-indol-2-yl)-N,N-dimethylcyclohexanamine (non-polar and polar diastereomer)

Hydrogenation with HBr/Sn

Ex. 26 (200 mg, 0.55 mmol) was dissolved in HBr/glacial acetic acid (33% HBr, 20 ml). Sn powder (700 mg, 5.9 mmol) was then added to the mixture in portions in the course of 60 min. When the addition had ended, the reaction mixture was stirred for a further 60 min.—For working up, ethanol (20 ml) was added to the mixture and the solvent mixture was concentrated to dryness on a rotary evaporator. The residue which remained was rendered basic by addition of 5 N NaOH (40 ml). Methylene chloride was added to the solution obtained and the mixture was extracted (4×20 ml). The combined organic phases were dried with $MgSO_4$ and then concentrated. The residue obtained (200 mg) was purified by column chromatography (mobile phase: non-polar isomer EtOAc, polar isomer EtOAc/EtOH 2:1)). 1-Benzyl-4-(5-fluoro-3-methyl-1H-indol-2-yl)-N,N-dimethylcyclohexanamine (less polar diastereomer) was obtained in this way in a yield of 87 mg (43%). The more polar diastereoisomer was obtained in a yield of 35 mg (17%).

Hydrogenation with $H_2$/Pd

Ex. 26 (137 mg, 0.38 mmol) was dissolved in ethanol (30 ml), the catalyst (Pd/charcoal 5%, 100 mg) was added and hydrogenation was carried out at RT under a hydrogen pressure of 3 bar for 2 h. The solid residue (128 mg) obtained after separating off the catalyst and removing the solvent was purified by column chromatography (mobile phase: non-polar isomer EtOAc, polar isomer EtOAc/EtOH 2:1). The less polar diastereoisomer was obtained in this way in a yield of 40 mg (29%), and the more polar diastereoisomer was obtained in a yield of 55 mg (40%).

1-Benzyl-4-(5-fluoro-3-methyl-1H-indol-2-yl)-N,N-dimethylcyclohexanamine, citrate (2:1), non-polar diastereomer 1-Benzyl-4-(5-fluoro-3-methyl-1H-indol-2-yl)-N,N-dimethylcyclohexanamine (non-polar isomer, 72 mg, 0.2 mmol) was dissolved in isopropanol (5 ml) at the boiling point and citric acid (40 mg, 0.21 mmol), dissolved in hot isopropanol (1 ml), was added. The solution was cooled to 5° C. (refrigerator) and left to stand for 17 h. The precipitate formed was separated off by means of a frit. Example 77 was obtained in this way in a yield of 87 mg (94%, melting point: 228-233° C., crystal conversion from 140° C.).

1-Benzyl-4-(5-fluoro-3-methyl-1H-indol-2-yl)-N,N-dimethylcyclohexanamine, citrate (1:1), polar diastereomer (1s,4s)-1-benzyl-4-(5-fluoro-3-methyl-1H-indol-2-yl)-N,N-dimethylcyclohexanamine (polar isomer, 80 mg, 0.22 mmol) was dissolved in isopropanol (3 ml) at the boiling point and citric acid (60 mg, 0.31 mmol), dissolved in hot isopropanol (2 ml), was added. The solution was cooled to 5° C. (refrigerator) and left to stand for 17 h. The precipitate formed was separated off by means of a frit. Example 78 was obtained in this way in a yield of 84 mg (68%, melting point: 183-184° C.).

Example 79

1-Butyl-4-(5-fluoro-3-methyl-1H-indol-2-yl)-N,N-dimethylcyclohexanamine hydrochloride

1-Butyl-4-(5-fluoro-3-methyl-1H-indol-2-yl)-N,N-dimethylcyclohexanamine (1 diastereomer)

5-Fluoro-3-methylindole (Ind-8) (596 mg, 4 mmol) was dissolved in methylene chloride (30 ml) together with ketone Ket-4 (788 mg, 4 mmol), and trifluoromethanesulfonic acid (500 µl, 5.63 mmol) was added. The mixture was stirred at RT for 24 h. Triethylsilane (2 ml, 12.4 mmol) was then added to the mixture. The reaction mixture was stirred at RT for 60 h. For working up, 2 N NaOH (30 ml) was added to the reaction mixture and the mixture was stirred at RT for 20 min. After the organic phase had been separated off, the aqueous phase was extracted with methylene chloride (3×15 ml). The combined organic extracts were dried over $Na_2SO_4$ and then concentrated. The crude product obtained (1.4 g) was purified by column chromatography [silica gel 60 (50 g); ethyl acetate (500 ml)] 1-Butyl-4-(5-fluoro-3-methyl-1H-indol-2-yl)-N,N-dimethylcyclohexanamine was obtained in a yield of 266 mg (22%) as a white solid. Only one of two possible diastereoisomers was obtained.

1-Butyl-4-(5-fluoro-3-methyl-1H-indol-2-yl)-N,N-dimethylcyclohexanamine hydrochloride 1-Butyl-4-(5-fluoro-3-methyl-1H-indol-2-yl)-N,N-dimethylcyclohexanamine (266 mg, 0.8 mmol) was dissolved in ethyl methyl ketone (30 ml). $Me_3SiCl$ (20.5 µl, 1.6 mmol) was then added dropwise at RT and the mixture was stirred for 1 h. A white precipitate precipitated out. The precipitate was filtered off with suction, washed with ethyl methyl ketone (2×5 ml) and then dried. Example 79 (193 mg, m.p. 255-265° C., 61%) was a white solid

Example 80

4-(5-Fluoro-3-methyl-1H-indol-2-yl)-N,N-dimethyl-1-phenylcyclohexanamine, citrate (2:1), non-polar diastereomer

Example 81

4-(5-Fluoro-3-methyl-1H-indol-2-yl)-N,N-dimethyl-1-phenylcyclohexanamine, citrate (1:1), polar diastereomer

4-(5-Fluoro-3-methyl-1H-indol-2-yl)-N,N-dimethyl-1-phenylcyclohexanamine (non-polar and polar diastereomer)

(±)-2-(4-(Dimethylamino)-4-phenylcyclohex-1-enyl)-3-methyl-5-fluoro-1H-indole (free base from Example 28) (420 mg, 1.2 mmol) was dissolved in HBr/glacial acetic acid (33% HBr, 25 ml). Sn powder (1.4 g, 12 mmol) was then added to the mixture in portions in the course of 40 min. When the addition had ended, the reaction mixture was stirred for a further 60 min.—For working up, the mixture was concentrated to dryness on a rotary evaporator. The residue which remained was rendered basic by addition of 5 N NaOH (40 ml). Methylene chloride was added to the solution obtained and the mixture was extracted (4×20 ml). The combined organic phases were dried with $MgSO_4$ and then concentrated. The residue obtained (360 mg) was boiled up in ethanol (30 ml), the substance only partly dissolving. The mixture was left at 5° C. for 1 h and the solid was then separated off. 4-(5-Fluoro-3-methyl-1H-indol-2-yl)-N,N-dimethyl-1-phenylcyclohexanamine (less polar isomer) was obtained in this way in a yield of 256 mg (60%, melting point: 199-205° C.).

The ethanolic mother liquor was concentrated. The residue which remained (162 mg) was purified by column chromatography (mobile phase: EtOAc/EtOH 2:1)). 4-(5-Fluoro-3-methyl-1H-indol-2-yl)-N,N-dimethyl-1-phenylcyclohexanamine (more polar diastereoisomer) was obtained in this way in a yield of 150 mg (35%).

4-(5-Fluoro-3-methyl-1H-indol-2-yl)-N,N-dimethyl-1-phenylcyclohexanamine, citrate (2:1), non-polar diastereomer 4-(5-Fluoro-3-methyl-1H-indol-2-yl)-N,N-dimethyl-1-phenylcyclohexanamine (less polar isomer) (250 mg, 0.71 mmol) was dissolved in isopropanol (300 ml) at the boiling point and citric acid (138 mg, 0.72 mmol), dissolved in hot isopropanol (5 ml), was added. The solution was concentrated to approx. 130 ml, cooled to 5° C. (refrigerator) and left to stand for 17 h. The precipitate formed was separated off by means of a frit. Example 80 was obtained in this way in a yield of 218 mg (68%, melting point: 224-229° C., crystal conversion from 205).

4-(5-Fluoro-3-methyl-1H-indol-2-yl)-N,N-dimethyl-1-phenylcyclohexanamine, citrate (1:1), polar diastereomer 4-(5-Fluoro-3-methyl-1H-indol-2-yl)-N,N-dimethyl-1-phenylcyclohexanamine (more polar diastereoisomer, 150 mg, 0.43 mmol) was dissolved in methanol (5 ml) at the boiling point and citric acid (84 mg, 0.44 mmol), dissolved in hot methanol (2 ml), was added. The solution was concentrated. The residue obtained was heated with isopropanol (10 ml), the substance remaining largely undissolved. The mixture was left at 5° C. for 1 h. The solid was then separated off by means of a frit. Example 81 was obtained in this way in a yield of 131 mg (56%, melting point: 190-194° C.).

Example 82

(±)-2-(4-(Dimethylamino)-4-butylcyclohex-1-enyl)-3-(2-(1H-benzo[d] imidazol-1-yl)ethyl)-5-fluoro-1H-indole 1-[2-(5-Fluoro-1H-indol-3-yl-ethyl]-1H-benzimidazole (Ind-19, 977 mg, 3.5 mmol) and ketone (Ket-4, 690 mg, 3.5 mmol) were dissolved in abs. methylene chloride (30 ml), and trifluoromethanesulfonic acid (0.93 ml, 10.5 mmol) was added rapidly. The mixture was stirred at RT for 48 h, during which a dark brown oil settled out. After addition of 1 N NaOH (20 ml) and $CH_2Cl_2$ (20 ml), the mixture was subsequently stirred for a further 20 min, the phases were separated, the aqueous phase was extracted twice with $CH_2Cl_2$, the combined organic phases were washed with water and dried ($Na_2SO_4$) and the solution was concentrated i. vac. The residue which remained was purified by flash chromatography with EA/EtOH (1:4).

Yield: 522 mg (33%), porous solid
$^1$H-NMR (DMSO-$d_6$): 0.88 (3H, t); 1.23 (10H, m); 2.11 (3H, bs); 2.22 (6H, bs); 3.22 (2H, t); 4.43 (2H, t); 5.62 (1H, s); 6.86 (1H, m); 7.20 (4H, m); 7.41 (1H, d); 7.61 (1H, d); 7.86 (1H, s); 10.83 (1H, s).

4-(3-(2-(1H-Benzo[d]imidazol-1-yl)ethyl)-5-fluoro-1H-indol-2-yl)-1-butyl-N,N-dimethylcyclohexan-amine, citrate (1:1):More polar diastereomer Tin (1.25 g) was added to a solution from of the olefin just prepared (450 mg, 0.98 mmol) in HBr/glacial acetic acid (35 ml) in the course of 20 min and the mixture was stirred at RT for 4 h. Ethanol was added to the mixture, the reaction mixture was concentrated to dryness and the residue was dissolved in 5 N NaOH (50 ml) and methylene chloride (30 ml). The phases were separated, the aqueous phase was extracted twice with $CH_2Cl_2$ and the combined organic phases were washed with water, dried over $Na_2SO_4$ and concentrated i. vac. The residue which remained was separated by flash chromatography with EA/EtOH (1:4→EtOH).

Yield: 304 mg (67%) non-polar diastereomer
119 mg (26%) polar diastereomer
The polar compound (107 mg, 0.232 mmol) was dissolved in hot ethanol (4 ml) and a solution of citric acid (45 mg, 0.232 mmol) in hot ethanol (3 ml) was added. After ether had been added and the mixture had stood in a refrigerator for 2 hours, the solid formed was filtered off with suction and dried i. vac.

Yield: 115 mg (Example 82; 76%), porous solid
$^1$H-NMR (DMSO-$d_6$): 0.92 (3H, t); 1.07 (2H, m); 1.23 (4H, m); 1.34 (2H, m); 1.48 (2H, m); 1.62 (2H, m); 1.80 (2H, m); 2.08 (1H, m); 2.57 (10H, m); 3.17 (2H, t); (4.46 (2H, t); 6.85 (1H, m); 7.24 (4H, m); 7.52 (1H, d); 7.63 (1H, d); 7.79 (1H, s); 10.77 (1 H, s), citrate.

Example 83

4-(3-(2-(1H-Benzo[d]imidazol-1-yl)ethyl)-5-fluoro-1H-indol-2-yl)-N,N-dimethyl-1-phenylcyclohexan-amine, citrate (1:1):Less Polar Diastereomer Tin (2.20 g) was added olefin Example 54 (836 mg, 1.74 mmol) in HBr/glacial acetic acid (70 ml) in the course of 20 min and the mixture was stirred at RT for 4 h. Ethanol was added to the mixture, the reaction mixture was concentrated to dryness and the residue was dissolved in 5 N NaOH (40 ml) and methylene chloride (30 ml). The phases were separated, the aqueous phase was extracted twice with $CH_2Cl_2$ and the combined organic phases were washed with water, dried over $Na_2SO_4$ and concentrated i. vac. The residue which remained was separated by flash chromatography with EA/EtOH (9:1→1:4).

Yield: 244 mg (29%), non-polar diastereomer
367 mg (44%), polar diastereomer
The less polar compound just obtained (225 mg 0.468 mmol) was dissolved in hot ethanol (8 ml), and a solution of citric acid (90 mg, 0.468 mmol) in hot ethanol (5 ml) was added. After the mixture had stood in a refrigerator for 2 hours, the solid formed was filtered off with suction and dried i. vac.

Yield: 206 mg, (83, 65%)
Melting point: 115-125° C.
$^1$H-NMR (DMSO-$d_6$): 1.17 (2H, m); 1.45 (2H, m); 2.10 (6H, s); 2.28 (1H, t); 2.64 (6H, m); 3.19 (2H, t); 4.44 (2H, t); 6.84 (1H, m); 7.11 (2H, m); 7.26 (8H, m); 7.48 (1H, m); 7.85 (1H, s); 10.67 (1H, s), citrate.

Example 84

4-(3-(2-(1H-Benzo[d]imidazol-1-yl)ethyl)-5-fluoro-1H-indol-2-yl)-N,N-dimethyl-1-phenylcyclohexan-amine, citrate (1:1):More polar diastereomer The more polar compound obtained under Example 83 (346 mg 0.72 mmol) was dissolved in hot ethanol (10 ml), and a solution of citric acid (138 mg, 0.72 mmol) in hot ethanol (6 ml) was added. After the mixture had stood in a refrigerator for 2 hours, the solid formed was filtered off with suction and dried i. vac.

Yield: 348 mg (72%), porous solid
$^1$H-NMR (DMSO-$d_6$): 1.21 (2H, m); 1.45 (2H, m); 2.27 (6H, s); 2.70 (4H, m); 3.13 (2H, t); 4.43 (2H, t); 6.78 (1H, m); 7.08 (1H, m); 7.24 (3H, m); 7.46 (5H, d); 7.66 (1H, d); 7.82 (1H, s); 10.41 (1H, s), citrate.

Example 85

(±)-2-(4-(Dimethylamino)-4-benzylcyclohex-1-enyl)-3-(2-(pyrrolidin-1-yl)ethyl)-5-fluoro-1H-indole Indole (Ind-36, 700 mg, 3.0 mmol) and ketone (Ket-3, 697 mg, 3.0 mmol) were dissolved in abs. $CH_2Cl_2$ (30 ml) at RT and trifluoromethanesulfonic acid (1.36 g, 0.80 ml. 9.0 mmol) was added swiftly. A black oil then precipitated out. The mixture was stirred at RT for 2 d. 1 N NaOH (30 ml) was added and the mixture was subsequently stirred for 20 min. The organic phase was separated off and the aqueous phase was extracted with $CH_2Cl_2$ (2×30 ml). The combined organic phases were washed with water (15 ml), dried over $Na_2SO_4$, filtered and concentrated i. vac. By flash chromatography with 50 g of silica gel and acetonitrile/methanol/aqueous 1 N ammonium chloride solution (9:1:1), the indole was obtained as the first fraction and the purified product as the second fraction. The second fraction was concentrated i. vac., the residue was rendered basic with 2 N NaOH, the mixture was extracted twice with $CH_2Cl_2$ and the extract was dried over $Na_2SO_4$ and concentrated i. vac.

Yield: 672 mg (50%), colourless solid
$^1$H-NMR (DMSO-$d_6$): 1.40 (2H; m); 1.67 (4H, m); 2.01 (4H, m); 2.31 (6H, m); 2.45 (5H, m); 2.75 (4H, m); 5.89 (1H, bs); 6.83 (1H, m); 7.20 (7H, m); 10.76 (1H, s).

1-Benzyl-4-(5-fluoro-3-(2-(pyrrolidin-1-yl)ethyl)-1H-indol-2-yl)-N,N-dimethylcyclohexanamine, citrate (1:1):Less Polar Diastereomer The olefin just obtained (650 mg, 1.46 mmol) was dissolved in HBr/glacial acetic acid (33% strength, 30 ml), and tin (1.90 g) was added in portions at RT in the course of 30 min. The mixture was stirred at RT for 4 h. Ethanol was added, the solvent mixture was removed i. vac. and the residue was dissolved with 5 N NaOH (60 ml) and $CH_2Cl_2$ (80 ml). The phases were separated, the aqueous phase was extracted twice with $CH_2Cl_2$ and the combined organic phases were washed with water, dried over $Na_2SO_4$, filtered and concentrated i. vac. The residue which remained was purified by flash chromatography with chloroform/methanol (20:1→4:1 in each case+1% triethylamine).

Yield: 351 mg (54%) non-polar compound, contained triethylamine 108 mg (17%) polar compound, contained triethylamine The less polar compound just prepared (274 mg 0.61 mmol) was dissolved hot in ethanol (4 ml), and a solution of citric acid (118 mg, 0.61 mmol) in ethanol (2 ml) was added. After 2 hours at RT, the precipitate formed was filtered off with suction and rinsed with ether.

Yield: 339 mg, (85, 87%)
Melting point: 200-202° C.
$^1$H-NMR (DMSO-$d_6$): 1.17 (2H, m); 1.43 (2H, m); 1.67 (2H, m); 1.96 (8H; m); 2.38 (6H, s); 2.59 (4H, m); 2.86 (2H, m); 3.11 (2H, t); 6.81 (1H, m); 7.24 (7H, m); 10.79 (1H, bs); 11.1 (1H, bs), citrate.

Example 86

1-Benzyl-4-(5-fluoro-3-(2-(pyrrolidin-1-yl)ethyl)-1H-indol-2-yl)-N,N-dimethylcyclohexanamine, citrate (1:1):More polar diastereomer The more polar compound obtained under Example 85 (94 mg, 0.21 mmol) was dissolved hot in ethanol (2 ml), and a solution of citric acid (40 mg, 0.21 mmol) in ethanol (1 ml) was added. After 2 hours at RT, the precipitate formed was filtered off with suction and rinsed with ether.

Yield: 76 mg (86, 57%); melting point: amorphous solid
$^1$H-NMR (DMSO-$d_6$): 1.73 (4H, m); 1.91 (3H, m); 2.02 (2H, m); 2.36 (6H, s); 2.57 (4H, m); 2.85-3.19 (7H, m); 6.85 (1H, m); 7.29 (7H, m); 11.0 (1H, s); 11.2 (2H, bs), citrate.

Example 87

(±)-2-(4-(Dimethylamino)-4-butylcyclohex-1-enyl)-3-(2-(pyrrolidin-1-yl)ethyl)-5-fluoro-1H-indole Indole (Ind-36, 1.00 g, 4.3 mmol) and ketone (Ket-4, 849 mg, 4.3 mmol) were dissolved in abs. $CH_2Cl_2$ (50 ml) at RT and trifluoromethanesulfonic acid (1.93 g, 1.15 ml. 12.9 mmol) was added swiftly. A black oil then precipitated out. The mixture was stirred at RT for 3 d. 1 N NaOH (50 ml) was added and the mixture was subsequently stirred for 20 min. The organic phase was separated off and the aqueous phase was extracted with $CH_2Cl_2$ (2×50 ml). The combined organic phases were washed with water (20 ml), dried over $Na_2SO_4$, filtered and concentrated i. vac. By flash chromatography with 50 g of silica gel and acetonitrile/methanol/aqueous 1 N ammonium chloride solution (9:1:1), the indole was obtained as the first fraction and the purified product as the second fraction. The second fraction was concentrated i. vac., the residue was rendered basic with 2 N NaOH, the mixture was extracted twice with $CH_2Cl_2$ and the extract was dried over $Na_2SO_4$ and concentrated i. vac.

Yield: 668 mg (37%), colourless solid
$^1$H-NMR (DMSO-$d_6$): 0.90 (3H; t); 1.24-1.60 (6H, m); 1.91 (4H, m); 2.11 (2H, m); 2.38 (6H, s); 2.57 (4H, m); 5.87 (1H, bs); 6.83 (1H, m); 7.22 (2H, m); 10.82 (1H, s).

1-Butyl-4-(5-fluoro-3-(2-(pyrrolidin-1-yl)ethyl)-1H-indol-2-yl)-N,N-dimethylcyclohexanamine, citrate (1:1) (87:Less polar diastereomer)

The olefin just prepared (640 mg, 1.55 mmol) was dissolved in HBr/glacial acetic acid (33% strength, 35 ml), and tin (2.02 g) was added in portions at RT in the course of 30 min. The mixture was stirred at RT for 4 h. Ethanol was added, the solvent mixture was removed i. vac. and the residue was dissolved with 5 N NaOH (60 ml) and $CH_2Cl_2$ (80 ml). The phases were separated, the aqueous phase was extracted twice with $CH_2Cl_2$ and the combined organic phases were washed with water, dried over $Na_2SO_4$, filtered and concentrated i. vac. The residue which remained was purified by flash chromatography with chloroform/methanol (20:1→4:1 in each case+1% triethylamine).

Yield: 285 mg (44%) non-polar compound, contained triethylamine 174 mg (27%) polar compound, contained triethylamine The less polar compound just obtained (261 mg 0.63 mmol) was dissolved hot in ethanol (ml), and a solution of citric acid (121 mg, 0.63 mmol) in ethanol (ml) was added. After 2 hours at RT, the precipitate formed was filtered off with suction and rinsed with ether.

Yield: 242 mg (63%); melting point: 168-186° C.
$^1$H-NMR (DMSO-$d_6$): 0.94 (3H, t); 1.25-1.55 (10H, m); 1.98 (6H, m); 2.38 (6H, s); 2.57 (4H, m); 2.97 (1H, m); 3.09 (2H, t); 3.13 (2H, t); 6.82 (1H, m); 7.30 (2H, m); 10.89 (1H, s); 11.1 (1H, bs), citrate.

Example 88

1-Butyl-4-(5-fluoro-3-(2-(pyrrolidin-1-yl)ethyl)-1H-indol-2-yl)-N,N-dimethylcyclohexanamine, citrate (1:1) (88:More polar diastereomer)

The more polar compound obtained under Example 87 (176 mg, 0.43 mmol) was dissolved hot in ethanol (ml), and a solution of citric acid (82 mg, 0.43 mmol) in ethanol (ml) was added. After 2 hours at RT, the precipitate formed was filtered off with suction and rinsed with ether.

Yield: 138 mg (88, 54%); amorphous solid
$^1$H-NMR (DMSO-$d_6$): 1.04 (3H, t); 1.40 (4H, m); 1.76 (12H, m); 2.02 (2H, m); 2.47 (6H, s); 2.59 (4H, m); 2.88-3.17 (5H, m); 6.85 (1H, m); 7.28 (2H, m); 10.9 (1H, s); 11.1 (2H, bs), citrate.

Example 89

(±)-2-(4-(Dimethylamino)-4-phenylcyclohex-1-enyl)-3-(2-(pyrrolidin-1-yl)ethyl)-5-fluoro-1H-indole Indole (Ind-36, 600 mg, 2.60 mmol) and ketone (Ket-10, 561 mg, 2.60 mmol) were dissolved in abs. $CH_2Cl_2$ (30 ml) at RT and trifluoromethanesulfonic acid (1.16 g, 0.69 ml, 7.7 mmol) was added swiftly. A black oil then precipitated out of the solution. The mixture was stirred at RT for 24 h. 1 N NaOH (30 ml) was added and the mixture was subsequently stirred for 20 min. The organic phase was separated off and the aqueous phase was extracted with $CH_2Cl_2$ (2×30 ml). The combined organic phases were washed with water (15 ml), dried over $Na_2SO_4$, filtered and concentrated i. vac. Flash chromatography of the residue with 50 g of silica gel and chloroform/methanol (9:1+1% triethylamine) gave a mixture of indole and product. By renewed flash chromatography of mixed fractions, which had been concentrated i. vac., with 50 g of silica gel and acetonitrile/methanol/aqueous 1 N ammonium chloride solution (9:1:1), the indole was obtained as the first fraction and the purified product as the second fraction. The second fraction was concentrated i. vac., the residue was rendered basic with 2 N NaOH, the mixture was extracted twice with $CH_2Cl_2$ and the extract was dried over $Na_2SO_4$ and concentrated i. vac.

Yield: 621 mg (55%), colourless solid $^1$H-NMR (DMSO-$d_6$): 1.66 (6H, m); 2.09 (8H, m); 2.40 (6H, m); 2.61 (4H, m); 6.20 (1H, bs); 6.82 (1H, m); 7.21 (5H, m); 7.45 (2H, m); 10.73 (1H, s).

4-(5-Fluoro-3-(2-(pyrrolidin-1-yl)ethyl)-1H-indol-2-yl)-N,N-dimethyl-1-phenylcyclohexanamine, citrate (1:1):Less polar diastereomer The olefin just prepared (600 mg, 1.40 mmol) was dissolved in HBr/glacial acetic acid (33% strength, 30 ml), and tin (1.82 g) was added in portions at RT in the course of 30 min. The mixture was stirred at RT for 4 h. Ethanol was added, the solvent mixture was removed i. vac. and the residue was dissolved with 5 N NaOH (60 ml) and $CH_2Cl_2$ (80 ml). The phases were separated, the aqueous phase was extracted twice with $CH_2Cl_2$ and the combined organic phases were washed with water, dried over $Na_2SO_4$, filtered and concentrated i. vac. The residue which remained was purified by flash chromatography with chloroform/methanol (20:1→4:1+1% triethylamine).

Yield: 352 mg (58%), non-polar compound, contained triethylamine 213 mg (35%), polar compound, contained triethylamine The less polar compound just obtained (295 mg 0.68 mmol) was dissolved hot in ethanol (7 ml), and a solution of citric acid (131 mg, 0.68 mmol) in ethanol (2 ml) was added. After 2 hours at RT, the precipitate formed was filtered off with suction and rinsed with ether.

Yield: 193 mg (45%); melting point: 219-222° C.

$^1$H-NMR (DMSO-$d_6$): 1.55 (2H, m); 1.67 (2H, m); 1.93 (4H; bs); 2.06 (6H, s); 2.14 (2H, m); 2.57 (2H, m); 2.86 (2H, d); 3.03 (4H, m); 3.20 (2H, t); 6.84 (1H, m); 7.32 (7H, m); 10.94 (1H, bs); 11.1 (1H, bs) citrate.

Example 90

4-(5-Fluoro-3-(2-(pyrrolidin-1-yl)ethyl)-1H-indol-2-yl)-N,N-dimethyl-1-phenylcyclohexanamine, citrate (1:1):More polar diastereomer The polar compound obtained under Example 89 (166 mg, 0.38 mmol) was dissolved hot in ethanol (2 ml), and a solution of citric acid (74 mg, 0.38 mmol) in ethanol (1 ml) was added. After 2 hours at RT, the precipitate formed was filtered off with suction and rinsed with ether.

Yield: 109 mg (90, 46%); melting point: 196-198° C.

$^1$H-NMR (DMSO-$d_6$): 1.41 (2H, m); 1.82 (2H, m); 1.96 (4H, m); 2.10 (2H; s); 2.35 (6H, s); 2.61 (4H, m); 3.08 (6H, t); 3.18 (2H, m); 6.77 (1H, m); 7.13 (1H, m); 7.32 (1H, m); 7.55 (3H, m); 7.67 (2H, m); 10.6 (1H, s), citrate.

Example 91

1-Benzyl-4-(5-fluoro-3-(2-(piperidin-1-yl)ethyl)-1H-indol-2-yl)-N,N-dimethylcyclohexanamine, citrate (1:1):Less polar diastereomer Olefin Example 55 (691 mg, 1.5 mmol) was dissolved in HBr/glacial acetic acid (33% strength, 30 ml), and tin (1.96 g) was added in portions at RT in the course of 30 min. The mixture was stirred at RT for 4 h. Ethanol was added, the solvent mixture was removed i. vac. and the residue was dissolved with 5 N NaOH (60 ml) and $CH_2Cl_2$ (80 ml). The phases were separated, the aqueous phase was extracted twice with $CH_2Cl_2$ and the combined organic phases were washed with water, dried over $Na_2SO_4$, filtered and concentrated i. vac. The residue which remained was purified by flash chromatography with 50 g of silica gel and chloroform/methanol (50:1→methanol).

Yield: 512 mg (74%), non-polar compound, 130 mg (19%), polar compound

The less polar compound just prepared (420 mg 0.91 mmol) was dissolved hot in ethanol (4 ml), and a solution of citric acid (175 mg, 0.91 mmol) in ethanol (2 ml) was added. After 2 hours at RT, the precipitate formed was filtered off with suction and rinsed with ethanol.

Yield: 426 mg (72%); melting point: 191-194° C.

$^1$H-NMR (DMSO-$d_6$): 1.54-1.75 (8H, m); 2.10 (6H, s); 2.56-2.65 (4H, m); 2.90 (4H, m); 3.06 (4H, bs); 6.85 (1H, m); 7.29 (3H, m); 7.40 (4H, m); 11.02 (1H, s), citrate.

Example 92

1-Benzyl-4-(5-fluoro-3-(2-(piperidin-1-yl)ethyl)-1H-indol-2-yl)-N,N-dimethylcyclohexanamine, citrate (2:3):More polar diastereomer The more polar compound prepared under Example 91 (111 mg, 0.24 mmol) was dissolved hot in ethanol (2 ml) and a solution of citric acid (46 mg, 0.24 mmol) in ethanol (1 ml) was added. Ether was added, and thereafter a precipitate precipitated out. This was filtered off with suction and washed with ether.

Yield: 80 mg (51%); melting point: amorphous solid $^1$H-NMR (DMSO-$d_6$): 1.50 (4H, m); 1.72 (8H, m); 2.13 (4H, m); 2.46 (2H, s); 2.90 (6H, m); 3.02 (3H, m); 6.77 (1H, m); 7.14 (2H, m); 7.23 (5H, m); 10.61 (H, bs), citrate.

Example 93

1-Butyl-4-(5-fluoro-3-(2-(piperidin-1-yl)ethyl)-1H-indol-2-yl)-N,N-dimethylcyclohexanamine, citrate (4:3):Less polar diastereomer Olefin Example 56 (972 mg, 2.30 mmol) was dissolved in HBr/glacial acetic acid (33% strength, 50 ml) and tin (2.98 g) was added in portions at RT in the course of 30 min. The mixture was stirred at RT for 4 h. Ethanol was added, the solvent mixture was removed i. vac. and the residue was dissolved with 5 N NaOH (120 ml) and $CH_2Cl_2$ (160 ml). The phases were separated, the aqueous phase was extracted twice with $CH_2Cl_2$ and the combined organic phases were washed with water, dried over $Na_2SO_4$, filtered and concentrated i. vac. The residue which remained was purified by flash chromatography with 100 g of silica gel and chloroform/methanol (50:1→methanol). The non-polar diastereomer was pure, but the polar diastereomer was highly contaminated with triethylamine hydrochloride, which was presumably contained in the silica gel used. The polar diastereomer was taken up in CHCl₃ and the mixture was washed with 1 N NaOH, The phases were separated and the aqueous phase was extracted with CHCl₃. The combined organic phases were dried over Na₂SO₄, filtered and concentrated i. vac.

Yield: 472 mg (48%), non-polar compound 45 mg (5%), polar compound

The non-polar compound just prepared (444 mg, 1.04 mmol) was dissolved hot in ethanol (5 ml), and a solution of citric acid (200 mg, 1.04 mmol) in ethanol (2 ml) was added. Ether was added, and thereafter a precipitate precipitated out. This was filtered off with suction and washed with ether.

Yield: 390 mg (93, 61%); amorphous solid $^1$H-NMR (DMSO-d₆): 0.96 (3H, t); 1.33 (6H, m); 1.62 (6H, m); 1.88 (6H, m); 2.01 (2H, m); 2.29 (2H, m); 2.73 (6H, s); 3.08 (6H, m); 6.84 (1H, m); 7.21 (1H, m); 7.39 (1H, m); 11.66 (1H, s), citrate.

Example 94

1-Butyl-4-(5-fluoro-3-(2-(piperidin-1-yl)ethyl)-1H-indol-2-yl)-N,N-dimethylcyclohexanamine, citrate (1:1):More polar diastereomer The more polar compound prepared under Example 93 (43 mg, 0.10 mmol) was dissolved hot in ethanol (1 ml), and a solution of citric acid (19 mg, 0.10 mmol) in ethanol (1 ml) was added. Scarcely any precipitate precipitated out, even after addition of ether, and thereafter the solvent mixture was removed i. vac.

Yield: 45 mg (94, 72%); amorphous solid $^1$H-NMR (DMSO-d₆): 0.96 (3H, t); 1.42 (6H, m); 1.75-1.93 (14H, m); 2.53-2.70 (10H, m); 3.16 or 3.34 (4H, m); 6.84 (1H, m); 7.28 (1H, m); 7.40 (1H, m); 11.22 (1H, s), citrate (sample still contained TEA×HCl).

Example 95

4-(5-Fluoro-3-(2-(piperidin-1-yl)ethyl)-1H-indol-2-yl)-N,N-dimethyl-1-phenylcyclohexanamine, citrate (1:1):Less polar diastereomer Olefin Example 57 (354 mg, 0.8 mmol) was dissolved in HBr/glacial acetic acid (33% strength, 15 ml) and tin (1.03 g) was added in portions at RT in the course of 30 min. The mixture was stirred at RT for 4 h. Ethanol was added, the solvent mixture was removed i. vac. and the residue was dissolved with 5 N NaOH (30 ml) and CH₂Cl₂ (40 ml). The phases were separated, the aqueous phase was extracted twice with CH₂Cl₂ and the combined organic phases were washed with water, dried over Na₂SO₄, filtered and concentrated i. vac. By flash chromatography of the residue with 50 g of silica gel chloroform/methanol (20:1→methanol), the non-polar diastereomer was obtained in only a highly contaminated form, and was purified by renewed flash chromatography with 25 g of silica gel and chloroform/methanol (50:1). The polar diastereomer was pure.

Yield: 161 mg (45%), non-polar compound 109 mg (30%), polar compound

The less polar compound just prepared (140 mg, 0.31 mmol) was dissolved hot in ethanol (3 ml) and a solution of citric acid (60 mg, 0.31 mmol) in ethanol (1 ml) was added. After 2 hours at RT, the precipitate formed was filtered off with suction and rinsed with ethanol.

Yield: 127 mg (63%); melting point: 220-223° C.

$^1$H-NMR (DMSO-d₆): 1.54-1.75 (8H, m); 2.10 (6H, s); 2.56-2.65 (4H, m); 2.90 (4H, m); 3.06 (4H, bs); 6.85 (1H, m); 7.29 (3H, m); 7.40 (4H, m); 11.02 (1H, s), citrate.

Example 96

4-(5-Fluoro-3-(2-(piperidin-1-yl)ethyl)-1H-indol-2-yl)-N,N-dimethyl-1-phenylcyclohexanamine, citrate (1:1):More polar diastereomer The polar compound prepared under Example 95 (93 mg, 0.21 mmol) was dissolved hot in ethanol (2 ml), and a solution of citric acid (40 mg, 0.21 mmol) in ethanol (1 ml) was added. After 2 hours at RT, the precipitate formed was filtered off with suction and rinsed with ethanol.

Yield: 73 mg (55%); melting point: 153-167° C.

$^1$H-NMR (DMSO-d₆): 1.50 (4H, m); 1.72 (8H, m); 2.13 (4H, m); 2.46 (2H, s); 2.90 (6H, m); 3.02 (3H, m); 6.77 (1H, m); 7.14 (2H, m); 7.23 (5H, m); 10.61 (H, bs) citrate.

Example 97

(±)-2-(4-(Dimethylamino)-4-benzylcyclohex-1-enyl)-3-(2-(1H-pyrazol-1-yl)ethyl)-5-fluoro-1H-indole Indole (Ind-38, 600 mg, 2.62 mmol) and ketone (Ket-3, 605 mg, 2.62 mmol) were dissolved in abs. methylene chloride (20 ml), and trifluoromethanesulfonic acid (0.70 ml, 7.9 mmol) was added rapidly. The mixture was stirred at RT for 48 h, during which a dark brown oil settled out. After addition of 1 N NaOH (20 ml) and CH₂Cl₂ (20 ml), the mixture was subsequently stirred for a further 20 min, the phases were separated, the aqueous phase was extracted twice with CH₂Cl₂, the combined organic phases were washed with water and dried (Na₂SO₄) and the solution was concentrated i. vac. The residue which remained was purified by flash chromatography with CHCl₃/MeOH (20:1).

Yield: 259 mg (22%), viscous oil $^1$H-NMR (DMSO-d₆): 1.96 (2H, m); 2.32 (6H, bs); 2.77 (6H, m); 3.17 (2H, t); 4.28 (2H, t); 5.78 (1H, bs); 6.12 (1H, s); 6.86 (2H, m); 7.17 (6H, d); 7.54 (1H, s); 10.85 (1H, s).

4-(3-(2-(1H-Pyrazol-1-yl)ethyl)-5-fluoro-1H-indol-2-yl)-1-benzyl-N,N-dimethylcyclohexanamine, citrate (2:3):Less polar diastereomer Tin (0.70 g) was added to a solution of the olefin just prepared (250 mg, 0.565 mmol) in HBr/glacial acetic acid (25 ml) in the course of 20 min and the mixture was stirred at RT for 4 h. Ethanol was added to the mixture, the reaction mixture was concentrated to dryness and the residue was dissolved in 5 N NaOH (30 ml) and methylene chloride (30 ml). The phases were separated, the aqueous phase was extracted twice with CH₂Cl₂ and the combined organic phases were washed with water, dried over Na₂SO₄ and concentrated i. vac. The residue which remained was separated by flash chromatography with CHCl₃/MeOH (9:1→MeOH). The non-polar compound was obtained as a salt (159 mg), and it was then possible to liberate this by stirring with 1 N NaOH and CH₂Cl₂. The phases were separated, the aqueous phase was extracted twice with CH₂Cl₂ and the combined organic phases were dried over Na₂SO₄, filtered and concentrated i. vac. The chloroform used was probably contaminated with HCl.

Yield: 85 mg (34%) non-polar diastereomer 37 mg (15%) polar diastereomer

The less polar compound just isolated (63 mg 0.14 mmol) was dissolved in hot ethanol (2 ml), and a solution of citric acid (27 mg, 0.14 mmol) in hot ethanol (2 ml) was added. Since no solid precipitated out, the substance mixture was concentrated i. vac. and the residue was dried.

Yield: 90 mg (Ex. 97, 100%), porous solid $^1$H-NMR (DMSO-d$_6$): 1.18 (2H, m); 1.31 (2H, m); 1.80 (2H; m); 2.03 (1H, m); 2.59 (6H, s); 2.79 (2H, m); 3.02 (2H, t); 4.19 (2H, t); 6.04 (1H, s); 6.78 (1H, m); 7.09 (1H, m); 7.29 (8H, m); 11.50 (1H, s), free base.

Example 98

4-(3-(2-(1H-Pyrazol-1-yl)ethyl)-5-fluoro-1H-indol-2-yl)-1-benzyl-N,N-dimethylcyclohexanamine, citrate (1:1):More polar diastereomer The more polar compound prepared under Example 97 (37 mg, 0.08 mmol) was dissolved in hot ethanol (2 ml), and a solution of citric acid (16 mg, 0.08 mmol) in hot ethanol (2 ml) was added. Since no solid precipitated out, the substance mixture was concentrated i. vac. and the residue was dried.

Yield: 53 mg (98, 100%), porous solid $^1$H-NMR (DMSO-d$_6$): 1.24 (4H, m); 1.66 (4H, m); 1.95 (4H, m); 2.57 (6H; s); 3.16 (2H, t); 4.26 (2H, t); 6.14 (1H, s); 6.62 (1H, m); 6.85 (2H, m); 7.25 (7H, m); 10.91 (1H, s), citrate.

Example 99

(±)-2-(4-(Dimethylamino)-4-butylcyclohex-1-enyl)-3-(2-(1H-pyrazol-1-yl)ethyl)-5-fluoro-1H-indole Indole (Ind-38, 730 mg, 3.18 mmol) and ketone (Ket-4, 628 mg, 3.18 mmol) were dissolved in abs. methylene chloride (25 ml), and trifluoromethanesulfonic acid (0.85 ml, 9.6 mmol) was added rapidly. The mixture was stirred at RT for 72 h, during which a dark brown oil settled out. After addition of 1 N NaOH (20 ml) and CH$_2$Cl$_2$ (20 ml), the mixture was subsequently stirred for a further 20 min, the phases were separated, the aqueous phase was extracted twice with CH$_2$Cl$_2$, the combined organic phases were washed with water and dried (Na$_2$SO$_4$) and the solution was concentrated i. vac. The residue which remained was purified by flash chromatography with CHCl$_3$/MeOH (20:1→9:1).

Yield: 402 mg (31%), porous solid $^1$H-NMR (DMSO-d$_6$): 0.89 (3H, t); 1.12-1.68 (6H, m); 2.00 (4H, m); 2.69 (6H, bs); 3.18 (2H, t); 4.33 (2H, t); 5.80 (1H, s); 6.16 (1H, s); 6.88 (1H, m); 7.18 (1H, m); 7.28 (1H, s); 7.44 (1H, d); 7.56 (1H, s); 11.07 (1H, s).

4-(3-(2-(1H-Pyrazol-1-yl)ethyl)-5-fluoro-1H-indol-2-yl)-1-butyl-N,N-dimethylcyclohexanamine, citrate (1:1):Less polar diastereomer Tin (1.20 g) was added to a solution from of the olefin just prepared (385 mg, 0.94 mmol) in HBr/glacial acetic acid (30 ml) in the course of 20 min and the mixture was stirred at RT for 4 h. Ethanol was added to the mixture, the reaction mixture was concentrated to dryness and the residue was dissolved in 5 N NaOH (40 ml) and methylene chloride (30 ml). The phases were separated, the aqueous phase was extracted twice with CH$_2$Cl$_2$ and the combined organic phases were washed with water, dried over Na$_2$SO$_4$ and concentrated i. vac. The residue which remained was separated by flash chromatography with CHCl$_3$/MeOH (9:1(MeOH). The non-polar compound was obtained as a salt (173 mg), and it was then possible to liberate this by stirring with 1 N NaOH and CH$_2$Cl$_2$. The phases were separated, the aqueous phase was extracted twice with CH$_2$Cl$_2$ and the combined organic phases were dried over Na$_2$SO$_4$, filtered and concentrated i. vac. The chloroform used was probably contaminated with HCl.

Yield: 122 mg (32%), non-polar diastereomer 46 mg (12%), polar diastereomer

The less polar compound just isolated (104 mg 0.25 mmol) was dissolved in hot ethanol (3 ml), and a solution of citric acid (49 mg, 0.25 mmol) in hot ethanol (2 ml) was added. Since no solid precipitated out, the substance mixture was concentrated i. vac. and the residue was dried.

Yield: 153 mg (99; 100%), porous solid $^1$H-NMR (DMSO-d$_6$): 0.95 (3H, t); 1.23-1.96 (14H, m); 2.64 (6H, s); 3.32 (2H, t); 4.27 (2H, t); 6.14 (1H, t); 6.82 (1H, m); 7.18 (1H, m); 7.28 (1H, m); 7.44 (1H, d); 7.54 (1H, d); 10.6 (1H, s), citrate.

Example 100

4-(3-(2-(1H-Pyrazol-1-yl)ethyl)-5-fluoro-1H-indol-2-yl)-1-butyl-N,N-dimethylcyclohexanamine, citrate (1:1):More polar diastereomer The more polar compound prepared under Example 99 (46 mg 0.11 mmol) was dissolved in hot ethanol (2 ml), and a solution of citric acid (21 mg, 0.11 mmol) in hot ethanol (2 ml) was added. After ether had been added and the mixture had stood in a refrigerator for 2 hours, the solid formed was filtered off with suction and dried i. vac.

Yield: 48 mg (100; 73%), porous solid $^1$H-NMR (DMSO-d$_6$): 0.96 (3H, t); 1.29 (2H, m); 1.37-1.83 (11H, m); 2.57 (7H, m); 3.12 (2H, t); 4.24 (2H, t); 6.14 (1H, t); 6.83 (1H, m); 7.20 (2H, m); 7.45 (1H, d); 7.52 (1H, d); 10.82 (1H, s), citrate.

Example 101

(±)-2-(4-(Dimethylamino)-4-phenylcyclohex-1-enyl)-3-(2-(1H-pyrazol-1-yl)ethyl)-5-fluoro-1H-indole Indole (Ind-38, 500 mg, 2.18 mmol) and ketone (Ket-10, 473 mg, 2.18 mmol) were dissolved in abs. methylene chloride (20 ml), and trifluoromethanesulfonic acid (0.58 ml, 6.54 mmol) was added rapidly. The mixture was stirred at RT overnight, during which a dark brown oil settled out. After addition of 1 N NaOH (20 ml) and CH$_2$Cl$_2$ (20 ml), the mixture was subsequently stirred for a further 20 min, the phases were separated, the aqueous phase was extracted twice with CH$_2$Cl$_2$, the combined organic phases were washed with water and dried (Na$_2$SO$_4$) and the solution was concentrated i. vac. The residue which remained was purified by flash chromatography with CHCl$_3$/MeOH (9:1).

Yield: 454 mg (49%), porous solid $^1$H-NMR (DMSO-d$_6$): 1.71 (2H, m); 2.14 (8H, m); 2.67 (H, d); 3.09 (2H, t); 4.16 (2H, t); 6.03 (1H, s); 6.18 (1H, s); 6.80 (1H, m); 7.07-7.32 (6H, m); 7.52 (3H, m); 10.81 H, s).

4-(3-(2-(1H-Pyrazol-1-yl)ethyl)-5-fluoro-1H-indol-2-yl)-N,N-dimethyl-1-phenylcyclohexanamine, citrate (2:1):Less polar diastereomer Tin (1.31 g) was added to a solution from of the olefin (450 mg, 1.05 mmol) in HBr/glacial acetic acid (30 ml) in the course of 20 min and the mixture was stirred at RT for 4 h. Ethanol was added to the mixture, the reaction mixture was concentrated to dryness and the residue was dissolved in 5 N NaOH (40 ml) and methylene chloride (20 ml). The phases were separated, the aqueous phase was extracted twice with $CH_2Cl_2$ and the combined organic phases were washed with water, dried over $Na_2SO_4$ and concentrated i. vac. The residue which remained was separated by flash chromatography with $CHCl_3$/MeOH (9:1) and purified.

Yield: 178 mg (39%), non-polar diastereomer 209 mg (46%), polar diastereomer

The less polar compound just obtained (167 mg 0.387 mmol) was dissolved in hot ethanol (5 ml), and a solution of citric acid (74 mg, 0.387 mmol) in hot ethanol (4 ml) was added. After the mixture had stood in a refrigerator for 2 hours, the solid formed was filtered off with suction and dried i. vac.

Yield: 155 mg (76%); melting point: 218-220° C.

$^1$H-NMR (DMSO-$d_6$): 1.56 (2H, m); 1.71 (2H, m); 2.19 (2H; m); 2.34 (6H, s); 2.65-2.71 (5H, m); 2.92 (2H, d); 3.15 (2H, t); 4.26 (2H, t); 6.13 (1H, s); 6.82 (1H, m); 7.19 (2H, m); 7.46 (7H, m); 11.0 (1H, bs), hemicitrate.

Example 102

4-(3-(2-(1H-Pyrazol-1-yl)ethyl)-5-fluoro-1H-indol-2-yl)-N,N-dimethyl-1-phenylcyclohexanamine, citrate (1:1):More polar diastereomer The more polar compound obtained under Example 101 (190 mg 0.44 mmol) was dissolved in hot ethanol (5 ml), and a solution of citric acid (85 mg, 0.44 mmol) in hot ethanol (5 ml) was added. After the mixture had stood in a refrigerator for 2 hours, the solid formed was filtered off with suction and dried i. vac.

Yield: 90 mg (33%); melting point: 115-116° C.

$^1$H-NMR (DMSO-$d_6$): 1.34 (2H, m); 1.58 (2H, m); 1.91 (2H, m); 2.40 (6H; s); 2.61 (5H, m); 2.99 (2H, m); 3.09 (2H, t); 4.23 (2H, t); 6.15 (1H, s); 6.76 (1H, m); 7.10 (2H, m); 7.54 (7H, m); 10.5 (1H, s), citrate.

Example 103

(±)-2-(4-(Dimethylamino)-4-benzylcyclohex-1-enyl)-3-(2-(1H-pyrazol-1-yl)ethyl)-5-fluoro-1H-indole Indole (Ind-39, 600 mg, 2.62 mmol) and ketone (Ket-3, 605 mg, 2.62 mmol) were dissolved in abs. methylene chloride (20 ml), and trifluoromethanesulfonic acid (0.70 ml, 7.9 mmol) was added rapidly. The mixture was stirred at RT for 48 h, during which a dark brown oil settled out. After addition of 1 N NaOH (20 ml) and $CH_2Cl_2$ (20 ml), the mixture was subsequently stirred for a further 20 min, the phases were separated, the aqueous phase was extracted twice with $CH_2Cl_2$, the combined organic phases were washed with water and dried ($Na_2SO_4$) and the solution was concentrated i. vac. The residue which remained was purified by flash chromatography with $CHCl_3$/MeOH (9:1).

Yield: 558 mg (48%), porous solid $^1$H-NMR (DMSO-$d_6$): 1.42 (1H, m); 1.95 (1H, m); 1.99 (1H, m); 2.27-2.40 (9H, m); 2.80 (2H, q); 3.13 (2H, t); 4.13 (2H, t); 5.71 (1H, s); 6.85 (2H, m); 7.09 (1H, s); 7.25-7.29 (7H, m); 7.47 (1H, s); 10.87 (1H, s).

4-(3-(2-(1H-Imidazol-1-yl)ethyl)-5-fluoro-1H-indol-2-yl)-1-benzyl-N,N-dimethylcyclohexanamine, citrate (1:1):Less polar diastereomer Tin (1.5 g) was added to a solution of the olefin just prepared (530 mg, 1.2 mmol) in HBr/glacial acetic acid (30 ml) in the course of 20 min and the mixture was stirred at RT for 4 h. Ethanol was added to the mixture, the reaction mixture was concentrated to dryness and the residue was dissolved in 5 N NaOH (40 ml) and methylene chloride (40 ml). The phases were separated, the aqueous phase was extracted twice with $CH_2Cl_2$, the combined organic phases were washed with water, dried over $Na_2SO_4$ and concentrated i. vac. The residue which remained was separated by flash chromatography with $CHCl_3$/MeOH (9:1→MeOH).

Yield: 248 mg (46%), non-polar diastereomer 62 mg (12%), polar diastereomer

The less polar diastereomer just obtained (230 mg 0.517 mmol) was dissolved in hot ethanol (5 ml), and a solution of citric acid (99 mg, 0.517 mmol) in hot ethanol (4 ml) was added. After the mixture had stood in a refrigerator for 2 hours, the solid formed was filtered off with suction and dried i. vac.

Yield: 180 mg (55%); melting point: 190-192° C.

$^1$H-NMR (DMSO-$d_6$): 1.30 (4H, m); 2.01 (4H; m); 2.37-2.80 (9H, m); 2.98 (2H, t); 4.0 (2H, t); 6.80 (2H, m); 7.09 (1H, s); 7.15-7.41 (8H, m); 11.0 (1H, bs), free base.

Example 104

4-(3-(2-(1H-Imidazol-1-yl)ethyl)-5-fluoro-1H-indol-2-yl)-1-benzyl-N,N-dimethylcyclohexanamine, citrate (1:1):More polar diastereomer The more polar diastereomer prepared under Example 103 (62 mg 0.139 mmol) was dissolved in hot ethanol (2 ml), and a solution of citric acid (27 mg, 0.139 mmol) in hot ethanol (2 ml) was added. After ether had been added and the mixture had stood in a refrigerator for 2 hours, the solid formed was filtered off with suction and dried i. vac.

Yield: 53 mg (60%), porous solid $^1$H-NMR (DMSO-$d_6$): 1.56 (4H, m); 1.90 (2H, m); 2.26 (8H; m); 2.62 (1H, m); 3.06 (2H, t); 3.41 (3H, m); 4.11 (2H, t); 6.82 (2H, m); 7.13-7.41 (9H, m); 11.01 (1H, s), (free base).

Example 105

(±)-2-(4-(Dimethylamino)-4-butylcyclohex-1-enyl)-3-(2-(1H-imidazol-1-yl)ethyl)-5-fluoro-1H-indole Indole (Ind-39, 800 mg, 3.49 mmol) and ketone (Ket-4, 690 mg, 3.49 mmol) were dissolved in abs. methylene chloride (25 ml), and trifluoromethanesulfonic acid (0.93 ml, 10.5 mmol) was added rapidly. The mixture was stirred at RT for 72 h, during which a dark brown oil settled out. After addition of 1 N NaOH (20 ml) and $CH_2Cl_2$ (20 ml), the mixture was subsequently stirred for a further 20 min, the phases were separated, the aqueous phase was extracted twice with $CH_2Cl_2$, the combined organic phases were washed with water and dried ($Na_2SO_4$) and the solution was concentrated i. vac. The residue which remained was purified by flash chromatography with $CHCl_3$/MeOH (9:1).

Yield: 548 mg (39%), porous solid

¹H-NMR (DMSO-d₆): 0.91 (3H, t); 1.27 (6H, m); 1.56 (2H, m); 1.83 (2H, m); 2.05 (2H, m); 2.31 (6H, s); 3.11 (2H, t); 4.15 (2H, t); 5.77 (1H, s); 6.87 (2H, m); 7.09 (1H, s); 7.26 (2H, m); 7.45 (1H, s); 10.94 (1H, s).

4-(3-(2-(1H-Imidazol-1-yl)ethyl)-5-fluoro-1H-indol-2-yl)-1-butyl-N,N-dimethylcyclohexanamine, citrate (2:3) (105:Less polar diastereomer)

Tin (1.60 g) was added to a solution of the olefin just prepared (528 mg, 1.29 mmol) in HBr/glacial acetic acid (35 ml) in the course of 20 min and the mixture was stirred at RT for 4 h. Ethanol was added to the mixture, the reaction mixture was concentrated to dryness and the residue was dissolved in 5 N NaOH (50 ml) and methylene chloride (30 ml). The phases were separated, the aqueous phase was extracted twice with CH₂Cl₂ and the combined organic phases were washed with water, dried over Na₂SO₄ and concentrated i. vac. The residue which remained was separated by flash chromatography with CHCl₃/MeOH (9:1→1:1+1% TEA).). The non-polar compound was obtained as a salt (350 mg), and it was then possible to liberate this by stirring with 1 N NaOH and CH₂Cl₂. The phases were separated, the aqueous phase was extracted twice with CH₂Cl₂ and the combined organic phases were dried over Na₂SO₄, filtered and concentrated i. vac. The chloroform used was probably contaminated with HCl.

Yield: 285 mg (54%) of non-polar diastereomer
123 mg (23%), polar diastereomer

The less polar diastereomer obtained (285 mg 0.694 mmol) was dissolved in hot ethanol (5 ml), and a solution of citric acid (133 mg, 0.694 mmol) in hot ethanol (5 ml) was added. After the mixture had stood in a refrigerator for 2 hours, the solid formed was filtered off with suction and dried i. vac.

Yield: 220 mg (53%), porous solid
¹H-NMR (DMSO-d₆): 0.96 (3H, t); 1.37 (6H, m); 1.73 (4H; m); 1.94 (5H, m); 2.71 (6H, m); 3.08 (2H, t); 4.12 (2H, t); 6.85 (2H, m); 7.24 (3H, s); 7.54 (1H, s); 11.4 (1H, bs), free base Example 106

4-(3-(2-(1H-Imidazol-1-yl)ethyl)-5-fluoro-1H-indol-2-yl)-1-butyl-N,N-dimethylcyclohexanamine, citrate (1:1):More polar diastereomer The more polar diastereomer prepared under Example 105 (123 mg 0.30 mmol) was dissolved in hot ethanol (3 ml), and a solution of citric acid (58 mg, 0.3 mmol) in hot ethanol (2 ml) was added. After the mixture had stood in a refrigerator for 2 hours, the solid formed was filtered off with suction and dried i. vac.

Yield: 129 mg (106, 71%), porous solid
¹H-NMR (DMSO-d₆): 0.95 (3H, t); 1.23 (8H, m); 1.63 (7H, m); 2.19 (6H; m); 3.05 (2H, t); 4.09 (2H, t); 6.81 (2H, m); 7.21 (3H, m); 7.41 (1H, s); 10.8 (1H, s), free base.

Example 107

(±)-2-(4-(Dimethylamino)-4-phenylcyclohex-1-enyl)-3-(2-(1H-imidazol-1-yl)ethyl)-5-fluoro-1H-indole Indole (Ind-39, 667 mg, 2.91 mmol) and ketone (Ket-4, 631 mg, 2.91 mmol) were dissolved in abs. methylene chloride (20 ml), and trifluoromethanesulfonic acid (0.78 ml, 8.7 mmol) was added rapidly. The mixture was stirred at RT overnight, during which a dark brown oil settled out. After addition of 1 N NaOH (20 ml) and CH₂Cl₂ (20 ml), the mixture was subsequently stirred for a further 20 min, the phases were separated, the aqueous phase was extracted twice with CH₂Cl₂, the combined organic phases were washed with water and dried (Na₂SO₄) and the solution was concentrated i. vac. The residue which remained was purified by flash chromatography with CHCl₃/MeOH (9:1→4:1).

Yield: 941 mg (75%), porous solid
¹H-NMR (DMSO-d₆): 1.71 (1H, m); 2.18 (8H, m); 2.39 (1H, d); 2.58 (1H, s); 2.83 (1H, d); 2.98/2H, m); 3.95 (2H, m); 6.02 (1H, s); 6.83 (2H, m); 7.04 (1H, s); 7.18-7.50 (8H, m); 10.82 (1H, s).

4-(3-(2-(1H-Imidazol-1-yl)ethyl)-5-fluoro-1H-indol-2-yl)-N,N-dimethyl-1-phenylcyclohexanamine, citrate (1:1):Less polar diastereomer Tin (2.54 g) was added to a solution of the olefin just prepared (900 mg, 2.1 mmol) in HBr/glacial acetic acid (50 ml) in the course of 20 min and the mixture was stirred at RT for 4 h. Ethanol was added to the mixture, the reaction mixture was concentrated to dryness and the residue was dissolved in 5 N NaOH (80 ml) and methylene chloride (50 ml). The phases were separated, the aqueous phase was extracted twice with CH₂Cl₂ and the combined organic phases were washed with water, dried over Na₂SO₄ and concentrated i. vac. The residue which remained was separated by flash chromatography with CHCl₃/MeOH (9:1→1:4).

Yield: 198 mg (22%) non-polar diastereomer
157 mg (17%) polar diastereomer

The less polar diastereomer just obtained (172 mg 0.4 mmol) was dissolved in hot dioxane (5 ml), and a solution of citric acid (77 mg, 0.4 mmol) in hot dioxane (4 ml) was added. After the mixture had stood in a refrigerator for 2 hours, the solid formed was filtered off with suction and dried i. vac.

Yield: 185 mg (74%); melting point: 236-238° C.
¹H-NMR (DMSO-d₆): 1.48 (4H, m); 2.10 (7H; bs); 2.74 (3H, m); 3.05 (2H, t); 4.10 (2H, t); 6.83 (2H, m); 7.20-7.52 (9H, m); 10.95 (1H, s), free base.

Example 108

4-(3-(2-(1H-Imidazol-1-yl)ethyl)-5-fluoro-1H-indol-2-yl)-N,N-dimethyl-1-phenylcyclohexanamine, citrate (2:3):More polar diastereomer The under Example 107 (144 mg, 0.33 mmol) was dissolved in hot ethanol (5 ml), and a solution of citric acid (64 mg, 0.33 mmol) in hot ethanol (4 ml) was added. After the mixture had stood in a refrigerator for 2 hours, the solid formed was filtered off with suction and dried i. vac.

Yield: 120 mg (57%), porous solid
¹H-NMR (DMSO-d₆): 1.40 (2H, m); 1.62 (2H, m); 1.90 (6H; s); 2.71 (3H, m); 3.01 (2H, t); 4.07 (2H, t); 6.73 (1H, m); 6.85 (1H, s); 7.11-7.43 (9H, m); 10.47 (1H, s), free base.

Example 109

(±)-2-(4-(Dimethylamino)-4-benzylcyclohex-1-enyl)-3-(2-(1H-benzo[d]imidazol-1-yl)ethyl)-5-fluoro-1H-indole Indole (Ind-40, 668 mg, 2.39 mmol) and ketone (Ket-3, 553 mg, 2.39 mmol) were dissolved in abs. methylene chloride (30 ml), and trifluoromethanesulfonic acid (0.64 ml, 7.2 mmol) was added rapidly. The mixture was stirred at RT for 72 h, during which a dark brown oil settled out. After addition of 1 N NaOH (20 ml) and CH$_2$Cl$_2$ (20 ml), the mixture was subsequently stirred for a further 20 min, the phases were separated, the aqueous phase was extracted twice with CH$_2$Cl$_2$, the combined organic phases were washed with water and dried (Na$_2$SO$_4$) and the solution was concentrated i. vac. The residue which remained was purified by flash chromatography with EA/EtOH (9:1→1:2).

Yield: 395 mg (33%), porous solid
$^1$H-NMR (DMSO-d$_6$): 1.23 (2H, m); 2.06 (2H, m); 2.41 (6H, bs); 3.22 (2H, t); 3.33 (2H, s); 4.43 (2H, t); 5.58 (1H, s); 6.84 (1H, m); 7.08 (3H, m); 7.29 (6H, m); 7.40 (1H, d); 7.56 (1H, d); 7.86 (1H, s); 10.92 (1H, s).

4-(3-(2-(1H-Benzo[d]imidazol-1-yl)ethyl)-5-fluoro-1H-indol-2-yl)-1-benzyl-N,N-dimethylcyclohexanamine, citrate (4:3):Less polar diastereomer Tin (1.00 g) was added to a solution of the olefin just prepared (395 mg, 0.8 mmol) in HBr/glacial acetic acid (30 ml) in the course of 20 min and the mixture was stirred at RT for 4 h. Ethanol was added to the mixture, the reaction mixture was concentrated to dryness and the residue was dissolved in 5 N NaOH (40 ml) and methylene chloride (30 ml). The phases were separated, the aqueous phase was extracted twice with CH$_2$Cl$_2$ and the combined organic phases were washed with water, dried over Na$_2$SO$_4$ and concentrated i. vac. The residue which remained was separated by flash chromatography with EA/EtOH (9:1→1:4).

Yield: 173 mg (44%), non-polar diastereomer, 57 mg (14%), polar diastereomer
The less polar diastereomer obtained (155 mg 0.313 mmol) was dissolved in hot ethanol (4 ml), and a solution of citric acid (60 mg, 0.313 mmol) in hot ethanol (2 ml) was added. After the mixture had stood in a refrigerator for 2 hours, the solid formed was filtered off with suction and dried i. vac.

Yield: 107 mg (50%); melting point: 215-217° C.
$^1$H-NMR (DMSO-d$_6$): 1.60 (2H, m); 1.75 (2H, m); 2.43 (6H, s); 2.63 (6H, m); 3.05 (2H, t); 3.20 (1H, m); 4.36 (2H, t); 6.79 (1H, m); 6.91 (1H, m); 7.08-7.44 (8H, m); 7.55 (1H, d); 7.61 (1H, s); 10.46 (1H, s), citrate.

Example 110

4-(3-(2-(1H-Benzo[d]imidazol-1-yl)ethyl)-5-fluoro-1H-indol-2-yl)-1-benzyl-N,N-dimethylcyclohexanamine, citrate (2:3):More polar diastereomer The polar diastereomer prepared under Example 109 (56 mg 0.11 mmol) was dissolved in hot ethanol (2 ml), and a solution of citric acid (22 mg, 0.11 mmol) in hot ethanol (2 ml) was added. After the mixture had stood in a refrigerator for 2 hours, the solid formed was filtered off with suction and dried i. vac.

Yield: 54 mg (110, 69%), porous solid
$^1$H-NMR (DMSO-d$_6$): 1.11 (2H, m); 1.58 (2H, m); 1.73 (2H, m); 2.11 (2H, m); 2.39 (6H, s); 2.58 (4H, m); 3.10 (2H, bs); 3.21 (2H, t); 3.45 (1H, m); (4.45 (2H, t); 6.85 (1H, m); 7.19 (9H, m); 7.60 (2H, m); 7.76 (1H, s); 10.83 (1H, s), citrate.

Example 111

4-(3-(2-(1H-Benzo[d]imidazol-1-yl)ethyl)-5-fluoro-1H-indol-2-yl)-1-butyl-N,N-dimethylcyclohexanamine, citrate (2:3):Less polar diastereomer Tin (1.25 g) was added to a solution of Example 82 (450 mg, 0.98 mmol) in HBr/glacial acetic acid (35 ml) in the course of 20 min and the mixture was stirred at RT for 4 h. Ethanol was added to the mixture, the reaction mixture was concentrated to dryness and the residue was dissolved in 5 N NaOH (50 ml) and methylene chloride (30 ml). The phases were separated, the aqueous phase was extracted twice with CH$_2$Cl$_2$ and the combined organic phases were washed with water, dried over Na$_2$SO$_4$ and concentrated i. vac. The residue which remained was separated by flash chromatography with EA/EtOH (1:4→EtOH).

Yield: 304 mg (67%) non-polar diastereomer
119 mg (26%) polar diastereomer
The less polar diastereomer just obtained (275 mg 0.597 mmol) was dissolved in hot ethanol (10 ml), and a solution of citric acid (115 mg, 0.597 mmol) in hot ethanol (5 ml) was added. After ether had been added and the mixture had stood in a refrigerator for 2 hours, the solid formed was filtered off with suction and dried i. vac.

Yield: 165 mg (42%), porous solid
$^1$H-NMR (DMSO-d$_6$): 0.97 (5H, m); 1.06 (4H, m); 1.42 (4H, m); 1.82 (4H, m); 2.07 (1H, m); 2.59 (10H, m); 3.19 (2H, t); 4.45 (2H, t); 6.83 (1H, m); 7.21 (4H, m); 7.62 (2H, d); 7.77 (1H, s); 10.99 (1H, s), citrate.

Example 112

4-(3-(2-(1H-1,2,3-Triazol-1-yl)ethyl)-5-fluoro-1H-indol-2-yl)-1-benzyl-N,N-dimethylcyclohexanamine, citrate (4:1):Less polar Diastereomer Tin (1.00 g) was added to a solution of Example 59 (356 mg, 0.8 mmol) in HBr/glacial acetic acid (30 ml) in the course of 20 min and the mixture was stirred at RT for 4 h. Ethanol was added to the mixture, the reaction mixture was concentrated to dryness and the residue was dissolved in 5 N NaOH (40 ml) and methylene chloride (40 ml). The phases were separated, the aqueous phase was extracted twice with CH$_2$Cl$_2$ and the combined organic phases were washed with water, dried over Na$_2$SO$_4$ and concentrated i. vac. The residue which remained was separated by flash chromatography with EA/EtOH (1:4→1:2+1% TEA).

Yield: 237 mg (66%), non-polar diastereomer
73 mg (20%), polar diastereomer
The less polar diastereomer just obtained (234 mg 0.525 mmol) was dissolved in hot ethanol (10 ml), and a solution of citric acid (101 mg, 0.525 mmol) in hot ethanol (5 ml) was added. After ether had been added and the mixture had stood in a refrigerator for 2 hours, the solid formed was filtered off with suction and dried i. vac.

Yield: 173 mg (112, 61%); melting point: 262-167° C.
$^1$H-NMR (DMSO-d$_6$): 1.34 (4H, m); 2.11 (2H, m); 2.46 (1H, m); 2.56 (2H, m); 2.75 (6H, s); 2.92 (2H, m); 3.14 (2H, t); 4.44 (2H, t); 6.79 (1H, m); 7.13 (2H, m); 7.28 (5H, m); 7.55 (1H, s); 7.90 (1H, s); 11.41 (1H, s), hemicitrate.

Example 113

4-(3-(2-(1H-1,2,3-Triazol-1-yl)ethyl)-5-fluoro-1H-indol-2-yl)-1-benzyl-N,N-dimethylcyclohexanamine, citrate (1:1):More polar diastereomer The polar diastereomer prepared under Example 112 (73 mg 0.163 mmol) was dissolved in hot ethanol (3 ml), and a solution of citric acid (31 mg, 0.163 mmol) in hot ethanol (2 ml) was added. After ether had been added and the mixture had stood in a refrigerator for 2 hours, the solid formed was filtered off with suction and dried i. vac.

Yield: 79 mg (113, 76%), porous solid $^1$H-NMR (DMSO-d$_6$): 1.64 (4H, m); 1.89 (4H, m); 2.47 (11H, m); 3.22 (2H, t); 4.55 (2H, t); 6.85 (1H, m); 7.27 (7H, m); 7.65 (1H, s); 8.01 (1H, s); 10.98 (1H, s), citrate.

Example 114

4-(3-(2-(1H-1,2,3-Triazol-1-yl)ethyl)-5-fluoro-1H-indol-2-yl)-1-butyl-N,N-dimethylcyclohexanamine, citrate (2:1):Less polar diastereomer Tin (1.40 g) was added to a solution of Example 60 (440 mg, 1.07 mmol) in HBr/glacial acetic acid (30 ml), in the course of 20 min and the mixture was stirred at RT for 4 h. Ethanol was added to the mixture, the reaction mixture was concentrated to dryness and the residue was dissolved in 5 N NaOH (40 ml) and methylene chloride (40 ml). The phases were separated, the aqueous phase was extracted twice with CH$_2$Cl$_2$ and the combined organic phases were washed with water, dried over Na$_2$SO$_4$ and concentrated i. vac. The residue which remained was separated by flash chromatography with EA/EtOH (1:4→1:2+1% TEA).

Yield: 265 mg (60%), non-polar diastereomer 134 mg (30%), polar diastereomer

The less polar diastereomer just obtained (245 mg 0.595 mmol) was dissolved in hot ethanol (10 ml), and a solution of citric acid (114 mg, 0.595 mmol) in hot ethanol (5 ml) was added. After ether had been added and the mixture had stood in a refrigerator for 2 hours, the solid formed was filtered off with suction and dried i. vac.

Yield: 121 mg (40%); melting point: 221-223° C.

$^1$H-NMR (DMSO-d$_6$): 1.03 (3H, t); 1.33 (6H, m); 1.57 (2H, m); 1.70 (2H, m); 1.99 (2H, m); 2.16 (2H, m); 2.66 (11H, m); 3.21 (2H, t); 4.53 (2H, t); 6.85 (1H, m); 7.21 (2H, m); 7.64 (1H, s); 8.02 (1H, s); 11.43 (1H, s), hemicitrate.

Example 115

4-(3-(2-(1H-1,2,3-Triazol-1-yl)ethyl)-5-fluoro-1H-indol-2-yl)-1-butyl-N,N-dimethylcyclohexanamine, citrate (1:1):More polar diastereomer The polar diastereomer prepared under Example 114 (130 mg 0.315 mmol) was dissolved in hot ethanol (5 ml), and a solution of citric acid (61 mg, 0.315 mmol) in hot ethanol (2 ml) was added. After ether had been added and the mixture had stood in a refrigerator for 2 hours, the solid formed was filtered off with suction and dried i. vac.

Yield: 110 mg (57%), porous solid $^1$H-NMR (DMSO-d$_6$): 1.03 (3H, t); 1.35 (6H, m); 1.86 (8H, m); 2.65 (11H, m); 3.22 (2H, t); 4.54 (2H, t); 6.85 (1H, m); 7.26 (2H, m); 7.65 (1H, s); 8.05 (1H, s); 10.90 (1H, s), citrate.

Example 116

4-(3-(2-(1H-1,2,3-Triazol-1-yl)ethyl)-5-fluoro-1H-indol-2-yl)-N,N-dimethyl-1-phenylcyclohexanamine, citrate (2:1):Less polar diastereomer Tin (2.10 g) was added to a solution of Example 61 (730 mg, 1.7 mmol) in HBr/glacial acetic acid (70 ml) in the course of 20 min and the mixture was stirred at RT for 4 h. Ethanol was added to the mixture, the reaction mixture was concentrated to dryness and the residue was dissolved in 5 N NaOH (70 ml) and methylene chloride (70 ml). The phases were separated, the aqueous phase was extracted twice with CH$_2$Cl$_2$ and the combined organic phases were washed with water, dried over Na$_2$SO$_4$ and concentrated i. vac. The residue which remained was separated by flash chromatography with EA/EtOH (9:1→EtOH).

Yield: 181 mg (25%), non-polar diastereomer 265 mg (36%), polar diastereomer

The less polar diastereomer just obtained (168 mg 0.389 mmol) was dissolved in hot ethanol (5 ml), and a solution of citric acid (75 mg, 0.389 mmol) in hot ethanol (3 ml) was added. After the mixture had stood in a refrigerator for 2 hours, the solid formed was filtered off with suction and dried i. vac.

Yield: 89 mg (37%); melting point: 228-229° C.

$^1$H-NMR (DMSO-d$_6$): 1.47 (4H, m); 2.04 (2H, m); 2.12 (6H, s); 2.67 (7H, m); 3.21 (2H, t); 4.54 (2H, t); 6.83 (1H, m); 7.30 (7H, m); 7.64 (1H, s); 8.01 (1H, s), citrate.

Example 117

4-(3-(2-(1H-1,2,3-Triazol-1-yl)ethyl)-5-fluoro-1H-indol-2-yl)-N,N-dimethyl-1-phenylcyclohexanamine, citrate (2:1):More polar diastereomer The more polar diastereomer prepared under Example 116 (248 mg 0.574 mmol) was dissolved in hot ethanol (8 ml), and a solution of citric acid (110 mg, 0.574 mmol) in hot ethanol (6 ml) was added. After the mixture had stood in a refrigerator for 2 hours, the solid formed was filtered off with suction and dried i. vac.

Yield: 262 mg (73%), porous solid $^1$H-NMR (DMSO-d$_6$): 1.33 (2H, m); 1.53 (2H, m); 1.80 (2H, m); 2.29 (6H, s); 2.57 (5H, m); 2.89 (2H, m); 3.19 (2H, t); 4.50 (2H, t); 6.77 (1H, m); 7.13 (2H, m); 7.45 (5H, s); 7.67 (1H, s); 7.98 (1H, s); 10.5 (1H, s), citrate.

Example 118

2-(4-(Dimethylamino)-4-phenylcyclohexyl)-3-methyl-1H-indol-5-ol, less polar diastereomer An approx. 1 M solution of BBr$_3$ in methylene chloride (3 ml, approx. 3 mmol) was added to a solution of the free base from Ex. 127 (less polar diastereoisomer, 205 mg, 0.57 mmol) in dry methylene chloride (30 ml) at RT, while stirring and with exclusion of moisture. After 10 min, a precipitate precipitated out. The mixture was stirred at RT for 18 h.—For working up, sat. NaHCO$_3$ solution (20 ml) was added to the mixture and the mixture was stirred for 30 min. The solid (156 mg) at the phase boundary was separated off. and stirred in a mixture of sat. NaHCO$_3$ solution (20 ml) and methanol (2 ml) for 3 d. The methanol was removed from the mixture on a rotary evaporator and the aqueous residue was extracted with methylene chloride (5×10 ml). The combined organic phases were dried over MgSO$_4$ and then concentrated. The residue obtained was recrystallized from methanol (1 ml). Example 118 was obtained in this way in a yield of 62 mg (31%, melting point: 227-235° C.) as a green/beige solid.

$^1$H NMR (400 MHz, DMSO-d$_6$) δ ppm: 1.20-1.55 (m, 2H), 1.57-1.69 (m, 2H), 2.02 (s, 6H), 2.05-2.15-2.1 (m, 5H), 2.73-2.90 (m, 3H), 6.48 (dd, J=8.49, 2.27 Hz, 1H), 6.66 (d, J=2.07 Hz, 1H), 7.06 (d, J=8.47 Hz, 1H), 7.37 (d, J=4.20 Hz, 4H), 8.40 (s, 1H), 10.22 (s, 1H).

$^{13}$C NMR (101 MHz, DMSO) □ ppm 8.5, 27.1, 33.2, 35.5, 37.7, 58.0, 101.5, 102.7, 109.6, 110.9, 126.2, 126.4, 127.2, 129.5, 129.6, 139.7, 140.9, 149.9

Example 119

2-(4-(Dimethylamino)-4-phenylcyclohexyl)-3-methyl-1H-indol-5-ol, polar diastereomer An approx. 1 M solution of $BBr_3$ in methylene chloride (5 ml, approx. 5 mmol) was added solution of the free base from Ex. 128 (more polar diastereoisomer, 340 mg, 0.94 mmol in dry methylene chloride (40 ml) at RT, while stirring and with exclusion of moisture. The mixture was stirred at RT for 18 h.—For working up, water (10 ml) was added to the mixture and the mixture formed was added to sat. $NaHCO_3$ solution (30 ml). The mixture was stirred at RT for 2 h and the was then separated off by means of a frit. The phases of the filtrate were separated. The aqueous phase was extracted with methylene chloride (2×20 ml). The combined organic phases were dried over $MgSO_4$ and then concentrated on a rotary evaporator. It was possible to isolate further product (90 mg) by purification by column chromatography [silica gel 60 G (10 g); EtOAc/EtOH 1:1 (100 ml)]. After recrystallization of the combined product fractions (methanol, 3 ml), Example 119 was obtained in a yield of 92 mg (28%, melting point: 164-169° C.) as an ochre-coloured solid.

$^1$H NMR (400 MHz, DMSO-$d_6$) δ ppm: 1.35-1.52 (m, 2H), 1.75-1.87 (m, 2H), 1.94-2.05 (s, 6H), 2.28-2.45 (m, 5H), 2.81-2.87 (m, 1H), 2.95-3.06 (m, 2H), 6.37-6.41 (m, 2H), 6.62 (s, 1H), 6.92 (d, J=8.49 Hz, 1H), 7.46-7.71 (m, 5H), 8.40 (s, 1H), 9.99 (s, 1H)

$^{13}$C NMR (101 MHz, DMSO-$d_6$) δ ppm: 8.4, 28.1, 30.9, 35.0, 37.4, 101.5, 103.2, 109.9, 110.7, 128.8, 129.2, 129.3, 129.4, 138.5, 149.96

Example 120

1-Benzyl-N,N-dimethyl-4-(3-methyl-5-(trifluoromethoxy)-1H-indol-2-yl)cyclohexanamine, citrate (1:1), polar diastereomer (±)-N-[1-Benzyl-4-(3-methyl-5-trifluoromethoxy-1H-indol-2-yl)cyclohex-3-enyl]-N,N-dimethylamine The ketone (Ket-3, 462 mg, 2 mmol) was dissolved in methylene chloride (25 ml) together with indole Ind-43 (430 mg, 2 mmol). The addition of trifluoromethanesulfonic acid (0.2 ml, 338 mg 2.25 mmol) then took place, the mixture becoming dark in colour. The solution was stirred at RT for 3 d. The course of the reaction was monitored by means of TLC. To separate off the unreacted ketone, water (3×15 ml) was added to the reaction mixture and the mixture was stirred for 10 min each time. After separation of the phases, 1 N NaOH (10 ml) was added to the organic phase and the mixture was stirred for 10 min. After separation of the phases, the aqueous phase was extracted with methylene chloride (2×10 ml). The combined organic phases were dried with sodium sulfate, filtered and concentrated in vacuo. 620 mg of a brown oil were obtained, which was separated by chromatography [silica gel 60 (60 g); ethyl acetate/methanol (10:1; 500 ml)]. (±)-N-[1-Benzyl-4-(3-methyl-5-trifluoromethoxy-1H-indol-2-yl)cyclohex-3-enyl]-N,N-dimethylamine was obtained in a yield of 27% (233 mg) as a colourless solid with a melting point of 74-75° C.

1-Benzyl-N,N-dimethyl-4-(3-methyl-5-(trifluoromethoxy)-1H-indol-2-yl)cyclohexanamine (polar diastereomer)

(±)-N-[1-Benzyl-4-(3-methyl-5-trifluoromethoxy-1H-indol-2-yl)cyclohex-3-enyl]-N,N-dimethylamine (230 mg, 0.53 mmol) was dissolved in methanol (40 ml) and ethanol (10 ml), while heating, and Pd/C (5%, 100 mg) was added under argon. Hydrogenation was carried out at 40° C. under 3 bar for 4 h. The catalyst was then filtered off with suction over Celite and the filtrate was concentrated. The solid colourless residue (227 mg) was separated by chromatography [silica gel 60 (30 g); ethyl acetate/methanol (20:1; 400 ml); (4:1; 500 ml) (2:1; 300 ml)]. 1-Benzyl-N,N-dimethyl-4-(3-methyl-5-(trifluoromethoxy)-1H-indol-2-yl)cyclohexanamine (more polar diastereomer) was obtained in a yield of 175 mg (77%) as a colourless solid.

1-Benzyl-N,N-dimethyl-4-(3-methyl-5-(trifluoromethoxy)-1H-indol-2-yl)cyclohexanamine, citrate (1:1), polar diastereomer 1-Benzyl-N,N-dimethyl-4-(3-methyl-5-(trifluoromethoxy)-1H-indol-2-yl)cyclohexanamine (more polar diastereoisomer) (159 mg, 0.37 mmol) was dissolved in ethanol (8 ml), while heating, and citric acid (78 mg, 0.4 mmol), dissolved in hot ethanol (5 ml), was added. After approx. 30 min a precipitate started to precipitate out. The mixture was stirred for 20 h and the precipitate was filtered off with suction. The filtrate was concentrated to half and diethyl ether (10 ml) was added. After stirring at RT for a further 2 h, it was possible for the precipitate which had precipitated out to be filtered off with suction. The two fractions were combined. Example 120 was obtained in a yield of 66% (153 mg).

Example 121

1-Butyl-N,N-dimethyl-4-(3-methyl-5-(trifluoromethoxy)-1H-indol-2-yl)cyclohexanamine, citrate (1:1), non-polar diastereomer

Example 122

1-Butyl-N,N-dimethyl-4-(3-methyl-5-(trifluoromethoxy)-1H-indol-2-yl)cyclohexanamine, citrate (1:1), polar diastereomer (±)-N-[1-Butyl-4-(3-methyl-5-trifluoromethoxy-1H-indol-2-yl)cyclohex-3-enyl]-N,N-dimethylamine The ketone (Ket-4, 513 mg, 2.6 mmol) was dissolved in methylene chloride (30 ml) together with indole Ind-43 (560 mg, 2.6 mmol). The addition of trifluoromethanesulfonic acid (0.26 ml, 439 mg, 2.86 mmol) then took place. The solution was stirred at RT for 3 d. The course of the reaction was monitored by means of TLC. To separate off the ketone, water (15 ml) was added and the mixture was stirred vigorously for 10 min. After separation of the phases, the organic phase was stirred with water (15 ml) again. The procedure was carried out three time in total. 1 N NaOH (10 ml) was then added to the organic phase and the mixture was stirred for 10 min. After separation of the phases, the aqueous phase was extracted with methylene chloride (2×10 ml). The combined organic phases were dried with sodium sulfate, filtered and concentrated in vacuo. 840 mg of a brown oil were obtained, which was separated by chromatography [silica gel 60 (60 g); ethyl acetate/methanol (10:1; 500 ml); (1:1; 500 ml)]. (±)-N-[1-Butyl-4-(3-methyl-5-trifluoromethoxy-1H-indol-2-yl)cyclohex-3-enyl]-N,N-dimethylamine was obtained in a yield of 31% (321 mg) as a pale brown oil.

1-Butyl-N,N-dimethyl-4-(3-methyl-5-(trifluoromethoxy)-1H-indol-2-yl)cyclohexanamine, (non-polar and polar diastereomer)

(±)-N-[1-Butyl-4-(3-methyl-5-trifluoromethoxy-1H-indol-2-yl)cyclohex-3-enyl]-N,N-dimethylamine (320 mg, 0.81 mmol) was dissolved in ethanol (50 ml), and Pd/C (5%, 140 mg) was added under argon. Hydrogenation was carried out under 3 bar for 1.5 h. The catalyst was then filtered off with suction over Celite and the filtrate was concentrated. The solid pale brown residue (341 mg) was separated by chromatography [silica gel 60 (30 g); ethyl acetate/methanol (1:1; 500 ml); (1:2; 300 ml)]. 1-Butyl-N,N-dimethyl-4-(3-methyl-5-(trifluoromethoxy)-1H-indol-2-yl)cyclohexanamine (less polar diastereoisomer) was obtained in a yield of 28 mg (9%) and the more polar diastereoisomer in a yield of 237 mg (75%), in each case as a colourless solid.

1-Butyl-N,N-dimethyl-4-(3-methyl-5-(trifluoromethoxy)-1H-indol-2-yl)cyclohexanamine, citrate (1:1), non-polar diastereomer 1-Butyl-N,N-dimethyl-4-(3-methyl-5-(trifluoromethoxy)-1H-indol-2-yl)cyclohexanamine (less polar diastereoisomer) (28 mg, 0.07 mmol) was dissolved in ethanol (5 ml) under the influence of heat and citric acid (15 mg, 0.08 mmol), dissolved in hot ethanol (1 ml), was added. The clear colourless solution was stirred for 24 h and then concentrated down to approx. 0.5 ml. After addition of diethyl ether (5 ml), the mixture was stirred at RT for 1 h and the precipitate was then filtered off with suction. Example 121 was obtained in a yield of 75% (31 mg) with a melting point of 246-253° C.

1-Butyl-N,N-dimethyl-4-(3-methyl-5-(trifluoromethoxy)-1H-indol-2-yl)cyclohexanamine, citrate (1:1), polar diastereomer 1-Butyl-N,N-dimethyl-4-(3-methyl-5-(trifluoromethoxy)-1H-indol-2-yl)cyclohexanamine (more polar diastereoisomer) (230 mg, 0.58 mmol) was dissolved in ethanol (15 ml) under the influence of heat and citric acid (122 mg, 0.64 mmol), dissolved in hot ethanol (2 ml), was added. The clear colourless solution was stirred for 24 h and then concentrated down to approx. 0.5 ml. After addition of diethyl ether (5 ml), the mixture was stirred at RT for 1 h and the precipitate was then filtered off with suction. Example 122 was obtained in a yield of 74% (252 mg) with a melting point of 166-168° C.

Example 123

N,N-Dimethyl-4-(3-methyl-5-(trifluoromethoxy)-1H-indol-2-yl)-1-phenylcyclohexanamine, citrate (2:1), non-polar diastereomer

Example 124

N,N-dimethyl-4-(3-methyl-5-(trifluoromethoxy)-1H-indol-2-yl)-1-phenylcyclohexanamine, citrate (1:1), polar diastereomer

(±)-N,N-Dimethyl-N-[4-(3-methyl-5-trifluoromethoxy-1H-indol-2-yl)-1-phenylcyclohex-3-enyl]amine The ketone (Ket-10, 313 mg, 1.44 mmol) was dissolved in methylene chloride (15 ml) together with Ind-43 (310 mg, 1.44 mmol). The addition of trifluoromethanesulfonic acid (0.144 ml, 1.6 mmol) then took place. The mixture was stirred at RT for 3 d. For working up, 1 N NaOH (10 ml) was added to the reaction mixture and the mixture was stirred for 10 min. After separation of the phases, the aqueous phase was extracted with methylene chloride (2×10 ml). The combined organic phases were dried with sodium sulfate, filtered and concentrated in vacuo. 676 mg of a pale brown solid were obtained, which was separated by chromatography [silica gel 60 (30 g); ethyl acetate/methanol 10:1; 500 ml)]. 491 mg (82%) of (±)-N,N-dimethyl-N-[4-(3-methyl-5-trifluoromethoxy-1H-indol-2-yl)-1-phenylcyclohex-3-enyl]amine were obtained.

N,N-dimethyl-4-(3-methyl-5-(trifluoromethoxy)-1H-indol-2-yl)-1-phenylcyclohexanamine (non-polar and polar diastereomer)

(±)-N,N-Dimethyl-N-[4-(3-methyl-5-trifluoromethoxy-1H-indol-2-yl)-1-phenylcyclohex-3-enyl]amine (350 mg, 0.84 mmol) was stirred with HBr/glacial acetic acid (33% HBr, 18 ml) until it had dissolved completely. Tin powder (0.98 g, 8.4 mmol) was then added to the mixture in portions in the course of 30 min. When the addition had ended, the reaction mixture was stirred for a further 1.5 h, and for working up it was then concentrated to dryness on rotary evaporator. The residue which remained was rendered basic by addition of 5 N NaOH (40 ml). The solution obtained was extracted with methylene chloride (4×30 ml). The combined organic phases were dried with $Na_2SO_4$ and then concentrated. The residue (410 mg) was separated by column chromatography [silica gel 60 (30 g); ethyl acetate/cyclohexane (1:1; 500 ml); ethyl acetate/methanol (2:1, (450 ml)]. N,N-dimethyl-4-(3-methyl-5-(trifluoromethoxy)-1H-indol-2-yl)-1-phenylcyclohexanamine (less polar diastereoisomer) was obtained in a yield of 132 mg (38%) as a colourless solid with a melting point of 78-84° C. The more polar diastereoisomer was obtained in a yield of 151 mg (43%) as a colourless solid with a melting point of 219-221° C.

N,N-Dimethyl-4-(3-methyl-5-(trifluoromethoxy)-1H-indol-2-yl)-1-phenylcyclohexanamine, citrate (2:1), non-polar diastereomer N,N-dimethyl-4-(3-methyl-5-(trifluoromethoxy)-1H-indol-2-yl)-1-phenylcyclohexanamine (less polar diastereoisomer) (132 mg, 0.317 mmol) was dissolved in ethanol (10 ml), and citric acid (67 mg, 0.349 mmol), dissolved in hot ethanol (2 ml), was added. After stirring at RT for 30 min, a colourless solid started to precipitate out. After stirring for 20 h, the mixture was filtered with suction. Example 123 was obtained in a yield of 52% (84 mg) with a melting point of 209-111° C.

N,N-dimethyl-4-(3-methyl-5-(trifluoromethoxy)-1H-indol-2-yl)-1-phenylcyclohexanamine, citrate (1:1), polar diastereomer N,N-dimethyl-4-(3-methyl-5-(trifluoromethoxy)-1H-indol-2-yl)-1-phenylcyclohexanamine (more polar diastereoisomer) (151 mg, 0.36 mmol) was dissolved in ethanol (10 ml), and citric acid (77 mg, 0.4 mmol), dissolved in hot ethanol (2 ml), was added. After stirring at RT for 20 h, the colourless solid which had precipitated out was filtered off with suction. Example 124 was obtained in a yield of 50% (109 mg) with a melting point of 198-199° C.

Example 125

1-Butyl-4-(5-methoxy-3-methyl-1H-indol-2-yl)-N,
N-dimethylcyclohexanamine, citrate (1:1), non-polar
diastereomer

Example 126

1-Butyl-4-(5-methoxy-3-methyl-1H-indol-2-yl)-N,
N-dimethylcyclohexanamine, citrate (1:1), polar
diastereomer (±)-N-[1-Butyl-4-(5-methoxy-3-methyl-1H-indol-2-
yl)cyclohex-3-enyl]-N,N-dimethylamine 5-Methoxyskatole (Ind-9, 806 mg, 5 mmol) was dissolved in methylene chloride (40 ml) together with Ket-4 (985 mg, 5 mmol), and trifluoromethanesulfonic acid (0.65 ml, 7.5 mmol) was added. The mixture was stirred at RT for 24 h.—For working up, 2 N NaOH (20 ml) was added to the reaction mixture and the mixture was stirred at RT for 20 min. After the organic phase had been separated off, the aqueous phase was extracted with methylene chloride (3×20 ml). The combined organic extracts were dried over $Na_2SO_4$ and then concentrated. The crude product was obtained in a yield of 1.69 g (99%) as a yellow oil and was employed in the next reaction without further purification.

1-Butyl-4-(5-methoxy-3-methyl-1H-indol-2-yl)-N,
N-dimethylcyclohexanamine (non-polar and polar
diastereomer)

(±)-N-[1-Butyl-4-(5-methoxy-3-methyl-1H-indol-2-yl)cyclohex-3-enyl]-N,N-dimethylamine (1.5 g, 4.4 mmol) was suspended in HBr/glacial acetic acid (33% HBr, 20 ml). Sn powder (2.6 g, 22 mmol) was then added to the mixture in portions at RT in the course of 30 min. When the addition had ended, the reaction mixture was stirred at RT for a further 24 h.—For working up, the mixture was diluted with EtOH (20 ml) and concentrated to dryness on a rotary evaporator. The residue which remained was rendered basic by addition of 5 N NaOH (100 ml). The aqueous mixture obtained was extracted with methylene chloride (4×20 ml). The combined organic phases were washed with water (50 ml), dried over $Na_2SO_4$ and then concentrated. The residue obtained (1.5 g) was purified by column chromatography [silica gel 60 (70 g); EtOAc (400 ml), methanol (400 ml)]. 1-Butyl-4-(5-methoxy-3-methyl-1H-indol-2-yl)-N,N-dimethylcyclohexanamine (less polar diastereomer) was obtained in a yield of 141 mg (10%) as a brown oil. The more polar product had to be purified by a second column chromatography [silica gel 60 (50 g); methanol (200 ml), MeCN/methanol/1 M $NH_4Cl$ soln. 9:1:1, (250 ml)]. It was obtained in a yield of 125 mg (8%) as a yellow oil.

1-Butyl-4-(5-methoxy-3-methyl-1H-indol-2-yl)-N,
N-dimethylcyclohexanamine, citrate (1:1), non-polar
diastereomer 1-Butyl-4-(5-methoxy-3-methyl-1H-indol-2-yl)-N,N-dimethylcyclohexanamine (less polar diastereomer) (50 mg, 0.14 mmol) was dissolved in hot isopropanol (20 ml), and isopropanolic citric acid solution (28 mg, 0.14 mmol in 2 ml) was added. The mixture was stirred at room temperature for 2 h. The white solid was filtered off with suction. Example 125 was obtained in a yield of 56 mg (71%) with a melting point of 115-121° C.

1-Butyl-4-(5-methoxy-3-methyl-1H-indol-2-yl)-N,
N-dimethylcyclohexanamine, citrate (1:1), polar
diastereomer 1-Butyl-4-(5-methoxy-3-methyl-1H-indol-2-yl)-N,N-dimethylcyclohexanamine (more polar diastereomer) (125 mg, 0.36 mmol) was dissolved in hot isopropanol (30 ml), and isopropanolic citric acid solution (70 mg, 0.36 mmol in 2 ml) was added. The mixture was stirred at room temperature for 2 h. The solid which had precipitated out was filtered off with suction. Example 126 was obtained in a yield of 130 mg (65%).

Example 127

4-(5-Methoxy-3-methyl-1H-indol-2-yl)-N,N-dimethyl-1-phenylcyclohexanamine, citrate (1:0.85),
non-polar diastereomer

Example 128

4-(5-Methoxy-3-methyl-1H-indol-2-yl)-N,N-dimethyl-1-phenylcyclohexanamine, citrate (4:3), polar
diastereomer 4-(5-Methoxy-3-methyl-1H-indol-2-yl)-N,N-dimethyl-1-phenylcyclohexanamine (non-polar and polar
diastereomer)

The free base from Example 29 (385 mg, 1.07 mmol) was suspended in HBr/glacial acetic acid (33% HBr, 15 ml). Sn powder (1.8 g, 15 mmol) was then added to the mixture in portions in the course of 30 min. When the addition had ended, the reaction mixture was stirred at RT for a further 30 min. A clear solution was formed by this procedure.—For working up, the mixture was diluted with EtOH (20 ml) and concentrated to dryness on a rotary evaporator. The residue which remained was rendered basic by addition of 5 N NaOH (60 ml). The aqueous mixture obtained was extracted with methylene chloride (4×20 ml). The combined organic phases were washed with water (50 ml), dried over $MgSO_4$ and then concentrated. The residue obtained (360 mg) was boiled up in boiling methanol (30 ml), not all the substance dissolving. The mixture was brought to RT and placed in a refrigerator for 17 h to bring the crystallization to completion. 4-(5-Methoxy-3-methyl-1H-indol-2-yl)-N,N-dimethyl-1-phenylcyclohexanamine ((163 mg (42%)), non-polar diastereomer) was separated off by filtration as a white solid with a melting point of 156-163° C. (from isopropanol). The methanolic mother liquor was concentrated and the residue was purified by column chromatography [silica gel 60 G (10 g); EtOAc/EtOH 1:1 (150 ml)]. The more polar diastereoisomer was obtained in this way in a yield of 82 mg (21%) as a white solid with a melting point of 227-236° C.

4-(5-Methoxy-3-methyl-1H-indol-2-yl)-N,N-dimethyl-1-phenylcyclohexanamine, citrate (1:0.85),
non-polar diastereomer 4-(5-Methoxy-3-methyl-1H-indol-2-yl)-N,N-dimethyl-1-phenylcyclohexanamine (non-polar diastereomer) (156 mg, 0.43 mmol) was dissolved in isopropanol (10 ml) at the boiling point and citric acid (82 mg, 0.43 mmol), dissolved in hot isopropanol (1 ml), was added. On cooling, a precipitate precipitated out. To bring the precipitation to completion, the mixture was cooled to 5° C. (refrigerator) and left at this temperature for 17 h. The precipitate was separated off by means of a frit and then dried. Example 127 was obtained in this way in a yield of 175 mg (75%) with a melting point of 221-225° C.

4-(5-Methoxy-3-methyl-1H-indol-2-yl)-N,N-dimethyl-1-phenylcyclohexanamine, citrate (4:3), polar diastereomer 4-(5-Methoxy-3-methyl-1H-indol-2-yl)-N,N-dimethyl-1-phenylcyclohexanamine (polar diastereomer, 82 mg, 0.22 mmol) was dissolved in isopropanol (10 ml) at the boiling point and citric acid (41 mg, 0.22 mmol), dissolved in hot isopropanol (1 ml), was added. On cooling, a precipitate precipitated out. To bring the precipitation to completion, the mixture was cooled to 5° C. (refrigerator) and left at this temperature for 17 h. The precipitate was separated off by means of a frit and then dried. Example 128 was obtained in this way in a yield of 85 mg (85%) with a melting point of 146-151° C.

Example 129

1-Benzyl-N,N-dimethyl-4-(3-methyl-1H-indol-2-yl)cyclohexanamine, citrate (1:1), polar diastereomer Example 130

1-Benzyl-N,N-dimethyl-4-(3-methyl-1H-indol-2-yl)cyclohexanamine, citrate (2:1), non-polar diastereomer 1-Benzyl-N,N-dimethyl-4-(3-methyl-1H-indol-2-yl)cyclohexanamine, (non-polar and polar diastereomer)

The free base from Example 30 (280 mg, 0.81 mmol) was dissolved in ethanol (30 ml), the catalyst (Pd/charcoal 5%, 200 mg) was added and hydrogenation was carried out at RT under a hydrogen pressure of 3 bar for 3 h (sample after 1 h: scarcely any reaction). The solid residue (270 mg) obtained after separating off the catalyst and removing the solvent was purified by column chromatography (mobile phase: EtOAc). 1-Benzyl-N,N-dimethyl-4-(3-methyl-1H-indol-2-yl)cyclohexanamine (non-polar diastereoisomer) was obtained in this way in a yield of 71 mg (25%) and the more polar diastereoisomer was obtained in a yield of 145 mg (51%).

1-Benzyl-N,N-dimethyl-4-(3-methyl-1H-indol-2-yl)cyclohexanamine, citrate (1:1), polar diastereomer 1-Benzyl-N,N-dimethyl-4-(3-methyl-1H-indol-2-yl)cyclohexanamine (polar isomer, 130 mg, 0.38 mmol) was dissolved in isopropanol (4 ml) at the boiling point and citric acid (80 mg, 0.41 mmol), dissolved in hot isopropanol (2 ml), was added. The solution was cooled to 5° C. (refrigerator) and left to stand for 17 h. The precipitate formed was separated off by means of a frit. Example 129 was obtained in this way in a yield of 126 mg (61%, melting point: 167-169° C.).

1-Benzyl-N,N-dimethyl-4-(3-methyl-1H-indol-2-yl)cyclohexanamine, citrate (2:1), non-polar diastereomer 1-Benzyl-N,N-dimethyl-4-(3-methyl-1H-indol-2-yl)cyclohexanamine (non-polar isomer, 68 mg, 0.20 mmol) was dissolved in methanol (30 ml) at the boiling point and citric acid (60 mg, 0.31 mmol), dissolved in hot methanol (5 ml), was added. The solution was cooled to 5° C. (refrigerator) and left to stand for 17 h. The precipitate formed was separated off by means of a frit. Example 130 was obtained in this way in a yield of 72 mg (63%, melting point: 193-196° C.).

Example 131

1-Butyl-N,N-dimethyl-4-(3-methyl-1H-indol-2-yl)cyclohexanamine, citrate (2:1), non-polar diastereomer Example 132

1-Butyl-N,N-dimethyl-4-(3-methyl-1H-indol-2-yl)cyclohexanamine, citrate (1:1), polar diastereomer 1-Butyl-N,N-dimethyl-4-(3-methyl-1H-indol-2-yl)cyclohexanamine, (non-polar and polar diastereomer)

3-Methylindole (Ind-10, 524 mg, 4 mmol) was dissolved in methylene chloride (30 ml) together with ketone Ket-4 (788 mg, 4 mmol), and trifluoromethanesulfonic acid (0.4 ml, 4.6 mmol) was added. The mixture was stirred at RT for 24 h. Triethylsilane (2 ml, 12.6 mmol) was then added to the mixture. The reaction mixture was stirred at RT for 60 h.—For working up, 2 N NaOH (10 ml) was added to the reaction mixture. The mixture was stirred for a further 20 min. After separation of the phases, the aqueous phase was extracted with methylene chloride (3×20 ml). The combined organic extracts were dried over $MgSO_4$ and then concentrated. The crude product obtained (1.8 g), which still contained triethylsilyl compounds, was purified by column chromatography (mobile phase: ethyl acetate). 1-Butyl-N,N-dimethyl-4-(3-methyl-1H-indol-2-yl)cyclohexanamine (non-polar isomer) was obtained in a yield of 122 mg (9%). The polar isomer was obtained in a yield of 230 mg (18%).

1-Butyl-N,N-dimethyl-4-(3-methyl-1H-indol-2-yl)cyclohexanamine, (polar diastereomer)

Ex. 31 (free base, 210 mg, 0.68 mg) was initially introduced into methanol (50 ml) together with the catalyst (5 per cent strength Pd/C, 100 mg) and hydrogenation was carried out at RT under a hydrogen pressure of 3 bar. After a reaction time of 1 h, no or scarcely any conversion was to be observed. After hydrogenation at RT for 6 h, the starting substance was no longer detectable.—For working up, the catalyst was separated off by means of a frit and washed with methanol (2×20 ml). After removal of the solvent, a residue of 198 mg was obtained. NMR analyses showed that the crude product was 1-butyl-N,N-dimethyl-4-(3-methyl-1H-indol-2-yl)cyclohexanamine (polar isomer) (94% yield) in an almost pure form.

1-Butyl-N,N-dimethyl-4-(3-methyl-1H-indol-2-yl)cyclohexanamine, citrate (2:1), non-polar diastereomer 1-Butyl-N,N-dimethyl-4-(3-methyl-1H-indol-2-yl)cyclohexanamine (non-polar diastereomer, 102 mg, 0.33 mmol) was dissolved in isopropanol (4 ml) at the boiling point and citric acid (62 mg, 0.32 mmol), dissolved in hot isopropanol (1 ml), was added. The solution was cooled to 5° C. in a refrigerator and left to stand for 3 h. The precipitate formed was separated off by means of a frit. The hemicitrate of the non-polar isomer Ex. 131 was obtained in this way in a yield of 108 mg (80%, melting point: 208-211° C.).

1-Butyl-N,N-dimethyl-4-(3-methyl-1H-indol-2-yl) cyclohexanamine, citrate (1:1), polar diastereomer 1-Butyl-N,N-dimethyl-4-(3-methyl-1H-indol-2-yl)cyclohexanamine (polar diastereomer, 200 mg, 0.63 mmol) was dissolved in isopropanol (2 ml) at the boiling point and citric acid (120 mg, 0.63 mmol), dissolved in hot isopropanol (1 ml), was added. After cooling the solution, a tacky precipitate precipitated out, which solidified to a vitreous solid on drying in vacuo. The substance was taken up in $H_2O$ (6 ml) and triturated. The solid formed was separated off by means of a frit. The citrate of the polar isomer Ex. 132 was obtained in this way in a yield of 152 mg (59%, melting point: 124-129° C.).

Example 133

1-Benzyl-4-(3-cyclopropyl-1H-indol-2-yl)-N,N-dimethylcyclohexanamine, citrate (1:1), non-polar diastereomer

Example 134

1-Benzyl-4-(3-cyclopropyl-1H-indol-2-yl)-N,N-dimethylcyclohexanamine, citrate (1:1), polar diastereomer

1-Benzyl-4-(3-cyclopropyl-1H-indol-2-yl)-N,N-dimethylcyclohexanamine (non-polar and polar diastereomer)

The free base from Example 33 (210 mg, 0.567 mmol) was dissolved in methanol (35 ml), and palladium on charcoal (5 per cent strength; 90 mg) was added. The reaction mixture was hydrogenated under 3 bar for 5 h. The catalyst was separated off over Celite and the filtrate was concentrated. The solid residue (185 mg) was separated by chromatography [silica gel 60 (40 g); ethyl acetate/methanol 10:1 (250 ml), ethyl acetate/methanol 4:1 (250 ml)]. 1-Benzyl-4-(3-cyclopropyl-1H-indol-2-yl)-N,N-dimethylcyclohexanamin (more polar diastereoisomer) was obtained in a yield of 50% (105 mg) with a melting point of 65-70° C. The less polar diastereoisomer was isolated in a yield of 26% (54 mg) together with by-products. This fraction was purified again by chromatography [silica gel 60 (20 g); trichloromethane/methanol 40:1 (250 ml)]. The less polar diastereoisomer was obtained by this procedure in a yield of 43 mg (20%) with traces of an impurity and was employed in this form for the citrate preparation.

1-Benzyl-4-(3-cyclopropyl-1H-indol-2-yl)-N,N-dimethylcyclohexanamine, citrate (1:1), non-polar diastereomer 1-Benzyl-4-(3-cyclopropyl-1H-indol-2-yl)-N,N-dimethylcyclohexanamine (less polar isomer) (41 mg, 0.11 mmol, contaminated) was dissolved in ethanol (7 ml) at 60° C. and an ethanolic solution (3 ml) of citric acid (24 mg, 0.12 mmol) was added. After a reaction time of 2 h at room temperature, the colourless solid was separated off by filtration and washed with ethanol (2 ml) and diethyl ether (2 ml). Example 133 was obtained in a yield of 48% (30 mg) with a melting point of 237-242° C.

1-Benzyl-4-(3-cyclopropyl-1H-indol-2-yl)-N,N-dimethylcyclohexanamine, citrate (1:1), polar diastereomer 1-Benzyl-4-(3-cyclopropyl-1H-indol-2-yl)-N,N-dimethylcyclohexanamine (more polar isomer) (105 mg, 0.29 mmol) was dissolved in ethanol (5 ml) at 40° C. and an ethanolic solution (3 ml) of citric acid (62 mg, 0.32 mmol) was added. After a reaction time of 16 h at room temperature, no salt had precipitated out. The reaction mixture was concentrated. The residue was dissolved in ethanol (1.5 ml). Diethyl ether (20 ml) was then added. After 30 min the colourless solid was separated off by filtration and washed with diethyl ether (3 ml). The citrate (Ex. 134) was isolated in a yield of 56% (91 mg).

Example 135

1-Butyl-4-(3-cyclopropyl-1H-indol-2-yl)-N,N-dimethylcyclohexanamine hydrochloride, polar diastereomer Ex. 34 (337 mg, 1.0 mmol) was dissolved in methanol (35 ml), and palladium on charcoal (5 per cent strength; 144 mg) was added. The reaction mixture was hydrogenated under 3 bar for 4 h. Since no reaction was visible, catalyst (Pd/C, 5 per cent strength, 144 g) was again added and hydrogenation was carried out under 3 bar for 2 h. After 2 h, the educt was no longer detectable. The catalyst was separated off over Celite and the filtrate was concentrated. The solid residue (297 mg) was separated by chromatography [silica gel 60 (50 g); methanol (600 ml)]. 1-Butyl-4-(3-cyclopropyl-1H-indol-2-yl)-N,N-dimethylcyclohexanamine (polar diastereomer) was obtained in a yield of 62% (209 mg) with a melting point of 257-263° C. No further diastereomer was obtained.

1-Butyl-4-(3-cyclopropyl-1H-indol-2-yl)-N,N-dimethylcyclohexanamine (polar diastereomer) (135 mg, 0.398 mmol) was dissolved in trichloromethane (15 ml) and methanol (10 ml), and a 5 N hydrochloric acid (0.16 ml. 0.8 mmol) in propan-2-ol was added. The lilac-coloured solution was concentrated and diethyl ether (40 ml) was added. After 30 min the hydrochloride was separated off as a lilac-coloured solid by filtration and washing with diethyl ether (2×2 ml). Example 135 was obtained in a yield of 56% (84 mg) with a melting point of 274-276° C.

Example 136

4-(3-Cyclopropyl-1H-indol-2-yl)-N,N-dimethyl-1-phenylcyclohexanamine, citrate (2:1), polar diastereomer Ex. 35 (329 mg, 0.92 mmol) was dissolved in methanol (100 ml), and palladium on charcoal (5 per cent strength; 124 mg) was added. The reaction mixture was hydrogenated under 3 bar for 5 h. Since the reaction was not complete, catalyst (40 mg) was again added and hydrogenation was carried out for a further 16 h. The catalyst was separated off over Celite and the filtrate was concentrated. The solid residue (306 mg) was separated by chromatography [silica gel 60 (45 g); ethyl acetate/methanol 4:1 (500 ml), methanol (200 ml)]. 4-(3-Cyclopropyl-1H-indol-2-yl)-N,N-dimethyl-1-phenylcyclohexanamine (polar diastereoisomer) was obtained in a yield of 62% (205 mg). 4-(3-Cyclopropyl-1H-indol-2-yl)-N,N-dimethyl-1-phenylcyclohexanamine (polar diastereoisomer) (246 mg, 0.686 mmol) was dissolved in ethanol (36 ml) at 60° C. and an ethanolic solution (3 ml) of citric acid (146 mg, 0.76 mmol) was added. After a reaction time of 16 h at room temperature, the colourless solid was separated off by filtration and washed (150 mg) with ethanol (2 ml). The filtrate was concentrated to 5 ml and diethyl ether (50 ml) was added. After 30 min further solid was separated off and washed (91 mg) with diethyl ether (2×5 ml). The two fractions were combined. Example 136 was obtained in this way in a yield of 64% with a melting point of 238-245° C.

Example 137

Methyl 2-(2-(4-(dimethylamino)-4-phenylcyclohexyl)-1H-indol-3-yl)acetate, citrate (2:1), non-polar diastereomer

Example 138

Methyl 2-(2-(4-(dimethylamino)-4-phenylcyclohexyl)-1H-indol-3-yl)acetate, citrate (2:1), polar diastereomer (+)-Methyl 2-(2-(4-(dimethylamino)-4-phenylcyclohex-1-enyl)-1H-indol-3-yl)acetate Methyl 2-(1H-indol-3-yl)acetate (Ind-47, 757 mg, 4 mmol) was dissolved in methylene chloride (80 ml), together with ketone Ket-10 (868 mg, 4 mmol), and trifluoromethanesulfonic acid (540 µl, 6 mmol) was added. The mixture was stirred at RT for 16 h. For working up, 2 N NaOH (50 ml) was added to the reaction mixture and the mixture was stirred at RT for 20 min. After the organic phase had been separated off, the aqueous phase was extracted with methylene chloride (3×20 ml). The combined organic extracts were dried over $Na_2SO_4$ and then concentrated. It was possible for the crude product obtained (1.52 g) to be purified by column chromatography [silica gel 60 (100 g); MeOH (500 ml)] (+)-Methyl 2-(2-(4-(dimethylamino)-4-phenylcyclohex-1-enyl)-1H-indol-3-yl)acetate was obtained in a yield of 936 mg (60%) as a yellow solid.

Methyl 2-(2-(4-(dimethylamino)-4-phenylcyclohexyl)-1H-indol-3-yl)acetate (non-polar and polar diastereomer)

(±)-Methyl 2-(2-(4-(dimethylamino)-4-phenylcyclohex-1-enyl)-1H-indol-3-yl)acetate (936 mg, 2.4 mmol) was dissolved in HBr/glacial acetic acid (33% HBr, 30 ml). Sn powder (2.88 g, 24 mmol) was then added to the mixture in portions at RT in the course of 1 h. When the addition had ended, the reaction mixture was stirred at RT for a further 16 h.—For working up, the mixture was diluted with EtOH (10 ml) and concentrated to dryness on a rotary evaporator. The residue which remained was rendered basic by addition of 2 N NaOH (100 ml). The aqueous mixture obtained was extracted with methylene chloride (4×40 ml). The combined organic phases were dried over $Na_2SO_4$ and then concentrated. The crude product obtained (900 mg) was purified by column chromatography [silica gel 60 (100 g); MeOH (1,000 ml)] Methyl 2-(2-(4-(dimethylamino)-4-phenylcyclohexyl)-1H-indol-3-yl)acetate (less polar diastereomer) was obtained in a yield of 290 mg (31%), and the polar diastereomer was obtained in a yield of 200 mg (21%). Both products were colourless oils.

Methyl 2-(2-(4-(dimethylamino)-4-phenylcyclohexyl)-1H-indol-3-yl)acetate, citrate (2:1), non-polar diastereomer Methyl 2-(2-(4-(dimethylamino)-4-phenylcyclohexyl)-1H-indol-3-yl)acetate (non-polar diastereomer) (290 mg, 0.74 mmol) was dissolved in hot methylene chloride (150 ml), and citric acid (143 mg, 0.74 mmol) was added. The clear solution was left to stand at 4° C. for 16 h. The colourless solid which had precipitated out was filtered off with suction and dried. Example 137 was obtained in a yield of 250 mg (67%) with a melting point of 226-229° C.

$^1$H NMR (400 MHz, DMSO-$d_6$) δ ppm: 1.52-1.73 (m, 4H), 2.12 (s, 2H), 2.43-2.75 (m, 4H), 2.76-2.88 (m, 2H), 2.90-3.02 (m, 2H), 3.17 (s, 1H), 3.57 (s, 3H), 3.71 (s, 1H), 6.87-7.07 (m, 2H), 7.23-7.51 (m, 7H), 10.76 (s, 1H)
$^{13}$C NMR (101 MHz, DMSO-$d_6$) δ ppm: 27.0, 29.5, 32.7, 34.7, 37.8, 43.2, 51.4, 56.0, 72.0, 102.0, 110.9, 117.5, 118.3, 120.1, 126.8, 127.5(s, 1C), 128.0, 135.2, 141.4, 171.2, 172.1, 175.3

Methyl 2-(2-(4-(dimethylamino)-4-phenylcyclohexyl)-1H-indol-3-yl)acetate, citrate (2:1), polar diastereomer

[Methyl 2-(2-(4-(dimethylamino)-4-phenylcyclohexyl)-1H-indol-3-yl)acetate (more polar diastereomer) (200 mg, 0.51 mmol) was dissolved in hot methylene chloride (100 ml), and citric acid (99 mg, 0.96 mmol) was added. The clear solution was left to stand at 4° C. for 16 h. The colourless solid which had precipitated out was filtered off with suction and dried. Example 138 was obtained in a yield of 170 mg (57%) with a melting point of 190-193° C.

$^1$H NMR (400 MHz, DMSO-$d_6$) δ ppm: 1.38-1.56 (m, 2H), 1.73-1.90 (m, 4H), 2.22 (s, 6H), 2.46-2.62 (m, 4H), 2.85-3.02 (m, 3H), 3.56 (s, 3H), 3.66 (s, 2H), 6.83-7.01 (m, 1H), 7.17 (d, J=7.78 Hz, 1H), 7.39-7.46 (m, 1H), 7.48-7.63 (m, 4H), 10.54 (s, 1H)
13C NMR (101 MHz, DMSO-d6) (ppm: 28.5, 29.4, 31.9, 35.3, 37.7, 44.2, 51.4, 64.4, 71.2, 102.2, 110.7, 117.4, 118.3, 120.1, 127.8, 127.9, 128.3, 128.6, 133.8, 135.0, 140.4, 171.2, 172.0, 176.8

Example 139

1-Benzyl-4-(3-(cyclohexylmethyl)-1H-indol-2-yl)-N,N-dimethylcyclohexanamine, citrate (2:1), non-polar diastereomer

Example 140

1-Benzyl-4-(3-(cyclohexylmethyl)-1H-indol-2-yl)-N,N-dimethylcyclohexanamine, citrate (1:1), polar diastereomer 1-Benzyl-4-(3-(cyclohexylmethyl)-1H-indol-2-yl)-N,N-dimethylcyclohexanamine (non-polar and polar diastereomer)

Ex. 36 (705 mg, 1.522 mmol) was dissolved in hydrogen bromide/glacial acetic acid (33% HBr, 35 ml). Tin powder (1.808 g, 15.23 mmol) was then added to the mixture in portions at room temperature in the course of 40 min and the mixture was stirred for a further 20 min. The mixture was then diluted with water (300 ml). The mixture was stirred at 5° C. for 1 h. The product precipitated out as the hydrobromide. This was filtered off and washed with water (2×5 ml). 1 N NaOH (50 ml) was added to the pink-coloured wet solid (5.0 g). The mixture was extracted with methylene chloride (3×30 ml). The combined organic phases were dried with $Na_2SO_4$ and filtered. The volatile constituents were removed completely in vacuo. The yellow oil (630 mg) was stirred with methanol (10 ml) at 5° C. for 1 h. 1-Benzyl-4-(3-(cyclohexylmethyl)-1H-indol-2-yl)-N,N-dimethylcyclohexanamine (less polar diastereoisomer) precipitated out as a white solid. This was filtered off with suction and washed (326 mg, 48%, m.p.: 120-126° C.) with methanol (2×1 ml). The filtrate was concentrated (165 mg of oil). After separation of this mixture by chromatography [silica gel 60 (20 g); chloroform/methanol 40:1 (410 ml)], the more polar diastereoisomer (95 mg, 15%) was obtained as a yellow oil.

1-Benzyl-4-(3-(cyclohexylmethyl)-1H-indol-2-yl)-N,N-dimethylcyclohexanamine, citrate (2:1), non-polar diastereomer 1-Benzyl-4-(3-(cyclohexylmethyl)-1H-indol-2-yl)-N,N-dimethylcyclohexanamine (less polar diastereoisomer, 285 mg, 0.641 mmol) was dissolved in hot ethanol (12 ml), and a similarly hot ethanolic citric acid solution (135 mg, 0.703 mmol in 2 ml) was added. The mixture was subsequently stirred at room temperature overnight and then filtered and the residue was washed with a little ethanol. Example 139 was obtained as a white solid in a yield of 99% (334 mg) with a melting point of 208-213° C.

1-Benzyl-4-(3-(cyclohexylmethyl)-1H-indol-2-yl)-N,N-dimethylcyclohexanamine, citrate (1:1), polar diastereomer 1-Benzyl-4-(3-(cyclohexylmethyl)-1H-indol-2-yl)-N,N-dimethylcyclohexanamine (more polar diastereomer) (92 mg, 0.215 mmol) and citric acid (44 mg, 0.229 mmol) were dissolved in hot ethanol (0.5 ml). Diethyl ether (10 ml) was slowly added dropwise to the clear solution at room temperature. The mixture was stirred at room temperature overnight. A white precipitate precipitated out, and was filtered off and washed with diethyl ether. Ex. 140 was obtained in a yield of 66% (88 mg) with a melting point of 110-115° C.

Example 141

1-Benzyl-4-(3-benzyl-1H-indol-2-yl)-N,N-dimethyl-cyclohexanamine, citrate (1:1), non-polar diastereomer Example 142

1-Benzyl-4-(3-benzyl-1H-indol-2-yl)-N,N-dimethyl-cyclohexanamine, citrate (1:1), polar diastereomer 1-Benzyl-4-(3-benzyl-1H-indol-2-yl)-N,N-dimethyl-cyclohexanamine (non-polar and polar diastereomer)

Ex. 37 (750 mg, 1.64 mmol) was dissolved in hydrogen bromide/glacial acetic acid (33% HBr, 40 ml). Tin powder (1.950 g, 16.43 mmol) was then added to the mixture in portions at RT in the course of 40 min. The mixture was stirred for a further 20 min. The mixture was then diluted with water (300 ml). The mixture was stirred at 5° C. for 1 h. The product precipitated out as the hydrobromide. This was filtered off and washed with water (2×5 ml). 1 N NaOH (50 ml) was added to the pink-coloured moist solid (5.0 g). The mixture was extracted with methylene chloride (3×30 ml). The combined organic phases were dried with Na₂SO₄ and then filtered. The volatile constituents of the filtrate were removed completely in vacuo. The solid (615 mg) was stirred with methanol (6 ml) at room temperature overnight. 1-Benzyl-4-(3-benzyl-1H-indol-2-yl)-N,N-dimethylcyclohexanamine (less polar diastereoisomer) precipitated out as a beige-coloured solid. It was filtered off and washed (277 mg) with methanol (2×1 ml) and diethyl ether (2×1 ml) The filtrate was concentrated (330 mg of oil). After separation of this oil by chromatography [silica gel 60 (40 g); ethyl acetate (1,500 ml)], further amounts of the less polar diastereoisomer (61 mg, 49% in total, m.p.: 140-143° C.) and the more polar diastereoisomer (207 mg, 30%, oil) were obtained.

1-Benzyl-4-(3-benzyl-1H-indol-2-yl)-N,N-dimethyl-cyclohexanamine, citrate (1:1), non-polar diastereomer 1-Benzyl-4-(3-benzyl-1H-indol-2-yl)-N,N-dimethylcyclohexanamine (less polar diasteroisomer) (304 mg, 0.719 mmol) was dissolved in a mixture of methylene chloride (4 ml) and ethanol (2 ml), and ethanolic citric acid solution (145 mg, 0.755 mmol in 4 ml) was added. The solution was concentrated to approx. 2 ml. The solid was filtered off with suction and washed with ethanol (2×0.5 ml). Example 141 was obtained in this way in a yield of 72% (320 mg) as a white solid with a melting point of 214-217° C.

1-Benzyl-4-(3-benzyl-1H-indol-2-yl)-N,N-dimethyl-cyclohexanamine, citrate (1:1), polar diastereomer)

1-Benzyl-4-(3-benzyl-1H-indol-2-yl)-N,N-dimethylcyclohexanamine (more polar diastereomer) (85 mg, 0.201 mmol) and citric acid (43 mg, 0.224 mmol) were dissolved in ethanol (2 ml). Diethyl ether (20 ml) was slowly added dropwise to the clear solution at room temperature. The mixture was stirred at room temperature for 1 h. A beige-coloured solid precipitated out, and was filtered off and washed with diethyl ether (2×1 ml). Example 142 was obtained in this way in a yield of 69% (76 mg) with a melting point of 110-115° C.

Example 143

1-Butyl-4-(3-(cyclohexylmethyl)-1H-indol-2-yl)-N,N-dimethylcyclohexanamine, citrate (2:1), non-polar diastereomer Example 144

1-Butyl-4-(3-(cyclohexylmethyl)-1H-indol-2-yl)-N,N-dimethylcyclohexanamine hydrochloride (1:1), polar diastereomer 1-Butyl-4-(3-(cyclohexylmethyl)-1H-indol-2-yl)-N,N-dimethylcyclohexanamine (non-polar and polar diastereomer)

Ex. 38 (777 mg, 1.811 mmol) was dissolved in hydrogen bromide/glacial acetic acid (33% HBr, 40 ml). Tin powder (2.150 g, 18.1 mmol) was then added to the mixture in portions at room temperature in the course of 40 min and the mixture was stirred for a further 20 min. The mixture was then diluted with water (250 ml). The mixture was stirred at 5° C. for 1 h. The product precipitated out as the hydrobromide. This was filtered off and washed with water (2×5 ml). 1 N NaOH (50 ml) was added to the beige-coloured wet solid (5.0 g). The mixture was extracted with methylene chloride (3×30 ml). The combined organic phases were dried with Na₂SO₄ and filtered and the volatile constituents were removed completely in vacuo. A yellow oil (650 mg) remained.

After separation of this mixture by chromatography [silica gel 60 (80 g); ethyl acetate/methanol 10:1 (1,100 ml), ethyl acetate/methanol (2:1 (540 ml)], 1-butyl-4-(3-(cyclohexylmethyl)-1H-indol-2-yl)-N,N-dimethylcyclohexanamine (less polar diastereoisomer, 306 mg, 43%, m.p.: 155-165° C.) and the more polar diastereoisomer (163 mg, 23%, m.p.: 258-264° C.) were obtained as white solids.

1-Butyl-4-(3-(cyclohexylmethyl)-1H-indol-2-yl)-N,N-dimethylcyclohexanamine, citrate (2:1), non-polar diastereomer 1-Butyl-4-(3-(cyclohexylmethyl)-1H-indol-2-yl)-N,N-dimethylcyclohexanamine (less polar diastereoisomer) (277 mg, 0.702 mmol) and citric acid (142 mg, 0.739 mmol) were dissolved in hot ethanol (20 ml). A solid precipitated out at room temperature. The mixture was left to stand at 5° C. overnight and then filtered and the residue was washed with a little ethanol. Example 143 was obtained in a yield of 72% (298 mg) with a melting point of 228-232° C.

1-Butyl-4-(3-(cyclohexylmethyl)-1H-indol-2-yl)-N,N-dimethylcyclohexanamine hydrochloride (1:1), polar diastereomer 1-Butyl-4-(3-(cyclohexylmethyl)-1H-indol-2-yl)-N,N-dimethylcyclohexanamine (polar diastereomer) (135 mg, 0.342 mmol) and citric acid (71 mg, 0.370 mmol) were dissolved in hot ethanol (4 ml). Diethyl ether (26 ml) was slowly added dropwise to the clear solution at room temperature. The mixture was stirred at room temperature overnight. The white solid was filtered off and washed with diethyl ether. was obtained in a yield of 50% (101 mg) with a melting point of 268-272° C. This product was identified as the hydrochloride.

Example 145

4-(3-benzyl-1H-indol-2-yl)-1-butyl-N,N-dimethylcyclohexanamine, citrate (1:1), non-polar diastereomer Example 146

4-(3-Benzyl-1H-indol-2-yl)-1-butyl-N,N-dimethyl-cyclohexanamine, citrate (1:1), polar diastereomer 4-(3-Benzyl-1H-indol-2-yl)-1-butyl-N,N-dimethyl-cyclohexanamine (non-polar and polar diastereomer Ex. 39 (438 mg, 1.133 mmol) was dissolved in hydrogen bromide/glacial acetic acid (33% HBr, 25 ml). Tin powder (1.345 g, 11.330 mmol) was then added to the mixture in portions at room temperature in the course of 40 min and the mixture was stirred for a further 20 min. The mixture was then diluted with water (100 ml). The mixture was stirred at 5° C. for 1 h. The product precipitated out as the hydrobromide. This was filtered off and washed with water (2×5 ml). 1 N NaOH (50 ml) was added to the moist yellow solid (4.0 g). The mixture was extracted with methylene chloride (3×30 ml). The combined organic phases were dried with $Na_2SO_4$ and filtered. The volatile constituents were removed completely in vacuo. An oil (425 mg) remained. After separation of this mixture by chromatography [silica gel 60 (40 g); ethyl acetate (500 ml), ethyl acetate/methanol 4:1 (750 ml)] 4-(3-benzyl-1H-indol-2-yl)-1-butyl-N,N-dimethylcyclohexanamine (less polar diastereoisomer, 210 mg, impure) and the more polar diastereoisomer (178 mg, 40%) was obtained as a yellow oil. The less polar diastereoisomer was purified further: Hot methanol (6 ml) was added and the mixture was left to stand at −10° C. overnight. The colourless solid which separated out (144 mg, 33%, melting point of 72-78° C. and 97-99° C.) was filtered off with suction and washed with cold methanol (2×0.5 ml).

4-(3-Benzyl-1H-indol-2-yl)-1-butyl-N,N-dimethyl-cyclohexanamine, citrate (1:1), non-polar diastereomer 4-(3-Benzyl-1H-indol-2-yl)-1-butyl-N,N-dimethylcyclohexanamine (less polar diastereoisomer, 121 mg, 0.311 mmol) dissolved in hot ethanol (2 ml), and ethanolic citric acid solution (63 mg, 0.328 mmol in 1 ml) added. The mixture was stirred at room temperature for 2 h. The solid which had precipitated out was filtered off with suction and washed with diethyl ether (2×1 ml). Example 145 was obtained in a yield of 61% (111 mg) with a melting point of 167-171° C.

4-(3-Benzyl-1H-indol-2-yl)-1-butyl-N,N-dimethyl-cyclohexanamine, citrate (1:1), polar diastereomer 4-(3-Benzyl-1H-indol-2-yl)-1-butyl-N,N-dimethylcyclohexanamine (more polar diastereoisomer, 157 mg, 0.404 mmol) was dissolved in diethyl ether (10 ml), and ethanolic citric acid solution (83 mg, 0.432 mmol in 0.5 ml) was added. The mixture was stirred at room temperature for 2 h. The solid which had precipitated out was filtered off with suction and washed with diethyl ether (2×1 ml). Example 146 (beige-coloured solid) was obtained in a yield of 55% (130 mg) with a melting point of 90-95° C. (HPLC purity approx. 88%).

Example 147

4-(3-(Cyclohexylmethyl)-1H-indol-2-yl)-N,N-dimethyl-1-phenylcyclohexanamine, citrate (2:1), non-polar diastereomer Example 148

4-(3-(Cyclohexylmethyl)-1H-indol-2-yl)-N,N-dimethyl-1-phenylcyclohexanamine, citrate (1:1), polar diastereomer 4-(3-(Cyclohexylmethyl)-1H-indol-2-yl)-N,N-dimethyl-1-phenylcyclohexanamine (non-polar and polar diastereomer)

Ex. 40 (913 mg, 2.033 mmol) was dissolved in hydrogen bromide/glacial acetic acid (33% HBr, 46 ml). Tin powder (2.415 g, 20.344 mmol) was then added to the mixture in portions at room temperature in the course of 40 min and the mixture was stirred for a further 20 min. The mixture was then diluted with water (300 ml). The mixture was stirred at 5° C. for 1 h. The product precipitated out as the hydrobromide. This was filtered off and washed with water (2×5 ml). 1 N NaOH (50 ml) was added to the pink-coloured wet solid (5.7 g). The mixture was extracted with methylene chloride (3×30 ml). The combined organic phases were dried with $Na_2SO_4$ and filtered and the volatile constituents were removed completely in vacuo. A yellow solid (776 mg) remained. After separation of this mixture by chromatography [silica gel 60 (80 g); ethyl acetate (500 ml), ethyl acetate/methanol 20:1 (525 ml), ethyl acetate/methanol 5:1 (600 ml), ethyl acetate/methanol 2:1 (600 ml)], 4-(3-(cyclohexylmethyl)-1H-indol-2-yl)-N,N-dimethyl-1-phenylcyclohexanamine less polar diastereoisomer) (472 mg, contaminated) and the more polar diastereoisomer (269 mg, 32%, m.p.: 195-198° C.) were obtained as white solids.

The less polar diastereomer was purified further: Methanol (15 ml) was added and the mixture was stirred overnight and then filtered. The residue was washed with methanol (3×1 ml). The white solid was obtained in a yield of 40% (336 mg) with a melting point of 206-209° C.).

4-(3-(Cyclohexylmethyl)-1H-indol-2-yl)-N,N-dimethyl-1-phenylcyclohexanamine, citrate (2:1), non-polar diastereomer 4-(3-(Cyclohexylmethyl)-1H-indol-2-yl)-N,N-dimethyl-1-phenylcyclohexanamine (non-polar diastereomer) (294 mg, 0.706 mmol) and citric acid (141 mg, 0.734 mmol) were dissolved in hot ethanol (7 ml). A solid precipitated out at room temperature. The mixture was stirred at room temperature overnight and then filtered and the residue was washed with a little ethanol. Example 147 was obtained in this way in a yield of 99% (355 mg) with a melting point of 224-228° C. as a white solid.

4-(3-(Cyclohexylmethyl)-1H-indol-2-yl)-N,N-dimethyl-1-phenylcyclohexanamine, citrate (1:1), polar diastereomer 4-(3-(Cyclohexylmethyl)-1H-indol-2-yl)-N,N-dimethyl-1-phenylcyclohexanamine (polar diastereomer) (245 mg, 0.588 mmol) and citric acid (122 mg, 0.635 mmol) were dissolved in hot ethanol (2 ml). Diethyl ether (12 ml) was slowly added dropwise to the clear solution at room temperature. The mixture was stirred at room temperature overnight. The white solid was filtered off and washed with diethyl ether. Example 148 was obtained in this way in a yield of 81% (290 mg) with a melting point of 190-192° C.

Example 149

4-(3-Benzyl-1H-indol-2-yl)-N,N-dimethyl-1-phenylcyclohexanamine, citrate (2:1), non-polar diastereomer Example 150

4-(3-Benzyl-1H-indol-2-yl)-N,N-dimethyl-1-phenylcyclohexanamine, citrate (1:1), polar diastereomer 4-(3-Benzyl-1H-indol-2-yl)-N,N-dimethyl-1-phenylcyclohexanamine (non-polar and polar diastereomer)

Ex. 41 (768 mg, 1.733 mmol) was dissolved in hydrogen bromide/glacial acetic acid (33% HBr, 40 ml). Tin powder (2.060 g, 17.353 mmol) was then added to the mixture in portions at room temperature in the course of 40 min and the mixture was stirred for a further 20 min. The mixture was then diluted with water (100 ml). The mixture was stirred at 5° C. for 1 h. The product precipitated out as the hydrobromide. This was filtered off and washed with water (2×5 ml). 1 N NaOH (50 ml) was added to the beige-coloured moist solid (4.3 g). The mixture was extracted with methylene chloride (3×30 ml). The combined organic phases were dried with Na$_2$SO$_4$ and then filtered. The volatile constituents were removed completely in vacuo. An oil (619 mg) remained. After separation of this mixture by chromatography [silica gel 60 (80 g); ethyl acetate (500 ml), ethyl acetate/methanol 20:1 (525 ml), ethyl acetate/methanol 5:1 (600 ml), ethyl acetate/methanol 2:1 (600 ml)], 4-(3-benzyl-1H-indol-2-yl)-N,N-dimethyl-1-phenylcyclohexanamine (less polar diastereoisomer) (186 mg, 26%, m.p.: 194-199° C.) and the more polar diastereoisomer (241 mg, 34%, m.p.: 205-209° C.) were obtained as beige-coloured solids.

4-(3-Benzyl-1H-indol-2-yl)-N,N-dimethyl-1-phenylcyclohexanamine, citrate (2:1), non-polar diastereomer (149)

4-(3-Benzyl-1H-indol-2-yl)-N,N-dimethyl-1-phenylcyclohexanamine (less polar diastereoisomer) (146 mg, 0.357 mmol) was dissolved in a mixture of methylene chloride (4 ml) and ethanol (0.5 ml), and ethanolic citric acid solution (73 mg, 0.380 mmol in 3.5 ml) was added. The solution was concentrated to approx. 2 ml. The solid which had precipitated out was filtered off with suction and washed with ethanol (2×0.5 ml). Ex. 149 was obtained in a yield of 96% (174 mg) as a white solid with a melting point of 220-223° C.

4-(3-Benzyl-1H-indol-2-yl)-N,N-dimethyl-1-phenylcyclohexanamine, citrate (1:1), polar diastereomer (150)

4-(3-Benzyl-1H-indol-2-yl)-N,N-dimethyl-1-phenylcyclohexanamine (more polar diastereoisomer) (150 mg, 0.367 mmol) was dissolved in methylene chloride (10 ml), and ethanolic citric acid solution (77 mg, 0.401 mmol in 10 ml) was added. The solution was concentrated to approx. 2 ml. The solid which had precipitated out was filtered off with suction and washed with ethanol (2×0.5 ml) and with diethyl ether (2×0.5 ml). Ex. 150 was obtained in a yield of 74% (163 mg) with a melting point of 140-143° C.

Example 151

N,N-Dimethyl-1-phenyl-4-(3-(pyridin-2-ylmethyl)-1H-indol-2-yl)cyclohexanamine, non-polar diastereomer Example 152

N,N-Dimethyl-1-phenyl-4-(3-(pyridin-2-ylmethyl)-1H-indol-2-yl)cyclohexanamine, polar diastereomer (±)-Dimethyl-[1-phenyl-4-(3-pyridin-2-ylmethyl-1H-indol-2-yl)cyclohex-3-enyl]amine Trifluoromethanesulfonic acid (3.95 g, 2.30 ml, 26 mmol) was added to a solution of Ind-49 (2.17 g 10.4 mmol) and Ket-10 (2.70 g, 12.5 mmol) in anhydrous methylene chloride (80 ml), while cooling with ice. The reaction mixture was stirred at room temperature for 2 d and 0.5 M sodium hydroxide solution (50 ml) was then added and the mixture was stirred at room temperature for 2 h. The phases were separated, the aqueous phase was extracted with methylene chloride (3×30 ml) and the combined organic phases were dried with sodium sulfate and concentrated i. vac. The crude product (6.45 g) was purified by flash chromatography (400 g, 20×7.6 cm) with chloroform/methanol (9:1).

Yield ((±)-Dimethyl-[1-phenyl-4-(3-pyridin-2-ylmethyl-1H-indol-2-yl)cyclohex-3-enyl]amine: 949 mg (22%), beige-coloured oil $^1$H-NMR (DMSO-d$_6$): 1.67-1.85 (m 2H); 1.99 (s, 2H); 2.09 (s, 6H); 2.57-2.77 (m, 2H); 4.17 (s, 2H); 6.23 (s, 1H); 6.85-6.90 (m, 2H); 6.99 (dt, 1H, J=7.0 and 1.0 Hz); 7.55 (dt, (ddd, 1H, J=7.4, 4.8 and 0.8 Hz); 7.18-7.40 (m, 5H); 7.45 (d, 2H, J=7.7 Hz); 7.55 (dt, 1H, J=7.6 and 1.8 Hz); 8.45 (d, 1H, J=3.9 Hz); 10.76 (1H, s).

N,N-Dimethyl-1-phenyl-4-(3-(pyridin-2-ylmethyl)-
1H-indol-2-yl)cyclohexanamine, non-polar diastereomer (Ex. 151) and N,N-Dimethyl-1-phenyl-4-(3-(pyridin-2-ylmethyl)-
1H-indol-2-yl)cyclohexanamine, polar diastereomer
(Ex. 152)

(±)-Dimethyl-[1-phenyl-4-(3-pyridin-2-ylmethyl-1H-indol-2-yl)cyclohex-3-enyl]amine (200 mg, 0.49 mmol) was dissolved in a 33% solution of hydrogen bromide in glacial acetic acid by stirring at room temperature for one hour. Tin powder (622 mg) was then added to the solution in portions in the course of 30 min. Thereafter, the mixture was stirred at room temperature overnight. Ethanol (10 ml) was added to the mixture and the mixture was concentrated i. vac. 5 N sodium hydroxide solution (25 ml) and methylene chloride (30 ml) were added to the very poorly soluble residue, the phases were separated and the aqueous phase was extracted with methylene chloride (5×30 ml). The combined organic phases were dried with sodium sulfate and concentrated i. vac. The crude product (135 mg) was purified by means of flash chromatography (10 g, 20×2.1 cm) with chloroform/methanol (4:1). It was possible to separate the non-polar and the polar diastereomer, which were obtained as the hydrochloride due to the chloroform used. In order to obtain the free base, sodium bicarbonate solution was added in each case and the mixture was extracted with methylene chloride (3×10 ml). The combined organic phases were dried with sodium sulfate and concentrated i. vac.

Yield: 25 mg (12%), yellowish amorphous solid.

$^1$H-NMR (DMSO-$d_6$): 1.46 (t, 2H, J=13.0 Hz); 1.58 (d, 2H, J=11.0 Hz); 2.01 (s, 6H); 2.11 (q, 2H, J=12.5 Hz); 2.79 (d, 2H, J=12.7 Hz); 3.04 (m, 1H); 4.16 (s, 2H); 6.86 (t, 1H, J=7.4 Hz); 6.96 (t, 1H, J=7.5 Hz); 7.06-7.16 (m, 2H); 7.22-7.43 (m, 7H); 7.59 (dt, 1H, J=7.7 and 1.8 Hz); 8.44 (d, 1H, J=3.9 Hz); 10.77 (s, 1H).

Yield (Ex. 152): 43 mg (21%), white solid; melting point: 205-210° C.

$^1$H-NMR (DMSO-$d_6$): 1.48 (t, 2H, J=12.3 Hz); 1.65 (t, 4H, J=12.1 Hz); 1.92 (s, 6H); 2.77 (d, 2H, J=11.3 Hz); 3.03 (t, 1H, J=11.8 Hz); 4.11 (s, 2H); 6.83 (t, 1H, J=7.3 Hz); 6.91 (t, 1H, J=7.0 Hz), 7.03 (d, 1H, J=7.8 Hz), 7.13 (dd, 1H, J=7.9 and 4.9 Hz); 7.17 (d, 1H, J=7.9 Hz), 7.30 (d, 2H, J=7.6 Hz); 7.36-7.46 (m, 4H); 7.59 (dt, 1H, J=7.6 and 1.8 Hz); 8.45 (d, 1H, J=3.8 Hz); 10.45 (s, 1H).

Example 153

3-(2-(4-(dimethylamino)-4-phenylcyclohexyl)-1H-
indol-3-yl)propionic acid hydrochloride, polar diastereomer 3-[2-(4-Dimethylamino-4-phenylcyclohexyl)-1H-
indol-3-yl]propionic acid (more polar diastereomer)

Ketone Ket-10 (1.9 g, 8.75 mmol) and indole Ind-50 (1.66 g, 8.75 mmol) were dissolved in HBr/glacial acetic acid (33% HBr, 50 ml) and the mixture was stirred at RT for 16 h. Sn powder (10.5 g, 87.5 mmol) was then added to the mixture in portions at RT in the course of 2 h. When the addition had ended, the reaction mixture was stirred at RT for a further 48 h.—For working up, the mixture was diluted with EtOH (20 ml) and concentrated to dryness on a rotary evaporator. It was possible for the crude product obtained to be purified by column chromatography [silica gel 60 (300 g); MeOH (3,000 ml)]. 3-[2-(4-Dimethylamino-4-phenylcyclohexyl)-1H-indol-3-yl]propionic acid (more polar diastereomer) was obtained in a yield of 419 mg (12%) as a white solid.

3-(2-(4-(dimethylamino)-4-phenylcyclohexyl)-1H-
indol-3-yl)propionic acid hydrochloride, polar diastereomer (153)

3-[2-(4-Dimethylamino-4-phenylcyclohexyl)-1H-indol-3-yl]propionic acid (more polar diastereomer) (419 mg, 1.08 mmol) was dissolved in ethyl acetate (50 ml). Me$_3$SiCl (276 µl, 1.16 mmol) was added dropwise at RT and the mixture was stirred for 16 h. The solvent was distilled off on a rotary evaporator and Example 153 (458 mg, m.p. 242-245° C., 100%) was obtained as a white solid.

Example 156

1-Benzyl-N,N-dimethyl-4-(3-propyl-1H-indol-2-yl)
cyclohexanamine, citrate (1:1), 1 diastereomer 1-Benzyl-N,N-dimethyl-4-(3-propyl-1H-indol-2-yl)
cyclohexanamine, (1 diastereomer)

Ex. 42 (956 mg, 2.57 mmol) was dissolved in methanol (60 ml), and Pd/C (5 per cent strength; 300 mg) was added and hydrogenation was carried out at 40° C. under 3 bar for 3 h, while stirring. For working up, the catalyst was filtered off over Celite and the methanol was removed in vacuo. After separation of the residue which remained (834 mg of yellow oil) by chromatography [silica gel 60 (70 g); cyclohexane/ethyl acetate 2:1 (450 ml), cyclohexane/ethyl acetate 1:1 (1,000 ml), ethyl acetate (500 ml), ethyl acetate/methanol 1:1 (300 ml)], a beige-coloured solid (432 mg) was obtained. This was suspended in ethyl acetate (3 ml) and then filtered off and washed with ethyl acetate (3×0.5 ml). One of the two possible diastereoisomers was obtained as a beige-coloured solid (208 mg, 22%, melting point: 232-250° C. 1-Benzyl-N,N-dimethyl-4-(3-propyl-1H-indol-2-yl)cyclohexanamine (200 mg, 0.534 mmol) and citric acid (105 mg, 0.547 mmol) were dissolved in hot methanol (6 ml). The clear solution was concentrated in vacuo. The residue was stirred overnight with ethyl acetate (5 ml) and then filtered off and washed with diethyl ether (2×2 ml). Example 156 was obtained in this way in a yield of 61% (185 mg) with a melting point of 250-265° C. (sublimes above 230° C.).

Example 157

1-Butyl-N,N-dimethyl-4-(3-propyl-1H-indol-2-yl)
cyclohexanamine hydrochloride, 1 diastereomer Example 158

1-Butyl-N,N-dimethyl-4-(3-propyl-1H-indol-2-yl)
cyclohexanamine, citrate (1:1), 1 diastereomer 1-Butyl-N,N-dimethyl-4-(3-propyl-1H-indol-2-yl)
cyclohexanamine (1 diastereomer) and 1-butyl-N,N-
dimethyl-4-(3-propyl-1H-indol-2-yl)cyclohexanamine hydrochloride, 1 diastereomer (157)

Pd/C (230 mg, 5 per cent strength) was added to a solution of Example 43 (736 mg, 2.17 mmol) in methanol (50 ml) and hydrogenation was carried out at 40° C. under 3 bar for 3 h. For working up, the catalyst was filtered off and the methanol was removed in vacuo. After separation of the residue which remained (769 mg of yellow oil) by chromatography [silica gel 60 (70 g); ethyl acetate/methanol 100:1 (500 ml), ethyl acetate/methanol 20:1 (525 ml), ethyl acetate/methanol 10:1 (1,100 ml), ethyl acetate/methanol 5:1 (350 ml), ethyl acetate/methanol 1:1 (300 ml)], a yellow mixture of oil and solid (550 mg) was obtained. This was suspended in diethyl ether (10 ml) and the suspension was then filtered. The solid filtered off was washed with diethyl ether (2×2 ml) and recrystallized from isopropyl alcohol (6 ml). Example 157 was obtained as a beige-coloured solid (244 mg, 16%, m.p.: 258-272° C.). The ethereal filtrate was concentrated and the residue was recrystallized from cyclohexane (3 ml). A white solid was obtained (1-butyl-N,N-dimethyl-4-(3-propyl-1H-indol-2-yl) cyclohexanamine, 1 diastereomer, 78 mg, 8%, m.p.: 127-130° C.).

1-Butyl-N,N-dimethyl-4-(3-propyl-1H-indol-2-yl)cyclo-hexanamine (1 diastereomer) (73 mg, 0.214 mmol) and citric acid (43 mg, 0.224 mmol) were dissolved in hot methanol (5 ml). The clear solution was concentrated in vacuo. The residue was stirred overnight with diethyl ether (15 ml) and then filtered off and washed with diethyl ether (2×1 ml). Example 158 was obtained as a white solid in a yield of 71% (81 mg) with a melting point of 83-90° C.

Example 159

N,N-Dimethyl-1-phenyl-4-(3-propyl-1H-indol-2-yl) cyclohexanamine, citrate (2:1), non-polar diastereomer Example 160

N,N-Dimethyl-1-phenyl-4-(3-propyl-1H-indol-2-yl) cyclohexanamine, citrate (2:1), polar diastereomer N,N-Dimethyl-1-phenyl-4-(3-propyl-1H-indol-2-yl) cyclohexanamine (non-polar and polar diastereomer)

Ex. 44 (1,057 mg, 2.948 mmol) was dissolved in hydrogen bromide/glacial acetic acid (33% HBr, 70 ml). Tin powder (5.250 g, 44.2 mmol) was then added to the mixture in portions at room temperature in the course of 1 h and the mixture was stirred for a further 1 h. The mixture was then diluted with methylene chloride (250 ml). 3 N sodium hydroxide solution (750 ml) was added, while cooling. The mixture was stirred at room temperature for 20 min. After separation of the phases, the aqueous phase was extracted with methylene chloride (3×20 ml). The combined organic extracts were dried over $Na_2SO_4$ and then concentrated (976 mg of beige-coloured solid). After separation of this mixture by chromatography [silica gel 60 (100 g); ethyl acetate/methanol 10:1 (550 ml), ethyl acetate/methanol 20:3 (575 ml), ethyl acetate/methanol 5:1 (1,200 ml), ethyl acetate/methanol 3:1 (400 ml)] N,N-dimethyl-1-phenyl-4-(3-propyl-1H-indol-2-yl)cyclohexan-amine (less polar diastereoisomer) (318 mg, 30%, m.p.: 177-181° C.) and the more polar diastereoisomer (267 mg, 25%, m.p.: 211-215° C.) were obtained as white and, respectively, beige-coloured solids.

N,N-Dimethyl-1-phenyl-4-(3-propyl-1H-indol-2-yl) cyclohexanamine, citrate (2:1), non-polar diastereomer (159)

N,N-Dimethyl-1-phenyl-4-(3-propyl-1H-indol-2-yl)cy-clohexanamine (less polar diastereoisomer) (155 mg, 0.430 mmol) was dissolved in hot methanol (80 ml), and a methanolic citric acid solution (85 mg, 0.442 mmol in 5 ml) was added. The mixture was subsequently stirred at 0 to 5° C. for 2 h and then filtered. Example 159 was obtained as a white solid in a yield of 77% (182 mg) with a melting point of 243-249° C.

N,N-Dimethyl-1-phenyl-4-(3-propyl-1H-indol-2-yl) cyclohexanamine, citrate (2:1), polar diastereomer N,N-Dimethyl-1-phenyl-4-(3-propyl-1H-indol-2-yl)cy-clohexanamine (more polar diastereoisomer) (248 mg, 0.688 mmol) and citric acid (136 mg, 0.707 mmol) were dissolved in methanol (5 ml). The clear solution was concentrated in vacuo. The residue was stirred with ethyl acetate (5 ml) for 1 h and then filtered off and washed with diethyl ether. Example 160 was obtained as a beige-coloured solid in a yield of 60% (187 mg) with a melting point of 188-192° C.

Example 161

1-Benzyl-N,N-dimethyl-4-(3-(2-(pyridin-4-yl)ethyl)-1H-indol-2-yl)cyclohexanamine, citrate (1:1):Less polar diastereomer The catalyst (110 mg, 5% Pd/C) was added to a solution of the olefin Example 45 (335 mg, 0.769 mmol) in methanol (40 ml) and hydrogenation was carried out at 40° C. under 3 bar for 4 h, while stirring. For working up, the catalyst was filtered off and the methanol was removed in vacuo. After separation of the residue which remained by chromatography [silica gel 60 (40 g); ethyl acetate/methanol (10:1, 550 ml), ethyl acetate/methanol (1:1, 450 ml), ethyl acetate/methanol (1:2, 480 ml), methanol (750 ml)], the less polar diastereoisomer (93 mg, 27% m.p.: 233-237° C.) and the more polar diastereoisomer (150 mg, 44%, m.p.: 198-203° C.) were obtained as a white solid.

Less Polar Diastereomer:
$^1$H NMR (400 MHz, $CDCl_3$) δ ppm: 1.10-1.35 (m, 4H), 1.72-1.95 (m, 4H), 2.22-2.48 (m, 7H), 2.67 (s, 2H), 2.81-2.92 (m, 2H), 2.92-3.03 (m, 2H), 6.94-7.02 (m, 2H), 7.02-7.22 (m, 4H), 7.22-7.40 (m, 4H), 7.44-7.52 (m, 4H), 7.48 (d, J=7.81 Hz, 1H), 8.33 (s, broad, 1H), 8.39 (dd, J=4.48, 1.48 Hz, 1H)
$^{13}$C NMR (101 MHz, $CDCl_3$) δ ppm: 25.1, 27.0, 32.3, 34.8, 36.4, 36.8, 37.0, 57.7 (broad), 108.4, 110.6, 117.8, 118.9, 120.9, 124.1, 125.9, 127.9, 128.0, 130.9, 135.3, 138.9 (broad), 140.2, 149.4, 151.2

More Polar Diastereomer:
$^1$H NMR (400 MHz, $CDCl_3$) δ ppm: 1.16-1.45 (m, 1H), 1.45-1.69 (m, 5H),1.69-1.87 (m, 2H), 2.22-2.50 (m, 6H), 2.50-2.72 (m, 1H), 2.78-2.96 (m, 4H),), 2.96-3.10 (m, 2H), 7.00 (d, J=4.76 Hz, 1H), 7.03-7.18 (m, 2H), 7.18-7.37 (m, 5H), 7.50 (d, J=7.51 Hz, 1H), 7.79 (s, 1H), 8.43 (d, J=4.79 Hz, 1H)
$^{13}$C NMR (101 MHz, $CDCl_3$) δ ppm: 25.5, 28.6, 31.8, 34.0, 36.27, 36.30, 37.8, 57.7, 108.9, 110.5, 117.9, 119.2, 121.1, 124.2, 126.0, 127.9, 128.0, 130.7, 135.2, 139.2, 139.9, 149.4, 151.2

The less polar diastereomer just prepared (70 mg, 0.160 mmol) was dissolved in a mixture of methanol (2 ml) and chloroform (2 ml), and citric acid (33 mg, 0.172 mmol), dissolved in methanol (2 ml), was added. The clear solution was concentrated in vacuo. The residue was dissolved in hot ethanol (4 ml). Ethyl acetate (4 ml) and diethyl ether (4 ml) was slowly added dropwise to the solution at RT. The desired citrate precipitated out as a white solid. The mixture was stirred at RT for a further 2 h and then filtered and the residue was washed with diethyl ether. The white solid was obtained in a yield of 81% (82 mg) with a melting point of 150-155° C.

¹H NMR (400 MHz, DMSO-d₆) δ ppm: 1.10-1.32 (m, 4H), 1.71-1.90 (m, 2H), 1.91-2.08 (m, 2H), 2.40-2.53 (m, 7H), 2.63 (dd, J=35.78, 15.32 Hz, 4H), 2.72-2.83 (m, 4H), 2.84-2.94 (m, 2H), 6.86-6.94 (m, 1H), 6.94-7.01 (m, 1H), 7.06-7.13 (m, 2H), 7.19-7.46 (m, 7H), 8.28-8.36 (m, 2H), 10.3 (s, 1H)

Example 162

1-Benzyl-N,N-dimethyl-4-(3-(2-(pyridin-4-yl)ethyl)-1H-indol-2-yl)cyclohexanamine, citrate (1:1):More polar diastereomer The more polar diastereomer obtained under Example 161 (135 mg, 0.308 mmol) and citric acid (60 mg, 0.312 mmol) were dissolved in methanol (4 ml). The clear solution was concentrated in vacuo and the residue was dissolved in hot isopropanol (10 ml). The mixture was stirred at 5° C. for 2 h. The desired citrate precipitated out as a white solid, and was filtered off and washed with diethyl ether. The product was obtained in a yield of 61% (119 mg) with a melting point of 122-150° C.

¹H NMR (400 MHz, DMSO-d₆) δ ppm: 1.04 (d, J=6.10 Hz, 3H), 1.34-1.49 (m, 2H), 1.53-1.72 (m, 2H), 1.73-1.89 (m, 2H), 1.89-2.06 (m, 2H), 2.50 (m, under DMSO), 2.55 (dd, J=32.28, 17.12 Hz, 4H), 2.82-2.92 (m, 2H), 2.95-3.06 (m, 2H), 3.23 (s,), 6.91-6.99 (m, 1H), 6.99-7.06 (m, 1H),), 7.11-7.19 (m, 2H), 7.23-7.44 (m, 6H), 7.48 (d, J=7.62 Hz, 1H), 8.40 (d, J=5.38 Hz, 2H), 10.74 (s, 1H)

Example 163

1-Butyl-N,N-dimethyl-4-(3-(2-(pyridin-4-yl)ethyl)-1H-indol-2-yl)cyclohexanamine, citrate (1:1):Less polar diastereomer The catalyst (140 mg, 5% Pd/C) was added to a solution of the olefin Example 46 (390 mg, 0.971 mmol) in methanol (40 ml) and hydrogenation was carried out at 40° C. under 3 bar for 2 h, while stirring. For working up, the catalyst was filtered off and the methanol was removed in vacuo. After separation of the residue which remained by chromatography [silica gel 60 (50 g); ethyl acetate/methanol (5:1, 250 ml), ethyl acetate/methanol (1:1, 450 ml), methanol (1,800 ml)], the less polar diastereoisomer (89 mg, 23%, m.p.: 210-250° C., sublimes above 200° C.) and the more polar diastereoisomer (221 mg, 56%, m.p.: 206-212° C.) were obtained as a white solid.

More Polar Diastereomer:
¹H NMR (300 MHz, CDCl₃) δ ppm: 0.75-0.92 (m, 3H), 0.97 (t, J=6.88 Hz, 2H), 1.11-1.65 (m, 15H), 1.75-1.90 (m, 1H), 2.08-2.36 (m, 1H), 2.36-2.51 (m, 1H), 2.51-2.79 (m, 3H),), 2.84-2.96 (m, 1H),), 2.96-3.10 (m, 1H), 6.90-7.00 (m, 2H), 7.00-7.16 (m, 2H), 7.39-7.57 (m, 2H), 8.39 (d, J=5.08 Hz, 2H), 10.59 (s, broad, 1H)
¹³C NMR (101 MHz, CDCl₃) δ ppm 13.9, 23.4, 25.6, 26.1, 26.6, 29.7, 31.1, 34.2, 36.4, 37.2, 107.6, 111.5, 117.5, 118.4, 120.8, 124.4, 127.3, 135.9, 138.8 (broad), 149.3, 151.5

For preparation of the citrate, the less polar diastereomer just obtained (63 mg, 0.156 mmol) and citric acid (31 mg, 0.161 mmol) was dissolved in hot methanol (20 ml). The clear solution was concentrated in vacuo and the residue was dissolved in hot ethanol (2 ml). Ethyl acetate (8 ml) and diethyl ether (30 ml) was slowly added dropwise to the solution at RT. The desired citrate precipitated out as a white solid. The mixture was stirred at RT overnight and then filtered and the residue was washed with diethyl ether. The yellow powder became in a yield of 61% (57 mg) with a melting point of 184-187° C.

¹H NMR (400 MHz, DMSO-d₆) δ ppm: 0.87-1.04 (m, 3H), 1.28-1.47 (m, 4H), 1.54-1.68 (m, 2H), 1.68-1.83 (m, 3H), 1.93-2.08 (m, 3H), 2.14-2.34 (m, 3H), 2.42-2.58 (m,), 2.61-2.80 (m,), 2.82-2.93 (m,), 6.88-6.97 (m, 1H), 6.97-7.06 (m, 1H), 7.12-7.21 (m, 2H), 7.21-7.28 (m, 1H), 7.41-7.51 (m, 1H), 8.36-8.46 (m, 2H), 11.14 (s, 1H)

Example 164

1-Butyl-N,N-dimethyl-4-(3-(2-(pyridin-4-yl)ethyl)-1H-indol-2-yl)cyclohexanamine, citrate (1:1):More polar diastereomer The more polar diastereomer obtained under Example 163 (234 mg, 0.580 mmol) and citric acid (113 mg, 0.588 mmol) were dissolved in hot methanol (20 ml). The clear solution was concentrated in vacuo and the residue was dissolved in hot ethanol (4 ml). Ethyl acetate (6 ml) and diethyl ether (20 ml) was slowly added dropwise to the solution at RT. The mixture was stirred at RT overnight. The desired citrate precipitated out as a yellow powder, and was filtered off and washed with diethyl ether. The product was obtained in a yield of 76% (261 mg) with a melting point of 97-103° C.

Example 165

N,N-Dimethyl-1-phenyl-4-(3-(2-(pyridin-4-yl)ethyl)-1H-indol-2-yl)cyclohexanamine, citrate (1:4):Less polar diastereomer Example 47 (400 mg, 0.95 mmol) was dissolved in HBr/glacial acetic acid (33% HBr, 25 ml). Sn powder (1.126 g, 9.49 mmol) was then added to the mixture in portions in the course of 40 min. Since according to TLC the reaction was not complete, further Sn powder (0.57 g, 4.8 mmol) was added and the mixture was stirred for a further 1 h. The mixture was then diluted with methylene chloride (250 ml). 3 N NaOH solution (280 ml) was then slowly added, while cooling, such that the temperature did not exceed 25° C. The mixture was stirred for 20 min. The phases were separated. The aqueous phase was extracted with methylene chloride (3×20 ml). The combined organic phases were dried with Na₂SO₄ and filtered and the volatile constituents were removed completely in vacuo. A yellow solid (369 mg) remained. After separation of this mixture by chromatography [silica gel 60 (50 g); chloroform/methanol (50:1, 250 ml), chloroform/methanol (25:1, 250 ml), ethyl acetate/methanol (10:1, 250 ml), ethyl acetate/methanol (5:1, 280 ml), ethyl acetate/methanol (10:3, 300 ml), ethyl acetate/methanol (5:2 (320 ml)], the less polar diastereoisomer (148 mg, 37%, m.p.: 267-270° C.) and the more polar diastereoisomer (81 mg, 20%, m.p.: 228-232° C.) were obtained as white solids.

Less Polar Diastereomer:
¹H NMR (400 MHz, DMSO-d₆+0.02 ml 20% DCl in D₂O) δ ppm: 1.51 (d, J=12.14 Hz, 2H), 1.75-2.05 (m, 2H), 2.25-2.69 (m, 9H), 2.86-3.33 (m, 6H), 6.83-7.13 (m, 2H), 7.24 (d, J=7.81 Hz, 1H), 7.38-7.63 (m, 4H), 7.63-7.81 (m, 2H), 7.90 (d, J=5.13 Hz, 1H), 8.75 (d, J=5.18 Hz, 1H)
¹³C NMR (101 MHz, DMSO-d₆+0.02 ml 20% DCl in D₂O) δ ppm: 24.4, 26.7, 30.9, 32.1, 36.3, 37.1, 38.1, 66.5, 107.0, 110.6, 117.9, 118.3, 120.6, 127.1, 127.6, 128.6, 128.7, 129.7, 134.1, 135.2, 140.4, 140.5, 163.4

More Polar Diastereomer:

$^1$H NMR (400 MHz, DMSO-d$_6$+0.02 ml 20% DCl in D$_2$O) δ ppm: 1.29-1.51 (m, 2H), 1.51-1.71 (m, 2H), 2.09-2.31 (m, 2H), 2.31-2.59 (m, 7H), 2.66-2.86 (m, 1H), 2.86-3.23 (m, 5H), 6.78-7.05 (m, 2H), 7.05-7.26 (m, 1H), 7.28-7.47 (m, 1H), 7.47-7.65 (m, 3H), 7.65-7.81 (m, 2H), 7.81-7.99 (m, 2H), 8.82 (d, J=4.83 Hz, 1H)

$^{13}$C NMR (101 MHz, DMSO-d$_6$+0.02 ml 20% DCl in D$_2$O) δ ppm: 24.4, 28.6, 30.4, 34.8, 36.8, 37.2, 38.9, 68.5, 107.2, 110.8, 117.6, 118.3, 120.4, 127.3, 127.6, 129.2, 129.6, 130.4, 135.1, 138.7, 140.5, 163.2

For preparation of the desired citrate, the less polar diastereomer just obtained (122 mg, 0.288 mmol) and citric acid (57 mg, 0.297 mmol) were dissolved in methanol (200 ml), while heating. The solution was concentrated to 10 ml and left to stand at 5° C. overnight. The citrate which had precipitated out was filtered off with suction and washed with methanol (2×0.5 ml). The white solid was obtained in a yield of 86% (153 mg) with a melting point of 198-203° C., and 273-278° C.

$^1$H NMR (300 MHz, DMSO-d$_6$) δ ppm: 1.26-1.45 (m, 2H), 1.45-1.67 (m, 2H), 1.87-2.26 (m, 9H), 2.65 (dd, J=30.24, 15.31 Hz, 4H), 2.77-2.92 (m, 4H), 2.92-3.04 (m, 2H), 6.88-7.05 (m, 2H), 7.12-7.21 (m, 2H), 7.26-7.36 (m, 2H), 7.36-7.54 (m, 5H), 8.39 (d, J=5.76 Hz, 2H), 10.51 (s, 1H)

$^{13}$C NMR (101 MHz, DMSO-d$_6$) δ ppm: 25.1, 27.2, 32.6, 34.7, 36.0, 37.8, 43.1, 72.0, 107.6, 110.8, 117.4, 118.0, 119.9, 124.1, 126.9, 127.5, 127.8, 135.4, 140.2, 149.1, 150.8, 166.8, 171.2, 175.2

Example 166

N,N-Dimethyl-1-phenyl-4-(3-(2-(pyridin-4-yl)ethyl)-1H-indol-2-yl)cyclohexanamine, citrate (2:1):More polar diastereomer The more polar diastereomer prepared under Example 165 (58 mg, 0.137 mmol) and citric acid (28 mg, 0.146 mmol) were dissolved in methanol (80 ml), while heating. The solution was concentrated to 10 ml and left to stand at 5° C. overnight. The citrate which had precipitated out was filtered off with suction and washed with methanol (2×0.5 ml). The white solid was obtained in a yield of 65% (55 mg) with a melting point of 223-225° C.

$^1$H NMR (300 MHz, DMSO-d$_6$) δ ppm: 1.28-1.58 (m, 3H), 1.60-1.82 (m, 1H), 2.05-2.29 (m, 3H), 2.42-2.62 (m), 2.62-2.74 (m, 1H), 2.74-2.84 (m, 2H), 2.84-2.94 (m, 2H), 6.84-6.99 (m, 2H), 7.06-7.20 (m, 3H), 7.33-7.60 (m, 6H), 8.42 (d, J=5.50 Hz, 2H), 10.33 (s, 1H)

Example 167

(±)-2-(4-(Dimethylamino)-4-phenylcyclohex-1-enyl)-3-(2-(1-methyl-1H-benzo[d]imidazol-2-yl)ethyl)-1H-indole Indole (Ind-54, 0.850 g, 3.08 mmol) and ketone (Ket-10; 668 mg, 3.08 mmol) were dissolved in abs. methylene chloride (30 ml), and trifluoromethanesulfonic acid (0.82 ml, 9.24 mmol) was added rapidly. The mixture was stirred at RT overnight, during which a dark brown oil settled out. After addition of 1 N NaOH (15 ml) and CH$_2$Cl$_2$ (20 ml), the mixture was subsequently stirred for a further 60 min, the phases were separated, the aqueous phase was extracted twice with CH$_2$Cl$_2$, the combined organic phases were washed with water and dried (Na$_2$SO$_4$) and the solution was concentrated i. vac. The residue which remained was purified by flash chromatography with CHCl$_3$/MeOH (9:1).

Yield: 777 mg (53%), porous solid $^1$H-NMR (DMSO-d$_6$): 1.74 (1H, m); 2.12 (8H, m); 2.37 (2H, m); 2.56 (1H, m); 2.98 (2H, t); 3.18 (2H, t); 3.49 (3H, s); 6.08 (1H, s); 6.88 (1H, t); 7.01 (1 H, m); 7.22 (6H, m); 7.44 (4H, m); 7.61 (1H, d); 10.66 (1H, s).

N,N-Dimethyl-4-(3-(2-(1-methyl-1H-benzo[d]imidazol-2-yl)ethyl)-1H-indol-2-yl)-1-phenylcyclohexanamine, citrate (1:1):Less polar diastereomer Tin (1.92 g) was added to a solution of the olefin just prepared (770 mg, 1.62 mmol) in HBr/glacial acetic acid (40 ml) in the course of 30 min and the mixture was stirred at RT for 5 h. Ethanol was added to the mixture, the reaction mixture was concentrated to dryness and the residue was dissolved in 5 N NaOH (40 ml) and methylene chloride (30 ml). The phases were separated, the aqueous phase was extracted twice with CH$_2$Cl$_2$ and the combined organic phases were washed with water, dried over Na$_2$SO$_4$ and concentrated i. vac. The residue which remained was separated by flash chromatography with CHCl$_3$/MeOH (20:1→1:1).

Yield: 223 mg (29%), non-polar diastereomer 176 mg (23%), polar diastereomer

The less polar diastereomer obtained (200 mg 0.42 mmol) was dissolved in hot ethanol (5 ml), and a solution of citric acid (80 mg, 0.42 mmol) in hot ethanol (5 ml) was added. After the mixture had stood in a refrigerator for 2 hours, the solid formed was filtered off with suction and dried i. vac.

Yield: 152 mg (54%); melting point: 171-172° C.

$^1$H-NMR (DMSO-d$_6$): 1.48 (4H, m); 2.18 (8H, m); 2.72 (7H, m); 3.16 (4H, m); 3.52 (3H, s); 6.98 (2H, m); 7.01 (2H, m); 7.16 (2H, m); 7.44 (9H, m); 10.67 (1 H, s).

Citrate: (ethanol)

Example 168

N,N-Dimethyl-4-(3-(2-(1-methyl-1H-benzo[d]imidazol-2-yl)ethyl)-1H-indol-2-yl)-1-phenylcyclohexanamine, citrate (1:1):More polar diastereomer The more polar diastereomer prepared under Example 167 (168 mg, 0.35 mmol) was dissolved in hot ethanol (5 ml), and a solution of citric acid (68 mg, 0.35 mmol) in hot ethanol (3 ml) was added. After diethyl ether had been added and the mixture had stood in a refrigerator for 2 hours, the solid formed was filtered off with suction and dried i. vac.

Yield: 87 mg (37%); melting point: >270° C. (decomp.)

$^1$H-NMR (DMSO-d$_6$): 1.35 (2H, m); 1.54 (2H, m); 2.00 (2H, m); 2.37 (6H; s); 2.61 (2H, m); 2.83 (4H, m); 3.14 (4H, m); 3.53 (3H, s); 6.88 (3H, m); 7.19 (3 H, m); 7.49 (7H, m); 10.36 (1H, s).

Citrate: (ethanol)

Example 169

(±)-2-(4-(Dimethylamino)-4-phenylcyclohex-1-enyl)-3-(2-(pyridin-2-yl)ethyl)-1H-indole 3-(2-Pyridin-2-yl-ethyl)-1H-indole (Ind-55, 444 mg, 2.0 mmol) and ketone (Ket-10; 434 mg, 2.0 mmol) were dissolved in abs. methylene chloride (20 ml), and trifluoromethanesulfonic acid (0.54 ml, 6.0 mmol) was added rapidly. The mixture was stirred at RT overnight, during which a dark brown oil settled out. After addition of 1 N NaOH (10 ml) and CH$_2$Cl$_2$ (10 ml), the mixture was subsequently stirred for a further 30 min, the phases were separated, the aqueous phase was extracted twice with $CH_2Cl_2$, the combined organic phases were washed with water and dried ($Na_2SO_4$) and the solution was concentrated i. vac. The residue which remained was purified by flash chromatography with $CHCl_3$/MeOH (9:1).

Yield: 320 mg (38%), porous solid $^1$H-NMR (DMSO-$d_6$): 1.75 (2H, m); 2.12 (8H, m); 2.40-2.69 (3H, m); 2.90 (2 H, m); 3.06 (2H, m); 6.15 (1H, bs); 6.89 (1H, m); 6.98 (1H, m); 7.09 (1H, m); 7.22 (5H, m); 7.39 (1H, m); 7.49 (2H, m); 7.64 (1H, m); 8.52 (1H, m); 10.58 (1H, s).

N,N-Dimethyl-1-phenyl-4-(3-(2-(pyridin-2-yl)ethyl)-1H-indol-2-yl)cyclohexanamine, citrate (1:1):Less polar diastereomer Tin (0.9 g) was added to a solution of the olefin just prepared (300 mg, 0.71 mmol) in HBr/glacial acetic acid (15 ml) in the course of 20 min and the mixture was stirred at RT for 3 h. Ethanol was added to the mixture, the reaction mixture was concentrated to dryness and the residue was dissolved in 5 N NaOH (20 ml) and methylene chloride (30 ml). The phases were separated, the aqueous phase was extracted twice with $CH_2Cl_2$ and the combined organic phases were washed with water, dried over $Na_2SO_4$ and concentrated i. vac. The residue which remained was separated by flash chromatography with $CHCl_3$/MeOH (9:1→4:1).

Yield: 141 mg (47%), non-polar diastereomer 58 mg (19%), polar diastereomer

The less polar diastereomer just obtained (116 mg 0.27 mmol) was dissolved in hot ethanol (3 ml), and a solution of citric acid (53 mg, 0.27 mmol) in hot ethanol (3 ml) was added. After the mixture had stood in a refrigerator for 2 hours, the solid formed was filtered off with suction and dried i. vac.

Yield: 120 mg (71%); melting point: 139-140° C.

$^1$H-NMR (DMSO-$d_6$): 1.42 (2H, m); 1.56 (2H, m); 2.01 (2H, m); 2.15 (6H, s); 2.64-2.77 (6H, m); 3.04 (2H, t); 3.45 (2H, t); 6.93 (2H, m); 7.14 (2H, m); 7.42 (6H, s); 7.62 (1H, m); 8.49 (1H, m); 10.49 (1H, s).

Citrate: (ethanol)

Example 170

N,N-Dimethyl-1-phenyl-4-(3-(2-(pyridin-2-yl)ethyl)-1H-indol-2-yl)cyclohexanamine, citrate (2:3):More polar diastereomer The more polar diastereomer obtained under Example 169 (58 mg 0.14 mmol) was dissolved in hot ethanol (3 ml), and a solution of citric acid (27 mg, 0.14 mmol) in hot ethanol (2 ml) was added. After the mixture had stood in a refrigerator for 2 hours, the solid formed was filtered off with suction and dried i. vac.

Yield: 40 mg (47%), porous solid $^1$H-NMR (DMSO-$d_6$): 1.40 (2H, m); 1.58 (2H, m); 1.88 (2H, m); 2.41 (6H, m); 2.54-2.66 (4H, m); 2.76 (1H, m); 2.99 (6H, m); 6.87 (2H, m); 7.04-7.23 (3H, m); 7.41 (1H, m); 7.61 (6H, m); 10.30 (1H, s).

Citrate: (ethanol), porous solid

Example 171

4-(2-(4-Benzyl-4-(dimethylamino)cyclohexyl)-1H-indol-3-yl)butanoic acid hydrochloride, 1 diastereomer 4-(2-(4-Benzyl-4-dimethylaminocyclohex-1-enyl)-1H-indol-3-yl)butanoic acid 4-(1H-Indol-3-yl)butanoic acid (Ind-56, 813 mg, 4 mmol) was dissolved in methylene chloride (80 ml), together with the ketone Ket-3 (926 mg, 4 mmol), and trifluoromethanesulfonic acid (540 µl, 6 mmol) was added. The mixture was stirred at RT for 48 h. For working up, $H_2O$ (20 ml) was added to the reaction mixture and the mixture was stirred at RT for 20 min. After the organic phase had been separated off, the aqueous phase was extracted with methylene chloride (3×20 ml). The combined organic extracts were dried over $Na_2SO_4$ and then concentrated. It was possible for the crude product obtained (1.39 g) to be purified by column chromatography [silica gel 60 (100 g); MeOH (1,000 ml)]. 4-[2-(4-Benzyl-4-dimethylaminocyclohex-1-enyl)-1H-indol-3-yl]butanoic acid was obtained in a yield of 1.35 g (81%) as a yellow foam.

4-(2-(4-Benzyl-4-(dimethylamino)cyclohexyl)-1H-indol-3-yl)butanoic acid (1 diastereomer)

Palladium as the catalyst (Pd/C, 5%, 120 mg) was added to 4-[2-(4-benzyl-4-dimethylaminocyclohex-1-enyl)-1H-indol-3-yl]butanoic acid (300 mg, 0.7 mmol) in abs. methanol (30 ml) and hydrogenation was carried out at RT for 6 h (hydrogen pressure: 3 bar). The catalyst was removed with the aid of a frit provided with a layer of Celite 1 cm high. The residue was rinsed thoroughly with methanol (500 ml). The solvent was distilled off in vacuo. 4-(2-(4-Benzyl-4-(dimethylamino)cyclohexyl)-1H-indol-3-yl)butanoic acid was obtained in a yield of 260 mg (86%) as a yellow solid (one of the two possible diastereoisomers).

4-(2-(4-Benzyl-4-(dimethylamino)cyclohexyl)-1H-indol-3-yl)butanoic acid hydrochloride, 1 diastereomer (171)

4-(2-(4-Benzyl-4-(dimethylamino)cyclohexyl)-1H-indol-3-yl)butanoic acid (260 mg, 0.6 mmol) was dissolved in ethyl acetate (50 ml). Me$_3$SiCl (153 µl, 1.2 mmol) was then added dropwise at RT and the mixture was stirred for 1 h. A white precipitate precipitated out. The precipitate was filtered off with suction, washed with ethyl acetate (2×5 ml) and then dried. Example 171 (197 mg, m.p. 90-93° C., 70%) was obtained as a white solid (purity <95%).

Example 172

4-(2-(4-(Dimethylamino)-4-phenylcyclohexyl)-1H-indol-3-yl)butanoic acid hydrochloride, 1 diastereomer (±)-4-[2-(4-Dimethylamino-4-phenyl-cyclohex-1-enyl)-1H-indol-3-yl]butanoic acid 4-(Indol-3-yl)butyric acid (Ind-56, 1.626 g, 8 mmol) was dissolved in methylene chloride (160 ml) together with ketone Ket-10 (1.736 g, 8 mmol), and trifluoromethanesulfonic acid (1.08 ml, 12 mmol) was added. The mixture was stirred at RT for 16 h. For working up, $H_2O$ (40 ml) was added to the reaction mixture and the mixture was stirred at RT for 20 min. After the organic phase had been separated off, the aqueous phase was extracted with methylene chloride (3×30 ml). The combined organic extracts were dried over Na$_2$SO$_4$ and then concentrated. It was possible for the crude product obtained (2 g) to be purified by column chromatography [silica gel 60 (100 g); MeOH (1,000 ml)]. (±)-4-[2-(4-Dimethylamino-4-phenyl-cyclohex-1-enyl)-1H-indol-3-yl]butanoic acid was obtained in a yield of 500 mg (15%) as a yellow solid.

4-[2-(4-(Dimethylamino)-4-phenylcyclohexyl)-1H-indol-3-yl]butanoic acid (1 diastereomer)

Palladium as the catalyst (Pd/C, 5%, 200 mg) was added to (±)-4-[2-(-4-dimethylamino-4-phenyl-cyclohex-1-enyl)-1H-indol-3-yl]butanoic acid (500 mg, 1.2 mmol) in abs. methanol (50 ml) and hydrogenation was carried out at RT for 6 h (hydrogen pressure: 3 bar). The catalyst was removed with the aid of a frit provided with a layer of Celite 1 cm high. The residue was rinsed thoroughly with methanol (500 ml). The solvent was distilled off in vacuo. 4-[2-(4-Dimethylamino-4-phenylcyclohexyl)-1H-indol-3-yl]butanoic acid was obtained in a yield of 340 mg (68%) as a white solid (one of the two possible diastereoisomers).

4-(2-(4-(Dimethylamino)-4-phenylcyclohexyl)-1H-indol-3-yl)butanoic acid hydrochloride, 1 diastereomer 4-[(2-(4-Dimethylamino-4-phenylcyclohexyl)-1H-indol-3-yl)butanoic acid (340 mg, 0.81 mmol) was dissolved in ethyl acetate (50 ml). Me$_3$SiCl (207 µl, 1.62 mmol) was then added dropwise at RT and the mixture was stirred for 16 h. The solvent distilled off on a rotary evaporator. Example 172 (370 mg, m.p. 227-230° C., 100%) was a beige-coloured solid.

Example 173

4-(2-(4-(Dimethylamino)-4-phenylcyclohexyl)-1H-indol-3-yl)butanol hydrochloride, non-polar diastereomer (±)-4-[2-(4-Dimethylamino-4-phenylcyclohex-1-enyl)-1H-indol-3-yl]butan-1-ol 4-(1H-indol-3-yl)butanol (Ind-57), (797 mg, 4.21 mmol was dissolved in methylene chloride (80 ml) together with the ketone Ket-10 (914 mg, 4.21 mmol), and trifluoromethanesulfonic acid (540 µl, 6 mmol) was added. The mixture was stirred at RT for 24 h. For working up, 5 N NaOH (30 ml) was added to the reaction mixture and the mixture was stirred at RT for 20 min. After the organic phase had been separated off, the aqueous phase was extracted with methylene chloride (3×30 ml). The combined organic extracts were dried over Na$_2$SO$_4$ and then concentrated. It was possible for the crude product obtained (2 g) to be purified by column chromatography [silica gel 60 (100 g); MeOH (1,000 ml)]. (±)-4-[2-(4-Dimethylamino-4-phenylcyclohex-1-enyl)-1H-indol-3-yl]butan-1-ol was obtained in a yield of 600 mg (37%) as a white foam.

4-[2-(4-(Dimethylamino)-4-phenylcyclohexyl)-1H-indol-3-yl]butanol (non-polar diastereomer)

(±)-4-[2-(4-Dimethylamino-4-phenylcyclohex-1-enyl)-1H-indol-3-yl]butan-1-ol (600 mg, 1.54 mmol) was dissolved in HBr/glacial acetic acid (33% HBr, 10 ml). Sn powder (1.81 g, 15.4 mmol) was then added to the mixture in portions at RT in the course of 2 h. When the addition had ended, the reaction mixture was stirred at RT for a further 16 h. For working up, the mixture was diluted with EtOH (10 ml) and concentrated to dryness on a rotary evaporator. The residue which remained was rendered basic by addition of 5 N NaOH (40 ml). The aqueous mixture obtained was extracted with methylene chloride (3×30 ml). The combined organic phases were dried over Na$_2$SO$_4$ and then concentrated. It was possible for the crude product obtained to be purified by column chromatography [silica gel 60 (50 g); MeOH (500 ml)]. 4-[2-(4-Dimethylamino-4-phenylcyclohexyl)-1H-indol-3-yl]butan-1-ol (less polar diastereomer) was obtained in a yield of 173 mg (29%) as a white solid.

4-(2-(4-(Dimethylamino)-4-phenylcyclohexyl)-1H-indol-3-yl)butanol hydrochloride, non-polar diastereomer 4-[(2-(4-Dimethylamino-4-phenylcyclohexyl)-1H-indol-3-yl)butan-1-ol (less polar diastereomer) (170 mg, 0.43 mmol) was dissolved in ethyl acetate (50 ml). Me$_3$SiCl (108 µl, 0.86 mmol) was then added dropwise at RT and the mixture was stirred for 1 h. A white precipitate precipitated out. The precipitate was filtered off with suction, washed with ethyl acetate (2×5 ml) and then dried. Example 173 (170 mg, m.p. 223-226° C., 91%) was obtained as a white solid.

Example 174

4-(2-(4-Benzyl-4-(dimethylamino)cyclohexyl)-1H-indol-3-yl)butyl acetate hydrochloride, non-polar diastereomer Example 175

4-(2-(4-Benzyl-4-(dimethylamino)cyclohexyl)-1H-indol-3-yl)butyl acetate hydrochloride, polar diastereomer 4-(2-(4-Benzyl-4-(dimethylamino)cyclohexyl)-1H-indol-3-yl)butyl acetate (non-polar and polar diastereomer)

The ketone Ket-3 (463 mg, 2 mmol) and Ind-57 (379 mg, 2 mmol) were dissolved in HBr/glacial acetic acid (33% HBr, 2 ml) and the mixture was stirred at RT for 24 h. Sn powder (2.4 g, 20 mmol) was then added to the mixture in portions at RT in the course of 1 h. When the addition had ended, the reaction mixture was stirred at RT for a further 16 h. For working up, the mixture was diluted with EtOH (10 ml) and concentrated to dryness on a rotary evaporator. The residue which remained was neutralized by addition of solid NaHCO$_3$, and H$_2$O (40 ml) was added. The aqueous mixture obtained was extracted with methylene chloride (4×20 ml). The combined organic phases were dried over Na$_2$SO$_4$ and then concentrated. It was possible for the crude product obtained (800 mg) to be purified by column chromatography [silica gel 60 (50 g); MeOH (500 ml)]. 4-(2-(4-Benzyl-4-(dimethylamino) cyclohexyl)-1H-indol-3-yl)butyl acetate (less polar product) was obtained in a yield of 120 mg (13%) as a yellow solid. The more polar diastereoisomer was obtained in a yield of 87 mg (10%) as a white solid.

4-(2-(4-Benzyl-4-(dimethylamino)cyclohexyl)-1H-indol-3-yl)butyl acetate hydrochloride, non-polar diastereomer 4-(2-(4-Benzyl-4-(dimethylamino)cyclohexyl)-1H-indol-3-yl)butyl acetate (less polar diastereomer) (120 mg, 0.27 mmol) was dissolved in ethyl acetate (10 ml), and $Me_3SiCl$ (68 μl, 0.54 mmol) was added dropwise at RT and the mixture was stirred for 1 h. A white precipitate precipitated out. The precipitate was filtered off with suction, washed with ethyl acetate (2×5 ml) and then dried. Example 174 (117 mg, m.p. 187-191° C., 90%) was obtained as a white solid

4-(2-(4-Benzyl-4-(dimethylamino)cyclohexyl)-1H-indol-3-yl)butyl acetate hydrochloride, polar diastereomer (175)

4-(2-(4-Benzyl-4-(dimethylamino)cyclohexyl)-1H-indol-3-yl)butyl acetate (more polar diastereomer) (87 mg, 0.19 mmol) was dissolved in ethyl acetate (7 ml). $Me_3SiCl$ (49 μl, 0.39 mmol) was then added dropwise at RT and the mixture was stirred for 1 h. A white precipitate precipitated out. The precipitate was filtered off with suction, washed with ethyl acetate (2×5 ml) and then dried. Example 175 (85 mg, m.p. 194-197° C., 90%) was obtained as a white solid.

Example 176

4-(2-(4-Butyl-4-(dimethylamino)cyclohexyl)-1H-indol-3-yl)butyl acetate hydrochloride, polar diastereomer

Example 177

4-(2-(4-Butyl-4-(dimethylamino)cyclohexyl)-1H-indol-3-yl)butyl acetate hydrochloride, non-polar diastereomer

4-(2-(4-Butyl-4-(dimethylamino)cyclohexyl)-1H-indol-3-yl)butyl acetate (non-polar and polar diastereomer)

The ketone Ket-4 (395 mg, 2 mmol) and Ind-57 (379 mg, 2 mmol) were dissolved in HBr/glacial acetic acid (33% HBr, 2 ml) and the mixture was stirred at RT for 24 h. Sn powder (2.4 g, 20 mmol) was then added to the mixture in portions at RT in the course of 1 h. When the addition had ended, the reaction mixture was stirred at RT for a further 16 h. For working up, the mixture was diluted with EtOH (10 ml) and concentrated to dryness on a rotary evaporator. The residue which remained was neutralized by addition of solid $NaHCO_3$, and 40 ml of $H_2O$ were added. The aqueous mixture obtained was extracted with methylene chloride (3×30 ml). The combined organic phases were dried over $Na_2SO_4$ and then concentrated. It was possible for the crude product obtained to be purified by column chromatography [silica gel 60 (50 g); MeOH (500 ml)]. 4-(2-(4-Butyl-4-(dimethylamino)cyclohexyl)-1H-indol-3-yl]butyl acetate (non-polar diastereomer) was obtained in a yield of 206 mg (25%) as a white solid. The more polar diastereoisomer was obtained in a yield of 124 mg (15%) as a white solid.

4-(2-(4-Butyl-4-(dimethylamino)cyclohexyl)-1H-indol-3-yl)butyl acetate hydrochloride, polar diastereomer (176)

Acetic acid 4-[2-(4-butyl-4-dimethylaminocyclohexyl)-1H-indol-3-yl]butyl ester (polar diastereomer) (124 mg, 0.3 mmol) was dissolved in ethyl acetate (50 ml). $Me_3SiCl$ (76 μl, 0.39 mmol) was then added dropwise at RT and the mixture was stirred for 1 h. A white precipitate precipitated out. The precipitate was filtered off with suction, washed with ethyl acetate (2×5 ml) and then dried. Example 176 (100 mg, m.p. 173-176° C., 74%) was obtained as a white solid.

4-(2-(4-Butyl-4-(dimethylamino)cyclohexyl)-1H-indol-3-yl)butyl acetate hydrochloride, non-polar diastereomer (177)

Acetic acid 4-[2-(4-butyl-4-dimethylaminocyclohexyl)-1H-indol-3-yl]butyl ester (non-polar diastereomer) (206 mg, 0.5 mmol) was dissolved in ethyl acetate (50 ml). $Me_3SiCl$ (126 μl, 1 mmol) was then added dropwise at RT and the mixture was stirred for 1 h. A white precipitate precipitated out. The precipitate was filtered off with suction, washed with ethyl acetate (2×5 ml) and then dried. Example 177 (150 mg, m.p. 128-131° C., 67%) was obtained as a white solid

Example 178

4-(2-(4-(Dimethylamino)-4-phenylcyclohexyl)-1H-indol-3-yl)butyl acetate hydrochloride, non-polar diastereomer

Example 179

4-(2-(4-(Dimethylamino)-4-phenylcyclohexyl)-1H-indol-3-yl)butyl acetate hydrochloride, polar diastereomer

4-(2-(4-(Dimethylamino)-4-phenylcyclohexyl)-1H-indol-3-yl)butyl acetate (non-polar and polar diastereomer)

The ketone Ket-10 (434 mg, 2 mmol) and Ind-57 (379 mg, 2 mmol; were dissolved in HBr/glacial acetic acid (33% HBr, 1.75 ml) and the mixture was stirred at RT for 24 h. Sn powder (2.4 g, 20 mmol) was then added to the mixture in portions at RT in the course of 1 h. When the addition had ended, the reaction mixture was stirred at RT for a further 16 h. For working up, the mixture was diluted with EtOH (10 ml) and concentrated to dryness on a rotary evaporator. The residue which remained was neutralized by addition of solid $NaHCO_3$, and 40 ml of $H_2O$ were added. The aqueous mixture obtained was extracted with methylene chloride (4×20 ml). The combined organic phases were dried over $Na_2SO_4$ and then concentrated. It was possible for the crude product obtained (865 mg) to be purified by column chromatography [silica gel 60 (50 g); MeOH (800 ml)]. 4-(2-(4-(Dimethylamino)-4-phenylcyclohexyl)-1H-indol-3-yl]butyl acetate (non-polar diastereomer) was obtained in a yield of 234 mg (27%) as a white solid. The more polar diastereoisomer was obtained in a yield of 112 mg (13%) as a white solid.

4-(2-(4-(Dimethylamino)-4-phenylcyclohexyl)-1H-indol-3-yl)butyl acetate hydrochloride, non-polar diastereomer 4-(2-(4-(Dimethylamino)-4-phenylcyclohexyl)-1H-indol-3-yl)butyl acetate (non-polar diastereomer) (234 mg, 0.54 mmol) was dissolved in ethyl acetate (50 ml). $Me_3SiCl$ (136 μl, 1.08 mmol) was then added dropwise at RT. The mixture was stirred for 1 h. A white precipitate precipitated out. The precipitate was filtered off with suction, washed with ethyl acetate (2×5 ml) and then dried. Example 178 (155 mg, m.p. 238-241° C., 61%, NMR purity <95%) was obtained as a white solid.

4-(2-(4-(Dimethylamino)-4-phenylcyclohexyl)-1H-indol-3-yl)butyl acetate hydrochloride, polar diastereomer 4-(2-(4-(Dimethylamino)-4-phenylcyclohexyl)-1H-indol-3-yl)butyl acetate (polar diastereomer) (112 mg, 0.26 mmol) was dissolved in ethyl acetate (20 ml). Me₃SiCl (65 µl, 0.52 mmol) was then added dropwise at RT and the mixture was stirred for 1 h. A white precipitate precipitated out. The precipitate was filtered off with suction, washed with ethyl acetate (2×5 ml) and then dried. Example 179 (97 mg, m.p. 165-169° C., 80%) was a white solid.

Example 180

3-(2-(4-Benzyl-4-(dimethylamino)cyclohexyl)-1H-indol-3-yl)propan-1-ol, citrate (1:1), non-polar diastereomer The free base from Example 48 (300 mg, 0.77 mmol) was dissolved in HBr/glacial acetic acid (33% HBr, 10 ml). Sn powder (906 mg, 7.7 mmol) was then added to the mixture in portions at RT in the course of 1 h. When the addition had ended, the reaction mixture was stirred at RT for a further 16 h. For working up, the mixture was diluted with EtOH (10 ml) and concentrated to dryness on a rotary evaporator. The residue which remained was rendered basic by addition of 2 N NaOH (40 ml). The aqueous mixture obtained was extracted with methylene chloride (4×20 ml). The combined organic phases were dried over Na₂SO₄ and then concentrated. It was possible for the crude product obtained (250 mg) to be purified by column chromatography [silica gel 60 (20 g); MeOH (500 ml)]. 3-(2-(4-Benzyl-4-(dimethylamino)cyclohexyl)-1H-indol-3-yl)propan-1-ol (less polar diastereomer) was obtained in a yield of 129 mg (43%) as a colourless oil.

The less polar diastereomer (129 mg, 0.33 mmol) was dissolved in isopropanol (4 ml) at the boiling point and citric acid (64 mg, 0.33 mmol), dissolved in hot isopropanol (2 ml), was added. The solution was cooled to 5° C. in a refrigerator and left to stand for 16 h.

The white precipitate formed was separated off by means of a frit. Example 180 was obtained in a yield of 100 mg (52%, melting point: 82-85° C.).

Example 181

3-(2-(4-Butyl-4-(dimethylamino)cyclohexyl)-1H-indol-3-yl)propan-1-ol hydrochloride, polar diastereomer Example 182

3-(2-(4-Butyl-4-(dimethylamino)cyclohexyl)-1H-indol-3-yl)propan-1-ol hydrochloride, non-polar diastereomer The free base from Example 49 (300 mg, 0.85 mmol) was dissolved in HBr/glacial acetic acid (33% HBr, 20 ml). Sn powder (1 g, 8.5 mmol) was then added to the mixture in portions at RT in the course of 1 h. When the addition had ended, the reaction mixture was stirred at RT for a further 16 h. For working up, the mixture was diluted with EtOH (10 ml) and concentrated to dryness on a rotary evaporator. The residue which remained was rendered basic by addition of 2 N NaOH (80 ml). The aqueous mixture obtained was extracted with methylene chloride (4×20 ml). The combined organic phases were dried over Na₂SO₄ and then concentrated. The crude product obtained (300 mg) was purified by column chromatography [silica gel 60 (20 g); MeOH (500 ml)]. 3-(2-(4-Butyl-4-(dimethylamino)cyclohexyl)-1H-indol-3-yl)propan-1-ol (less polar diastereomer) was obtained in a yield of 111 mg (37%) as a colourless oil. The more polar product was obtained in a yield of 54 mg (18%) as a colourless oil.

3-(2-(4-Butyl-4-(dimethylamino)cyclohexyl)-1H-indol-3-yl)propan-1-ol hydrochloride, polar diastereomer 3-(2-(4-Butyl-4-(dimethylamino)cyclohexyl)-1H-indol-3-yl)propan-1-ol (more polar diastereomer) (54 mg, 0.15 mmol) was dissolved in ethyl acetate (5 ml). Me₃SiCl (38 µl, 0.3 mmol) was then added dropwise at RT and the mixture was stirred for 1 h. A white precipitate precipitated out. The precipitate was filtered off with suction, washed with ethyl acetate (2×3 ml) and then dried. Example 181 (57 mg, m.p. 128-132° C., 95%) was obtained as a white solid.

3-(2-(4-Butyl-4-(dimethylamino)cyclohexyl)-1H-indol-3-yl)propan-1-ol hydrochloride, non-polar diastereomer 3-(2-(4-Butyl-4-(dimethylamino)cyclohexyl)-1H-indol-3-yl)propan-1-ol (less polar diastereomer) (110 mg, 0.25 mmol) was dissolved in ethyl acetate (10 ml). Me₃SiCl (63 µl, 0.5 mmol) was then added dropwise at RT and the mixture was stirred for 1 h. A white precipitate precipitated out. The precipitate was filtered off with suction, washed with ethyl acetate (2×5 ml) and then dried. Example 182 (104 mg, m.p. 218-222° C., 85%) was obtained as a white solid.

Example 183

3-(2-(4-(Dimethylamino)-4-phenylcyclohexyl)-1H-indol-3-yl)propan-1-ol hydrochloride, polar diastereomer Example 184

3-(2-(4-(Dimethylamino)-4-phenylcyclohexyl)-1H-indol-3-yl)propan-1-ol hydrochloride, non-polar diastereomer (±)-3-[2-(4-Dimethylamino-4-phenylcyclohex-1-enyl)-1H-indol-3-yl]propan-1-ol Indole Ind-16 (701 mg, 4 mmol) was dissolved in methylene chloride (80 ml) together with ketone Ket-10 (868 mg, 4 mmol), and trifluoromethanesulfonic acid (540 µl, 6 mmol) was added. The mixture was stirred at RT for 24 h. For working up, 5 N NaOH (30 ml) was added to the reaction mixture and the mixture was stirred at RT for 20 min. After the organic phase had been separated off, the aqueous phase was extracted with methylene chloride (3×30 ml). The combined organic extracts were dried over Na₂SO₄ and then concentrated. It was possible for the crude product obtained (1.55 g) to be purified by column chromatography [silica gel 60 (100 g); MeOH (500 ml)]. (±)-3-[2-(4-Dimethylamino-4-phenyl-cyclohex-1-enyl)-1H-indol-3-yl]propan-1-ol was obtained in a yield of 985 mg (66%) as a white solid.

3-(2-(4-(Dimethylamino)-4-phenylcyclohexyl)-1H-indol-3-yl)propan-1-ol (non-polar and polar diastereomer)

(±)-3-[2-(4-Dimethylamino-4-phenylcyclohex-1-enyl)-1H-indol-3-yl]propan-1-ol (500 mg, 1.335 mmol) was dissolved in HBr/glacial acetic acid (33% HBr, 10 ml). Sn powder (1.57 g, 13.35 mmol) was then added to the mixture in portions at RT in the course of 2 h. When the addition had ended, the reaction mixture was stirred at RT for a further 16 h. For working up, the mixture was diluted with EtOH (10 ml) and concentrated to dryness on a rotary evaporator. The residue which remained was rendered basic by addition of 5 N NaOH (40 ml). The aqueous mixture obtained was extracted with methylene chloride (4×20 ml). The combined organic phases were dried over $Na_2SO_4$ and then concentrated. It was possible for the crude product obtained to be purified by column chromatography [silica gel 60 (50 g); MeOH (600 ml)]. 3-(2-(4-(Dimethylamino)-4-phenylcyclohexyl)-1H-indol-3-yl]propan-1-ol (non-polar diastereomer) was obtained in a yield of 160 mg (32%) as a white solid. The more polar diastereomer was obtained in a yield of 130 mg (26%) as a white solid.

3-(2-(4-(Dimethylamino)-4-phenylcyclohexyl)-1H-indol-3-yl)propan-1-ol hydrochloride, polar diastereomer (Ex. 183)

3-(2-(4-(Dimethylamino)-4-phenylcyclohexyl)-1H-indol-3-yl)propan-1-ol (polar diastereomer) (130 mg, 0.35 mmol) was dissolved in ethyl acetate (15 ml). $Me_3SiCl$ (88 μl, 0.7 mmol) was then added dropwise at RT and the mixture was stirred for 1 h. A white precipitate precipitated out. The precipitate was filtered off with suction, washed with ethyl acetate (2×5 ml) and then dried. Example 183 (125 mg, m.p. 210-214° C., 87%, NMR purity <95%) was a white solid.

3-(2-(4-(Dimethylamino)-4-phenylcyclohexyl)-1H-indol-3-yl)propan-1-ol hydrochloride, non-polar diastereomer (Ex. 184)

3-(2-(4-(Dimethylamino)-4-phenylcyclohexyl)-1H-indol-3-yl)propan-1-ol (non-polar diastereomer) (160 mg, 0.43 mmol) was dissolved in ethyl acetate (20 ml). $Me_3SiCl$ (108 μl, 0.86 mmol) was then added dropwise at RT and the mixture was stirred for 1 h. A white precipitate precipitated out. The precipitate was filtered off with suction, washed with ethyl acetate (2×5 ml) and then dried. Example 184 (159 mg, m.p. 248-250° C., 90%, NMR purity <95%) was obtained as a white solid.

Example 185

3-(2-(4-(Dimethylamino)-4-phenylcyclohexyl)-1H-indol-3-yl)propyl acetate hydrochloride, polar diastereomer

Example 186

3-(2-(4-(Dimethylamino)-4-phenylcyclohexyl)-1H-indol-3-yl)propyl acetate hydrochloride, non-polar diastereomer

3-(2-(4-(Dimethylamino)-4-phenylcyclohexyl)-1H-indol-3-yl)propyl acetate (non-polar and polar diastereomer)

The ketone Ket-10 (434 mg, 2 mmol) and Ind-16 (350 mg, 2 mmol) were dissolved in HBr/glacial acetic acid (33% HBr, 2 ml) and the mixture was stirred at RT for 24 h. Sn powder (2.4 g, 20 mmol) was then added to the mixture in portions at RT in the course of 1 h. When the addition had ended, the reaction mixture was stirred at RT for a further 16 h. For working up, the mixture was diluted with EtOH (10 ml) and concentrated to dryness on a rotary evaporator. The residue which remained was neutralized by addition of solid $NaHCO_3$, and 40 ml of $H_2O$ were added. The aqueous mixture obtained was extracted with methylene chloride (4×30 ml). The combined organic phases were dried over $Na_2SO_4$ and then concentrated. It was possible for the crude product obtained (640 mg) to be purified by column chromatography [silica gel G (50 g); MeOH (600 ml)]. 3-(2-(4-(Dimethylamino)-4-phenylcyclohexyl)-1H-indol-3-yl]propyl acetate (less polar diastereomer) was obtained in a yield of 190 mg (25%) as a white solid. The more polar diastereomer was obtained in a yield of 60 mg (8%) as a white solid.

3-(2-(4-(Dimethylamino)-4-phenylcyclohexyl)-1H-indol-3-yl)propyl acetate hydrochloride, polar diastereomer (Ex. 185)

3-(2-(4-(Dimethylamino)-4-phenylcyclohexyl)-1H-indol-3-yl)propyl acetate (more polar diastereomer) (60 mg, 0.16 mmol) was dissolved in ethyl acetate (20 ml). $Me_3SiCl$ (40 μl, 0.32 mmol) was then added dropwise at RT and the mixture was stirred for 1 h. A white precipitate precipitated out. The precipitate was filtered off with suction, washed with ethyl acetate (1×5 ml) and then dried. Example 185 (55 mg, m.p. 229-232° C., 84%) was a white solid.

$^1$H NMR (400 MHz, DMSO-$d_6$) δ ppm: 1.40-1.59 (m, 2H), 1.71-187 (m, 3H), 1.87-2.02 (m, 1H), 2.07 (s, 3H), 2.19-2.33 (m, 2H), 2.44 (d, J=4.73, 6H), 2.58-2.70 (m, 2H), 2.82-2.96 (m, 1H), 3.09 (d, J=12.32 Hz, 2H), 3.91 (t, J=6.36, 6.36 Hz, 2H), 6.81-6.98 (m, 2H), 7.15 (d, J=7.77 Hz, 1H), 7.35 (d, J=7.67 Hz, 1H), 7.52-7.65 (3H), 7.70-7.81 (m, 2H), 10.40 (s, 1H), 11.20-11.31 (m, 1H), $^{13}$C NMR (101 MHz, DMSO-$d_6$) δ ppm 19.7, 20.9, 28.6, 29.3, 30.4, 34.8, 37.0, 63.1, 68.3, 108.1, 110.7, 117.4, 118.0, 120.0, 127.7, 129.0, 129.4, 129.6, 130.4, 135.3, 138.4, 170.4

3-(2-(4-(Dimethylamino)-4-phenylcyclohexyl)-1H-indol-3-yl)propyl acetate hydrochloride, non-polar diastereomer 3-(2-(4-(Dimethylamino)-4-phenylcyclohexyl)-1H-indol-3-yl)propyl acetate (less polar diastereomer) (190 mg, 0.51 mmol) was dissolved in ethyl acetate (50 ml). $Me_3SiCl$ (128 μl, 1.02 mmol) was then added dropwise at RT. The mixture was stirred for 1 h. A white precipitate precipitated out. The precipitate was filtered off with suction, washed with ethyl acetate (2×5 ml) and then dried. Example 186 (120 mg, m.p. 217-220° C., 58%) was a white solid $^1$H NMR (300 MHz, DMSO-$d_6$) δ ppm: 1.68-2.03-(m, 10H), 2.37-2.47 (m, 1H), 2.54-2.62 (m, 6H), 2.68-2.78 (m, 2H), 2.98-3.11 (m, 1H), 3.12-3.22 (m, 2H), 3.93 (t, J=6.50, 6.50 Hz, 2H), 6.87-7.06 (m, 2H), 7.25 (d, J=7.80 Hz, 1H), 7.42 (d, J=7.80, 1 H) 7.48-7.60 (m, 3H), 7.67-7.82-(m, 2H), 10.00 (s, 1H), 11.34 (s, 1H)

Example 187

1-(2-(2-(4-(Dimethylamino)-4-phenylcyclohex-1-enyl)-1H-indol-3-yl)ethyl)pyrrolidine-2.5-dione The indole (Ind-61, 3.00 g, 12.4 mmol) and the aminoketone (Ket-10, 2.70 g, 12.4 mmol) were dissolved in methylene chloride (160 m), trifluoromethanesulfonic acid (3.0 ml) was added and the mixture was stirred at RT overnight. 3.5 N NaOH (50 ml) was added to the mixture, the aqueous phase was separated off and extracted with $CH_2Cl_2$ (two times 140 ml) and the organic phases were combined, dried ($Na_2SO_4$) and concentrated i. vac. The residue was purified by flash chromatography with MeOH/ethyl acetate (1:1).

Yield: 3.30 g (57%)

$^1$H-NMR (DMSO-$d_6$): 1.68 (2H, m); 2.18 (8H, m); 2.62 (6H, m); 2.85 (2H, t); 3.47 (2H, t); 6.30 (1H, s); 6.96 (2H, m); 7.21 (4H, m); 7.46 (2H, m); 10.69 (1 H, bs).

1-(2-(2-(4-(Dimethylamino)-4-phenylcyclohexyl)-1H-indol-3-yl)ethyl)pyrrolidine-2.5-dione: Less polar diastereomer The olefin just prepared (1.50 g, 3.00 mmol) was dissolved in 33% strength HBr in glacial acetic acid (50 ml). Tin powder (3.56 g, 30 mmol) was added in portions in the course of one hour, while cooling with ice. After 1 h the mixture was concentrated i. vac. After addition of 5 N NaOH (100 ml) and $CH_2Cl_2$ (50 ml), the aqueous phase was separated off and extracted with $CH_2Cl_2$ (two times 50 ml) and the organic phases were combined, dried ($Na_2SO_4$) and concentrated i. vac. The residue was purified by flash chromatography with methanol/ethyl acetate (1:1). Both the more polar and the less polar diastereomer was obtained.

Yield: 350 mg (27%) Less polar diastereomer 484 mg (37%) More polar diastereomer The less polar diastereomer just obtained is presented as Example 187, $^1$H-NMR (DMSO-$d_6$): 1.47 (2H, m); 1.68 (2H, m); 2.13 (8H, m); 2.46 (2H, m); 2.87 (4H, m); 3.51 (2H, t); 6.98 (2H, m); 7.38 (7H, m); 10.76 (1H, bs).

Example 188

1-(2-(2-(4-(Dimethylamino)-4-phenylcyclohexyl)-1H-indol-3-yl)ethyl)pyrrolidine-2.5-dione: more polar diastereomer The more polar diastereomer obtained under Example 187 we presented as Example 188.

Yield: 484 mg (37%)

$^1$H-NMR (DMSO-$d_6$): 1.48 (2H, m); 1.66 (4H, m); 1.99 (6H, s); 2.59 (4H, m); 2.81 (4H, m); 3.50 (2H, m); 6.91 (2H, m); 7.17 (1H, m); 7.38 (6H, m); 10.42 (1 H, bs).

Example 189

(±)-2-(4-(Dimethylamino)-4-phenylcyclohex-1-enyl)-3-(2-(3,4-dihydroquinolin-1(2H)-yl)ethyl)-1H-indole The amino-ketone (Ket-10, 2.58 g, 11.9 mmol) was dissolved in methylene chloride (200 ml) with the indole (Ind-62, 3.28 g, 11.9 mmol). A rapid addition of trifluoromethanesulfonic acid (3.62 ml, 41.7 mmol) then took place at room temperature. The mixture stirred at room temperature for 24 h. For working up, 2 N NaOH (200 ml) was added to the mixture and the mixture was stirred at room temperature for 20 min. The organic phase was separated off and the aqueous phase was extracted with methylene chloride (2×25 ml). The combined organic phases were dried over $Na_2SO_4$ and concentrated to dryness i. vac. The crude product was purified by means of flash chromatography with cyclohexane/EA (2:1→1:1→EA) and methanol, the product being obtained completely only with methanol.

Yield: 2.22 g (40%)

$^1$H-NMR ($CDCl_3$): 1.80 (4H, m); 2.09 (8H, m); 2.64 (4H, m); 2.87 (2H, m); 3.09 (2H; m); 6.22 (1H, s); 6.48 (1H, t); 6.61 (1H, d); 7.02 (4H, m); 7.26 (4H, m); 7.45 (3H, m); 10.69 (1H, s).

4-(3-(2-(3,4-Dihydroquinolin-1 (2H)-yl)ethyl)-1H-indol-2-yl)-N,N-dimethyl-1-phenylcyclohexanamine, citrate (4:3):Less polar diastereomer Tin (5.00 g) was added to a solution of the olefin just prepared (2.00 g, 4.2 mmol) in HBr/glacial acetic acid (85 ml) in the course of 20 min. The reaction mixture then subsequently stirred at room temperature for 2 h. Ethanol was added to the mixture and the mixture was concentrated to dryness i. vac. 5 N NaOH (120 ml) was added to the residue and the mixture was extracted with methylene chloride (3×50 ml). The combined organic phases were dried over $Na_2SO_4$. The crude product was purified by means of flash chromatography and cyclohexane/EA (3:1→1:1 and methanol), the non-polar product being obtained with cyclohexane/EA (1:1) and the polar product with methanol.

Yield: 0.140 g (7%), non-polar diastereomer 0.650 g (33%), polar diastereomer

The less polar diastereomer just obtained (0.140 g, 0.293 mmol) was dissolved in hot ethanol (4 ml), and citric acid (0.056 g, 0.29 mmol), dissolved in hot ethanol (2 ml), was added at room temperature. The mixture stirred at room temperature for 2 h. A solid remained, which was filtered off with suction and dried i. vac.

Yield: 74 mg (Ex. 189, 8%), porous solid

1H-NMR (DMSO-d6): 1.66 (6H, m);); 2.11 (6H, m); 2.58 (4H, m); 2.63 (4H; m); 2.88 (4H, m); 6.41 (2H, m); 6.63 (1H, m); 6.95 (3H, m); 7.34 (6H, m); 10.64 (1 H, s), citrate.

Example 190

4-(3-(2-(3,4-Dihydroquinolin-1(2H)-yl)ethyl)-1H-indol-2-yl)-N,N-dimethyl-1-phenylcyclohexanamine, citrate (1:1):More polar diastereomer The more polar diastereomer prepared under Example 189 (0.650 g 1.36 mmol) was dissolved in hot ethanol (20 ml), and citric acid (0.260 g, 1.36 mmol), dissolved in hot ethanol (10 ml), was added at room temperature. The mixture stirred at room temperature for 2 h. Since it was not possible to observe formation of a precipitate, the solution was concentrated i. vac. and the residue was stirred thoroughly with ether. A solid remained, which was filtered off with suction and dried i. vac.

Yield: 272 mg (Ex. 190, 30%), porous solid $^1$H-NMR (DMSO-$d_6$):): 1.52 (2H, m);); 1.80 (6H, m); 2.36 (6H; s); 2.64 (4 H, m); 2.86 (4H, m); 2.97 (4H, m); 6.50 (1H, t); 6.62 (1H, d); 6.91 (2H, m); 7.03 (1 H, m); 7.17 (1H, m); 7.54 (6H, m); 10.46 (1H, s), citrate.

Example 191

Methyl 1-(2-(2-(4-(dimethylamino)-4-phenylcyclohex-1-enyl)-1H-indol-3-yl)ethyl)-1H-1,2,3-triazole-4-carboxylate 3-[2-(1H-Indol-3-yl)-ethyl]-3H-[1,2,3]triazole-4-carboxylic acid methyl ester (320 mg, 1.18 mmol) and 4-dimethylamino-4-phenyl-cyclohexanone (256 mg, 1.18 mmol) were dissolved in abs. methylene chloride (15 ml), and trifluoromethanesulfonic acid (0.21 ml, 2.4 mmol) was added rapidly. The mixture was stirred at RT overnight, during which a dark oil settled out. After addition of 1 N NaOH (10 ml) and $CH_2Cl_2$ (10 ml), the mixture was subsequently stirred for a further 20 min, the phases were separated, the aqueous phase was extracted twice with $CH_2Cl_2$, the combined organic phases were washed with water and dried ($Na_2SO_4$) and the solution was concentrated i. vac. The residue which remained was purified by flash chromatography with $CHCl_3$/MeOH (9:1).

Yield: 245 mg (44%)

$^1$H-NMR (DMSO-$d_6$): 1.71-2.60 (12H, m); 3.28 (2H; m); 3.80 (3H, s); 4.49 (2 H, m); 6.06 (1H, bs); 6.92 (2H, m); 7.24 (4H, m); 7.44 (3H, m); 8.62 (1H, s); 10.72 (1H, s).

$^{13}$C-NMR (DMSO-$d_6$): 25.61; 26.53; 27.00; 32.43; 38.14; 50.30; 51.63; 60.11; 105.42; 110.82; 117.74; 118.54; 121.08; 126.13; 126.36; 126.97; 127.43; 127.99; 128.99; 129.29; 135.07; 136.77; 138.31; 142.57; 160.74.

Methyl 1-(2-(2-(4-(dimethylamino)-4-phenylcyclohexyl)-1H-indol-3-yl)ethyl)-1H-1,2,3-triazole-4-carboxylate, citrate (1:1) Less polar diastereomer Tin (0.60 g) was added to a solution of the olefin just prepared (218 mg, 0.46 mmol) in HBr/glacial acetic acid (10 ml) in the course of 20 min and the mixture was stirred at RT for 3 h. Ethanol was added to the mixture, the solvent mixture was concentrated to dryness and the residue was dissolved in 5 N NaOH (20 ml) and methylene chloride (30 ml). The phases were separated, the aqueous phase was extracted twice with $CH_2Cl_2$ and the combined organic phases were washed with water and dried over ($Na_2SO_4$). The methylene chloride phase was filtered off with suction (was cloudy) over Celite and the solution was concentrated i. vac. The residue which remained was purified by flash chromatography with $CHCl_3$/MeOH (20:1→9:1).

Yield: 70 mg (32%) of non-polar diastereomer 39 mg (18%) of polar diastereomer

The less polar diastereomer obtained (66 mg 0.14 mmol) was dissolved in hot ethanol (3 ml), and a solution of citric acid (27 mg, 0.14 mmol) in hot ethanol (2 ml) was added. The citrate did not precipitate out, and the solvent was therefore removed and the residue was dried i. vac.

Yield: 93 mg (100%)

$^1$H-NMR (DMSO-$d_6$): 1.40 (4H, m); 2.04 (8H; m); 2.58 (1H, m) 2.72 (2H, m); 3.26 (2H, t); 3.79 (3H, s); 4.60 (2H, t); 6.94 (2H, t); 7.38 (6H, m); 7.47 (1 H, m); 8.73 (1H, s); 10.73 (1H, bs), free base.

Example 192

Methyl 1-(2-(2-(4-(dimethylamino)-4-phenylcyclohexyl)-1H-indol-3-yl)ethyl)-1H-1,2,3-triazole-4-carboxylate, citrate (1:1):More polar diastereomer The more polar diastereomer obtained under Example 191 (39 mg, 0.082 mmol) was dissolved in hot ethanol (2 ml), and a solution of citric acid (16 mg, 0.082 mmol) in hot ethanol (2 ml) was added. The citrate did not precipitate out, and the solvent was therefore removed and the residue was dried i. vac.

Yield: 55 mg (100%)

$^1$H-NMR (DMSO-$d_6$): 1.39 (4H, m); 1.64 (2H m); 1.98 (6H; m); 2.50 (1H, m); 2.71 (2H, m); 3.22 (2H, t); 3.85 (3H, s); 4.57 (2H, t); 6.92 (2H, t); 7.17 (1 H, m); 7.42 (6H, m); 8.72 (1H, s); 10.40 (1H, bs), free base.

Example 193

(±)-2-(4-(Dimethylamino)-4-phenylcyclohex-1-enyl)-3-(2-(isoindolin-2-yl)ethyl)-1H-indole Indole (Ind-64, 1.05 g, 4.0 mmol) and ketone (Ket-10; 868 mg, 4.0 mmol) were dissolved in abs. methylene chloride (30 ml), and trifluoromethanesulfonic acid (1.06 ml, 12.0 mmol) was added rapidly. The mixture was stirred at RT overnight, during which a dark brown oil settled out. After addition of 1 N NaOH (20 ml) and $CH_2Cl_2$ (30 ml), the mixture was subsequently stirred for a further 30 min, the phases were separated, the aqueous phase was extracted twice with $CH_2Cl_2$, the combined organic phases were washed with water and dried ($Na_2SO_4$) and the solution was concentrated i. vac. The residue which remained was purified by flash chromatography with $CHCl_3$/MeOH (20:1).

Yield: 605 mg (33%), porous solid $^1$H-NMR (DMSO-$d_6$): 1.83 (1H, m); 2.16 (7H, m); 2.57 (1H, m); 2.72 (4H, m); 2.88 (2H, m); 3.80 (4H, s); 6.22 (1H, s); 6.98 (2H, s); 7.26 (8H, m); 7.47 (3 H, m); 10.66 (1H, s).

4-(3-(2-(Isoindolin-2-yl)ethyl)-1H-indol-2-yl)-N,N-dimethyl-1-phenylcyclohexanamine, citrate (1:1): Less polar diastereomer Tin (1.50 g) was added to a solution of the olefin just prepared (588 mg, 1.27 mmol) in HBr/glacial acetic acid (30 ml) in the course of 30 min and the mixture was stirred at RT for 4 h. Ethanol was added to the mixture, the reaction mixture was concentrated to dryness and the residue was dissolved in 5 N NaOH (40 ml) and methylene chloride (30 ml). The phases were separated, the aqueous phase was extracted twice with $CH_2Cl_2$ and the combined organic phases were washed with water, dried over $Na_2SO_4$ and concentrated i. vac. The residue which remained was separated by flash chromatography with $CHCl_3$/MeOH (20:1→9:1).

Yield: 304 mg (52%) non-polar diastereomer 108 mg (18%) polar diastereomer

The less polar diastereomer just obtained (264 mg 0.57 mmol) was dissolved in hot ethanol (5 ml), and a solution of citric acid (109 mg, 0.57 mmol) in hot ethanol (5 ml) was added. After the mixture had stood in a refrigerator for 2 hours, the solid formed was filtered off with suction and dried i. vac.

Yield: 289 mg (77%); melting point: 225° C.

$^1$H-NMR (DMSO-$d_6$): 1.66 (4H, m); 2.08 (6H, m); 2.18 (2H, m); 2.57-2.66 (4 H, m); 2.85 (2H, d); 3.04 (3H, m); 3.20 (2H, t); 4.36 (4H, s); 6.98 (2H, s); 7.32 (10H, m); 7.49 (1H, m); 10.75 (1H, s).

Citrate: (ethanol)

Example 194

4-(3-(2-(Isoindolin-2-yl)ethyl)-1H-indol-2-yl)-N,N-dimethyl-1-phenylcyclohexanamine, citrate (1:1): More polar diastereomer The more polar diastereomer obtained under Example 193 (93 mg 0.20 mmol) was dissolved in hot ethanol (3 ml), and a solution of citric acid (38 mg, 0.20 mmol) in hot ethanol (2 ml) was added. After the mixture had stood in a refrigerator for 2 hours, the solid formed was filtered off with suction and dried i. vac.

Yield: 103 mg (78%), porous solid
$^1$H-NMR (DMSO-$d_6$): 1.50 (2H, m); 1.80 (2H, m); 1.98 (2H, m); 2.32 (6H, s); 2.58 (4H, m); 2.96 (6H, m); 4.15 (4H, s); 6.91 (2H, s); 7.15-7.34 (5H, m); 7.43-7.65 (5H, m); 10.48 (1H, s).
Citrate: (ethanol), porous solid

Example 195

(±)-2-(4-(Dimethylamino)-4-phenylcyclohex-1-enyl)-3-(2-(3,4-dihydroisoquinolin-2(1H)-yl)ethyl)-1H-indole Indole (Ind-65, 1.10 g, 4.0 mmol) and ketone (Ket-10, 868 mg, 4.0 mmol) were dissolved in abs. methylene chloride (30 ml), and trifluoromethanesulfonic acid (1.06 ml, 12.0 mmol) was added rapidly. The mixture was stirred at RT overnight, during which a dark brown oil settled out. After addition of 1 N NaOH (20 ml) and $CH_2Cl_2$ (30 ml), the mixture was subsequently stirred for a further 30 min, the phases were separated, the aqueous phase was extracted twice with $CH_2Cl_2$, the combined organic phases were washed with water and dried ($Na_2SO_4$) and the solution was concentrated i. vac. The residue which remained was purified by flash chromatography with $CHCl_3$/MeOH (20:1).
Yield: 637 mg (33%), porous solid
$^1$H-NMR (DMSO-$d_6$): 1.75 (2H, m); 1.94 (2H, m); 2.11 (6H, s); 2.55-2.89 (8 H, m); 3.82 (1H, m); 6.22 (1H, s); 6.91 (13H, m); 10.62 (1H, s).

4-(3-(2-(3,4-Dihydroisoquinolin-2(1H)-yl)ethyl)-1H-indol-2-yl)-N,N-dimethyl-1-phenylcyclohexanamine, citrate (1:1):Less polar diastereomer Tin (1.50 g) was added to a solution of the olefin just prepared (600 mg, 1.26 mmol) in HBr/glacial acetic acid (30 ml) in the course of 30 min and the mixture was stirred at RT for 4 h. Ethanol was added to the mixture, the reaction mixture was concentrated to dryness and the residue was dissolved in 5 N NaOH (40 ml) and methylene chloride (30 ml). The phases were separated, the aqueous phase was extracted twice with $CH_2Cl_2$ and the combined organic phases were washed with water, dried over $Na_2SO_4$ and concentrated i. vac. The residue which remained was separated by flash chromatography with $CHCl_3$/MeOH (20:1→9:1).
Yield: 207 mg (34%) non-polar diastereomer
128 mg (21%) polar diastereomer
The less polar diastereomer obtained (195 mg 0.41 mmol) was dissolved in hot ethanol (10 ml), and a solution of citric acid (78 mg, 0.41 mmol) in hot ethanol (3 ml) was added. After the mixture had stood in a refrigerator for 2 hours, the solid formed was filtered off with suction and dried i. vac.
Yield: 197 mg (72%); melting point: 153-154° C.
$^1$H-NMR (DMSO-$d_6$): 1.60 (4H, m); 2.08 (6H, m); 2.17 (2H, m); 2.57-2.61 (6 H, m); 3.02 (8H, m); 4.14 (2H, s); 6.98 (2H, m); 7.16 (3H, m); 7.34 (6H, m); 7.49 (1H, m); 10.77(1H, s).
Citrate: (ethanol)

Example 196

4-(3-(2-(3,4-Dihydroisoquinolin-2(1H)-yl)ethyl)-1H-indol-2-yl)-N,N-dimethyl-1-phenylcyclohexanamine, citrate (2:3):More polar diastereomer The more polar diastereomer obtained under Example 195 (102 mg 0.21 mmol) was dissolved in hot ethanol (3 ml), and a solution of citric acid (41 mg, 0.21 mmol) in hot ethanol (2 ml) was added. After the mixture had stood in a refrigerator for 2 hours, the solid formed was filtered off with suction and dried i. vac.
Yield: 75 mg (52%), porous solid
$^1$H-NMR (DMSO-$d_6$): 1.53 (2H, m); 1.81 (2H, m); 2.01 (2H, m); 2.37 (6H, s); 6H, s); 2.60 (4H, m); 2.90 (10H, m); 4.00 (2H, t); 6.93 (2H, m); 7.18 (5H, m); 7.17-7.68 (6H, m); 10.48 (1H, s).
Citrate: (ethanol), porous solid

Example 197

(±)-2-(4-(Dimethylamino)-4-phenylcyclohex-1-enyl)-3-(2-(pyrrolidin-1-yl)ethyl)-1H-indole Indole (Ind-66, 1.00 g, 4.7 mmol) and ketone (Ket-10, 1.01 g, 4.7 mmol) were dissolved in abs. $CH_2Cl_2$ (50 ml) at RT and trifluoromethanesulfonic acid was added swiftly. A black oil then precipitated out. The mixture was stirred at RT for 24 h, 1 N NaOH (50 ml) was added and the mixture was stirred for 20 min. The organic phase was separated off and the aqueous phase was extracted with $CH_2Cl_2$ (2×50 ml). The combined organic phases were washed with water (20 ml), dried over $Na_2SO_4$, filtered and concentrated i. vac. The residue was purified by flash chromatography with chloroform/methanol (9/1+1% triethylamine).
Yield: 789 mg (41%), yellow solid.
$^1$H-NMR (DMSO-$d_6$): 1.75 (4H, m); 2.09 (8H; m); 2.62 (6H, m); 2.82 (4H, m); 6.19 (1H, s); 6.97 (2H, m); 7.21-7.48 (7H, m); 10.62 (1H, s).

N,N-Dimethyl-1-phenyl-4-(3-(2-(pyrrolidin-1-yl)ethyl)-1H-indol-2-yl)cyclohexanamine, citrate (1:1): Less polar diastereomer The olefin just prepared (666 mg, 1.6 mmol) was dissolved in 33% strength HBr/glacial acetic acid (35 ml), and tin (2.10 g) was added in portions at RT in the course of 30 min. The mixture was stirred at RT for 4 h. Ethanol was added, the solvent mixture was removed i. vac. and the residue was dissolved with 5 N NaOH (70 ml) and $CH_2Cl_2$ (100 ml). The phases were separated, the aqueous phase was extracted with $CH_2Cl_2$ (2×) and the combined organic phases were washed with water, dried over $Na_2SO_4$, filtered and concentrated i. vac. The residue which remained was purified by flash chromatography with chloroform/methanol (20:1→9:1).
Yield: 544 mg (82%), non-polar compound, contained triethylamine and impurity 259 mg (39%), polar compound, contained triethylamine and impurity
In the reaction of the less polar diastereomer just obtained with a molar amount of citric acid in ethanol, the citrate precipitated out as a yellow solid.
Yield: 308 mg, non-polar diastereomer; melting point: 209-210° C.
$^1$H-NMR (DMSO-$d_6$): 1.57 (4H, m); 1.94 (4H, m); 2.08 (8H, m); 2.58 (4H, m); 2.83-3.41 (10H, m); 6.99 (2H, m); 7.41 (6H, m); 7.51 (1H, m); 10.88 (1H, s).

Example 198

N,N-Dimethyl-1-phenyl-4-(3-(2-(pyrrolidin-1-yl)ethyl)-1H-indol-2-yl)cyclohexanamine, citrate (1:1) More polar diastereomer In the reaction of the more polar diastereomer obtained under Example 197 with a molar amount of citric acid in ethanol, only little precipitate precipitated out, and after addition of ether the citrate precipitated out as a yellow solid.

Yield: 204 mg, polar diastereomer; melting point: amorphous solid

¹H-NMR (DMSO-d₆): 1.15 (2H, m); 1.44 (2H, m); 1.75 (2H, m); 1.94-2.06 (5 H, m); 2.30 (4H, m); 2.58 (4H, m); 3.09 (6H, m); 3.43 (5H, m); 6.94 (2H, m); 7.18 (1H, m); 7.53 (6H, m); 10.55 (1H, s).

Example 199

N,N-Dimethyl-1-phenyl-4-(3-(2-(piperidin-1-yl)ethyl)-1H-indol-2-yl)cyclohexanamine, citrate (1:1): One of 2 possible diastereomers Sn powder (0.57 g) was added to a solution of Example 58 (0.209 g, 0.488 mmol) in HBr/glacial acetic acid (10 ml) in the course of 20 min. The reaction mixture then stirred at room temperature for 2.5 h. Ethanol was added to the mixture and the mixture was concentrated to dryness i. vac. 5 N NaOH (20 ml) was added to the residue and the mixture was extracted with methylene chloride (3×20 ml), the organic phase was dried with Na₂SO₄ and concentrated i. vac. and the residue was purified by means of flash chromatography with chloroform/methanol (15:1).

Yield: 0.05 g (24%)

The reaction product just obtained (0.050 g, 0.116 mmol) was dissolved in hot ethanol (1.4 ml), and citric acid (0.022 g, 0.116 mmol), dissolved in hot ethanol (0.865 ml), was added. After 2 h a precipitate formed, which was filtered off, washed with ethanol and dried i. vac.

Yield: 0.055 g; melting point: 214-215° C.

¹H-NMR (DMSO-d₆): 1.51-1.72 (10H, m); 2.05 (6H, s); 2.19 (6H, m); 2.56 (4 H, m); 2.92 (4H, m); 3.04 (2H, s); 6.94 (3H, m); 7.29 (2H, m); 7.40 (3H, m); 7.48 (1H, m); 10.82 (1H, s).

Example 200

(±)-2-(4-(Dimethylamino)-4-phenylcyclohex-1-enyl)-3-(2-(4-methylpiperazin-1-yl)ethyl)-1H-indole Indole (Ind-68, 1.23 g, 5.05 mmol) and ketone (Ket-10, 1.09 g, 5.05 mmol) were initially introduced into abs. CH₂Cl₂ (60 ml) under argon and trifluoromethanesulfonic acid (1.77 ml, 20.2 mmol) was added. The mixture was stirred at RT overnight. For working up, 1 N NaOH was added to the solution and the mixture was stirred for 30 min. The phases were separated and the aqueous phase was extracted with CH₂Cl₂ (3×20 ml). The organic phase was dried over Na₂SO₄ and concentrated i. vac. The residue was purified by flash chromatography with CHCl₃/MeOH (1:1).

Yield: 382 mg (17%)

¹H-NMR (DMSO-d₆): 1.77 (2H, m); 2.10 (6H, m); 2.16 (3H, s); 2.06-2.44 (12 H, m); 2.77 (2H, m); 3.27 (2H, m); 6.18 (1H, m); 6.96 (2H, m); 7.22 (6H, m); 7.46 (2H, m); 10 61 (1H, s).

¹³C-NMR (DMSO-d₆): 22.01; 26.50; 27.03; 32.69; 38.18; 45.78; 52.52; 54.76; 59.11; 60.17; 108.51; 110.71; 117.83; 118.28; 120.86; 125.25; 126.36; 127.00; 127.46; 128.49; 129.83; 135.17; 135.63; 142.72.

N,N-dimethyl-4-(3-(2-(4-methylpiperazin-1-yl)ethyl)-1H-indol-2-yl)-1-phenylcyclohexanamine, citrate (1:1): One of 2 possible diastereomers The olefin just obtained (375 mg. 0.847 mmol) was initially introduced into HBr/glacial acetic acid (18 ml), tin (988 mg) was added in the course of 30 min and the mixture was subsequently stirred at RT for 3 h. The mixture was diluted with ethanol, stirred at RT for 20 h and concentrated i. vac. 5 N NaOH was added to the residue and the mixture was extracted with methylene chloride (3×20 ml). The organic phase was dried over Na₂SO₄ and concentrated i. vac. The residue was purified by flash chromatography with CHCl₃/MeOH (9:1).

Yield: 160 mg (43%)

In the reaction with a molar amount of citric acid in ethanol, the citrate precipitated out as a white solid.

Yield: 151 mg (70%); melting point: 210-213° C.

¹H-NMR (DMSO-d₆): 1.53 (4H, m); 2.06 (6H, m); 2.54-2.69 (10H, m); 2.81 (10 H, m); 6.96 (2H, s); 7.29 (2H, m); 7.40 (5H, m); 10.72 (1H, s).

Example 201

(±)-2-(4-(Dimethylamino)-4-phenylcyclohex-1-enyl)-3-(2-morpholinoethyl)-1H-indole Indole (Ind-69, 1.05 g, 4.56 mmol) and ketone (Ket-10, 0.99 g, 4.56 mmol) were dissolved in abs. CH₂Cl₂ (50 ml) at RT and trifluoromethanesulfonic acid (2.05 g, 2.2 ml. 13.7 mmol) was added swiftly, and a black oil then precipitated out. The mixture was stirred at RT for 3 d. After addition of 1 N NaOH (50 ml), the mixture was stirred for 20 min and the organic phase was then separated off and the aqueous phase was extracted with CH₂Cl₂ (2×50 ml). The combined organic phases were washed with water (20 ml), dried over Na₂SO₄, filtered and concentrated i. vac.

The residue obtained was purified by flash chromatography with 100 g of silica gel and chloroform/methanol (9:1).

Yield: 644 mg (33%)

¹H-NMR (DMSO-d₆): 1.78 (2H, m); 2.11 (6H, s); 2.37 (8H, m); 2.80 (4H, d); 3.59 (4 H, d); 6.19 (1H, s); 6.94 (2H, m); 7.21-7.50 (7H, m); 10.64 (1H, s).

N,N-dimethyl-4-(3-(2-morpholinoethyl)-1H-indol-2-yl)-1-phenylcyclohexanamine, citrate (1:1):Less polar diastereomer The olefin just prepared (617 mg, 1.4 mmol) was dissolved in 33% strength HBr/glacial acetic acid (30 ml), and tin (1.87 g) was then added in portions at RT in the course of 30 min. The mixture was stirred at RT for 4 h. Ethanol was added, the solvent mixture was removed i. vac. and the residue was dissolved with 5 N NaOH (60 ml) and CH₂Cl₂ (90 ml). The phases were separated, the aqueous phase was extracted twice with CH₂Cl₂ and the combined organic phases were washed with water, dried over Na₂SO₄ and filtered and the solution was concentrated i. vac.

The residue which remained was purified by flash chromatography with chloroform/methanol (9:1→4:1).

Yield: 334 mg (54%) non-polar compound 119 mg (19%) polar compound

In the reaction of the less polar diastereomer just obtained with a molar amount of citric acid in ethanol, the citrate precipitated out as a colourless solid.

Yield: 346 mg, non-polar compound; melting point: 234-242° C.

¹H-NMR (DMSO-d₆): 1.63 (4H, m); 2.11 (8H; m); 2.55-2.91 (14H, m); 3.68 (4 H, m); 6.96 (2H, m); 7.37 (7H, m); 10.71 (1H, s).

Example 202

N,N-dimethyl-4-(3-(2-morpholinoethyl)-1H-indol-2-yl)-1-phenylcyclohexanamine, citrate (1:1): Polar diastereomer In the reaction of the more polar diastereomer obtained under Example 201 with a molar amount of citric acid in ethanol, the citrate precipitated out as a colourless solid.

Yield: 75 mg, polar compound; melting point: 224-228° C.
$^1$H-NMR (DMSO-$d_6$): 1.51 (2H, m); 1.83 (2H, m); 2.00 (2H, m); 2.36 (6H; s); 2.59 (8H, m); 2.78 (2H, t); 3.02 (3H, m); 3.65 (4H, m); 6.90 (2H, m); 7.16 (1 H, d); 7.35 (1 H, d); 7.56 (5H, m); 10.44 (1H, s).

Example 203

(±)-2-(4-(Dimethylamino)-4-phenylcyclohex-1-enyl)-3-(2-(1H-benzo[d]imidazol-1-yl)ethyl)-1H-indole Indole (Ind-70, 650 mg, 2.5 mmol) and ketone (Ket-10, 542 mg, 2.5 mmol) were dissolved in abs. methylene chloride (20 ml), and trifluoromethanesulfonic acid (0.66 ml, 7.5 mmol) was added rapidly. The mixture was stirred at RT overnight, during which a dark brown oil settled out. After addition of 1 N NaOH (10 ml) and $CH_2Cl_2$ (20 ml), the mixture was subsequently stirred for a further 30 min, the phases were separated, the aqueous phase was extracted twice with $CH_2Cl_2$, the combined organic phases were washed with water and dried ($Na_2SO_4$) and the solution was concentrated i. vac. The residue which remained was purified by flash chromatography with $CHCl_3$/MeOH (9:1).

Yield: 454 mg (39%), porous solid
$^1$H-NMR (DMSO-$d_6$): 2.09 (10H, m); 2.41 (2H, m); 3.19 (2H, m); 4.29 (2H, m); 5.83 (1H, s); 6.89-7.28 (7H, m); 7.41 (6H, m); 7.65 (1H, s); 10.64 (1H, bs).
$^{13}$C-NMR (DMSO-$d_6$): 30.41; 30.91; 42.48; 47.93; 63.48; 71.61; 108.19; 125.46; 126.90; 127.96; 144.23.

4-(3-(2-(1H-benzo[d]imidazol-1-yl)ethyl)-1H-indol-2-yl)-N,N-dimethyl-1-phenylcyclohexanamine, citrate (1:1):Less polar diastereomer Tin (1.20 g) was added to a solution of the olefin just prepared (429 mg, 0.93 mmol) in HBr/glacial acetic acid (20 ml) in the course of 20 min and the mixture was stirred at RT for 3 h. Ethanol was added to the mixture, the reaction mixture was concentrated to dryness and the residue was dissolved in 5 N NaOH (40 ml) and methylene chloride (30 ml). The phases were separated, the aqueous phase was extracted twice with $CH_2Cl_2$ and the combined organic phases were washed with water, dried over $Na_2SO_4$ and concentrated i. vac. The residue which remained was separated by flash chromatography with $CHCl_3$/MeOH (20:1→9:1).

Yield: 165 mg (38%), non-polar diastereomer
144 mg (33%), polar diastereomer

The less polar diastereomer just obtained (143 mg 0.31 mmol) was dissolved in hot ethanol (5 ml), and a solution of citric acid (59 mg, 0.31 mmol) in hot ethanol (3 ml) was added. After the mixture had stood in a refrigerator for 2 hours, the solid formed was filtered off with suction and dried i. vac.

Yield: 101 mg (50%); melting point: 227-228° C.
$^1$H-NMR (DMSO-$d_6$): 1.19 (4H, m); 1.89 (2H, m); 2.09 (6H, s); 2.33 (2H, t); 2.67 (4H, m); 3.21 (2H, t); 4.45 (2H, t); 7.00 (2H, m); 7.14 (2H, m); 7.32-7.61 (9 H, m); 7.84 (1 H, s); 10.55 (1H, s).

Citrate: (ethanol)

Example 204

4-(3-(2-(1H-benzo[d]imidazol-1-yl)ethyl)-1H-indol-2-yl)-N,N-dimethyl-1-phenylcyclohexanamine, citrate (1:1):More polar diastereomer The more polar diastereomer obtained under Example 203 (135 mg 0.27 mmol) was dissolved in hot ethanol (5 ml), and a solution of citric acid (52 mg, 0.27 mmol) in hot ethanol (3 ml) was added. After the mixture had stood in a refrigerator for 2 hours, the solid formed was filtered off with suction and dried i. vac.

Yield: 68 mg (36%), porous solid
$^1$H-NMR (DMSO-$d_6$): 1.61 (2H, m); 2.33 (2H, m); 2.41 (6H, s); 2.63-2.83 (6 H, m); 3.18 (2H, t); 4.43 (2H, t); 6.93 (3H, m); 7.20 (3H, m); 7.42-7.67 (7H, m); 7.83 (1H, s); 10.33 (1H, s).

Citrate: (ethanol), porous solid

Example 205

(±)-2-(4-(Dimethylamino)-4-phenylcyclohex-1-enyl)-3-(2-(1H-imidazol-1-yl)ethyl)-1H-indole Indole (Ind-71, 490 mg, 2.32 mmol) and ketone (Ket-10, 503 mg, 2.32 mmol) were dissolved in abs. methylene chloride (20 ml), and trifluoromethanesulfonic acid (0.62 ml, 7 mmol) was added rapidly. The mixture was stirred at RT overnight, during which a dark brown oil settled out. After addition of 1 N NaOH (10 ml) and $CH_2Cl_2$ (20 ml), the mixture was subsequently stirred for a further 90 min, the phases were separated, the aqueous phase was extracted twice with $CH_2Cl_2$, the combined organic phases were washed with water and dried ($Na_2SO_4$) and the solution was concentrated i. vac. The residue which remained was purified by flash chromatography with $CHCl_3$/MeOH (4:1).

Yield: 311 mg (33%), viscous oil
$^1$H-NMR (DMSO-$d_6$): 1.68 (2H, m); 1.88 (1H, m); 2.08 (6H, s); 2.38 (1H, d); 2.60 (2H, d); 3.06 (2H, m); 4.02 (2H, m); 6.00 (1H, s); 6.78-7.03 (4H, m); 7.19-7.48 (8H, m); 10 70 (1H, s).
$^{13}$C-NMR (DMSO-$d_6$): 26.59; 26.77; 27.23; 32.42; 38.15; 46.61; 60.21; 106.31; 110.73; 117.92; 118.45; 119.15; 120.99; 126.00; 126.40; 127.07; 127.43; 128.11; 129.41; 135.09; 136.64; 136.88; 142.29.

4-(3-(2-(1H-imidazol-1-yl)ethyl)-1H-indol-2-yl)-N,N-dimethyl-1-phenylcyclohexanamine, citrate (1:1): Less polar diastereomer Tin (0.90 g) was added to a solution of the olefin just prepared (300 mg, 0.708 mmol) in HBr/glacial acetic acid (15 ml) in the course of 20 min and the mixture was stirred at RT for 3 h. Ethanol was added to the mixture, the reaction mixture was concentrated to dryness and the residue was dissolved in 5 N NaOH (20 ml) and methylene chloride (30 ml). The phases were separated, the aqueous phase was extracted twice with $CH_2Cl_2$ and the combined organic phases were washed with water, dried over $Na_2SO_4$ and concentrated i. vac. The residue which remained was separated by flash chromatography with $CHCl_3$/MeOH (20:1→1:1).

Yield: 111 mg (38%), non-polar diastereomer
33 mg (11%), polar diastereomer

The less polar diastereomer just obtained (87 mg 0.21 mmol) was dissolved in hot ethanol (3 ml), and a solution of citric acid (40 mg, 0.21 mmol) in hot ethanol (2 ml) was added. After the mixture had stood in a refrigerator for 2 hours, the solid formed was filtered off with suction and dried i. vac.

Yield: 91 mg (72%); melting point: 203° C.

$^1$H-NMR (DMSO-$d_6$): 1.46 (4H, m); 2.03 (6H; s); 2.10 (1H, m); 2.70 (3H, m); 3.08 (2H, t); 4.13 (2H, t); 6.85 (1H, s); 6.99 (2H, m); 7.15 (1H, s); 7.25 bis 7.49 (8H, m); 10.74 (1H, s), (free base).

Citrate: (ethanol)

Example 206

4-(3-(2-(1H-imidazol-1-yl)ethyl)-1H-indol-2-yl)-N,N-dimethyl-1-phenylcyclohexanamine, citrate (1:1): More polar diastereomer The more polar diastereomer obtained under Example 205 (33 mg 0.08 mmol) was dissolved in hot ethanol (2 ml), and a solution of citric acid (15 mg, 0.08 mmol) in hot ethanol (2 ml) was added. The citrate did not precipitate out, and the solvent was therefore removed and the residue was dried i. vac.

Yield: 48 mg (100%), porous solid $^1$H-NMR (DMSO-$d_6$): 1.39 (2H, m); 1.51 (2H, m); 1.60 (2H, m); 1.99 (6H; s); 2.69 (3H, m); 3.04 (2H, t); 4.08 (2H, t); 6.91 (3H, m); 7.18 (2H, m); 7.42 (7H, m); 10.40 (1H, s), (free base).

Citrate: (ethanol) porous solid

Example 207

(±)-2-(4-(Dimethylamino)-4-phenylcyclohex-1-enyl)-3-(2-(1H-1,2,4-triazol-1-yl)ethyl)-1H-indole Indole (Ind-72, 800 mg, 3.77 mmol) and ketone (Ket-10, 819 mg, 3.77 mmol) were dissolved in abs. methylene chloride (20 ml), and trifluoromethanesulfonic acid (1.0 ml, 11.3 mmol) was added rapidly. The mixture was stirred at RT overnight, during which a dark brown oil settled out. After addition of 1 N NaOH (20 ml) and CH$_2$Cl$_2$ (20 ml), the mixture was subsequently stirred for a further 30 min, the phases were separated, the aqueous phase was extracted twice with CH$_2$Cl$_2$, the combined organic phases were washed with water and dried (Na$_2$SO$_4$) and the solution was concentrated i. vac. The residue which remained was purified by flash chromatography with CHCl$_3$/MeOH (9:1).

Yield: 465 mg (30%), colourless solid $^1$H-NMR (DMSO-$d_6$): 1.70 (2H, m); 2.11 (8H, m); 2.63 (2H, m); 3.17 (2H, t); 4.25 (2H, t); 6.08 (1H, s); 6.94 (2H, m); 7.32 (5H, m); 7.48 (2H, m); 7.99 (1H, s); 8.28 (1H, s); 10.74 (1H, s).

4-(3-(2-(1H-1,2,4-triazol-1-yl)ethyl)-1H-indol-2-yl)-N,N-dimethyl-1-phenylcyclohexanamine, citrate (1:1):Less polar diastereomer Tin (1.3 g) was added to a solution of the olefin just prepared (450 mg, 1.09 mmol) in HBr/glacial acetic acid (25 ml) in the course of 30 min and the mixture was stirred at RT for 6 h. Ethanol was added to the mixture, the reaction mixture was concentrated to dryness and the residue was dissolved in 5 N NaOH (40 ml) and methylene chloride (30 ml). The phases were separated, the aqueous phase was extracted twice with CH$_2$Cl$_2$ and the combined organic phases were washed with water, dried over Na$_2$SO$_4$ and concentrated i. vac. The residue which remained was separated by flash chromatography with CHCl$_3$/MeOH (20:1→9:1).

Yield: 191 mg (42%) non-polar diastereomer 131 mg (29%) polar diastereomer

The less polar diastereomer just obtained (174 mg, 0.42 mmol) was dissolved in hot ethanol/dioxane (1:1, 10 ml), and a solution of citric acid (81 mg, 0.42 mmol) in hot ethanol (3 ml) was added. After the mixture had stood in a refrigerator for 2 hours, the solid formed was filtered off with suction and dried i. vac.

Yield: 107 mg (42%); melting point: 234-236° C.

$^1$H-NMR (DMSO-$d_6$): 1.47 (4H, m); 2.01 (2H, m); 2.36 (6H, s); 2.58-2.64 (6H, m); 3.12 (2H, t); 4.33 (2H, t); 6.92 (2H, m); 7.15 (1H, m); 7.39-7.64 (6H, m); 8.00 (1H, s); 8.21 (1H, s); 10.43 (1H, s).

Citrate: (ethanol/dioxane)

Example 208

4-(3-(2-(1H-1,2,4-triazol-1-yl)ethyl)-1H-indol-2-yl)-N,N-dimethyl-1-phenylcyclohexanamine, citrate (1:1):More polar diastereomer The more polar diastereomer obtained under Example 207 (120 mg, 0.29 mmol) was dissolved in hot ethanol (5 ml), and a solution of citric acid (56 mg, 0.29 mmol) in hot ethanol (3 ml) was added. After the mixture had stood in a refrigerator for 2 hours, the solid formed was filtered off with suction and dried i. vac.

Yield: 80 mg (45%); melting point: 183-184° C.

$^1$H-NMR (DMSO-$d_6$): 1.52 (4H, m); 2.06 (2H, m); 2.12 (6H, s); 2.51-2.83 (6H, m); 3.17 (2H, t); 4.34 (2H, t); 6.99 (2H, m); 7.41 (7H, m); 7.94 (1H, s); 8.25 (1H, s); 10.68 (1H, s).

Citrate: (ethanol)

Example 209

(±)-2-(4-(Dimethylamino)-4-phenylcyclohex-1-enyl)-3-(2-(thiazolidin-3-yl)ethyl)-1H-indole Indole (Ind-73, 542 mg, 2.33 mmol) and ketone (Ket-10, 503 mg, 2.33 mmol) were initially introduced into abs. CH$_2$Cl$_2$ (50 ml) under argon and trifluoromethanesulfonic acid (612 µl, 6.99 mmol) was added. The mixture was stirred at RT overnight. For working up, 1 N NaOH was added to the solution and the mixture was stirred for 30 min. The phases were separated, the aqueous phase was extracted with CH$_2$Cl$_2$ (3×20 ml) and the organic phase was dried over Na$_2$SO$_4$ and concentrated i. vac. The residue was purified by flash chromatography with CHCl$_3$/MeOH (1:1).

Yield: 417 mg (42%)

$^1$H-NMR (DMSO-$d_6$): 1.77 (2H, m); 2.08 (8H, m); 2.10-2.68 (8H, m); 2.92 (2H, m); 3.17 (2H, s); 6.18 (1H, bs); 6.94 (2H, m); 7.23 (2H, m); 7.32 (2H, m); 7.48 (3H, m); 10.67 (1H, s).

N,N-dimethyl-1-phenyl-4-(3-(2-(thiazolidin-3-yl)ethyl)-1H-indol-2-yl)cyclohexanamine, citrate (1:1) (209:Less polar diastereomer The olefin just obtained (417 mg. 0.96 mmol) was initially introduced into HBr/glacial acetic acid (30 ml), tin (1.13 g) was added in the course of 30 min and the mixture was stirred at RT for 3 h. For working up, the mixture was diluted with ethanol, stirred at RT for 20 min and then concentrated i. vac. 5 N NaOH was added to the residue, the mixture was extracted with CH$_2$Cl$_2$ (3×20 ml) and the organic phase was dried over Na$_2$SO$_4$ and concentrated i. vac. The residue was purified by flash chromatography with CHCl$_3$/MeOH (4:1→1:1).

Yield: 86 mg (20%) of non-polar diastereomer
$^1$H-NMR (DMSO-d$_6$): 1.51 (2H, m); 1.67 (2H, m); 2.03 (6H; s); 2.16 (2H, m); 2.85 (10H, m); 6.95 (2H, m); 7.32 (5H, m); 7.60 (2H, m); 10.74 (1H, s).

Yield: 119 mg (28%) of polar diastereomer
$^1$H-NMR (DMSO-d$_6$): 1.50 (2H, m); 1.75 (6H, m); 1.94 (6H; s); 2.54-2.72 (10H, m); 6.89 (2H, m); 7.17 (1H, m); 7.34 (6H, m); 10.38 (1H, s).

The less polar diastereomer just obtained (86 mg, 0.198 mmol) was dissolved in hot ethanol (5 ml). Citric acid (37 mg, 0.198 mmol) was dissolved in hot ethanol (1 ml) and added. The mixture was cooled to RT, a precipitate thereby precipitating out. The precipitate was dried i. vac.

Yield: 69 mg (55%) non-polar; melting point: 185-188° C.

Example 210

N,N-dimethyl-1-phenyl-4-(3-(2-(thiazolidin-3-yl)ethyl)-1H-indol-2-yl)cyclohexanamine, citrate (1:1): More polar diastereomer The more polar diastereomer obtained under Example 209 (119 mg, 0.274 mmol) was dissolved in hot ethanol (5 ml). Citric acid (51 mg, 0.274 mmol) was dissolved in hot ethanol (1 ml) and added. The mixture was cooled to RT, a precipitate thereby precipitating out. The precipitate was dried i. vac.

Yield: 58 mg (34%) polar; melting point: 138-141° C.

Example 211

(±)-2-(4-(Dimethylamino)-4-phenylcyclohex-1-enyl)-3-(2-(5-methyl-2H-tetrazol-2-yl)ethyl)-1H-indole Indole (Ind-74, 620 mg, 2.72 mmol) and ketone (Ket-10, 592 mg, 2.72 mmol) were dissolved in abs. methylene chloride (15 ml), and trifluoromethanesulfonic acid (0.73 ml, 8.2 mmol) was added rapidly. The mixture was stirred at RT overnight, during which a dark brown oil settled out. After addition of 1 N NaOH (10 ml) and CH$_2$Cl$_2$ (20 ml), the mixture was subsequently stirred for a further 60 min, the phases were separated, the aqueous phase was extracted twice with CH$_2$Cl$_2$, the combined organic phases were washed with water and dried (Na$_2$SO$_4$) and the solution was concentrated i. vac. The residue which remained was purified by flash chromatography with CHCl$_3$/MeOH (9:1).

Yield: 443 mg (Ind-74, 38%)
$^1$H-NMR (DMSO-d$_6$): 1.74 (2H, m); 2.13 (8H, m); 2.42 (3H, s); 2.61 (2H, m); 3.31 (2H, m); 4.63 (2H, t); 6.07 (1H, s); 6.90 (1H, m); 7.01 (1H, m); 7.24 (5H, m); 7.50 (2H, m); 10.76 (1H, s).

N,N-dimethyl-4-(3-(2-(5-methyl-2H-tetrazol-2-yl)ethyl)-1H-indol-2-yl)-1-phenylcyclohexanamine, citrate (2:1):Less polar diastereomer Tin (1.20 g) was added to a solution of the olefin just prepared (418 mg, 0.98 mmol) in HBr/glacial acetic acid (30 ml) in the course of 20 min and the mixture was stirred at RT for 3 h. Ethanol was added to the mixture, the reaction mixture was concentrated to dryness and the residue was dissolved in 5 N NaOH (40 ml) and methylene chloride (30 ml). The phases were separated, the aqueous phase was extracted twice with CH$_2$Cl$_2$ and the combined organic phases were washed with water, dried over Na$_2$SO$_4$ and concentrated i. vac. The residue which remained was separated by flash chromatography with CHCl$_3$/MeOH (20:1→9:1).

Yield: 91 mg (22%), non-polar diastereomer
139 mg (33%), polar diastereomer

The less polar diastereomer just obtained (91 mg, 0.212 mmol) was dissolved in hot ethanol (2 ml), and a solution of citric acid (41 mg, 0.212 mmol) in hot ethanol (2 ml) was added. After the mixture had stood in a refrigerator for 2 hours, the solid formed was filtered off with suction and dried i. vac.

Yield: 72 mg (211, 54%); melting point: 208-209° C.
$^1$H-NMR (DMSO-d$_6$): 1.46 (2H, m); 1.65 (2H, m); 2.17 (4H, m); 2.28 (8H; s); 2.41 (3H, s); 2.93 (2H, m); 4.77 (2H, t); 6.98 (2H, m); 7.27 (1H, d); 7.43 (4H, m); 7.55 (2H, m); 10.92 (1H, s), citrate.

Example 212

N,N-dimethyl-4-(3-(2-(5-methyl-2H-tetrazol-2-yl)ethyl)-1H-indol-2-yl)-1-phenylcyclohexanamine, citrate (1:1):More polar diastereomer The more polar diastereomer prepared the under Example 211 (133 mg, 0.31 mmol) was dissolved in hot ethanol (3 ml), and a solution of citric acid (60 mg, 0.31 mmol) in hot ethanol (2 ml) was added. After the mixture had stood in a refrigerator for 2 hours, the solid formed was filtered off with suction and dried i. vac.

Yield: 103 mg (212, 53%), porous solid
$^1$H-NMR (DMSO-d$_6$): 1.40 (4H, m); 1.88 (2H, m); 2.41 (9H; m); 2.57 (4H, m); 3.01 (2H, m); 3.34 (2H, m); 4.73 (2H, t); 6.91 (2H, m); 7.13 (1H, m); 7.39 (1H, m); 7.53 (5H, m); 10.45 (1H, s), citrate.

Example 213

(±)-2-(4-(Dimethylamino)-4-phenylcyclohex-1-enyl)-3-((1H-pyrazol-1-yl)ethyl)-1H-indole Indole (Ind-75, 615 mg, 2.9 mmol) and ketone (Ket-10, 632 mg, 2.9 mmol) were dissolved in abs. methylene chloride (20 ml), and trifluoromethanesulfonic acid (0.77 ml, 8.7 mmol) was added rapidly. The mixture was stirred at RT overnight, during which a dark brown oil settled out. After addition of 1 N NaOH (20 ml) and CH$_2$Cl$_2$ (20 ml), the mixture was subsequently stirred for a further 60 min, the phases were separated, the aqueous phase was extracted twice with CH$_2$Cl$_2$, the combined organic phases were washed with water and dried (Na$_2$SO$_4$) and the solution was concentrated i. vac. The residue which remained was purified by flash chromatography with CHCl$_3$/MeOH (9:1).

Yield: 233 mg (20%), porous solid
$^1$H-NMR (DMSO-d$_6$): 1.74 (2H, m); 2.11 (9H, m); 3.13 (2H, t); 3.85 (1H, m); 4.18 (2H, t); 6.01 (1H, s); 6.19 (1H, s); 6.90 (1H, m); 7.01 (1H, m); 7.22 bis 7.49 (9H, m); 10.68 (1H, s).

4-(3-(2-(1H-pyrazol-1-yl)ethyl)-1H-indol-2-yl)-N,N-dimethyl-1-phenylcyclohexanamine, citrate (1:1): Less polar diastereomer Tin (0.8 g) was added to a solution of the olefin just prepared (230 mg, 0.56 mmol) in HBr/glacial acetic acid (10 ml) in the course of 20 min and the mixture was stirred at RT for 3 h. Ethanol was added to the mixture, the reaction mixture was concentrated to dryness and the residue was dissolved in 5 N NaOH (20 ml) and methylene chloride (30 ml). The phases were separated, the aqueous phase was extracted twice with $CH_2Cl_2$ and the combined organic phases were washed with water, dried over $Na_2SO_4$ and concentrated i. vac. The residue which remained was separated by flash chromatography with $CHCl_3$/MeOH (9:1).

Yield: 48 mg (21%) of non-polar diastereomer
47 mg (20%) of polar diastereomer

The less polar diastereomer obtained (48 mg 0.116 mmol) was dissolved in hot ethanol (3 ml) and a solution of citric acid (22 mg, 0.116 mmol) in hot ethanol (2 ml) was added.

After the mixture had stood in a refrigerator for 2 hours, the solid formed was filtered off with suction and dried i. vac.

Yield: 34 mg (47%); melting point: 130° C.
$^1$H-NMR (DMSO-$d_6$): 1.51 (4H, m); 2.04 (2H, m); 2.17 (6H, s); 2.60-2.83 (7H, m); 3.18 (2H, t); 4.28 (2H, t); 6.15 (1H, d); 6.99 (2H, m); 7.31-7.55 (9H, m); 10.61 (1H, s).
Citrate: (ethanol)

Example 214

4-(3-(2-(1H-pyrazol-1-yl)ethyl)-1H-indol-2-yl)-N,N-dimethyl-1-phenylcyclohexanamine, citrate (1:2): More polar diastereomer The more polar diastereomer obtained under Example 213 (47 mg 0.114 mmol) was dissolved in hot ethanol (3 ml), and a solution of citric acid (22 mg, 0.114 mmol) in hot ethanol (2 ml) was added. The citrate did not precipitate out, and the solvent was therefore removed and the residue was dried i. vac.

Yield: 74 mg (100%), viscous oil
$^1$H-NMR (DMSO-$d_6$): 1.41 (2H, m); 1.61 (2H, m); 1.95 (2H, m); 2.14 (2H, m); 2.61 (6H, s); 2.66-2.70 (5H, m); 3.03 (2H, t); 4.23 (2H, t); 6.17 (1H, d); 6.93 (2H, m); 7.14 (1H, m); 7.41-7.60 (6H, m); 7.68 (2H, m); 10.39 (1H, s).
Citrate: (ethanol), viscous oil

Example 215

(±)-2-(4-(Dimethylamino)-4-phenylcyclohex-1-enyl)-3-(2-(1H-1,2,3-triazol-1-yl)ethyl)-1H-indole Indole (Ind-76, 500 mg, 2.35 mmol) and ketone (Ket-10, 511 mg, 2.35 mmol) were dissolved in abs. methylene chloride (20 ml), and trifluoromethanesulfonic acid (0.62 ml, 7.0 mmol) was added rapidly. The mixture was stirred at RT overnight, during which a dark brown oil settled out. After addition of 1 N NaOH (20 ml) and $CH_2Cl_2$ (20 ml), the mixture was subsequently stirred for a further 60 min, the phases were separated, the aqueous phase was extracted twice with $CH_2Cl_2$, the combined organic phases were washed with water and dried ($Na_2SO_4$) and the solution was concentrated i. vac. The residue which remained was purified by flash chromatography with $CHCl_3$/MeOH (9:1).

Yield: 327 mg (34%), colourless oil
$^1$H-NMR (DMSO-$d_6$): 1.70 (2H, m); 2.14 (6H, m); 2.37 (2H, m); 2.65 (2H, m); 3.23 (2H, t); 4.45 (2H, t); 6.04 (1H, s); 6.95 (2H, m); 7.21-7.51 (7H, m); 7.67 (1H, s); 7.94 (1H, s); 10.74 (1H, s).

4-(3-(2-(1H-1,2,3-triazol-1-yl)ethyl)-1H-indol-2-yl)-N,N-dimethyl-1-phenylcyclohexanamine, citrate (2:1):Less polar diastereomer Tin (0.90 g) was added to a solution of the olefin just prepared (300 mg, 0.73 mmol) in HBr/glacial acetic acid (20 ml) in the course of 20 min and the mixture was stirred at RT for 5 h. Ethanol was added to the mixture, the reaction mixture was concentrated to dryness and the residue was dissolved in 5 N NaOH (40 ml) and methylene chloride (30 ml). The phases were separated, the aqueous phase was extracted twice with $CH_2Cl_2$ and the combined organic phases were washed with water, dried over $Na_2SO_4$ and concentrated i. vac. The residue which remained was separated by flash chromatography with $CHCl_3$/MeOH (20:1→9:1).

Yield: 96 mg (32%) non-polar diastereomer
77 mg (26%) polar diastereomer

The less polar diastereomer just obtained (84 mg, 0.20 mmol) was dissolved in hot ethanol (3 ml), and a solution of citric acid (39 mg, 0.20 mmol) in hot ethanol (2 ml) was added. After the mixture had stood in a refrigerator for 2 hours, the solid formed was filtered off with suction and dried i. vac.

Yield: 86 mg (70%); melting point: 230-232° C.
$^1$H-NMR (DMSO-$d_6$): 1.47 (4H, m); 2.02 (2H, m); 2.12 (6H, s); 2.57-2.83 (6H, m); 3.21 (2H, t); 4.55 (2H, t); 6.97 (2H, m); 7.39 (7H, m); 7.65 (1H, s); 8.02 (1H, s); 10.70 (1H, s).
Citrate: (ethanol)

Example 216

-(3-(2-(1H-1,2,3-triazol-1-yl)ethyl)-1H-indol-2-yl)-N,N-dimethyl-1-phenylcyclohexanamine, citrate (1:1):More polar diastereomer The more polar diastereomer obtained under Example 215 (73 mg, 0.17 mmol) was dissolved in hot ethanol (3 ml), and a solution of citric acid (34 mg, 0.17 mmol) in hot ethanol (2 ml) was added. After the mixture had stood in a refrigerator for 2 hours, the solid formed was filtered off with suction and dried i. vac.

Yield: 62 mg (58%), porous solid
$^1$H-NMR (DMSO-$d_6$): 1.40 (2H, m); 1.58 (2H, m); 1.88 (2H, m); 2.40 (6H, m); 2.57 (8H, m); 2.99 (1H, m); 3.20 (2H, t); 4.54 (2H, t); 6.91 (1H, m); 7.14 (1H, m); 7.42-7.67 (8H, m); 7.95 (1H, s); 10.45 (1H, s).
Citrate: (ethanol), porous solid

Example 217

(±)-2-(4-(Dimethylamino)-4-phenylcyclohex-1-enyl)-3-(2-(5-methyl-1H-tetrazol-1-yl)ethyl)-1H-indole Indole (Ind-77, 900 mg, 3.96 mmol) and ketone (Ket-10, 860 mg, 3.96 mmol) were dissolved in abs. methylene chloride (40 ml), and trifluoromethanesulfonic acid (1.06 ml, 12 mmol) was added rapidly. The mixture was stirred at RT overnight, during which a dark brown oil settled out. After addition of 1 N NaOH (20 ml) and $CH_2Cl_2$ (40 ml), the mixture was subsequently stirred for a further 60 min, the phases were separated, the aqueous phase was extracted twice with $CH_2Cl_2$, the combined organic phases were washed with water and dried ($Na_2SO_4$) and the solution was concentrated i. vac. The residue which remained was purified by flash chromatography with $CHCl_3$/MeOH (9:1).

Yield: 700 mg (41%), porous solid
$^1$H-NMR (DMSO-$d_6$): 1.69 (2H, m); 2.02-2.32 (11H, m); 2.61 (2H, m); 3.19 (2H, m); 4.36 (2H, m); 6.02 (1H, s); 6.90 (1H, m); 7.01 (1H, m); 7.22 (5H, m); 7.48 (2H, m); 10.78 (1H, s).

N,N-dimethyl-4-(3-(2-(5-methyl-1H-tetrazol-1-yl) ethyl)-1H-indol-2-yl)-1-phenylcyclohexanamine, citrate (2:1):Less polar diastereomer Tin (1.90 g) was added to a solution of the olefin just prepared (670 mg, 1.57 mmol) in HBr/glacial acetic acid (40 ml) in the course of 20 min and the mixture was stirred at RT for 3 h. Ethanol was added to the mixture, the reaction mixture was concentrated to dryness and the residue was dissolved in 5 N NaOH (40 ml) and methylene chloride (30 ml). The phases were separated, the aqueous phase was extracted twice with $CH_2Cl_2$ and the combined organic phases were washed with water, dried over $Na_2SO_4$ and concentrated i. vac. The residue which remained was separated by flash chromatography with $CHCl_3$/MeOH (9:1→1:1).

Yield: 107 mg (16%) non-polar diastereomer
145 mg (22%) polar diastereomer

The less polar diastereomer just obtained (103 mg, 0.24 mmol) was dissolved in hot ethanol (2 ml), and a solution of citric acid (46 mg, 0.24 mmol) in hot ethanol (2 ml) was added. After the mixture had stood in a refrigerator for 2 hours, the solid formed was filtered off with suction and dried i. vac.

Yield: 86 mg (217, 58%); melting point: 198-199° C.
$^1$H-NMR (DMSO-$d_6$): 1.40 (2H, m); 1.59 (2H, m); 1.97 (3H, s); 2.10 (2H; m); 2.25 (6H, s); 2.57-2.74 (4H, m); 3.31 (2H, t); 4.52 (2H, t); 6.96 (2H, m); 7.39 (7H, m); 10.86 (1H, s), citrate.

Example 218

N,N-dimethyl-4-(3-(2-(5-methyl-1H-tetrazol-1-yl) ethyl)-1H-indol-2-yl)-1-phenylcyclohexanamine, citrate (2:1):More polar diastereomer The more polar diastereomer obtained under Example 217 (130 mg, 0.30 mmol) was dissolved in hot ethanol (3 ml), and a solution of citric acid (58 mg, 0.30 mmol) in hot ethanol (2 ml) was added. After the mixture had stood in a refrigerator for 2 hours, the solid formed was filtered off with suction and dried i. vac.

Yield: 106 mg (218, 56%); melting point: 252-253° C.
$^1$H-NMR (DMSO-$d_6$): 1.41 (2H, m); 1.50 (2H, m); 1.96 (3H, s); 2.05 (2H; m); 2.37 (6H, s); 2.61 (2H, m); 3.02 (2H, m); 3.17 (2H, t); 4.50 (2H, t); 6.93 (2H, m); 7.16 (1H, m); 7.29 (1H, m); 7.51 (3H, m); 7.68 (2H, m); 10.48 (1H, s), citrate.

Example 219

2-[2-(4-Dimethylamino-4-phenyl-cyclohexyl)-1H-indol-3-yl]-ethanol, 1 diastereomer (219a)

Ex. 220 (1.70 g, 4.2 mmol) was suspended in methanol (35 ml), a solution of KOH (800 mg, 14.4 mmol) in water (7 ml) was added and the mixture was boiled under reflux. After 16 h further KOH (2.66 g, 47 mmol) in solid form was added and the mixture was stirred at RT for 72 h. The precipitate was filtered off with suction. The precipitate was washed with water, and thereby dissolved. The aqueous solution was extracted six times with $CHCl_3$ and the organic phase was dried over $Na_2SO_4$, filtered and concentrated.

Yield (219): 645 mg (42%, 1 diastereomer); melting point: 125-127° C.
$^1$H-NMR (DMSO-$d_6$): 1.47 (2H, m); 1.70 (4H, m); 1.93 (6H, s); 2.78 (4H, m); 2.92 (1H, t); 3.51 (2H, m); 4.57 (1H; s); 6.91 (2H, m); 7.15 (1H, m); 7.38 (6H, m); 10.31 (1H, bs).

$^{13}$C-NMR (DMSO-$d_6$): 28.04; 29.23; 33.11; 35.86; 37.97; 60.79; 61.91; 105.92; 110.64; 117.36; 117.85; 119.61; 126.16; 127.68; 127.85; 128.20; 135.20; 136.82; 140.14.

Example 220

2-(2-(4-(Dimethylamino)-4-phenylcyclohexyl)-1H-indol-3-yl)ethyl acetate, 1 diastereomer

2-(2-(4-(Dimethylamino)-4-phenylcyclohex-1-enyl)-1H-indol-3-yl)ethyl acetate 2-(1H-Indol-3-yl)-ethanol (Ind-5, 6.44 g, 40 mmol) and Ket-10 (8.68 g, 40 mmol) were dissolved in 33% strength HBr/glacial acetic acid (35 ml), under argon and while cooling with ice, and the mixture was stirred at RT for 3 d.

The amount of $NaHCO_3$ required for neutralizing the HBr (93.7 g, 1.12 mol) was added in portions in solid form, while cooling with ice, and the mixture was stirred at 40° C. for 3 h until no further gas formed. The acetic acid was removed i. vac., ethyl acetate was added to the residue and the mixture was stirred with saturated $NaHCO_3$ solution at 40° C. for 1 h until no further gas formed. The aqueous phase was separated off and extracted three times with ethyl acetate. The combined organic phases were washed with saturated $NaHCO_3$ solution and water and dried over $Na_2SO_4$. The organic phase was filtered and concentrated i. vac. and the residue was purified by flash chromatography with 500 g of silica gel and chloroform/methanol (20:1).

Yield (2-(2-(4-(Dimethylamino)-4-phenylcyclohex-1-enyl)-1H-indol-3-yl)ethyl acetate): 15.7 g (98%), yellow solid; melting point: 146-148° C.

$^1$H-NMR (DMSO-$d_6$): 1.72 (2H, m); 1.98 (3H, s); 2.14 (7H, m); 2.58 (1H, m); 2.77 (1H, m); 3.01 (2H, m); 4.08 (2H; t); 6.22 (1H, bs); 6.94 (2H, m); 7.31 (4H, m); 7.45 (3H, m); 10.7 (1H, bs).

$^{13}$C-NMR (DMSO-$d_6$): 20.70; 24.04; 26.61; 27.00; 32.61; 37.93; 60.19; 63.93; 105.68; 110.77; 117.84; 118.45; 120.96; 125.81; 126.32; 127.42; 128.42; 129.48; 135.14; 136.51; 142.61; 170.20.

2-(2-(4-(Dimethylamino)-4-phenylcyclohexyl)-1H-indol-3-yl)ethyl acetate, 1 diastereomer (220)

2-(2-(4-(Dimethylamino)-4-phenylcyclohex-1-enyl)-1H-indol-3-yl)ethyl acetate (6.80 g, 16.9 mmol) was dissolved in acetic acid (300 ml), palladium/active charcoal 10% strength (2.10 g) was added and hydrogenation was carried out with hydrogen at 50° C. under 3 bar for 16 h, further hydrogenation was then carried out at RT for 16 h and the catalyst was then filtered off over Celite.

The acetic acid was removed i. vac. The diastereomer mixture obtained (6.24 g, 90%) was slightly contaminated and was therefore washed with ether. A diastereomer was isolated by this procedure.

Yield (220): 1.70 g (25%); melting point: 164-172° C.
$^1$H-NMR (DMSO-$d_6$): 1.51 (2H, m); 1.70 (3H, m); 1.90-1.99 (10H, m); 2.79 (2H, m); 2.89 (3H, m); 4.08 (2H; t); 6.88 (2H, m); 6.95 (1H, m); 7.31 (6H, m); 10.44 (1H, bs).

Example 221

N,N-Dimethyl-4-(3-methyl-1H-pyrrolo[3,2-c]pyridin-2-yl)-1-phenylcyclohexanamine, citrate (1:2), non-polar diastereomer

Example 222

N,N-Dimethyl-4-(3-methyl-1H-pyrrolo[3,2-c]pyridin-2-yl)-1-phenylcyclohexanamine, citrate (1:2), polar diastereomer 4-(Dimethylamino)-4-phenyl-1-(prop-1-ynyl)cyclohexanol The ketone Ket-10 (3,000 mg, 13.81 mmol) was initially introduced into tetrahydrofuran (absolute, 50 ml) at −78° C. Prop-1-ynyl magnesium bromide (31.8 ml, 15.88 mmol, 0.5 M in tetrahydrofuran) was added dropwise under argon. The reaction mixture was then stirred at −78° C. for 15 min. Thereafter, it was warmed to room temperature and stirred at this temperature for 1 h. Ammonium chloride solution (50 ml; 1.0 M) was then added. The phases were separated. The aqueous phase was extracted with tetrahydrofuran (3×50 ml). The combined organic phases were dried with sodium sulfate and the volatile constituents were then removed completely in vacuo. A pale brown oil remained, to which diethyl ether (20 ml) was added. A white solid precipitated out (990 mg, 4-dimethylamino-4-phenyl-1-(prop-1-ynyl)cyclohexanol, non-polar diastereomer). The wash solution was concentrated down to 5 ml in vacuo. A white solid again precipitated out (1,350 mg, diastereomer mixture). The wash solution was evaporated slowly to 3 ml. A product fraction again precipitated out (410 mg; both diastereomers).

Yield (4-(Dimethylamino)-4-phenyl-1-(prop-1-ynyl)cyclohexanol): 2,750 mg (10.68 mmol; 77%, diastereomer mixture)

4-Dimethylamino-1-(3-methyl-1H-pyrrolo[3,2-c]pyridin-2-yl)-4-phenylcyclohexanol

4-Amino-3-iodopyridine (2,331 mg, 10.60 mmol), 4-(dimethylamino)-4-phenyl-1-(prop-1-ynyl)cyclohexanol (3,000 mg, 11.66 mmol, diastereomer mixture), lithium chloride (472 mg, 11.13 mmol) and sodium carbonate (3,369 mg, 31.79 mmol) were combined in dimethylformamide (absolute, 45 ml) in an argon atmosphere. The catalyst ([Pd(dppf)Cl$_2$×CH$_2$Cl$_2$], 865 mg, 1.06 mmol) was then added. The red solution was heated at 100° C. (oil bath temperature) for 4 h. The black reaction mixture was cooled to room temperature and water (50 ml; stirring for 10 min), methylene chloride (50 ml) and saturated sodium chloride solution (100 ml for better phase separation) were added in succession. The phases were separated. The mixture was filtered over kieselguhr beforehand. The aqueous phase was extracted with methylene chloride (3×30 ml). The combined organic phases were washed with saturated sodium chloride solution (3×20 ml), dried with sodium sulfate and filtered and the volatile constituents were then removed completely in vacuo. The residue was absorbed on silica gel and separated by chromatography (silica gel [200 g]; chloroform/ethanol [9:1 1,000 ml, 5:1, 500 ml, 3:1, 500 ml, 1:1, 500 ml and 1:3, 500 ml]). 800 mg of 4-dimethylamino-1-(3-methyl-1H-pyrrolo[3,2-c]pyridin-2-yl)-4-phenylcyclohexanol (non-polar diastereoisomer) were isolated as a colourless solid and 765 mg of the polar diastereoisomer were isolated as a colourless solid.

(±)-N,N-Dimethyl-N-[4-(3-methyl-1H-pyrrolo[3,2-c]pyridin-2-yl)-1-phenylcyclohex-3-enyl]amine P$_4$O$_{10}$ (approx. 1 g, two spatula-tips) was added to a solution of 4-dimethylamino-1-(3-methyl-1H-pyrrolo[3,2-c]pyridin-2-yl)-4-phenylcyclohexanol (600 mg, 1.72 mmol) in methanesulfonic acid (20 ml). The slightly pale brown-coloured solution was stirred at 77° C. (oil bath temperature) for 3 h. Water (10 ml) was added to the reaction mixture and this was rendered basic with sodium hydroxide solution (5 M). Methylene chloride (30 ml) was then added and the mixture was stirred for 10 min. The phases were separated. The aqueous phase was extracted with methylene chloride (3×35 ml). The combined organic phases were dried over sodium sulfate. The volatile constituents were then removed completely in vacuo. 425 mg of (±)-N,N-dimethyl-N-[4-(3-methyl-1H-pyrrolo[3,2-c]pyridin-2-yl)-1-phenylcyclohex-3-enyl]amine remained (dark brown solid, slightly contaminated).

N,N-Dimethyl-4-(3-methyl-1H-pyrrolo[3,2-c]pyridin-2-yl)-1-phenylcyclohexanamine, (non-polar and polar diastereomer)

Tin powder (3.00 g, 45 mmol) was added to N,N-Dimethyl-N-[4-(3-methyl-1H-pyrrolo[3.2-c]pyridin-2-yl)-1-phenylcyclohex-3-enyl]amine (525 mg, 1.58 mmol) in HBr/glacial acetic acid (33 per cent strength; 30 ml) in the course of 150 min (vigorous evolution of gas). The reaction mixture became dark brown in colour. The mixture was stirred at room temperature overnight. The reaction mixture was then evaporated to dryness in vacuo and 5 N sodium hydroxide solution (20 ml) was added to the residue. Methylene chloride (20 ml) was added to the pale-coloured suspension and the mixture was stirred for 10 min. Insoluble grey powder was then filtered off. Thereafter, the phases of the filtrate were separated. The aqueous phase was extracted with methylene chloride (2×20 ml) and trichloromethane/ethanol (2×20 ml; 1:1). The combined organic phases were dried with sodium sulfate and the volatile constituents were then removed completely in vacuo. The residue (250 mg of pale yellow powder) was separated by chromatography [silica gel 60 (100 g), ethyl acetate/methanol 1:1 (500 ml); methanol (1,000 ml)]. 20 mg (0.06 mmol; 4%) of N,N-dimethyl-4-(3-methyl-1H-pyrrolo[3,2-c]pyridin-2-yl)-1-phenylcyclohexanamine (non-polar diastereoisomer) and 78 mg (0.41 mmol; 15%) of the polar diastereoisomer were isolated.

N,N-Dimethyl-4-(3-methyl-1H-pyrrolo[3,2-c]pyridin-2-yl)-1-phenylcyclohexanamine, citrate (1:2), non-polar diastereomer Dimethyl-4-(3-methyl-1H-pyrrolo[3,2-c]pyridin-2-yl)-1-phenylcyclohexanamine (less polar diastereoisomer) (20 mg, 0.06 mmol) was suspended in ethanol (5 ml), and citric acid (13 mg, 0.07 mmol) was added. The reaction mixture was stirred vigorously at the boiling point for 1 h and then cooled to room temperature and concentrated to approx. 3 ml in vacuo. The solution was left to stand at room temperature overnight. A colourless solid precipitated out. The precipitation was brought to completion by adding diethyl ether (5 ml). The mixture was left to stand at room temperature for 3 h. The supernatant solution was siphoned off. The solid was washed with diethyl ether (10 ml) and dried in vacuo. Example 221 (m.p. 103-105° C.) was obtained as a pale brown solid (28 mg, 0.04 mmol, 89%). $^1$H NMR (400 MHz, RT, pyridine-D$_5$) δ ppm: 1.70 (psq, 2H), 1.94 (psd, 2H), 2.60 (pst, 2H) 2.19 (s, 6H), 2.29 (s, 3H), 2.85 (psd, 2H), 3.17 (pst, 1H), 3.67 (dd, 8H), 7.28 (t, 2H), 7.35 (psd, 2H), 7.39-7.46 (m, 1H), 7.48-7.54 (m, 1H), 8.44 (psq, 1H), 9.15 (s, 1H), 9.20-10.4 (s, br, 12 [incl. H$_2$O]), 12.38 (s, 1H).
$^{13}$C NMR (101 MHz, pyridine-D$_5$) δ ppm: 8.3, 29.3, 33.0, 36.2, 38.0, 45.0, 63.3, 74.3, 106.3, 106.9, 126.6, 127.6, 128.0, 128.5, 128.7, 137.0, 138.9, 140.7, 142.9, 173.7, 178.1.

N,N-Dimethyl-4-(3-methyl-1H-pyrrolo[3,2-c]pyridin-2-yl)-1-phenylcyclohexanamine, citrate (1:2), polar diastereomer N,N-Dimethyl-4-(3-methyl-1H-pyrrolo[3,2-c]pyridin-2-yl)-1-phenylcyclohexanamine (more polar diastereoisomer) (78 mg, 0.23 mmol) was suspended in ethanol (5 ml), and citric acid (49 mg, 0.26 mmol) was added. The mixture was stirred vigorously at the boiling point for 1 h. The reaction mixture was cooled to room temperature and left to stand at room temperature overnight. A colourless solid precipitated out. The precipitation was brought to completion by adding diethyl ether (5 ml). The mixture was left to stand at room temperature for 3 h. The supernatant solution was siphoned off. The solid washed with diethyl ether (10 ml) and dried in vacuo. Example 222 m.p. 116-119° C.) was obtained as an ochre-coloured solid (114 mg, 0.16 mmol; 93%).
$^1$H NMR (400 MHz, RT, pyridine-D$_5$) δ ppm: 1.69 (pst, 2H), 1.86 (psd, 2H), 2.32 (s, br. 9H), 2.64 (psd, 2H), 2.96 (psd, 2H), 3.11 (pst, 1H), 3.67 (dd, 8H), 7.42-7.59 (m, 6H), 8.48 (s, 1H), 9.16 (s, 1H, lies over the following signal on top), 8.80-10.0 (s, br, 10 [incl. H$_2$O]), 13.37 (s, 1H).
$^{13}$C NMR (101 MHz, pyridine-D$_5$) δ ppm: 8.3, 27.3, 33.1, 34.7, 37.8, 44.8, 61.0 (br), 74.3, 106.5, 107.4, 126.4, 127.6, 127.9, 128.3, 137.7, 141.2, 144.4, 173.7, 178.1, 2 signals in the aromatic region (n.d.).

Example 223

N,N-Dimethyl-4-(3-methyl-1H-pyrrolo[2,3-b]pyridin-2-yl)-1-phenylcyclohexanamine, citrate (1:1), non-polar diastereomer Example 224

N,N-dimethyl-4-(3-methyl-1H-pyrrolo[2,3-b]pyridin-2-yl)-1-phenylcyclohexanamine, citrate (1:1), polar diastereomer N,N-dimethyl-4-(3-methyl-1H-pyrrolo[2,3-b]pyridin-2-yl)-1-phenylcyclohexanamine, (non-polar and polar diastereomer)

Tin powder (1,500 mg) was added to a suspension of the free base from Example 32 (325 mg, 0.98 mmol) in HBr/glacial acetic acid (35%; 20 ml) in the course of 90 min. The reaction mixture became dark brown in colour. The mixture was stirred for 3 h. The reaction mixture was then evaporated to dryness in vacuo and 5 N sodium hydroxide solution (20 ml) was added to the residue. The pale-coloured suspension was extracted with methylene chloride (3×20 ml). Insoluble constituents in the form of a grey powder were filtered off with suction. The combined organic phases were dried with sodium sulfate. The volatile constituents were then removed completely in vacuo. The residue (pale yellow powder) was separated by chromatography (silica gel [100 g]; chloroform/ethanol [19:1, 500 ml]; [9:1, 500 ml]; [5:1; 1,000 ml]). It was possible to isolate 85 mg (0.26 mmol; 26%) of N,N-dimethyl-4-(3-methyl-1H-pyrrolo[2,3-b]pyridin-2-yl)-1-phenylcyclohexanamine (non-polar diastereomer) and 137 mg (0.41 mmol; 42%) of the polar diastereoisomer as a colourless powder.

N,N-Dimethyl-4-(3-methyl-1H-pyrrolo[2,3-b]pyridin-2-yl)-1-phenylcyclohexanamine, citrate (1:1), non-polar diastereomer (223)

N,N-dimethyl-4-(3-methyl-1H-pyrrolo[2,3-b]pyridin-2-yl)-1-phenylcyclohexanamine (non-polar diastereomer) (70 mg, 0.18 mmol) was suspended in ethanol (10 ml), and citric acid (44 mg, 0.23 mmol) was added. The mixture was stirred vigorously at the boiling point for 1 h. The reaction mixture was cooled to room temperature and left to stand overnight. The supernatant solution was siphoned off from the colourless precipitate and discarded. Example 223 (25 mg; 23%) was isolated as a colourless solid (melting point: 176-179° C.).

N,N-dimethyl-4-(3-methyl-1H-pyrrolo[2,3-b]pyridin-2-yl)-1-phenylcyclohexanamine, citrate (1:1), polar diastereomer (224)

N,N-dimethyl-4-(3-methyl-1H-pyrrolo[2,3-b]pyridin-2-yl)-1-phenylcyclohexanamine (polar diastereomer) (100 mg, 0.30 mmol) was suspended in ethanol (10 ml), and citric acid (63 mg, 0.32 mmol) was added. The mixture was stirred vigorously at the boiling point for 1 h. The reaction mixture was cooled to room temperature and stored overnight. A colourless solid precipitated out. The supernatant solution was siphoned off from the colourless precipitate and discarded. 114 mg (0.22 mmol; 72%) of Example 224 (melting point: 194-197° C.) were isolated.

Example 225

N,N-dimethyl-4-(3-methylbenzofuran-2-yl)-1-phenylcyclohexanamine, citrate (1:1):More polar diastereomer The olefin prepared under Example 240 (500 mg, 1.9 mmol) was dissolved in HBr/glacial acetic acid (33% HBr, 20 ml), and tin powder (1.4 g, 12 mmol) was added in portions at RT in the course of 30 min. When the addition had ended, the reaction mixture was stirred for a further 14 h.—For working up, the mixture was concentrated to dryness on a rotary evaporator. The residue which remained was rendered basic by addition of 5 N NaOH (40 ml). Methylene chloride was added to the solution obtained and the mixture was extracted (4×20 ml). The combined organic phases were dried with MgSO$_4$ and then concentrated. The residue obtained (442 mg) was purified by column chromatography (mobile phase: 1. EtOAc/EtOH 10:1; 2. EtOAc/EtOH 2:1). The non-polar diastereoisomer (156 mg, 31%, m.p.: from 128° C., main amount 136-141° C.) and the polar diastereoisomer (250 mg, 49%, m.p.: 136-138° C.) were obtained in this manner.

The more polar amine diastereoisomer just isolated (157 mg, 0.47 mmol) was dissolved in isopropanol (5 ml) at the boiling point and citric acid (96 mg, 0.5 mmol), dissolved in hot isopropanol (5 ml), was added. The solvent volume was reduced to about 5 ml. The solution which remained was cooled to 5° C. (refrigerator) and left to stand for 17 h. The precipitate formed was separated off by means of a frit. The citrate of the polar amine was obtained in this way in a yield of 135 mg (54%, melting point: 169-171° C.).

Example 226

N,N-dimethyl-4-(3-methylbenzofuran-2-yl)-1-phenylcyclohexanamine, citrate (1:1):Less polar diastereomer The less polar diastereomer prepared under Example 225 (146 mg, 0.44 mmol) was dissolved in isopropanol (10 ml) at the boiling point and citric acid (96 mg, 0.5 mmol), dissolved in hot isopropanol (1 ml), was added. The solution was cooled to 5° C. (refrigerator) and left to stand for 17 h. The precipitate formed was separated off by means of a frit. The hemicitrate of the non-polar amine, compound, was obtained in this way in a yield of 167 mg (88%, melting point: 184-185° C.).

Example 227

4-(1H-indol-3-yl)-N,N-dimethyl-1-phenylcyclohexanamine, citrate (1:1):One of 2 possible diastereomers 1H-indole (351 mg, 3 mmol) was dissolved in methylene chloride (20 ml) together with the ketone (Ket-10, 651 mg, 3 mmol), and trifluoromethanesulfonic acid (0.3 ml, 3.4 mmol) was added. After approx. 30 min a precipitate precipitated out. The mixture was stirred at RT for 17 h. Triethylsilane (1 ml, 6.2 mmol) was then added to the mixture and the mixture was stirred at RT for a further 2 d. Since a precipitate existed throughout the entire time, ethanol (10 ml) was added to the mixture until a clear solution formed. Triethylsilane (1 ml, 6.2 mmol) was added to the reaction mixture obtained and the mixture was stirred for 20 h (this treatment is probably superfluous, since in an experiment in which a homogeneous solution was already generated by means of ethanol before the first addition of the silane, in that it was not possible to isolate the desired product).—For working up, 2 N NaOH (10 ml) was added to the reaction mixture. The mixture was stirred for a further 10 min and saturated $NH_4Cl$ solution (30 ml) was added in order to facilitate a phase separation. After the organic phase had been separated off, the aqueous phase was extracted with methylene chloride (3×20 ml). The combined organic extracts were dried over $MgSO_4$ and then concentrated. Ethyl acetate (approx. 20 ml) was added to the crude product obtained (1.12 g) and the insoluble contents were separated off by means of a frit. The solution obtained was concentrated and the residue was purified by column chromatography (mobile phase: EtOAc). One of the two possible isomers was obtained in this way in a yield of 140 mg (11%, melting point 210-214° C., after recrystallization from 2-propanol).

The amine just obtained (120 mg, 0.38 mmol) was dissolved in isopropanol (10 ml) at the boiling point and citric acid (80 mg, 0.4 mmol), dissolved in hot isopropanol (4 ml), was added. Directly after the addition of the acid, a precipitate precipitated out. To bring the precipitation to completion, the mixture was cooled to 5° C. (refrigerator) and left to stand for 12 h. The precipitate was separated off by means of a frit and then dried. The desired product was obtained in this way in a yield of 111 mg (71%, melting point: from 197-201° C.) as the hemicitrate.

Example 228

(±)-3-(4-(Dimethylamino)-4-benzylcyclohex-1-enyl)-1H-pyrrolo[2,3-b]pyridine

7-Azaindole (Ind-86) (637 mg, 5.39 mmol) and ketone Ket-3 (1.247 g, 5.39 mmol) were dissolved in 2 N KOH/MeOH (50 ml) and the solution was boiled under reflux for 16 h. For working up, MeOH was distilled off and $H_2O$ (60 ml) was added to the reaction mixture. The aqueous phase was extracted with methylene chloride (3×30 ml). The combined organic extracts were dried over $Na_2SO_4$ and then concentrated. The residue was recrystallized from MeOH (20 ml). Example 228 was obtained in a yield of 929 mg as a white solid (52%, melting point: 222-225° C.

$^1$H NMR (300 MHz, DMSO-$d_6$) δ ppm: 1.25-1.52 (m, 1H), 1.84-1.99 (m, 1H), 1.99-2.13 (m, 1H), 2.30 (s, 6H), 2.32-2.39 (m, 2H), 2.39-2.46 (m, 1H), 2.75 (dd, J=13.42, 6.72 Hz, 2H), 5.97-6.12 (m, 1H), 7.05 (dd, J=7.92, 4.71 Hz, 1H), 7.10-7.22 (m, 1H), 7.22-7.31 (m, 4H), 7.42 (s, 1H), 8.12-8.22 (m, 2H), 11.54 (s, 1H)

Example 229

(±)-3-(4-(Dimethylamino)-4-butylcyclohex-1-enyl)-1H-pyrrolo[2,3-b]pyridine

7-Azaindole (Ind-86) (591 mg, 5 mmol) and Ket-4 (987 mg, 5 mmol) were dissolved in 2 N KOH/MeOH (50 ml) and the solution was boiled under reflux for 16 h. For working up, MeOH was distilled off and $H_2O$ (100 ml) was added to the reaction mixture. The aqueous phase was extracted with methylene chloride (4×30 ml). The combined organic extracts were dried over $Na_2SO_4$ and then concentrated. The residue was recrystallized from MeOH (20 ml). Example 229 was obtained in a yield of 553 mg as a white solid (37%, melting point: 142-145° C.).

$^1$H NMR (300 MHz, DMSO-$d_6$) δ ppm: 0.87 (t, J=6.91 Hz, 3H), 1.10-1.55 (m, 6H), 1.55-1.68 (m, 1H), 1.68-1.48 (m, 1H), 1.85-2.02 (m, 1H), 2.03-2.60 (m, 9H), 6.02-6.23 (m, 1H), 7.06 (dd, J=7.91, 4.70 Hz, 1H), 7.45 (s, 1H), 8.13-8.23 (m, 2H), 11.54 (s, 1H)

$^{13}$C NMR (101 MHz, DMSO-$d_6$) δ ppm: 14.1, 23.0, 25.1, 25.8, 28.2, 29.8, 31.8, 37.6, 55.2, 115.3, 115.5, 116.9, 119.2, 122.4, 128.3, 130.1, 142.4, 149.0

Example 230

(±)-3-(4-(Dimethylamino)-4-phenylcyclohex-1-enyl)-1H-pyrrolo[2,3-b]pyridine, citrate (1:2)

(±)-3-(4-(Dimethylamino)-4-phenylcyclohex-1-enyl)-1H-pyrrolo[2,3-b]pyridine

7-Azaindole (Ind-86) (294 mg, 2.49 mmol) and Ket-10 (540 mg, 2.58 mmol) were dissolved in 2 N KOH/MeOH (20 ml) and the solution was boiled under reflux for 10 h. For working up, MeOH was distilled off and $H_2O$ (40 ml) was added to the reaction mixture. The aqueous phase was extracted with methylene chloride (3×20 ml). The combined organic extracts were dried over $Na_2SO_4$ and then concentrated. (±)-3-(4-(Dimethylamino)-4-phenylcyclohex-1-enyl)-1H-pyrrolo[2,3-b]pyridine was obtained in a yield of 740 mg (94%) as a beige solid.

(±)-N,N-Dimethyl-N-[1-phenyl-4-(1H-pyrrolo[2,3-b]pyridin-3-yl)cyclohex-3-enyl]ammonium citrate (±)-2-(4-(Dimethylamino)-4-phenylcyclohex-1-enyl)-1H-pyrrolo[2,3-b]pyridine (640 mg, 2 mmol) was dissolved in isopropanol (20 ml) at the boiling point and citric acid (385 mg, 2 mmol), dissolved in hot isopropanol (5 ml), was added. The mixture was left to stand at 5° C. for 16 h. The white precipitate formed was separated off by means of a frit. Example 230 was obtained in a yield of 670 mg (65%, melting point: 107-110° C.).

$^1$H NMR (300 MHz, DMSO-$d_6$) δ ppm: 1.78-1.90 (m, 1H), 2.16-2.32 (m, 1H), 2.42 (s, 6H) 2.53-2.70 (m, 6H), 2.72-2.90 (m, 1H) 3.05-3.19 (m, 1H), 6.25 (m, 1H), 7.08 (dd, J=7.90, 4.62 Hz, 1H), 7.28-7.50 (m, 4H), 7.63 (d, J=7.49 Hz, 2H), 8.12-8.23 (m, 2H), 11.58 (s, 1H)

$^{13}$C NMR (101 MHz, DMSO-$d_6$) δ ppm: 25.9, 27.9, 30.1, 37.8, 38.9, 43.6, 62.0, 71.7, 114.3, 115.6, 116.7, 117.1, 123.0, 127.9, 128.2, 130.6, 136.5, 142.6, 148.9, 171.2, 176.0

Example 231

(±)-3-(4-(Dimethylamino)-4-phenylcyclohex-1-enyl)-1H-indole

1H-Indole (468 mg, 4 mmol) was dissolved in methylene chloride (40 ml) together with the ketone (Ket-10, 868 mg, 4 mmol), and trifluoromethanesulfonic acid (0.4 ml, 4.6 mmol) was added. The mixture was stirred at RT for 20 h.—For working up, 2 N NaOH (20 ml) was added to the reaction mixture. The mixture was stirred for a further 20 min. After separation of the phases, the aqueous phase was extracted with methylene chloride (2×20 ml). The combined organic extracts were dried over $Na_2SO_4$ and then concentrated. Ethyl acetate (approx. 10 ml) was added to the crude product obtained (1.2 g) and the insoluble contents were separated off by means of a frit. The clear solution obtained was purified by column chromatography (mobile phase: EtOAc). A mixture (230 mg) was obtained which, in addition to the desired product, contained small amounts of an isomer (probably substitution in the 2-position of the indole). By trituration with ethanol (approx. 5 ml), the desired product was obtained in a yield of 173 mg (13%, m.p.: 164-172° C.) in crystalline form.

The olefin obtained (158 mg, 0.5 mmol) was dissolved in isopropanol (20 ml) at the boiling point and citric acid (100 mg, 0.52 mmol), dissolved in hot isopropanol (4 ml), was added. Directly after the addition of the acid, a precipitate precipitated out. To bring the precipitation to completion, the mixture was cooled to 5° C. (refrigerator) and left to stand for 12 h. The precipitate was separated off by means of a frit and then dried. The desired product was obtained in this way in a yield of 109 mg (52%, melting point: from 98-102° C.) as the hemicitrate.

Example 232

(±)-3-(4-(Dimethylamino)-4-phenylcyclohex-1-enyl)-1H-indole

KOH (56 mg, 1 mmol) is dissolved in MeOH (10 ml). 1H-Indole (234 mg, 2 mmol) and ketone (Ket-10, 434 mg, 2 mmol) are added and the mixture is boiled under reflux for 12 h. The course of the reaction is monitored by TLC. The white solid formed is filtered off with suction and rinsed with $H_2O$ (3×5 ml). After drying of the solid, the desired olefin is obtained in a yield of 250 mg (39%). To prepare the hydrochloride, the olefin (250 mg, 0.785 mmol) is dissolved in ethyl methyl ketone, and 1.85 N 1.85 N EtOH/HCl (0.65 ml) is added. The white solid thereby formed is dried. The desired product 265 mg (37%) is obtained in this way with a melting point of 193-195° C.

Example 233

2-(3-(4-(dimethylamino)-4-phenylcyclohex-1-enyl)benzo[b]thiophen-2-yl)ethanol hydrochloride The ketone (Ket-10, 217 mg, 1 mmol) was dissolved in absolute methylene chloride (5 ml) together with 2-benzo[b]thiophen-2-ylethanol (Ind-89, 178 mg, 1 mmol) under argon. The addition of methanesulfonic acid (3 ml) then took place. The mixture was stirred at RT for 24 h. For working up, ice (30 g) was added to the reaction mixture. A colourless solid thereby precipitated out, and was suspended in 1 N sodium hydroxide solution (10 ml) and trichloromethane (30 ml), and the mixture was stirred for 30 min. The organic phase was separated off and the aqueous phase was extracted with trichloromethane (30 ml). After drying, the organic extracts were concentrated and the residue (295 mg) was separated by chromatography on silica gel (40 g) with ethyl acetate/methanol (4:1). The desired olefin was obtained in a yield of 14% (45 mg) as a colourless solid with a melting point of 151-153° C.

The olefin isolated (47 mg, 0.124 mmol) was dissolved in ethanol (5 ml), and 5 N isopropanolic hydrochloric acid (0.04 ml, 0.2 mmol) was added. After 1 h the clear solution was concentrated to 3 ml, diethyl ether (40 ml) was added and the mixture was stirred for 1 h. The desired hydrochloride was obtained as a colourless solid in a yield of 75% (38 mg) with a melting point of 219-221° C.

Example 234

2-(3-(4-(dimethylamino)-4-(pyridin-2-yl)cyclohex-1-enyl)benzo[b]thiophen-2-yl)ethanol hydrochloride The ketone (Ket-11, 218 mg, 1 mmol) was dissolved in absolute methylene chloride (5 ml) together with 2-benzo[b]thiophen-2-ylethanol (Ind-89, 178 mg, 1 mmol) under argon. The addition of methanesulfonic acid (3 ml) then took place. The mixture was stirred at RT for 3 d. For working up, ice (5 g) and water (30 ml) were added to the reaction mixture. After neutralization with $NaHCO_3$ (4.4 g, 52 mmol) and addition of 5 N NaOH (1 ml), methylene chloride (10 ml) was added. The organic phase was separated off and the aqueous phase was extracted with methylene chloride (2×30 ml). After drying, the organic extracts were concentrated and the residue (375 mg) was separated by chromatography on silica gel (45 g) with ethyl acetate/methanol (10:1), (4:1) and methanol. The desired olefin was obtained in a yield of 26% (100 mg) the as a colourless oily compound.

The olefin just isolated (100 mg, 0.264 mmol) was dissolved in ethanol (5 ml), and 5 N isopropanolic hydrochloric acid (0.104 ml, 0.52 mmol) was added. After 2.5 h the clear solution was concentrated to 3 ml, diethyl ether (30 ml) was added and the mixture was stirred for 1.5 h. The hydrochloride was obtained as a colourless solid in a yield of 67% (73 mg). It was not possible to determine a melting point.

Example 235

(±)-2-(4-(Dimethylamino)-4-phenylcyclohex-1-enyl)-1H-indole

1-Phenylsulfonyl-1H-indole (Ind-90, 1.2 g, 4.66 mmol) was dissolved in dry THF, and n-butyllithium (2.2 ml, 2.5 N solution in THF, 5.5 mmol) was added at −5° C. (ice/sodium chloride mixture) in the course of 30 min. The reaction mixture was stirred at 0° C. for 2 h, before the ketone (Ket-10, 986 mg, 4.66 mmol), dissolved in dry THF (10 ml), was added in the course of 15 min, while maintaining the temperature. The reaction mixture was then stirred at 0° C. for a further hour and, after removal of the cooling, at RT for 5 d.—For working up, NH$_4$Cl solution (30 ml) was added to the mixture and the mixture was stirred for 2 h. Water (20 ml) and ethyl acetate (50 ml) were then added to the reaction mixture. The organic phase was separated off and the aqueous phase was extracted with ethyl acetate (3×20 ml). The combined organic extracts were dried over MgSO$_4$ and then concentrated. Since it was not possible for the desired product to be isolated in adequate purity from the crude product obtained (1.8 g) by crystallization from 2-propanol (10 ml), purification by column chromatography was carried out [silica gel 60 (100 g); EtOAc (1,000 ml)]. The desired olefin was obtained in this way in a yield of 490 mg (33%, melting point 141-146° C.).

4-(1H-indol-2-yl)-N,N-dimethyl-1-phenylcyclohexanamine, citrate (1:1):More polar diastereomer The olefin just isolated (450 mg, 1.42 mmol) was dissolved in HBr/glacial acetic acid (33% HBr, 20 ml). Sn powder (2 g, 16.95 mmol) was then added to the mixture in portions at RT in the course of 2 h. When the addition had ended, the reaction mixture was stirred at RT for a further 60 min.—For working up, the mixture was diluted with EtOH (20 ml) and concentrated to dryness on a rotary evaporator. The residue which remained was rendered basic by addition of 5 N NaOH (60 ml). The aqueous mixture obtained was extracted with methylene chloride (4×20 ml). The combined organic phases were washed with water (50 ml), dried over MgSO$_4$ and then concentrated. After it emerged that purification by recrystallization was possible to only a limited extent, the crude product obtained (400 mg) was purified by column chromatography [silica gel 60 G (10 g); ethyl acetate, ethyl acetate/ethanol 2:1, methanol (in total 250 ml)]. The less polar product was obtained in a yield of 106 mg (23%, melting point: 159-164° C.), and the more polar product was obtained in a yield of 135 mg [30%, melting point: 205-211° C. (from 2-propanol)].

The more polar diastereomer just isolated (68 mg, 0.21 mmol) was dissolved in isopropanol (5 ml) at the boiling point and citric acid (59 mg, 0.3 mmol), dissolved in hot isopropanol (1 ml), was added. Directly after the addition of the acid, a precipitate precipitated out. To bring the precipitation to completion, the mixture was cooled to 5° C. (refrigerator) and left to stand for 17 h. The precipitate was separated off by means of a frit and then dried. The desired product was obtained in this way in a yield of 83 mg (76%, melting point: from 194-197° C.) as the citrate.

Example 236

4-(1H-indol-2-yl)-N,N-dimethyl-1-phenylcyclohexanamine, citrate (2:1):Less polar diastereomer The less polar diastereomer isolated under Example 235 (100 mg, 0.31 mmol) was dissolved in isopropanol (5 ml) at the boiling point and citric acid (60 mg, 0.31 mmol), dissolved in hot isopropanol (2 ml), was added. Directly after the addition of the acid, a precipitate precipitated out. To bring the precipitation to completion, the mixture was cooled to 5° C. (refrigerator) and left to stand for 17 h. The precipitate was separated off by means of a frit and then dried. The desired product was obtained in this way in a yield of 103 mg (79%, melting point: from 231-233° C.) as the hemicitrate.

Example 237

1-Benzyl-N,N-dimethyl-4-(1H-pyrrolo[2,3-b]pyridin-3-yl)cyclohexanamine hydrochloride, diastereomer mixture Palladium catalyst (Pd/C, 5%, 216 mg) was added to Ex. 228 (540 mg, 1.63 mmol) in abs. methanol (100 ml) and hydrogenation was carried out at RT for 36 h (hydrogen pressure: 3 bar). The catalyst was removed with the aid of a frit provided with a layer of Celite 1 cm high. The frit was washed thoroughly with methanol (1,000 ml). The solvent was distilled off in vacuo. 1-Benzyl-N,N-dimethyl-4-(1H-pyrrolo[2,3-b]pyridin-3-yl)cyclohexanamine was obtained in a yield of 350 mg (65%) as a white solid. It was a mixture of the two diastereoisomers.

The diastereoisomer mixture (350 mg, 1.05 mmol) was dissolved in ethyl acetate (100 ml). Me$_3$SiCl (265 µl, 2.1 mmol) was added dropwise at RT and the mixture was stirred for 1 h. A white precipitate precipitated out. The precipitate was filtered off with suction, washed with ethyl acetate (2×5 ml) and then dried.

Ex. 237 (350 mg, m.p. 215-219° C., 90%) was obtained as a white solid.

$^1$H NMR (400 MHz, DMSO-d$_6$) δ ppm: 1.39-1.94 (m, 4H), 2.01-2.316 (m, 4H), 2.57, 2.58 (2s, 6H), 2.80-3.00 (m, 3H), 7.23-7.48 (m, 6H), 7.53-7.91 (m, Hz, 1H), 8.30-8.44 (m, 1H), 8.53-8.80 (m, 1H), 10.03, 10.89 (2s, 1H), 12.65 (s, 1H)

$^{13}$C NMR (101 MHz, DMSO-d$_6$) δ ppm: 26.5, 28.8, 30.0, 31.4, 32.4, 32.6, 34.5, 37.3, 37.4, 66.02, 66.1, 114.6, 114.8, 119.8, 120.5, 123.1, 123.8, 124.8, 126.2, 127.0, 127.2, 128.2, 128.6, 130.7, 131.2, 133.9, 134.2, 134.9, 135.3, 136.0, 138.9, 140.2

Example 238

1-Butyl-N,N-dimethyl-4-(1H-pyrrolo[2,3-b]pyridin-3-yl)cyclohexanamine hydrochloride, 1 diastereomer (238)

Palladium catalyst (Pd/C, 5%, 200 mg) was added to Ex. 229 (500 mg, 1.68 mmol) in abs. methanol (100 ml) and hydrogenation was carried out at RT for 36 h (hydrogen pressure: 3 bar). The catalyst was removed with the aid of a frit provided with a layer of Celite 1 cm high. The frit was washed thoroughly with methanol (1,000 ml). The solvent was distilled off in vacuo. 1-Butyl-N,N-dimethyl-4-(1H-pyrrolo[2,3-b]pyridin-3-yl)cyclohexanamine was obtained in a yield of 428 mg (85%) as a white solid. Only one of two possible diastereoisomers was obtained.

1-Butyl-N,N-dimethyl-4-(1H-pyrrolo[2,3-b]pyridin-3-yl)cyclohexanamine (425 mg, 1.42 mmol) was dissolved in ethyl acetate (100 ml). Me$_3$SiCl (358 µl, 2.84 mmol) was then added dropwise at RT and the mixture was stirred for 1 h. A white precipitate precipitated out. The precipitate was filtered off with suction, washed with ethyl acetate (2×10 ml) and then dried. Example 238 (435 mg, 91%) was a colourless solid $^1$H NMR (300 MHz, DMSO-d$_6$) δ ppm: 0.79-0.97 (m, 4H), 1.21-1.48 (m, 5H), 1.53-1.71 (m, 3H), 1.74-1.88 (m, 3H), 1.97 (s, 6H) 2.69-2.96 (m, 3H), 7.44-7.52 (m, 1H), 7.57-7.60 (m, 1H), 8.40-846 (m, 1H), 8.68 (d, J=7.51 Hz, 1H), 10.62-10.43 (m, 1H), 12.88 (s, 1H)

$^{13}$C NMR (101 MHz, DMSO-d$_6$) δ ppm: 13.8, 22.6, 24.6, 26.7, 28.7, 29.5, 32.6, 37.1, 37.3, 66.00 (s, 1C), 114.8, 120.2, 123.7, 125.0, 134.1, 134.9, 139.3

Example 239

4-(Benzofuran-2-yl)-1-benzyl-N,N-dimethylcyclohex-3-enamine hydrochloride

A solution of benzo[b]furan (Ind-92, 612 mg, 5.12 mmol) in dry THF (40 ml) was cooled to −8° C. under a stream of argon. Thereafter, tert-butyllithium (6.22 mmol, 4.14 ml of a 1.5 M pentane solution) was added dropwise such that a reaction temperature of −5° C. was not thereby exceeded. When the addition had ended, the reaction mixture was stirred at −5° C. for 2 h. Thereafter, a solution of ketone (Ket-3, 1.198 g, 5.18 mmol) in dry THF (10 ml) was added dropwise at 0° C. The mixture was stirred at 0° C. for 1 h and then at room temperature for 4 d. The reaction mixture was quenched with saturated ammonium chloride solution (20 ml), the organic phase was separated off and the aqueous phase was extracted with methylene chloride (4×30 ml). The combined organic phases were dried over sodium sulfate. Thereafter, the solvent was removed in vacuo. Purification was carried out by means of flash chromatography [silica gel, cyclohexane/EtOAc (8:2)]. 380 mg (21%) of the cyclohexanol with a melting point of 121-124° C. were obtained A solution of the cyclohexanol just isolated (250 mg, 0.72 mmol) in hydrobromic acid (5 ml, 48%) was heated under reflux for 15 min. The cooled reaction mixture was adjusted to a pH of 9 with 5 N NaOH solution. Thereafter, the mixture was extracted with methylene chloride (4×10 ml). The combined organic phases were dried over sodium sulfate. Thereafter, the solvent was removed in vacuo. Purification was carried out by means of flash chromatography [silica gel, cyclohexane/EtOAc (1:1)]. 170 mg (71%) of the desired olefin were obtained.

For preparation of the hydrochloride, the olefin just isolated (170 mg, 0.512 mmol) was dissolved in ethyl methyl ketone (5 ml), chlorotrimethylsilane (105 mg, 0.769 mol) was added and the mixture was stirred at room temperature in the open reaction vessel for 45 min. The solid thereby formed was filtered off with suction. The hydrochloride was obtained in this way in a yield of 160 mg (61%) as a white solid with a melting point of 115-119° C.

Example 240

N,N-Dimethyl-4-(3-methylbenzofuran-2-yl)-1-phenylcyclohex-3-enamine, citrate (1:1)

3-Methylbenzofuran (354 mg, 3 mmol) was dissolved in methylene chloride (25 ml) together with the ketone (Ket-10, 651 mg, 3 mmol), and trifluoromethanesulfonic acid (0.3 ml, 3.4 mmol) was added. The mixture was stirred at RT for 20 h.—For working up, 2 N NaOH (10 ml) was added to the reaction mixture. The mixture was stirred for a further 20 min. After separation of the phases, the aqueous phase was extracted with methylene chloride (3×20 ml). The combined organic extracts were dried over MgSO$_4$ and then concentrated. The crude product obtained (950 mg) was purified by column chromatography (mobile phase: EtOAc). The desired olefin was obtained in a 348 mg yield (35%) as a tacky oil.

The olefin just isolated (331 mg, 1 mmol) was dissolved in isopropanol (10 ml) at the boiling point and citric acid (192 mg, 1 mmol), dissolved in hot isopropanol (5 ml), was added. The solution was kept at 5° C. for 15 h. The crystals formed were separated off by means of a frit. The crystals deliquesced in air, and for this reason they were rapidly introduced into a sample tube and then dried in vacuo. The desired citrate was obtained in this way in a yield of 185 mg (35%) as a vitreous solid.

Example 241

2-(2-(4-(Dimethylamino)-4-phenylcyclohex-1-enyl)benzofuran-3-yl)ethanethiol, citrate (1:1)

The ketone (Ket-10, 2.06 g, 9.5 mmol) was dissolved in absolute methylene chloride (25 ml) together with 2-(benzofuran-3-yl)ethanethiol (Ind-94, 1.70 g) under argon. The addition of methanesulfonic acid (680 µl, 10.45 mmol) then took place. The mixture was stirred at RT for 4 d. For working up, H$_2$O (15 ml) was added to the mixture. The aqueous phase was separated off and extracted with methylene chloride (3×20 ml). The combined organic phases were dried with 2 N H$_2$SO$_4$. The methylene chloride phase was concentrated on a rotary evaporator. The tacky yellow residue was washed with diethyl ether (3×10 ml). The ethereal wash solution was discarded. 2 N NaOH (20 ml) was then added to the residue which remained. The mixture obtained was extracted with diethyl ether (3×15 ml). The ethereal phase was dried over sodium sulfate and concentrated on a rotary evaporator. From the residue obtained in this way, the desired olefin i was obtained with the aid of column chromatography [silica gel 60 (100 g); ethyl acetate, ethanol (9:1)] as a viscous oil in a yield of 381 mg (10%, based on the ketone employed).

The olefin just isolated (350 mg, 0.928 mmol) was dissolved in boiling ethanol (8 ml), a solution of citric acid (178 mg, 0.928 mmol) in hot ethanol (2 ml) was added and the mixture was stirred for 10 min and allowed to come to RT. The mixture was then brought to 5° C. in a refrigerator. A white precipitate thereby precipitated out, the consistency of which was not stable at room temperature. The ethanol was therefore poured off at approx. 5° C. and the solid residue which remained was dried in vacuo. The citrate of the olefin was obtained as a vitreous solid in a yield of 252 mg (47%) with a melting point of 55-57° C.

Example 242

N,N-Dimethyl-4-(3-methylbenzo[b]thiophen-2-yl)-1-phenylcyclohex-3-enamine, citrate (1:1)

3-Methylbenzo[b]thiophene (Ind-95, 0.27 ml, 2 mmol) was dissolved in methylene chloride (20 ml) together with the ketone (Ket-10, 434 mg, 2 mmol), and trifluoromethanesulfonic acid (0.2 ml, 2.3 mmol) was added. The mixture was stirred at RT for 2 days, a brown oil precipitating out.—For working up, 2 N NaOH (10 ml) was added to the reaction mixture. The mixture was stirred for a further 20 min. After separation of the phases, the aqueous phase was extracted with methylene chloride (2×20 ml). The combined organic extracts were dried over MgSO$_4$ and then concentrated. The crude product obtained (856 mg) was purified by column chromatography (mobile phase: EtOAc). The desired olefin was obtained in this way in a 380 mg yield (54%) as a tacky oil. Crystal formation was achieved by trituration with methanol (3 ml). The solid obtained (295 mg, m.p.: 49-52° C.) became tacky again on standing.

The olefin just isolated (295 mg, 0.85 mmol) was dissolved in methanol (30 ml) at the boiling point and citric acid (163 mg, 0.85 mmol), dissolved in hot methanol (2 ml), was added. Since no precipitate precipitated out, the solvent was stripped off. And the desired citrate (458 mg, 100%) obtained.

Example 243

N,N-dimethyl-4-(3-methylbenzo[b]thiophen-2-yl)-1-phenylcyclohexanamine, citrate (1:1)

3-Methylbenzo[b]thiophene (Ind-95, 0.27 ml, 2 mmol) was dissolved in HBr/glacial acetic acid (33% HBr, 20 ml) together with the ketone (Ket-10, 434 mg, 2 mmol) and the solution was stirred at RT for 50 h. Sn powder (1 g, 8.5 mmol) was then added to the mixture in portions at RT in the course of 30 min. When the addition had ended, the reaction mixture was stirred for a further 20 h.—For working up, the mixture was concentrated to dryness on a rotary evaporator. The residue which remained was rendered basic by addition of 5 N NaOH (40 ml). Methylene chloride was added to the solution obtained and the mixture was extracted (4×20 ml). The combined organic phases were dried with MgSO$_4$ and then concentrated. The residue obtained (552 mg) was purified by column chromatography (mobile phase: 1. EtOAc; 2. EtOAc/EtOH 2:1). In addition to olefin (120 mg), one of the two possible diastereoisomer reduction products was obtained in this way in a yield of 200 mg (28%).

The reduction product isolated (224 mg, 0.64 mmol) was dissolved in methanol (5 ml) at the boiling point and citric acid (124 mg, 0.64 mmol), dissolved in hot methanol (2 ml), was added. Since no precipitate precipitated out, the solvent was stripped off. The solid residue obtained was triturated with methylene chloride. The desired product (271 mg, 78%) was obtained in this way as the citrate with a melting point of 178-179° C.

Example 244

N,N-Dimethyl-1-phenyl-4-(1H-pyrrolo[2,3-b]pyridin-3-yl)cyclohexanamine, citrate (1:1), 1 diastereomer Palladium catalyst (Pd/C, 5%, 120 mg) was added to the free base from Example 230 (300 mg, 0.95 mmol) in abs. methanol (40 ml) and hydrogenation was carried out at RT for 36 h (hydrogen pressure: 3 bar). The progress of the reaction was monitored by TLC. The catalyst was removed with the aid of a frit provided with a layer of Celite 1 cm high. The frit was washed thoroughly with methanol (1,000 ml). The solvent was distilled off in vacuo. It was possible for the crude product obtained (310 mg) to be purified by column chromatography [silica gel 60 (20 g); MeOH (500 ml)]. N,N-Dimethyl-1-phenyl-4-(1H-pyrrolo[2,3-b]pyridin-3-yl)cyclohexanamine (1 diastereomer) was obtained in a yield of 180 mg (60%) as a white solid. The solid (180 mg, 0.56 mmol) was dissolved in isopropanol (10 ml) at the boiling point and citric acid (108 mg, 0.56 mmol), dissolved in hot isopropanol (3 ml), was added. The mixture was left to stand at 5° C. for 16 h. The white precipitate formed was separated off by means of a frit. Example 244 was obtained in a yield of 173 mg (60%, melting point: 130-133° C.).

$^1$H NMR (300 MHz, DMSO-d$_6$) δ ppm: 1.18-1.45 (m, 2H), 1.84-2.15 (m, 4H), 2.40 (s, 6H), 2.52-2.67 (m, 4H), 2.78-3.02 (m, 3H), 6.82-6.96 (m, 1H), 7.00 (S, 1H), 7.39-7.59 (m, 3H), 7.59-7.77 (m, 3H), 8.03-8.18 (m, 1H), 11.24 (s, 1H)

$^{13}$C NMR (101 MHz, DMSO-d$_6$) δ ppm: 29.2, 31.1, 34.1, 37.5, 44.0, 66.6, 71.4, 114.5, 117.6, 118.1, 120.9, 126.6, 128.6, 128.7, 129.2, 132.2, 142.2, 148.7, 171.21, 176.5

Example 246

1-(Dimethylamino)-3-(2-(4-(dimethylamino)-4-phenylcyclohexyl)-3-methyl-1H-indol-1-yl)propan-2-ol, non-polar diastereomer Dimethylamine (324 mg, 2.36 mmol; 33 per cent strength in ethanol, 0.76 g/ml) was added to a suspension of Example 247 (free base) (115 mg, 0.40 mmol) in ethanol (15 ml) at room temperature. The reaction mixture was stirred at 59° C. (oil bath temperature) for 9 h. The reaction mixture was then freed completely from volatile constituents in vacuo. Diethyl ether (3 ml) was added to the residue. The mixture was stored at 0° C. for 3 days. A precipitate precipitated out. The supernatant solution was decanted off. Example 244 (m.p. 54-57° C. was obtained as a colourless solid in a yield of 50% (64 mg, 0.15 mmol).

Example 247

(±)-N,N-Dimethyl-4-(3-methyl-1-(oxiran-2-ylmethyl)-1H-indol-2-yl)-1-phenylcyclohexanamine, citrate (1:1), non-polar diastereomer The free base from Example 17 (non-polar diastereomer, 279 mg, 0.84 mmol) was dissolved in dimethylformamide/tetrahydrofuran (20 ml, 1:1), and sodium hydride (60 per cent strength suspension in mineral oil, 70 mg, 1.75 mmol) was added to the clear pale yellow solution. A light-coloured solid then precipitated out of the reaction mixture. The mixture was stirred at 57° C. (oil bath temperature) for 1 h. The epichlorohydrin (163 mg, 1.76 mmol; 1.183 g/ml) was then added at this temperature. The mixture was stirred at 57° C. (oil bath temperature) for 1 h. Water (30 ml) and diethyl ether (20 ml) were then added to the reaction mixture. The mixture was stirred for 10 min. The phases were then separated. The aqueous phase was extracted with ethyl acetate (2×20 ml). The combined organic phases (ethyl acetate and diethyl ether) were washed with saturated sodium chloride solution (3×10 ml), dried with sodium sulfate and filtered. The volatile constituents were then removed completely in vacuo. 406 mg of (±)-N,N-dimethyl-4-(3-methyl-1-(oxiran-2-ylmethyl)-1H-indol-2-yl)-1-phenylcyclohexanamine remained. The crude product was reacted further without further purification.

(±)-N,N-Dimethyl-4-(3-methyl-1-(oxiran-2-ylmethyl)-1H-indol-2-yl)-1-phenylcyclohexanamine (62 mg, 0.16 mmol) was dissolved in boiling ethanol (5 ml). Citric acid (34 mg, 0.18 mmol) was then added. The clear solution was stirred at the boiling point for 3 h. The reaction mixture was then cooled to room temperature and left to stand at this temperature for 24 h. A colourless microcrystalline precipitate precipitated out. This was filtered off and washed with ethanol (2×5 ml). 69 mg (0.12 mmol; 75%) of Example 247 (m.p.: 175-178° C.) were obtained.

Example 248

4-(1.3-Dimethyl-1H-indol-2-yl)-N,N-dimethyl-1-phenylcyclohexanamine, non-polar diastereomer The free base from Example 17 (non-polar diastereomer, 176 mg, 0.53 mmol) was initially introduced into dry dimethylformamide (15 ml) under an argon atmosphere and sodium hydride (60 per cent strength suspension in mineral oil, 21 mg, 0.53 mmol) was added. The reaction mixture was stirred at room temperature for 1 h and then cooled to 0° C. in an ice bath. Methyl iodide (150 mg, 0.06 ml, 1.06 mmol, 2.28 g/ml) was added to the yellowish solution, after which immediate decolorization started. The reaction mixture was warmed to room temperature in the course of 2 h and stirred at room temperature overnight. For working up, 2 N sodium hydroxide solution (10 ml) and water (10 ml) were added to the reaction mixture and the mixture was stirred for 10 min. The cloudy mixture was left to stand overnight and filtered the next day. The colourless solid obtained was dried in vacuo. 135 mg (0.39 mmol; 73%) of Example 248 (m.p.: 209-212° C.) were isolated.

Example 249

2-(4-Butyl-4-(dimethylamino)cyclohexyl)-3-methyl-1H-indol-5-ol, citrate (1:2), non-polar diastereomer A 1 M solution of $BBr_3$ in methylene chloride (1 ml, 1 mmol) was added to a solution of the free base from Example 125 (less polar diastereoisomer, 115 mg, 0.33 mmol) in dry methylene chloride (20 ml) at RT, while stirring and with exclusion of moisture. After 10 min a precipitate precipitated out. The mixture was stirred at RT for 24 h.—For working up, sat. $NaHCO_3$ solution (15 ml) was added to the mixture and the mixture was stirred for 24 h. The organic phase was separated off and the aqueous phase was extracted with methylene chloride (3×10 ml). The combined organic phases were dried over $Na_2SO_4$ and then concentrated. 2-(4-Butyl-4-(dimethylamino)cyclohexyl)-3-methyl-1H-indol-5-ol was obtained in this way in a yield of 107 mg (99%).

2-(4-Butyl-4-(dimethylamino)cyclohexyl)-3-methyl-1H-indol-5-ol (non-polar diastereomer, 107 mg, 0.32 mmol) was dissolved in hot isopropanol (50 ml), and isopropanolic citric acid solution (62 mg, 0.32 mmol in 2 ml) was added. The mixture was stirred at room temperature for 2 h. The white solid which had precipitated out was filtered off with suction and Example 249 was obtained in a yield of 47 mg (27%) with a melting point of 197-208° C.

Example 250

2-(4-Butyl-4-(dimethylamino)cyclohexyl)-3-methyl-1H-indol-5-ol, citrate (1:1), polar diastereomer A 1 M solution of $BBr_3$ in methylene chloride (0.66 ml, 0.66 mmol) was added to a solution to a solution of the free base of Example 126 (more polar diastereoisomer, 263 mg, 0.77 mmol) in dry methylene chloride (40 ml) at RT, while stirring and with exclusion of moisture. After 10 min a precipitate precipitated out. The mixture was stirred at RT for 24 h.—For working up, sat. $NaHCO_3$ solution (15 ml) was added to the mixture and the mixture was stirred for 24 h. The solid (100 mg) at the phase boundary was separated off. was stirred in a mixture of sat. $NaHCO_3$ solution (20 ml) and ethyl acetate (10 ml) for 1 h. The organic phase was separated off. The aqueous residue was extracted with ethyl acetate (5×10 ml). The combined organic phases were dried over $Na_2SO_4$ and then concentrated. 2-(4-Butyl-4-(dimethylamino)cyclohexyl)-3-methyl-1H-indol-5-ol was obtained in this way in a yield of 35 mg (13%). The filtrate was extracted again with methylene chloride (4×10 ml). The combined organic phases were dried over $Na_2SO_4$ and then concentrated. 2-(4-Butyl-4-(dimethylamino)cyclohexyl)-3-methyl-1H-indol-5-ol (more polar diastereoisomer) was obtained in total in a yield of 135 mg (53%).

2-(4-Butyl-4-(dimethylamino)cyclohexyl)-3-methyl-1H-indol-5-ol (more polar diastereoisomer) (135 mg, 0.41 mmol) was dissolved in hot isopropanol (30 ml), and isopropanolic citric acid solution (79 mg, 0.41 mmol in 3 ml) was added. The mixture was stirred at room temperature for 2 h. The beige solid was filtered off with suction and Example 250 was obtained in a yield of 160 mg (74%) with a melting point of 145-159° C.

Example 251

(±)-2-(4-(Dimethylamino)-4-(thiophen-2-yl)-cyclohex-1-enyl)-3-(2-(pyridin-4-yl)ethyl)-1H-indole Ind-14 (667 mg, 3 mmol) was dissolved in abs. methylene chloride (45 ml) together with ketone Ket-12 (671 mg, 3 mmol), and trifluoromethanesulfonic acid (0.660 ml, 7.43 mmol) was added. The mixture was stirred at RT for 64 h, a brown oil precipitating out. For working up, 1 N NaOH (30 ml) and methanol (10 ml) were added to the reaction solution. The mixture was stirred for a further 60 min. After separation of the phases, the aqueous phase was extracted with methylene chloride (3×10 ml). The combined organic extracts were dried over $Na_2SO_4$ and then concentrated. The crude product obtained (1.33 g) was purified by column chromatography [silica gel 60 (100 g); ethyl acetate/methanol 10:1 (1,650 ml), ethyl acetate/methanol 5:1 (600 ml)]. Ex. 251 was obtained as a yellow solid (373 mg, 29%, m.p.: 189-193° C.).

Example 252

±)-2-(4-(Dimethylamino)-4-(3-fluorophenyl)-cyclohex-1-enyl)-3-(2-(pyridin-4-yl)ethyl)-1H-indole Ind-14 (667 mg, 3 mmol) was dissolved in abs. methylene chloride (45 ml) together with Ket-13 (706 mg, 3 mmol), and trifluoromethanesulfonic acid (0.660 ml, 7.43 mmol) was added. The mixture was stirred at RT for 64 h, a brown oil precipitating out. For working up, 1 N NaOH (30 ml) and methanol (10 ml) were added to the reaction solution. The mixture was stirred for a further 60 min. After separation of the phases, the aqueous phase was extracted with methylene chloride (3×10 ml). The combined organic extracts were dried over $Na_2SO_4$ and then concentrated. The crude product obtained (1.33 g) was purified by column chromatography [silica gel 60 (100 g); ethyl acetate/methanol 10:1 (1,100 ml), ethyl acetate/methanol 5:1 (900 ml)]. The product obtained (425 mg) was recrystallized (at −5° C.) from methyl ethyl ketone (2.5 ml) and Example 252 was obtained as a pale yellow solid (309 mg, 23%, m.p.: 194-198° C.).

Example 253

±)-2-(4-Butyl-4-(pyrrolidin-1-yl)cyclohex-1-enyl)-3-(2-(pyridin-4-yl)ethyl)-1H-indole Ind-14 (667 mg, 3 mmol) was dissolved in abs. methylene chloride (45 ml) together with Ket-14 (671 mg, 3 mmol), and trifluoromethanesulfonic acid (0.613 ml, 6.9 mmol) was added. The mixture was stirred at RT for 64 h, a brown oil precipitating out. For working up, 1 N NaOH (30 ml) and methanol (10 ml) were added to the reaction solution. The mixture was stirred for a further 60 min. After separation of the phases, the aqueous phase was extracted with methylene chloride (3×10 ml). The combined organic extracts were dried over $Na_2SO_4$ and then concentrated. The crude product obtained (1.35 g) was purified by column chromatography [silica gel 60 (90 g); ethyl acetate/methanol 1:1 (2,400 ml)]. Ex. 253 was obtained as a beige-coloured solid (292 mg, 23%, m.p.: 187-195° C.).

Example 254

(±)-2-(4-(Methylamino)-4-phenylcyclohex-1-enyl)-3-(2-(pyridin-4-yl)ethyl)-1H-indole (254)

Ind-14 (667 mg, 3 mmol) was dissolved in abs. methylene chloride (45 ml) together with Ket-15 (610 mg, 3 mmol), and trifluoromethanesulfonic acid (0.613 ml, 6.9 mmol) was added. The mixture was stirred at RT for 64 h, a brown oil precipitating out. For working up, 1 N NaOH (30 ml) and methanol (10 ml) were added to the reaction solution. The mixture was stirred for a further 60 min. After separation of the phases, the aqueous phase was extracted with methylene chloride (3×10 ml). The combined organic extracts were dried over $Na_2SO_4$ and then concentrated. The crude product obtained (1.47 g) was purified by column chromatography [silica gel 60 (90 g); ethyl acetate/methanol 5:1 (1,200 ml), ethyl acetate/methanol 1:1 (1,200 ml)]. Ex. 254 was obtained as a pale yellow solid (578 mg, 47%, m.p.: 168-172° C.).

Example 255

(±)-2-(4-(Dimethylamino)-4-(thiophen-2-yl)-cyclohex-1-enyl)-3-methyl-1H-indole, citrate (1:1)

Ind-10 (686 mg, 5.24 mmol) was dissolved in methylene chloride (40 ml) together with Ket-12 (1.17 g, 5.24 mmol), and trifluoromethanesulfonic acid (0.5 ml, 5.6 mmol) was added. The mixture was stirred at RT for 20 h.—For working up, $H_2O$ (20 ml) was added to the reaction mixture, a tacky precipitate precipitating out. The mixture was stirred for 10 min and the aqueous phase, which contained small amounts of unreacted ketone (<100 mg), was then separated off. Sat. $NaHCO_3$ solution (20 ml) was added to the organic phase and the tacky solid. The solvent mixture was stirred at RT (60 min) until all the substance had dissolved. After the organic phase had been separated off, the aqueous phase was extracted with methylene chloride (3×20 ml). The combined organic extracts were washed with water, dried over $MgSO_4$ and then concentrated. It was possible for the crude product obtained (2 g) to be purified by column chromatography [silica gel 60 G (10 g); EtOAc (100 ml)]. (±)-2-(4-(Dimethylamino)-4-(thiophen-2-yl)-cyclohex-1-enyl)-3-methyl-1H-indole was obtained in a yield of 882 mg (50%) as a solid (melting point: 183-192° C.).

(±)-2-(4-(Dimethylamino)-4-(thiophen-2-yl)-cyclohex-1-enyl)-3-methyl-1H-indole (168 mg, 0.5 mmol) was dissolved in isopropanol (15 ml) at the boiling point, and citric acid (102 mg, 0.53 mmol), dissolved in hot isopropanol (2 ml), was added. After the addition of the acid, a precipitate precipitated out. To bring the precipitation to completion, the mixture was cooled to 5° C. (refrigerator) and left at this temperature for 17 h. The precipitate was separated off by means of a frit and then dried. Example 255 was obtained in this way in a yield of 163 mg (61% as a solid.

Example 256

N,N-Dimethyl-4-(3-methyl-1H-indol-2-yl)-1-(thiophen-2-yl)cyclohexanamine, citrate (2:1), non-polar diastereomer Example 257

N,N-Dimethyl-4-(3-methyl-1H-indol-2-yl)-1-(thiophen-2-yl)cyclohexanamine, citrate (2:1), polar diastereomer N,N-Dimethyl-4-(3-methyl-1H-indol-2-yl)-1-(thiophen-2-yl)cyclohexanamine (non-polar and polar diastereomer)

The free base from Example 255 (436 mg, 1.3 mmol) was taken up in HBr/glacial acetic acid (33% HBr, 30 ml). Sn powder (4 g, 33 mmol) was then added to the mixture in portions at RT in the course of 4 h. When the addition had ended, the reaction mixture was stirred at RT for a further 18 h.—For working up, the mixture was diluted with EtOH (20 ml) and the solvent volume was concentrated to approx. 10 ml on a rotary evaporator. The residue which remained was added to 200 ml of water. The solid which had precipitated out was separated off by means of filtration and 2 N NaOH (50 ml) was then added. The mixture obtained was extracted with methylene chloride (4×20 ml). The combined organic phases were washed with water (50 ml), dried over $MgSO_4$ and then concentrated. The residue obtained (380 mg) was purified by column chromatography [silica gel 60 G (10 g); EtOAc (150 ml)]. N,N-Dimethyl-4-(3-methyl-1H-indol-2-yl)-1-(thiophen-2-yl)cyclohexanamine (less polar diastereomer) was obtained in a yield of 108 mg (24%) as a white solid with a melting point of 191-197° C. (from methanol). The more polar diastereoisomer was obtained in a yield of 70 mg (16% yield) as a white solid with a melting point of 218-225° C.

N,N-Dimethyl-4-(3-methyl-1H-indol-2-yl)-1-(thiophen-2-yl)cyclohexanamine, citrate (2:1), non-polar diastereomer N,N-Dimethyl-4-(3-methyl-1H-indol-2-yl)-1-(thiophen-2-yl)cyclohexanamine (less polar diastereomer) (91 mg, 0.27 mmol) was dissolved in isopropanol (4 ml) at the boiling point and citric acid (60 mg, 0.31 mmol), dissolved in hot isopropanol (1 ml), was added. A precipitate precipitated out immediately. To bring the precipitation to completion, the mixture was cooled to 5° C. (refrigerator) and left at this temperature for 2 h. The precipitate was separated off by means of a frit and then dried. Example 256 was obtained in this way in a yield of 81 mg (68%, melting point: 196-198° C.).

N,N-Dimethyl-4-(3-methyl-1H-indol-2-yl)-1-(thiophen-2-yl)cyclohexanamine, citrate (2:1), polar diastereomer N,N-Dimethyl-4-(3-methyl-1H-indol-2-yl)-1-(thiophen-2-yl)cyclohexanamine (more polar diastereomer) (64 mg, 0.19 mmol) was dissolved in isopropanol (4 ml) at the boiling point and citric acid (52 mg, 0.27 mmol), dissolved in hot isopropanol (1 ml), was added. The solvent was removed and the residue was taken up in methanol (10 ml). Water was then added (3 ml) to the solution and the methanol was stripped off on a rotary evaporator. The precipitate obtained in this way was separated off by means of a frit and then dried. Example 257 was obtained in this way in a yield of 62 mg (75%, melting point from 168° C.).

Example 258

(±)-2-(4-Butyl-4-(pyrrolidin-1-yl)cyclohex-1-enyl)-3-methyl-1H-indole

The ketone Ket-14 (800 mg, 3.58 mmol) and Ind-10 (470 mg, 3.58 mmol) were dissolved in abs. methylene chloride (50 ml), trifluoromethanesulfonic acid (0.953 ml, 1.61 g, 10.74 mmol) was added and the mixture was stirred at room temperature for 18 h. Water (20 ml) and 1 N sodium hydroxide solution (15 ml) were added to the mixture and the mixture was stirred for 1 h. The phases were separated. The aqueous phase was extracted with methylene chloride (2×20 ml). The organic phases were combined, washed with water (20 ml), dried with sodium sulfate and concentrated. The residue was a brown oil (1.24 g), which was separated by chromatography [silica gel 60 (100 g); ethyl acetate/methanol (4:1 (500 ml), methanol (600 ml)]. Example 258 was obtained as a beige-coloured solid in a yield of 36% (426 mg).

Example 259

N-Methyl-4-(3-methyl-1H-indol-2-yl)-1-phenylcyclohexanamine hydrobromide, non-polar diastereomer Example 260

N-Methyl-4-(3-methyl-1H-indol-2-yl)-1-phenylcyclohexanamine, citrate (1:1), polar diastereomer (±)-N-Methyl-N-[4-(3-methyl-1H-indol-2-yl)-1-phenylcyclohex-3-enyl]amine 3-Methylindole (Ind-10, 393 mg, 3 mmol) was dissolved in methylene chloride (25 ml) together with Ket-15 (609 mg, 3 mmol), and trifluoromethanesulfonic acid (0.4 ml, 4.5 mmol) was added. The mixture was stirred at RT for 24 h.—For working up, 2 N NaOH (20 ml) was added to the reaction mixture and the mixture was stirred at RT for 20 min. After the organic phase had been separated off, the aqueous phase was extracted with methylene chloride (2×20 ml). The combined organic extracts were dried over $Na_2SO_4$ and then concentrated. The crude product ((±)-N-methyl-N-[4-(3-methyl-1H-indol-2-yl)-1-phenylcyclohex-3-enyl]amine) was obtained in a yield of 945 mg (99%) as a yellow oil and was employed in the next reaction without further purification.

N-Methyl-4-(3-methyl-1H-indol-2-yl)-1-phenylcyclohexanamine hydrobromide, non-polar diastereomer (259) and N-methyl-4-(3-methyl-1H-indol-2-yl)-1-phenylcyclohexanamine (polar diastereomer)

(±)-N-Methyl-N-[4-(3-methyl-1H-indol-2-yl)-1-phenylcyclohex-3-enyl]amine (900 mg, 2.8 mmol) was dissolved in HBr/glacial acetic acid (33% HBr, 30 ml). Sn powder (1.66 g, 14 mmol) was then added to the mixture in portions at RT in the course of 20 min. When the addition had ended, the reaction mixture was stirred at RT for 9 d (a considerably shorter reaction time is probably sufficient). A clear solution was formed by this procedure.—For working up, the mixture was diluted with EtOH (20 ml) and concentrated to dryness on a rotary evaporator. The residue which remained was rendered basic by addition of 5 N NaOH (50 ml). The aqueous mixture obtained was extracted with ethyl acetate (4×20 ml). The combined organic phases were washed with water (50 ml), dried over $Na_2SO_4$ and then concentrated. The crude product (1 g) was obtained as a mixture of base and hydrobromide and it was possible to separate it by column chromatography [silica gel 60 (50 g); ethyl acetate (250 ml), methanol (250 ml)]. The less polar product (259) was obtained as the hydrobromide in a yield of 67 mg (6%) with a melting point of 288-298° C. The more polar product (N-Methyl-4-(3-methyl-1H-indol-2-yl)-1-phenylcyclohexanamine) was isolated as the base in a yield of 390 mg (39%).

$^1$H NMR (300 MHz, RT, DMSO-$D_6$) δ ppm: 1.80 (psd, 2H), 2.03 (pst, 2H), 2.19 (s, 3H), 2.21 (s, 3H), 2.36-2.70 (m, 4H, [over the DMSO-D5-resonance]), 3.05 (pst, 1H), 4.43 (d, 1H), 6.94 (t, 1H), 7.02 (t, 1H), 7.32-7.58 (m, 4H), 7.68 (psd, 1H), 9.37 (s, vbr, 2H), 11.10 (s, 1H).

$^{13}$C NMR (101 MHz, RT, DMSO-$D_6$) δ ppm: 8.3, 26.3, 26.8, 32.1, 32.4, 61.2, 103.8, 110.3, 117.6, 117.9, 120.2, 126.2, 128.4, 128.6, 128.9, 135.1, 139.1, 139.2 [br].

N-Methyl-4-(3-methyl-1H-indol-2-yl)-1-phenylcyclohexanamine, citrate (1:1), polar diastereomer N-Methyl-4-(3-methyl-1H-indol-2-yl)-1-phenylcyclohexanamine (more polar diastereomer) (390 mg, 1.22 mmol) was dissolved in hot isopropanol (250 ml), and ethanolic citric acid solution (234 mg, 1.22 mmol in 5 ml) was added. The mixture was stirred at room temperature for 2 h. The solid which had precipitated out was filtered off with suction. Example 260 was obtained in a yield of 270 mg (43%, white solid) with a melting point from 189° C.

$^1$H NMR (300 MHz, RT, DMSO-$D_6$) δppm: 1.54 (psq, 2H), 1.83 (psd, 2H), 2.05-2.20 (m, 8H), 2.76-3.03 (m, 3H), 3.38 (s, br, 3H [water underneath]), 6.91 (dqu, 2H), 7.15 (dd, 1H), 7.32 (psd, 1H), 7.40-7.65 (m, 4H), 7.71 (psd, 1H), 10.41 (s, 1H).

$^{13}$C NMR (101 MHz, RT, DMSO-$D_6$) (ppm: 8.3, 25.8, 27.8, 32.2, 35.2, 61.7, 104.0, 110.5, 117.3, 117.9, 119.9, 128.3, 128.6, 128.8, 129.0, 134.4, 135.0, 138.1.

Example 261

1-(3-Fluorophenyl)-N,N-dimethyl-4-(3-methyl-1H-indol-2-yl)cyclohexanamine, citrate (2:1), non-polar diastereomer Example 262

1-(3-Fluorophenyl)-N,N-dimethyl-4-(3-methyl-1H-indol-2-yl)cyclohexanamine, citrate (2:1), polar diastereomer 1-(3-Fluorophenyl)-N,N-dimethyl-4-(3-methyl-1H-indol-2-yl)cyclohexanamine (non-polar and polar diastereomer)

Ex. 263 (450 mg, 1.3 mmol) was suspended in HBr/glacial acetic acid (33% HBr, 15 ml). Sn powder (771 mg, 6.5 mmol) was then added to the mixture in portions at RT in the course of 10 min. When the addition had ended, the reaction mixture was stirred at RT for 48 h. A clear solution was formed by this procedure.—For working up, the mixture was diluted with EtOH (20 ml) and concentrated to dryness on a rotary evaporator. The residue which remained was rendered basic by addition of 5 N NaOH (30 ml). The aqueous mixture obtained was extracted with methylene chloride (4×20 ml). The combined organic phases were washed with water (50 ml), dried over $Na_2SO_4$ and then concentrated. It was possible for the crude product obtained (300 mg) to be purified by column chromatography [silica gel 60 (30 g); 1. ethyl acetate (150 ml), 2. methanol (150 ml)]. 1-(3-Fluorophenyl)-N,N-dimethyl-4-(3-methyl-1H-indol-2-yl)cyclohexanamine (less polar diastereoisomer) was obtained in a yield of 130 mg (29%). The more polar diastereoisomer was isolated in a yield of 130 mg (29%).

1-(3-Fluorophenyl)-N,N-dimethyl-4-(3-methyl-1H-indol-2-yl)cyclohexanamine, citrate (2:1), non-polar diastereomer (261)

1-(3-Fluorophenyl)-N,N-dimethyl-4-(3-methyl-1H-indol-2-yl)cyclohexanamine (less polar diastereoisomer) (120 mg, 0.34 mmol) was dissolved in hot isopropanol (110 ml), and an ethanolic citric acid solution (66 mg, 0.34 mmol in 3 ml) was added. The mixture was stirred at room temperature for 2 h. The solid which had precipitated out was filtered off with suction. Example 261 was obtained in a yield of 90 mg (59%, white solid) with a melting point of 228-237° C.

$^1$H NMR (300 MHz, RT, DMSO-$D_6$) δ ppm: 1.4-1.72 (m, 4H), 2.02-2.24 (m, 9H), 2.66 (dd, 2H), 2.78 (psd, 2H), 2.93 (pst, 1H), 6.90 (dqu, 2H), 7.14 (psd, 1H), 7.27-7.43 (m, 2H), 7.46-7.69 (m, 3H), 10.38 (s, 1H).

$^{13}$C NMR (101 MHz, RT, DMSO-$D_6$) δ ppm: 8.4, 29.9, 32.8, 34.9, 37.7, 59.1 (br), 72.09, 103.7, 110.6, 113.4 (d), 113.7 (d), 117.2, 117.8, 119.7, 122.7 (d), 128.8, 129.1 (d), 135.1, 139.5, 142.1 (br), 162.0 (d), 172.2, 175.1.

1-(3-Fluorophenyl)-N,N-dimethyl-4-(3-methyl-1H-indol-2-yl)cyclohexanamine, citrate (2:1), polar diastereomer (262)

1-(3-Fluorophenyl)-N,N-dimethyl-4-(3-methyl-1H-indol-2-yl)cyclohexanamine (more polar diastereoisomer) (120 mg, 0.34 mmol) was dissolved in hot isopropanol (50 ml), and an ethanolic citric acid solution (66 mg, 0.34 mmol in 3 ml) was added. The mixture was stirred at room temperature for 2 h. The solid which had precipitated out was filtered off with suction. Example 262 was obtained in a yield of 64 mg (42%) with a melting point of 276-285° C.

$^1$H NMR (300 MHz, RT, DMSO-$D_6$) δ ppm: 1.45 (psq, 2H), 1.81 (psd, 2H), 2.06-2.25 (m, 5H), 2.35 (s, br, 6H), 2.91 (pst, 1H), 2.99 (psd, 2H), 6.90 (dqu, 2H), 7.14 (psd, 1H), 7.27-7.43 (m, 2H), 7.46-7.69 (m, 3H), 10.38 (s, 1H).

$^{13}$C NMR (101 MHz, RT, DMSO-$D_6$) δ ppm: 8.3, 28.1, 30.9, 34.8, 37.3, 66.4 (br), 104.0, 110.5, 115.7 (d), 116.5 (d), 117.3, 117.9, 119.9, 125.5, 128.6, 130.6 (d), 135.0, 138.1, 162.6 (d), a $C_{ipso}$ (n.d.).

Example 263

(±)-2-(4-(Dimethylamino)-4-(3-fluorophenyl)-cyclohex-1-enyl)-3-methyl-1H-indole

3-Methylindole (Ind-10, 393 mg, 3 mmol) was dissolved in methylene chloride (25 ml) together with Ket-13 (705 mg, 3 mmol), and trifluoromethanesulfonic acid (0.4 ml, 4.5 mmol) was added. The mixture was stirred at RT for 24 h.—For working up, 2 N NaOH (20 ml) was added to the reaction mixture and the mixture was stirred at RT for 20 min. After the organic phase had been separated off, the aqueous phase was extracted with methylene chloride (2×20 ml). The combined organic extracts were dried over $Na_2SO_4$ and then concentrated. The crude product was obtained in a yield of 1 g (100%) as a yellow oil. The oil was dissolved in hot methanol (10 ml). The mixture was brought to RT and placed in a refrigerator for 17 h to bring the crystallization to completion. Example 263 was separated off by filtration in a yield of 480 mg (48%) as a pale yellow solid with a melting point of 157-163° C.

$^1$H NMR (300 MHz, RT, DMSO-$D_6$) δ ppm: 1.74 (pst, 1H), 2.05-2.15 s over m, 8H), 2.23 (s, 3H), 2.46 (m [under DMSO-$D_5$], br, 1H), 2.67 (psq, 2H), 6.17 (s, 1H), 6.88-7.10 (m, 3H), 7.18-7.42 (m, 5H), 10.56 (s, 1H).

Example 264

2-(4-Benzyl-4-(dimethylamino)cyclohexyl)-3-methyl-1H-indol-5-ol, citrate (1:1), polar diastereomer Example 265

2-(4-Benzyl-4-(dimethylamino)cyclohexyl)-3-methyl-1H-indol-5-ol, citrate (1:1), non-polar diastereomer (±)-N-[1-Benzyl-4-(5-methoxy-3-methyl-1H-indol-2-yl)cyclohex-3-enyl]-N,N-dimethylamine 5-Methoxyskatole (Ind-9, 806 mg, 5 mmol) was dissolved in methylene chloride (40 ml) together with Ket-3 (1.15 g, 5 mmol), and trifluoromethanesulfonic acid (0.65 ml, 7.5 mmol) was added. The mixture was stirred at RT for 24 h.—For working up, 2 N NaOH (20 ml) was added to the reaction mixture and the mixture was stirred at RT for 20 min. After the organic phase had been separated off, the aqueous phase was extracted with methylene chloride (3×20 ml). The combined organic extracts were dried over $Na_2SO_4$ and then concentrated. The crude product was obtained in a yield of 2 g (98%) as a yellow oil and was employed in the next reaction without further purification.

1-Benzyl-4-(5-methoxy-3-methyl-1H-indol-2-yl)-N,N-dimethylcyclohexanamine (non-polar and polar diastereomer)

(±)-N-[1-Benzyl-4-(5-methoxy-3-methyl-1H-indol-2-yl)cyclohex-3-enyl]-N,N-dimethylamine (1.97 g, 5.26 mmol) was suspended in HBr/glacial acetic acid (33% HBr, 30 ml). Sn powder (3.12 g, 26.3 mmol) was then added to the mixture in portions in the course of 30 min. When the addition had ended, the reaction mixture was stirred at RT for a further 48 h.—For working up, the mixture was diluted with EtOH (20 ml) and concentrated to dryness on a rotary evaporator. The residue which remained was rendered basic by addition of 5 N NaOH (100 ml). The aqueous mixture obtained was extracted with methylene chloride (4×20 ml). The combined organic phases were washed with water (50 ml), dried over $Na_2SO_4$ and then concentrated. The residue obtained (1.7 g) was dissolved in ethyl acetate (10 ml). The mixture was placed in a refrigerator for 2 h for crystallization. 1-Benzyl-4-(5-methoxy-3-methyl-1H-indol-2-yl)-N,N-dimethylcyclohexanamine (less polar diastereoisomer) was separated off by filtration in a yield of 500 mg (25%) as a beige solid. The mother liquor was concentrated and the residue was purified by column chromatography [silica gel 60 G (150 g); EtOAc (1,000 ml)]. The polar product was obtained in a yield of 134 mg (7%) as a brown oil.

2-(4-Benzyl-4-(dimethylamino)cyclohexyl)-3-methyl-1H-indol-5-ol, citrate (1:1), polar diastereomer (264)

A 1 M solution of BBr$_3$ in methylene chloride (1.03 ml, 1.03 mmol) was added to a solution of 1-benzyl-4-(5-methoxy-3-methyl-1H-indol-2-yl)-N,N-dimethylcyclohexanamine (more polar diastereoisomer, 130 mg, 0.345 mmol) in dry methylene chloride (20 ml) at RT, while stirring and with exclusion of moisture. After 10 min a precipitate precipitated out. The mixture was stirred at RT for 24 h.—For working up, sat. NaHCO$_3$ solution (15 ml) was added to the mixture and the mixture was stirred for 48 h. The organic phase was separated off and the aqueous phase was extracted with methylene chloride (3×10 ml). The combined organic phases were dried over Na$_2$SO$_4$ and then concentrated. 2-(4-Benzyl-4-(dimethylamino)cyclohexyl)-3-methyl-1H-indol-5-ol (polar diastereomer) was obtained in this way in a yield of 63 mg (50%).

2-(4-Benzyl-4-(dimethylamino)cyclohexyl)-3-methyl-1H-indol-5-ol (polar diastereomer) (63 mg, 0.173 mmol) was dissolved in hot isopropanol (10 ml), and isopropanolic citric acid solution (34 mg, 0.173 mmol in 2 ml) was added. The mixture was stirred at room temperature for 2 h. The white solid was filtered off with suction. Example 264 was obtained in a yield of 55 mg (57%) with a melting point of 165-173° C.

$^1$H NMR (300 MHz, RT, DMSO-D$_6$) δ ppm: 1.64-2.08 (m, 10H), 2.10 (s, 3H), 2.30-2.40 (m, 2H), 2.54 (dd, 8H), 2.62-2.90 (m, 3H), 3.24 (s, br, 2H), 4.33 (s, br, 1H), 6.52 (dd, 1H), 6.68 (d, 1H), 7.05 (d, 1H), 7.30-7.45 (m, 5H), 8.47 (s, br, 1H), 10.40 (s, 1H), 10.50-12.00 (s, vbr, 2H).

2-(4-Benzyl-4-(dimethylamino)cyclohexyl)-3-methyl-1H-indol-5-ol, citrate (1:1), non-polar diastereomer (265)

A 1 M solution of BBr$_3$ in methylene chloride (3.48 ml, 3.48 mmol) was added to a solution of 1-benzyl-4-(5-methoxy-3-methyl-1H-indol-2-yl)-N,N-dimethylcyclohexanamine (less polar diastereoisomer, 437 mg, 1.16 mmol) in dry methylene chloride (50 ml) at RT, while stirring and with exclusion of moisture. After 10 min a precipitate precipitated out. The mixture was stirred at RT for 24 h.—For working up, sat. NaHCO$_3$ solution (20 ml) was added to the mixture and the mixture was stirred for 48 h. The organic phase was separated off and the aqueous phase was extracted with methylene chloride (3×10 ml). The combined organic phases were dried over Na$_2$SO$_4$ and then concentrated. 2-(4-Benzyl-4-(dimethylamino)cyclohexyl)-3-methyl-1H-indol-5-ol (less polar diastereoisomer) was obtained in this way in a yield of 291 mg (69%).

N-[1-Benzyl-4-(5-hydroxy-3-methyl-1H-indol-2-yl)cyclohexyl]-N,N-dimethylamine (less polar diastereoisomer) (291 mg, 0.8 mmol) was dissolved in hot isopropanol (30 ml), and isopropanolic citric acid solution (154 mg, 0.8 mmol in 2 ml) was added. The mixture was stirred at room temperature for 2 h. The white solid was filtered off with suction. Example 265 was obtained in a yield of 300 mg (67%) with a melting point of 224-239° C.

$^1$H NMR (300 MHz, RT, DMSO-D$_6$) δ ppm: 1.25 (t, 2H), 1.47 (d, 2H), 1.75-2.20 (m, br, 7H), 2.53 (s, br, 6H), 2.64 (dd, 4H), 2.71-2.89 (m, 3H), 6.47 (dd, 1H), 6.63 (d, 1H), 7.05 (d, 1H), 7.19-7.38 (m, 5H), 8.82 (s, br, 1H), 10.05 (s, 1H), 10.20-11.80 (s, vbr, 4H).

$^{13}$C NMR (101 MHz, RT, DMSO-D$_6$) δ ppm: 8.3, 25.9, 31.4, 34.7, 36.4, 36.9, 43.8, 59.7 (br), 71.7, 101.6, 102.9, 109.8, 110.8, 126.0, 127.9, 129.4, 129.5, 130.8, 137.7, 139.9, 150.0, 171.4, 176.3.

Example 266

2-(4-Butyl-4-(pyrrolidin-1-yl)cyclohexyl)-3-(2-(pyridin-4-yl)ethyl)-1H-indole, citrate (1:1), non-polar diastereomer

Example 267

2-(4-Butyl-4-(pyrrolidin-1-yl)cyclohexyl)-3-(2-(pyridin-4-yl)ethyl)-1H-indole, citrate (1:1), polar diastereomer 2-[4-Butyl-4-(pyrrolidin-1-yl)cyclohexyl]-3-(2-pyridin-4-ylethyl)-1H-indole (non-polar and polar diastereomer)

Ex. 253 (228 mg, 0.533 mmol) was dissolved in HBr/glacial acetic acid (33% HBr, 10 ml). Sn powder (0.633 g, 5.33 mmol) was then added to the mixture in portions in the course of 40 min. The mixture was stirred for a further 20 min. The mixture was then diluted with methylene chloride (100 ml). 5 N NaOH solution (60 ml) was then slowly added, while cooling, such that the temperature did not exceed 25° C. The mixture was stirred for 30 min. The phases were separated. The aqueous phase was extracted with methylene chloride (3×20 ml). The combined organic phases were dried with Na$_2$SO$_4$ and filtered and the volatile constituents were removed completely in vacuo. An oil (230 mg) remained. After separation of this mixture by chromatography [silica gel 60 (20 g); ethyl acetate/methanol 10:1 (550 ml), ethyl acetate/methanol 1:1 (500 ml), methanol (800 ml)], 2-(4-Butyl-4-(pyrrolidin-1-yl)cyclohexyl)-3-(2-(pyridin-4-yl)ethyl)-1H-indole (less polar diastereoisomer, 106 mg, white solid, 46%, m.p.: 176-179° C.) and the more polar diastereoisomer (46 mg, 20%, m.p.: 165-175° C.) were obtained as a beige-coloured solid.

2-(4-Butyl-4-(pyrrolidin-1-yl)cyclohexyl)-3-(2-(pyridin-4-yl)ethyl)-1H-indole, citrate (1:1), non-polar diastereomer (266)

2-(4-Butyl-4-(pyrrolidin-1-yl)cyclohexyl)-3-(2-(pyridin-4-yl)ethyl)-1H-indole (less polar diastereoisomer, 80 mg, 0.186 mmol) was dissolved in methylene chloride (1 ml), and citric acid (40 mg, 0.208 mmol), dissolved in ethyl acetate (6 ml) was added. During the addition of the acid, a precipitate precipitated out. The mixture was subsequently stirred at 23° C. for 2 h and then filtered. The precipitate was washed with ethyl acetate (2×0.5 ml). Example 266 was obtained as a white solid in a yield of 94% (109 mg) with a melting point of 132-139° C.

$^1$H NMR (400 MHz, CD$_3$OD) δ ppm: 1.01 (t, J=6.94, 3H), 1.14-1.49 (m, 6H), 1.49-1.64 (m, 2H), 1.62-1.85 (m, 4H), 1.85-2.23 (m, 6H), 2.42-2.63 (m, 1H), 2.71-2.93 (m, 4H), 2.93-3.01 (m, 2H), 3.01-3.13 (m, 2H), 3.16-3.62 (m, 4H), 6.91-7.07 (m, 2H), 7.12 (d, J=5.05 Hz, 2H), 7.37 (s, 1H), 7.45 (d, J=7.59 Hz, 1H), 8.30 (d, J=4.83 Hz, 2H)

$^{13}$C NMR (101 MHz, CD$_3$OD) δ ppm: 14.3, 24.3, 25.6, 26.3, 27.2, 27.5, 32.4, 32.9, 35.0, 37.4, 45.0, 49.3, 67.3, 74.5, 109.1, 112.2, 118.7, 119.6, 121.9, 126.3, 129.2, 137.3, 140.2, 149.2, 154.8, 175.2, 179.4

2-(4-Butyl-4-(pyrrolidin-1-yl)cyclohexyl)-3-(2-(pyridin-4-yl)ethyl)-1H-indole, citrate (1:1), polar diastereomer (267)

2-(4-Butyl-4-(pyrrolidin-1-yl)cyclohexyl)-3-(2-(pyridin-4-yl)ethyl)-1H-indole (more polar diastereoisomer, 44 mg, 0.102 mmol) was dissolved in methylene chloride (0.5 ml), and citric acid (22 mg, 0.114 mmol), dissolved in ethyl acetate (4 ml) was added. During the addition of the acid, a precipitate precipitated out. The mixture was subsequently stirred at 23° C. for 2 h and then filtered and the precipitate was washed with ethyl acetate (2×0.5 ml). Example 267 was obtained as a beige-coloured solid in a yield of 93% (59 mg) with a melting point of 105-112° C.

$^1$H NMR (400 MHz, CD$_3$OD) δ ppm: 1.04 (t, J=7.05 Hz, 3H), 1.28-1.56 (m, 6H), 1.62-1.81 (m, 4H), 1.81-1.93 (m, 2H), 1.93-2.02 (m, 2H), 2.02-2.15 (m, 4H), 2.46-2.66 (m, 1H), 2.80 (dd, J=35.74, 15.44 Hz, 4H), 2.93-3.04 (m, 2H), 3.04-3.15 (m, 2H), 3.34-3.50 (m, 4H), 6.92-7.01 (m, 1H), 7.01-7.08 (m, 1H), 7.13 (d, J=5.15 Hz, 2H), 7.26 (d, J=7.94 Hz, 1H), 7.46 (d, J=7.81 Hz, 1H), 8.26-8.42 (m, 2H)

$^{13}$C NMR (101 MHz, CD$_3$OD) δ ppm: 14.3, 24.1, 24.7, 25.6, 26.3, 29.3, 31.2, 32.2, 35.7, 37.3, 44.7, 48.4, 49.1, 67.6, 74.1, 109.2, 111.7, 118.8, 119.6, 121.8, 126.3, 129.2, 137.5, 139.8, 149.2, 154.8, 174.7, 179.0

Example 268

(±)-2-(4-(azetidin-1-yl)-4-phenylcyclohex-1-enyl)-3-methyl-1H-indole

Indole (Ind-10, 525 mg, 4 mmol) was dissolved in methylene chloride (80 ml) together with the ketone (Ket-16, 917 mg, 4 mmol), and trifluoromethanesulfonic acid (0.54 ml, 6 mmol) was added. The mixture was stirred at RT for 24 h. For working up, 5 N NaOH (40 ml) was added to the reaction mixture and the mixture was stirred at RT for 20 min. After the organic phase had been separated off, the aqueous phase was extracted with methylene chloride (2×30 ml). The combined organic extracts were dried over Na$_2$SO$_4$ and then concentrated. The crude product was purified by column chromatography [silica gel 60 (50 g); methanol (500 ml)]. Nevertheless, however, it still contained the educt ketone (approx. 40%). 730 mg (53%) of olefin-ketone mixture were obtained. This was employed for the next reaction without further purification.

2-(4-(Azetidin-1-yl)-4-phenylcyclohexyl)-3-methyl-1H-indole, citrate (1:1):More polar diastereomer The olefin just prepared (730 mg, 2.11 mmol) was dissolved in HBr/glacial acetic acid (33% HBr, 20 ml). Sn powder (2.5 g, 21 mmol) was then added to the mixture in portions at RT in the course of 40 min. When the addition had ended, the reaction mixture was stirred at RT for 16 h. A clear solution was formed by this procedure.—For working up, the mixture was diluted with EtOH (20 ml) and concentrated to dryness on a rotary evaporator. The residue which remained was rendered basic by addition of 5 N NaOH. The aqueous mixture obtained was extracted with methylene chloride (4×30 ml). The combined organic phases were washed with water (50 ml), dried over Na$_2$SO$_4$ and then concentrated. It was possible for the crude product (0.6 g) to be purified by column chromatography [silica gel 60 (50 g); methanol (500 ml)]. The less polar diastereomer was obtained in a yield of 220 mg (30%). The more polar diastereomer was obtained in a yield of 165 mg (22%).

For preparation of the citrate, the more polar diastereomer just prepared (165 mg, 0.48 mmol) was dissolved in hot methanol (100 ml), and citric acid (185 mg, 0.96 mmol) was added. The clear solution was left to stand at 4° C. for 16 h. The white citrate which had precipitated out was filtered off with suction and dried. The citrate (Example 268) was obtained in a yield of 180 mg (67%) with a melting point of 150-155° C.

$^1$H NMR (300 MHz, DMSO-d$_6$) δ ppm: 1.34-1.59 (m, 2H), 1.65-2.02 (m, 6H), 2.11 (s, 3H), 2.55 (dd, J=25.02, 15.10 Hz, 2H), 2.59-2.74 (m, 2H), 2.86-3.06 (m, 1H), 3.40-3.62 (m, 4H), 6.80-7.00 (m, 2H), 7.10-7.21 (m, 1H), 7.08-7.19 (m, 1H), 7.41-7.51 (m, 1H), 7.51-7.59 (m, 2H), 7.59-7.71 (m, 2H), 10.34 (s, 1H)

$^{13}$C NMR (101 MHz, DMSO-d$_6$) δ ppm: 8.3, 15.4, 27.7, 29.5, 35.2, 44.3, 47.1, 62.4, 71.3, 103.8, 110.5, 117.2, 117.9, 119.8, 128.3, 128.6, 128.8, 134.1, 135.0, 138.5, 171.3, 176.8

Example 269

2-(4-(Azetidin-1-yl)-4-phenylcyclohexyl)-3-methyl-1H-indole, citrate (1:1):Less polar diastereomer For preparation of the citrate, the less polar diastereomer prepared under Example 268 (220 mg, 0.68 mmol) was dissolved in hot methanol (150 ml), and citric acid (243 mg, 1.26 mmol) was added. The clear solution was left to stand at 4° C. for 16 h. The white citrate which had precipitated out was filtered off with suction and dried. The citrate (Example 269) was obtained in a yield of 183 mg (54%) with a melting point of 165-167° C.

$^1$H NMR (300 MHz, DMSO-d$_6$) δ ppm: 1.51-1.74 (m, 4H), 1.74-1.92 (m, 2H), 2.05-2.34 (m, 6H), 2.34-2.49 (m, 1H), 2.65 (dd, J=29.23, 15.25 Hz, 2H), 2.78-2.99 (m, 1H), 3.02-3.58 (m, 4H), 6.82-7.09 (m, 2H), 7.22-7.34 (m, 1H), 7.34-7.44 (m, 2H), 7.44-7.62 (m, 4H), 10.68 (s, 1H)

$^{13}$C NMR (101 MHz, DMSO-d$_6$) δ ppm: 8.4, 15.3, 27.1, 30.8, 30.8, 34.1, 43.3, 46.9, 58.5, 71.9, 103.7, 110.6, 117.3, 117.8, 119.8, 125.9, 127.2, 127.4 127.9, 128.7, 135.1, 139.5, 171.2, 175.5

Example 270

(±)-2-(4-(azetidin-1-yl)-4-phenylcyclohex-1-enyl)-3-(2-(pyridin-4-yl)ethyl)-1H-indole lindole (Ind-14, 667 mg, 3 mmol) was dissolved in abs. methylene chloride (45 ml) together with the ketone (Ket-16, 688 mg, 2 mmol), and trifluoromethanesulfonic acid (0.613 ml, 6.9 mmol) was added. The mixture was stirred at RT for 64 h, a brown oil precipitating out. For working up, 1 N NaOH (30 ml) and methanol (10 ml) were added to the reaction solution. The mixture was stirred for a further 60 min. After separation of the phases, the aqueous phase was extracted with methylene chloride (3×10 ml). The combined organic extracts were dried over Na$_2$SO$_4$ and then concentrated. The crude product obtained (1.42 g) was purified by column chromatography [silica gel 60 (90 g); ethyl acetate/methanol 5:1 (1,800 ml), ethyl acetate/methanol 2:1 (600 ml)]. The olefin was isolated as a beige-coloured solid (315 mg, 24%, m.p. 213-219° C.).

2-(4-(Azetidin-1-yl)-4-phenylcyclohexyl)-3-(2-(pyridin-4-yl)ethyl)-1H-indole hydrochloride:More polar diastereomer The olefin prepared (288 mg, 0.66 mmol) was suspended in HBr/glacial acetic acid (33% HBr, 10 ml). Sn powder (797 mg, 6.6 mmol) was then added to the mixture in portions at RT in the course of 30 min. When the addition had ended, the reaction mixture was stirred at RT for 24 h. For working up, the mixture was diluted with EtOH (20 ml) and concentrated to dryness on a rotary evaporator. The residue which remained was rendered basic by addition of 5 N NaOH (75 ml), and methylene chloride (70 ml) was added. This mixture was stirred at room temperature for 2 h. The organic phase was separated off and the aqueous phase was extracted with methylene chloride (3×30 ml). The combined organic phases were dried over $Na_2SO_4$ and then concentrated. It was possible for the crude product obtained (196 mg) to be purified by column chromatography [silica gel 60 (20 g); methanol (150 ml)]. The less polar diastereoisomer was obtained in a yield of 100 mg (35%). The more polar diastereoisomer was isolated in a yield of 36 mg (12%).

The more polar diastereomer prepared (36 mg, 0.08 mmol) was dissolved in methylene chloride (50 ml). $Me_3SiCl$ (20 µl, 0.16 mmol) was then added dropwise at RT and the mixture was stirred for 1 h. Since the solid which had precipitated out was hygroscopic, the solvent was removed on a rotary evaporator. The more polar hydrochloride (Example 270) (39 mg, m.p. 250-254° C., yield 100%) was a white solid.

$^1$H NMR (400 MHz, DMSO-$d_6$) δ ppm: 1.33-1.51 (m, 2H), 1.52-1.67 (m, 2H), 1.72-1.89 (m, 1H), 1.94-2.12 (m, 2H), 2.14-2.32 (m, 1H), 2.68-2.88 (m, 3H), 2.94-3.03 (m, 2H), 3.03-3.12 (m, 2H), 3.58-3.73 (m, 2H), 3.81-4.00 (m, 2H), 6.83-6.99 (m, 2H), 7.11-7.19 (d, 1H), 7.37-7.46 (d, 1H), 7.50-7.65 (m, 3H), 7.01-7.81 (m, 4H), 8.76 (d, J=6.42 Hz, 2H), 10.44 (s, 1H), 11.53-11.70 (m, 1H)

Example 271

-(4-(Azetidin-1-yl)-4-phenylcyclohexyl)-3-(2-(pyridin-4-yl)ethyl)-1H-indole hydrochloride:Less polar diastereomer The less polar diastereomer prepared under Example 270 (100 mg, 0.23 mmol) was dissolved in methylene chloride (150 ml). $Me_3SiCl$ (50 µl, 0.4 mmol) was then added dropwise at RT and the mixture was stirred for 1 h. Since the solid which had precipitated out was hygroscopic, the solvent was removed on a rotary evaporator. The less polar hydrochloride (Example 271) (108 mg, m.p. 242-245° C., yield 100%) was a white solid.

$^1$H NMR (400 MHz, DMSO-$d_6$) δ ppm: 6.89-6.99 (m, 1H), 6.99-7.08 (m, 1H), 7.21-7.29 (d, 1H), 7.44-7.53 (d, 2H), 7.53-7.66 (m, 2H), 7.71-7.88 (m, 4H), 8.65-8.74 (d, 2H), 10.64-10.86 (m, 1H), 11.29 (s, 1H)

Example 272

(±)-2-(4-butyl-4-(pyrrolidin-1-yl)cyclohexyl)-3-methyl-1H-indole

The ketone (Ket-17, 800 mg, 3.58 mmol) and skatole (Ind-10, 470 mg, 3.58 mmol) were dissolved in abs. methylene chloride (50 ml), trifluoromethanesulfonic acid (0.953 ml, 1.61 g, 10.74 mmol) was added and the mixture was stirred at room temperature for 18 h. Water (20 ml) and 1 N sodium hydroxide solution (15 ml) were added to the mixture and the mixture was stirred for 1 h. The phases were separated. The aqueous phase was extracted with methylene chloride (2×20 ml). The organic phases were combined, washed with water (20 ml), dried with sodium sulfate and concentrated. The residue was a brown oil (1.24 g), which was separated by chromatography [silica gel 60 (100 g); ethyl acetate/methanol 4:1 (500 ml), methanol (600 ml)]. The olefin was obtained as a beige-coloured solid in a yield of 36% (426 mg). It was not possible to determine a melting point.

2-(4-Butyl-4-(pyrrolidin-1-yl)cyclohexyl)-3-methyl-1H-indole, citrate (1:1):More polar diastereomer Variant 1: The olefin just prepared (211 mg, 0.627 mmol) was dissolved in methanol (30 ml), and palladium on charcoal (5 per cent strength, 50 mg) was added. The reaction mixture was hydrogenated under 3 bar for 3.5 h. The catalyst was separated off over Celite and the filtrate was concentrated. The residue (200 mg, pale brown oil) was separated by chromatography [silica gel 60 (20 g); ethyl acetate/methanol (10:1 (200 ml), ethyl acetate/methanol 4:1, (200 ml), methanol (200 ml)]. The less polar diastereoisomer was obtained in a yield of 10% (20 mg), and the more polar diastereoisomer was obtained in a yield of 67% (143 mg). Both diastereoisomers were in the form of colourless salts after the chromatography.

Variant 2: The olefin just prepared (180 mg, 0.535 mmol) was dissolved with HBr/glacial acetic acid (33% HBr, 10 ml) at room temperature in the course of 1 h. Tin powder (64 mg, 0.535 mmol) was then added to the mixture in portions in the course of 10 min. When the addition had ended, the reaction mixture was stirred for a further 30 min. Water (20 ml) was added to the mixture, while cooling with ice, and the mixture was stirred at room temperature for 15 min. The beige-coloured solid which had precipitated out was filtered off with suction and washed with water (4×5 ml) and with methylene chloride (2×5 ml). The hydrobromide of the diastereoisomer mixture was obtained in a yield of 69% (155 mg). The salt was taken up in a mixture of methylene chloride (30 ml), water (30 ml) and 1 N sodium hydroxide solution (20 ml) and the mixture was stirred at room temperature for 30 min. The phases were separated. The aqueous phase was extracted with methylene chloride (20 ml). The organic phases were combined, dried with sodium sulfate and concentrated. The residue (107 mg, beige-coloured oil) was separated by chromatography [silica gel 60 (20 g); ethyl acetate/methanol 10:1 (200 ml), ethyl acetate/methanol 4:1, (200 ml), methanol (200 ml)]. The less polar diastereoisomer was obtained in a yield of 31% (56 mg) and the more polar diastereoisomer was obtained in a yield of 17% (31 mg). Both diastereoisomers were in the form of colourless salts after the chromatography.

The more polar diastereomer just prepared (105 mg, 0.29 mmol) was dissolved in ethanol (5 ml), and an ethanolic solution (2 ml) of citric acid (63 mg, 0.326 mmol) was added. After a reaction time of 16 h at room temperature, the citrate (Example 272) was separated off by filtration as a colourless solid and washed with diethyl ether (2×2 ml). The salt was obtained in a yield of 51% (80 mg) with a melting point of 239-240° C.

$^1$H NMR (400 MHz, DMSO-$d_6$) δ ppm: 0.98 (t, 3H), 1.25-1.48 (m, 4H), 1.60-1.90 (m, 14H), 2.17 (s, 3H), 2.50 (dd, 4H), 2.85 (t, 1H), 2.90-3.08 (m, 4H), 6.88-6.95 (m, 1H), 6.95-7.02 (m, 1H), 7.26 (d, 1H), 7.36 (d, 1H), 10.61 (s, 1H)

Example 273

4-(dimethylamino)-4-phenyl-1-(5-(tetrahydro-2H-pyran-2-yloxy)pent-1-ynyl)cyclohexanol 2-(4-Pentynyloxy)tetrahydro-2H-pyran (2,394 mg, 13.81 mmol; 97%) were dissolved in absolute tetrahydrofuran (50 ml) under an argon atmosphere and the solution was cooled to −78° C. Lithium diisopropylamide solution (17.95 mmol, 9.9 ml, 1.8 M) was then slowly added dropwise. When the addition had ended, the now reddish solution was warmed to room temperature in the meantime (15 min), the solution becoming lighter in colour. The ketone (Ket-10, 3,000 mg, 13.81 mmol) was dissolved in tetrahydrofuran (15 ml) and the solution was slowly added dropwise at −78° C. to the organolithium compound prepared in situ. After 10 min the cooling was removed and the pale brown solution was stirred for 17 h. For working up of the reaction mixture, saturated ammonium chloride solution (50 ml) was added, while cooling with ice. A white solid was thereby formed, which was dissolved with a little water (10 ml). The phases were separated. The aqueous phase was extracted with diethyl ether (3×50 ml). The combined organic phases were dried over sodium sulfate and the volatile constituents were then removed completely in vacuo. A red-brown oil remained. This was purified by chromatography [silica gel 60 (200 g), cyclohexane/ethyl acetate 5:1, (100 ml), chloroform/ethanol (19:1 (1,000 ml)]. It was possible to obtain the desired alcohol in a yield of 50% (2,643 mg, 6.86 mmol) as a red-brown paste.

4-(dimethylamino)-4-phenyl-1-(3-(3-(tetrahydro-2H-pyran-2-yloxy)propyl)-1H-pyrrolo[2,3-b]pyridin-2-yl)cyclohexanol 4-(Dimethylamino)-4-phenyl-1-(5-(tetrahydro-2H-pyran-2-yloxy)pent-1-ynyl)cyclohexanol (700 mg, 1.82 mmol), 2-amino-3-iodopyridine (363 mg, 1.65 mmol), lithium chloride (74 mg, 1.73 mmol) and sodium carbonate (525 mg, 4.95 mmol) was dissolved in dimethylformamide (20 ml) under an argon atmosphere. Argon was subsequently allowed to flow through the solution for 10 min and the catalyst ([Pd(dppf)Cl$_2$×CH$_2$Cl$_2$], 135 mg, 0.17 mmol) was then added. The reaction mixture was heated at 105° C. (oil bath temperature) for 3 h. A TLC showed that the starting substances had been used up completely. The black reaction mixture was cooled to room temperature and water (50 ml; stirring for 10 min), methylene chloride (50 ml) and saturated sodium chloride solution (for phase separation, 80 ml) were added in succession. The phases were separated and the aqueous phase was extracted with methylene chloride (3×20 ml). The combined organic phases were washed with water (20 ml) and with saturated sodium chloride solution (3×20 ml), dried over sodium sulfate and filtered and the volatile constituents were then removed completely in vacuo. The residue was separated by chromatography [silica gel 60 (200 g); chloroform/ethanol 19:1 (500 ml), 9:1 (500 ml), 4:1 (500 ml), methanol (1,000 ml)]. It was possible to obtain a diastereoisomer of the alcohol (4-(dimethylamino)-4-phenyl-1-(3-(3-(tetrahydro-2H-pyran-2-yloxy)propyl)-1H-pyrrolo[2,3-b]pyridin-2-yl)cyclohexanol) (m.p.: 238° C.) in a yield of 28% (221 mg, 0.46 mmol) as a white powder.

3-(2-(4-(Dimethylamino)-4-phenylcyclohex-1-enyl)-1H-pyrrolo[2,3-b]pyridin-3-yl)propan-1-ol The alcohol just prepared (662 mg, 1.39 mmol) was dissolved in methanesulfonic acid (45 ml), and P$_4$O$_{10}$ (approx. 2 g) was added. The red-coloured reaction mixture was stirred at 73° C. (oil bath temperature) for 3 h. The colour of the reaction mixture had not changed. 5 N sodium hydroxide solution (130 ml), water (70 ml) and methylene chloride (40 ml) were added to the reaction solution, while cooling with ice, and the mixture was stirred for 10 min. The phases were then separated. The aqueous phase was extracted with methylene chloride (2×30 ml). The combined organic phases were dried over sodium sulfate and filtered and the volatile constituents were then removed completely in vacuo. An orange foam (478 mg) remained. Diethyl ether (10 ml) was added to the residue, the mixture was placed in an ultrasound bath for 5 min, the ethereal phase was siphoned off and the residue which remained was dried in vacuo. It was possible to obtain the desired olefin in a yield of 74% (386 mg, 1.03 mmol) as a yellow powder.

3-(2-(4-(dimethylamino)-4-phenylcyclohexyl)-1H-pyrrolo[2,3-b]pyridin-3-yl)propan-1-ol, citrate (1:1):
One of two possible diastereoisomers Tin (1,430 mg, 12.05 mmol) was added to a suspension of the olefin just obtained (341 mg, 0.91 mmol) in HBr/glacial acetic acid (20 ml, 35%) in the course of 60 min (evolution of gas). The mixture was stirred at room temperature for 20 h. The reaction mixture became pale brown in colour. The reaction mixture was evaporated to dryness in vacuo and 5 N sodium hydroxide solution (20 ml) and methylene chloride (20 ml) were added to the pale brown residue. The mixture was filtered, the solid obtained was dissolved in methanol (5 ml) and the solution was combined with the organic phase. The aqueous phase was separated off and extracted with methylene chloride (2×20 ml). The organic phases were combined, dried over sodium sulfate and then concentrated to approx. 5 ml in vacuo. A crystalline yellow solid precipitated out of the solution overnight. The solid was removed with a frit. The yellow filtrate was evaporated completely (706 mg) and the residue was separated by chromatography [silica gel 60 (200 g); chloroform/ethanol 19:1 (500 ml), 9:1 (1,000 ml), 4:1, (1,000 ml), methanol (500 ml)]. It was possible to obtain a diastereoisomer of the desired alcohol in a yield of 24% (83 mg, 0.22 mmol) as a yellow powder.

The alcohol just prepared (76 mg, 0.20 mmol) was initially introduced into ethanol (5 ml) and the cloudy, weakly yellow solution was heated to the boiling point. Citric acid (39 mg, 0.20 mmol) was added and the reaction solution was stirred at the boiling point for 30 min. The solution was cooled to 5° C. in a refrigerator and left to stand for 16 h. A colourless precipitate precipitated out. The supernatant solution was siphoned off and the residue was dried in vacuo. It was possible to isolate 67 mg (0.12 mmol; 59%) of the target compound (m.p.: 220-223° C.).

$^1$H NMR (400 MHz, RT, DMSO-D$_6$) δ ppm 1.64 (pst, br, 2H), 1.80 (psd, br, 2H), 1.86-2.20 (m, 4H), 2.46 (s, br, 6H), 2.63 (dd, 4H), 2.67-2.78 (m, br, 2H), 2.88-3.13 (m, br, 2H), 2.46 (t, 2H), 4.16 (t, 1H), 6.93 (dd, 1H), 7.51-7.63 (m, 3H), 7.71 (psd, 2H), 7.79 (dd, 1H), 8.04 (dd, 1H), 11.22 (s, 1H), additionally from 1.5-4.5 (very br).

$^{13}$C NMR (101 MHz, RT, DMSO-D$_6$) δ ppm: 20.4, 28.2, 30.8, 33.3, 35.0, 37.4, 43.4 44.9, 68.1, 71.9, 106.6, 114.7, 120.0, 125.3, 128.9, 129.3, 129.5, 139.6, 141.4, 148.1, 171.4, 175.7.

Example 274

1-(2-(4-(dimethylamino)-4-phenylcyclohexyl)-3-methyl-1H-indol-1-yl)-3-(methylamino)propan-2-ol, citrate:More polar diastereomer Methylamine (49 mg, 1.59 mmol; 2 M in tetrahydrofuran, 0.79 ml) was added to a suspension of the more polar epoxide (220 mg, 0.57 mmol) in ethanol (15 ml) at room temperature. Since no reaction started at room temperature, the reaction mixture was stirred at 59° C. (oil bath temperature) for 5 h. The reaction mixture was then concentrated to approx. 5 ml in vacuo. A colourless solid precipitated out. Diethyl ether (3 ml) was added. The mixture was stored at 0° C. for 3 d. The supernatant solution was decanted off. It was possible to obtain the polar product quantitatively (234 mg, 0.57 mmol).

The polar amino alcohol just prepared (298 mg, 0.71 mmol) was initially introduced into boiling ethanol (15 ml). Citric acid (150 mg, 0.78 mmol) was then added and the clear solution was stirred at the boiling point for 3 h. The reaction mixture was then cooled to room temperature and left to stand at this temperature for 24 h. A colourless microcrystalline precipitate precipitated out. The precipitate was filtered off and washed with ethanol. It was possible to obtain the desired product (Example 274) as a colourless solid (m.p.: 173-180° C.) in a yield of 60% (260 mg, 0.43 mmol).

$^1$H NMR (400 MHz, RT, DMSO-D$_6$) δ ppm: 1.50-2.00 (m, 9H), 2.25 (s, 6H), 2.46 (s, br, 3H) 2.53 (dd, 4H), 2.80-3.10 (m, 4H), 3.90-4.25 (m, 3H), 6.89 (t, 1H), 6.99 (t, 1H), 7.23 (d, 1H), 7.31 (d, 1H), 7.41 (pst, 1H), 7.50 (pst, 2H), 7.55 (pst, 2H), 8.00-11.00 (s, br, 6H).

$^{13}$C NMR (101 MHz, RT, DMSO-D$_6$) δ ppm: 8.7, 26.8, 27.1, 31.4, 31.5, 32.9, 33.7, 37.6, 44.4, 46.4, 51.3, 64.9, 66.1, 71.5, 104.5, 109.5, 117.1, 118.4, 120.3, 127.9, 128.4, 128.8, 129.1, 133.4, 135.3, 139.5, 171.6, 177.1.

Example 275

(±)-1-Benzyl-3-(2-(2-(4-(dimethylamino)-4-phenyl-cyclohex-1-enyl)-1H-indol-3-yl)ethyl)-urea Indole (Ind-100, 820 mg, 2.8 mmol) and ketone (Ket-10, 608 mg, 2.8 mmol) were dissolved in abs. methylene chloride (30 ml), and trifluoromethanesulfonic acid (1.00 ml, 11.2 mmol) was added rapidly. The mixture was stirred at RT for 3 d, during which a dark brown oil settled out. After addition of 1 N NaOH (50 ml) and CH$_2$Cl$_2$ (20 ml), the mixture was subsequently stirred for 1 h until the oil had dissolved. The phases were separated, the aqueous phase was extracted three times with CH$_2$Cl$_2$, the combined organic phases were washed with water and dried (Na$_2$SO$_4$) and the solution was concentrated i. vac. The residue which remained was purified by flash chromatography with 50 g of silica gel and CHCl$_3$/MeOH (9:1→1:1). Yield: 647 mg (47%)

1-Benzyl-3-(2-(2-(4-(dimethylamino)-4-phenylcyclohexyl)-1H-indol-3-yl)ethyl)-urea, citrate (1:1): Less polar diastereomer Tin (2.27 g) was added to a solution of the olefin just prepared (871 mg, 1.77 mmol) in HBr/glacial acetic acid (35 ml) in the course of 20 min and the mixture was stirred at RT for 4 h. Ethanol was added to the mixture, the reaction mixture was concentrated to dryness and the residue was dissolved in 5 N NaOH (100 ml) and methylene chloride (150 ml). The phases were separated, the aqueous phase was extracted three times with CH$_2$Cl$_2$ and the combined organic phases were washed with water, dried over Na$_2$SO$_4$ and concentrated i. vac. The residue which remained was separated by flash chromatography with 50 g of silica gel and CHCl$_3$/MeOH (20:1→9:1→4:1→1:1). According to NMR the two diastereomers were in the form of a salt, and therefore 1 N NaOH (10 ml) was added in each case and the mixture was extracted 7× with CH$_2$Cl$_2$, and the organic phases were in each case dried (Na2SO4) and concentrated i. vac.

Yield: 126 mg (14%), non-polar diastereomer
189 mg (22%), polar diastereomer

Citrate Non-Polar:

The less polar diastereomer just prepared (108 mg, 0.22 mmol) was dissolved hot in ethanol (10 ml), and a solution of citric acid (42 mg, 0.22 mmol) in ethanol (0.5 ml) was added. Since scarcely any precipitate precipitated out, the solution was concentrated to half i. vac. and left to stand in a refrigerator overnight. The precipitate which had precipitated out was filtered off with suction and rinsed with ether. Yield: 85 mg (57%)

$^1$H-NMR (DMSO-d$_6$): 1.64-1.71 (4H, m); 2.20 (8H, s); 2.59-2.75 (4H, m); 2.74-2.86 (6H, m); 2.91-2.99 (1H, m); 3.17-3.23 (2H, m); 4.19 (2H, d); 5.94 (1H, t); 6.32 (1H, t); 6.90-7.01 (2H, m); 7.17-7.49 (12H, m); 10.62 (1H, s); 11.10 (4H, bs).

Example 276

1-Benzyl-3-(2-(2-(4-(dimethylamino)-4-phenylcyclohexyl)-1H-indol-3-yl)ethyl)-urea, citrate (1:1): More polar diastereomer Citrate Polar:

The more polar diastereomer prepared under Example 275 (175 mg, 0.35 mmol) was dissolved hot in ethanol (5 ml), and a solution of citric acid (68 mg, 0.35 mmol) in ethanol (0.5 ml) was added. Since scarcely any precipitate precipitated out, the solution was concentrated to half i. vac. and left to stand in a refrigerator overnight. The precipitate was filtered off with suction and rinsed with ether. Yield: 108 mg (44%)

$^1$H-NMR (DMSO-d$_6$): 1.44-1.54 (2H, m); 1.79-1.92 (4H, m); 2.30 (6H, s); 2.49-2.61 (4H, m); 2.76 (2H, s); 2.93-2.96 (3H, m); 3.17-3.18 (2H, m); 4.24 (2H, d); 5.93 (1H, t); 6.34 (1H, t); 6.87-6.94 (2H, m); 7.14-7.34 (6H, m); 7.41-7.61 (6H, m); 10.37 (1H, s); 11.10 (4H, bs).

Example 277

(±)-1-(2-(2-(4-(dimethylamino)-4-phenylcyclohex-1-enyl)-1H-indol-3-yl)ethyl)-3-phenyl-urea Indole (Ind-101, 600 mg, 2.15 mmol) and ketone (Ket-10, 467 mg, 2.15 mmol) were dissolved in abs. methylene chloride (30 ml), and trifluoromethanesulfonic acid (0.76 ml, 8.6 mmol) was added rapidly. The mixture was stirred at RT for 3 d, during which a dark brown oil settled out. After addition of 1 N NaOH (40 ml) and CH$_2$Cl$_2$ (30 ml), the mixture was subsequently stirred for a further 2 h until the oil had dissolved. The phases were separated, the aqueous phase was extracted with CH$_2$Cl$_2$ (3×40 ml), the combined organic phases were washed with water (10 ml) and dried (Na$_2$SO$_4$) and the solution was concentrated i. vac. The residue which remained was purified by flash chromatography with 100 g of silica gel and CHCl$_3$/MeOH (9:1). Yield: 927 mg (90%)

1-(2-(2-(4-(Dimethylamino)-4-phenylcyclohexyl)-1H-indol-3-yl)ethyl)-3-phenyl-urea, citrate (1:1): Less polar diastereomer Tin (1.50 g) was added to a solution of the olefin just prepared (638 mg, 1.33 mmol) in HBr/glacial acetic acid (25 ml) in the course of 20 min and the mixture was stirred at RT for 4 h. Ethanol was added to the mixture, the reaction mixture was concentrated to dryness and the residue was dissolved in 5 N NaOH (75 ml) and chloroform (175 ml). After 2 h the phases were separated, the aqueous phase was extracted with CHCl$_3$ (3×100 ml) and the combined organic phases were washed with water (30 ml), dried over Na$_2$SO$_4$ and concentrated i. vac. The residue which remained was separated by flash chromatography with 50 g of silica gel and CHCl$_3$/MeOH (20:1→9:1→4:1→1:1). According to NMR the two diastereomers were in the form of a salt. 1 N NaOH (10 ml) was added to the non-polar diastereomer and the mixture was extracted 7× with CH$_2$Cl$_2$. The organic phase was dried (Na$_2$SO$_4$) and concentrated i. vac. 28 mg of a non-crystalline solid were obtained, which was not investigated further. Ethyl acetate (40 ml) was added to the aqueous phase, but the phases did not subsequently separate again. On concentration i. vac., the non-polar diastereomer precipitated out as a white solid, and this was filtered off with suction, rinsed with water and dried i. vac. 1 N NaOH (10 ml) was added to the polar diastereomer and the mixture was extracted with CHCl$_3$ (4×20 ml). The organic phase was dried over Na$_2$SO$_4$ and concentrated i. vac.

Yield: 62 mg (10%), non-polar diastereomer 261 mg (41%), polar diastereomer

Citrate Non-Polar:

The less polar diastereomer just obtained (61 mg, 0.13 mmol) was dissolved hot in a mixture of ethanol (10 ml) and methanol (2 ml), citric acid (24 mg, 0.13 mmol) was added and the mixture was heated again. The solubility of the substance was improved visibly by addition of citric acid, and the solvent was therefore removed i. vac. until the solution became cloudy. The precipitate which had precipitated out after subsequent standing in a refrigerator was filtered off with suction and rinsed with ether. Yield: 51 mg (60%)

$^1$H-NMR (DMSO-d$_6$): 1.44-1.53 (2H, m); 1.64-1.68 (2H, m); 2.09 (8H, s); 2.56-2.71 (4H, m); 2.71-2.91 (5H, m); 3.26-3.32 (2H, m); 6.08 (1H, t); 6.84-7.01 (3H, m); 7.18 (2H, t); 7.28-7.37 (8H, m); 7.49 (1H, d); 8.37 (1H, s); 10.64 (1H, s); 11.10 (4H, bs).

Example 278

1-(2-(2-(4-(Dimethylamino)-4-phenylcyclohexyl)-1H-indol-3-yl)ethyl)-3-phenyl-urea, citrate (1:1): More polar diastereomer Citrate Polar:

The more polar diastereomer prepared under Example 277 (236 mg, 0.49 mmol) was dissolved hot in ethanol (5 ml), and citric acid (94 mg, 0.49 mmol) was added. The solution was briefly heated again. Since scarcely any precipitate precipitated out, the solution was concentrated to half i. vac. and placed in a refrigerator overnight. The precipitate which had precipitated out was filtered off with suction and rinsed with ether.

Yield: 71 mg (21%)

$^1$H-NMR (DMSO-d$_6$): 1.44-1.53 (2H, m); 1.79-1.87 (4H, m); 2.25 (6H, s); 2.49-2.62 (4H, m); 2.78-2.96 (5H, m); 3.23-3.28 (2H, m); 6.11 (1H, t); 6.87-6.95 (3H, m); 7.15-7.25 (3H, m); 7.41-7.59 (8H, m); 8.42 (1H, s); 10.39 (1H, s); 11.10 (4H, bs).

Example 279

(±)-1-Cyclopentyl-3-(2-(2-(4-(dimethylamino)-4-phenylcyclohex-1-enyl)-1H-indol-3-yl)ethyl)-urea Indole (Ind-102, 1.21 g, 4.5 mmol) and ketone (Ket-10, 968 mg, 4.5 mmol) were dissolved in abs. methylene chloride (50 ml), and trifluoromethanesulfonic acid (1.58 ml, 17.8 mmol) was added rapidly. The mixture was stirred at RT for 3 d, during which a dark brown oil settled out. After addition of 1 N NaOH (80 ml) and CH$_2$Cl$_2$ (120 ml), the mixture was subsequently stirred for 3 h until the oil had dissolved. The phases were separated, the aqueous phase was extracted with CH$_2$Cl$_2$ (3×80 ml), the combined organic phases were washed with water and dried (Na$_2$SO$_4$) and the solution was concentrated i. vac. The residue which remained was purified by flash chromatography with 100 g of silica gel and CHCl$_3$/MeOH (9:1→1:1).

Yield: 1.39 mg (66%)

1-Cyclopentyl-3-(2-(2-(4-(dimethylamino)-4-phenylcyclohexyl)-1H-indol-3-yl)ethyl)-urea, citrate (1:1): Less polar diastereomer Tin (3.28 g) was added to a solution of the olefin just prepared (1.37 g, 2.91 mmol) in HBr/glacial acetic acid (50 ml) in the course of 20 min and the mixture was stirred at RT for 4 h. Ethanol was added to the mixture, the reaction mixture was concentrated to dryness and the residue was dissolved in 5 N NaOH (80 ml) and methylene chloride (170 ml). The phases were separated, the aqueous phase was extracted with CH$_2$Cl$_2$ (3×80 ml) and the combined organic phases were washed with water (20 ml), dried over Na$_2$SO$_4$ and concentrated i. vac. The residue which remained was separated by flash chromatography with 100 g of silica gel and CHCl$_3$/MeOH (20:1→9:1→4:1→1:1). According to NMR the two diastereomers were in the form of a salt, and therefore 1 N NaOH (10 ml) was added in each case and the mixture was extracted 7× with CHCl$_3$, and the organic phases were in each case dried (Na$_2$SO$_4$) and concentrated i. vac.

Yield: 125 mg (9%), non-polar diastereomer 293 mg (21%), polar diastereomer

Citrate Non-Polar:

The less polar diastereomer just obtained (109 mg, 0.23 mmol) was dissolved hot in ethanol (10 ml) and methanol (5 ml), citric acid (44 mg, 0.23 mmol) was added and the mixture was heated briefly to the boiling point. Since scarcely any precipitate precipitated out, the solution was concentrated to half i. vac. and left to stand in a refrigerator. The precipitate which had precipitated out was filtered off with suction and rinsed with ether. Yield: 95 mg (62%)

$^1$H-NMR (DMSO-d$_6$): 1.20-1.28 (2H, m); 1.43-1.57 (4H, m); 2.14-2.17 (2H, m); 2.23 (6H, s); 2.60-2.74 (4H, m); 2.74-2.95 (5H, m); 3.13-3.18 (2H, m); 3.82 (1H, qu); 5.66 (1H, t); 5.77 (1H, d); 6.90-7.00 (2H, m); 7.31-7.50 (7H, m); 10.63 (1H, s); 11.10 (4H, bs).

Example 280

1-Cyclopentyl-3-(2-(2-(4-(dimethylamino)-4-phenylcyclohexyl)-1H-indol-3-yl)ethyl)-urea, citrate (1:1): More polar diastereomer Citrate Polar:

The more polar diastereomer obtained under Example 279 (274 mg, 0.58 mmol) was dissolved hot in ethanol (5 ml) and methanol (2 ml), citric acid (111 mg, 0.58 mmol) was added and the mixture was heated briefly to the boiling point. Since scarcely any precipitate precipitated out, the solution was concentrated to half i. vac. and then left to stand in a refrigerator. The precipitate which had precipitated out was filtered off with suction and rinsed with ether. Yield: 230 mg (60%)

$^1$H-NMR (DMSO-d$_6$): 1.25-1.32 (2H, m); 1.44-1.61 (6H, m); 1.77-1.83 (4H, m); 1.91-1.97 (2H, m); 2.36 (6H, s); 2.52-2.64 (4H, m); 2.72 (2H, t); 2.90-3.00 (3H, m); 3.11-3.16 (2H, m); 3.87-3.92 (1H, m); 5.67 (1H, t); 5.80 (1H, d); 6.86-6.94 (2H, m); 7.15 (1H, d); 7.41 (1H, d); 7.54-7.66 (5H, m); 10.36 (1H, s); 11.10 (4H, bs).

Example 281

N-(2-(2-(4-(dimethylamino)-4-phenylcyclohex-1-enyl)-1H-indol-3-yl)ethyl)cyclopentanesulfonamide Indole (Ind-103, 736 mg, 2.5 mmol) and ketone (Ket-10, 547 mg, 2.5 mmol) were dissolved in abs. methylene chloride (30 ml), and trifluoromethanesulfonic acid (0.89 ml, 10.1 mmol) was added rapidly. The mixture was stirred at RT for 3 d, during which a dark brown oil settled out. After addition of 1 N NaOH (40 ml) and $CH_2Cl_2$ (30 ml), the mixture was stirred for 2 h until the oil had dissolved. The phases were separated, the aqueous phase was extracted with $CH_2Cl_2$ (3×40 ml), the combined organic phases were washed with water (10 ml) and dried ($Na_2SO_4$) and the solution was concentrated i. vac. The residue which remained was purified by flash chromatography with 100 g of silica gel and $CHCl_3$/MeOH (9:1). Yield: 1.04 g (84%)

N-(2-(2-(4-(dimethylamino)-4-phenylcyclohexyl)-1H-indol-3-yl)ethyl)cyclopentanesulfonamide, citrate (1:1):Less polar diastereomer Tin (1.07 g) was added to a solution of the olefin just isolated (464 mg, 0.94 mmol) in HBr/glacial acetic acid (20 ml) in the course of 20 min and the mixture was stirred at RT for 4 h. Ethanol was added to the mixture, the reaction mixture was concentrated to dryness and the residue was dissolved in 5 N NaOH (50 ml) and methylene chloride (150 ml). The phases were separated, the aqueous phase was extracted with $CH_2Cl_2$ (3×50 ml) and the combined organic phases were washed with water, dried over $Na_2SO_4$ and concentrated i. vac. The residue which remained was separated by flash chromatography with 25 g of silica gel and $CHCl_3$/MeOH (100:1→1:1). According to NMR the two diastereomers were in the form of a salt, and therefore 1 N NaOH (10 ml) was added in each case and the mixture was extracted 7× with $CHCl_3$, and the organic phases were in each case dried ($Na_2SO_4$) and concentrated i. vac.

Yield: 177 mg (38%), non-polar diastereomer
203 mg (44%), polar diastereomer
Citrate Non-Polar:
The less polar diastereomer just isolated (155 mg, 0.31 mmol) was dissolved hot in a mixture of ethanol (5 ml) and methanol (15 ml), citric acid (60 mg, 0.31 mmol) was added and the mixture was heated again. The precipitate which had precipitated out after subsequent standing in a refrigerator was filtered off with suction and rinsed with ether.

Yield: 126 mg (72%)
$^1$H-NMR (DMSO-$d_6$): 1.47-1.71 (8H, m); 1.78-1.82 (4H, m); 2.15 (6H, s); 2.58-2.73 (4H, m); 2.83-3.00 (5H, m); 3.06-3.13 (2H, m); 3.38-3.49 (1H, m); 6.91-7.02 (2H, m); 7.08 (1H, t); 7.31-7.47 (7H, m); 10.69 (1H, s); 11.10 (4H, bs).

Example 282

N-(2-(2-(4-(dimethylamino)-4-phenylcyclohexyl)-1H-indol-3-yl)ethyl)cyclopentanesulfonamide, citrate (1:1):More polar diastereomer Citrate Polar:
The more polar diastereomer isolated under Example 281 (176 mg, 0.36 mmol) was dissolved hot in ethanol (5 ml) and methanol (15 ml), citric acid (68 mg, 0.36 mmol) was added and the mixture was heated briefly to the boiling point and placed in a refrigerator. Since scarcely any precipitate precipitated out, the solution was concentrated to half i. vac. and left to stand in a refrigerator overnight. The precipitate which had precipitated out was filtered off with suction and rinsed with ether. Yield: 63 mg (26%)

$^1$H-NMR (DMSO-$d_6$): 1.42-1.68 (6H, m); 1.80-1.92 (8H, m); 2.29 (6H, s); 2.48-2.61 (4H, m); 2.82-3.08 (7H, m); 3.40-3.47 (1H, m); 6.87-6.95 (2H, m); 7.07-7.16 (2H, m); 7.35-7.62 (6H, m); 10.42 (1H, s); 11.10 (4H, bs).

Example 283

(±)-N-(2-(2-(4-(dimethylamino)-4-phenylcyclohex-1-enyl)-1H-indol-3-yl)ethyl)benzenesulfonamide Ketone (Ket-10, 1.33 g, 6.15 mmol) and indole (Ind-104, 1.85 g, 6.15 mmol) were dissolved in abs. methylene chloride (40 ml) under argon. Trifluoromethanesulfonic acid (1.07 ml, 12.3 mmol) was then added rapidly and the mixture was stirred at RT for 16 h. For working up, the mixture was rendered basic with 1 N NaOH and subsequently stirred at RT for 15 min. The phases were separated off. The aqueous phase was extracted with methylene chloride (3×20 ml). The organic phase was dried over $Na_2SO_4$ and concentrated i. vac. $CHCl_3$/MeOH (9:1, 10 ml) was added to the residue and an insoluble solid thereby precipitated out. This solid was filtered off with suction and dried i. vac. Yield: 1.14 g (37%)

N-(2-(2-(4-(dimethylamino)-4-phenylcyclohexyl)-1H-indol-3-yl)ethyl)benzenesulfonamide, citrate (1:1):More polar diastereomer The olefin obtained (1.14 g/2.28 mmol) was dissolved in HBr/glacial acetic acid (55 ml). Tin (2.64 g/2.28 mmol) was added in the course of 30 min and the mixture was stirred at RT for 4 h. Ethanol was added to the mixture and the mixture was stirred at RT overnight. (however, 20 min is actually sufficient). The mixture was then concentrated to dryness i. vac., 5 N NaOH was added and the mixture was extracted with methylene chloride (3×20 ml). The organic phase was dried over $Na_2SO_4$ and concentrated i. vac. The residue was purified by flash chromatography EA/EtOH (2:1).

Yield: 45 mg (4%) non-polar
285 mg (25%) polar
Citrate Polar:
The more polar diastereomer just isolated (280 mg/0.558 mmol) was dissolved in hot ethanol (5 ml). Citric acid (106 mg/0.558 mmol) was dissolved in hot ethanol (1 ml) and added. The mixture was cooled to RT, a precipitate thereby precipitating out. The precipitate was filtered off with suction and dried i. vac.

Yield: 154 mg (40%); melting point: 145-149° C.
$^1$H-NMR (DMSO-$d_6$): 1.40-1.49 (2H, m); 1.72 (2H, d); 1.85 (2H, t); 2.22 (6H, s); 2.40-2.59 (4H, m); 2.70-2.74 (2H, m); 2.82-2.93 (5H, m); 6.83-6.92 (2H, m); 7.12-7.23 (2H, dd); 7.42 (1H, t); 7.49-7.64 (7H, m); 7.80 (2H, d); 10.38 (1H, s); 11.42 (4H, bs).

Example 284

(±)-N-(2-(2-(4-(dimethylamino)-4-phenylcyclohex-1-enyl)-1H-indol-3-yl)ethyl)thiophene-2-sulfonamide Ketone (Ket-10, 975 mg, 4.5 mmol) and indole (Ind-105, 1.38 g, 4.5 mmol) were dissolved in abs. methylene chloride (40 ml) under argon. Trifluoromethanesulfonic acid (781 µl, 9.0 mmol) was then added rapidly and the mixture was stirred at RT for 16 h. For working up, the mixture was rendered basic with 1 N NaOH and subsequently stirred at RT for 15 min. The phases were separated. The aqueous phase was extracted with methylene chloride (3×20 ml). The organic phase was dried over $Na_2SO_4$ and concentrated i. vac. The residue was purified by flash chromatography $CHCl_3$/MeOH (15:1, 1:1, MeOH+1% TEA).

Yield: 1.26 g (55%)

N-(2-(2-(4-(dimethylamino)-4-phenylcyclohexyl)-1H-indol-3-yl)ethyl)thiophene-2-sulfonamide, citrate (1:1):Less polar diastereomer The olefin just isolated (1.26 g, 2.49 mmol) was dissolved in HBr/glacial acetic acid (50 ml). Tin (2.88 g, 2.49 mmol) was added in the course of 30 min and the mixture was stirred at RT for 3 h. Ethanol was added to the mixture and the mixture was stirred at RT for 10 min. The mixture was then concentrated to dryness i. vac., 5 N NaOH was added and the mixture was extracted with methylene chloride (3×20 ml). The organic phase was dried over $Na_2SO_4$ and concentrated i. vac. The residue was separated by flash chromatography $CHCl_3$/MeOH (20:1, 4:1, MeOH+1% TEA).

Yield: 268 mg (22%) of less polar diastereomer
262 mg (20%) of more polar diastereomer
Citrate Non-Polar:
The less polar diastereomer just obtained (268 mg/0.528 mmol) was dissolved in hot ethanol (15 ml) and methanol (5 ml). Citric acid (101 mg/0.528 mmol) was dissolved in hot ethanol (1 ml) and added. The mixture was cooled to RT, a precipitate thereby precipitating out. The precipitate was filtered off with suction and dried i. vac.

Yield: 232 mg (62%); melting point: 233-235° C.

$^1$H-NMR (DMSO-$d_6$): 1.51-1.64 (4H, m); 2.11 (8H, s); 2.57-2.72 (4H, m); 2.80-2.97 (7H, m); 6.88-7.00 (2H, m); 7.13-7.15 (1H, m); 7.29-7.45 (7H, m); 7.55-7-56 (1H, m); 7.87-7.94 (2H, m) 10.65 (1H, s); 11.1 (4H, bs).

Example 285

N-(2-(2-(4-(dimethylamino)-4-phenylcyclohexyl)-1H-indol-3-yl)ethyl)thiophene-2-sulfonamide, citrate (1:1):More polar diastereomer Citrate Polar:
The more polar diastereomer obtained under Example 284 (262 mg/0.516 mmol) was dissolved in hot ethanol (15 ml) and methanol (5 ml). Citric acid (98 mg/0.516 mmol) was dissolved in hot ethanol (1 ml) and added. The mixture was cooled to RT, a precipitate thereby precipitating out. The precipitate was filtered off with suction and dried i. vac.

Yield: 229 mg (63%); melting point: 143-145° C.

$^1$H-NMR (DMSO-$d_6$): 1.40-1.52 (2H, m); 1.71-1.86 (4H, m); 2.21 (6H, s); 2.47-2.60 (4H, m); 2.74-2.94 (7H, m); 6.84-6.94 (2H, m); 7.13-7.28 (3H, m); 7.42-7.59 (6H, m); 7.92-7.94 (2H, m) 10.41 (1H, s); 11.1 (4H, bs).

Example 286

(±)-N-(2-(2-(4-(dimethylamino)-4-phenylcyclohex-1-enyl)-1H-indol-3-yl)ethyl)nicotinamide Ketone (Ket-10, 392 mg, 1.81 mmol) and indole (Ind-106, 482 mg, 1.81 mmol) were dissolved in abs. methylene chloride (40 ml) under argon. Trifluoromethanesulfonic acid (471 µl, 5.43 mmol) was then added rapidly and the mixture was stirred at RT for 16 h. For working up, the mixture was rendered basic with 1 N NaOH and subsequently stirred at RT for 15 min. The phases were separated off. The aqueous phase was extracted with methylene chloride (3×20 ml). The organic phase was dried over $Na_2SO_4$ and concentrated i. vac. The residue was purified by flash chromatography $CHCl_3$/MeOH (20:1, 1:1, MeOH).

Yield: 277 mg (33%)

N-(2-(2-(4-(dimethylamino)-4-phenylcyclohexyl)-1H-indol-3-yl)ethyl)nicotinamide, citrate (1:1):Less polar diastereomer The olefin just isolated (333 mg/0.716 mmol) was dissolved in HBr/glacial acetic acid (25 ml). Tin (828 mg/0.716 mmol) was added in the course of 30 min and the mixture was stirred at RT for 3 h. Ethanol was added to the mixture and the mixture was stirred at RT for 10 min. The mixture was then concentrated to dryness i. vac., 5 N NaOH was added and the mixture was extracted with methylene chloride (3×20 ml). The organic phase was dried over $Na_2SO_4$ and concentrated i. vac. The residue was purified by flash chromatography $CHCl_3$/MeOH (50:1).

Yield: 91 mg (27%) of less polar diastereomer
248 mg (74%) of more polar diastereomer, slightly contaminated
Citrate Non-Polar:
The less polar diastereomer just obtained (86 mg/0.184 mmol) was dissolved in hot ethanol (8 ml). Citric acid (35 mg/0.184 mmol) was dissolved in hot ethanol (1 ml) and added. The mixture was concentrated to dryness i. vac. and ether was added. The precipitate which had precipitated out was filtered off with suction and dried i. vac.

Yield: 59 mg (48%); melting point: 263-265° C.

$^1$H-NMR (DMSO-$d_6$): 1.67-1.71 (4H, m); 2.33 (8H, s); 2.92-2.97 (5H, m); 3.44 (2H, qu); 6.91-7.03 (2H, m); 7.28 (1H, d); 7.44-7.54 (7H, m); 8.14-8.18 (1H, m); 8.67-8.69 (1H, m); 8.82 (1H, t); 8.98 (1H, d); 11.1 (1H, s).

Example 287

N-(2-(2-(4-(dimethylamino)-4-phenylcyclohexyl)-1H-indol-3-yl)ethyl)nicotinamide, citrate (1:1):More polar diastereomer Citrate Polar:
The more polar diastereomer obtained under Example 286 (248 mg/0.531 mmol) was dissolved in hot ethanol (10 ml) and methanol (5 ml). Citric acid (101 mg/0.531 mmol) was dissolved in hot ethanol (1 ml) and added. The mixture was cooled to RT, a precipitate thereby precipitating out. The precipitate was filtered off with suction and dried i. vac.

Yield: 49 mg (14%); melting point: 205-210° C.

$^1$H-NMR (DMSO-$d_6$): 1.41-1.54 (2H, m); 1.78-1.83 (2H, m); 2.08-2.20 (2H, m); 2.38 (6H, s); 2.49-2.62 (4H, m); 2.86-3.16 (5H, m); 3.40-3.45 (2H, m) 6.88-6.93 (2H, m); 7.14-16 (1H, m); 7.48-7.59 (5H, m); 7.72 (2H, d); 8.24-8.27 (1H, m); 8.69-8.71(1H, m); 8.99-9.03 (2H, m); 10.42 (1H, s); 11.45 (4H, bs).

Example 288

4-(3-(2-Bromoethyl)-1H-indol-2-yl)-N,N-dimethyl-1-phenylcyclohexanamine

2-[2-(4-Dimethylamino-4-phenyl-cyclohexyl)-1H-indol-3-yl]-ethanol (Example 219, 3.20 g, 8.8 mmol) was dissolved in abs. $CH_2Cl_2$ (50 ml) at RT and tetrabromomethane (4.39 g, 13.2 mmol) was added. Triphenylphosphine (3.61 g, 12.6 mmol) was then added at RT. The solution was stirred at RT for 2.5 h and then concentrated i. vac. Flash chromatography of the residue with 300 g of silica gel and ethyl acetate/ethanol (1:2) gave 1.98 g of contaminated product, 1 N NaOH was added to this and the mixture was extracted three times with $CHCl_3$. The organic phase was dried over $Na_2SO_4$ and concentrated i. vac. Yield: 1.57 g (42%)

4-(3-(2-aminoethyl)-1H-indol-2-yl)-N,N-dimethyl-1-phenylcyclohexanamine

The bromide just prepared (868 mg, 2.0 mmol) was dissolved in 2 N $NH_3$ solution in ethanol (15 ml) and the solution was stirred in a pressure vessel at 100° C. for 7 h. The solution was concentrated i. vac. The residue obtained was washed with ethanol and then dried i. vac.

Yield: 924 mg (>100%), diastereomer mixture $^1$H-NMR (DMSO-$d_6$): 1.43-1.52 (2H, m); 1.76-1.79 (2H, m); 2.17 (6H, s); 2.89-3-06 (7H, m); 6.91-6.95 (2H, m); 7.17 (1H, d); 7.39-7.62 (6H, m); 8.08 (2H, bs); 10.48/10.49 (1H, 2s).

N-(2-(2-(4-(dimethylamino)-4-phenylcyclohexyl)-1H-indol-3-yl)ethyl)benzamide, citrate (1:1): One of two possible diastereomers The 4-(3-(2-aminoethyl)-1H-indol-2-yl)-N,N-dimethyl-1-phenylcyclohexanamine just prepared (200 mg, 0.55 mmol) was suspended in abs. $CH_2Cl_2$ (5 ml). Triethylamine (78 μl, 0.63 mmol) and benzoyl chloride (73 μl, 0.63 mmol) were then added at RT and the mixture was stirred at RT for 1 d. Water was added to the mixture and the mixture was extracted three times with $CH_2Cl_2$. The organic phase was dried over $Na_2SO_4$ and concentrated i. vac. The residue obtained was purified by flash chromatography with 50 g of silica gel and ethyl acetate/ethanol (1:1→1:2→1:4).

Yield: 129 mg (50%), diastereomer mixture

Citrate:

Since the spectrum of the compound just prepared indicated a salt, 1 N NaOH was added to it (119 mg, 0.26 mmol), the mixture was extracted several times with $CH_2Cl_2$ and the organic phase was then dried over $Na_2SO_4$ and concentrated i. vac. The pure compound obtained (52 mg, 0.11 mmol) was dissolved hot in ethanol (1 ml), and citric acid (22 mg, 0.11 mmol), dissolved in ethanol (0.5 ml), was added. After 2 hours the precipitate which had precipitated out was filtered off with suction and rinsed with ether.

Yield: 15 mg (20%)

$^1$H-NMR (DMSO-$d_6$): 1.40-1.55 (2H, m); 1.74-1.84 (4H, m); 2.31 (6H, s); 2.49-2.63 (4H, m); 2.89-2.93 (5H, m); 3.36-3.42 (2H, m); 6.87-6.95 (2H, m); 7.14-7.16 (1H, m); 7.45-7.61 (9H, m); 7.86-7.89 (2H, m); 8.61 (1H, t); 10.40 (1H, s); 11.10 (4H, bs).

Example 289

1-(3-Fluorophenyl)-N,N-dimethyl-4-(3-(2-(pyridin-4-yl)ethyl)-1H-indol-2-yl)cyclohexanamine, non-polar diastereomer

Example 290

1-(3-Fluorophenyl)-N,N-dimethyl-4-(3-(2-(pyridin-4-yl)ethyl)-1H-indol-2-yl)cyclohexanamine, citrate (1:1), polar diastereomer

1-(3-Fluorophenyl)-N,N-dimethyl-4-(3-(2-(pyridin-4-yl)ethyl)-1H-indol-2-yl)cyclohexanamine (polar diastereomer) and

1-(3-Fluorophenyl)-N,N-dimethyl-4-(3-(2-(pyridin-4-yl)ethyl)-1H-indol-2-yl)cyclohexanamine, non-polar diastereomer (289)

Ex. 252 (257 mg, 0.58 mmol) was dissolved in HBr/glacial acetic acid (33% HBr, 15 ml). Sn powder (2 g, 16.8 mmol) was then added to the mixture in portions at RT in the course of 60 min. The mixture was stirred at RT overnight (18 h). The yellow solid which had precipitated out was separated off by means of a frit. The filter cake was washed with glacial acetic acid (10 ml), heated to the boiling point in ethanol (10 ml) and then separated off by filtration. 2 N NaOH (10 ml) and ethyl acetate (20 ml) were added to the solid and the mixture was stirred for 20 min. The solid (1-(3-fluorophenyl)-N,N-dimethyl-4-(3-(2-(pyridin-4-yl)ethyl)-1H-indol-2-yl)cyclohexanamine, polar diastereomer) at the phase boundary was separated off by means of a frit and dried (158 mg, melting point: 301-314° C., 61% yield) and was employed for the citrate formation (see Ex. 290).—The glacial acetic acid/HBr solution, the ethyl acetate phase and the ethanolic solution were concentrated to dryness on a rotary evaporator and the particular residues were combined. The mixture obtained in this way was rendered basic with 5 N NaOH (10 ml) and extracted with ethyl acetate (5×20 ml). The combined organic phases were washed with water (50 ml), dried over $MgSO_4$ and then concentrated. The residue was purified by column chromatography [silica gel 60 G (10 g); EtOAc/EtOH 1:1 (150 ml)]. Example 289 (less polar diastereoisomer) was obtained in this way in a yield of 30 mg (11%) as a white solid with a melting point of 211-218° C. $^1$H NMR (300 MHz, $CDCl_3$) δ ppm: 1.18-1.36 (m, 2H), 1.39-1.52 (m, 2H), 1.58-1.74 (m, 2H), 2.08 (s, 6H), 2.46-2.50 (m, 1H), 2.63-2.75 (m, 1H), 2.86-3.08 (m, 4H), 6.90-7.15-(m, 6H), 7.18-7.32 (m, 1H), 7.34-7.45 (m, 1H), 7.48-7.54 (m, 2H), 8.43 (dd, J=4.44, 1.57 Hz, 2H)

$^{13}$C NMR (101 MHz, $CDCl_3$. δ)ppm: 25.5, 29.4, 33.5, 35.7, 36.2, 38.1, 61.5, 108.9, 110.5, 113.7, 113.9, 115.0, 115.2, 117.9, 119.2, 121.2, 123.8, 124.2, 128.1, 129.4, 129.5, 135.1, 139.0, 149.37, 151.2, 161.8, 164.3

1-(3-Fluorophenyl)-N,N-dimethyl-4-(3-(2-(pyridin-4-yl)ethyl)-1H-indol-2-yl)cyclohexanamine, citrate (1:1), polar diastereomer (290)

1-(3-Fluorophenyl)-N,N-dimethyl-4-(3-(2-(pyridin-4-yl) ethyl)-1H-indol-2-yl)cyclohexanamine (more polar diastereomer, 140 mg, 0.36 mmol) was heated to the boiling point in isopropanol (100 ml). Still undissolved particles were separated off by means of a frit. Citric acid (160 mg, 0.83 mmol), dissolved in hot isopropanol (3 ml), was added to the solution obtained. The solvent volume was reduced to approx. 20 ml on a rotary evaporator and the mixture was then cooled to 5° C. (refrigerator) and left at this temperature for 2 h. The precipitate formed was separated off by means of a frit and then dried in a high vacuum. Example 290 was obtained in this way in a yield of 84 mg (41%) with a melting point of 143-151° C.

$^1$H NMR (300 MHz, DMSO-d$_6$) δ ppm: 1.29-1.49 (m, 4H), 2.02 (s, 6H), 2.52-2.67 (m, 6H), 2.67-2.78 (m, 3H), 2.79-3.03 (m, 4H), 6.86-7.03 (m, 2H), 7.05-7.26 (m, 5H), 7.26-7.33 (m 1H), 7.36-7.50 (m, 2H), 8.39 (dd, J=4.53, 1.36 Hz, 2H), 10.60 (s, 1H)

Example 291

-Methyl-1-phenyl-4-(3-(2-(pyridin-4-yl)ethyl)-1H-indol-2-yl)cyclohexanamine, citrate (2:1), non-polar diastereomer Example 292

-Methyl-1-phenyl-4-(3-(2-(pyridin-4-yl)ethyl)-1H-indol-2-yl)cyclohexanamine, citrate (1:1), polar diastereomer N-Methyl-1-phenyl-4-(3-(2-(pyridin-4-yl)ethyl)-1H-indol-2-yl)cyclohexanamine (non-polar and polar diastereomer)

Ex. 254 (350 mg, 0.86 mmol) was dissolved in hydrogen bromide/glacial acetic acid (33% HBr, 18 ml). Tin powder (1.02 g, 8.6 mmol) was then added to the mixture in portions at room temperature in the course of 40 min. A yellow suspension was formed. The mixture was stirred for a further 20 h. The mixture was then diluted with methylene chloride (50 ml) and rendered alkaline with 5 N sodium hydroxide solution (50 ml), while cooling with ice. The phases were separated. The aqueous phase was extracted with methylene chloride (3×30 ml). The combined organic phases were dried with Na$_2$SO$_4$ and then filtered. The volatile constituents of the filtrate were removed completely in vacuo. A pale yellow solid (534 mg) remained. This was separated by chromatography [silica gel 60 (50 g); ethyl acetate/methanol 4:1 (500 ml); methanol/ethyl acetate 3:2 (500 ml); 4:1 (500 ml)]. It was possible for N-methyl-1-phenyl-4-(3-(2-(pyridin-4-yl) ethyl)-1H-indol-2-yl)cyclohexanamine (less polar diastereoisomer) (178 mg, 50%, m.p.: 251-256° C.) and the more polar diastereoisomer (97 mg, 28%, m.p.: 224-227° C.) to be obtained in this way.

N-Methyl-1-phenyl-4-(3-(2-(pyridin-4-yl)ethyl)-1H-indol-2-yl)cyclohexanamine, citrate (2:1), non-polar diastereomer N-Methyl-1-phenyl-4-(3-(2-(pyridin-4-yl)ethyl)-1H-indol-2-yl)cyclohexanamine (less polar diastereoisomer) (178 mg, 0.43 mmol) was dissolved in ethanol (20 ml), while heating, and citric acid (100 mg, 0.52 mmol), dissolved in hot ethanol (4 ml), was added. The solution was stirred for 17 h and then concentrated down to approx. 3 ml, and diethyl ether (5 ml) was added until crystallization occurred. The colourless precipitate which had precipitated out was filtered off with suction and washed with diethyl ether (5 ml). Example 291 was obtained in this way in a yield of 53% (115 mg) with a melting point of 267-277° C.

$^1$H NMR (400 MHz, DMSO-d$_6$) δ ppm: 1.30-1.48 (m, 2H), 1.80-1.99 (m, 2H), 2.18 (s, 3H), 2.21-2.38 (m, 2H), 2.38-2.49 (m, 2H), 2.60 (dd, J=33.53, 15.20 Hz, 2H), 2.72-2.93 (m, 3H), 2.93-3.08 (m, 2H), 6.90-6.99 (m, 1H), 6.99-7.08 (m, 1H), 7.11-7.20 (m, 2H), 7.23-7.31 (m, 1H), 7.37-7.45 (m, 1H), 7.45-7.55 (m, 3H), 7.59-7.69 (m, 2H), 8.39 (d, J=5.09 Hz, 2H), 10.98 (s, 1H)

$^{13}$C NMR (101 MHz, DMSO-d$_6$) δ ppm: 24.8, 26.4, 26.9, 32.3, 32.5, 36.0, 43.7, 60.8, 71.6, 107.6, 110.5, 117.7, 118.1, 120.2, 124.2, 126.1, 127.4, 128.4, 128.8, 135.2, 139.8, 149.1, 150.7, 171.2, 176.1

N-Methyl-1-phenyl-4-(3-(2-(pyridin-4-yl)ethyl)-1H-indol-2-yl)cyclohexanamine, citrate (1:1), polar diastereomer (292)

N-Methyl-1-phenyl-4-(3-(2-(pyridin-4-yl)ethyl)-1H-indol-2-yl)cyclohexanamine (more polar diastereoisomer) (97 mg, 0.284 mmol) was dissolved in ethanol (10 ml), while heating, and citric acid (55 mg, 0.284 mmol), dissolved in hot ethanol (2 ml), was added. After stirring at room temperature for 1 h, a colourless solid started to precipitate out. This was filtered off and washed with diethyl ether (5 ml). Example 292 was obtained in a yield of 52% (74 mg) with a melting point of 243-245° C.

$^1$H NMR (300 MHz, DMSO-d$_6$) δ ppm: 1.33-1.58 (m, 4H), 1.62-1.87 (m, 2H), 2.01 (s, 3H), 2.51 (dd, J=24.19, 15.02 Hz, +DMSO), 2.60-2.75 (m, 3H), 2.75-2.86 (m, 2H), 2.86-2.99 (m, 2H), 6.84-7.01 (m, 2H), 7.06-7.13 (m, 2H), 7.13-7.22 (m, 1H), 7.33-7.54 (m, 4H), 7.54-7.66 (m, 2H), 8.37-8.48 (m, 2H), 10.41 (s, 1H)

$^{13}$C NMR (101 MHz, DMSO-d$_6$) δ ppm: 25.1, 26.9, 28.5, 33.8, 35.7, 36.0, 44.6, 59.9, 71.1, 107.7, 110.7, 117.4, 118.0, 120.0, 124.0, 127.7, 127.8, 128.7, 135.2, 137.8, 139.2, 149.2, 150.7, 171.5, 177.2

Example 293

-(4-Butyl-4-(pyrrolidin-1-yl)cyclohexyl)-3-methyl-1H-indole, citrate (2:1), non-polar diastereomer 2-(4-Butyl-4-(pyrrolidin-1-yl)cyclohexyl)-3-methyl-1H-indole (non-polar and polar diastereomer)

Variant 1: Example 258 (211 mg, 0.627 mmol) was dissolved in methanol (30 ml), and palladium on charcoal (5 per cent strength, 50 mg) was added. The reaction mixture was hydrogenated under 3 bar for 3.5 h. The catalyst was separated off over Celite and the filtrate was concentrated. The residue (200 mg, pale brown oil) was separated by chromatography [silica gel 60 (20 g); ethyl acetate/methanol (10:1 (200 ml), ethyl acetate/methanol 4:1 (200 ml), methanol (200 ml)]. 2-(4-Butyl-4-(pyrrolidin-1-yl)cyclohexyl)-3-methyl-1H-indole (less polar diastereoisomer) was obtained in a yield of 10% (20 mg), and the more polar diastereoisomer was obtained in a yield of 67% (143 mg). Both diastereoisomers were in the form of colourless salts after the chromatography.

Variant 2: Example 258 (180 mg, 0.535 mmol) was dissolved with HBr/glacial acetic acid (33% HBr, 10 ml) at room temperature in the course of 1 h. Tin powder (64 mg, 0.535 mmol) was then added to the mixture in portions in the course of 10 min. When the addition had ended, the reaction mixture was stirred for a further 30 min. Water (20 ml) was added to the mixture, while cooling with ice, and the mixture was stirred at room temperature for 15 min. The beige-coloured solid which had precipitated out was filtered off with suction and washed with water (4×5 ml) and with methylene chloride (2×5 ml). The hydrobromide of the diastereoisomer mixture was obtained in a yield of 69% (155 mg). The salt was taken up in a mixture of methylene chloride (30 ml), water (20 ml) and 1 N sodium hydroxide solution (2 ml) and the mixture was stirred at room temperature for 30 min. The phases were separated. The aqueous phase was extracted with methylene chloride (20 ml). The organic phases were combined, dried with sodium sulfate and concentrated. The residue (107 mg, beige-coloured oil) was separated by chromatography [silica gel 60 (20 g); ethyl acetate/methanol (10:1 (200 ml), ethyl acetate/methanol 4:1 (200 ml), methanol (200 ml)]. The less polar diastereoisomer was obtained in a yield of 31% (56 mg) and the more polar diastereoisomer was obtained in a yield of 17% (31 mg). Both diastereoisomers were in the form of colourless salts after the chromatography.

2-(4-Butyl-4-(pyrrolidin-1-yl)cyclohexyl)-3-methyl-1H-indole, citrate (2:1), non-polar diastereomer
(293)

The salt of the less polar diastereomer (76 mg) was taken up in a mixture of methylene chloride (30 ml), water (20 ml) and 1 N sodium hydroxide solution (1 ml) and the mixture was stirred at room temperature for 1 h. The phases were separated. The aqueous phase was extracted with methylene chloride (20 ml). The combined organic phases were dried with sodium sulfate and concentrated. The residue (beige-coloured oil, 75 mg, 0.221 mmol) was dissolved in ethanol (5 ml), and an ethanolic solution (1.5 ml) of citric acid (46 mg, 0.24 mmol) was added. A precipitation was immediately visible. After 30 min diethyl ether (15 ml) was added. After a reaction time of 1 h at room temperature, the colourless solid was separated off by filtration and washed with diethyl ether (2×ml). Example 293 was obtained in a yield of 70% (67 mg) with a melting point of 214-216° C.

$^1$H NMR (300 MHz, DMSO-d$_6$) δ ppm: 0.94 (t, 3H), 1.12-1.37 (m, 5H), 1.37-1.70 (m, 7H), 1.70-2.03 (m, 8H), 2.18 (s, 3H), 2.54 (dd, 2H), 2.63-3.11 (m, 3H), 6.88-7.02 (m, 2H), 7.30 (d, 1H), 7.36 (d, 1H), 10.32 (s, 1H)

Example 294

(±)-3-(4-(Dimethylamino)-4-phenylcyclohex-1-enyl)-(1-(phenylsulfonyl)-1H-indole)

1-Benzenesulfonyl-1H-indole (504 mg, 2 mmol) was dissolved in methylene chloride (20 ml) together with the ketone (Ket-10, 434 mg, 2 mmol), and trifluoromethanesulfonic acid (0.2 ml, 2.3 mmol) was added. The mixture was stirred at RT for 15 h. Since according to TLC the reaction was not complete, the mixture was stirred for a further 3 d.—For working up, 2 N NaOH (10 ml) was added to the reaction solution. The mixture was stirred for a further 20 min. After separation of the phases, the aqueous phase was extracted with methylene chloride (3×20 ml). The combined organic extracts were dried over Na$_2$SO$_4$ and then concentrated. The crude product obtained (917 mg) was purified by column chromatography (mobile phase: EtOAc). In addition to a bisindole compound (178 mg, m.p.: 237-242° C.), the desired olefin was obtained in a yield of 440 mg (48%, m.p.: 165-167° C.) in crystalline form.

N,N-dimethyl-1-phenyl-4-(1-(phenylsulfonyl)-1H-indol-2-yl)cyclohexanamine: Less polar diastereomer The olefin just obtained (300 mg, 0.66 mmol) was dissolved in HBr/glacial acetic acid (33% HBr, 10 ml) (not all the substance was dissolved and a larger amount of HBr therefore seems appropriate). Sn powder (0.8 g, 7 mmol) was then added to the mixture in portions at RT in the course of 40 min. When the addition had ended, the reaction mixture was stirred for a further 3 h.—For working up, the mixture was concentrated to dryness on a rotary evaporator. The residue which remained was rendered basic by addition of 5 N NaOH (20 ml). Methylene chloride was added to the solution obtained and the mixture was extracted (4×20 ml). The combined organic phases were dried with MgSO$_4$ and then concentrated. The residue obtained (290 mg) was purified by column chromatography (mobile phase: 1) EtOAc; 2) EtOAc/EtOH 2:1; 3) EtOH). The less polar diastereoisomer, which ran in the vicinity of the solvent front in the thin layer chromatogram when EtOAc was used, was obtained in this way in a yield of 29 mg (9%) in the form of a yellowish oil. The more polar diastereoisomer, which remained in the vicinity of the starting spot in the thin layer chromatogram when EtOAc was used, was obtained in a yield of 132 mg (43%) as a white solid (m.p.: 139-142° C.). The starting substance was recovered to the extent of 40%.

$^1$H NMR (300 MHz, CDCl$_3$) δ ppm: 1.54-1.78 (m, 2H), 1.82-1.96 (m, 2H), 1.99-2.17 (m, 8H), 2.65-2.90 (m, 3H), 7.17-7.64 (m, 12H), 7.82-8.03 (m, 3H)

$^{13}$C NMR (101 MHz, CDCl$_3$.) δ ppm: 27.7, 33.3, 34.7, 37.8, 58.8, 113.8, 119.9, 121.7, 122.9, 124.5, 126.8, 127.5, 129.0, 129.2, 130.6, 133.5, 135.4, 138.5, 139.8

Example 295

N-dimethyl-1-phenyl-4-(1-(phenylsulfonyl)-1H-indol-2-yl)cyclohexanamine:More polar diastereoisomer The more polar diastereomer obtained under Example 294 is presented as Example 295 in the following.

$^1$H NMR (300 MHz, CDCl$_3$) δ ppm: 1.30-1.51 (m, 2H), 1.87-2.07 (m, 4H), 2.19 (s, 6H), 2.75-2.94 (m, 3H), 7.09 (s, 1H), 7.12-7.20 (m, 1H), 7.21-7.29 (m, 1H), 7.31-7.52 (m, 9H), 7.33-7.81 (m, 2H), 7.91 (d, J=8.21 Hz, 1H)

$^{13}$C NMR (101 MHz, CDCl$_3$.) δ ppm: 29.1, 33.0, 34.7, 38.1, 63.1, 113.7, 119.7, 121.2, 122.9, 124.5, 126.6, 127.3, 127.8, 128.3, 129.1, 130.2, 133.5, 134.8, 135.4, 138.2

Example 296

(±)-2-(4-(Dimethylamino)-4-phenylcyclohex-1-enyl)-3-(methyl)-(1-(oxiran-2-ylmethyl)-1H-indole): diastereomer mixture The free base of Example 16 (350 mg, 1.06 mmol) was initially introduced into dimethylformamide/tetrahydrofuran (20 ml, 1:1). Sodium hydride (60 per cent strength suspension in mineral oil, 110 mg, 2.75 mmol) was added to the clear pale yellow solution at room temperature. The reaction mixture gassed first. A light-coloured solid then precipitated out of the reaction mixture. The mixture was stirred at 57° C. (oil bath temperature) for 1 h. The epichlorohydrin (255 mg, 0.22 ml, 2.75 mmol; 1.183 g/ml) was then added at this temperature. The reaction mixture started to boil. The mixture was stirred at 57° C. (oil bath temperature) for 1 h. Water (30 ml) and diethyl ether (20 ml) were then added to the reaction mixture. The mixture was stirred for 10 min. The phases were then separated. The aqueous phase was extracted with ethyl acetate (2×20 ml). The combined organic phases were washed with saturated aqueous NaCl solution (3×10 ml), dried with sodium sulfate and filtered. The volatile constituents were then removed completely in vacuo. A pale yellow oil which still contained dimethylformamide remained. A colourless solid crystallized out of the oil overnight. This did not dissolve in methanol. The solid was filtered off and dried in vacuo (100 mg, 0.26 mmol; 24% of both diastereoisomers). The filtrate was absorbed on coarse silica gel and separated by chromatography [silica gel 60 (150 g); ethyl acetate (500 ml); ethyl acetate/methanol 5:1 (500 ml), 2:1 (500 ml)]. Further epoxide (200 mg, 0.52 mmol; 49%; both diastereoisomers, m.p. 147-150° C.) was isolated.

$^1$H NMR (400 MHz, RT, DMSO-D$_6$) δ ppm: 1.56 (s, br, 1H), 1.88-2.25 (m, br, 12H), 2.36 (psd, 1H), 2.53-3.03 (m, 4H), 3.77-3.83 (m, 1H), 3.90-4.14 (m, 1H), 5.96 (s, br, 1H), 6.97 (pst, 1H), 7.06 (pst, 1H), 7.27 (pst, 1H), 7.36 and 7.51 (pst and psd, 6H).

$^{13}$C NMR (101 MHz, RT, DMSO-D$_6$) δ ppm: 8.66, 8.68, 26.93, 26.99, 28.96, 29.01, 32.71, 32.75, 44.66, 44.84, 44.94, 45.19, 50.71, 50.75, 60.18, 60.20, 106.12, 106.16, 110.08, 110.09, 117.94, 117.95, 118.66, 118.67, 120.84, 120.86, 126.45, 127.17, 127.19, 127.47, 127.49, 127.95, 127.96, 129.23, 129.25, 131.00, 135.99, 136.02, 138.42, 138.49, 142.26, 142.27.

Example 297

N,N-dimethyl-4-(3-methyl-1-(oxiran-2-ylmethyl)-1H-indol-2-yl)-1-phenylcyclohexanamine, citrate (1:1):More polar diastereomer The free base of the more polar skatole derivative Example 18 (500 mg, 1.50 mmol) was initially introduced into dimethylformamide/tetrahydrofuran (20 ml, 1:1), and sodium hydride (60 per cent strength suspension in mineral oil, 210 mg, 3.13 mmol) was added to the clear pale yellow solution. The reaction mixture gassed. A light-coloured solid then precipitated out of the reaction mixture. The mixture was stirred at 57° C. (oil bath temperature) for 1 h. The epichlorohydrin (290 mg, 0.122 ml, 3.13 mmol; 1.183 g/ml) was then added at this temperature. The reaction mixture started to boil. The mixture was stirred at 57° C. (oil bath temperature) for 1 h. Water (30 ml) and diethyl ether (20 ml) were then added to the reaction mixture. The mixture was stirred for 10 min. The phases were then separated. The aqueous phase was extracted with ethyl acetate (2×20 ml). An attempt was made to extract the aqueous phase with methylene chloride. However, this was unsuccessful. It was not possible to extract an epoxide. The combined organic phases (ethyl acetate and diethyl ether) were washed with saturated aqueous NaCl solution (3×10 ml), dried with sodium sulfate and filtered. The volatile constituents were then removed completely in vacuo. An attempt was made to separate the residue by chromatography [silica gel 60 (150 g), ethyl acetate/methanol 1:1 (1,500 ml)]. It was possible for 215 mg (0.55 mmol; 37%) of the polar target compound to be isolated as a colourless powder.

Citrate Polar:

The more polar skatole derivative just obtained (50 mg, 0.129 mmol) was dissolved in boiling ethanol (3 ml). Citric acid (27 mg, 0.14 mmol) was then added. The clear solution was stirred at the boiling point for 30 min. The reaction mixture was then cooled to room temperature and left to stand at this temperature for 24 h. A colourless microcrystalline precipitate precipitated out. This was filtered off and washed with ethanol (2×5 ml). 52 mg (0.090 mmol; 69%) of the polar citrate (m.p. 182-184° C.) were obtained.

Example 298

1-(Dimethylamino)-3-(2-(4-(dimethylamino)-4-phenylcyclohex-1-enyl)-3-methyl-1H-indol-1-yl)propan-2-ol, citrate (1:1): racemate Example 296 (150 mg, 0.39 mmol) was suspended in ethanol (15 ml). Dimethylamine (35 mg, 0.78 mmol, 33 per cent strength in ethanol, 0.14 ml; 0.76 g/ml) was added to the suspension at room temperature. Since no reaction started at room temperature, the reaction mixture was stirred at 59° C. (oil bath temperature) for 10 h. The reaction mixture was then concentrated to dryness in vacuo. The amino alcohol was isolated in a slightly contaminated form as a pale yellow oil (120 mg, 0.26 mmol; 67%) and was employed in this form for the citrate formation.

Citric acid (54 ml, 0.28 mmol) was added to a solution of the amino alcohol just prepared (110 mg, 0.26 mmol) in boiling ethanol (3 ml). The clear solution was stirred at the boiling point for 30 min. The reaction mixture was then cooled to room temperature. A pale yellow solid precipitated out. This was filtered off and washed with ethanol (3×1 ml). 48 mg (0.08 mmol; 30%) of the citrate (Example 298) (m.p. 170-173° C.) were isolated.

Example 299

1-(Dimethylamino)-3-(2-(4-(dimethylamino)-4-phenylcyclohexyl)-3-methyl-1H-indol-1-yl)propan-2-ol, citrate (1:1): more polar diastereomer Dimethylamine (37 mg, 0.82 mmol; 33 per cent strength in ethanol, 0.15 ml; 0.76 g/ml) was added to the free base of the polar epoxide Example 297 (160 mg, 0.41 mmol) in ethanol (15 ml) at room temperature. Since no reaction started at room temperature, the reaction mixture was stirred at 59° C. (oil bath temperature) for 4 h and at room temperature overnight. The reaction mixture was then concentrated to approx. 5 ml in vacuo. A colourless solid precipitated out. This was filtered off. 132 mg (0.30 mmol; 74%) of the polar amino alcohol were isolated.

Citrate Polar:

Citric acid (55 mg, 0.284 mmol) was added to a solution of the polar amino alcohol just isolated (112 mg, 0.26 mmol) in boiling ethanol (3 ml). The clear solution was stirred at the boiling point for 30 min. The reaction mixture was then cooled to room temperature and left to stand at this temperature for 24 h. A colourless microcrystalline precipitate already precipitated out of the warm ethanol. This precipitate was filtered off and dried in vacuo. 128 mg (0.21 mmol; 79%) of the polar citrate (Example 299) were isolated.

Example 300

(±)-2-(3-(4-(Dimethylamino)-4-phenylcyclohex-1-enyl)-1H-indol-1-yl)ethanol hydrochloride The ketone (Ket-10, 217 mg, 1 mmol) was initially introduced into absolute methylene chloride (10 ml) together with 2-indol-1-yl-ethanol (Ind-107, 161 mg, 1 mmol) under an inert gas. The addition of trifluoromethanesulfonic acid trimethylsilyl ester (0.2 ml, 1.03 mmol) then took place. The mixture was stirred at RT for 24 h. For working up, 1 N sodium hydroxide solution (10 ml) was added to the clear lilac-coloured solution, after which decolorization occurred. The mixture was stirred for 30 min. The phases were separated. The aqueous phase was extracted with methylene chloride (2×10 ml). The combined organic phases were washed with water, dried over $Na_2SO_4$ and concentrated. The product was purified by chromatography on silica gel 60 [40 g; methanol/$NH_3$ (500:1)]. The desired olefin was obtained as a pale brown oil in a yield of 30% (104 mg).

Citrate:

Chlorotrimethylsilane (0.06 ml, 0.45 mmol) was added to a solution of the olefin just isolated (104 mg, 0.3 mmol) in ethyl methyl ketone (5 ml) and the mixture was stirred at room temperature for 2 h. The reaction mixture became reddish in colour. The hydrochloride (Example 300) was obtained as a salmon-coloured solid in a yield of 68% (81 mg) with a melting point of 217-219° C.

$^1$H NMR (400 MHz, DMSO-$d_6$) δ ppm: 1.84-2.04 (m, 1H), 2.34-2.27 (m), 2.80-2.94 (m, 1H), 2.94-3.08 (m, 1H), 3.36-3.49 (m, 1H), 3.64 (t, J=5.53 Hz, 2H), 4.01-4.20 (m, 2H), 4.81 (s, 1H), 6.10-6.21 (m, 1H), 6.98-7.07 (m, 1H), 7.07-7.17 (m, 1H), 7.26 (s, 1H), 7.35-7.56 (m, 4H), 7.69-7.75 (m, 1H), 7.75-7.85 (m, 2H), 10.64-10.88 (m, 1H)

Example 301

(±)-3-(4-(Dimethylamino)-4-phenylcyclohex-1-enyl)-(1-(phenylsulfonyl)-1H-indole) hydrochloride, citrate (1:1)

The olefin N,N-dimethyl-1-phenyl-4-(1-(phenylsulfonyl)-1H-indol-2-yl)cyclohex-3-enamine prepared under Example 294 (150 mg, 0.33 mmol) was dissolved in ethanol (20 ml) at the boiling point and citric acid (65 mg, 0.34 mmol), dissolved in hot ethanol (3 ml), was added. Since no precipitate precipitated out even after cooling of the mixture, the solvent was concentrated on a rotary evaporator. The residue was dissolved in isopropanol (12 ml) at the boiling point. On cooling, a tacky precipitate precipitated out, which became crystalline after trituration and prolonged standing. The solid was separated off with the aid of a frit and then dried. The desired product was obtained in this way in a yield of 171 mg (63%, melting point: 198-200° C.) as the citrate (Example 301).

$^1$H NMR (400 MHz, DMSO-$d_6$) δ ppm: 1.68-1.88 (m, 1H), 2.13-2.41 (m, 9H), 2.45-2.76 (m, 4H), 2.67-2.76 (m, 1H), 2.93-3.06 (m, 1H), 6.37 (s, 1H), 7.21-7.45 (m, 5H), 7.49-7.61 (m, 4H), 7.61-7.69 (m, 2H), 7.72-7.80 (m, 1H), 7.89-8.01 (m, 3H)

$^{13}$C NMR (101 MHz, DMSO) δ ppm: 26.4, 278, 30.8, 38.0, 62.7, 71.6 (s, 1C), 113.3, 121.2, 122.6, 123.0, 123.3, 123.7, 124.9, 126.6, 127.5, 127.9, 128.1, 128.9, 129.8, 134.6, 134.7, 136.8, 138.5, 171.2, 176.2

Example 302

(±)-2-(4-(Dimethylamino)-4-benzylcyclohex-1-enyl)-1H-indole hydrochloride

4-Benzyl-4-dimethylamino-1-(1-methyl-1H-indol-2-yl)cyclohexanol

A solution of 2-methylindole (500 mg, 3.81 mmol) in dry THF (20 ml) is cooled to −5° C. under a stream of argon. Thereafter, tert-butyllithium (4.19 mmol, 2.47 ml of a 1.7 M pentane solution) is cautiously added dropwise such that a reaction temperature of 0° C. is not thereby exceeded. When the addition has ended, the reaction mixture is stirred at 0° C. for 2 h. Thereafter, a solution of 4-benzyl-4-dimethylaminocyclohexanone (Ket-3, 880 mg, 3.81 mmol) in dry THF (7 ml) is added dropwise at 0° C. The mixture is stirred at 0° C. for 15 min and then at room temperature for 4 h. The reaction mixture is quenched with saturated ammonium chloride solution (20 ml), the organic phase is separated off and the aqueous phase is extracted four times with methylene chloride (20 ml). The combined organic phases are dried over sodium sulfate and thereafter the solvent is removed in vacuo. Purification is carried out by means of flash chromatography (silica gel, cyclohexane/EtOAc 8:2). 456 mg (33%) of the desired cyclohexanol with a melting point of m.p.=105-107° C. are obtained. Only 1 of 2 possible diastereoisomers is formed.

[1-Benzyl-4-(1-methyl-1H-indol-2-yl)cyclohex-3-enyl]dimethylamine

A solution of the cyclohexanol just prepared (500 mg, 1.53 mmol) in hydrobromic acid (5 ml, 48%) was heated under reflux for 15 min. The cooled reaction mixture was adjusted to a pH of 9 with 5 N NaOH solution. Thereafter, the mixture was extracted with methylene chloride (4-10 ml). The combined organic phases were dried over sodium sulfate and thereafter the solvent was removed in vacuo. Purification was carried out by means of flash chromatography [silica gel, cyclohexane/EtOAc (1:1)]. 230 mg (44%) of the desired olefin were obtained.

[1-Benzyl-4-(1-methyl-1H-indol-2-yl)cyclohex-3-enyl]dimethylamine hydrochloride (302)

For preparation of the hydrochloride, the olefin just obtained (220 mg, 0.638 mmol) was dissolved in ethyl methyl ketone (5 ml), chlorotrimethylsilane (105 mg, 0.96 mol) was added and the mixture was stirred at room temperature in the open reaction vessel for 1 h. The solid thereby formed was filtered off with suction. The hydrochloride (302) was obtained in this way in a yield of 160 mg (66%) as a white solid with a melting point of 244-246° C.

Example 303

N,N-Dimethyl-4-(3-(2-(pyridin-4-yl)ethyl)-1H-indol-2-yl)-1-(thiophen-2-yl)cyclohexanamine hydrochloride, non-polar diastereomer Example 304

N,N-dimethyl-4-(3-(2-(pyridin-4-yl)ethyl)-1H-indol-2-yl)-1-(thiophen-2-yl)cyclohexanamine hydrochloride, polar diastereomer N,N-dimethyl-4-(3-(2-(pyridin-4-yl)ethyl)-1H-indol-2-yl)-1-(thiophen-2-yl)cyclohexanamine (non-polar and polar diastereomer)

Ex. 251 (316 mg, 0.74 mmol) was suspended in HBr/glacial acetic acid (33% HBr, 10 ml). Sn powder (439 mg, 3.7 mmol) was then added to the mixture in portions at RT in the course of 10 min. When the addition had ended, the reaction mixture was stirred at RT for 24 h. A clear solution was formed by this procedure.—For working up, the mixture was diluted with EtOH (20 ml) and concentrated to dryness on a rotary evaporator. The residue which remained was rendered basic by addition of 5 N NaOH (75 ml), and ethyl acetate (70 ml) was added. This mixture was stirred at room temperature for 24 h. The organic phase was separated off and the aqueous phase was extracted with ethyl acetate (4×20 ml). The combined organic phases were washed with water (50 ml), dried over Na$_2$SO$_4$ and then concentrated. It was possible for the crude product obtained (220 mg) to be purified by column chromatography [silica gel 60 (30 g); methanol (300 ml)]. N,N-dimethyl-4-(3-(2-(pyridin-4-yl)ethyl)-1H-indol-2-yl)-1-(thiophen-2-yl)cyclohexanamine (less polar diastereoisomer) was obtained in a yield of 60 mg (19%). The more polar diastereoisomer was isolated in a yield of 43 mg (13%).

N,N-dimethyl-4-(3-(2-(pyridin-4-yl)ethyl)-1H-indol-2-yl)-1-(thiophen-2-yl)cyclohexanamine hydrochloride, non-polar diastereomer N,N-dimethyl-4-(3-(2-(pyridin-4-yl)ethyl)-1H-indol-2-yl)-1-(thiophen-2-yl)cyclohexanamine (less polar diastereoisomer) (60 mg, 0.13 mmol) was dissolved in ethyl acetate (20 ml). Me$_3$SiCl (25 µl, 0.2 mmol) was then added dropwise at RT and the mixture was stirred for 1 h. A white precipitate precipitated out. The precipitate was filtered off with suction, washed with ethyl acetate (2×5 ml) and then dried. Example 303 (59 mg, m.p. 199-204° C., yield 90%) was a white solid.
$^1$H NMR (400 MHz, RT, DMSO-D$_6$) δ ppm: 1.49 (psd, 2H), 2.08 (pst, 1H), 2.38 (psq, 2H), 2.65 (psd, 6H), 2.90 (psd, 2H), 2.99 (psqt, 1H), 3.08 (pst, 4H), 6.94 (pst, 1H), 7.02 (pst, 1H), 7.22-7.27 (m, 2H), 7.48 (psd, 1H), 7.51 (psd, 1H), 7.76 (d, 2H), 7.82 (psd, 1H), 8.69 (d, 2H), 10.19 (s, br, 1H), 11.36 (s, 1H).

N,N-dimethyl-4-(3-(2-(pyridin-4-yl)ethyl)-1H-indol-2-yl)-1-(thiophen-2-yl)cyclohexanamine hydrochloride, polar diastereomer (304)

N,N-dimethyl-4-(3-(2-(pyridin-4-yl)ethyl)-1H-indol-2-yl)-1-(thiophen-2-yl)cyclohexanamine (more polar diastereoisomer) (43 mg, 0.1 mmol) was dissolved in ethyl acetate (20 ml). Me$_3$SiCl (19 µl, 0.15 mmol) was then added dropwise at RT and the mixture was stirred for 1 h. A white precipitate precipitated out. The precipitate was filtered off with suction, washed with ethyl acetate (2×5 ml) and then dried. Example 304 (40 mg, m.p. 188-191° C., yield 87%) was a white solid.
$^1$H NMR (300 MHz, DMSO-d$_6$) δ ppm: 1.47-1.67-(m, 4H), 2.17-2.37-(m, 2H), 2.51-2.57 (m, 6H), 2.57-2.65 (m, 1H), 2.70-2.83 (m, 2H), 2.95-3.14 (m, 4), 6.83-7.04 (m, 2H), 7.12-7.21 (m, 1H), 7.25-7.33 (m, 1H), 7.38-7.48-(m, 1H), 7.49-7.55 (m, 1H), 7.71-7.81 (m, 2H), 7.86-7.93 (m, 1H), 8.78 (d, J=6.43 Hz, 2H), 10.57 (s, 1H), 11.33 (s, 1H)

Example 305

N-Methyl-4-(3-methyl-1H-indol-2-yl)-1-(4-methylthiazol-2-yl)cyclohexanamine, polar diastereomer Example 306

N-methyl-4-(3-methyl-1H-indol-2-yl)-1-(4-methylthiazol-2-yl)cyclohexanamine, non-polar diastereomer (±)-2-(4-(Methylamino)-4-(4-methylthiazol-2-yl) cyclohex-1-enyl)-3-methyl-1H-indole 3-Methylindole (Ind-10, 367 mg, 2.8 mmol) was dissolved in methylene chloride (25 ml) together with the ketone Ket-18 (750 mg, 3.3 mmol), and trifluoromethanesulfonic acid (0.4 ml, 4.5 mmol) was added. The mixture was stirred at RT for 24 h.—For working up, 2 N NaOH (20 ml) was added to the reaction mixture and the mixture was stirred at RT for 20 min. After the organic phase had been separated off, the aqueous phase was extracted with ethyl acetate (2×20 ml). The combined organic extracts were dried over Na$_2$SO$_4$ and then concentrated. The crude product ((±)-2-(4-(methylamino)-4-(4-methylthiazol-2-yl)cyclohex-1-enyl)-3-methyl-1H-indole) was obtained in a yield of 940 mg (99%) as a yellow oil and was employed in the next reaction without further purification.

N-Methyl-4-(3-methyl-1H-indol-2-yl)-1-(4-methylthiazol-2-yl)cyclohexanamine, polar diastereomer (305) and N-methyl-4-(3-methyl-1H-indol-2-yl)-1-(4-methylthiazol-2-yl)cyclohexanamine, non-polar diastereomer (306)

(±)-2-(4-(Methylamino)-4-(4-methylthiazol-2-yl)cyclohex-1-enyl)-3-methyl-1H-indole (935 mg, 2.7 mmol) was suspended in HBr/glacial acetic acid (33% HBr, 40 ml). Sn powder (1.6 g, 13.8 mmol) was then added to the mixture in portions at RT in the course of 30 min. When the addition had ended, the reaction mixture was stirred at RT for a further 24 h.—For working up, the mixture was diluted with EtOH (20 ml) and concentrated to dryness on a rotary evaporator. The residue which remained was rendered basic by addition of 5 N NaOH (100 ml) and the mixture was stirred with ethyl acetate (30 ml) at room temperature for 18 h. The phases were separated. The aqueous phase was extracted with ethyl acetate (4×20 ml). The combined organic phases were washed with water (30 ml), dried over Na$_2$SO$_4$ and then concentrated. The residue obtained (1 g) was purified by column chromatography [silica gel 60 (70 g); EtOAc (400 ml), methanol (400 ml)]. Example 305 was obtained in a yield of 416 mg (30%) as a yellow oil. Example 306 was obtained in a yield of 249 mg (18%) as a yellow oil.
$^1$H NMR (300 MHz, DMSO-d$_6$) δ ppm: 1.66-1.87 (m, 3H), 1.89-2.01 (m, 3H), 2.15 (s, 3H), 2.17 (s, 3H), 2.31-2.39 (m, 1H), 2.42-2.47 (m, 3H), 2.56-2.72 (m, 2H), 2.82-2.98-(m, 1H), 6.83-7.01 (m, 2H), 7.08-7.24 (m, 1H), 7.34 (d, J=7.22 Hz, 1H), 7.47 (s, 1H), 10.45 (s, 1H)
$^1$H NMR (400 MHz, DMSO-d$_6$) δ ppm: 1.60-1.67 (m, 2H), 1.91-2.05 (m, 6H), 2.19 (S, 3H), 2.20 (s, 3H), 2.34 (s, 3H), 2.52-2.62 (m, 1H), 2.85-297 (m, 1H), 6.89-6.95 (m, 1H), 6.96-7.01 (m, 1H), 7.08-7.12 (m, 1H), 7.24-7.31 (m, 1H), 7.35-7.38 (m, 1H) 10.55 (s, 1H)
$^{13}$C NMR (101 MHz, DMSO) δ ppm: 8.3, 17.0, 26.9, 28.9, 34.1, 35.1, 58.6, 103.6, 110.4, 113.8, 117.4, 117.8, 119.9, 128.6, 135.1, 139.8, 151.2, 180.2

Example 307

2-(2-(4-(Dimethylamino)-4-phenylcyclohexyl)-1H-indol-3-yl)ethanol, diastereomer mixture 2-(2-(4-(Dimethylamino)-4-phenylcyclohexyl)-1H-indol-3-yl)ethanol, diastereomer mixture (219b)

Ket-10 (8.8 g, 40.48 mmol) and Ind-5 (6.52 g, 40.48 mmol) were initially introduced into abs. methylene chloride (250 ml) at 0° C. Trifluoromethanesulfonic acid silyl ester (8.76 ml, 44.52 mmol) in abs. methylene chloride (10 ml) was then added rapidly and the mixture was stirred for 20 min, while cooling with ice. The mixture was stirred at RT overnight. For working up, 1 N NaOH (120 ml) was added to the reaction mixture and the mixture was stirred at RT for 10 min, the mixture becoming yellow in colour and a precipitate precipitating out. The mixture was stirred further for 20 min, while cooling with ice, and the precipitate which had precipitated out was filtered off with suction, suspended again in ethanol, filtered off with suction and dried i. vac. This mixture was employed for the further synthesis.

Yield: 8.63 g (59%, 1:1 mixture of 2-(2-(4-(dimethylamino)-4-phenylcyclohex-1-enyl)-1H-indol-3-yl)ethanol and N,N-dimethyl-4-phenyl-4',9'-dihydro-3'H-spiro[cyclohexane-1,1'-pyrano[3,4-b]indol]-4-amine) The mixture (8.63 g, 23.88 mmol) was initially introduced into conc. HCl (730 ml) and the mixture was stirred at RT overnight. Tin (35.1 g, 303.33 mmol) was then added in portions in the course of 2 h (a precipitate always thereby precipitated out and dissolved again after prolonged stirring, and at the end of the addition the colour changed from red/orange to grey) and the mixture was subsequently stirred at RT for 2.5 h. For working up, 5 N NaOH (approx. 1,500 ml) was added to the mixture, while cooling with ice, and the mixture was stirred at RT for 10 min, a white precipitate precipitating out. The precipitate was filtered off with suction over Celite and rinsed with $CH_2Cl_2$ (2×50 ml). The phases were separated. The aqueous phase was extracted with $CH_2Cl_2$ (3×100 ml). The organic phase was dried over $Na_2SO_4$ and concentrated i. vac. (only 412 g of product isolated). The Celite was boiled thoroughly with $CH_2Cl_2$ (2×100 ml) and with ethanol (3×100 ml) and then filtered off. The filtrate was concentrated i. vac. The solid residue was recrystallized from toluene.

Yield (307): 4.29 g (49%, diastereomer mixture); melting point: 205-210° C.

Diastereomer 1:
$^1$H-NMR (DMSO-$d_6$): 1.49 (2H, m); 1.62 (2H, m); 2.03 (6H, s); 2.15 (2H, m); 2.81 (4H; m); 3.49 (2H, m); 4.57 (1H, t, OH); 6.90 (2H, m); 7.28 (2H, m); 7.38 (5H, m); 10.64 (1H, s).

Diastereomer 2:
$^1$H-NMR (DMSO-$d_6$): 1.48 (2H, m); 1.80 (2H, m); 1.96 (2H, m); 2.38 (6H, s); 2.56-2.64 (4H, m); 2.81 (2H; m); 2.96 (2H, m); 3.49 (2H, m); 6.89 (2H, m); 7.14 (1H, m); 7.35 (1H, m); 7.51 (5H, m); 10.35 (1H, s), citrate.

The following examples were identified via HPLC-MS analysis:

| Example | MS peak |
|---|---|
| 1 | 363.2 |
| 3 | 403.2 |
| 6 | 375.2 |
| 8 | 403.2 |
| 9 | 428.1 |
| 10 | 379.2 |
| 16 | 286.3 |
| 17 | 333.3 |
| 18 | 288.3 |
| 22 | 370.2 |
| 23 | 311.2 |
| 24 | 379.2 |
| 25 | 399.2 |
| 26 | 363.2 |
| 27 | 329.3 |
| 28 | 304.2 |
| 29 | 316.2 |
| 30 | 345.3 |
| 31 | 311.3 |
| 33 | 371.2 |
| 34 | 337.3 |
| 35 | 312.3 |
| 36 | 427.2 |
| 37 | 421.2 |
| 38 | 393.3 |
| 39 | 387.3 |
| 40 | 368.2 |
| 41 | 407.2 |
| 42 | 373.2 |
| 43 | 339.3 |
| 44 | 314.3 |
| 45 | 298.2 |
| 48 | 389.2 |
| 49 | 355.3 |
| 51 | 490.2 |
| 62 | 440.3 |
| 63 | 402.2 |
| 64 | 438.3 |
| 65 | 409.2 |
| 66 | 448.3 |
| 67 | 405.2 |
| 68 | 372.2 |
| 69 | 372.2 |
| 70 | 338.3 |
| 71 | 338.3 |
| 72 | 358.2 |
| 73 | 415.2 |
| 74 | 415.2 |
| 75 | 381.2 |
| 76 | 401.2 |
| 77 | 365.2 |
| 78 | 365.2 |
| 79 | 331.3 |
| 80 | 351.2 |
| 81 | 351.3 |
| 120 | 431.2 |
| 121 | 397.2 |
| 122 | 397.2 |
| 123 | 417.2 |
| 124 | 417.2 |
| 125 | 343.3 |
| 126 | 343.3 |
| 127 | 363.2 |
| 128 | 318.2 |
| 129 | 347.3 |
| 130 | 347.3 |
| 131 | 313.3 |
| 132 | 313.3 |
| 133 | 373.2 |
| 134 | 373.2 |
| 135 | 339.3 |
| 136 | 314.3 |
| 139 | 429.3 |
| 140 | 429.2 |
| 141 | 423.2 |
| 142 | 423.2 |
| 143 | 395.3 |
| 144 | 395.3 |
| 145 | 389.3 |
| 146 | 389.3 |
| 147 | 415.3 |
| 148 | 415.3 |
| 149 | 409.2 |
| 150 | 409 |
| 153 | 391.2 |
| 156 | 375.2 |
| 157 | 341.3 |
| 158 | 341.3 |
| 159 | 361.3 |
| 160 | 316.3 |
| 164 | 359.3 |
| 171 | 419.2 |
| 172 | 405.2 |
| 173 | 433.2 |
| 174 | 447.2 |
| 175 | 447.2 |
| 176 | 413.3 |
| 177 | 41.3 |
| 178 | 433.3 |
| 179 | 433.2 |
| 180 | 391.2 |
| 181 | 357.3 |
| 182 | 357.3 |
| 183 | 377.3 |
| 184 | 377.3 |
| 219 | 363.2 |

-continued

| Example | MS peak |
|---|---|
| 220 | 405.2 |
| 223 | 289.3 |
| 224 | 289.3 |
| 225 | 289.3 |
| 226 | 334.3 |
| 227 | 274.3 |
| 231 | 272.3 |
| 232 | 272.3 |
| 233 | 378.2 |
| 234 | 379.1 |
| 235 | 274.3 |
| 236 | 274.3 |
| 239 | 332.3 |
| 240 | 287.3 |
| 241 | 333.2 |
| 242 | 303.2 |
| 243 | 350.2 |

Pharmacological Studies:

Measurement of the ORL1 Binding

The compounds according to the invention were investigated in a receptor binding assay with $^3$H-nociceptin/orphanin FQ with membranes from recombinant CHO-ORL1 cells. This test system was conducted in accordance with the method described by Ardati et al. (Mol. Pharmacol., 51, 1997, S. 816-824). The concentration of $^3$H-nociceptin/orphanin FQ in these experiments was 0.5 nM. The binding assays were carried out with in each case 20 µg of membrane protein per 200 µl batch in 50 mM hepes, pH 7.4, 10 mM $MgCl_2$ and 1 mM EDTA. The binding to the ORL1 receptor was determined using in each case 1 mg of WGA-SPA beads (Amersham-Pharmacia, Freiburg) by incubation of the batch at RT for one hour and subsequent measurement in a Trilux scintillation counter (Wallac, Finland). The affinity is stated in Table 1 as the nanomolar $K_i$ value in or % inhibition at c=1 µM.

Measurement of the µ Binding

The receptor affinity for the human µ opiate receptor was determined in a homogeneous set-up in microtitre plates. For this, dilution series of the compound to be tested in each case were incubated with a receptor membrane preparation (15-40 µg of protein per 250 µl of incubation batch) of CHO-K1 cells which express the human µ opiate receptor (RB-HOM receptor membrane preparation from NEN, Zaventem, Belgium) in the presence of 1 nmol/l of the radioactive ligand [$^3$H]-naloxone (NET719, NEN, Zaventem, Belgium) and 1 mg of WGA-SPA-Beads (wheat germ agglutinin SPA beads from Amersham/Pharmacia, Freiburg, Germany) in a total volume of 250 µl for 90 minutes at room temperature. 50 mmol/l of Tris-HCl supplemented with 0.05 wt. % of sodium azide and with 0.06 wt. % of bovine serum albumin was used as the incubation buffer. 25 µmol/l of naloxone was additionally added for determination of the non-specific binding. After the end of the ninety-minute incubation time, the microtitre plates were centrifuged for 20 minutes at 1,000 g and the radioactivity was measured in a β-counter (Microbeta-Trilux, PerkinElmer Wallac, Freiburg, Germany). The percentage displacement of the radioactive ligand from its binding to the human µ opiate receptor was determined at a concentration of the test substances of 1 µmol/l and stated as the percentage inhibition (% inhibition) of the specific binding. Starting from the percentage displacement by various concentrations of the substances of the general formula I to be tested, $IC_{50}$ inhibitory concentrations which cause a 50 per cent displacement of the radioactive ligand were calculated in some cases. By conversion by means of the Cheng-Prusoff relationship, $K_i$ values for the test substances were obtained.

Testing of Analgesia in the Tail Flick Test in Mice

The mice were in each case placed individually in a test cage and the base of the tail was exposed to the focused heat ray of an electric lamp (Tail-flick type 50/08/1.bc, Labtec, Dr Hess). The intensity of the lamp was adjusted such that in the case of untreated mice the time between switching on of the lamp to sudden pulling away of the tail (pain latency) was 3 to 5 seconds. Before administration of the solutions containing the compound according to the invention or the particular comparison solutions, the mice were pretested twice in the course of five minutes and the mean of these measurements was calculated as the pretest mean.

The solutions of the compound of the general formula I according to the invention and the comparison solutions were then administered intravenously. The pain was measured in each case 10, 20, 40 and 60 minutes after the intravenous administration. The analgesic action was determined as the increase in pain latency (% of the maximum possible antinociceptive effect) according to the following formula:

$$[(T_1-T_0)/(T_2-T_0)]\times 100$$

In this formula, the time $T_0$ is the latency period before the administration and the time $T_1$ the latency period after the administration of the active compound combination and the time $T_2$ is the maximum duration of exposure (12 seconds).

Testing of Analgesia in the Tail Flick Test in Rats

The analgesic activity of the test compounds was investigated in the focal ray (tail flick) test in rats in accordance with the method of D'Amour and Smith (J. Pharm. Exp. Ther. 72, 74 79 (1941). Female Sprague-Dawley weighing between 134 and 189 g were used for this. The animals were placed individually in special test cages and the base of the tail was exposed to a focused heat ray of a lamp (Tail-flick type 50/08/1.bc, Labtec, Dr Hess). The intensity of the lamp was adjusted such that in the case of untreated animals the time between switching on of the lamp to sudden pulling away of the tail (pain latency) was 2.5-5 seconds. Before administration of a test compound, the animals were pretested twice in the course of 30 minutes and the mean of these measurements was calculated as the pretest mean The pain was measured 20, 40 and 60 min after intravenous administration. The analgesic action was determined as the increase in pain latency (% MPE) according to the following formula:

$$[(T_1-T_0)/(T_2-T_0)]\times 100$$

In this formula, $T_0$ is the latency period before and $T_1$ the latency period after administration of the substance, $T_2$ is the maximum exposure time (12 sec).

To determine the dose dependency, the particular test compound was administered in 3-5 logarithmically increasing doses, which included the threshold and the maximum active dose in each case, and the $ED_{50}$ values were determined with the aid of regression analysis. The $ED_{50}$ calculation was performed at the action maximum, 20 minutes after intravenous administration of the substance.

The following values were determined by way of example:

| Example | % inhibition (ORL1) at 1 µM or $K_i$ [µM] | % inhibition (µ) at 1 µM or $K_i$ [µM] | Tail-flick, i.v. |
|---|---|---|---|
| 1 | 0.0012 | 0.0044 | 99% MPE at 100 µg/kg (mouse) |
| 3 | 58% | 0.1100 | |
| 4 | 0.0200 | 0.0092 | |

| Example | % inhibition (ORL1) at 1 µM or Ki [µM] | % inhibition (µ) at 1 µM or Ki [µM] | Tail-flick, i.v. |
|---|---|---|---|
| 6 | 66% | 0.0240 | |
| 7 | 2 | 40% | |
| 8 | — | — | |
| 9 | 39% | 0.0370 | |
| 10 | 37% | 0.0330 | |
| 11 | 49% | 0.3200 | |
| 13 | 10% | 23% | |
| 14 | 3 | 0.0360 | |
| 15 | — | 64% | |
| 16 | 16% | 51% | |
| 17 | 0.0009 | 0.0004 | 79% MPE at 100 µg/kg (mouse) |
| 18 | 0.0140 | 0.0130 | |
| 19 | 70% | 89% | |
| 20 | 100% | 102% | |
| 21 | 53% | 60% | |
| 22 | — | 62% | |
| 23 | 87% | 96% | |
| 24 | 73% | 0.1400 | |
| 25 | 27% | 53% | |
| 26 | — | 61% | |
| 27 | 58% | 93% | |
| 28 | 12% | 39% | |
| 29 | 35% | 58% | |
| 30 | 75% | 89% | |
| 31 | 96% | 100% | |
| 32 | 35% | 60% | |
| 33 | — | 30% | |
| 34 | 26% | 50% | |
| 35 | 17% | 41% | |
| 36 | — | 20% | |
| 37 | — | 13% | |
| 38 | 11% | — | |
| 39 | 55% | 78% | |
| 40 | — | — | |
| 41 | 29% | 40% | |
| 42 | 50% | 73% | |
| 43 | 48% | 0.5300 | |
| 44 | 17% | 37% | |
| 45 | 16% | 97% | |
| 46 | 78% | 101% | |
| 47 | 62% | 92% | |
| 48 | 64% | 95% | |
| 49 | 74% | 98% | |
| 51 | 36% | 61% | |
| 52 | 35% | 100% | |
| 53 | 88% | 100% | |
| 54 | 89% | 95% | |
| 55 | 31% | 90% | |
| 56 | 80% | 98% | |
| 57 | 66% | 83% | |
| 58 | 90% | 92% | |
| 59 | 84% | 96% | |
| 60 | 52% | 97% | |
| 61 | 52% | 86% | |
| 62 | 78% | 96% | |
| 63 | 79% | 98% | |
| 64 | 63% | 99% | |
| 65 | 65% | 98% | |
| 66 | — | 21% | |
| 67 | 46% | 98% | |
| 68 | 13% | 83% | |
| 69 | 46% | 98% | |
| 70 | 68% | 97% | |
| 71 | 10% | 50% | |
| 72 | 38% | 54% | |
| 73 | 18% | 60% | |
| 74 | 57% | 67% | |
| 75 | — | 21% | |
| 76 | 18% | 24% | |
| 77 | — | 75% | |
| 78 | 55% | 90% | |
| 79 | 92% | 102% | |
| 80 | 94% | 0.0012 | |
| 81 | 24% | 0.5600 | |
| 82 | 38% | 74% | |
| 83 | 102% | 97% | |
| 84 | — | — | |
| 85 | 81% | 100% | |
| 86 | 32% | 68% | |
| 87 | 99% | 100% | |
| 88 | 19% | 41% | |
| 89 | 98% | 100% | |
| 90 | 27% | 36% | |
| 91 | 89% | 100% | |
| 92 | 26% | 64% | |
| 93 | 99% | 99% | |
| 94 | 91% | 98% | |
| 95 | 100% | 101% | |
| 96 | 87% | 91% | |
| 97 | 57% | 98% | |
| 98 | 19% | 48% | |
| 99 | 98% | 100% | |
| 100 | 10% | 34% | |
| 101 | 99% | 99% | |
| 102 | 50% | 57% | |
| 103 | 80% | 99% | |
| 104 | — | 42% | |
| 105 | 99% | 100% | |
| 106 | 14% | 38% | |
| 107 | 99% | 98% | |
| 108 | 37% | 43% | |
| 109 | 62% | 99% | |
| 110 | 23% | 53% | |
| 111 | 101% | 100% | |
| 112 | 72% | 98% | |
| 113 | 55% | 83% | |
| 114 | 99% | 100% | |
| 115 | 38% | 62% | |
| 116 | 99% | 100% | |
| 117 | 42% | 55% | |
| 118 | 87% | 94% | |
| 119 | 19% | 56% | |
| 120 | — | — | |
| 121 | 30% | 94% | |
| 122 | — | 16% | |
| 123 | 29% | 77% | |
| 124 | 67% | 65% | |
| 125 | 69% | 97% | |
| 126 | — | 61% | |
| 127 | 70% | 94% | |
| 128 | 27% | 38% | |
| 129 | 15% | 51% | |
| 130 | 68% | 93% | |
| 131 | 97% | 99% | |
| 132 | 62% | 85% | |
| 133 | 63% | 83% | |
| 134 | 18% | 35% | |
| 135 | 18% | 27% | |
| 136 | 32% | 28% | |
| 137 | 98% | 99% | |
| 138 | 52% | 72% | |
| 139 | — | 10% | |
| 140 | 11% | 21% | |
| 141 | 35% | 37% | |
| 142 | 28% | 47% | |
| 143 | 61% | 79% | |
| 144 | — | 12% | |
| 145 | 95% | 95% | |
| 146 | 62% | 87% | |
| 147 | 73% | 87% | |
| 148 | 18% | 29% | |
| 149 | 93% | 94% | |
| 150 | 27% | 26% | |
| 151 | 98% | 100% | |
| 152 | 76% | 92% | |
| 153 | 84% | 99% | |
| 156 | 11% | 41% | |
| 157 | — | 76% | |
| 158 | 17% | 54% | |

-continued

| Example | % inhibition (ORL1) at 1 μM or Ki [μM] | % inhibition (μ) at 1 μM or Ki [μM] | Tail-flick, i.v. |
|---|---|---|---|
| 159 | 95% | 98% | |
| 160 | — | 29% | |
| 161 | 77% | 98% | |
| 162 | 87% | 100% | |
| 163 | 100% | 102% | |
| 164 | 84% | 99% | |
| 165 | 99% | 101% | |
| 166 | 98% | 100% | |
| 167 | 99% | 99% | |
| 168 | 45% | 84% | |
| 169 | 99% | 101% | 100% MPE at 100 μg/kg (rat) |
| 170 | 88% | 95% | |
| 171 | 36% | 88% | |
| 172 | 83% | 99% | |
| 173 | 99% | 100% | |
| 174 | 55% | 90% | |
| 175 | 67% | 96% | |
| 176 | 66% | 81% | |
| 177 | 99% | 100% | |
| 178 | 99% | 95% | |
| 179 | 38% | 66% | |
| 180 | 86% | 98% | |
| 181 | 64% | 91% | |
| 182 | 99% | 101% | 100% MPE at 100 μg/kg (rat) |
| 183 | 79% | 82% | |
| 184 | 99% | 101% | |
| 185 | 69% | 65% | |
| 186 | 98% | 101% | |
| 187 | 100% | 100% | |
| 188 | 41% | 68% | |
| 189 | 100% | 98% | |
| 190 | 76% | 87% | |
| 191 | 99% | 100% | |
| 192 | 71% | 86% | |
| 193 | 98% | 101% | |
| 194 | 96% | 96% | |
| 195 | 100% | 101% | |
| 196 | 95% | 99% | |
| 197 | 100% | 100% | |
| 198 | 78% | 80% | |
| 199 | 99% | 95% | |
| 200 | 99% | 0.0003 | |
| 201 | 100% | 0.0003 | |
| 202 | 72% | 0.1100 | |
| 203 | 99% | 101% | 96% MPE at 100 μg/kg (rat) |
| 204 | 87% | 98% | |
| 205 | 99% | 101% | 100% MPE at 100 μg/kg (rat) |
| 206 | 87% | 94% | |
| 207 | 99% | 0.0003 | 100% MPE at 10 μg/kg (rat) |
| 208 | 56% | 0.4500 | |
| 209 | 100% | 99% | |
| 210 | 63% | 65% | |
| 211 | 100% | 102% | |
| 212 | 73% | 65% | |
| 213 | 99% | 100% | |
| 214 | 82% | 89% | |
| 215 | 100% | 102% | |
| 216 | 72% | 89% | |
| 217 | 99% | 100% | |
| 218 | 43% | 43% | |
| 219 | 54% | 60% | |
| 220 | 23% | 62% | |
| 221 | 81% | 97% | |
| 222 | 35% | 88% | |
| 223 | 80% | 95% | |
| 224 | 31% | 59% | |
| 225 | 15% | 26% | |
| 226 | 40% | 89% | |
| 227 | 50% | 67% | |
| 228 | 32% | 80% | |
| 229 | 12% | 49% | |
| 230 | 37% | 72% | |
| 231 | 16% | 13% | |
| 232 | 27% | n.d. | |
| 233 | 65% | 0.2100 | |
| 234 | — | 31% | |
| 235 | 47% | 65% | |
| 236 | 96% | 101% | |
| 237 | 22% | 36% | |
| 238 | 74% | 64% | |
| 239 | — | n.d. | |
| 240 | — | 20% | |
| 241 | 56% | 0.0320 | |
| 242 | — | 42% | |
| 243 | — | 14% | |
| 244 | 39% | 62% | |
| 246 | 95% | 97% | |
| 247 | 95% | 97% | |
| 248 | 67% | 91% | |
| 249 | 63% | 97% | |
| 250 | 15% | 54% | |
| 251 | n.d. | 92% | |
| 252 | n.d. | 67% | |
| 253 | n.d. | 35% | |
| 254 | n.d. | 85% | |
| 255 | n.d. | 64% | |
| 256 | n.d. | 99% | |
| 257 | n.d. | 29% | |
| 258 | n.d. | 20% | |
| 259 | 91% | 101% | |
| 260 | 68% | 73% | |
| 261 | 94% | 99% | |
| 262 | 23% | 11% | |
| 263 | 40% | 38% | |
| 264 | — | 35% | |
| 265 | — | 58% | |
| 266 | 73% | 97% | |
| 267 | 58% | 78% | |
| 268 | 77% | 79% | |
| 269 | 94% | 97% | |
| 270 | 20% | 49% | |
| 271 | 90% | 97% | |
| 272 | — | 15% | |
| 273 | 67% | 88% | |
| 274 | 57% | 57% | |
| 294 | 13% | 67% | |
| 295 | 21% | 25% | |
| 296 | 29% | 64% | |
| 297 | 14% | 42% | |
| 298 | 23% | 43% | |
| 299 | 24% | 52% | |
| 300 | 20% | 0.8100 | |
| 301 | 32% | 18% | |
| 302 | 0.1300 | 0.1033 | |
| 307 | 99% | 99% | |

Parenteral Solution of a Spirocyclic Derivative According to the Invention 3 g of one of the substituted indole derivatives according to the invention, here Example 1, is dissolved in 1 l of water for injection purposes at room temperature and the solution is then adjusted to isotonic conditions by addition of anhydrous glucose for injection purposes.

The invention claimed is:
1. Substituted heteroaryl derivatives of the formula I

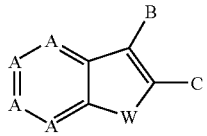

wherein
A represents N or $CR^{7-10}$, wherein A represents N at most twice
W represents O, S or $NR^4$
with the proviso that if W represents O or S, A denotes $CR^{7-10}$;
one of the radicals B or C represents H; $C_{1-8}$-alkyl, in each case saturated or unsaturated, branched or unbranched, mono- or polysubstituted or unsubstituted, $COR^{12}$; $SO_2R^{12}$; aryl, $C_{3-8}$-cycloalkyl or heteroaryl bonded via $C_{1-3}$-alkyl and in each case mono- or polysubstituted or unsubstituted, aryl or heteroaryl, in each case mono- or polysubstituted or unsubstituted; $C_{3-8}$-cycloalkyl, in each case mono- or polysubstituted or unsubstituted; and the other particular radical B or C represents

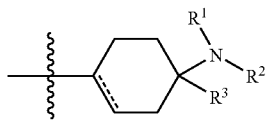

wherein
⇌ represents a single bond or a double bond,
$R^1$ and $R^2$ independently of one another represent H; $C_{1-5}$-alkyl, in each case saturated or unsaturated, branched or unbranched, mono- or polysubstituted or unsubstituted, except that neither $R^1$ nor $R^2$ may represent alkyl substituted by unsubstituted or substituted O-phenyl; $C_{3-8}$-cycloalkyl, in each case mono- or polysubstituted or unsubstituted; aryl or heteroaryl, in each case mono- or polysubstituted or unsubstituted; or aryl, $C_{3-8}$-cycloalkyl or heteroaryl, bonded via $C_{1-3}$-alkyl and in each case mono- or polysubstituted or unsubstituted;
or the radicals $R^1$ and $R^2$ together represent $CH_2CH_2OCH_2CH_2$, $CH_2CH_2NR^{11}CH_2CH_2$ or $(CH_2)_{3-6}$,
wherein $R^{11}$ denotes H; $C_{1-5}$-alkyl, in each case saturated or unsaturated, branched or unbranched, mono- or polysubstituted or unsubstituted; $C_{3-8}$-cycloalkyl, in each case mono- or polysubstituted or unsubstituted; aryl or heteroaryl, in each case mono- or polysubstituted or unsubstituted; or aryl, $C_{3-8}$-cycloalkyl or heteroaryl, bonded via $C_{1-3}$-alkyl and in each case mono- or polysubstituted or unsubstituted; C(O)phenyl, C(O)heteroaryl, $C(O)C_{1-5}$-alkyl, in each case substituted or unsubstituted;
and
$R^3$ represents $C_{1-8}$-alkyl, in each case saturated or unsaturated, branched or unbranched, mono- or polysubstituted or unsubstituted; $C_{3-8}$-cycloalkyl, in each case mono- or polysubstituted or unsubstituted; aryl or heteroaryl, in each case unsubstituted or mono- or polysubstituted; aryl, heteroaryl or $C_{3-8}$-cycloalkyl, bonded via $C_{1-3}$-alkyl group and in each case unsubstituted or mono- or polysubstituted;
$R^4$ represents H; $C_{1-5}$-alkyl, saturated or unsaturated, branched or unbranched, unsubstituted or mono- or polysubstituted; aryl, or heteroaryl, in each case substituted or unsubstituted; aryl, heteroaryl or cycloalkyl, bonded via a $C_{1-3}$-alkyl group and in each case mono- or polysubstituted or unsubstituted; $COR^{12}$; $SO_2R^{12}$,
wherein $R^{12}$ denotes H; $C_{1-5}$-alkyl, in each case saturated or unsaturated, branched or unbranched, mono- or polysubstituted or unsubstituted; $C_{3-8}$-cycloalkyl, in each case saturated or unsaturated, mono- or polysubstituted or unsubstituted; aryl or heteroaryl, in each case mono- or polysubstituted or unsubstituted; or aryl, $C_{3-8}$-cycloalkyl or heteroaryl, bonded via $C_{1-3}$-alkyl and in each case mono- or polysubstituted or unsubstituted; $OR^{13}$; $NR^{14}R^{15}$;
$R^7$, $R^8$, $R^9$ and $R^{10}$ independently of one another represent H, F, Cl, Br, I, $NO_2$, $CF_3$, $OR^{13}$, $SR^{13}$, $SO_2R^{13}$, $SO_2OR^{13}$, CN, $COOR^{13}$, $NR^{14}R^{15}$, $NHC(O)NHR^{13}$, $NHC(O)R^{13}$, $NH(CNR^{13})NHR^{13}$, $SO_2NHR^{13}$; $C_{1-5}$-alkyl, $C_{3-8}$-cycloalkyl, unsubstituted or mono- or polysubstituted; aryl or heteroaryl, unsubstituted or mono- or polysubstituted; or aryl, $C_{3-8}$-cycloalkyl or heteroaryl, bonded via $C_{1-3}$-alkyl and unsubstituted or mono- or polysubstituted;
wherein $R^{13}$ denotes H; $C_{1-5}$-alkyl, in each case saturated or unsaturated, branched or unbranched, unsubstituted or mono- or polysubstituted; $C_{3-8}$-cycloalkyl, in each case saturated or unsaturated, unsubstituted or mono- or polysubstituted; aryl or heteroaryl, unsubstituted or mono- or polysubstituted; or aryl, $C_{3-8}$-cycloalkyl or heteroaryl, bonded via $C_{1-3}$-alkyl and unsubstituted or mono- or polysubstituted;
or $R^7$, $R^8$ and $R^9$ have the abovementioned meaning and $R^{10}$ together with B represents —$CH_2CH_2CH_2$— and $R^{10}$ and B therefore form a six-membered ring,
$R^{14}$ and $R^{15}$ independently of one another denote H; $C_{1-5}$-alkyl, in each case saturated or unsaturated, branched or unbranched, unsubstituted or mono- or polysubstituted; or $C_{3-8}$-cycloalkyl, in each case saturated or unsaturated, unsubstituted or mono- or polysubstituted; aryl or heteroaryl, unsubstituted or mono- or polysubstituted; or aryl, $C_{3-8}$-cycloalkyl or heteroaryl, bonded via $C_{1-3}$-alkyl and unsubstituted or mono- or polysubstituted;
or $R^{14}$ and $R^{15}$ together form $CH_2CH_2OCH_2CH_2$, $CH_2CH_2NR^{16}CH_2CH_2$ or $(CH_2)_{3-6}$,
wherein $R^{16}$ denotes H; $C_{1-5}$-alkyl, saturated or unsaturated, branched or unbranched, unsubstituted or mono- or polysubstituted;
in the form of the racemate; of the enantiomers, diastereomers, mixtures of the enantiomers or diastereomers or of an individual enantiomer or diastereomer; of the bases and/or salts of physiologically acceptable acids.

2. Substituted heteroaryl derivatives according to claim 1, wherein
the $C_{1-8}$-alkyls, $C_{1-5}$-alkyls, $C_{1-3}$-alkyls or $C_{1-3}$-alkylenes or $C_{3-8}$-cycloalkyl radicals can in each case be mono- or polysubstituted by F, Cl, Br, I, —CN, $NH_2$, NH—$C_{1-6}$-alkyl, NH—$C_{1-6}$-alkyl-OH, N($C_{1-6}$-alkyl)$_2$, N($C_{1-6}$-alkyl-OH)$_2$, $NO_2$, SH, S—$C_{1-6}$-alkyl, S-benzyl, $OCF_3$, O—$C_{1-6}$-alkyl, OH, O—$C_{1-6}$-alkyl-OH, =O, $C_{1-6}$-alkyl, benzyl, O-benzyl, O-phenyl, C(=O)$C_{1-6}$-alkyl, $CO_2H$, NHC(=O)$C_{1-6}$-alkyl, OC(=O)$C_{1-6}$-alkyl, $CO_2$—$C_{1-6}$-alkyl,
the aryl or heteroaryl radicals can in each case be mono- or polysubstituted by F, Cl, Br, I, CN, $NH_2$, NH—$C_{1-6}$-alkyl, NH—$C_{1-6}$-alkyl-OH, N(C$_{1-6}$alkyl)$_2$, N(C$_{1-6}$-alkyl-OH)$_2$, NO$_2$, SH, S—C$_{1-6}$-alkyl, OH, O—C$_{1-6}$-alkyl, O—C$_{1-6}$alkyl-OH, C(=O)C$_{1-6}$-alkyl, CO$_2$H, CO$_2$—C$_{1-6}$-alkyl, CF$_3$, OCF$_3$, C$_{1-6}$-alkyl or phenoxy,
in the form of the racemate; of the enantiomers, diastereomers, mixtures of the enantiomers or diastereomers or of an individual enantiomer or diastereomer; of the bases and/or salts of physiologically acceptable acids.

3. Heteroaryl derivatives according to claim 1, wherein R$^1$ and R$^2$ independently of one another represent H; C$_{1-5}$-alkyl, saturated or unsaturated, branched or unbranched, mono- or polysubstituted or unsubstituted;
or the radicals R$^1$ and R$^2$ together form a ring and denote CH$_2$CH$_2$OCH$_2$CH$_2$, CH$_2$CH$_2$NR$^{11}$CH$_2$CH$_2$ or (CH$_2$)$_{3-6}$,
wherein R$^{11}$ denotes H; C$_{1-5}$-alkyl, saturated or unsaturated, branched or unbranched, mono- or polysubstituted or unsubstituted.

4. Heteroaryl derivatives according to claim 3, wherein R$^1$ and R$^2$ independently of one another represent CH$_3$ or H, wherein R$^1$ and R$^2$ do not simultaneously denote H.

5. Substituted heteroaryl derivatives according to claim 1, wherein R$^3$ denotes butyl, phenyl, thiophenyl, thiazolyl, cyclopentyl, cyclohexyl, naphthyl, benzyl, benzofuranyl, 1,2,4-triazolyl, benzimidazolyl, benzodioxanyl, benzodioxolanyl, pyridyl or benzothiophenyl, in each case unsubstituted or mono- or polysubstituted; phenyl, furyl or thiophenyl bonded via a saturated, unbranched C$_{1-3}$-alkyl group and in each case unsubstituted or mono- or polysubstituted.

6. Substituted heteroaryl derivatives according to claim 5, wherein R$^3$ denotes phenyl, 4-fluorophenyl, benzyl, butyl or benzothiophenyl.

7. Substituted heteroaryl derivatives according to claim 1, wherein B or C represents (CH$_2$)$_{1-4}$—R$^{21}$, wherein R$^{21}$ represents H, OH, SH, COOC$_{1-6}$-alkyl, COOH, OC(=O)C$_{1-6}$-alkyl, NH$_2$, NHC(=O)C$_{1-6}$-alkyl; or C$_{3-8}$-cycloalkyl, aryl or heteroaryl, in each case unsubstituted or mono- or polysubstituted.

8. Substituted heteroaryl derivatives according to claim 7, wherein R$^{21}$ represents OH, SH, COOCH$_3$, COOH, OC(=O)CH$_3$, NH$_2$, NHC(=O)CH$_3$, NHC(=O)CH$_2$C(CH$_3$)$_2$; or benzimidazole, pyridyl, triazolyl, phenyl, pyrazolyl, tetrazolyl or imidazolyl, in each case unsubstituted or substituted by COOCH$_3$, CH$_3$; or cyclopropyl, cyclohexyl, pyrrolidinyl tetrahydroquinolinyl, pyrrolidinyl, piperidyl, tetrahydroisoquinolinyl, isoindolinyl, piperazinyl, morpholinyl or thiazolinyl, in each case unsubstituted or substituted by =O or CH$_3$.

9. Substituted heteroaryl derivatives according to claim 1, wherein R$^7$, R$^8$, R$^9$ and R$^{10}$ independently of one another represent H; methyl; ethyl; propyl; butyl; pyridyl, O-benzyl, F, Cl, Br, I, CN, CF$_3$, OCF$_3$, OH, OCH$_3$, NH$_2$, COOH, COOCH$_3$, NHCH$_3$ or N(CH$_3$)$_2$ or NO$_2$.

10. Substituted heteroaryl derivatives according to claim 9, wherein R$^7$, R$^8$, R$^9$ and R$^{10}$ independently of one another represent H, F, Cl, NO$_2$, CN, CF$_3$, OCH$_3$, OCF$_3$ or OH.

11. Substituted heteroaryl derivatives according to claim 1, which are selected from the group consisting of:
(1) 2-(2-(4-(dimethylamino)-4-phenylcyclohexyl)-1H-indol-3-yl)ethanol, citrate;
(3) (±) 2-(2-(4-(dimethylamino)-4-phenylcyclohex-1-enyl)-1H-indol-3-yl)ethyl acetate hydrochloride;
(4) (±) 2-(4-(dimethylamino)-4-phenylcyclohex-1-enyl)-3-(3-aminopropyl)-1H-indole, citrate;
(6) (±) 3-(2-(4-(dimethylamino)-4-phenylcyclohex-1-enyl)-1H-indol-3-yl)propan-1-ol hydrochloride;
(7) (±) 2-(5,6-dichloro-2-(4-(dimethylamino)-4-phenylcyclohex-1-enyl)-1H-indol-3-yl)ethanol, citrate;
(8) (±) 2-(2-(4-morpholino-4-phenylcyclohex-1-enyl)-1H-indol-3-yl)ethanol, citrate;
(9) (±) 2-(4,6-dichloro-2-(4-(dimethylamino)-4-phenylcyclohex-1-enyl)-1H-indol-3-yl)ethanol, citrate;
(10) (±) 2-(2-(4-(dimethylamino)-4-phenylcyclohex-1-enyl)-5-fluoro-1H-indol-3-yl)ethanol, citrate;
(11) (±) 2-(2-(4-(dimethylamino)-4-phenylcyclohex-1-enyl)-5-(pyridin-3-yl)-1H-indol-3-yl)ethanol, citrate;
(13) (±) 2-(2-(4-(dimethylamino)-4-phenylcyclohex-1-enyl)-5-nitro-1H-indol-3-yl)ethanol, citrate;
(14) (±) 2-(2-(4-(benzo[b]thiophen-2-yl)-4-(dimethylamino)cyclohex-1-enyl)-1H-indol-3-yl)ethanol, citrate;
(15) (±) 2-(2-(4-(benzo[b]thiophen-2-yl)-4-(dimethylamino)cyclohex-1-enyl)-5-fluoro-1H-indol-3-yl)ethanol, citrate;
(16) (±) 2-(4-(dimethylamino)-4-phenylcyclohex-1-enyl)-3-methyl-1H-indole, citrate;
(17) N,N-dimethyl-4-(3-methyl-1H-indol-2-yl)-1-phenylcyclohexanamine, citrate;
(18) N,N-dimethyl-4-(3-methyl-1H-indol-2-yl)-1-phenylcyclohexanamine, citrate;
(19) 2-(2-(2-(4-(dimethylamino)-4-phenylcyclohexyl)-1H-indol-3-yl)ethyl)isoindoline-1,3-dione, citrate;
(20) N-(2-(2-(4-(dimethylamino)-4-phenylcyclohexyl)-1H-indol-3-yl)ethyl)acetamide, citrate;
(21) N-(2-(2-(4-(dimethylamino)-4-phenylcyclohexyl)-1H-indol-3-yl)ethyl)acetamide, citrate;
(22) (±)-2-(4-benzyl-4-(dimethylamino)cyclohex-1-enyl)-3-methyl-1H-indole-5-carbonitrile;
(23) (±)-2-(4-(dimethylamino)-4-phenylcyclohex-1-enyl)-3-methyl-1H-indole-5-carbonitrile;
(24) (±)-2-(4-(dimethylamino)-4-butylcyclohex-1-enyl)-3-methyl-5-trifluoromethyl-1H-indole;
(25) (±)-2-(4-(dimethylamino)-4-phenylcyclohex-1-enyl)-3-methyl-5-trifluoromethyl-1H-indole, citrate;
(26) (±)-2-(4-(dimethylamino)-4-benzylcyclohex-1-enyl)-3-methyl-5-fluoro-1H-indole, citrate;
(27) (±)-2-(4-(dimethylamino)-4-butylcyclohex-1-enyl)-3-methyl-5-fluoro-1H-indole, citrate;
(28) (±)-2-(4-(dimethylamino)-4-phenylcyclohex-1-enyl)-3-methyl-5-fluoro-1H-indole, citrate;
(29) (±)-2-(4-(dimethylamino)-4-phenylcyclohex-1-enyl)-3-methyl-5-methoxy-1H-indole, citrate;
(30) (±)-2-(4-(dimethylamino)-4-benzylcyclohex-1-enyl)-3-methyl-1H-indole, citrate;
(31) (±)-2-(4-(dimethylamino)-4-butylcyclohex-1-enyl)-3-methyl-1H-indole, citrate;
(32) (±)-2-(4-(dimethylamino)-4-phenylcyclohex-1-enyl)-3-methyl-1H-pyrrolo[2,3-b]pyridine, citrate;
(33) (±)-2-(4-(dimethylamino)-4-benzylcyclohex-1-enyl)-3-cyclopropyl-1H-indole hydrochloride;
(34) (±)-2-(4-(dimethylamino)-4-butylcyclohex-1-enyl)-3-cyclopropyl-1H-indole;
(35) (±)-2-(4-(dimethylamino)-4-phenylcyclohex-1-enyl)-3-cyclopropyl-1H-indole;
(36) (±)-2-(4-(dimethylamino)-4-benzylcyclohex-1-enyl)-3-(cyclohexylmethyl)-1H-indole;
(37) (±)-2-(4-(dimethylamino)-4-benzylcyclohex-1-enyl)-3-benzyl-1H-indole hydrochloride;
(38) (±)-2-(4-(dimethylamino)-4-butylcyclohex-1-enyl)-3-(cyclohexylmethyl)-1H-indole hydrochloride;
(39) (±)-2-(4-(dimethylamino)-4-butylcyclohex-1-enyl)-3-benzyl-1H-indole;
(40) (±)-2-(4-(dimethylamino)-4-phenylcyclohex-1-enyl)-3-(cyclohexylmethyl)-1H-indole hydrochloride;

(41) (±)-2-(4-(dimethylamino)-4-phenylcyclohex-1-enyl)-3-benzyl-1H-indole hydrochloride;
(42) (±)-2-(4-(dimethylamino)-4-benzylcyclohex-1-enyl)-3-propyl-1H-indole;
(43) (±)-2-(4-(dimethylamino)-4-butylcyclohex-1-enyl)-3-propyl-1H-indole;
(44) (±)-2-(4-(dimethylamino)-4-phenylcyclohex-1-enyl)-3-propyl-1H-indole;
(45) (±) 2-(4-(dimethylamino)-4-benzylcyclohex-1-enyl)-3-(2-(pyridin-4-yl)ethyl)-1H-indole;
(46) (±) 2-(4-(dimethylamino)-4-butylcyclohex-1-enyl)-3-(2-(pyridin-4-yl)ethyl)-1H-indole;
(47) (±) 2-(4-(dimethylamino)-4-phenylcyclohex-1-enyl)-3-(2-(pyridin-4-yl)ethyl)-1H-indole;
(48) (±)-3-(2-(4-benzyl-4-(dimethylamino)cyclohex-1-enyl)-1H-indol-3-yl)propan-1-ol, citrate;
(49) (±)-3-(2-(4-butyl-4-(dimethylamino)cyclohex-1-enyl)-1H-indol-3-yl)propan-1-ol, citrate;
(51) (±) 2-(2-(2-(4-(dimethylamino)-4-phenylcyclohex-1-enyl)-1H-indol-3-yl)ethyl)isoindoline-1,3-dione;
(52) (±) 2-(4-(dimethylamino)-4-benzylcyclohex-1-enyl)-3-(2-(1H-benzo[d]imidazol-1-yl)ethyl)-5-fluoro-1H-indole;
(53) (±) 2-(4-(dimethylamino)-4-butylcyclohex-1-enyl)-3-(2-(1H-benzo[d]imidazol-1-yl)ethyl)-5-fluoro-1H-indole;
(54) (±) 2-(4-(dimethylamino)-4-phenylcyclohex-1-enyl)-3-(2-(1H-benzo[d]imidazol-1-yl)ethyl)-5-fluoro-1H-indole;
(55) (±) 2-(4-(dimethylamino)-4-benzylcyclohex-1-enyl)-3-(2-(piperidin-1-yl)ethyl)-5-fluoro-1H-indole;
(56) (±) 2-(4-(dimethylamino)-4-butylcyclohex-1-enyl)-3-(2-(piperidin-1-yl)ethyl)-5-fluoro-1H-indole;
(57) (±) 2-(4-(dimethylamino)-4-phenylcyclohex-1-enyl)-3-(2-(piperidin-1-yl)ethyl)-5-fluoro-1H-indole;
(58) (±) 2-(4-(dimethylamino)-4-phenylcyclohex-1-enyl)-3-(2-(piperidin-1-yl)ethyl)-1H-indole, citrate;
(59) (±) 2-(4-(dimethylamino)-4-benzylcyclohex-1-enyl)-3-(2-(1H-1,2,3-triazol-1-yl)ethyl)-5-fluoro-1H-indole;
(60) (±) 2-(4-(dimethylamino)-4-butylcyclohex-1-enyl)-3-(2-(1H-1,2,3-triazol-1-yl)ethyl)-5-fluoro-1H-indole;
(61) (±) 2-(4-(dimethylamino)-4-phenylcyclohex-1-enyl)-3-(2-(1H-1,2,3-triazol-1-yl)ethyl)-5-fluoro-1H-indole;
(62) N-(2-(2-(4-butyl-4-(dimethylamino)cyclohexyl)-1H-indol-3-yl)ethyl)-3,3-dimethylbutanamide, citrate;
(63) (±) N-(2-(2-(4-(dimethylamino)-4-phenylcyclohex-1-enyl)-1H-indol-3-yl)ethyl)acetamide;
(64) (±) N-(2-(2-(4-butyl-4-(dimethylamino)cyclohex-1-enyl)-1H-indol-3-yl)ethyl)-3,3-dimethylbutanamide;
(65) (±)-2-(2-(4-(dimethylamino)-4-phenylcyclohex-1-enyl)-5-fluoro-6-methoxy-1H-indol-3-yl)ethanol, citrate;
(66) (±)-2-(2-(4-benzyl-4-(4-methylpiperazin-1-yl)cyclohex-1-enyl)-5-fluoro-1H-indol-3-yl)ethanol;
(67) (±)-2-(5-fluoro-2-(4-phenyl-4-(pyrrolidin-1-yl)cyclohex-1-enyl)-1H-indol-3-yl)ethanol;
(68) 2-(4-benzyl-4-(dimethylamino)cyclohexyl)-3-methyl-1H-indole-5-carbonitrile, citrate;
(69) 2-(4-benzyl-4-(dimethylamino)cyclohexyl)-3-methyl-1H-indole-5-carbonitrile, citrate;
(70) 2-(4-butyl-4-(dimethylamino)cyclohexyl)-3-methyl-1H-indole-5-carbonitrile, citrate;
(71) 2-(4-butyl-4-(dimethylamino)cyclohexyl)-3-methyl-1H-indole-5-carbonitrile, citrate;
(72) 2-(4-(dimethylamino)-4-phenylcyclohexyl)-3-methyl-1H-indole-5-carbonitrile, citrate;
(73) 1-benzyl-N,N-dimethyl-4-(3-methyl-5-(trifluoromethyl)-1H-indol-2-yl)cyclohexanamine, citrate;
(74) 1-benzyl-N,N-dimethyl-4-(3-methyl-5-(trifluoromethyl)-1H-indol-2-yl)cyclohexanamine, citrate;
(75) 1-butyl-N,N-dimethyl-4-(3-methyl-5-(trifluoromethyl)-1H-indol-2-yl)cyclohexanamine, citrate;
(76) N,N-dimethyl-4-(3-methyl-5-(trifluoromethyl)-1H-indol-2-yl)-1-phenylcyclohexanamine, citrate;
(77) 1-benzyl-4-(5-fluoro-3-methyl-1H-indol-2-yl)-N,N-dimethylcyclohexanamine, citrate;
(78) 1-benzyl-4-(5-fluoro-3-methyl-1H-indol-2-yl)-N,N-dimethylcyclohexanamine, citrate;
(79) 1-butyl-4-(5-fluoro-3-methyl-1H-indol-2-yl)-N,N-dimethylcyclohexanamine hydrochloride;
(80) 4-(5-fluoro-3-methyl-1H-indol-2-yl)-N,N-dimethyl-1-phenylcyclohexanamine, citrate;
(81) 4-(5-fluoro-3-methyl-1H-indol-2-yl)-N,N-dimethyl-1-phenylcyclohexanamine, citrate;
(82) 4-(3-(2-(1H-benzo[d]imidazol-1-yl)ethyl)-5-fluoro-1H-indol-2-yl)-1-butyl-N,N-dimethylcyclohexanamine, citrate;
(83) 4-(3-(2-(1H-benzo[d]imidazol-1-yl)ethyl)-5-fluoro-1H-indol-2-yl)-N,N-dimethyl-1-phenylcyclohexanamine, citrate;
(84) 4-(3-(2-(1H-benzo[d]imidazol-1-yl)ethyl)-5-fluoro-1H-indol-2-yl)-N,N-dimethyl-1-phenylcyclohexanamine, citrate;
(85) 1-benzyl-4-(5-fluoro-3-(2-(pyrrolidin-1-yl)ethyl)-1H-indol-2-yl)-N,N-dimethylcyclohexanamine, citrate;
(86) 1-benzyl-4-(5-fluoro-3-(2-(pyrrolidin-1-yl)ethyl)-1H-indol-2-yl)-N,N-dimethylcyclohexanamine, citrate;
(87) 1-butyl-4-(5-fluoro-3-(2-(pyrrolidin-1-yl)ethyl)-1H-indol-2-yl)-N,N-dimethylcyclohexanamine, citrate;
(88) 1-butyl-4-(5-fluoro-3-(2-(pyrrolidin-1-yl)ethyl)-1H-indol-2-yl)-N,N-dimethylcyclohexanamine, citrate;
(89) 4-(5-fluoro-3-(2-(pyrrolidin-1-yl)ethyl)-1H-indol-2-yl)-N,N-dimethyl-1-phenylcyclohexanamine, citrate;
(90) 4-(5-fluoro-3-(2-(pyrrolidin-1-yl)ethyl)-1H-indol-2-yl)-N,N-dimethyl-1-phenylcyclohexanamine, citrate;
(91) 1-benzyl-4-(5-fluoro-3-(2-(piperidin-1-yl)ethyl)-1H-indol-2-yl)-N,N-dimethylcyclohexanamine, citrate;
(92) 1-benzyl-4-(5-fluoro-3-(2-(piperidin-1-yl)ethyl)-1H-indol-2-yl)-N,N-dimethylcyclohexanamine, citrate (2:3);
(93) 1-butyl-4-(5-fluoro-3-(2-(piperidin-1-yl)ethyl)-1H-indol-2-yl)-N,N-dimethylcyclohexanamine, citrate (4:3);
(94) 1-butyl-4-(5-fluoro-3-(2-(piperidin-1-yl)ethyl)-1H-indol-2-yl)-N,N-dimethylcyclohexanamine, citrate;
(95) 4-(5-fluoro-3-(2-(piperidin-1-yl)ethyl)-1H-indol-2-yl)-N,N-dimethyl-1-phenylcyclohexanamine, citrate;
(96) 4-(5-fluoro-3-(2-(piperidin-1-yl)ethyl)-1H-indol-2-yl)-N,N-dimethyl-1-phenylcyclohexanamine, citrate;
(97) 4-(3-(2-(1H-pyrazol-1-yl)ethyl)-5-fluoro-1H-indol-2-yl)-1-benzyl-N,N-dimethylcyclohexanamine, citrate (2:3);
(98) 4-(3-(2-(1H-pyrazol-1-yl)ethyl)-5-fluoro-1H-indol-2-yl)-1-benzyl-N,N-dimethylcyclohexanamine, citrate;
(99) 4-(3-(2-(1H-pyrazol-1-yl)ethyl)-5-fluoro-1H-indol-2-yl)-1-butyl-N,N-dimethylcyclohexanamine, citrate;
(100) 4-(3-(2-(1H-pyrazol-1-yl)ethyl)-5-fluoro-1H-indol-2-yl)-1-butyl-N,N-dimethylcyclohexanamine, citrate;
(101) 4-(3-(2-(1H-pyrazol-1-yl)ethyl)-5-fluoro-1H-indol-2-yl)-N,N-dimethyl-1-phenylcyclohexanamine, citrate;
(102) 4-(3-(2-(1H-pyrazol-1-yl)ethyl)-5-fluoro-1H-indol-2-yl)-N,N-dimethyl-1-phenylcyclohexanamine, citrate;

(103) 4-(3-(2-(1H-imidazol-1-yl)ethyl)-5-fluoro-1H-indol-2-yl)-1-benzyl-N,N-dimethylcyclohexanamine, citrate;
(104) 4-(3-(2-(1H-imidazol-1-yl)ethyl)-5-fluoro-1H-indol-2-yl)-1-benzyl-N,N-dimethylcyclohexanamine, citrate;
(105) 4-(3-(2-(1H-imidazol-1-yl)ethyl)-5-fluoro-1H-indol-2-yl)-1-butyl-N,N-dimethylcyclohexanamine, citrate (2:3);
(106) 4-(3-(2-(1H-imidazol-1-yl)ethyl)-5-fluoro-1H-indol-2-yl)-1-butyl-N,N-dimethylcyclohexanamine, citrate;
(107) 4-(3-(2-(1H-imidazol-1-yl)ethyl)-5-fluoro-1H-indol-2-yl)-N,N-dimethyl-1-phenylcyclohexanamine, citrate;
(108) 4-(3-(2-(1H-imidazol-1-yl)ethyl)-5-fluoro-1H-indol-2-yl)-N,N-dimethyl-1-phenylcyclohexanamine, citrate (2:3);
(109) 4-(3-(2-(1H-benzo[d]imidazol-1-yl)ethyl)-5-fluoro-1H-indol-2-yl)-1-benzyl-N,N-dimethylcyclohexanamine, citrate (4:3);
(110) 4-(3-(2-(1H-benzo[d]imidazol-1-yl)ethyl)-5-fluoro-1H-indol-2-yl)-1-benzyl-N,N-dimethylcyclohexanamine, citrate (2:3);
(111) 4-(3-(2-(1H-benzo[d]imidazol-1-yl)ethyl)-5-fluoro-1H-indol-2-yl)-1-butyl-N,N-dimethylcyclohexanamine, citrate (2:3);
(112) 4-(3-(2-(1H-1,2,3-triazol-1-yl)ethyl)-5-fluoro-1H-indol-2-yl)-1-benzyl-N,N-dimethylcyclohexanamine, citrate (4:1);
(113) 4-(3-(2-(1H-1,2,3-triazol-1-yl)ethyl)-5-fluoro-1H-indol-2-yl)-1-benzyl-N,N-dimethylcyclohexanamine, citrate;
(114) 4-(3-(2-(1H-1,2,3-triazol-1-yl)ethyl)-5-fluoro-1H-indol-2-yl)-1-butyl-N,N-dimethylcyclohexanamine, citrate;
(115) 4-(3-(2-(1H-1,2,3-triazol-1-yl)ethyl)-5-fluoro-1H-indol-2-yl)-1-butyl-N,N-dimethylcyclohexanamine, citrate;
(116) 4-(3-(2-(1H-1,2,3-triazol-1-yl)ethyl)-5-fluoro-1H-indol-2-yl)-N,N-dimethyl-1-phenylcyclohexanamine, citrate;
(117) 4-(3-(2-(1H-1,2,3-triazol-1-yl)ethyl)-5-fluoro-1H-indol-2-yl)-N,N-dimethyl-1-phenylcyclohexanamine, citrate;
(118) 2-(4-(dimethylamino)-4-phenylcyclohexyl)-3-methyl-1H-indol-5-ol;
(119) 2-(4-(dimethylamino)-4-phenylcyclohexyl)-3-methyl-1H-indol-5-ol;
120) 1-benzyl-N,N-dimethyl-4-(3-methyl-5-(trifluoromethoxy)-1H-indol-2-yl)cyclohexanamine, citrate;
(121) 1-butyl-N,N-dimethyl-4-(3-methyl-5-(trifluoromethoxy)-1H-indol-2-yl)cyclohexanamine, citrate;
(122) 1-butyl-N,N-dimethyl-4-(3-methyl-5-(trifluoromethoxy)-1H-indol-2-yl)cyclohexanamine, citrate;
(123) N,N-dimethyl-4-(3-methyl-5-(trifluoromethoxy)-1H-indol-2-yl)-1-phenylcyclohexanamine, citrate;
(124) N,N-dimethyl-4-(3-methyl-5-(trifluoromethoxy)-1H-indol-2-yl)-1-phenylcyclohexanamine, citrate;
(125) 1-butyl-4-(5-methoxy-3-methyl-1H-indol-2-yl)-N,N-dimethylcyclohexanamine, citrate;
(126) 1-butyl-4-(5-methoxy-3-methyl-1H-indol-2-yl)-N,N-dimethylcyclohexanamine, citrate;
(127) 4-(5-methoxy-3-methyl-1H-indol-2-yl)-N,N-dimethyl-1-phenylcyclohexanamine, citrate;
(128) 4-(5-methoxy-3-methyl-1H-indol-2-yl)-N,N-dimethyl-1-phenylcyclohexanamine, citrate; (4:3);
(129) 1-benzyl-N,N-dimethyl-4-(3-methyl-1H-indol-2-yl)cyclohexanamine, citrate;
(130) 1-benzyl-N,N-dimethyl-4-(3-methyl-1H-indol-2-yl)cyclohexanamine, citrate;
(131) 1-butyl-N,N-dimethyl-4-(3-methyl-1H-indol-2-yl)cyclohexanamine, citrate;
(132) 1-butyl-N,N-dimethyl-4-(3-methyl-1H-indol-2-yl)cyclohexanamine, citrate;
(133) 1-benzyl-4-(3-cyclopropyl-1H-indol-2-yl)-N,N-dimethylcyclohexanamine, citrate;
(134) 1-benzyl-4-(3-cyclopropyl-1H-indol-2-yl)-N,N-dimethylcyclohexanamine, citrate;
(135) 1-butyl-4-(3-cyclopropyl-1H-indol-2-yl)-N,N-dimethylcyclohexanamine hydrochloride;
(136) 4-(3-cyclopropyl-1H-indol-2-yl)-N,N-dimethyl-1-phenylcyclohexanamine, citrate;
(137) methyl 2-(2-(4-(dimethylamino)-4-phenylcyclohexyl)-1H-indol-3-yl)acetate, citrate;
(138) methyl 2-(2-(4-(dimethylamino)-4-phenylcyclohexyl)-1H-indol-3-yl)acetate, citrate;
(139) 1-benzyl-4-(3-(cyclohexylmethyl)-1H-indol-2-yl)-N,N-dimethylcyclohexanamine, citrate;
(140) 1-benzyl-4-(3-(cyclohexylmethyl)-1H-indol-2-yl)-N,N-dimethylcyclohexanamine, citrate;
(141) 1-benzyl-4-(3-benzyl-1H-indol-2-yl)-N,N-dimethylcyclohexanamine, citrate;
(142) 1-benzyl-4-(3-benzyl-1H-indol-2-yl)-N,N-dimethylcyclohexanamine, citrate;
(143) 1-butyl-4-(3-(cyclohexylmethyl)-1H-indol-2-yl)-N,N-dimethylcyclohexanamine, citrate;
(144) 1-butyl-4-(3-(cyclohexylmethyl)-1H-indol-2-yl)-N,N-dimethylcyclohexanamine hydrochloride;
(145) 4-(3-benzyl-1H-indol-2-yl)-1-butyl-N,N-dimethylcyclohexanamine, citrate;
(146) 4-(3-benzyl-1H-indol-2-yl)-1-butyl-N,N-dimethylcyclohexanamine, citrate;
(147) 4-(3-(cyclohexylmethyl)-1H-indol-2-yl)-N,N-dimethyl-1-phenylcyclohexanamine, citrate;
(148) 4-(3-(cyclohexylmethyl)-1H-indol-2-yl)-N,N-dimethyl-1-phenylcyclohexanamine, citrate;
(149) 4-(3-benzyl-1H-indol-2-yl)-N,N-dimethyl-1-phenylcyclohexanamine, citrate;
(150) 4-(3-benzyl-1H-indol-2-yl)-N,N-dimethyl-1-phenylcyclohexanamine, citrate;
(151) N,N-dimethyl-1-phenyl-4-(3-(pyridin-2-ylmethyl)-1H-indol-2-yl)cyclohexanamine;
(152) N,N-dimethyl-1-phenyl-4-(3-(pyridin-2-ylmethyl)-1H-indol-2-yl)cyclohexanamine;
(153) 3-(2-(4-(dimethylamino)-4-phenylcyclohexyl)-1H-indol-3-yl)propanoic acid hydrochloride;
(156) 1-benzyl-N,N-dimethyl-4-(3-propyl-1H-indol-2-yl)cyclohexanamine, citrate;
(157) 1-butyl-N,N-dimethyl-4-(3-propyl-1H-indol-2-yl)cyclohexanamine hydrochloride;
(158) 1-butyl-N,N-dimethyl-4-(3-propyl-1H-indol-2-yl)cyclohexanamine, citrate;
(159) N,N-dimethyl-1-phenyl-4-(3-propyl-1H-indol-2-yl)cyclohexanamine, citrate;
(160) N,N-dimethyl-1-phenyl-4-(3-propyl-1H-indol-2-yl)cyclohexanamine, citrate;
(161) 1-benzyl-N,N-dimethyl-4-(3-(2-(pyridin-4-yl)ethyl)-1H-indol-2-yl)cyclohexanamine, citrate;
(162) 1-benzyl-N,N-dimethyl-4-(3-(2-(pyridin-4-yl)ethyl)-1H-indol-2-yl)cyclohexanamine, citrate;
(163) 1-butyl-N,N-dimethyl-4-(3-(2-(pyridin-4-yl)ethyl)-1H-indol-2-yl)cyclohexanamine, citrate;

(164) 1-butyl-N,N-dimethyl-4-(3-(2-(pyridin-4-yl)ethyl)-1H-indol-2-yl)cyclohexanamine, citrate;
(165) N,N-dimethyl-1-phenyl-4-(3-(2-(pyridin-4-yl)ethyl)-1H-indol-2-yl)cyclohexanamine, citrate (1:4);
(166) N,N-dimethyl-1-phenyl-4-(3-(2-(pyridin-4-yl)ethyl)-1H-indol-2-yl)cyclohexanamine, citrate;
(167) N,N-dimethyl-4-(3-(2-(1-methyl-1H-benzo[d]imidazol-2-yl)ethyl)-1H-indol-2-yl)-1-phenylcyclohexanamine, citrate;
(168) N,N-dimethyl-4-(3-(2-(1-methyl-1H-benzo[d]imidazol-2-yl)ethyl)-1H-indol-2-yl)-1-phenylcyclohexanamine, citrate;
(169) N,N-dimethyl-1-phenyl-4-(3-(2-(pyridin-2-yl)ethyl)-1H-indol-2-yl)cyclohexanamine, citrate;
(170) N,N-dimethyl-1-phenyl-4-(3-(2-(pyridin-2-yl)ethyl)-1H-indol-2-yl)cyclohexanamine, citrate (2:3);
(171) 4-(2-(4-benzyl-4-(dimethylamino)cyclohexyl)-1H-indol-3-yl)butanoic acid hydrochloride;
(172) 4-(2-(4-(dimethylamino)-4-phenylcyclohexyl)-1H-indol-3-yl)butanoic acid hydrochloride;
(173) 4-(2-(4-(dimethylamino)-4-phenylcyclohexyl)-1H-indol-3-yl)butan-1-ol hydrochloride;
(174) 4-(2-(4-benzyl-4-(dimethylamino)cyclohexyl)-1H-indol-3-yl)butyl acetate hydrochloride;
(175) 4-(2-(4-benzyl-4-(dimethylamino)cyclohexyl)-1H-indol-3-yl)butyl acetate hydrochloride;
(176) 4-(2-(4-butyl-4-(dimethylamino)cyclohexyl)-1H-indol-3-yl)butyl acetate hydrochloride;
(177) 4-(2-(4-butyl-4-(dimethylamino)cyclohexyl)-1H-indol-3-yl)butyl acetate hydrochloride;
(178) 4-(2-(4-(dimethylamino)-4-phenylcyclohexyl)-1H-indol-3-yl)butyl acetate hydrochloride;
(179) 4-(2-(4-(dimethylamino)-4-phenylcyclohexyl)-1H-indol-3-yl)butyl acetate hydrochloride;
(180) 3-(2-(4-benzyl-4-(dimethylamino)cyclohexyl)-1H-indol-3-yl)propan-1-ol, citrate;
(181) 3-(2-(4-butyl-4-(dimethylamino)cyclohexyl)-1H-indol-3-yl)propan-1-ol hydrochloride;
(182) 3-(2-(4-butyl-4-(dimethylamino)cyclohexyl)-1H-indol-3-yl)propan-1-ol hydrochloride;
(183) 3-(2-(4-(dimethylamino)-4-phenylcyclohexyl)-1H-indol-3-yl)propan-1-ol hydrochloride;
(184) 3-(2-(4-(dimethylamino)-4-phenylcyclohexyl)-1H-indol-3-yl)propan-1-ol hydrochloride;
(185) 3-(2-(4-(dimethylamino)-4-phenylcyclohexyl)-1H-indol-3-yl)propyl acetate hydrochloride;
(186) 3-(2-(4-(dimethylamino)-4-phenylcyclohexyl)-1H-indol-3-yl)propyl acetate hydrochloride;
(187) 1-(2-(2-(4-(dimethylamino)-4-phenylcyclohexyl)-1H-indol-3-yl)ethyl)pyrrolidine-2,5-dione;
(188) 1-(2-(2-(4-(dimethylamino)-4-phenylcyclohexyl)-1H-indol-3-yl)ethyl)pyrrolidine-2,5-dione;
(189) 4-(3-(2-(3,4-dihydroquinolin-1(2H)-yl)ethyl)-1H-indol-2-yl)-N,N-dimethyl-1-phenylcyclohexanamine, citrate (4:3);
(190) 4-(3-(2-(3,4-dihydroquinolin-1(2H)-yl)ethyl)-1H-indol-2-yl)-N,N-dimethyl-1-phenylcyclohexanamine, citrate;
(191) methyl 1-(2-(2-(4-(dimethylamino)-4-phenylcyclohexyl)-1H-indol-3-yl)ethyl)-1H-1,2,3-triazole-4-carboxylate, citrate;
(192) methyl 1-(2-(2-(4-(dimethylamino)-4-phenylcyclohexyl)-1H-indol-3-yl)ethyl)-1H-1,2,3-triazole-4-carboxylate, citrate;
(193) 4-(3-(2-(isoindolin-2-yl)ethyl)-1H-indol-2-yl)-N,N-dimethyl-1-phenylcyclohexanamine, citrate;
(194) 4-(3-(2-(isoindolin-2-yl)ethyl)-1H-indol-2-yl)-N,N-dimethyl-1-phenylcyclohexanamine, citrate;
(195) 4-(3-(2-(3,4-dihydroisoquinolin-2(1H)-yl)ethyl)-1H-indol-2-yl)-N,N-dimethyl-1-phenylcyclohexanamine, citrate;
(196) 4-(3-(2-(3,4-dihydroisoquinolin-2(1H)-yl)ethyl)-1H-indol-2-yl)-N,N-dimethyl-1-phenylcyclohexanamine, citrate (2:3);
(197) N,N-dimethyl-1-phenyl-4-(3-(2-(pyrrolidin-1-yl)ethyl)-1H-indol-2-yl)cyclohexanamine, citrate;
(198) N,N-dimethyl-1-phenyl-4-(3-(2-(pyrrolidin-1-yl)ethyl)-1H-indol-2-yl)cyclohexanamine, citrate;
(199) N,N-dimethyl-1-phenyl-4-(3-(2-(piperidin-1-yl)ethyl)-1H-indol-2-yl)cyclohexanamine, citrate;
(200) N,N-dimethyl-4-(3-(2-(4-methylpiperazin-1-yl)ethyl)-1H-indol-2-yl)-1-phenylcyclohexanamine, citrate;
(201) N,N-dimethyl-4-(3-(2-morpholinoethyl)-1H-indol-2-yl)-1-phenylcyclohexanamine, citrate;
(202) N,N-dimethyl-4-(3-(2-morpholinoethyl)-1H-indol-2-yl)-1-phenylcyclohexanamine, citrate;
(203) 4-(3-(2-(1H-benzo[d]imidazol-1-yl)ethyl)-1H-indol-2-yl)-N,N-dimethyl-1-phenylcyclohexanamine, citrate;
(204) 4-(3-(2-(1H-benzo[d]imidazol-1-yl)ethyl)-1H-indol-2-yl)-N,N-dimethyl-1-phenylcyclohexanamine, citrate;
(205) 4-(3-(2-(1H-imidazol-1-yl)ethyl)-1H-indol-2-yl)-N,N-dimethyl-1-phenylcyclohexanamine, citrate;
(206) 4-(3-(2-(1H-imidazol-1-yl)ethyl)-1H-indol-2-yl)-N,N-dimethyl-1-phenylcyclohexanamine, citrate;
(207) 4-(3-(2-(1H-1,2,4-triazol-1-yl)ethyl)-1H-indol-2-yl)-N,N-dimethyl-1-phenylcyclohexanamine, citrate;
(208) 4-(3-(2-(1H-1,2,4-triazol-1-yl)ethyl)-1H-indol-2-yl)-N,N-dimethyl-1-phenylcyclohexanamine, citrate;
(209) N,N-dimethyl-1-phenyl-4-(3-(2-(thiazolidin-3-yl)ethyl)-1H-indol-2-yl)cyclohexanamine, citrate;
(210) N,N-dimethyl-1-phenyl-4-(3-(2-(thiazolidin-3-yl)ethyl)-1H-indol-2-yl)cyclohexanamine, citrate;
(211) N,N-dimethyl-4-(3-(2-(5-methyl-2H-tetrazol-2-yl)ethyl)-1H-indol-2-yl)-1-phenylcyclohexanamine, citrate;
(212) N,N-dimethyl-4-(3-(2-(5-methyl-2H-tetrazol-2-yl)ethyl)-1H-indol-2-yl)-1-phenylcyclohexanamine, citrate;
(213) 4-(3-(2-(1H-pyrazol-1-yl)ethyl)-1H-indol-2-yl)-N,N-dimethyl-1-phenylcyclohexanamine, citrate;
(214) 4-(3-(2-(1H-pyrazol-1-yl)ethyl)-1H-indol-2-yl)-N,N-dimethyl-1-phenylcyclohexanamine, citrate;
(215) 4-(3-(2-(1H-1,2,3-triazol-1-yl)ethyl)-1H-indol-2-yl)-N,N-dimethyl-1-phenylcyclohexanamine, citrate;
(216) 4-(3-(2-(1H-1,2,3-triazol-1-yl)ethyl)-1H-indol-2-yl)-N,N-dimethyl-1-phenylcyclohexanamine, citrate;
(217) N,N-dimethyl-4-(3-(2-(5-methyl-1H-tetrazol-1-yl)ethyl)-1H-indol-2-yl)-1-phenylcyclohexanamine, citrate;
(218) N,N-dimethyl-4-(3-(2-(5-methyl-1H-tetrazol-1-yl)ethyl)-1H-indol-2-yl)-1-phenylcyclohexanamine, citrate;
(219) 2-(2-(4-(dimethylamino)-4-phenylcyclohexyl)-1H-indol-3-yl)ethanol;
(220) 2-(2-(4-(dimethylamino)-4-phenylcyclohexyl)-1H-indol-3-yl)ethyl acetate;
(221) N,N-dimethyl-4-(3-methyl-1H-pyrrolo[3,2-c]pyridin-2-yl)-1-phenylcyclohexanamine, citrate;
(222) N,N-dimethyl-4-(3-methyl-1H-pyrrolo[3,2-c]pyridin-2-yl)-1-phenylcyclohexanamine, citrate;

(223) N,N-dimethyl-4-(3-methyl-1H-pyrrolo[2,3-b]pyridin-2-yl)-1-phenylcyclohexanamine, citrate;
(224) N,N-dimethyl-4-(3-methyl-1H-pyrrolo[2,3-b]pyridin-2-yl)-1-phenylcyclohexanamine, citrate;
(225) N,N-dimethyl-4-(3-methylbenzofuran-2-yl)-1-phenylcyclohexanamine, citrate;
(226) N,N-dimethyl-4-(3-methylbenzofuran-2-yl)-1-phenylcyclohexanamine, citrate;
(227) 4-(1H-indol-3-yl)-N,N-dimethyl-1-phenylcyclohexanamine, citrate;
(228) (±)-3-(4-(dimethylamino)-4-benzylcyclohex-1-enyl)-1H-pyrrolo[2,3-b]pyridine;
(229) (±)-3-(4-(dimethylamino)-4-butylcyclohex-1-enyl)-1H-pyrrolo[2,3-b]pyridine;
(230) (±)-3-(4-(dimethylamino)-4-phenylcyclohex-1-enyl)-1H-pyrrolo[2,3-b]pyridine, citrate;
(231) (±)-4-(1H-indol-3-yl)-N,N-dimethyl-1-phenylcyclohex-3-enamine, citrate;
(232) (±)-4-(1H-indol-3-yl)-N,N-dimethyl-1-phenylcyclohex-3-enamine;
(233) (±)-2-(3-(4-(dimethylamino)-4-phenylcyclohex-1-enyl)benzo[b]thiophen-2-yl)ethanol hydrochloride;
(234) (±)-2-(3-(4-(dimethylamino)-4-(pyridin-2-yl)cyclohex-1-enyl)benzo[b]thiophen-2-yl)ethanol hydrochloride;
(235) 4-(1H-indol-2-yl)-N,N-dimethyl-1-phenylcyclohexanamine, citrate;
(236) 4-(1H-indol-2-yl)-N,N-dimethyl-1-phenylcyclohexanamine, citrate;
(237) 1-benzyl-N,N-dimethyl-4-(1H-pyrrolo[2,3-b]pyridin-3-yl)cyclohexanamine hydrochloride;
(238) 1-butyl-N,N-dimethyl-4-(1H-pyrrolo[2,3-b]pyridin-3-yl)cyclohexanamine hydrochloride;
(239) (±)-4-(benzofuran-2-yl)-1-benzyl-N,N-dimethylcyclohex-3-enamine hydrochloride;
(240) (±)-N,N-dimethyl-4-(3-methylbenzofuran-2-yl)-1-phenylcyclohex-3-enamine, citrate;
(241) (±)-2-(2-(4-(dimethylamino)-4-phenylcyclohex-1-enyl)benzofuran-3-yl)ethanethiol, citrate;
(242) (±)-N,N-dimethyl-4-(3-methylbenzo[b]thiophen-2-yl)-1-phenylcyclohex-3-enamine, citrate;
(243) N,N-dimethyl-4-(3-methylbenzo[b]thiophen-2-yl)-1-phenylcyclohexanamine, citrate;
(244) N,N-dimethyl-1-phenyl-4-(1H-pyrrolo[2,3-b]pyridin-3-yl)cyclohexanamine, citrate;
(245) 1-(dimethylamino)-3-(2-(4-(dimethylamino)-4-phenylcyclohexyl)-3-methyl-1H-indol-1-yl)propan-2-ol;
(247) N,N-dimethyl-4-(3-methyl-1-(oxiran-2-ylmethyl)-1H-indol-2-yl)-1-phenylcyclohexanamine;
(248) 4-(1,3-dimethyl-1H-indol-2-yl)-N,N-dimethyl-1-phenylcyclohexanamine;
(249) 2-(4-butyl-4-(dimethylamino)cyclohexyl)-3-methyl-1H-indol-5-ol, citrate;
(250) 2-(4-butyl-4-(dimethylamino)cyclohexyl)-3-methyl-1H-indol-5-ol, citrate;
(251) (±)-2-(4-(dimethylamino)-4-(thiophen-2-yl)-cyclohex-1-enyl)-3-(2-(pyridin-4-yl)ethyl)-1H-indole;
(252) (±)-2-(4-(dimethylamino)-4-(3-fluorophenyl)-cyclohex-1-enyl)-3-(2-(pyridin-4-yl)ethyl)-1H-indole;
(253) (±)-2-(4-butyl-4-(pyrrolidin-1-yl)cyclohex-1-enyl)-3-(2-(pyridin-4-yl)ethyl)-1H-indole;
(254) (±)-2-(4-(methylamino)-4-phenylcyclohex-1-enyl)-3-(2-(pyridin-4-yl)ethyl)-1H-indole;
(255) (±)-2-(4-(dimethylamino)-4-(thiophen-2-yl)-cyclohex-1-enyl)-3-methyl-1H-indole, citrate;
(256) N,N-dimethyl-4-(3-methyl-1H-indol-2-yl)-1-(thiophen-2-yl)cyclohexanamine, citrate;
(257) N,N-dimethyl-4-(3-methyl-1H-indol-2-yl)-1-(thiophen-2-yl)cyclohexanamine, citrate;
(258) 2-(4-butyl-4-(pyrrolidin-1-yl)cyclohex-1-enyl)-3-methyl-1H-indole;
(259) N-methyl-4-(3-methyl-1H-indol-2-yl)-1-phenylcyclohexanamine hydrobromide;
(260) N-methyl-4-(3-methyl-1H-indol-2-yl)-1-phenylcyclohexanamine, citrate;
(261) 1-(3-fluorophenyl)-N,N-dimethyl-4-(3-methyl-1H-indol-2-yl)cyclohexanamine, citrate;
(262) 1-(3-fluorophenyl)-N,N-dimethyl-4-(3-methyl-1H-indol-2-yl)cyclohexanamine, citrate;
(263) (±)-2-(4-(dimethylamino)-4-(3-fluorophenyl)-cyclohex-1-enyl)-3-methyl-1H-indole;
(264) 2-(4-benzyl-4-(dimethylamino)cyclohexyl)-3-methyl-1H-indol-5-ol, citrate;
(265) 2-(4-benzyl-4-(dimethylamino)cyclohexyl)-3-methyl-1H-indol-5-ol, citrate;
(266) 2-(4-butyl-4-(pyrrolidin-1-yl)cyclohexyl)-3-(2-(pyridin-4-yl)ethyl)-1H-indole, citrate;
(267) 2-(4-butyl-4-(pyrrolidin-1-yl)cyclohexyl)-3-(2-(pyridin-4-yl)ethyl)-1H-indole, citrate;
(268) 2-(4-(azetidin-1-yl)-4-phenylcyclohexyl)-3-methyl-1H-indole, citrate;
(269) 2-(4-(azetidin-1-yl)-4-phenylcyclohexyl)-3-methyl-1H-indole, citrate;
(270) 2-(4-(azetidin-1-yl)-4-phenylcyclohexyl)-3-(2-(pyridin-4-yl)ethyl)-1H-indole hydrochloride;
(271) 2-(4-(azetidin-1-yl)-4-phenylcyclohexyl)-3-(2-(pyridin-4-yl)ethyl)-1H-indole hydrochloride;
(272) 2-(4-butyl-4-(pyrrolidin-1-yl)cyclohexyl)-3-methyl-1H-indole, citrate;
(273) 3-(2-(4-(dimethylamino)-4-phenylcyclohexyl)-1H-pyrrolo[2,3-b]pyridin-3-yl)propan-1-ol, citrate;
(274) 1-(2-(4-(dimethylamino)-4-phenylcyclohexyl)-3-methyl-1H-indol-1-yl)-3-(methylamino)propan-2-ol, citrate;
(275) 1-benzyl-3-(2-(2-(4-(dimethylamino)-4-phenylcyclohexyl)-1H-indol-3-yl)ethyl)urea, citrate;
(276) 1-benzyl-3-(2-(2-(4-(dimethylamino)-4-phenylcyclohexyl)-1H-indol-3-yl)ethyl)urea, citrate;
(277) 1-(2-(2-(4-(dimethylamino)-4-phenylcyclohexyl)-1H-indol-3-yl)ethyl)-3-phenylurea, citrate;
(278) 1-(2-(2-(4-(dimethylamino)-4-phenylcyclohexyl)-1H-indol-3-yl)ethyl)-3-phenylurea, citrate;
(279) 1-cyclopentyl-3-(2-(2-(4-(dimethylamino)-4-phenylcyclohexyl)-1H-indol-3-yl)ethyl)urea, citrate;
(280) 1-cyclopentyl-3-(2-(2-(4-(dimethylamino)-4-phenylcyclohexyl)-1H-indol-3-yl)ethyl)urea, citrate;
(281) N-(2-(2-(4-(dimethylamino)-4-phenylcyclohexyl)-1H-indol-3-yl)ethyl)-cyclopentanesulfonamide, citrate;
(282) N-(2-(2-(4-(dimethylamino)-4-phenylcyclohexyl)-1H-indol-3-yl)ethyl)cyclopentanesulfonamide, citrate;
(283) N-(2-(2-(4-(dimethylamino)-4-phenylcyclohexyl)-1H-indol-3-yl)ethyl)benzenesulfonamide, citrate;
(284) N-(2-(2-(4-(dimethylamino)-4-phenylcyclohexyl)-1H-indol-3-yl)ethyl)thiophene-2-sulfonamide, citrate;
(285) N-(2-(2-(4-(dimethylamino)-4-phenylcyclohexyl)-1H-indol-3-yl)ethyl)thiophene-2-sulfonamide, citrate;
(286) N-(2-(2-(4-(dimethylamino)-4-phenylcyclohexyl)-1H-indol-3-yl)ethyl)nicotinamide, citrate;
(287) N-(2-(2-(4-(dimethylamino)-4-phenylcyclohexyl)-1H-indol-3-yl)ethyl)nicotinamide, citrate;
(288) N-(2-(2-(4-(dimethylamino)-4-phenylcyclohexyl)-1H-indol-3-yl)ethyl)benzamide, citrate;

(289) 1-(3-fluorophenyl)-N,N-dimethyl-4-(3-(2-(pyridin-4-yl)ethyl)-1H-indol-2-yl)cyclohexanamine;

(290) 1-(3-fluorophenyl)-N,N-dimethyl-4-(3-(2-(pyridin-4-yl)ethyl)-1H-indol-2-yl)cyclohexanamine, citrate;

(291) N-methyl-1-phenyl-4-(3-(2-(pyridin-4-yl)ethyl)-1H-indol-2-yl)cyclohexanamine, citrate;

(292) N-methyl-1-phenyl-4-(3-(2-(pyridin-4-yl)ethyl)-1H-indol-2-yl)cyclohexanamine, citrate;

(293) 2-(4-butyl-4-(pyrrolidin-1-yl)cyclohexyl)-3-methyl-1H-indole, citrate;

(294) N,N-dimethyl-1-phenyl-4-(1-(phenylsulfonyl)-1H-indol-2-yl)cyclohexanamine;

(295) N,N-dimethyl-1-phenyl-4-(1-(phenylsulfonyl)-1H-indol-2-yl)cyclohexanamine;

(296) N,N-dimethyl-4-(3-methyl-1-(oxiran-2-ylmethyl)-1H-indol-2-yl)-1-phenylcyclohex-3-enamine;

(297) N,N-dimethyl-4-(3-methyl-1-(oxiran-2-ylmethyl)-1H-indol-2-yl)-1-phenylcyclohexanamine, citrate;

(298) 1-(dimethylamino)-3-(2-(4-(dimethylamino)-4-phenylcyclohex-1-enyl)-3-methyl-1H-indol-1-yl)propan-2-ol, citrate;

(299) 1-(dimethylamino)-3-(2-(4-(dimethylamino)-4-phenylcyclohexyl)-3-methyl-1H-indol-1-yl)propan-2-ol, citrate;

(300) 2-(3-(4-(dimethylamino)-4-phenylcyclohex-1-enyl)-1H-indol-1-yl)ethanol hydrochloride;

(301) (±) 3-(4-(dimethylamino)-4-phenylcyclohex-1-enyl)-(1-(phenylsulfonyl)-1H-indole) hydrochloride;

(302) 1-benzyl-N,N-dimethyl-4-(1-methyl-1H-indol-2-yl)cyclohex-3-enamine; hydrochloride;

(303) N,N-dimethyl-4-(3-(2-(pyridin-4-yl)ethyl)-1H-indol-2-yl)-1-(thiophen-2-yl)cyclohexanamine hydrochloride;

(304) N,N-dimethyl-4-(3-(2-(pyridin-4-yl)ethyl)-1H-indol-2-yl)-1-(thiophen-2-yl)cyclohexanamine hydrochloride;

(305) N-methyl-4-(3-methyl-1H-indol-2-yl)-1-(4-methylthiazol-2-yl)cyclohexanamine;

(306) N-methyl-4-(3-methyl-1H-indol-2-yl)-1-(4-methylthiazol-2-yl)cyclohexanamine; and (307) 2-(2-(4-(dimethylamino)-4-phenylcyclohexyl)-1H-indol-3-yl)ethanol;

in the form of the racemate; of the enantiomers, diastereomers, mixtures of the enantiomers or diastereomers or of an individual enantiomer or diastereomer; of the bases and/or salts of physiologically acceptable acids.

12. Process for the preparation of substituted heteroaryl derivatives of the formula Ic

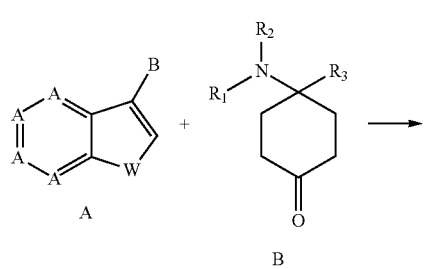

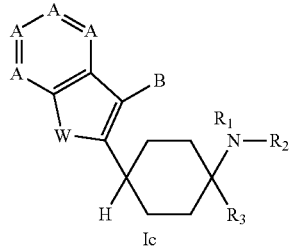

comprising reacting ketones of the formula B with heteroaromatics of the formula A in organic solvents or solvent mixtures with the addition of an organic or inorganic acid, or without a solvent in an organic or inorganic acid or acid mixtures at temperatures of between 0° C. and 150° C., optionally using microwave irradiation, and then reacting with the addition of an organic or inorganic reducing agent at temperatures of between 0° C. and 150° C., optionally using microwave irradiation.

13. Process for the preparation of substituted heteroaryl derivatives of the general formula Id or Ie

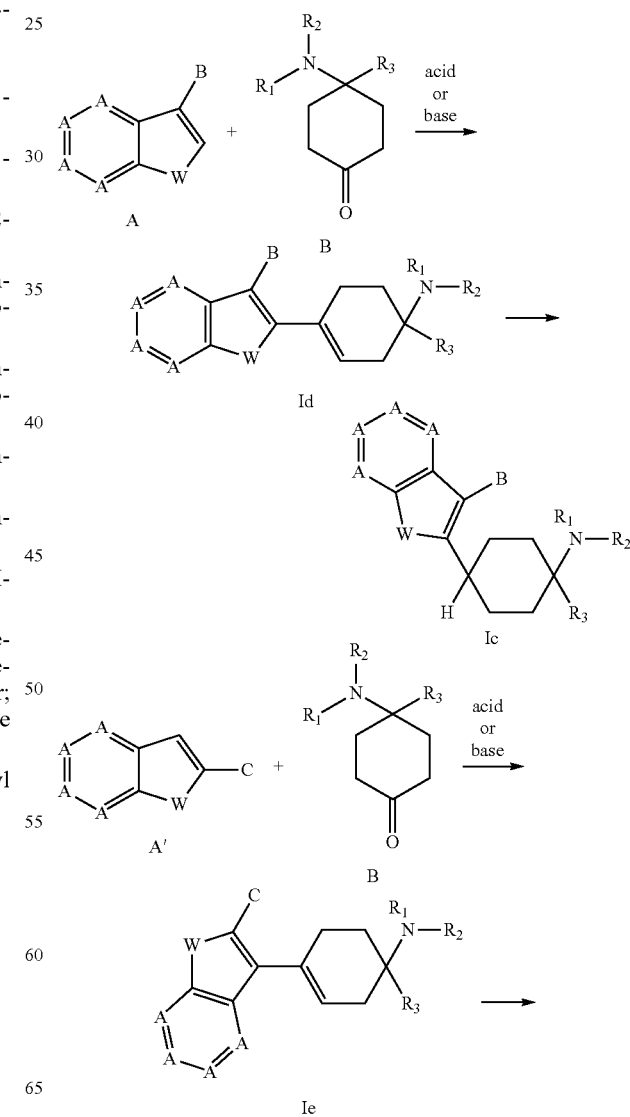

-continued

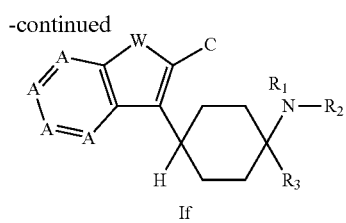

If comprising reacting heteroaromatics of the formula A or A' with cyclohexanones of the formula B in organic solvents or solvent mixtures with the addition of an organic or inorganic acid at temperatures of between 0° C. and 150° C., optionally using microwave irradiation;

or reacting heteroaromatics of the formula A or A' with cyclohexanones of the formula B with the addition of a base in an organic solvent at temperatures of between 20 and 100° C.

14. Process for the preparation of substituted heteroaryl derivatives of the formulae Ic or If

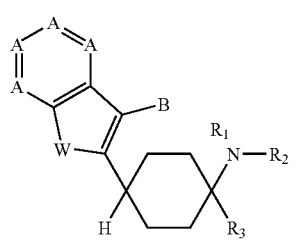

Ic

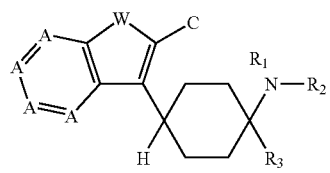

If comprising reducing compounds Id or Ie by means of hydrogen in the form of HBr/glacial acetic acid/Sn or HCl/Sn (nascent hydrogen) or $H_2$ in the presence of a metal catalyst in a suitable solvent or solvent mixture at temperatures of between 0° C. and 150° C.

15. A pharmaceutical composition comprising at least one substituted heteroaryl derivative according claim 1, optionally in the form of its racemate, of the pure stereoisomers, of a mixture of multiple stereoisomers in any desired mixture ratio; in the form of its acids or of its bases or in the form of its salts; and optionally containing suitable additives and/or auxiliary substances and/or optionally further active compounds.

16. A method of treating pain, selected from the group consisting of acute pain, chronic pain, and neuropathic pain, in a patient in need of such treatment, said method comprising administering to said patient an effective amount therefor of a substituted heteroaryl derivative according to claim 1, optionally in the form of its racemate, of the pure stereoisomers, of a mixture of multiple stereoisomers in any desired mixture ratio; in the form of its acids or of its bases or in the form of its salts.

17. Substituted heteroaryl derivatives according to claim 1, which has the formula:

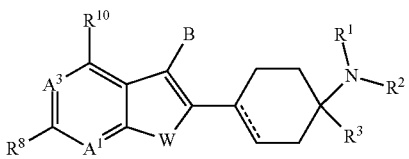

wherein

⇌ represents a single bond or a double bond,
$A^1$ represents N or $CR^7$;
$A^3$ represents N or $CR^9$; and
W represents O, S or $NR^4$;
with the proviso that if W represents O or S, then $A^1$ represents $CR^7$ and $A^3$ represents $CR^9$;

B represents $(CH_2)_{1-4}$—$R^{21}$, wherein $R^{21}$ represents H, OH, SH, $COOC_{1-6}$-alkyl, COOH, $OC(=O)C_{1-6}$-alkyl, $NH_2$, $NHC(=O)C_{1-6}$-alkyl; or $C_{3-8}$-cycloalkyl, aryl or heteroaryl, in each case unsubstituted or mono- or polysubstituted;

$R^1$ and $R^2$ independently of one another represent H; $C_{1-5}$-alkyl, saturated, branched or unbranched, unsubstituted;
or the radicals $R^1$ and $R^2$ together form a ring and denote $CH_2CH_2OCH_2CH_2$, $CH_2CH_2NR^{11}CH_2CH_2$ or $(CH_2)_{3-6}$;
wherein $R^{11}$ denotes H; $C_{1-5}$-alkyl, saturated, branched or unbranched, unsubstituted;

$R^3$ represents $C_{1-8}$-alkyl, in each case saturated or unsaturated, branched or unbranched, mono- or polysubstituted or unsubstituted; $C_{3-8}$-cycloalkyl, in each case mono- or polysubstituted or unsubstituted; aryl or heteroaryl, in each case unsubstituted or mono- or polysubstituted; aryl, heteroaryl or $C_{3-8}$-cycloalkyl, bonded via $C_{1-3}$-alkyl group and in each case unsubstituted or mono- or polysubstituted;

$R^4$ represents H; $C_{1-5}$-alkyl, saturated or unsaturated, branched or unbranched, unsubstituted or mono- or polysubstituted; or cycloalkyl, bonded via a $C_{1-3}$-alkyl group and in each case mono- or polysubstituted or unsubstituted; $COR^{12}$; $SO_2R^{12}$;
wherein $R^{12}$ denotes H; $C_{1-5}$-alkyl, saturated, branched or unbranched, unsubstituted; or aryl, mono- or polysubstituted or unsubstituted;

$R^7$ and $R^9$ independently of one another represent H, methyl, ethyl, propyl, butyl, pyridyl, O-benzyl, F, Cl, Br, I, CN, $CF_3$, $OCF_3$, OH, $OCH_3$, $NH_2$, COOH, $COOCH_3$, $NHCH_3$ or $N(CH_3)_2$ or $NO_2$;

in the form of the racemate; of the enantiomers, diastereomers, mixtures of the enantiomers or diastereomers or of an individual enantiomer or diastereomer; of the bases and/or salts of physiologically acceptable acids.

* * * * *